(12) United States Patent
Hsei et al.

(10) Patent No.: US 7,842,789 B2
(45) Date of Patent: *Nov. 30, 2010

(54) ANTIBODY FRAGMENT-POLYMER CONJUGATES AND USES OF SAME

(75) Inventors: Vanessa Hsei, San Jose, CA (US); Iphigenia Koumenis, Winston-Salem, NC (US); Steven Leong, Berkeley, CA (US); Zahra Shahrokh, San Francisco, CA (US); Gerardo Zapata, Berwyn, PA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/291,750

(22) Filed: Nov. 12, 2008

(65) Prior Publication Data

US 2009/0098147 A1    Apr. 16, 2009

Related U.S. Application Data

(63) Continuation of application No. 11/541,145, filed on Sep. 28, 2006, now Pat. No. 7,507,405, which is a continuation of application No. 11/259,232, filed on Oct. 25, 2005, now Pat. No. 7,214,776, which is a continuation of application No. 09/489,394, filed on Jan. 21, 2000, now Pat. No. 7,122,636.

(60) Provisional application No. 60/116,787, filed on Jan. 21, 1999.

(51) Int. Cl.
C07K 16/00 (2006.01)

(52) U.S. Cl. .................................. 530/387.1
(58) Field of Classification Search ........... None
See application file for complete search history.

(56) References Cited

U.S. PATENT DOCUMENTS

| | | | |
|---|---|---|---|
| 4,002,531 A | 1/1977 | Royer | |
| 4,179,337 A | 12/1979 | Davis et al. | |
| 4,515,893 A | 5/1985 | Kung et al. | |
| 4,732,863 A | 3/1988 | Tomasi et al. | |
| 5,091,313 A | 2/1992 | Chang | |
| 5,147,537 A | 9/1992 | Sada et al. | |
| 5,166,322 A | 11/1992 | Shaw et al. | |
| 5,169,627 A | 12/1992 | Cunningham-Rundles | |
| 5,527,528 A | 6/1996 | Allen et al. | |
| 5,532,150 A | 7/1996 | Snow et al. | |
| 5,595,732 A | 1/1997 | Hakini et al. | |
| 5,618,920 A | 4/1997 | Robinson et al. | |
| 5,620,689 A | 4/1997 | Allen et al. | |
| 5,622,700 A | 4/1997 | Jardieu et al. | |
| 5,643,575 A | 7/1997 | Martinez et al. | |
| 5,661,020 A | 8/1997 | Snow et al. | |
| 5,670,132 A | 9/1997 | Griffiths et al. | |
| 5,672,347 A | 9/1997 | Aggarwal et al. | |
| 5,677,426 A | 10/1997 | Fong et al. | |
| 5,679,532 A | 10/1997 | Repine et al. | |
| 5,686,070 A | 11/1997 | Doerschuck et al. | |
| 5,693,762 A | 12/1997 | Queen et al. | |
| 5,695,760 A * | 12/1997 | Faanes et al. | 424/178.1 |
| 5,698,196 A | 12/1997 | Matsushima et al. | |
| 5,702,946 A | 12/1997 | Doerschuk et al. | |
| 5,707,622 A | 1/1998 | Fong et al. | |
| 5,714,338 A | 2/1998 | Wai Fei et al. | |
| 5,725,856 A | 3/1998 | Hudziak et al. | |
| 5,726,037 A | 3/1998 | Bodary et al. | |
| 5,739,277 A | 4/1998 | Presta et al. | |
| 5,766,897 A * | 6/1998 | Braxton | 435/463 |
| 5,874,080 A | 2/1999 | Herbert et al. | |
| 6,025,158 A | 2/2000 | Gonzalez et al. | |
| 6,117,980 A | 9/2000 | Gonzalez et al. | |
| 6,133,426 A | 10/2000 | Gonzalez et al. | |
| 6,458,355 B1 | 10/2002 | Hsei et al. | |
| 6,468,532 B1 | 10/2002 | Hsei et al. | |
| 6,870,033 B1 | 3/2005 | Hsei et al. | |
| 7,005,504 B2 | 2/2006 | Hsei et al. | |
| 7,122,636 B1 | 10/2006 | Hsei et al. | |
| 7,214,776 B2 | 5/2007 | Hsei et al. | |
| 7,507,405 B2 | 3/2009 | Hsei et al. | |

FOREIGN PATENT DOCUMENTS

EP    0239400    9/1987

(Continued)

OTHER PUBLICATIONS

Zapata et al (FASEB J. 9:A1476, 1995).*

(Continued)

*Primary Examiner*—Sean E Aeder
(74) *Attorney, Agent, or Firm*—Craig Svoboda; James A. Fox; Ginger R. Dreger

(57) ABSTRACT

Described are conjugates formed by an antibody fragment covalently attached to a non-proteinaceous polymer, wherein the apparent size of the conjugate is at least about 500 kD. The conjugates exhibit substantially improved half-life, mean residence time, and/or clearance rate in circulation as compared to the underivatized parental antibody fragment. Also described are conjugates directed against human vascular endothelial growth factor (VEGF), human p185 receptor-like tyrosine kinase (HER2), human CD20, human CD18, human CD11a, human IgE, human apoptosis receptor-2 (Apo-2), human tumor necrosis factor-α (TNF-α), human tissue factor (TF), human $\alpha_4\beta_7$ integrin, human GPIIb-IIIa integrin, human epidermal growth factor receptor (EGFR), human CD3, and human interleukin-2 receptor α-chain (TAC) for diagnostic and therapeutic applications.

36 Claims, 144 Drawing Sheets

FOREIGN PATENT DOCUMENTS

| | | |
|---|---|---|
| EP | 420937 B1 | 11/1994 |
| EP | 770628 | 5/1997 |
| WO | WO 92/04372 | 3/1992 |
| WO | WO 93/04173 | 9/1993 |
| WO | WO 94/10202 | 5/1994 |
| WO | WO 94/11026 | 5/1994 |
| WO | WO 94/12219 | 6/1994 |
| WO | WO 94/21235 | 9/1994 |
| WO | WO 95/11987 | 5/1995 |
| WO | WO 95/15769 | 6/1995 |
| WO | WO 95/23813 | 9/1995 |
| WO | WO 95/23865 | 9/1995 |
| WO | WO 95/32003 | 11/1995 |
| WO | WO 96/02576 | 2/1996 |
| WO | WO 96/09325 | 3/1996 |
| WO | WO 96/22785 | 8/1996 |
| WO | WO 96/23065 | 8/1996 |
| WO | WO 96/34015 | 10/1996 |
| WO | WO 96/40210 | 12/1996 |
| WO | WO 96/40731 | 12/1996 |
| WO | WO 97/01354 | 1/1997 |
| WO | WO 97/10847 | 3/1997 |
| WO | WO 97/26912 | 7/1997 |
| WO | WO 97/40215 | 10/1997 |
| WO | WO 98/06248 | 2/1998 |
| WO | WO 98/23761 | 6/1998 |
| WO | WO 98/25971 | 6/1998 |
| WO | WO 98/37200 | 8/1998 |
| WO | WO 98/45331 | 10/1998 |
| WO | WO 98/51793 | 11/1998 |
| WO | WO 99/01556 | 1/1999 |
| WO | WO 99/37779 | 7/1999 |

OTHER PUBLICATIONS

Rathjen et al (Br. J. Cancer, 1992, 65: 852-856).*

Abuchowski and Davis, "Soluble Polymer-Enzyme Adducts" *Enzymes as Drugs*, Holcenberg, JS; Roberts, J. eds., New York; Wiley, Chapter 13, pp. 367-383 (1981).

Adagen Label *Physicans Desk Reference* (Product Information) 48 edition, Montvale, NJ; Medical Economics Data Production Company pp. 917-918 (1994).

Allen et al., "A new strategy for attachment of antibodies to sterically stabilized lipsomes resulting in efficient targeting to cancer cells" *Biochimica et Biophysica Acta* 1237 (2):99-108 (Jul. 26, 1995).

Anderson and Tomasi, "Polymer modification of antibody to eliminate immune complex and Fc binding" *Journal of Immunological Methods* 109(1): 37-42 (Apr. 22, 1988).

Beauchamp et al., "A new peocedure for the synthesis of polythylene glycol-protein adducts; effects on function, receptor recognition, and clearance of superoxide dismutase, lactoferrin, and $\alpha_2$-macroglobulin—Analytical Biochemistry 131 (1)": 25-33 (1983).

Bernard et al., "The American-European Consensus Conferences on ARDS. Definitions, mechanisms, relevant outcomes, and clinical trail coordination" *American Journal of Respiratory & Critical Care medicine* 149 (3 pt 1):818-824 (Mar. 1994).

Brooks and Stocks, "Use of polyacrylamide-derivatized antibody in dextran-poly (ethylene glycol) systems" *Methods in Enzymology* 228:390-395 (1994).

Brumeanu et al., Derivatization with monomethoxypolyethylene glycol of Igs experssing viral epitopes obviates adjuvant requirements :*Journal of Immunology* 154(7):3088-3095 (Apr. 1, 1995).

Carter et al., "Preparation and uses of Fab' fragments from *Esherichia coli*" *Antibody Engineering: a Practical Approach*, Hoogenboom, H., McCafferty, J. Chiswell, D., eds., Oxford, UK:IRK Press, Chpt. 13 pp. 291-308 (1996).

Chamow et al., Modification of CD4 immunoadhesin with monomethoxypoly (ethylene glycol) aldehyde via reductive alkylation: *BioconjugateChemistry* 5 (2): 133-140 (Mar.-Apr. 1994).

Chapman, et al., Therapeutic antibody fragments with prolonged in vivo hlaf-lives *Nature Biotechnology* 17 (8):780-783 (Aug. 1999).

Clark et al., "Long-acting growth hormones produced by conjugation with polyethylene glycol" *Journal of Biological Chemistry* 271 (36):21969-21977 (Sep. 6, 1996).

Cunningham-Rundles, et al., Biological activites of polyethylene-glycol immunoglobulin conjugates. Resistance to enzymatic degradation: *Journal of Immunological Methods* 152 (2):177-190 (Aug. 10, 1992).

Delgado et al., "Analytical partitioning of poly (ethylene glycol) modified proteins" *Journal of Biological Chromotography B* 692 (2):263-272 (May 9, 1997).

Delgado, et al., "Distinct Influence of PEGylation on the Tumour Localisation of Transferrin and a Tumour-specific Fab Fragment (f9)" *Journal of Cellular Biochemistry* (Abst. A4-101, Keystone Symposium held at Hilton Head Island, SC, Jan. 7-13, 1995) Suppl. 19A:171 (1995).

Delgado, et al., "Enhanced tumour specificaity of an anti-carcinoembrionic antigen Fab' fragment by poly (ethylene glycol) (PEG) modification" *British Journal of Cancer* 73(2): 175-182 (Jan. 1996).

Delgado, et al., "The uses and properties of PEG-linked proteins" *Crtical Reviews in Therapeutic Drug Carrier Systems* 9 (3-4):249-304 (1992).

Duel, et al., "Amino acid Sequence of human platelet factor 4" *Proc. Natl. Acad. Sci.* 74:2256-2258 (1977).

Donnelly, et al., :Interleukin-8 and development of adult respiratory distress syndrome in at-risk patient groups *Lancet* 341 (8846):643-647 (Mar. 13, 1993).

Elling and Kula, Immunoaffinity partitoning: synthesis and use of polyethylene glycol-oxirane for coupling to bovine scrum albumin and monoclonal antibodies: *Biotechnology and Applied Biochemistry* 13 (3):354-362 (Jun. 1994).

Eno-Amooquaye et al., "Altered biodistribution of an antibody-enzyme conjugate modified with polyethylene glycol" *British Journal of Cancer* 73(11):1323-1327 (Jun. 1996).

Folkesson, et al., "Acid aspiration-induced lung injury in rabbits is mediated by interleukin-8-dependent mechanisms" *Journal of Clinical Investigation* 96 (1):107-116 (Jul. 1995).

Gonzalez et al., "Humanization of Murine 6G425:An Anti-IL8 Monoclonal Antibody which blocks binding of IL8 to human neutrophils" *1996 Keystone Symposia on Exploring and Exploiting Antibody and Ig Superfamily Combining Sites* (Poster) pp. 1-21 (Feb. 1996).

Harding et al., "Immunogenicity and pharmacokinetic attributes of poly (ethylene glycol)-grafted immunoliposomes" *Biochimica et Biophysica Acta* 1327(2):181-192 (Jul. 25, 1997).

Harris et al., "Synthesis and applications of a new poly (ethylene Glycol) derivative" *J. Polym. Sci Polym. Chem. Ed.* 22 (2):341-352 (1984).

Haselgrubler et al., "Synthesis amd applications of a new poly (theylene glycol) derivative for the crosslinking of amines with thiols" *Bioconjugate Chemistry* 6 (3):242-248 (May-Jun. 1995).

Hebert et al., "Endothelial and Leukocyte Forms of IL-8: Conversion by Thrombin and interactions with Neutrophils" *J. Immunol.* 145 (9):3033-3040 (Nov. 1, 1990).

Hebert e al., "Interleukin-8: A Review" *Cancer Investigation* 11 (6):743-750 (1993).

Hebert, C., "Humanized anti IL-8 antibodies: potential therapy for shock and ARDS?" (Summary of seminar presented at the 1997 Keystone Symposia on "The Role of Chemokines in Leukocyte Trafficking and Disease" held at the Copper Mountain Resort, Co on Mar. 31-Apr. 5, 1997.) pp. 4.

Holliger et al., ":Diabodies: Small bivalent and bispecific antibody fragments" *Proc. Natl. Acad Sci. USA* 90:6444-6448 (Jul. 1993).

Karr et al., "Use of poly (ethylene glycol)-modified antibody in cell extraction" *Methods in Enzymology* 228:377-390 (1994).

Katre N., "The Conjugation of Proteins with Polyethylene Glycol and other Polymers. Altering properties of proteins to enhance their therapeutic potential." *Advanced Drug Delivery Reviews* 10(1):91-114 (1993).

Kawamura et a;., "Immune response to polyethylene glycol modified L-asparaginase in mice" *International Archives of Allergy & Applied Immunology* 76(4):324-330 (1985).

Kirpotin et al., "Sterically stabilized anti-HER2 immunoliposomes: design and targeting to human breast cancer cells in vitro" *Biochemistry* 36(1):66-75 (Jan. 7, 1997).

Kitamura et al., "Chemical engineering of the monoclonal antibody A7 by polyethylene glycol for targeting cancer chemotherapy" *Cancer Research* 51(16):4310-4315 (Aug. 15, 1991).

Kitamura et a;., "Polyethylene glycol modification of the monoclonal antibody A7 enhances its tumor localization" Biochemical & Biophysical Research Communications 171(3):1387-1394 (Sep. 28, 1990).

Knauf et al., "Relationship of effective molecular size to systemic clearance in ratos of recomninant Interleukin-2 chemically modified with wate soluble polymers" *The Journal of Biological Chemistry* 263(29):15064-15070 (Oct. 15, 1988).

Ko et al., "A sensitive enzyme-linked immunosorbent assay for human interleukin-8" *J. Immunol. Methods* 149:227-235 (1992).

Koumenis et al., "Tailoring antibody fragments with PEGylation without loss in biological activity" *Protein Science* (Abstract 109-M, presented at the Proetin Society's Twelfth Symposium in San Diego, CA on Jul. 25-29, 1998) 7 (Suppl. 1) 73 (Jul. 1998).

Lang et al., "Suppression of antibodies responses in rats to murine anti-CD4 monocloncal antibodies by conjugates with monomethoxypolyethylene glycol" *Immunology Letters* 32(3):247-252 (May 1992).

Lee and Sehon, "Suppression of reaginic antibodies with modified allergens. I. Reducation in allergenicity of protein allergens by conjugation to polythylene glycol" *International Archives of Allergy & Applied Immunology* 56(2):159-170 (1978).

Mainolfi, E. et al., "Reduction of Immunogenicity of a Murine ANTI-ICAM-1 Antibody through Pegylation Chemistry" *The 9th International Congress of Immunology* (abstract book) (abstract #5247) pp. 885 (1995).

Maiti et al., "Tolerogenic conjugates of xenogenic monoclonal antibodies with monomethoxpolyethylene glycol. I. Induction of long-lasting tolerance to xenogenic monoclonal antibodies" *International Journal of Cancer* Suppl. 3:17-22 (1988).

Maruyama et al., "Immunoliposomes bearing polyethyleneglycol-coupled Fab' fragment show prolonged circulation time and high extravasation into targeted solid tumors in vivo" *FEBS Letters* 413(1):177-180 (Aug. 11, 1997).

Maruyama ct al., "Targeting efficiency of PEG-immunoliposomes-conjugated antibodies at PEG terminals" *Advanced Drug Delivery Reviews* 24:235-242 (1997).

Matsimoto et al., "Prevention of cerebral edema and infarct in cerebral reperfusion injury by an antibody to interleukin-8" *Laboratory Investigation* 77(2):119-125 (Aug. 1997).

McCafferty et al., "Phage anitbodies: filamentous phage displaying antibody variable domanins" *Nature* 348:552-554 (1990).

Mulligan, et al., "Inhibition of Lung Inflammatory Reactions in rats by an anti-human IL-8 Antibody" *J. Immunol.* 150(12):5585-5595 (Jun. 15, 1993).

Nordvall et al., "IgG and IgE antibody patterns after immunotherapy with monomethoxy polyethylenglycol modified honey bee venom" *Allergy: European Journal of Allergy & Clinical Immunology* 41(2):89-94 (Feb. 1986).

Pedley et al., "The potential for enhanced tumour localisation by poly (ethylene glycol) modification of anti-CEA antibody" *British Journal of Cancer* 70(6):1126-1130 (Dec. 1994).

Sekido et al., "Prevention of lung reperfusion injury in rabbits by a monoclonal antibody against interleukin-8" *Nature* 365:654-657 (Oct. 14, 1993).

Shahinian and Silvius, "A novel strategy affords high yield coupling of antibody Fab fragments to liposomes" *Biochemica et Biophysica Acta* 1239 (2):157-167 (Nov. 1, 1995).

Sharp et al., "Synthesis and application of a poly (ethylene glycol)-antibody affinity ligand for cell separations in aqueous polymer two-phase systems" *Analytical Biochemistry* 154(1):110-117 (Apr. 1986).

(Shearwater Polymers, Inc.'s Jan. 1996 Catalog of Polyethylene Glycol Derivatices) pp. 1-50.

St. John et al., "Immunologic Therapy for ARDS, Septic Shock, and Multiple-Organ Failure" Chest 103:932-943 (1993).

Sticherling et al., Immunohistochemical studies on NAP-1/IL-8 in contact eczema and atopic dermatitis *Arch. Dermatol. Res.* 284:82-85 (1992).

Sticherling et al., "Production and Characterization of monoclonal antibodies against the novel neutrophil activating peptide NAP/IL8" *J. Immunol* 143(5):1628-1634 (Sep. 1, 1998).

Suzuki et al., Physicochemical and biological properties of poly (ethylene glycol)-coupled immunoglobulin G. part II. Effect of molecular weight of poly (ethylene glycol) *Journal of Biomaterials Science, Polymer Edition* 1(2):71-84 (1989).

Suzuki et al., "Preparation and characteristics of magnetite-labelled antibody with the use of poly (ethylene glycol) derivatives" *Biotechnology & Applied Biochemistry* 21 (pt 3):335-345 (Jun. 1995).

Tanaka et al., "Synthesis and biological characterization of monocyte-derived neutrophil chemotactic factor" *FEBS Letters* 236(2):467-470 (Aug. 1988).

Van Damme et al., "Purification of granulocyte chemotactic peptide/interleukin-8 reveals N-terminal sequence heterogeneity similar to that of β-thromboglobulin" *European Journal of Biochemistry* 181:337-344 (1989).

Veronese et al., "Improvement of pharmacokinetic, immunological and stability properties of asparaginase by conjugation to linear and branched monomethoxy poly(ethylene glycol)" *Journal of Controlled Release* 40:199-209 (1996).

Wie et al., "Suppression of reaginic antibodies with modified allergens. III. Preparation of tolergenic conjugates of common allergens with monomethoxypolyethylene glycols of different molecular weights by the mixed anhydride method" *International Archives of Allergy & Applied Immunology* 64(1):84-99 (1981).

Yokoi et al., "Prevention of endotoxemia-induced acute respiratory distress syndrome-like lung injury in rabbits by a monoclonal antibody to IL-8" *Laboratory Investigation* 76(3):375-384 (Mar. 1997).

Yoshimoto et al., "Chemical modification of tryptophanase from *E. coli* with polyethylene glycol to reduce its immunoreactivity towards anti-tryptophanase antibodies" *Enzyme* 36(4):261-265 (1986).

Yoshimura et al., "Neutrophil attractant/activation protein-1 and monocyte chemoacctractant protein-1 in rabbit. CDNA cloning and their expression in spleen cells" *J. Immunol.* 146:3483-3488 (1991).

Zapata et al., "Site-Specific Coupling of Monomethoxypoly (ethylene glycol) to a Single-Sulfhydryl Humanized Fab'" (poster presented at the American Society for Biochemistry and Molecular Biology FASEB Meeting in San Francisco, CA on May 21, 25, 1995) pp. 1-27.

Zapata et al., "Site-Specific Coupling of Monomethoxypoly (ethylene glycol) to a Single-Sulfhydryl Humanized Fab'" (Abstract #1288, presented at the American Society for Biochemistry and Molecular Biology FASEB Meeting in San Francisco, CA on May 21, 25, 1995) 9(6):A1479 (1995).

Cruse et al. (illustrated Dictionary of Immunology, CRC Press, p. 107, 1995.

Cruse et al (Illustrated Dictionary if Immunology, CRC Press, p. 107, 1995).

Haber, biochemistry 52:1099-1106 1964.

Tout et al., Clinical and Diagnostic Laboratory Immunol. 4:147-155 1997.

Zapata et al., FASEB J.9:A1479, abstract 1288 1995.

Harlow et al., Anntibodies A Laboratory Manual, Cold Spring Harbor Laboratory 1998.

Davis et al., "Soluble, Nonantigenic Polyethylene Glycol-Bound Enzymes" *Biomedical Polymers: Polymeric Materials and Pharamceuticals for Biomedical Use*, Goldberg E. and Nakajima, A. eds., New York:Academic Press pp. 441-452 (1980).

\* cited by examiner

FIG. 12

Neutrophil emigration index (%) vs Group (n=5 rabbits per group): S. pneumoniae (isotype control ~100%, anti IL8 ~15%), E. coli (isotype control ~100%, anti IL8 ~15%), P. aeruginosa (isotype control ~100%, anti IL8 ~45%).

Light Chain Primers:

MKLC-1, 22mer   FIG. 13

5'    CAGTCCAACTGTTCAGGACGCC 3'

MKLC-2, 22mer

5'    GTGCTGCTCATGCTGTAGGTGC 3'

MKLC-3, 23mer

5'    GAAGTTGATGTCTTGTGAGTGGC    3'

Heavy Chain Primers:

IGG2AC-1, 24mer

5'    GCATCCTAGAGTCACCGAGGAGCC    3'

IGG2AC-2, 22mer

5'    CACTGGCTCAGGGAAATAACCC 3'

IGG2AC-3, 22mer

5'    GGAGAGCTGGGAAGGTGTGCAC 3'

FIG. 14

Light chain forward primer

SL001A-2  35 mer

5' ACAAACGCGTACGCT GACATCGTCATGACCCAGTC 3'
                         T  T         T
                                       A

Light chain reverse primer

SL001B  37 mer

5' GCTCTTCGAATG GTGGGAAGATGGATACAGTTGGTGC 3'

Heavy chain forward primer

FIG. 15

SL002B    39 mer

5' CGATGGGCCGG ATAGACCGATGGGGCTGTTGTTTTGGC 3'
                        T              C
                        G
                        A

Heavy chain reverse primer

SL002B    39-MER

5' CGATGGGCCGG ATAGACCGATGGGGCTGTTGTTTTGGC   3'
                        T
                        A
                        G

```
  1 GACATTGTCA TGACACAGTC TCAAAAATTC ATGTCCACAT CAGTAGGAGA CAGGGTCAGC
    CTGTAACAGT ACTGTGTCAG AGTTTTTAAG TACAGGTGTA GTCATCCTCT GTCCCAGTCG
  1 D  I  V  M  T  Q  S  Q  K  F  M  S  T  S  V  G  D  R  V  S

61 GTCACCTGCA AGGCCAGTCA GAATGTGGGT ACTAATGTAG CCTGGTATCA ACAGAAACCA
    CAGTGGACGT TCCGGTCAGT CTTACACCCA TGATTACATC GGACCATAGT TGTCTTTGGT
 21 V  T  C  K  A  S  Q  N  V  G  T  N  V  A  W  Y  Q  Q  K  P
                          *  *  *  *  *  *  *  *
                                 CDR #1

121 GGGCAATCTC CTAAAGCACT GATTTACTCG TCATCCTACC GGTACAGTGG AGTCCCTGAT
    CCCGTTAGAG GATTTCGTGA CTAAATGAGC AGTAGGATGG CCATGTCACC TCAGGGACTA
 41 G  Q  S  P  K  A  L  I  Y  S  S  S  Y  R  Y  S  G  V  P  D
                              *  *  *  *  *  *  *
                                    CDR #2

181 CGCTTCACAG GCAGTGGATC TGGGACAGAT TTCACTCTCA CCATCAGCCA TGTGCAGTCT
    GCGAAGTGTC CGTCACCTAG ACCCTGTCTA AAGTGAGAGT GGTAGTCGGT ACACGTCAGA
 61 R  F  T  G  S  G  S  G  T  D  F  T  L  T  I  S  H  V  Q  S

241 GAAGACTTGG CAGACTATTT CTGTCAGCAA TATAACATCT ATCCTCTCAC GTTCGGTCCT
    CTTCTGAACC GTCTGATAAA GACAGTCGTT ATATTGTAGA TAGGAGAGTG CAAGCCAGGA
 81 E  D  L  A  D  Y  F  C  Q  Q  Y  N  I  Y  P  L  T  F  G  P
                             *  *  *  *  *  *  *  *  *
                                      CDR #3

301 GGGACCAAGC TGGAGTTGAA ACGGGCTGAT GCTGCACCAC CAACTGTATC CATCTTCCCA
    CCCTGGTTCG ACCTCAACTT TGCCCGACTA CGACGTGGTG GTTGACATAG GTAGAAGGGT
101 G  T  K  L  E  L  K  R  A  D  A  A  P  P  T  V  S  I  F  P

BstBI
361 CCATTCGAA
    GGTAAGCTT
121 P  F  E
```

FIG. 16

```
  1 TTCTATTGCT ACAAACGCGT ACGCTGAGGT GCAGCTGGTG GAGTCTGGGG GAGGCTTAGT
    AAGATAACGA TGTTTGCGCA TGCGACTCCA CGTCGACCAC CTCAGACCCC CTCCGAATCA
  1                                 E  V  Q  L  V  E  S  G  G  G  L  V

61 GCCGCCTGGA GGGTCCCTGA AACTCTCCTG TGCAGCCTCT GGATTCATAT TCAGTAGTTA
    CGGCGGACCT CCCAGGGACT TTGAGAGGAC ACGTCGGAGA CCTAAGTATA GTCATCAAT
 13 P  P  G  G  S  L  K  L  S  C  A  A  S  G  F  I  F  S  S  Y
                                                 *  *
                                                 CDR #1

121 TGGCATGTCT TGGGTTCGCC AGACTCCAGG CAAGAGCCTG GAGTTGGTCG CAACCATTAA
    ACCGTACAGA ACCCAAGCGG TCTGAGGTCC GTTCTCGGAC CTCAACCAGC GTTGGTAATT
 33 G  M  S  W  V  R  Q  T  P  G  K  S  L  E  L  V  A  T  I  N
    *  *  *                                            *  *  *

181 TAATAATGGT GATAGCACCT ATTATCCAGA CAGTGTGAAG GGCCGATTCA CCATCTCCCG
    ATTATTACCA CTATCGTGGA TAATAGGTCT GTCACACTTC CCGGCTAAGT GGTAGAGGGC
 53 N  N  G  D  S  T  Y  Y  P  D  S  V  K  G  R  F  T  I  S  R
    *  *  *  *  *  *  *  *  *  *  *  *  *
              CDR #2

241 AGACAATGCC AAGAACACCC TGTACCTGCA AATGAGCAGT CTGAAGTCTG AGGACACAGC
    TCTGTTACGG TTCTTGTGGG ACATGGACGT TTACTCGTCA GACTTCAGAC TCCTGTGTCG
 73 D  N  A  K  N  T  L  Y  L  Q  M  S  S  L  K  S  E  D  T  A

301 CATGTTTTAC TGTGCAAGAG CCCTCATTAG TTCGGCTACT TGGTTTGGTT ACTGGGGCCA
    GTACAAAATG ACACGTTCTC GGGAGTAATC AAGCCGATGA ACCAAACCAA TGACCCCGGT
 93 M  F  Y  C  A  R  A  L  I  S  S  A  T  W  F  G  Y  W  G  Q
                         *  *  *  *  *  *  *  *  *  *
                         CDR #3

361 AGGGACTCTG GTCACTGTCT CTGCAGCCAA AACAACAGCC CCATCTGTCT
    TCCCTGAGAC CAGTGACAGA GACGTCGGTT TTGTTGTCGG GGTAGACAGA
113 G  T  L  V  T  V  S  A  A  K  T  T  A  P  S  V  Y

ApaI
411 ATCCGGG
    TAGGCCC
130   P
```

VL.front        31-MER

5' ACAA<u>ACGCG</u>TACGCT<u>GATATC</u>GTCATGACAG        3'

VL.rear 31-MER

5' GCAGCATCAGCTC<u>TTCGAA</u>GCTCCAGCTTGG        3'

VH.front.SPE    21-MER

5' CC<u>ACTAGT</u>ACGCAAGTTCACG        3'

VH.rear 33-MER

5' GAT<u>GGGCCC</u>TTGGTGGAGGCTGCAGAGACAGTG        3'

```
  1 ATGAAGAAGA ATATCGCATT TCTTCTTGCA TCTATGTTCG TTTTTTCTAT TGCTACAAAC
    TACTTCTTCT TATAGCGTAA AGAAGAACGT AGATACAAGC AAAAAAGATA ACGATGTTTG
-23 M   K   K   N   I   A   F   L   L   A   S   M   F   V   F   S   I   A   T   N

61 GCGTACGCTG ATATCGTCAT GACACAGTCT CAAAAATTCA TGTCCACATC AGTAGGAGAC
    CGCATGCGAC TATAGCAGTA CTGTGTCAGA GTTTTTAAGT ACAGGTGTAG TCATCCTCTG
 -3 A   Y   A   D   I   V   M   T   Q   S   Q   K   F   M   S   T   S   V   G   D

121 AGGGTCAGCG TCACCTGCAA GGCCAGTCAG AATGTGGGTA CTAATGTAGC CTGGTATCAA
    TCCCAGTCGC AGTGGACGTT CCGGTCAGTC TTACACCCAT GATTACATCG GACCATAGTT
 18 R   V   S   V   T   C   K   A   S   Q   N   V   G   T   N   V   A   W   Y   Q
                                    *   *   *   *   *   *   *   *   *   *   *
                                              CDR #1

181 CAGAAACCAG GGCAATCTCC TAAAGCACTG ATTTACTCGT CATCCTACCG GTACAGTGGA
    GTCTTTGGTC CCGTTAGAGG ATTTCGTGAC TAAATGAGCA GTAGGATGGC CATGTCACCT
 38 Q   K   P   G   Q   S   P   K   A   L   I   Y   S   S   S   Y   R   Y   S   G
                                            *   *   *   *   *   *   *
                                                        CDR #2

241 GTCCCTGATC GCTTCACAGG CAGTGGATCT GGGACAGATT TCACTCTCAC CATCAGCCAT
    CAGGGACTAG CGAAGTGTCC GTCACCTAGA CCCTGTCTAA AGTGAGAGTG GTAGTCGGTA
 58 V   P   D   R   F   T   G   S   G   S   G   T   D   F   T   L   T   I   S   H

301 GTGCAGTCTG AAGACTTGGC AGACTATTTC TGTCAGCAAT ATAACATCTA TCCTCTCACG
    CACGTCAGAC TTCTGAACCG TCTGATAAAG ACAGTCGTTA TATTGTAGAT AGGAGAGTGC
 78 V   Q   S   E   D   L   A   D   Y   F   C   Q   Q   Y   N   I   Y   P   L   T
                                                    *   *   *   *   *   *   *   *
                                                              CDR #3
              BstBI
361 TTCGGTCCTG GGACCAAGCT GGAGCTTCGA AGAGCTGTGG CTGCACCATC TGTCTTCATC
    AAGCCAGGAC CCTGGTTCGA CCTCGAAGCT TCTCGACACC GACGTGGTAG ACAGAAGTAG
 98 F   G   P   G   T   K   L   E   L   R   R   A   V   A   A   P   S   V   F   I

421 TTCCCGCCAT CTGATGAGCA GTTGAAATCT GGAACTGCTT CTGTTGTGTG CCTGCTGAAT
    AAGGGCGGTA GACTACTCGT CAACTTTAGA CCTTGACGAA GACAACACAC GGACGACTTA
118 F   P   P   S   D   E   Q   L   K   S   G   T   A   S   V   V   C   L   L   N

481 AACTTCTATC CCAGAGAGGC CAAAGTACAG TGGAAGGTGG ATAACGCCCT CCAATCGGGT
    TTGAAGATAG GGTCTCTCCG GTTTCATGTC ACCTTCCACC TATTGCGGGA GGTTAGCCCA
138 N   F   Y   P   R   E   A   K   V   Q   W   K   V   D   N   A   L   Q   S   G

541 AACTCCCAGG AGAGTGTCAC AGAGCAGGAC AGCAAGGACA GCACCTACAG CCTCAGCAGC
    TTGAGGGTCC TCTCACAGTG TCTCGTCCTG TCGTTCCTGT CGTGGATGTC GGAGTCGTCG
158 N   S   Q   E   S   V   T   E   Q   D   S   K   D   S   T   Y   S   L   S   S

601 ACCCTGACGC TGAGCAAAGC AGACTACGAG AAACACAAAG TCTACGCCTG CGAAGTCACC
    TGGGACTGCG ACTCGTTTCG TCTGATGCTC TTTGTGTTTC AGATGCGGAC GCTTCAGTGG
178 T   L   T   L   S   K   A   D   Y   E   K   H   K   V   Y   A   C   E   V   T

661 CATCAGGGCC TGAGCTCGCC CGTCACAAAG AGCTTCAACA GGGGAGAGTG
    GTAGTCCCGG ACTCGAGCGG GCAGTGTTTC TCGAAGTTGT CCCCTCTCAC
198 H   Q   G   L   S   S   P   V   T   K   S   F   N   R   G   E   C

711 TTAA
    AATT
216 O
```

FIG. 19

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M   K   K    I   A   F   L   L   A   S   M   F   V   F   S   I   A   T   N

61 GCGTACGCTG AGGTGCAGCT GGTGGAGTCT GGGGGAGGCT TAGTGCCGCC TGGAGGGTCC
    CGCATGCGAC TCCACGTCGA CCACCTCAGA CCCCCTCCGA ATCACGGCGG ACCTCCCAGG
 -3 A   Y   A   E   V   Q   L   V   E   S   G   G   G   L   V   P   P   G   G   S

121 CTGAAACTCT CCTGTGCAGC CTCTGGATTC ATATTCAGTA GTTATGGCAT GTCTTGGGTT
    GACTTTGAGA GGACACGTCG GAGACCTAAG TATAAGTCAT CAATACCGTA CAGAACCCAA
 18 L   K   L   S   C   A   A   S   G   F   I   F   S   S   Y   G   M   S   W   V
                                    *   *   *   *   *   *   *   *
                                        CDR #1

181 CGCCAGACTC CAGGCAAGAG CCTGGAGTTG GTCGCAACCA TTAATAATAA TGGTGATAGC
    GCGGTCTGAG GTCCGTTCTC GGACCTCAAC CAGCGTTGGT AATTATTATT ACCACTATCG
 38 R   Q   T   P   G   K   S   L   E   L   V   A   T   I   N   N   N   G   D   S
                                                        *   *   *   *   *   *   *   *

241 ACCTATTATC AGACAGTGT  GAAGGGCCGA TTCACCATCT CCCGAGACAA TGCCAAGAAC
    TGGATAATAG GTCTGTCACA CTTCCCGGCT AAGTGGTAGA GGGCTCTGTT ACGGTTCTTG
 58 T   Y   Y   P   D   S   V   K   G   R   F   T   I   S   R   D   N   A   K   N
    *   *   *   *   *   *   *   *
            CDR #2

301 ACCCTGTACC TGCAAATGAG CAGTCTGAAG TCTGAGGACA CAGCCATGTT TTACTGTGCA
    TGGGACATGG ACGTTTACTC GTCAGACTTC AGACTCCTGT GTCGGTACAA AATGACACGT
 78 T   L   Y   L   Q   M   S   S   L   K   S   E   D   T   A   M   F   Y   C   A

361 AGAGCCCTCA TTAGTTCGGC TACTTGGTTT GGTTACTGGG GCCAAGGGAC TCTGGTCACT
    TCTCGGGAGT AATCAAGCCG ATGAACCAAA CCAATGACCC CGGTTCCCTG AGACCAGTGA
 98 R   A   L   I   S   S   A   T   W   F   G   Y   W   G   Q   G   T   L   V   T
        *   *   *   *   *   *   *   *   *   *   *   *
                    CDR #3
                        ApaI
421 GTCTCTGCAG CCTCCACCAA GGGCCCATCG GTCTTCCCCC TGGCACCCTC CTCCAAGAGC
    CAGAGACGTC GGAGGTGGTT CCCGGGTAGC CAGAAGGGGG ACCGTGGGAG GAGGTTCTCG
118 V   S   A   A   S   T   K   G   P   S   V   F   P   L   A   P   S   S   K   S

481 ACCTCTGGGG GCACAGCGGC CCTGGGCTGC CTGGTCAAGG ACTACTTCCC CGAACCGGTG
    TGGAGACCCC CGTGTCGCCG GGACCCGACG GACCAGTTCC TGATGAAGGG GCTTGGCCAC
138 T   S   G   G   T   A   A   L   G   C   L   V   K   D   Y   F   P   E   P   V

541 ACGGTGTCGT GGAACTCAGG CGCCCTGACC AGCGGCGTGC ACACCTTCCC GGCTGTCCTA
    TGCCACAGCA CCTTGAGTCC GCGGGACTGG TCGCCGCACG TGTGGAAGGG CCGACAGGAT
158 T   V   S   W   N   S   G   A   L   T   S   G   V   H   T   F   P   A   V   L

601 CAGTCCTCAG GACTCTACTC CCTCAGCAGC GTGGTGACCG TGCCCTCCAG CAGCTTGGGC
    GTCAGGAGTC CTGAGATGAG GGAGTCGTCG CACCACTGGC ACGGGAGGTC GTCGAACCCG
178 Q   S   S   G   L   Y   S   L   S   S   V   V   T   V   P   S   S   S   L   G
```

FIG. 20A

```
661 ACCCAGACCT ACATCTGCAA CGTGAATCAC AAGCCCAGCA ACACCAAGGT GGACAAGAAA
    TGGGTCTGGA TGTAGACGTT GCACTTAGTG TTCGGGTCGT TGTGGTTCCA CCTGTTCTTT
198 T   Q   T   Y   I   C   N   V   N   H   K   P   S   N   T   K   V   D   K   K

721 GTTGAGCCCA AATCTTGTGA CAAAACTCAC ACATGA
    CAACTCGGGT TTAGAACACT GTTTTGAGTG TGTACT
218 V   E   P   K   S   C   D   K   T   H   T   Q
```

FIG. 20B

Light Chain Primers:

MKLC-1, 22mer

5'    CAGTCCAACTGTTCAGGACGCC 3'

MKLC-2, 22mer

5'    GTGCTGCTCATGCTGTAGGTGC 3'

MKLC-3, 23mer

5'    GAAGTTGATGTCTTGTGAGTGGC    3'

Heavy Chain Primers:

IGG2AC-1, 24mer

5'    GCATCCTAGAGTCACCGAGGAGCC    3'

IGG2AC-2, 22mer

5'    CACTGGCTCAGGGAAATAACCC 3'

IGG2AC-3, 22mer

5'    GGAGAGCTGGGAAGGTGTGCAC 3'

FIG. 21

Light chain forward primer

6G4.light.Nsi  36-MER

```
5' CCAATGCATACGCT GAC ATC GTG ATG ACC CAG ACC CC 3'
                     T   T           T       T
                                     A       A
```

Light chain reverse primer

6G4.light.Mun  35-MER

5' AGA TGT CAA TTG CTC ACT GGA TGG TGG GAA GAT GG 3'

FIG. 22

Heavy chain forward primer

6G4.heavy.Mlu  32-MER

```
5' CAAACGCGTACGCT GAG ATC CAG CTG CAG CAG  3'
                         T           C
```

Heavy chain reverse primer

SL002B  39-MER

```
5' CGATGGGCCCGG ATAGACCGATGGGGCTGTTGTTTTGGC  3'
                         T
                         A
                         G
```

FIG. 23

```
 70 G ATATCGTGAT GACACAGACA CCACTCTCCC TGCCTGTCAG TCTTGGAGAT
    C TATAGCACTA CTGTGTCTGT GGTGAGAGGG ACGGACAGTC AGAACCTCTA
  1   D  I  V  M  T  Q  T  P  L  S  L  P  V  S  L  G  D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18  Q  A  S  I  S  C  R  S  S  Q  S  L  V  H  G  I  G  N  T  Y
                              *  *  *  *  *  *  *  *  *  *  *  *  *
                                           CDR #1

181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38  L  H  W  Y  L  Q  K  P  G  Q  S  P  K  L  L  I  Y  K  V  S
     *  *                                                  *  *  *
                                                         CDR #2

241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58  N  R  F  S  G  V  P  D  R  F  S  G  S  G  S  G  T  D  F  T
     *  *  *  *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78  L  R  I  S  R  V  E  A  E  D  L  G  L  Y  F  C  S  Q  S  T
                                                         *  *  *
                                                         CDR #3

361 CATGTTCCGC TCACGTTCGG TGCTGGGACC AAGCTGGAGC TGAAACGGGC TGATGCTGCA
    GTACAAGGCG AGTGCAAGCC ACGACCCTGG TTCGACCTCG ACTTTGCCCG ACTACGACGT
 98  H  V  P  L  T  F  G  A  G  T  K  L  E  L  K  R  A  D  A  A
     *  *  *  *  *
                                                    MunI
421 CCAACTGTAT CCATCTTCCC ACCATCCAGT GAGCAATTGA
    GGTTGACATA GGTAGAAGGG TGGTAGGTCA CTCGTTAACT
118  P  T  V  S  I  F  P  P  S  S  E  Q  L  K
```

FIG. 24

```
 70 G AGATTCAGCT GCAGCAGTCT GGACCTGAGC TGATGAAGCC TGGGGCTTCA
    C TCTAAGTCGA CGTCGTCAGA CCTGGACTCG ACTACTTCGG ACCCCGAAGT
  1 E   I   Q   L   Q   Q   S   G   P   E   L   M   K   P   G   A   S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V   K   I   S   C   K   A   S   G   Y   S   F   S   S   H   Y   M   H   W   V
                                        ─────────────────── *   *   *   *   *
                                              CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K   Q   S   H   G   K   S   L   E   W   I   G   Y   I   D   P   S   N   G   E
                                                        *   *   ─── ─── ─── *
                                                              CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T   T   Y   N   Q   K   F   K   G   K   A   T   L   T   V   D   T   S   S   S
    *   *   *   *   *   *   *   *   *

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T   A   N   V   H   L   S   S   L   T   S   D   D   S   A   V   Y   F   C   A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R   G   D   Y   R   Y   N   G   D   W   F   F   D   V   W   G   A   G   T   T
                ─── ─── ─── ─── ─── ─── ─── ─── ─── ───  *   *   *   *   *
                              CDR #3
    BstEII                                                        ApaI
421 GTCACCGTCT CCTCCGCCAA AACCGACAGC CCCATCGGTC TATCCGGGCC
    CAGTGGCAGA GGAGGCGGAT TTGGCTGTCG GGGTAGCCAG ATAGGCCCGG
118 V   T   V   S   S   A   K   T   D   S   P   I   G   L   S   G   P

471 CATC
    GTAG
135  I
```

FIG. 25

5' CTTGGTGGAGGCGGAGGAGACG 3'

Mutagenesis Primer for 6G425VL

DS/VF  38MER

5' GAAACGGGCTGTTGCTGCACCAACTGTATTCATCTTCC 3'

SYN.BstEII  31 MER

5' GTCACCGTCT CCTCCGCCTC CACCAAGGGC C 3'

SYN.Apa  22 MER

5' CTTGGTGGAGGCGGAGGAGACG    3'

FIG. 26

```
  1 ATGAAGAAGA ATATCGCATT TCTTCTTGCA TCTATGTTCG TTTTTTCTAT TGCTACAAAT
    TACTTCTTCT TATAGCGTAA AGAAGAACGT AGATACAAGC AAAAAAGATA ACGATGTTTA
-23 M  K  K    I  A  F    L  L  A    S  M  F    V  F  S  I  A  T  N

61 GCATACGCTG ATATCGTGAT GACACAGACA CCACTCTCCC TGCCTGTCAG TCTTGGAGAT
    CGTATGCGAC TATAGCACTA CTGTGTCTGT GGTGAGAGGG ACGGACAGTC AGAACCTCTA
 -3 A  Y  A   D  I  V  M  T  Q  T    P  L  S    P  V  S    L  G  D

121 CAGGCCTCCA TCTCTTGCAG ATCTAGTCAG AGCCTTGTAC ACGGTATTGG AAACACCTAT
    GTCCGGAGGT AGAGAACGTC TAGATCAGTC TCGGAACATG TGCCATAACC TTTGTGGATA
 18 Q  A  S  I  S  C  R   S  S  Q    S  L  V  H  G  I  G   N  T  Y
                          *  *  *  *  *  *  *  *  *  *  *  *  *  *
                                    CDR #1
```
```
181 TTACATTGGT ACCTGCAGAA GCCAGGCCAG TCTCCAAAGC TCCTGATCTA CAAAGTTTCC
    AATGTAACCA TGGACGTCTT CGGTCCGGTC AGAGGTTTCG AGGACTAGAT GTTTCAAAGG
 38 L  H  W  Y  L  Q  K   P  G  Q    S  P  K  L  L  I  Y   K  V  S
    *  *                                                   *  *  *
                                                          CDR #2
```
```
241 AACCGATTTT CTGGGGTCCC AGACAGGTTC AGTGGCAGTG GATCAGGGAC AGATTTCACA
    TTGGCTAAAA GACCCCAGGG TCTGTCCAAG TCACCGTCAC CTAGTCCCTG TCTAAAGTGT
 58 N  R  F  S  G  V  P   D  R  F    S  G  S  G  S  G  T   D  F  T
    *  *  *  *

301 CTCAGGATCA GCAGAGTGGA GGCTGAGGAT CTGGGACTTT ATTTCTGCTC TCAAAGTACA
    GAGTCCTAGT CGTCTCACCT CCGACTCCTA GACCCTGAAA TAAAGACGAG AGTTTCATGT
 78 L  R  I  S  R  V  E   A  E  D    L  G  L  Y  F  C  S   Q  S  T
                                                           *  *  *
                                                          CDR #3
```
```
361 CATGTTCCGC TCACGTTCGG TGCTGGGACC AAGCTGGAGC TGAAACGGGC TGTTGCTGCA
    GTACAAGGCG AGTGCAAGCC ACGACCCTGG TTCGACCTCG ACTTTGCCCG ACAACGACGT
 98 H  V  P  L  T  F  G   A  G  T    K  L  E  L  K  R  A   V  A  A
    *  *  *  *  *

421 CCAACTGTAT TCATCTTCCC ACCATCCAGT GAGCAATTGA AATCTGGAAC TGCCTCTGTT
    GGTTGACATA AGTAGAAGGG TGGTAGGTCA CTCGTTAACT TTAGACCTTG ACGGAGACAA
118 P  T  V  F  I  F  P   P  S  S    E  Q  L  K  S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L  N  N  F   Y  P  R    E  A  K  V  Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S  G  N  S   Q  E  S    V  T  E  Q  D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S  S  T  L   T  L  S    K  A  D  Y  E  K  H   K  V  Y
```

FIG. 27A

```
661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198  A  C  E  V  T  H  Q  G  L  S  S  P  V  T  K  S  F  N  R  G

721 GAGTGTTAA
    CTCACAATT
218  E  C  O
```

FIG. 27B

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K    I  A  F    L  L  A    S  M  F    V  F  S  I  A  T  N

61 GCGTACGCTG AGATTCAGCT GCAGCAGTCT GGACCTGAGC TGATGAAGCC TGGGGCTTCA
    CGCATGCGAC TCTAAGTCGA CGTCGTCAGA CCTGGACTCG ACTACTTCGG ACCCCGAAGT
 -3 A  Y  A  E  I  Q  L  Q  Q  S    G  P  E  L  M  K  P    G  A  S

121 GTGAAGATAT CCTGCAAGGC TTCTGGTTAT TCATTCAGTA GCCACTACAT GCACTGGGTG
    CACTTCTATA GGACGTTCCG AAGACCAATA AGTAAGTCAT CGGTGATGTA CGTGACCCAC
 18 V  K  I  S  C  K  A  S  G  Y  S  F  S  S  H  Y  M    H  W  V
                           ─  ─  ─  ─  ─  ─
                              CDR #1

181 AAGCAGAGCC ATGGAAAGAG CCTTGAGTGG ATTGGCTACA TTGATCCTTC CAATGGTGAA
    TTCGTCTCGG TACCTTTCTC GGAACTCACC TAACCGATGT AACTAGGAAG GTTACCACTT
 38 K  Q  S  H  G  K  S  L  E  W  I  G  Y  I  D  P  S  N  G  E
                                                  ─  ─  ─  ─
                                                     CDR #2

241 ACTACTTACA ACCAGAAATT CAAGGGCAAG GCCACATTGA CTGTAGACAC ATCTTCCAGC
    TGATGAATGT TGGTCTTTAA GTTCCCGTTC CGGTGTAACT GACATCTGTG TAGAAGGTCG
 58 T  T  Y  N  Q  K  F  K  G  K  A  T  L  T  V  D  T    S  S  S
    ─  ─  ─  ─  ─  ─  ─  ─  ─

301 ACAGCCAACG TGCATCTCAG CAGCCTGACA TCTGATGACT CTGCAGTCTA TTTCTGTGCA
    TGTCGGTTGC ACGTAGAGTC GTCGGACTGT AGACTACTGA GACGTCAGAT AAAGACACGT
 78 T  A  N  V  H  L  S  S  L  T  S  D  D  S    A  V  Y  F  C  A

361 AGAGGGGACT ATAGATACAA CGGCGACTGG TTTTTCGATG TCTGGGGCGC AGGGACCACG
    TCTCCCCTGA TATCTATGTT GCCGCTGACC AAAAAGCTAC AGACCCCGCG TCCCTGGTGC
 98 R  G  D  Y  R  Y  N  G  D  W  F  F  D  V    W  G  A  G  T  T
          ─  ─  ─  ─  ─  ─  ─  ─  ─  ─  ─
          CDR #3

421 GTCACCGTCT CCTCCGCCTC CACCAAGGGC CCATCGGTCT TCCCCCTGGC ACCCTCCTCC
    CAGTGGCAGA GGAGGCGGAG GTGGTTCCCG GGTAGCCAGA AGGGGGACCG TGGGAGGAGG
118 V  T  V  S  S  A  S  T  K  G    P  S  V  F  P  L  A  P  S  S

481 AAGAGCACCT CTGGGGGCAC AGCGGCCCTG GGCTGCCTGG TCAAGGACTA CTTCCCCGAA
    TTCTCGTGGA GACCCCCGTG TCGCCGGGAC CCGACGGACC AGTTCCTGAT GAAGGGGCTT
138 K  S  T  S  G  G  T    A  A  L  G  C  L  V  K  D  Y  F  P  E

541 CCGGTGACGG TGTCGTGGAA CTCAGGCGCC CTGACCAGCG GCGTGCACAC CTTCCCGGCT
    GGCCACTGCC ACAGCACCTT GAGTCCGCGG GACTGGTCGC CGCACGTGTG GAAGGGCCGA
158 P  V  T  V  S  W  N    S  G  A  L  T  S  G  V  H  T  F  P  A

601 GTCCTACAGT CCTCAGGACT CTACTCCCTC AGCAGCGTGG TGACCGTGCC CTCCAGCAGC
    CAGGATGTCA GGAGTCCTGA GATGAGGGAG TCGTCGCACC ACTGGCACGG GAGGTCGTCG
178 V  L  Q  S  S  G  L    Y  S  L  S  S  V  V  T  V  P  S  S  S
```

FIG. 28A

```
661  TTGGGCACCC AGACCTACAT CTGCAACGTG AATCACAAGC CCAGCAACAC CAAGGTGGAC
     AACCCGTGGG TCTGGATGTA GACGTTGCAC TTAGTGTTCG GGTCGTTGTG GTTCCACCTG
198   L  G  T   Q  T  Y   I  C  N   V  N  H   K  P  S   N  T  K   V  D

721  AAGAAAGTTG AGCCCAAATC TTGTGACAAA ACTCACACAT GA
     TTCTTTCAAC TCGGGTTTAG AACACTGTTT TGAGTGTGTA CT
218   K  K  V   E  P  K   S  C  D   K  T  H   T  Q
```

FIG. 28B

Variable Light Chain Domain

```
                10        20      abcde 30          40
6G425    DIVMTQTPLSLPVSLGDQASISCRSSQSLVHGIGNTYLHWYLQKPGQSPKLLIY
          #  # # ## #  ###  #                      #    ##
F(ab)-1  DIQMTQSPSSLSASVGDRVTITCRSSQSLVHGIGNTYLHWYQQKPGKAPKLLIY
                              #  ##########
humκI    DIQMTQSPSSLSASVGDRVTITCRASKTI-----SKYLAWYQQKPGKAPKLLIY
                                  ===========
                              +++++++++++++++
                                     L1

50        60        70        80        90       100
6G425    YKVSNRFSGVPDRFSDSGSGTDFTLRISRVEAEDLGLYFCSQSTHVPLTFGAGTKLELKR
           # #           #  ##### ### #                    #   # #
F(ab)-1  YKVSNRFSGVPSRFSGSGSGTDFTLTISSLQPEDFATYYCSQSTHVPLTFGQGTKVEIKR
         ## ###                                    # ####
humκI    YSGSTLESGVPSRFSGSGSGTDFTLTISSLQPEDFATYYCQQHNEYPLTFGQGTKVEIKR
         ===                                      ======
         +++++++                                  +++++++++
            L2                                       L3
```

Variable Heavy Chain Domain

```
                10        20        30        40
6G425    EIQLQQSGPELMKPGASVKISCKASGYSFSSHYMHWVKQSHGKSLEWI
          #  ##  ## ##  #  ### #           # ##  #   #
F(ab)-1  EVQLVESGGGLVQPGGSLRLSCAASGYSFSSHYMHWVRQAPGKGLEWV
                                 #  ## # #
humIII   EVQLVESGGGLVQPGGSLRLSCAASGFSFTGHWMNWVRQAPGKGLEWV
                                  =======
                                         ++++
                                          H1

50 a               70        80 abc     90       100       110
6G425    GYIDPSNGETTYNQKFKGKATLTVDTSSSTANVHLSSLTSDDSAVYFCAARGDYRYNGDWFFDVWGAGT
                           ## ### # ## ###### ### #   #                      #
F(ab)-1  GYIDPSNGETTYNQKFKGRFTISRDNSKNTLYLQMNSLRAEDTAVYYCAARGDYRYNGDWFFDVWGQGT
          # #  ## # ####                                    # # # ###  #
humIII   GMIHPSDSETRYADSVKGRFTISRDNSKNTLYLQMNSLRAEDTAVYYCAARGIYFY-GTTYFDYWGQGT
         ====                                              ===========
         ++++++++++++++++++                                +++++++++++
               H2                                              H3
```

Amino Acid Sequence of the humanized anti-IL-8 6G4.2.5V11 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V11 Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

Amino Acid Sequence of the peptide linker and M13 Phage Coat (gene-III)

SGGGSSGSGDFDYEKMANANKGAMTENADENALQSDAKGKLDSVATDYGAAIDGFIGDVS
GLANGNGATGDFAGSSNSQMAQVGDGDNSPLMNNFRQYLPSLPQSVECRPFVFSAGKPY
EFSIDCDKINLFRGVAFLLYVATFMYVFSTFANILRNKES

FIG. 31A

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K   N  I  A  F   L  L  A   S  M  F  V   F  S  I  A   T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A  D   I  Q  M   T  Q  S   P  S  S   L  S  A  S   V  G  D

121 AGGGTCACCA TCACCTGCAG GTCAAGTCAA AGCTTAGTAC ATGGTATAGG TAACACGTAT
    TCCCAGTGGT AGTGGACGTC CAGTTCAGTT TCGAATCATG TACCATATCC ACGATGCATA
 18 R  V  T  I   T  C  R   S  S  Q   S  L  V  H   G  I  G   N  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W  Y   Q  Q  K   P  G  K   A  P  K  L   L  I  Y   K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F  S   G  V  P   S  R  F   S  G  S   G  S  G  T   D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I  S   S  L  Q   P  E  D   F  A  T  Y   Y  C  S   Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P  L   T  F  G   Q  G  T   K  V  E  I   K  R  T   V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V  F   I  F  P   P  S  D   E  Q  L  K   S  G  T   A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L   N  N  F   Y  P  R   E  A  K  V   Q  W  K   V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S   G  N  S   Q  E  S   V  T  E  Q   D  S  K   D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S   S  T  L   T  L  S   K  A  D  Y   E  K  H   K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E  V   T  H  Q   G  L  S   S  P  V  T   K  S  F   N  R  G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  O
```

FIG. 31B

Amino Acid Sequence of the humanized anti-IL-8 6G4.2.5V19 Light Chain

MKKNIAFLLASMFVFSIATNAYADIQMTQSPSSLSASVGDRVTITCRSSQSLVHGIGNTY
LHWYQQKPGKAPKLLIYKVSNRFSGVPSRFSGSGSGTDFTLTISSLQPEDFATYYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V19 Heavy Chain

MKKNIAFLLASMFVFSIATNAYAEVQLVESGGGLVQPGGSLRLSCAASGYSFSSHYMH
WVKQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

FIG. 31C

Amino Acid Sequence of the humanized anti-IL-8 6G4.2.5V11N35A Light Chain

MKKNIAFLLASMFVFSIATNAYADIQMTQSPSSLSASVGDRVTITCRSSQSLVHGIGATY
LHWYQQKPGKAPKLLIYKVSNRFSGVPSRFSGSGSGTDFTLTISSLQPEDFATYCSQST
HVPLTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSFNRG
EC

Amino Acid Sequence of the humanized anti-IL-8 6G4.2.5V11N35A Heavy Chain

MKKNIAFLLASMFVFSIATNAYAEVQLVQSGGGLVQPGGSLRLSCAASGYSFSSHYMH
WVRQAPGKGLEWVGYIDPSNGETTYNQKFKGRFTLSRDNSKNTAYLQMNSLRAEDTAVYY
CARGDYRYNGDWFFDVWGQGTLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTK
VDKKVEPKSCDKTHT

Amino Acid Sequence of the putative Pepsin Cleavage Site and GCN4 Leucine Zipper

CPPCPAPELLGGRMKQLEDKVEELLSKNYHLENEVARLKKLVGER

FIG. 35

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M  K  K  N   I  A  F    L  L  A    S  M  F    V  F  S    I  A  T  N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A  Y  A  D   I  Q  M    T  Q  S    P  S  S    L  S  A    S  V  G  D

121 AGGGTCACCA TCACCTGCAG GTCAAGTCAA AGCTTAGTAC ATGGTATAGG TGCTACGTAT
    TCCCAGTGGT AGTGGACGTC CAGTTCAGTT TCGAATCATG TACCATATCC ACGATGCATA
 18 R  V  T  I   T  C  R    S  S  Q    S  L  V    H  G  I    G  A  T  Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L  H  W  Y   Q  Q  K    P  G  K    A  P  K  L   L  I  Y    K  V  S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N  R  F  S   G  V  P    S  R  F    S  G  S    G  S  G    T  D  F  T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L  T  I  S   S  L  Q    P  E  D    F  A  T    Y  Y  C    S  Q  S  T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H  V  P  L   T  F  G    Q  G  T    K  V  E    I  K  R    T  V  A  A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P  S  V  F   I  F  P    P  S  D    E  Q  L    K  S  G    T  A  S  V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V  C  L  L   N  N  F    Y  P  R    E  A  K    V  Q  W    K  V  D  N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A  L  Q  S   G  N  S    Q  E  S    V  T  E    Q  D  S    K  D  S  T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y  S  L  S   S  T  L    T  L  S    K  A  D    Y  E  K    H  K  V  Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A  C  E  V   T  H  Q    G  L  S    S  P  V    T  K  S    F  N  R  G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E  C  Q
```

FIG. 36

```
 781 AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
  -1                                  M  K  K  N  I  A  F  L  L  A

841 TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
 -11 S  M  F  V  F  S  I  A  T  N  A  Y  A  E  V  Q  L  V  Q  S

901 GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
   8 G  G  G  L  V  Q  P  G  G  S  L  R  L  S  C  A  A  S  G  Y

961 TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
  28 S  F  S  S  H  Y  M  H  W  V  R  Q  A  P  G  K  G  L  E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
  48 V  G  Y  I  D  P  S  N  G  E  T  T  Y  N  Q  K  F  K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
  68 F  T  L  S  R  D  N  S  K  N  T  A  Y  L  Q  M  N  S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
  88 A  E  D  T  A  V  Y  Y  C  A  R  G  D  Y  R  Y  N  G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
 108 F  F  D  V  W  G  Q  G  T  L  V  T  V  S  S  A  S  T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
 128 P  S  V  F  P  L  A  P  S  S  K  S  T  S  G  G  T  A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
 148 G  C  L  V  K  D  Y  F  P  E  P  V  T  V  S  W  N  S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
 168 L  T  S  G  V  H  T  F  P  A  V  L  Q  S  S  G  L  Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
 188 S  S  V  V  T  V  P  S  S  S  L  G  T  Q  T  Y  I  C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
 208 N  H  K  P  S  N  T  K  V  D  K  K  V  E  P  K  S  C  D  K

1561 ACTCACACAT GCCCGCCGTG CCCAGCACCA GAACTGCTGG GCGGCCGCAT GAAACAGCTA
     TGAGTGTGTA CGGGCGGCAC GGGTCGTGGT CTTGACGACC CGCCGGCGTA CTTTGTCGAT
 228 T  H  T  C  P  P  C  P  A  P  E  L  L  G  G  R  M  K  Q  L
```

FIG. 37A

```
1621 GAGGACAAGG TCGAAGAGCT ACTCTCCAAG AACTACCACC TAGAGAATGA AGTGGCAAGA
     CTCCTGTTCC AGCTTCTCGA TGAGAGGTTC TTGATGGTGG ATCTCTTACT TCACCGTTCT
 248 E   D   K   V   E   E   L   L   S   K   N   Y   H   L   E   N   E   V   A   R

1681 CTCAAAAAGC TTGTCGGGGA GCGCTAA
     GAGTTTTTCG AACAGCCCCT CGCGATT
 268 L   K   K   L   V   G   E   R   O
```

FIG. 37B

```
                                                           aluI
                                                           hindIII                              pleI
                       pflMI                               tru9I                                mboII    taqI
     ecoRI             bslI                  nlaIII        mseI cac8I                           earI/ksp632I
     apoI                                                              ddeI        bsrDI        mboII    hinfI
   1 GAATCAACT TCTCCATACT TTGGATAAGG AAATACAGAC ATGAAAAATC TCATTGCTGA GTTGTTATTT AAGCTTGCCC AAAAAGAAGA AGAGTCGAAT
     CTTAAGTTGA AGAGGTATGA AACCTATTCC TTTATGTCTG TACTTTTTAG AGTAACGACT CAACAATAAA TTCGAACGGG TTTTTCTTCT TCTCAGCTTA bspMI                                                                       sau3AI
              hinPI                                                                           mboI/ndeII[dam-]
              hhaI/cfoI                                                                       dpnI[dam+]
         mstI                       alul                                       hinPI          dpnII[dam-]
         avIII/fspI   hindIII                  msII                      hhaI/cfoI     acII   bcII[dam-] mnII
                                               maeIII bsrDI                            dspBII              bclI[dam-] mnlI
 101 GAACTGTGTG CGCAGGTAGA AGCTTTGGAG ATTATCGTCA CTGCAATGCT TCGCAATATG GCGCAAAATG ACCAACAGCG GTTGATTGAT CAGGTAGAGG
     CTTGACACAC GCGTCCATCT TCGAAACCTC TAATAGCAGT GACGTTACGA AGCGTTATAC CGCGTTTTAC TGGTTGTCGC CAACTAACTA GTCCATCTCC thaI
                                                           fnu4HI                  maeII
                                                           bsoFI
                                                           bbvI                    mnlI
                                                           fnu4HI bstUI   snaBI
                                                           bsoFI bsh1236I                         foKI
                                               hinPI       bbvI hinPI bsaAI                       sfaNI
                                   cac8I       hhaI/cfoI  aluI hhaI/cfoI
              hinPI
              hhaI/cfoI   mnlI      sfaNI  bsmI
         haeII csp6I
     rsaI
 201 GGGCGCTGTA CGAGGTAAAG CCCGATGCCA GCATTCCTGA CGACGATACG GAGCTGCTGC GCGATTACGT AAAGAAGTTA TTGAAGCATC CTCGTCAGTA
     CCCGCGACAT GCTCCATTTC GGGCTACGGT CGTAAGGACT GCTGCTATGC CTCGACGACG CGCTAATGCA TTTCTTCAAT AACTTCGTAG GAGCAGTCAT aluI
                                                                                                           sstI
                                                                                                           sacI
                                      haeIII/palI                                                          hglJII
                                      mcrI                                                                 hgiAI/aspHI
                                      eagI/xmaIII/eclXI                                                    ecl136II
                                      eaeI                                                                 ecoRI bsp1286
                                      cfrI                                                                 bslEI bs1HKAI
              aluI               bslEI    ahdI/eam1105I                                                    rmaI        bmyI
         tru9I    pvuII             bsmAI                                            tru9I                 maeI        taqI
         mseI dspBII   maeIII                                                        mseI       maeIII     bfaI apoI banII
 301 AAAAGTTAAT CTTTTCAACA GCTGTCATAA AGTTGTCACG GCCGAGACTT ATAGTCGCTT TGTTTTTATT TTTTAATGTA TTTGTAACTA AACATTGAT AACATTGAT
     TTTTCAATTA GAAAAGTTGT CGACAGTATT TCAACAGTGC CGGCTCTGAA TATCAGCGAA ACAAAAATAA AAAATTACAT AAACATTGAT CTTAAGCTCG
```

FIG. 41A

```
                        scrFI
                        ncII
                        mspI
                        hpaII
                        dsaV
                        xmaI/pspAI
                        smaI
                        scrFI
                        acII
                        dsaV
                        cauII       xhoI
                        bsaJI       mnlI
                        avaI
                  rsaI       sau3AI taqI
                  csp6I      mboI/ndeII[dam-]
                  nlaIV      dpnI[dam+]
                  nlaIV      nlaIV  paeR7I
                  kpnI cauII dpnII[dam-]
                  hgiCI      bstYI/xhoI
                  banI bsaJI alwI[dam-]
                  asp718     bamHI  avaI
                  acc65I     alwI[dam-] mnlI  mnlI                                                           mboII        sfaNI
401 TCGGTACCCG GGGATCCTCT CGAGGTGAG GTCCAACTC CGTGATTTTAT GAAAAAGAAT ATCGCATTTC TTCTTGCATC TATGTTCGTT TTTTCTATTG CTACAAACGC
    AGCCATGGGC CCCTAGGAGA GCTCCAACTC CACTAAAATA CTTTTTCTTA TAGCGTAAAG AAGAACGTAG ATACAAGCAA AAAAGATAAC GATGTTTGCG
-23                   M  K  K  N  I  A  F  L  L  A  S  M  F  V  F  S  I  A  T  N  A  ^ a mutation was found that inactivated the mluI site. The penultimate nucleotide was changed fr G tot ^
                                        sstI
                                        sacI
                                        hgiJII
                                        hgiAI/aspHI
                                        ecl136II
                                        bsp1286
                                        bsiBKAI
                        bsmFI bmyI                                                                                    bspMI
                        bsrI avaI aluI                                        mnlI                           hphI    scfI
                tth111I/aspI banII acII                          bstEII hphI bsgI    maeIII    bspMI       sse8387I     pstI                ddeI    nlaIII
      ecoRV                                                                                                                                  aluI    rsaI
                                                                                                                                             hindIII csp6I
501 ATACGCTGAT ATCCAGATGA ATCCAGTCCCC GAGCTCCCTG TCCGCCTCTG TGGGCGATAG GGTCACCATC ACCTGCAGT CAAGTCAAAG CTTAGTACAT
    TATGCGACTA TAGGTCTACT TAGGTCAGGGG CTCGAGGGAC AGGCGGAGAC ACCCGCTATC CCAGTGGTAG TGGACGTCCA GTTCAGTTTC GAATCATGTA
 -2   Y  A  D  I  Q  M  T  Q  S  P  S  S  L  S  A  S  V  G  D  R  V  T  I  T  C  R  S  S  Q  S  L  V  H
```

FIG. 41B

```
                                              scrFI
                                              mvaI
                                              ecoRII
                                              dsaV                                           hinfI       tfiI
                                              bstNI                                          taqI    bpmI/gsuI[dcm-]  bsmFI
                                              apyI[dcm+]                                             claI/bspl06     pleI
                           bsrI                                                                      bspDI[dam-]     hinfI
601 GGTATAGGTG CTACGTATTT ACACTGGTAT CAACAGAAAC CAGGAAAAGC TCCGAAACTA CTGATTACA AAGTATCCAA CTGATTCTCT GGAGTCCCTT
    CCATATCCAC GATGCATAAA TGTGACCATA GTTGTCTTTG GTCCTTTTCG AGGCTTTGAT GACTAATGT TTCATAGGTT AGCTAAGAGA CCTCAGGGAA
 32  G  I  G  A  T  Y  L  H  W  Y  Q  Q  K  P  G  K  A  P  K  L  L  I  Y  K  V  S  N  R  F  S  G  V  P  S
                      mspI
                      hpaII
                      bslI
                      bsaWI
                      sau3AI
                      mboI/ndeII[dam-]
                      dpnI[dam+]
                      dpnII[dam-]
                      alwI[dam-]
                      nlaIV                                                        fnu4HI
                      bstYI/xhoII                                                  bsoFI               rsaI
                      bamHI                                                        bbvI               csp6I
                      alwI[dam-]  bsmFI                                     scfI   mboII             scaI nlaIII
701 CTCGCTTCTC TGGATCCGGT TCTGGGACGG ATTTCACTCT GACCATCAGC AGTCTGCAGC CAGAAGACTT CGCAACTTAT TACTGTTCAC AGAGTACTCA
    GAGCGAAGAG ACCTAGGCCA AGACCCTGCC TAAAGTGAGA CTGGTAGTCG TCAGACGTCG GTCTTCTGAA GCGTTGAATA ATGACAAGTG TCTCATGAGT
 66  R  F  S  G  S  G  S  G  T  D  F  T  L  T  I  S  S  L  Q  P  E  D  F  A  T  Y  C  S  Q  S  T  H
                                  styI                                                pstI
                                  bsaJI                                               bsgI
                                  rsaI
                                  csp6I
                                  nlaIV
                                  kpnI                                                   mboII
                                  hglCI                           sau3AI                 bpuAI     acII
                                  banI                            mboI/ndeII[dam+]  fnu4HI  bbsI
                                  asp718                          dpnI[dam+]        bsoFI
                   bsrBI          acc65I                          dpnII[dam-]       bbvI        mboII
                   acII
801 TGTCCCGCTC AGTTTGGAC AGGTACCAA AAACGAACTG GGTGGAGATC TGGCTGCACC ATCTGTCTTC ATCTTCCCGC CATCTGATGA GCAGTTGAAA
    ACAGGGCGAG TCAAACCTG TCCATGGTT TTTGCTTGAC CCACCTCTAG ACCGACGTGG TAGACAGAAG TAGAAGGGCG GTAGACTACT CGTCAACTTT
 99  V  P  L  T  F  G  Q  G  T  K  V  E  I  K  R  T  V  A  A  P  S  V  F  I  F  P  P  S  D  E  Q  L  K
```

FIG. 41C

```
                                                                                                       scrFI
                                                                                                       mvaI
                                                                                                       ecoRII
                                                                                                       dsaV
                                              haeIII/palI                                              bstNI
                                              haeI  rsaI                                      mnlI     bsaJI
       xmnI                                   mnlI  csp6I                                      bslI    maeIII apyI[dcm+]
       asp700         cac8I    xmnI
 901 TCTGGAACTG CTTCTGTGT GTGCCTGCTG AATAACTTCT ATCCCAGAGA GGCCAAAGTA CAGTGGAAGG TGGATAACGC CCTCCAATCG GGTAACTCCC
     AGACCTTGAC GAAGACACA CACGGACGAC TTATTGAAGA TAGGGTCTCT CCGGTTTCAT GTCACCTTCC ACCTATTGCG GGAGGTTAGC CCATTGAGGG
 132  S  G  T  A  S  V  V   C  L  L  N  N  F  Y  P   R  E  A  K  V  Q  W  K  V   D  N  A  L  Q  S   G  N  S  Q fnu4HI
                                                     bsoFI                celII/espI
                     maeIII                ddeI      mnlI bbvI  hgaI ddeI  blpI/bpu1102I          accI cac8I
1001 AGGAGAGTGT CACAGAGCAG GACAGCAAGG ACAGCACCTA CAGCCTCAGC CGCTGAGCAA CGCTGAGCGA AGCAGACTAC GAGAAACACA AGTCTACGC
     TCCTCTCACA GTGTCTCGTC CTGTCGTTCC TGTCGTGGAT GTCGGAGTCG TCGTGGGACT GCGACTCGTT TCGTCTGATG CTCTTTGTGT TTCAGATGCG
 166  E  S  V  T  E  Q   T  A  S   T  T  P   Q  P  S   R  R  V   R  R  L   S  R  K  H  K   S  T  R cac8I
                      aluI
                      sstI
                      sacI
                      hgiJII
                      hgiAI/aspHI
                      ecl136II
                      bspl286
                      bsiHKAI
                      bmyI
               haeIII/palI                                                                                rmaI
               sau96I banII                                                                               maeI
               asuI ddeI                                                                                  bfaI
         hphI  ecoO109I/draII                                                          mnlI               sau96I
         maeIII  alwNI[dcm-]                                            aluI           sau3AI             haeIII/palI
                                                                        tru9I  mboI/ndeII[dam-] hgaI      asuI
                                                                        mseI   dpnI[dam+]      mspI       hpaII sfaNI
1101 CTGCGAAGTC ACCCATGCAGG CCTGAGCTC GCCCGTCACA AAGAGCTTCA ACAGGGGAGA GTGTTAAGCT GATCCTCTAC GCCGGACGCA TCGTGCCCCT
     GACGCTTCAG TGGGTAGTCC GGACTCGAG CGGGCAGTGT TTCTCGAAGT TGTCCCCTCT CACAATTCGA CTAGGAGATG CGGCCTGCGT AGCACCGGGA
 199  C  E  V  T   H  Q  G  L  S  S   P  V  T  K  S  F   N  R  G  E  C   Q
```

```
                              bsaJI             dsaV
                              avaI              bstNI
                              bsaJI             bsII
           plaI     sau96I    sau96I            apyI[dcm+]                       bsII
           hinfI    avaII     nlaIV             sau96I                           sau3AI
        taqI        asuI      haeIII/palI                              mboI/hdeII[dam-]
        xhoI        nlaIV     asuI              avaI                   dpnI[dam+]              maeII
        paeR7I                                  ecoO109I/draII         dpnII[dam-]             hphI   snaBI
        avaI maeIII bsrI      ecoO109I/draII haeIII/palI                          alwI[dam-]          hphI      bsaAI
1401 CTTCTCGAGT CACTATATGC ACTGGGTCCG TCAGGCCCCG GGTAAGGGCC TGGAAATGGGT TGGATATATT GATCCTTCCA ATGGTGAAAC TACGTATAAT
     GAAGAGCTCA GTGATATACG TGACCCAGGC AGTCCGGGGC CCATTCCCGG ACCTTTACCCA ACCTATATAA CTAGGAAGGT TACCACTTTG ATGCATATTA
  29  F  S  S  H  Y  M  H  W  V  R  Q  A  P  G  K  R  G  L  E  W  V  G  Y  I  D  P  S  N  G  E  T  T  Y  N thaI
                              fnuDII/mvnI                                         scfI
                haeIII/palI   bstUI                                               pstI
                sau96I        bshI236I                                            bsgI          cac8I    mnII
                asuI          nruI                                                bspMI         cac8I    ddeI   drdI
1501 CAAAAGTTCA AGGGCCGTTT CACTTTATCT CGGACAACT CCAAAAACAC AGCATACCTG CAGATGAACA GCCTGCGTGC TGAGGACACT CCGTCTATT
     GTTTTCAAGT TCCCGGCAAA GTGAAATAGA GCCGTGTTGA GGTTTTTGTG TCGTATGGAC GTCTACTTGT CGGACGCACG ACTCCTGTGA CGGCAGATAA
  62  Q  K  F  K  G  R  F  T  L  S  R  D  N  S  K  N  T  A  Y  L  Q  M  N  S  L  R  A  E  D  T  A  V  Y  Y sau96I
                                                                                                              haeIII/palI
                                                                maeIII                                        sau96I
                                                                bstEII                                        nlaIV
                                                                scrFI                                         hgiJII
                                                                mvaI             mnII                         bsp1286
                                                                ecoRII  bsaJI                      bmyI       bsp120I
                                                      maeII     dsaV    bseRI    esp3I                        banII
                                           maeIII     hinfI/acyI bstNI                                 asuI
                                           hphI bsrI mboII aatII ahaII/bsaBI     bsaJI hphI bsmBI      apaI    bsaJI
      mnII                                 taqI                                 bsaJI apyI[dcm+] bsmAI  styI asuI
1601 ACTGTGCAAG AGGGGATTAT CGCTACAATG GTGACTGGTT CTTCGACGTC GAACCCTGGT TGGGGTCAAG GAACCCTCTCC TCGGCCTCCA CCAAGGGCCC
     TGACACGTTC TCCCCTAATA GCGATGTTAC CACTGACCAA GAAGCTGCAG CTTGGGACCA ACCCCAGTTC CTTGGGAGAGG AGCCGGAGGT GGTTCCCGGG
   96 C  A  R  G  D  Y  R  I  N  G  D  W  F  F  D  V  W  G  Q  G  T  L  V  T  V  S  S  A  S  T  K  G  P haeIII/palI ecoO109I/draII
                                                                                                         mnII      nlaIV
                                                                                                 seq right is from p6G425chIm2.fab2
```

```
                                                                                                    fnu4HI
                                                                                                    bsoFI
                                                                            haeIII/palI             haeIII/palI
                                                            sau96I                                                    acII  eaeI
                                                            scrFI                                                           cfrI
                                            ncII                                                    hgiAI/aspHI       mcrI
                                    rsaI   mspI mnII                               hinPI            bsp1286           bsiEI
              sfaNI                        csp6I hpaII                             hhaI/cfoI        bsiHKAI
              scrFI                        mspI   dsaV bsII                        mstI  bsII       bmyI
              mvaI                         hpaII  cauII                            avIII/fspI                         mnII
              ecoRII                       cfr10I/bsrFI asuI                                          ACGGCTTTGG        sau3AI
              dsaV                                       acII                                                          mboI/ndeII[dam-]
              bstNI                                     ecoRV                                                          dpnI[dam+]
              bsaJI                                                                                                    dpnII[dam-]
                                                                                                                       alwI[dam-]
                                                                                                                       nlaIV
     nlaIV                                                                                                             bstYI/xhoI     hgaI
     mnII hgiCI                                                                                                        bamHI         mspI
     bsaJI    banI                                 hinPI                                                               alwI[dam-]   hpaII    sfaNI
     fokI     maeIII  fokI  scfI                   hhaI/cfoI                                                                bsII hphI  apyI[dcm+]                                    rmaI
hinPI                                               maeI
hhaI/cfoI                                           nheI
                           fnu4HI  haeII
                           bsoFI   eco47III
                           bbvI    bfaI
                  maeIII   cacBI
      sfaNI bsrI
2301 AATGCGCTCA TCGTCATCCT CGGCACCGTC ACCCTGGTT ATGCCGGGCCT ATGCCGGGCCT CTTGCGGGAT ATCGTCCATT
     TTACGCGAGT AGCAGTAGGA GCCGTGGCAG TGGGACCAA TACGCCCGTA TCGGACCCGA GAACGCCCTA TAGCAGTTAA sfaNI
2401 CCGACAGCAT CGCCAGTCAC TATGGCGTGC TGCTAGCGCT ATATGCGGTTG ATGCAATTTC TATGCGCACC CGTTCTCGGA GCACTGTCCG ACCGCTTTGG
     GGCTGTCGTA GCGGTCAGTG ATACCGCACG ACGATCGCGA TATACGCAAC TACGTTAAAG ATACGCGTGG GCAAGAGCCT CGTGACAGGC TGGCGAAACC thaI
                                                                              fnuDII/mvnI
     acII                                                                     bstUI     nlaIII
     fnu4HI                                                        sau3AI
     bsoFI                                                         mboI/ndeII[dam-]
     acII bsrI    cacBI                   nlaIV       taqI  bsh1236I           dpnI[dam+]                               bsII
2501 CCGCCGCCCA GTCCTGCTCG CTTCGGCTACT TGGAGCCACT ATCGACTACG CGATCATGGC GACCACACCC GTCCTGTGGA TCCTCTACGC CGGACGCATC
     GGCGGCGGGT CAGGACGAGC GAAGCGATGA ACCTCGGTGA TAGCTGATGC GCTAGTACCG CTGGTGTGGG CAGGACACCT AGGAGATGCG GCCTGCGTAG

```
                                                                fnu4HI
                                                                mspI hinPI
                                                                naeI haeII
                                                                cfr10I/bsrFI
                                                                cac8I eco47III
                                               fnu4HI           nlaIV bsoFI                              sau96I
                                               bsoFI            hglCI bbvI                              nlaIV
        acII                                   mboII            nlaIII banI hpaII hhaI/cfoI  mnlI       avaII
        thaI                        acII       bpuAI                                                   asuI
        fnuDII/mvnI  acII  fnu4HI   bsoFI      bbsI                                                    bsrI  acII
        bstUI  nlaIII fnu4HI                                                                           maeII bsmFI
        bshl236I                         thaI
        hinPI bcgI                       fnuDII/mvnI       haeIII/palI
        hhaI/cfoI                        bstUI
                                         bshl236I  sau3AI                  acII       tfiI
                   acII                  hinPI     mboI/ndeII[dam-]               hinfI  cac8I mnlI
                   sau96I                hhaI/cfoI dpnI[dcm-] dpnII[dam-]  cac8I
                   avaII                 bpmI/gsuI[dcm-]                                                  thaI  fnuDII/mvnI
                   asuI                                                                                  hgaI
2901 TGGGCGCGGG GCATGACTAT CGTCGCCGCA CTTATGACTG TCTTCTTTAT CATGCAACTC GTAGGACAGG TGCCGGCAGC GCTCTGGGTC ATTTTCGGCG
     ACCCGCGCCC CGTACTGATA GCAGCGGCGT GAATACTGAC AGAAGAAATA GTACGTTGAG CATCCTGTCC ACGGCCGTCG CGAGACCCAG TAAAAGCCGC mcrI
                                                      eagI/xmaIII/eclXI
                                                      eaeI      hinPI
                                                      cfrI      hhaI/cfoI
                                                      bslEI  thaI
                                              mspI    fnu4HI fnuDII/mvnI
                                              naeI    bsoFI  bstUI
                                              cfr10I/bsrFI   bshl236I
                                              bsoFI   acII   hgaI       bshl236I mnlI  haeI
                                haeIII/palI           bglI nlaIII haeIII/palI  maeII cac8I  nruI bshl236I fokI haeIII/palI
       maeII      haeI          haeI          cac8I
       pspl406I   cac8I
3001 AGGACCGCTT TCGCTGGAGC GCGACGATGA TCGGCCTGTC GCTTGCGGTA TTCGGAATCT TGCACGCCCT CGCTCAAGCC TTCGTCACTG GTCCCGCCAC
     TCCTGGCGAA AGCGACCTCG CGCTGCTACT AGCCGGACAG CGAACGCCAT AAGCCTTAGA ACGTGCGGGA GCGAGTTCGG AAGCAGTGAC CAGGGCGGTG 3101 CAAACGTTTC GGCGAGAAGC AGGCCATTAT CGCCGGCATG CCCGGGCACG CGCTGGGCTA CGTCTTGCTG CGGTTCGCGA CGGGAGGCTG GATGGCCTTC
     GTTTGCAAAG CCGCTCTTCG TCCGGTAATA GCGGCCGTAC GGGCCCGTGC GCGACCCGAT GCAGAACGAC GCCAAGCGCT GCCCTCCGAC CTACCGGAAG
```

FIG. 41K

```
                                                                                bspMI
                                                                                scrFI
                                              thaI                              mvaI
                                              fnuDII/mvnI                       ecoRII
                                              bstUI                             dsaV
                    fnu4HI                    cacBI      haeI                   bstNI
                    bsoFI
                    acII
          mspI mslI sfaNI bsh1236I haeIII/palI                            bsmFI aluI      alwI[dam-]
     tfiI hpaII sfaNI fokI acII cacBI nlaIII  apyI[dcm+]  TAGATGACGA CCATCAGGA CAGCTTCAAG
     hinfI
3201 CCCATTATGA TTCTTCTCGC TTCCGGCGGC ATCGGGATGC CCGGTTGCA GGCCATGCTG TCCAGGCAGG  TCCAGGCAGG  CCATCAGGA  CAGCTTCAAG
     GGGTAATACT AAGAAGAGCG AAGGCCGCCG TAGCCCTACG GGCCAACGT CCGGTACGAC AGGTCCGTCC ATCTACTGCT GGTAGTCCCT GTCGAAGTTC fnu4HI
              bsoFI
              acII
              thaI                                                                        mnlI
              fnuDII/mvnI                sau96I                               mnlI        hgiAI/aspHI
              bstUI                      avaII                                beaJI       bsp1286
         cacBI                      bsrI       sau3AI                               acII  bslHKAI
         sau3AI bsh1236I       sau3AI asuI     mboI/ndeII[dam-]                     fnu4HI  bmyI
         mboI/ndeII[dam-]      mboI/ndeII[dam+] nspBII        maeIII                bsoFI
         dpnI[dam+]            dpnI[dam-]                     dpnI[dam+]              bglI    cac8I   nlaIII  nlaIII
         dpnII[dam-]                                  taqI[dam-]  acII dpnII[dam-]    TTTATGCCGC CTCGGCGAGC ACATGGAACG GGTTGGCATG
3301 GATCGCTCGC GGCTCTTACC AGCCTAACTT CGATCACTGG ACCGCTGATC GTCACGGCGA TTTATGCCGC CTCGGCGAGC ACATGGAACG GGTTGGCATG
     CTAGCGAGCC CCGAGAATGG TCGGATTGAA GCTAGTGACC TGGCGACTAG CAGTGCCGCT AAATACGGCG GAGCCGCTCG TGTACCTTGC CCAACCGTAC fnu4HI
            bsoFI
            hinPI                                              haeIII/palI
            hhaI/cfoI                                          sau96I                                    fnu4HI
            nlaIV                                              scrFI                                     bsoFI
            narI                                               ncII                                      acII
            kasI                                  thaI         mspI                                        mspI    mnlI
            hinII/acyI                            fnuDII/mvnI  hpaII                                       hpaII nlaIV
            hgiCI                                 bstUI        dsaV                                        naeI  hgiCI
            haeII                                 bsh1236I     hgaI acII asuI  cauII mnlI                  cfr10I/bsrFI
            banI acII                                                                                     cac8I banI
            ahaII/bsaBI     mnlI acII CCTCCCCGCG TTGCGTCGCG GTGCATGGAG CCGGGCCACC TCGACCTGAA TGGAAGCCGG CGGCACCTCG
3401 GATTGTAGGC GCCGCCCTAT ACCTTGTCTG CCTCCCCGCG TTGCGTCGCG GTGCATGGAG CCGGGCCACC TCGACCTGAA TGGAAGCCGG CGGCACCTCG
     CTAACATCCG CGGCGGGATA TGGAACAGAC GGAGGGGCGC AACGCAGCGC CACGTACCTC GGCCCGGTGG AGCTGGACTT ACCTTCGGCC GCCGTGGAGC
```

```
                                                              sau3AI
                                                              mboI/ndeII[dam-]
                                                              nanI[dam-]
                                                              dpnI[dam+]
                                                              dpnII[dam-]
                                                              bstYI/xhoII
                                                              alwI[dam-]
                                                         mspI
                                                         hpaII
                                                         mroI bsaBI[dam-]             fnu4HI
                                                         bspMII                       bsoFI
                                                         bspEI[dam-]                  bbvI
                         acII                            bsaWI     sfaNI
                    thaI                                 accIII[dam-] GATCTGCATC  GCAGGATGCT  GCTGGCTACC
                    fnuDII/mvnI hinPI
              mboII bstUI       hhaI/cfoI                                           foki   cac8I
              bpuAI beh1236I  haeII             msII
              bbsI
3801 TGGTCTTCGG TTTCCGTGTT TCGTAAAGTC TGGAAACGCG GAAGTCAGCG CCCTGCACCA TTATGTTCCG GATCTGCATC GCAGGATGCT GCTGGCTACC
     ACCAGAAGCC AAAGGCACAA AGCATTTCAG ACCTTTGCGC CTTCAGTCGC GGGACGTGGT AATACAAGGC CTAGACGTAG CGTCCTACGA CGACCGATGG acII
                                cac8I                               bsmFI    foki
                                hinPI                               sau96I   sfaNI
                                hhaI/cfoI                           nlaIV  acII
                      tru9I  haeII                                  avaII fnu4HI        bsrI
                      mseI  eco47III            ddeI                asuI bsoFI          acII         mnII
3901 CTGTGGAACA CCTACATCTG TATTAACGAA GGGCTGGCAT TGACCCTGAG TGATTTTTCT CTGGTCCCGC CGCATCCATA CGGCCAGTTG TTTACCCTCA
     GACACCTTGT GGATGTAGAC ATAATTGCTT CCCGACCGTA ACTGGGACTC ACTAAAAAGA GACCAGGGCG GCGTAGGTAT GCCGGTCAAC AAATGGGAGT nspI
              scrFI
              ncII                                        mnII
              mspI                                        foki
        bsrI  hpaII                                       sfaNI
        bsII  dsaV nlaIII
     maeII    cauII
     psp1406I maeIII bspHI      maeIII                            nlaIII          apoI  bsII
4001 CAACGTTCCA GTAACCGGGC ATGTTCATCA TCAGTAACCC GTTTCATCG CATCCTCTCT CGTTTCATCG GTATCATTAC CCCATGAAC AGAAATTCCC
     GTTGCAAGGT CATTGGCCCG TACAAGTAGT AGTCATTGGG GCAAAGTAGC GTAGAGAGA GCAAAGTAGC CATAGTAATG GGGGTACTTG TCTTTAAGGG

FIG. 41N
```

```
                                                                                cac8I
                                                                                sau96I
                                                     acII bsII nlaIII acII       haeIII/palI                                     tru9I
           mnII           sfaNI                        msel   tru9I                asuI                                          mseI    bpmI/gsuI[dcm-]
4101 CCTTACACGG AGGCATCAAG TGACCAAACA GGAAAAAACC GCCCTTAACA TGGCCCGCTT TATCAGAAGC CAGACATTAA CGCTTCTGGA GAAACTCAAC
     GGAATGTGCC TCCGTAGTTC ACTGGTTTGT CCTTTTTTGG CGGGAATTGT ACCGGGCGAA ATAGTCTTCG GTCTGTAATT GCGAAGACCT CTTTGAGTTG fnu4HI    thaI
                                                                                                          bsoFI     fnuDII/mvnI
                                                                                                           aluI      bstUI
             acII                                                                                          pvuII     hinPI
             thaI                                                                                          nspBII    hhaI/cfoI
             fnuDII/mvnI                     xmnI                                                          fnu4HI    thaI
             bstUI                           tfII                                                          bsoFI     fnuDII/mvnI
             bsh1236I                        hinfI                                                         bcgI      bstUI
       aluI hgaI fokI                        asp700                        msII           aluI   acII  bbvI bbvI  mnII bsh1236I hphI
4201 GAGCTGGACG CGGATGAACA GGCAGACATC TGTGAATCGC TTCACGACCA CGCTGATGAG CTTTACCGCA CGTGCCTCGC GGTTTCGGT GATGACGGTG
     CTCGACCTGC GCCTACTTGT CCGTCTGTAG ACACTTAGCG AAGTGCTGGT GCGACTACTC GAAATGGCGT GCACGGAGCG CCAAAGCCA CTACTGCCAC esp3I
                            bsmBI
                            bsmAI
                mspI  hpaII                              scrFI                                             hgaI
          fnu4HI  scrFI                                  ncII                                              thaI
          bsoFI   ncII                                   mspI                                              fnuDII/mvnI
           bbvI   dsaV                                   hpaII                                             bstUI   acII
           nlaIII                                        sfaNI                                             bsh1236I
           nspI   cauII       aluI                       fokI dsaV                                         hinPI nspBII
       mnII dspHI aluI bsII   maeIII                     acII   cauII      drdI                            hhaI/cfoI   acII
4301 AAAACCTCTG ACACATGCAG CTCCCGGAGA CGTCACAGC TTGTCTGTAA GCGGATGCCG GGAGCAGACA AGCCCGTCAG GGGGGTCAG CGGGTGTTGG
     TTTTGGAGAC TGTGTACGTC GAGGGCCTCT GCCAGTGTCG AACAGACATT CGCCTACGGC CCTCGTCTGT TCGGGCAGTC CCCCCAGTC GCCCACAACC
```

```
                                                                                                             mspI                          haeII/palI
                                          bsmAI                                                              hpaII                         sau96I hinPI
                                          bsaI                                       bpmI/gsuI[dcm-]         bglI              haeII/palI  asuI hhaI/cfoI
              bsrI                        thaI                           mspI                     cac8I      GCCAGCCGGA        AGGGGCCAGC
              sau96I    fnu4HI            fouDII/mvnI                    hpaII                    CGGTCGGGCCT                  TCCCGGCTCG
              nlaIV     bsoFI             bstUI                          cfr10I/bsrFI
              haeIII/palI bsrDI           bshl236I
              asuI      bbvI              aclI                           hphI  nlaIV
                                                                                                                                           maeII
                                                                                      scrFI                                                hinPI
                                                                                      nciI                                                 hhaI/cfoI
                                                                                      mspI                                                 mstI pspl406I
             sau96I                                        tru9I         hpaII  rmaI                         tru9I              bsrI       avIII/fspI
             avaII                       mblI   bsrI       mseI          dsaV   maeI                         mseI               maeI       TGCGCAACGT
             asuI              acII      foki             aseI/asnI/vspI cauII  bfaI                                                       ACGCGTTGCA
5601 GGCTTACCAT CTGGCCCCAG TGCTGCAATG ATACCGCGAG ACCCAGCGTC ACCGGGCTCC ATTATTCAG CAATAAACCA GATTTATCAG CAATGAACCA GTTATTCGTT CTAAATAGTC GTTATATTAGCT ATCAAGCGGT CAATTATCAA
     CCGAATGGTA GACCGGGGTC ACGACGTTAC TATGGCGCTC TGGGTCGCAG CGGGCCCTTC GCTACGAGT CGACTCAT   CTAAATAGTC GATCCATGTC   CAATTGAA GTTATATTAGCT                                  ACGCGTTGCA
                                                                                                                                           sau3AI
                                                                                                                                           mboI/ndeII[dam-]
                                                                                                                                           dpnI[dam+]
                                                                                                                nlaIV           sau3AI     dpnII[dam-]
                                                                                                                mspI            mboI/ndeII[dam-]
                                                                                                                bsaWI           dpnI[dam+]  nlaIII
                                                                                                                aluI hpaII      dpnII[dam-] maeII alwI[dam-]
5701 GCAGAAGTGG TCCTGCAACT GCTGTCAGCC CGGCCTGCGT ACGGTCGTCG TTTGGTATGG CTTCATTCAG CTCCGGTTCC CAACGATCAA GGGCAGTTAC ATGATCCCC TACTAGGGGG
     CGTCTTCACC AGGACGTTGA CGACGAGTCGG TGCCAGCAGC AAACCATACC GAAGTAAGTC GAGGCCAAGG GTTGCTAGTT CCGCTCAATG TACTAGGGGG
              cacBI
              scfI
              pstI                                                                                              aclI
              fnu4HI                     sau3AI                                                                 fnu4HI
              bsoFI                      mboI/ndeII[dam-]                                                       bsoFI
              bbvI      malI             dpnI[dam+]                                                             haeIII/palI                fnu4HI
              bsrDI bsgI sfaNI           mallI dpnII pvuI/bspCI                                                 eaeI                       bsoFI
                                         sau96I avaII mcrI                                                      cfrI                       bbvI
                                         avaII asuI bstEI
5801 TCGTTGCCATT GCTTCGAGGG ACGTCGTGTC ACGGTCGTCG TGGTGTGTCA TCGTTGTCAG AGCAACAGTC TTCATTCAAC CGGGGTCACA ATAGTGAGTA CCAATACCGT CGTGACGTAT
     ACAACGGTAA CGAAGGCTCC TGCAGCACAG TGCCAGCAGC ACCACACAGT AGCAACAGTC TTCATTCAAC CGGGGTCACA ATAGTGAGTA CCAATACCGT CGTGACGTAT
              aclI
              aclI    aluI                                                                                      nlaIII
                                                                                                                mslI
5901 ATGTGTGCA AAAAGCCGT TAGCTCCTTC GGTCCTCCGA TCGTGTCAG AAGTAAGTTG GCCGCAGTGT TATCACTCAT GGTTATGCCA GCACTGCATA
     TACACACCGT TTTTTCGGCA ATCGAGGAAG CCAGGAGGCT AGCACACAGTC TTCATTCAAC CGGCGTCACA ATAGTGAGTA CCAATACCGT CGTGACGTAT
```

FIG. 41T

```
                                                                                              maeII
                                                                                              hinfI/acyI
                                                   hinPI                                      ahaII/bsaHI
                                                   thaI                                       aatII ddeI
                                                   fnuDII/mvnI
                                                   bstUI
                                                   bsh1236I
                                                   aciI
                                           ulaIV hhaI/cfoI
        nlaIII
        rcaI                                  sau96I
        bspRI  aciI                           haeIII/palI
        bsmAI  bsr8I                          asuI      mboII
                                              ecoO109I/draII
                                              mnlI   bpuAI
                  nlaIII                      bssSI  bbsI
                  rcaI    tru9I
                  bspHI   mseI
6401 TTGTCTCATG AGCGGATACA TATTTGAATG TATTTAGAAA AATAAACAAA TAGGGGTTCC GCGCACATTT CCCCGAAAAG TGCCACCTGA CGTCTAAGAA
     AACAGAGTAC TCGCCTATGT ATAAACTTAC ATAAATCTTT TTATTTGTTT ATCCCCAAGG CGCGTGTAAA GGGGCTTTTC ACGGTGGACT GCAGATTCTT 6501 ACCATTATTA TCATGACATT AACCTATAAA AATAGGGGTA TCACGAGGCC CTTCGTCTT CAA
     TGGTAATAAT AGTACTGTAA TTGGATATTT TTATCCCCAT AGTGCTCCGG GAAGCAGAA GTT

FIG. 41U
```

```
>length: 6563 aatII(GACGTC):           1645 6489
acc65I(GGTACC):          403 823
accI(GTMKAC):            1093 1963 4449
accIII(TCCGGA):          3867[dam-]
aclI(CCGC):              178 542 805 877 1340 1750 1826 2011 2039 2043 2182 2242 2384 2492 2501 2504
                         2628 2781 2784 2787 2906 2926 3005 3045 3094 3141 3226 3241 3309 3342 3367 3412
                         3436 3448 3490 3544 3597 3613 3619 3700 3838 3967 3970 3981 4139 4155 4210 4266
                         4351 4390 4400 4442 4467 4505 4518 4544 4561 4604 4611 4632 4723 4751 4878 4897
                         5018 5128 5263 5272 5634 5725 5916 5962 6083 6127 6204 6313 6412 6459
acyI                     see hinII
aflIII(ACRYGT):          1307 4678
ageI(ACCGGT):            1788
ahaII/bsaHI(GRCGYC):     1645 1813 2616 2637 2751 3408 6107 6489
ahaIII/draI(TTTAAA):     5435 5454 6146
ahdI/eam1105I(GACNNNNNGTC): 346 5566
aluI(AGCT):              72 121 252 320 398 532 589 648 1126 1144 1167 1325 1386 1906 2054 2075 2126
                         2218 2233 2889 3292 4202 4259 4270 4319 4338 4619 4845 4935 4981 5238 5759 5859
                         5922
alw44I/snoI(GTGCAC):     1831 4494 4992 6238
alwI[dam-](GGATC):       412 413 712 713 1171 1471 2578 2579 3300 3870 5245 5319 5331 5416 5429 589
                         6196 6214
alwNI[dcm-](CAGNNNCTG):  1117 1385 5089
apaI(GGGCCC):            1695
apaLI/snoI(GTGCAC):      1831 4494 4992 6238
apoI(RAATTY):            1 391 4093
apyI[dcm+](CCWGG):       640 999 1347 1357 1449 1665 1713 1755 1764 2333 3262 3645 4705 4826 4839
aseI/asnI/vspI(ATTAAT):  5742
asnI                     see aseI
asp700(GAANNNNTTC):      905 930 4234 6166
asp718(GGTACC):          403 823
aspHI                    see hgiAI
aspI                     see tth111I
asuI(GGNCC):             1119 1195 1425 1434 1446 1512 1695 1696 1752 2155 2375 2727 3002 3090 3339 3463
```

FIG. 41V

Stop Template Primer

SL.97.2    5' CAT GGT ATA GGT <u>TAA</u> ACT TAT TTA CAC 3'

NNS Randomization Primer

SL.97.3    5' CAT GGT ATA GGT <u>NNS</u> ACT TAT TTA CAC 3'

FIG. 42

Randomization of Position N35 of Variable Light Chain CDR-1
Amino Acid Frequency

*Phage Display (NNS Codon Library) Sort #3*

| Amino Acid | Frequency | % Total | IC50 (nM) |
|---|---|---|---|
| Asparagine (wt) | 1 | 5.6 | 4.9 |
| Glycine | 6 | 16.6 | 3.1 |
| Aspartic Acid | 3 | 16.6 | 3.1 |
| Glutamic Acid | 4 | 22.2 | 0.1 |
| Alanine | 2 | 5.6 | 0.2 |
| Lysine | 1 | 5.6 | ND |
| Serine | 1 | 1.9 | ND |

FIG. 43A

Representative Conc versus Time Plot. Shown is the kinetic data for 6G4V11N35A.F(ab')2.

| SAMPLE | ka | kd | Kd |
|---|---|---|---|
| 6G4V11N35A-Fab | ND | ND | 114pM |
| 6G4V11N35A-F(ab')$_2$ | 2.0x10$^6$ | 2.1x10$^{-4}$ | 109pM |
| 6G4V11N35E-Fab | 4.7x10$^6$ | 2.6x10$^{-4}$ | 54pM |

```
  1 ATGAAAAAGA ATATCGCATT TCTTCTTGCA TCTATGTTCG TTTTTTCTAT TGCTACAAAC
    TACTTTTTCT TATAGCGTAA AGAAGAACGT AGATACAAGC AAAAAAGATA ACGATGTTTG
-23 M   K   K   N   I   A   F   L   L   A   S   M   F   V   F   S   I   A   T   N

61 GCATACGCTG ATATCCAGAT GACCCAGTCC CCGAGCTCCC TGTCCGCCTC TGTGGGCGAT
    CGTATGCGAC TATAGGTCTA CTGGGTCAGG GGCTCGAGGG ACAGGCGGAG ACACCCGCTA
 -3 A   Y   A   D   I   Q   M   T   Q   S   P   S   S   L   S   A   S   V   G   D

121 AGGGTCACCA TCACCTGCAG GTCAAGTCAA AGCTTAGTAC ATGGTATAGG TGAGACGTAT
    TCCCAGTGGT AGTGGACGTC CAGTTCAGTT TCGAATCATG TACCATATCC ACTCTGCATA
 18 R   V   T   I   T   C   R   S   S   Q   S   L   V   H   G   I   G   E   T   Y

181 TTACACTGGT ATCAACAGAA ACCAGGAAAA GCTCCGAAAC TACTGATTTA CAAAGTATCC
    AATGTGACCA TAGTTGTCTT TGGTCCTTTT CGAGGCTTTG ATGACTAAAT GTTTCATAGG
 38 L   H   W   Y   Q   Q   K   P   G   K   A   P   K   L   L   I   Y   K   V   S

241 AATCGATTCT CTGGAGTCCC TTCTCGCTTC TCTGGATCCG GTTCTGGGAC GGATTTCACT
    TTAGCTAAGA GACCTCAGGG AAGAGCGAAG AGACCTAGGC CAAGACCCTG CCTAAAGTGA
 58 N   R   F   S   G   V   P   S   R   F   S   G   S   G   S   G   T   D   F   T

301 CTGACCATCA GCAGTCTGCA GCCAGAAGAC TTCGCAACTT ATTACTGTTC ACAGAGTACT
    GACTGGTAGT CGTCAGACGT CGGTCTTCTG AAGCGTTGAA TAATGACAAG TGTCTCATGA
 78 L   T   I   S   S   L   Q   P   E   D   F   A   T   Y   Y   C   S   Q   S   T

361 CATGTCCCGC TCACGTTTGG ACAGGGTACC AAGGTGGAGA TCAAACGAAC TGTGGCTGCA
    GTACAGGGCG AGTGCAAACC TGTCCCATGG TTCCACCTCT AGTTTGCTTG ACACCGACGT
 98 H   V   P   L   T   F   G   Q   G   T   K   V   E   I   K   R   T   V   A   A

421 CCATCTGTCT TCATCTTCCC GCCATCTGAT GAGCAGTTGA AATCTGGAAC TGCTTCTGTT
    GGTAGACAGA AGTAGAAGGG CGGTAGACTA CTCGTCAACT TTAGACCTTG ACGAAGACAA
118 P   S   V   F   I   F   P   P   S   D   E   Q   L   K   S   G   T   A   S   V

481 GTGTGCCTGC TGAATAACTT CTATCCCAGA GAGGCCAAAG TACAGTGGAA GGTGGATAAC
    CACACGGACG ACTTATTGAA GATAGGGTCT CTCCGGTTTC ATGTCACCTT CCACCTATTG
138 V   C   L   L   N   N   F   Y   P   R   E   A   K   V   Q   W   K   V   D   N

541 GCCCTCCAAT CGGGTAACTC CCAGGAGAGT GTCACAGAGC AGGACAGCAA GGACAGCACC
    CGGGAGGTTA GCCCATTGAG GGTCCTCTCA CAGTGTCTCG TCCTGTCGTT CCTGTCGTGG
158 A   L   Q   S   G   N   S   Q   E   S   V   T   E   Q   D   S   K   D   S   T

601 TACAGCCTCA GCAGCACCCT GACGCTGAGC AAAGCAGACT ACGAGAAACA CAAAGTCTAC
    ATGTCGGAGT CGTCGTGGGA CTGCGACTCG TTTCGTCTGA TGCTCTTTGT GTTTCAGATG
178 Y   S   L   S   S   T   L   T   L   S   K   A   D   Y   E   K   H   K   V   Y

661 GCCTGCGAAG TCACCCATCA GGGCCTGAGC TCGCCCGTCA CAAAGAGCTT CAACAGGGGA
    CGGACGCTTC AGTGGGTAGT CCCGGACTCG AGCGGGCAGT GTTTCTCGAA GTTGTCCCCT
198 A   C   E   V   T   H   Q   G   L   S   S   P   V   T   K   S   F   N   R   G

721 GAGTGTTAAG CTGATCCTCT ACGCCGGACG CATCGTGGCC CTAGTACGCA ACTAGTCGTA
    CTCACAATTC GACTAGGAGA TGCGGCCTGC GTAGCACCGG GATCATGCGT TGATCAGCAT
218 E   C   Q
```

FIG. 45

N35AH1upr

5'-CTAGTGCAGTCTGGGCGGTGGCCTGGTGCAGCCAGGGGCTCACTCCGTTTGTCCTGTGCAGCTTCTGGCTACTCCTTC-3'

N35AH1lwr

5'-TCGAGAAGGAGTAGCCAGAAGCTGCACAGGACAAACGGAGTGAGCCCCTGGCTGCACCAGGCCACCGCCCAGACTGCACT
AG-3'

Bold indicates nucleotide change destroying PvuII site.

FIG. 47

```
> Wed May  7 18:27:36 1997
> /home/ruby/vc/Immbio/afan/ss.pRK7v11.N35A.choSD
> sites: std
> length: 8120 (circular)
> This has the pSVI backbone with the pRK7 cloning linker (pSVI7) and the intron DHFR(ID)
> made from pSVI WTSD.D by adding a linearization linker(LL) into the HpaI site cac8I
              aluI
              sstI
              sacI
              hgiJII
              hgiAI/aspHI                             scrFI
              ecl136II            sau3AI  aluI        mvaI
              bsp1286             mboI/ndeII(dam-)    ecoRII
              bslHKAI             dpnI(dam+)          dsaV
              bmyI                pvuI/bspCI          bstNI
              banII         rmaI  plei  dpnII(dam-)   apyI(dcm+)
              taqI          maeI  mcrI  pvuII         bsaJI
                            bfaI  belEI nspBII        bsmFI  nlaIV    cac8I
    1 TTCGAGCTCG CCCGACATTG ATTATTGACT AGAGTCGATC GACAGCTGTG GAATGTGTGT CAGTTAGGGT GTGGAAAGTC CCCAGGCTCC CCAGCAGGCA
      AAGCTCGAGC GGGCTGTAAC TAATAACTGA TCTCAGCTAG CTGTCGACAC CTTACACACA GTCAATCCCA CACCTTTCAG GGTCCGAGG GGTCGTCCGT
                                sfaNI                                                           sfaNI
                                ppu10I                    scrFI                                 ppu10I
                                nsiI/avaIII               mvaI                                  nsiI/avaIII
                                nlaIII                    ecoRII                                       nlaIII
                                sphI                      dsaV                                  sphI
                                nspI                      bstNI                                 nspI
                                nspHI                     apyI(dcm+)                            nspHI
                                cac8I                     bsaJI                                 cac8I
                                                   sexAI        bsmFI  nlaIV  cac8I
  101 GAAGTATGCA AAGCATGCAT CTCAATTAGT CAGCAACCAG GTGTGGAAAG TCCCCAGGCT CCCCAGCAGG CAGAAGTATG CAAAGCATGC ATCTCAATTA
      CTTCATACGT TTCGTACGTA GAGTTAATCA GTCGTTGGTC CACACCTTTC AGGGGTCCGA GGGGTCGTCC GTCTTCATAC GTTTCGTACG TAGAGTTAAT
                                                                                nlaIII
                                                                                styI
                                                                                ncoI
                                                                       acII  baII dsaI
                                                 acII  barI  acII      ccgcccatg  acII  bsaJI
                 acII            acII            ccgcccagttc  cgcccattct CCGCCCATG GCGGGGGTAC GCTGACTAAT TTTTTTTATT
                 bsmFI  acII  foxI  acII         CCCCTAACTC  GCCCATCCCG
  201 GTCAGCAACC ATAGTCCCGC CCCTAACTCC GCCCATCCCG CCCCTAACTC GCCCATCCCG CCCCTAACTC GCCCATCCCG CGCCCCATG GCGGGGGTAC GCTGACTAAT TTTTTTTATT
      CAGTCGTTGG TATCAGGGCG GGGATTGAGG CGGGTAGGGC GGGGATTGAGG CGGGTAGGGC GGGGATTGAGG CGGGTAGGGC GCGGGGTAC CGACTGATTA AAAAAAATAA
```

```
                                                                                                         hgaI
                                                                                                         hinII/acyI
                                                                                                         ahaII/bsaHI
                                                                                                         scrFI
                                                                                                         mvaI        mnlI
                                                                                                         ecoRII
                   nlaIII                                                                                dsaV
              sau3AI                                                                                     bstNI       ecoNI
              mboII/ndeII[dam-]                                                                          apyI[dcm+]    mnlI
              dpnI[dam+]                                    maeII                                        bsaJI      bsII ddeI
              dpnII[dam-]                         aflIII                                         mnlI
     maeIII alwI[dam-]   apoI    maeII
 901 GTGACAAGGA TCATGCAGGA ATTTGAAAGT GACACGTTTT TCCCAGAAAT TGATTGGGGG AAATATAAAC CTCTCCCAGA ATACCCAGGC GTCCTCTCTG
     CACTGTTCCT AGTACGTCCT TAAACTTTCA CTGTGCAAAA AGGGTCTTTA ACTAAACCCC TTTATATTTG GAGAGGGTCT TATGGGTCCG CAGGAGAGAC scrFI
     mvaI
     ecoRII
     dsaV
     bstNI
     apyI[dcm+]                                                                           sfaNI
     sau96I                                                          accI     mboII       mboII
     avaII                                                                                mnlI     aluI
     asuI    mnlI      sfaNI                                  styI                        mnlI
1001 AGGTCCAGGA GGAAAAAGGC ATCAAGTATA AGTTTGAAGT CTACGAGAAG AAAGACTAAC AGGAAGATGC TTTCAAGTTC TCTGCTCCCC TCCTAAAGCT
     TCCAGGTCCT CCTTTTTCCG TAGTTCATAT TCAAACTTCA GATGCTCTTC TTTCTGATTG TCCTTCTACG AAGTTCAAG AGACGAGGGG AGGATTTCGA
                                                             bsaJI                        ^END DHFR styI
                                                  bsaJI
                                                  sau3AI
                                                  mboII/ndeII[dam-]
                                                  dpnI[dam+]                        aluI       tru9I
                            nlaIII                dpnII[dam-]                       fnu4HI     mseI
                            styI                  alwI[dam-]                        bsoFI      aseI/asnI/vspI
                ppu10I      ncoI    desaI bsmFI   bstYI/xhoII                       bbvI
                nsiI/avaIII bsaJI   cac8I
1101 ATGCATTTTT ATAAGACCAT GGGACTTTTG CTGGCTTAGA ATCCCCTTGG ACCGAGCTAC CTTCGTTAGA ACCGAGCTAC TGCGTCGATG ATTGGAATAC ATAGTATGTG
     TACGTAAAAA TATTCTGGTA CCCTGAAAAC GACCGAAATC TAGGGGAACC TGGCTCGATG GAAGCAATCT TGGCTCGACG ACGCAGCTAC TAACCTTATG TATCATACAC sau96I
                                                                                            avaII
                                                                                            asuI
                                                                                            scrFI
                                                                                            mvaI
                                                                                            ecoRII
```

```
                                                                     scrFI
                                                                     nciI
                                                                     mspI
                                                                     hpaII
                                                                     dsaV          scrFI
                                                                     cauII         mvaI
                                                                     xmaI/pspAI    ecoRII       scrFI
                                                                     smaI          dsaV         mvaI
                                                                     scrFI         bstNI        ecoRII
                                                                     nciI          apyI[dcm+]   dsaV
                                                          rsaI       dsaV          sexAI        bstNI
                                                          csp6I      cauII                      apyI[dcm+]
                                             bsp1407I/bsrGI GTACACCCTG CCCCCATCCC  GGGAAGAGAT GACCAAGAAC CAGTCAGCC  bspMI
         avaI    raeI   bslI bsaJI bslI avaI  foki                    earI/xsp632I                         TGACCTGCCT GGTCAAAGGC TTCTATCCA
2401 CAGCCCGAG AACCACAGGT GTACACCCTG CCCCCATCCC GGGAAGAGAT GACCAAGAAC CAGTCAGCC TGACCTGCCT GGTCAAAGGC TTCTATCCA
     GTCGGGCTC TTGGTGTCCA CATGTGGGAC GGGGTAGGG CCCTTCTCTA CTGGTTCTTG GTCAGTCGG ACTGGACGGA CCAGTTTCCG AAGATAGGGT
 347  Q  P  R  E  P  Q  V  Y  T  L  P  P  S  R  E  E  M  T  K  N  Q  V  S  L  T  C  L  V  K  G  F  Y  P  S mspI
                                                      hpaII
                            dsaI           fnu4HI     mnlI                                         pleI
                            bslI           bsoFI                                                   hinfI   nlaIV mboII
                  msII bsaJI    bsrDI      bbvI                                                                      mnlI
2501 GCGACATCGC CGTGGAGTGG GAGAGCAATG GCCAGCCGGA GAACAACTAC AAGACCACGC CTCCCGTGCT GGACTCCGAC CTCTCTACAG
     CGCTGTAGCG GCACCTCACC CTCTCGTTAC CGGTCGGCCT CTTGTTGATG TTCTGGTGCG GAGGGCACGA CCTGAGGCTG GAGAGATGTC
 381  D  I  A  V  E  W  E  S  N  G  Q  P  E  N  N  Y  K  T  T  P  P  V  L  D  S  D  G  S  F  F  L  Y  S mboII                                             sapI
              dsaI           fnu4HI         maeII        bpuAI         nlaIII                              mboII mnlI
              hphI           bsoFI   xmnI bbsI           ppu10I        nsiI/avaIII                         earI/xsp632I
          aluI bsaJI  bspMI bbvI     asp700          nlaIII            sfaNI      mnlI
2601 CAAGCTCACC GTGGACAAGA GCAGGTGGCA GCAGGGAAC GTCTTCTCAT GCTCCGTGAT GCATGAGGCT CTGCACAACC ACTACACGCA GAAGAGCCTC
     GTTCGAGTGG CACCTGTTCT CGTCCACCGT CGTCCCCTTG CAGAAGAGTA CGAGGCACTA CGTACTCCGA GACGTGTTGG TGATGTGCGT CTTCTCGGAG
 414  K  L  T  V  D  K  S  R  W  Q  Q  G  N  V  F  S  C  S  V  M  H  E  A  L  H  N  H  Y  T  Q  K  S  L
```

```
                                                                sfaNI                       scrFI
                 scrFI                                          ppuI0I               mvaI
                 mvaI                                       nsII/avaIII              ecoRII
                 ecoRII                                        nlaIII                 daeV
                 daeV                                           sphI                  bstNI
                 bstNI                                          nspI                apyI[dcm+]
               apyI[dcm+]                                       nspHI                 sexAI
                 bsaJI                                          cac8I                           bsmFI
               bsmFI   nlaIV   cac8I
3001 GAATGTGTGT CAGTTAGGGT GTGAAAGTC CCCAGGCTCC GAAGTATGCA AGCAGGCA CTCAATTAGT CAGCAACCAG GTGTGGAAAG
     CTTACACACA GTCAATCCCA CACCTTTCAG GGGTCCGAGG CTTCATACGT TCGTACGTA GAGTTAATCA GTCGTTGGTC CACACCTTTC nlaIV                    sfaNI
            scrFI                   ppuI0I
            mvaI                 nsII/avaIII
            ecoRII                 nlaIII                                       acII
            daeV                   sphI                                        bsmFI       acII    fokI    acII
            bstNI                  nspI                                                                
          apyI[dcm+]               nspHI
            bsaJI     cac8I        cac8I
3101 TCCCCAGGCT CCCAGCAGG CAGAAGTATG CAAAGCATGC ATCTCAATTA GTCAGCAACC ATAGTCCCGC CCCTAACTCC CCCTAACTC
     AGGGGTCCGA GGGTCGTCC GTCTTCATAC GTTTCGTACG TAGAGTTAAT CAGTCGTTGG TATCAGGGCG GGGATTGAGG GGGATTGAG fnu4HI
                                                                bsoFI
                                                                bglI
                                                                sfiI
              nlaIII                                         haeIII/palI
              styI                                mnlI          mnlI        ddeI
              ncoI                                haeIII/palI bsaJI  mnlI   aluI      mnlI
           balI  daeI                             mnlI bsaJI acII       haeIII/palI         bseRI
         bsrI acII acII
3201 CGGCCAGTTC CGCCCATTCT CCGCCCCATG GCTGACTAAT TTTTTTATT TATGCAGAGG GCTGACTAAT ATACGTCTCC GCTGACTAAT AGAAGTAGTG
     GCCGGTCAAG GCGGGTAAGA GGCGGGGTAC CGACTGATTA AAAAAATAA ATACGTCTCC GACTGATTA TATGCAGAGG CGACTATTG TCTTCATCAC
```

```
                                                                                    sau3AI
                                                                                    mboI/ndeII(dam-)
                                                                                    dpnI(dam+)
                                                              sau96I
                                                              haeIII/palI
                                                              asuI        dpnII(dam+)
                                                              mnlI acII   pvuI/bspCI
                                             cac8I            mboII cac8I mcrI                                        hinPI
                                             aluI             earI/ksp632I bslEI                                      thaI
                                             pvuII                                                                    fnuDII/mvnI
                                             nspBII                                                                   bstUI scfI
                          fnu4HI             cac8I                                                                    bshl236I
            tru9I         bsoFI                                                                                       rsaI hhaI/cfoI
     maeIII msnI          bbvI      fokI            ACATCCCCCC TTCGCCAGCT GGCGTAATAG CGAAGAGGCC CGCACCGATC GCCCTTCCCA  csp6I  bslI     ACAGTTGCGT
5001 TGGCGTTACC CAACTTAATC GCCTTGCAGC CGGAATTAG    ACATCCCCCC TTCGCCAGCT GGCGTAATAG CGAAGAGGCC CGCACCGATC GCCCTTCCCA ACAGTTGCGT
     ACCGCAATGG GTTGAATTAG CGGAACGTCG             TGTAGGGGGG AAGCGGTCGA CCGCATTATC GCTTCTCCGG GCGTGGCTAG CGGGAAGGGT TGTCAACGCA
           hinPI
           hhaI/cfoI
           nlaIV
           narI
           kasI                                                                                          hinPI
           hinII/acyI                                                                                    hhaI/cfoI
           hglCI                                                               acII    maeII             rmaI
           haeII     acII                                                                                hinPI haeII
           banI      sfaNI                        sfaNI   acII    acII         TACGTCAAAG CAACCATAGT ACGGGCCCTG
     bglI  ahaII/bsaHI                                                                                            hhaI/cfoI      barBI
5101 AGCCTGAATG GCGAATGGCG CCTGATGCGG TATTTCTCTC TTACGCATCT GTGCGGTATT TCACACCGCA TACGTCAAAG CAACCATAGT ACGGGCCCTG
     TCGGACTTAC CGCTTACCGC GGACTACGCC ATAAAGAGAG AATGCGTAGA CACGCCATAA AGTGTGGCGT ATGCAGTTTC GTTGGTATCA TGCGCGGGAC
                  acII
                  fnu4HI
                  bsoFI
                  thaI                      fnu4HI                                       hinPI
                  fnuDII/mvnI                bsoFI                                       hhaI/cfoI
           hinPI  bstUI                      hinPI                                       thaI          bfaI acII
     fnu4HI       hhaI/cfoI                  hhaI/cfoI                                   haeII maeI    cac8I
     bsoFI        tru9I acII                 thaI                                        cac8I                    mboII
     acII         msnI bshl236I              fnuDII/mvnI                                 maeIII bbvI maeIII
5201 TAGCGGGCGCA TTAAGCGCGG CGGGTGTGGT GGTTACGCCGG AGCGTGACCG CTACACTGCC CAGCGGCCCTA GGCGCCCGCTC CTTTCGCTTT CTTCCCTTCC
     ATCGCCCGCGT AATTCGCGCC GCCCACACCA CCAATGCGCC TCGCACTGGC GATGTGAACG GTCGCGGGAT CGCGGGCGAG GAAAGCGAAA GAAGGGAAGG

FIG. 48R
```

```
                                                                                          nlaIV
                                                                                          hg1CI   taqI
                                                                                          banI    mnlI
                       mspI                                            nlaIV
                       hpaII                                           hg1JII
                       naeI                                            bsp1286
                       cfr10I/bsrFI           aluI                     bmyI
             maeII                                                     banII                                                                    nlaIV
5301 TTTCTCGCCA CGTTCGCCGG CTTTCCCCGT CAAGCTCTAA ATCGGGGGCT CCCTTTAGGG TTCCGATTTA GTGCTTTACG GCACCTGAC CCCAAAAAC
     AAGAGCGGGT GCAAGCGGCC GAAAGGGGCA GTTCGAGATT TAGCCCCCGA GGGAAATCCC AAGGCTAAAT CACGAAATGC CGTGGAGCTG GGGTTTTTTG maeII     haeIII/palI                                     maeII  pleI           tru9I      pleI
                             draIII    sau96I                                          drdI   hinfI   maeII  mseI       hinfI
             hphI    bsaAI   asuI
5401 TTGATTTGGG TGATGGTTCA CGTAGTGGGC CATCGCCCTG ATAGACGGTT TTTCGCCCTT TGACGTTGGA GTCCACGTTC TTTAATAGTG GACTCTTGTT
     AACTAAACCC ACTACCAAGT GCATCACCCG GTAGCGGGAC TATCTGCCAA AAAGCGGGAA ACTGCAACCT CAGGTGCAAG AAATTATCAC CTGAGAACAA tru9I
                     bslI                                                                      mseI                              tru9I
             bsrI    bslI  avaI                                                haeIII/palI            aluI                       mseI
5501 CCAAACTGGA ACAACACTCA ACCTATCTC GGGCTATTCT TTTGATTTAT AAGGGATTTT GCCGATTTCG GCCTATTGGT TAAAAAATGA GCTGATTTAA
     GGTTTGACCT TGTTGTGAGT TGGATAGAG CCCGATAAGA AAACTAAATA TTCCCTAAAA CGGCTAAAGC CGGATAACCA ATTTTTTACT CGACTAAATT hg1AI/aspHI
                                                    bsp1286
                     thaI                           bsiHKAI
                     fnuDII/mvnI            maeII   bmyI    ddeI      rsaI                     acII
             tru9I   apoI  tru9I            psp1406I        apaLI/snoI                         fnu4HI             tru9I
             mseI    bstUI mseI             tru9I           alw44I/snoI csp6I                  bsoFI              mseI         acII
     apoI    bsh1236I                spI   mseI                                                       sfaNI                   fnu4HI
5601 CAAAATTTA ACGGAATTT TAACAAATA TTAACGTTA CAATTTTATG GTGCACTCTC AGTACAATCT GCTCTGATGC CGCATAGTTA AGCCAACTCC
     GTTTTTAAAT TGCCTTAAA ATTGTTTAT AATTGCAAAT GTTAAAATAC CACGTGAGAG TCATGTTAGA CGAGACTACG GCGTATCAAT TCGGTTGAGG hinPI
                                                       hhaI/cfoI                                                         sfaNI
                             hinPI                     thaI                                                              mspI
                             fnu4HI                    fnuDII/mvnI                                                       hpaII
                             bsoFI                     bstUI                                                             scrFI
             maeIII          nlaIII  hhaI/cfoI         nspBII  bsh1236I                                 drdI             ncII
             maeII  bsrI           nlaIII hhaI/cfoI    acII    hgaI       drdI                                           daeV   fokI    acII
     bsaAI  tth111I/aspI bbvI                         acII                                                               cauII          acII
5701 GCTATCGCTA CGTGACTGGG TCATGGCTGC GCCCCGACAC CCGGCCACAC CCGCTGACGC GCCCCGACGG GCTTGTCTGC TCCCGGCATC CGCTTACAGA
     CGATAGCGAT GCACTGACCC AGTACCGACG CGGGGCTGTG GGCGGTGTGT GGCGACTGCG CGGGGCTGCC CGAACAGACG AGGGCCGTAG GCGAATGTCT
```

FIG. 48S

```
                                                                              thaI
                                                                              fnuDII/mvnI
                                                                              bstUI
                                                                              bshl236I
                                                                              hinPI                                        mnlI
                                                                              hhaI/cfoI                                    haeIII/palI
               scrFI                                                          thaI mnlI                             mboII  sau96I
               ncII                                                           fnuDII/mvnI                           bpuAI  asuI bssSI
               mspI                            nspI                           bstUI                                 bbsI   eco0109I/draII
               hpaII                           nspHI                          bshl236I
               dsaV                       fnu4HI                  hphI        hphI
          esp3I                           bsoFI
          bsmBI                           bbvI
     maeIII bsmAI
     alul    bsII  cauII aluI nlaIII  mnlI
5801 CAAGCTGTGA CCGTCTCCGG GAGCTGCATG TGTCAGAGGT TTTCACCGTC ATCACCGAAA CGGCGGAGGC AGTATTCTTG AAGACGAAAG GGCCTCGTGA
     GTTCGACACT GGCAGAGGCC CTCGACGTAC ACAGTCTCCA AAAGTGGCAG TAGTGGCTTT GCGCGGCTCCG TCATAAGAAC TTCTGCTTTC CCGGAGCACT
                                                                                           nlaIV
                                                                                    acII
                                                                                    thaI
                                                                                    fnuDII/mvnI
                                                                                    bstUI
                                                                                    bshl236I
                                                          hinII/acyI                hinPI
                                                          ahaII/bsaHI               hhaI/cfoI
                                                          aatII
                                                          ddeI maeII
5901 TACGCCTATT TTTATAGGTT AATGTCATGA TAATAATGGT TTCTAGACG TCAGGTGGCA CTTTTCGGGG AAATGTGCGC GGAACCCCTA TTTGTTTATT
     ATGCGGATAA AAATATCCAA TTACAGTACT ATTATTACCA AAGATCTGC AGTCCACCGT GAAAAGCCCC TTTACACGCG CCTTGGGGAT AAACAAATAA
                                               rcaI
                                               bspHI
                                          bsrBI bsmAI
                                          acII  nlaIII
                   tru9I  nlaIII                                     mboII
                   msel   rcaI                                       earI/kspS32I                   mblI
                          bspHI                           sspI       mboII                          mblI
6001 TTTCTAAATA CATTCAAATA TGTATCCGCT CATGAGACAA TAACCCTGAT AAATGCTTCA ATATATTGA AAAAGGAAGA GTATGAGTAT TCAACATTTC
     AAAGATTTAT GTAAGTTTAT ACATAGGCGA GTACTCTGTT ATTGGGACTA TTTACGAAGT TATATAACT TTTTCCTTCT CATACTCATA AGTTGTAAAG
                                                                                                        hg1AI/aspHI
                                                                                                        bsp1286
                                                                                                        bslHKAI
                                                                                            sau3AI
                                                                                            mboI/ndeII[dam-]
                                                                                            dpnI[dam+] bmyI
                                                                                            dpnII[dam-]
           fnu4HI                                                                                apaLI/snoI
           bsoFI                                                         eco57I                  alw44I/snoI
           acII                                          hphI            sfaNI mboII[dam-]
6101 CGTGTCGCCC TTATTCCCTT TTTTGCGGCA TTTGCCTTC CTGTTTTGC CTGTTTTGC ACGCTGGTGA AGTAAAAGA TGCTGAAGAT CAGTTGGGTG
     GCACAGCGGG AATAAGGGAA AAAACGCCGT AAACGGAAG GACAAAACG AGTGGCTT TGCGACCACT TCATTTTCT ACGACTTCTA GTCAACCCAC
```

```
                                                                                                              sau3AI
                    sau3AI                                                                                    mboI/ndeII(dam-)
                    mboI/ndeII(dam-)                                                                          dpnI(dam+)
      mboII(dam-)   dpnI(dam+)                                                                                dpnII(dam-)
      mboI/ndeII(dam-) dpnII(dam-)                                                                            alwI(dam-)
      dpnI(dam+)    alwI(dam-)                                                                       mspI
      dpnII(dam-)   bstYI/xhoII                                                       acII         hpaII     aluI
      bstYI/xhoII   alwI(dam-)                           tha I                        nspBII   ACCAGCGGTG GTTTGTTTGC CGGATCAAGA
      alwI(dam-)                                         fnuDII/mvnI                                TGGTCGCCAC CAAACAAACG GCCTAGTCT
7101 TCAAAGGATC TTCTTGAGAT CTTTTTTTC TGCGCGTAAT CTGCCGCTG CAAACAAAAA AACCACCGCT ACCAGCGGTG GTTTGTTTGC CGGATCAAGA
     AGTTCCTAG AAGAACTCTA GAAAAAAAAG ACGCGCATTA GACGGCGAAC GTTTGTTTTT TTGGTGGCGA TGGTCGCCAC CAAACAAACG GCCTAGTCT rmaI
                                                                          maeI                 haeIII/palI
                                           hinPI                          bfaI                 haeI
                          bsrI             hhaI/cfoI                                   bslI
                          maeIII   eco57I                                                               scrFI
                                                                                                        ncII
                                                                                                        mspI
                                                                                                        hpaII
                                                                                                        dsaV    pleI
                                                                                                        cauII   hinfI
7201 GCTACCAACT CTTTTTCCGA AGGTAACTGG CCTTCAGCAGA GCGCAGATAC CAAATACTGT CCTTCTAGTG TAGCCGTAGT TAGGCCACCA CTTCAAGAAC
     CGATGGTTGA GAAAAAGGCT TCCATTGACC GAAGTCGTCT CGCGTCTATG GTTTATGACA GGAAGATCAC ATCGGCATCA ATCCGGTGGT GAAGTTCTTG fnu4HI
                                           bsoFI
                                           bbvI
                                      fnu4HI
                                      bsoFI
                              alwNI(dcm-)
                              bsrI bbvI  bsrI
             acII
             nspBII
             fnu4HI              mnlI    maeIII
     scfI    bsoFI
7301 TCTGTAGCAC CGCCTACATA CCTCGCTCTG CTAATCCTGT TACCAGTGGC TGCTGCCAGT GGCGATAAGT CGTGTCTTAC CGGGTTGGAC TCAAGACGAT
     AGACATCGTG GCGGATGTAT GGAGCGAGAC GATTAGGACA ATGGTCACCG ACGACGGTCA CCGCTATTCA GCACAGAATG GCCCAACCTG AGTTCTGCTA hglAI/aspHI
                    bsp1286
                    bsIHKAI
     mspI           bmyI
     hpaII          apaLI/snoI
     bsaWI          alw44I/snoI    aluI                                                           ddeI    scfI
     maeIII  hhaI/cfoI
7401 AGTTACCGGA TAAGGCGCAG CGGTCGGGCT GAACGGGGGG TTCGTGCACA CAGCCCAGCT TGGAGCGAAC GACCTACACC GAACTGAGAT ACCTACAGCG
     TCAATGGCCT ATTCCGCGTC GCCAGCCCGA CTTGCCCCCC AAGCACGTGT GTCGGGTCGA ACCTCGCTTG CTGGATGTGG CTTGACTCTA TGGATGTCGC
```

FIG. 48W

```
                                                                                                                                        scrFI
                                                                                                                                        mvaI
                                                                                                                                        ecoRII
                                                                                                                                        dsaV
                                                                                                                                        bstNI
                                                                                                              bssSI                     bsaJI
                                                                                                              hinPI mnlI
                                          hinPI                                                               hhaI/cfoI aluI apyI[dcm+]
                                          hhaI/cfoI                                                           
                                          haeII                                          mspI
                                                                                          hpaII fnu4HI
                                                                                          bslI  bsoFI
                                                                              acII        bsaWI acII
       7501 TGAGCATTGA GAAAGCGCCA CGCTTCCCGA AGGGAGAAAG GCGGACAGGT ATCCGGTAAG CGGCAGGGTC GGAACAGGAG AGCGCACGAG GGAGCTTCCA
            ACTCGTAACT CTTTCGCGGT GCGAAGGGCT TCCCTCTTTC CGCCTGTCCA TAGGCCATTC GCCGTCCCAG CCTTGTCCTC TCGCGTGCTC CCTCGAAGGT nlaIV
                         scrFI                                                                     acII
                         mvaI
                         ecoRII
                         dsaV
                         bstNI                                                      taqI
                         apyI[dcm+]                               mnlI drdI         hgaI      sfaNI
       7601 GGGGAAACG CCTGGTATCT TTATAGTCCT GTCGGGTTTC GCCACCTCTG ACTTGAGCGT CGATTTTTGT GATGCTCGTC AGGGGGGCGG AGCCTATGGA
            CCCCCTTTGC GGACCATAGA AATATCAGGA CAGCCCAAAG CGGTGGAGAC TGAACTCGCA GCTAAAACA CTACGAGCAG TCCCCCCGCC TCGGATACCT haeIII/palI    haeIII/palI
                         fnu4HI         scrFI
                         bsoFI          mvaI bslI
                         bbvI           ecoRII
                         acII           dsaV                                                                  tfiI
                         thaI bslI      bstNI                  haeIII/palI                                    hinfI
                         fnuDII/mvnI    apyI[dcm+]             haeI                                  nspHI
                         bstUI          nlaIV  haeI            cac8I                                 aflIII
                  cac8I bsh1236I
       7701 AAAACGCCAG CAACGCGGCC TTTTTACGGT TCCTGGCCTT TTGCTGGCCT TTGCTCACA TGTTCTTTCC CCTGATTCTG TGGATAACCG
            TTTTGCGGTC GTTGCGCCGG AAAAATGCCA AGGACCGGAA AACGACCGGA AACGAGTGT ACAAGAAAGG GGACTAAGAC ACCTATTGGC fnu4HI                                              sapI hinPI
                                    bsoFI                                 fnu4HI        mboII hhaI/cfoI
                                    bbvI                                  bsoFI         earI/ksp632I
                         cac8I acII                                       bbvI pleI
                         barBI fnu4HI               mcrI         hinPI hinfI            mnlI acII       haeII
                acII     acII  bsoFI                bslEI        hhaI/cfoI
       7801 TATTACCGCC TTTGAGTGAG CTGATACCGC TCGCCGCAGC CGAACGACCG AGCGCAGCGA GTCAGTGAGC GAGGAAGCGG AAGAGCGCCC AATACGCAAA
            ATAATGGCGG AAACTCACTC GACTATGGCG AGCGGCGTCG GCTTGCTGGC TCGCGTCGCT CAGTCACTCG CTCCTTCGCC TTCTCGCGGG TTATGCGTTT
```

FIG. 48X

```
                                                   thaI
                                                   fnuDII/mvnI                                                              tru9I
                                                   bstUI                                                                    mseI          maeIII
                                                   bsh1236I                                     cac8I               hinPI   aseI/asnI/vspI
                                                   hinPI                                        aclI                hhaI/cfoI
                                                   hhaI/cfoI                             bsrI                                                   
                    thaI                                 cac8I
                    fnuDII/mvnI                          aluI
                    bstUI  haeIII/palI                                       
                    bsh1236I    tru9I  pvuII
       mnlI  bslI  eaeI  tfII aseI/asnI/vspI
       aclI  aclI  cfrI hinfI mseI nspBII
7901 CCGCGCTCTCC CCGCGCGGTTG GCCGATTCAT TAATCCAGCT GGCACGACAG GTTTCCCGAC TGGAAAGCGG GCAGTGAGCG CAACGCAATT AATGTGAGTT
     GGCGCGAGAGG GGCGCGCCAAC CGGCTAAGTA ATTAGGTCGA CCGTGCTGTC CAAAGGGCTG ACCTTTCGCC CGTCACTCGC GTTGCGTTAA TTACACTCAA scrFI
           mvaI
           ecoRII
           deaV                                              mspI             aclI
           nlaIV bstNI                                       hpaII            bsrBI                         aluI
           hgiCI apyI[dcm+]
     mnlI  banI bsaJI
8001 ACCTCACTCA TTAGGCACCC CAGGCTTTAC ACTTTATGCT TCCGGCTCGT ATGTTGTGTG GAATTGTGAG CGGATAACAA TTTCACACAG GAAACAGCTA
     TGGAGTGAGT AATCCGTGGG GTCCGAAATG TGAAATACGA AGGCCGAGCA TACAACACAC CTTAACACTC GCCTATTGTT AAAGTGTGTC CTTTGTCGAT
```

FIG. 48Y

Representative Conc versus Time Plot. Shown is the kinetic data for 6G4V11N35A.IgG1

| SAMPLE | ka | kd | Kd |
|---|---|---|---|
| Murine 6G4.2.5 IgG2a | $8.3 \times 10^5$ | $2.9 \times 10^{-4}$ | 350pM |
| 6G4V11N35A-IgG1 | $8.7 \times 10^5$ | $7.7 \times 10^{-5}$ | 88pM |
| 6G4V11N35E-IgG1 | $3.0 \times 10^6$ | $1.4 \times 10^{-4}$ | 49pM |

```
 781 AAAAGGGTAT CTAGAGGTTG AGGTGATTTT ATGAAAAAGA ATATCGCATT TCTTCTTGCA
     TTTTCCCATA GATCTCCAAC TCCACTAAAA TACTTTTTCT TATAGCGTAA AGAAGAACGT
  -1                                           M  K  K  N   I  A  F   L  L  A

841 TCTATGTTCG TTTTTTCTAT TGCTACAAAC GCGTACGCTG AGGTTCAGCT AGTGCAGTCT
     AGATACAAGC AAAAAAGATA ACGATGTTTG CGCATGCGAC TCCAAGTCGA TCACGTCAGA
 -11 S  M  F   V  F  S  I   A  T  N   A  Y  A  E   V  Q  L   V  Q  S

901 GGCGGTGGCC TGGTGCAGCC AGGGGGCTCA CTCCGTTTGT CCTGTGCAGC TTCTGGCTAC
     CCGCCACCGG ACCACGTCGG TCCCCCGAGT GAGGCAAACA GGACACGTCG AAGACCGATG
   8 G  G  G   L  V  Q  P   G  G  S   L  R  L   S  C  A  A   S  G  Y

961 TCCTTCTCGA GTCACTATAT GCACTGGGTC CGTCAGGCCC CGGGTAAGGG CCTGGAATGG
     AGGAAGAGCT CAGTGATATA CGTGACCCAG GCAGTCCGGG GCCCATTCCC GGACCTTACC
  28 S  F  S   S  H  Y  M   H  W  V   R  Q  A  P   G  K  G   L  E  W

1021 GTTGGATATA TTGATCCTTC CAATGGTGAA ACTACGTATA ATCAAAAGTT CAAGGGCCGT
     CAACCTATAT AACTAGGAAG GTTACCACTT TGATGCATAT TAGTTTTCAA GTTCCCGGCA
  48 V  G  Y   I  D  P  S   N  G  E   T  T  Y   N  Q  K  F   K  G  R

1081 TTCACTTTAT CTCGCGACAA CTCCAAAAAC ACAGCATACC TGCAGATGAA CAGCCTGCGT
     AAGTGAAATA GAGCGCTGTT GAGGTTTTTG TGTCGTATGG ACGTCTACTT GTCGGACGCA
  68 F  T  L   S  R  D  N   S  K  N   T  A  Y  L   Q  M  N   S  L  R

1141 GCTGAGGACA CTGCCGTCTA TTACTGTGCA AGAGGGGATT ATCGCTACAA TGGTGACTGG
     CGACTCCTGT GACGGCAGAT AATGACACGT TCTCCCCTAA TAGCGATGTT ACCACTGACC
  88 A  E  D   T  A  V  Y   Y  C  A   R  G  D  Y   R  Y  N   G  D  W

1201 TTCTTCGACG TCTGGGGTCA AGGAACCCTG GTCACCGTCT CCTCGGCCTC CACCAAGGGC
     AAGAAGCTGC AGACCCCAGT TCCTTGGGAC CAGTGGCAGA GGAGCCGGAG GTGGTTCCCG
 108 F  F  D   V  W  G  Q   G  T  L   V  T  V  S   S  A  S   T  K  G

1261 CCATCGGTCT TCCCCCTGGC ACCCTCCTCC AAGAGCACCT CTGGGGGCAC AGCGGCCCTG
     GGTAGCCAGA AGGGGGACCG TGGGAGGAGG TTCTCGTGGA GACCCCCGTG TCGCCGGGAC
 128 P  S  V   F  P  L  A   P  S  S   K  S  T   S  G  G  T   A  A  L

1321 GGCTGCCTGG TCAAGGACTA CTTCCCCGAA CCGGTGACGG TGTCGTGGAA CTCAGGCGCC
     CCGACGGACC AGTTCCTGAT GAAGGGGCTT GGCCACTGCC ACAGCACCTT GAGTCCGCGG
 148 G  C  L   V  K  D  Y   F  P  E   P  V  T  V   S  W  N   S  G  A

1381 CTGACCAGCG GCGTGCACAC CTTCCCGGCT GTCCTACAGT CCTCAGGACT CTACTCCCTC
     GACTGGTCGC CGCACGTGTG GAAGGGCCGA CAGGATGTCA GGAGTCCTGA GATGAGGGAG
 168 L  T  S   G  V  H  T   F  P  A   V  L  Q  S   S  G  L   Y  S  L

1441 AGCAGCGTGG TGACCGTGCC CTCCAGCAGC TTGGGCACCC AGACCTACAT CTGCAACGTG
     TCGTCGCACC ACTGGCACGG GAGGTCGTCG AACCCGTGGG TCTGGATGTA GACGTTGCAC
 188 S  S  V   V  T  V  P   S  S  S   L  G  T  Q   T  Y  I   C  N  V

1501 AATCACAAGC CCAGCAACAC CAAGGTCGAC AAGAAAGTTG AGCCCAAATC TTGTGACAAA
     TTAGTGTTCG GGTCGTTGTG GTTCCAGCTG TTCTTTCAAC TCGGGTTTAG AACACTGTTT
 208 N  H  K   P  S  N  T   K  V  D   K  K  V  E   P  K  S   C  D  K

1561 ACTCACACAT GCCCGCCGTGA
     TGAGTGTGTA CGGGCGGCACT
 228 T  H  T   C  P  P  Q
```

FIG. 53

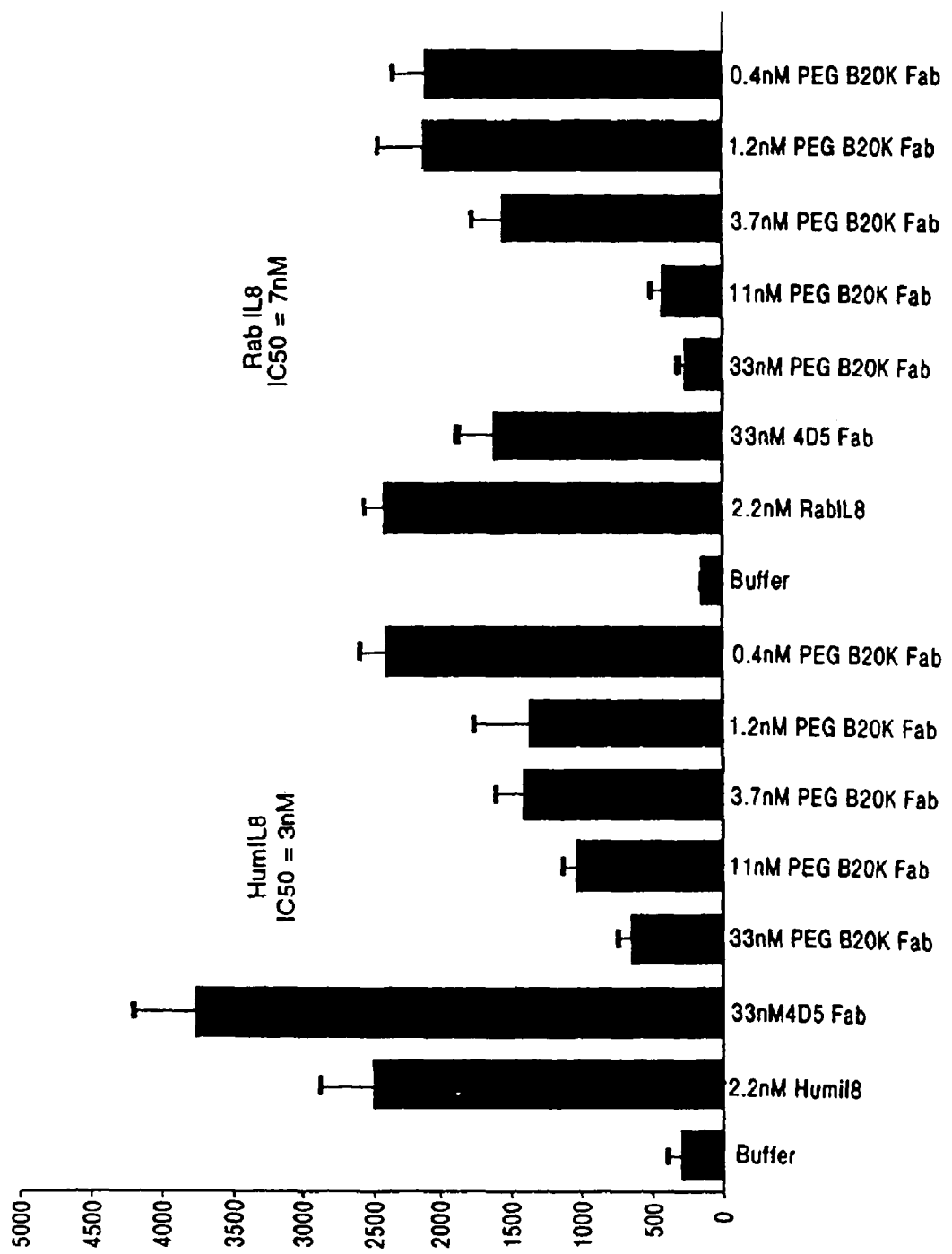

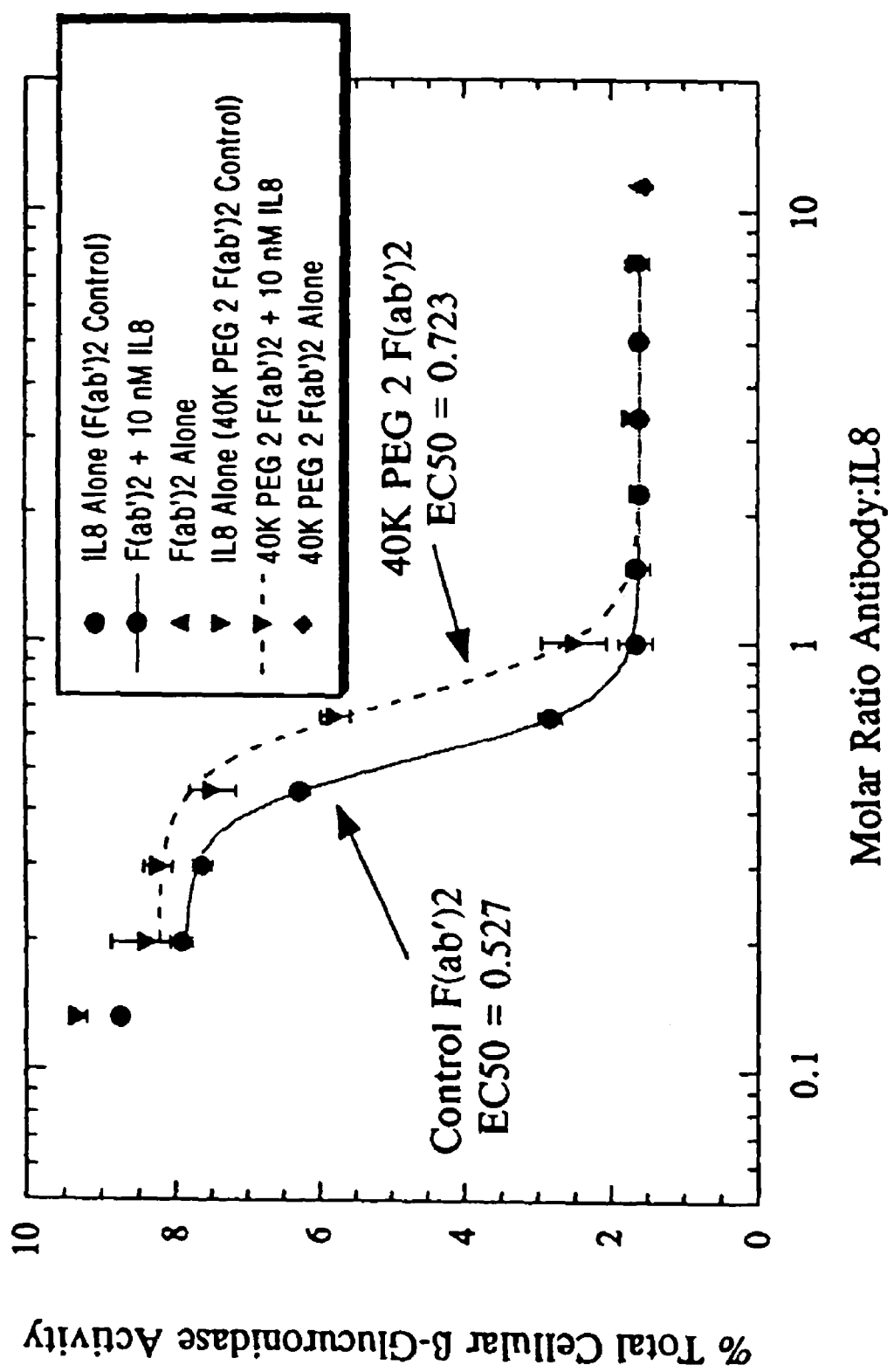

Figure 72: 20K and 40K PEG rhuMAb VEGF Fab (approximately 3 mg/kg Serum concentrations following IV administration Figure 73: 20K and 40K PEG rhuMAb VEGF Fab (approximately 3 mg/kg Serum concentrations following IP administration

ANTIBODY FRAGMENT-POLYMER CONJUGATES AND USES OF SAME

This application is a continuation of U.S. patent application Ser. No. 11/541,145, filed Sep. 28, 2006, now U.S. Pat. No. 7,507,405, which is a continuation of U.S. patent application Ser. No. 11/259,232, filed Oct. 25, 2005, now U.S. Pat. No. 7,214,776, which is a continuation of U.S. patent application Ser. No. 09/489,394, filed Jan. 21, 2000, now U.S. Pat. No. 7,122,636, which is a non-provisional application filed under 37 CFR 1.53(b)(1), claiming priority under 35 USC 119(e) to provisional application No. 60/116,787, filed Jan. 21, 1999, the contents of which non-provisional and provisional applications are hereby incorporated herein by reference in their entireties.

FIELD OF THE INVENTION

This application relates to the field of antibody fragments derivatized with polymers, and in particular to the use of such derivatization to increase the circulation half-lives of antibody fragment-polymer conjugates. This application also relates to the use of such antibody fragment-polymer conjugates in the treatment of diseases.

BACKGROUND

Modification of proteins with polyethylene glycol ("PEGylation") has the potential to increase residence time and reduce immunogenicity in vivo. For example, Knauf et al., *J. Biol. Chem.*, 263: 15064-15070 (1988) reported a study of the pharmacodynamic behavior in rats of various polyoxylated glycerol and polyethylene glycol modified species of interleukin-2. Despite the known advantage of PEGylation, PEGylated proteins have not been widely exploited for clinical applications. In the case of antibody fragments, PEGylation has not been shown to extend serum half-life to useful levels. Delgado et al., *Br. J. Cancer,* 73: 175-182 (1996), Kitamura et al., *Cancer Res.,* 51: 4310-4315 (1991), Kitamura et al., *Biochem. Biophys. Res. Comm.,* 171: 1387-1394 (1990), and Pedley et al., *Br. J. Cancer,* 70: 1126-1130 (1994) reported studies characterizing blood clearance and tissue uptake of certain anti-tumor antigen antibodies or antibody fragments derivatized with low molecular weight (5 kD) PEG. Zapata et al., *FASEB J.,* 9: A1479 (1995) reported that low molecular weight (5 or 10 kD) PEG attached to a sulfhydryl group in the hinge region of a Fab' fragment reduced clearance compared to the parental Fab' molecule.

It is now well established that angiogenesis is implicated in the pathogenesis of a variety of disorders. These include solid tumors, intraocular neovascular syndromes such as proliferative retinopathies or age-related macular degeneration (AMD), rheumatoid arthritis, and psoriasis (Folkman et al. *J. Biol. Chem.* 267:10931-10934 (1992); Klagsbrun et al. *Annu. Rev. Physiol.* 53:217-239 (1991); and Garner A, *Vascular diseases. In: Pathobiology of ocular disease. A dynamic approach.* Garner A, Klintworth G K, Eds. 2nd Edition Marcel Dekker, NY, pp 1625-1710 (1994)). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner et al. *N Engl J Med* 324:1-6 (1991); Horak et al. *Lancet* 340:1120-1124 (1992); and Macchiarini et al. *Lancet* 340:145-146 (1992)).

Work done over the last several years has established the key role of vascular endothelial growth factor (VEGF) in the regulation of normal and abnormal angiogenesis (Ferrara et al. *Endocr. Rev.* 18:4-25 (1997)). The finding that the loss of even a single VEGF allele results in embryonic lethality points to an irreplaceable role played by this factor in the development and differentiation of the vascular system (Ferrara et al.). Furthermore, VEGF has been shown to be a key mediator of neovascularization associated with tumors and intraocular disorders (Ferrara et al.). The VEGF mRNA is overexpressed by the majority of human tumors examined (Berkman et al. *J Clin Invest* 91:153-159 (1993); Brown et al. *Human Pathol.* 26:86-91 (1995); Brown et al. *Cancer Res.* 53:4727-4735 (1993); Mattern et al. *Brit. J. Cancer.* 73:931-934 (1996); and Dvorak et al. *Am J. Pathol.* 146:1029-1039 (1995)). Also, the concentration of VEGF in eye fluids are highly correlated to the presence of active proliferation of blood vessels in patients with diabetic and other ischemia-related retinopathies (Aiello et al. *N. Engl. J. Med.* 331:1480-1487 (1994)). Furthermore, recent studies have demonstrated the localization of VEGF in choroidal neovascular membranes in patients affected by AMD (Lopez et al. *Invest. Ophialmo. Vis. Sci.* 37:855-868 (1996)). Anti-VEGF neutralizing antibodies suppress the growth of a variety of human tumor cell lines in nude mice (Kim et al. *Nature* 362:841-844 (1993); Warren et al. *J. Clin. Invest.* 95:1789-1797 (1995); Borgström et al. *Cancer Res.* 56:4032-4039 (1996); and Melnyk et al. *Cancer Res.* 56:921-924 (1996)) and also inhibit intraocular angiogenesis in models of ischemic retinal disorders (Adamis et al. *Arch. Ophthalmol.* 114:66-71 (1996)). Therefore, anti-VEGF monoclonal antibodies or other inhibitors of VEGF action are promising candidates for the treatment of solid tumors and various intraocular neovascular disorders.

Proto-oncogenes that encode growth factors and growth factor receptors have been identified to play important roles in the pathogenesis of various human malignancies, including breast cancer. It has been found that the human erbB2 gene (also known as HER2, or c-erbB-2), which encodes a 185-kd transmembrane glycoprotein receptor (p185$^{HER2}$) related to the epidermal growth factor receptor (EGFR), is overexpressed in about 25% to 30% of human breast cancer (Slamon et al., *Science* 235:177-182 [1987]; Slamon et al., *Science* 244:707-712 [1989]).

Several lines of evidence support a direct role for ErbB2 in the pathogenesis and clinical aggressiveness of ErbB2-overexpressing tumors. The introduction of ErbB2 into non-neoplastic cells has been shown to cause their malignant transformation (Hudziak et al., *Proc. Natl. Acad. Sci. USA* 84:7159-7163 [1987]; DiFiore et al., *Science* 237:78-182 [1987]). Transgenic mice that express HER2 were found to develop mammary tumors (Guy et al., *Proc. Natl. Acad. Sci. USA* 89:10578-10582 [1992]).

Antibodies directed against human erbB2 protein products and proteins encoded by the rat equivalent of the erbB2 gene (neu) have been described. Drebin et al., *Cell* 41:695-706 (1985) refer to an IgG2a monoclonal antibody which is directed against the rat neu gene product. This antibody called 7.16.4 causes down-modulation of cell surface p185 expression on B104-1-1 cells (NIH-3T3 cells transfected with the neu protooncogene) and inhibits colony formation of these cells. In Drebin et al. *PNAS (USA)* 83:9129-9133 (1986), the 7.16.4 antibody was shown to inhibit the tumorigenic growth of neu-transformed NIH-3T3 cells as well as rat neuroblastoma cells (from which the neu oncogene was initially isolated) implanted into nude mice. Drebin et al. in *Oncogene* 2:387-394 (1988) discuss the production of a panel of antibodies against the rat neu gene product. All of the antibodies were found to exert a cytostatic effect on the growth of neu-transformed cells suspended in soft agar. Antibodies of the IgM, IgG2a and IgG2b isotypes were able to mediate significant in vitro lysis of neu-transformed cells in the presence of complement, whereas none of the antibodies were able to mediate high levels of antibody-dependent cellular cytotoxicity (ADCC) of the neu-transformed cells. Drebin et al. *Oncogene* 2:273-277 (1988) report that mixtures of antibodies reactive with two distinct regions on the p185 molecule result in synergistic anti-tumor effects on neu-transformed NIH-3T3 cells implanted into nude mice. Biological effects of anti-neu antibodies are reviewed in Myers et al., *Meth. Enzym.* 198:277-290 (1991). See also WO94/22478 published Oct. 13, 1994.

Hudziak et al., *Mol. Cell. Biol.* 9(3):1165-1172 (1989) describe the generation of a panel of anti-ErbB2 antibodies which were characterized using the human breast tumor cell line SKBR3. Relative cell proliferation of the SKBR3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel, including 7C2 and 7F3, reduced cellular proliferation to a lesser extent in this assay. Hudziak et al. conclude that the effect of the 4D5 antibody on SKBR3 cells was cytostatic rather than cytotoxic, since SKBR3 cells resumed growth at a nearly normal rate following removal of the antibody from the medium. The antibody 4D5 was further found to sensitize p185erbB2-overexpressing breast tumor cell lines to the cytotoxic effects of TNF-α. See also WO89/06692 published Jul. 27, 1989. The anti-ErbB2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); and D'souza et al. *Proc. Natl. Acad. Sci.* 91:7202-7206 (1994).

Tagliabue et al. *Int. J. Cancer* 47:933-937 (1991) describe two antibodies which were selected for their reactivity on the lung adenocarcinoma cell line (Calu-3) which overexpresses ErbB2. One of the antibodies, called MGR3, was found to internalize, induce phosphorylation of ErbB2, and inhibit tumor cell growth in vitro.

McKenzie et al. *Oncogene* 4:543-548 (1989) generated a panel of anti-ErbB2 antibodies with varying epitope specificities, including the antibody designated TA1. This TA1 antibody was found to induce accelerated endocytosis of ErbB2 (see Maier et al. *Cancer Res.* 51:5361-5369 (1991)). Bacus et al. *Molecular Carcinogenesis* 3:350-362 (1990) reported that the TA1 antibody induced maturation of the breast cancer cell lines AU-565 (which overexpresses the erbB2 gene) and MCF-7 (which does not). Inhibition of growth and acquisition of a mature phenotype in these cells was found to be associated with reduced levels of ErbB2 receptor at the cell surface and transient increased levels in the cytoplasm.

Stancovski et al. *PNAS (USA)* 88:8691-8695 (1991) generated a panel of anti-ErbB2 antibodies, injected them i.p. into nude mice and evaluated their effect on tumor growth of murine fibroblasts transformed by overexpression of the erbB2 gene. Various levels of tumor inhibition were detected for four of the antibodies, but one of the antibodies (N28) consistently stimulated tumor growth. Monoclonal antibody N28 induced significant phosphorylation of the ErbB2 receptor, whereas the other four antibodies generally displayed low or no phosphorylation-inducing activity. The effect of the anti-ErbB2 antibodies on proliferation of SKBR3 cells was also assessed. In this SKBR3 cell proliferation assay, two of the antibodies (N12 and N29) caused a reduction in cell proliferation relative to control. The ability of the various antibodies to induce cell lysis in vitro via complement-dependent cytotoxicity (CDC) and antibody-mediated cell-dependent cytotoxicity (ADCC) was assessed, with the authors of this paper concluding that the inhibitory function of the antibodies was not attributed significantly to CDC or ADCC.

Bacus et al. *Cancer Research* 52:2580-2589 (1992) further characterized the antibodies described in Bacus et al. (1990) and Stancovski et al. of the preceding paragraphs. Extending the i.p. studies of Stancovski et al., the effect of the antibodies after i.v. injection into nude mice harboring mouse fibroblasts overexpressing human ErbB2 was assessed. As observed in their earlier work, N28 accelerated tumor growth whereas N12 and N29 significantly inhibited growth of the ErbB2-expressing cells. Partial tumor inhibition was also observed with the N24 antibody. Bacus et al. also tested the ability of the antibodies to promote a mature phenotype in the human breast cancer cell lines AU-565 and MDA-MB453 (which overexpress ErbB2) as well as MCF-7 (containing low levels of the receptor). Bacus et al. saw a correlation between tumor inhibition in vivo and cellular differentiation; the tumor-stimulatory antibody N28 had no effect on differentiation, and the tumor inhibitory action of the N12, N29 and N24 antibodies correlated with the extent of differentiation they induced.

Xu et al. *Int. J. Cancer* 53:401-408 (1993) evaluated a panel of anti-ErbB2 antibodies for their epitope binding specificities, as well as their ability to inhibit anchorage-independent and anchorage-dependent growth of SKBR3 cells (by individual antibodies and in combinations), modulate cell-surface ErbB2, and inhibit ligand stimulated anchorage-independent growth. See also WO94/00136 published Jan. 6, 1994 and Kasprzyk et al. *Cancer Research* 52:2771-2776 (1992) concerning anti-ErbB2 antibody combinations. Other anti-ErbB2 antibodies are discussed in Hancock et al. *Cancer Res.* 51:4575-4580 (1991); Shawver et al. *Cancer Res.* 54:1367-1373 (1994); Arteaga et al. *Cancer Res.* 54:3758-3765 (1994); and Harwerth et al. *J. Biol. Chem.* 267:15160-15167 (1992).

A recombinant humanized anti-ErbB2 monoclonal antibody (a humanized version of the murine anti-ErbB2 antibody 4D5, referred to as rhuMAb HER2 or HERCEPTIN®) has been clinically active in patients with ErbB2-overexpressing metastatic breast cancers that had received extensive prior anticancer therapy. (Baselga et al., *J. Clin. Oncol.* 14:737-744 [1996]).

ErbB2 overexpression is commonly regarded as a predictor of a poor prognosis, especially in patients with primary disease that involves axillary lymph nodes (Slamon et al., [1987] and [1989], supra; Ravdin and Chamness, *Gene* 159:19-27 [1995]; and Flynes and Stern, *Biochim Biophys Acta* 1198: 165-184 [1994]), and has been linked to sensitivity and/or resistance to hormone therapy and chemotherapeutic regimens, including CMF (cyclophosphamide, methotrexate, and fluorouracil) and anthracyclines (Baselga et al., *Oncology* 11(3 Suppl 1):43-48 [1997]). However, despite the association of ErbB2 overexpression with poor prognosis, the odds of HER2-positive patients responding clinically to treatment with taxanes were greater than three times those of HER2-negative patients (Ibid). rhuMab HER2 was shown to enhance the activity of paclitaxel (TAXOL®) and doxorubicin against breast cancer xenografts in nude mice injected with BT-474 human breast adenocarcinoma cells, which express high levels of HER2 (Baselga et al., *Breast Cancer, Proceedings of ASCO*, Vol. 13, Abstract 53 [1994]).

Lymphocyte adherence to endothelium is a key event in the process of inflammation. There are at least three known pathways of lymphocyte adherence to endothelium, depending on the activation state of the T cell and the endothelial cell. T cell immune recognition requires the contribution of the T cell receptor as well as adhesion receptors, which promote attachment of T cells to antigen-presenting cells and transduce regulatory signals for T cell activation. The lymphocyte function associated (LFA) antigen-1 (LFA-1, CD11a, α-chain/CD18, β-chain) has been identified as the major integrin receptor on lymphocytes involved in these cell adherence interactions leading to several pathological states. ICAM-1, the endothelial cell immunoglobulin-like adhesion molecule, is a known ligand for LFA-1 and is implicated directly in graft rejection, psoriasis, and arthritis.

LFA-1 is required for a range of leukocyte functions, including lymphokine production of helper T cells in response to antigen-presenting cells, killer T cell-mediated target cell lysis, and immunoglobulin production through T cell-B cell interactions. Activation of antigen receptors on T cells and B cells allows LFA-1 to bind its ligand with higher affinity.

Monoclonal antibodies (MAbs) directed against LFA-1 led to the initial identification and investigation of the function of LFA-1. Davignon et al., *J. Immunol.*, 127: 590 (1981). LFA-1 is present only on leukocytes [Krenskey et al., *J. Immunol.*, 131: 611 (1983)], and ICAM-1 is distributed on activated leukocytes, dermal fibroblasts, and endothelium. Dustin et al., *J. Immunol.*, 137: 245 (1986).

Previous studies have investigated the effects of anti-CD11a MAbs on many T-cell-dependent immune functions in vitro and a limited number of immune responses in vivo. In vitro, anti-CD11a MAbs inhibit B-cell activation [Kuypers et al., *Res. Immunol.*, 140: 461 (1989)], T-cell-dependent B-cell proliferation and differentiation [Davignon et al., supra; Fischer et al., *J. Immunol.*, 136: 3198 (1986)], target cell lysis by cytotoxic T lymphocytes [Krensky et al., supra], formation of immune conjugates (Sanders et al., *J. Immunol.*, 137: 2395 (1986); Mentzer et al., *J. Immunol.*, 135: 9 (1985)), and the adhesion of T-cells to vascular endothelium. Lo et al., *J. Immunol.*, 143: 3325 (1989). Also, the antibody 5C6 directed against CD11b/CD18 was found to prevent intra-islet infiltration by both macrophages and T cells and to inhibit development of insulin-dependent diabetes mellitus in mice. Hutchings et al., *Nature*, 348: 639 (1990).

IgE is a member of the immunoglobulin family that mediates allergic responses such as asthma, food allergies, and other type I hypersensitivity reactions. IgE is secreted by and expressed on the surface of B-cells or B-lymphocytes. IgE binds to B-cells (as well as monocytes, eosinophils and platelets) through its Fc region to a low affinity IgE receptor ($Fc_\epsilon RII$). Upon exposure of a mammal to an allergen, B-cells bearing a membrane-bound IgE antibody specific for the antigen are activated to form IgE-secreting plasma cells. The allergen-specific, soluble IgE secreted by plasma cells circulates through the bloodstream and binds to the surface of mast cells in tissues and basophils in the blood, through the high affinity IgE receptor ($Fc_\epsilon RI$). The mast cells and basophils thereby become sensitized for the allergen. Subsequent exposure to the allergen results in cross linking of allergen-specific IgE bound to basophilic and mast cellular $Fc_\epsilon RI$, which induces a release of histamine, leukotrienes and platelet activating factors, eosinophil and neutrophil chemotactic factors and the cytokines IL-3, IL-4, IL-5 and GM-CSF, which are responsible for clinical hypersensitivity and anaphylaxis.

The pathological condition hypersensitivity is characterized by an excessive immune response to (an) allergen(s) resulting in gross tissue changes if the allergen is present in relatively large amounts or if the humoral and cellular immune state is at a heightened level.

Physiological changes in anaphylactic hypersensitivity can include intense constriction of the bronchioles and bronchi of the lungs, contraction of smooth muscle and dilation of capillaries. Predisposition to this condition appears to result from an interaction between genetic and environmental factors. Common environmental allergens which induce anaphylactic hypersensitivity are found in pollen, foods, house dust mites, animal danders, fungal spores and insect venoms. Atopic allergy is associated with anaphylactic hypersensitivity and includes disorders such as asthma, allergic rhinitis and conjunctivitis (hay fever), eczema, urticaria and food allergies. Anaphylactic shock, a dangerous life-threatening condition that can occur in the progression of anaphylaxis, is usually provoked by insect stings or parenteral medication.

Recently, a treatment strategy has been pursued for Type 1 hypersensitivity or anaphylactic hypersensitivity which blocks IgE from binding to the high-affinity receptor ($Fc_\epsilon RI$) found on basophils and mast cells, and thereby prevents the release of histamine and other anaphylactic factors resulting in the pathological condition.

Interleukin-8 (IL-8) is neutrophil chemotactic peptide secreted by a variety of cells in response to inflammatory mediators (for a review see Hebert et al. *Cancer Investigation* 11(6):743 (1993)). IL-8 can play an important role in the pathogenesis of inflammatory disorders, such as adult respiratory distress syndrome (ARDS), septic shock, and multiple organ failure. Immune therapy for such inflammatory disorders can include treatment of an affected patient with anti-IL-8 antibodies.

Sticherling et al. (*J. Immunol.* 143:1628 (1989)) disclose the production and characterization of four monoclonal antibodies against IL-8. WO 92/04372, published Mar. 19, 1992, discloses polyclonal antibodies which react with the receptor-interacting site of IL-8 and peptide analogs of IL-8, along with the use of such antibodies to prevent an inflammatory response in patients. St. John et al. (*Chest* 103:932 (1993)) review immune therapy for ARDS, septic shock, and multiple organ failure, including the potential therapeutic use of anti-IL-8 antibodies. Sekido et al. (*Nature* 365:654 (1993)) disclose the prevention of lung reperfusion injury in rabbits by a monoclonal antibody against IL-8. Mulligan et al. (*J. Immunol.* 150:5585 (1993)), disclose protective effects of a murine monoclonal antibody to human IL-8 in inflammatory lung injury in rats.

WO 95/23865 (International Application No. PCT/US95/02589 published Sep. 8, 1995) demonstrates that anti-IL-8 monoclonal antibodies can be used therapeutically in the treatment of other inflammatory disorders, such as bacterial pneumonias and inflammatory bowel disease.

Anti-IL-8 antibodies are additionally useful as reagents for assaying IL-8. For example, Sticherling et al. (*Arch. Dermatol. Res.* 284:82 (1992)), disclose the use of anti-IL-8 monoclonal antibodies as reagents in immunohistochemical studies. Ko et al. (*J. Immunol. Methods* 149:227 (1992)) disclose the use of anti-IL-8 monoclonal antibodies as reagents in an enzyme-linked immunoabsorbent assay (ELISA) for IL-8.

SUMMARY OF THE INVENTION

One aspect of the invention is a conjugate consisting essentially of one or more antibody fragments covalently attached to one or more nonproteinaceous polymer molecules, wherein the apparent size of the conjugate is at least about 500 kD.

Another aspect of the invention is a conjugate formed by one or more antibody fragments covalently attached to one or more nonproteinaceous polymer molecules, wherein the apparent size of the conjugate is at least about 500 kD, and wherein the covalent structure of the conjugate is free of any matter other than the antibody fragment and nonproteinaceous polymer molecules.

Yet another aspect of the invention is a conjugate formed by the one or more antibody fragments covalently attached to one or more nonproteinaceous polymer molecules, wherein the covalent structure of the conjugate further incorporates one or more nonproteinaceous labels, wherein the covalent structure of the conjugate is free of any matter other than the antibody fragment, nonproteinaceous polymer and nonproteinaceous label molecules, and wherein the apparent size of the conjugate is at least about 500 kD.

Still another aspect of the invention is a conjugate consisting essentially of one or more antibody fragments covalently attached to one or more nonproteinaceous polymer molecules, wherein the apparent size of the conjugate is at least about 500 kD, and wherein at least one antibody fragment comprises an antigen binding site that binds to a polypeptide selected from the group consisting of human vascular endothelial growth factor (VEGF), human p185 receptor-like tyrosine kinase (HER2), human CD20, human CD18, human CD11a, human IgE, human apoptosis receptor-2 (Apo-2), human tumor necrosis factor-α (TNF-α), human tissue factor, human $\alpha_4\beta_7$ integrin, human GPIIb-IIIa integrin, human epidermal growth factor receptor (EGFR), human CD3, and human interleukin-2 receptor α-chain (TAC).

BRIEF DESCRIPTION OF THE FIGURES

FIG. 11A depicts myeloperoxidase levels in tissue; FIG. 11B depicts IL-8 levels in tissue; FIG. 11C depicts colon weight; FIG. 11D depicts gross inflammation; FIG. 11E depicts edema; FIG. 11F depicts extent of necrosis; FIG. 11G depicts severity of necrosis; FIG. 11H depicts neutrophil margination; FIG. 11I depicts neutrophil infiltration; and FIG. 11J depicts mononuclear infiltration.

FIG. 12 is a graph depicting the effect of anti-IL-8 monoclonal antibody treatment on the number of neutrophils in bronchioalveolar lavage (BAL) fluid in animals infected with *Streptococcus pneumoniae, Escherichia coli,* or *Pseudomonas aeruginosa.* Treatment with 6G4.2.5 significantly reduced the number of neutrophils present in the BAL fluid compared to animals treated with isotype control mouse IgG (FIG. 12).

FIG. 13 depicts the DNA sequences (SEQ ID NOS: 1-6) of three primers designed for each of the light and heavy chains. Multiple primers were designed in order to increase the chances of primer hybridization and efficiency of first strand cDNA synthesis for cloning the variable light and heavy regions of monoclonal antibody 5.12.14.

FIG. 14 depicts the DNA sequences (SEQ ID NOS: 7-10) of one forward primer and one reverse primer for the 5.12.14 light chain variable region amplification.

FIG. 15 depicts the DNA sequences (SEQ ID NOS: 11-15) of one forward primer and one reverse primer for the 5.12.14 heavy chain variable region amplification.

FIG. 16 depicts the DNA sequence (SEQ ID NO: 16) and the amino acid sequence (SEQ ID NO: 17) of the 5.12.14 light chain variable region and partial murine constant light region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable light region is amino acids 1 to 109. The partial murine constant light region is amino acids 110 to 123 (in italics).

FIG. 17 depicts the DNA sequence (SEQ ID NO: 18) and the amino acid sequence (SEQ ID NO: 19) of the 5.12.14 heavy chain variable region and partial murine constant heavy region. CDRs are indicated by either X-ray crystallography (underlined amino acids) or by Kabat sequence comparison (amino acids denoted with asterisk). Important restriction sites are indicated in italics. The signal peptide of STII is amino acids −23 to −1. The murine variable heavy region is amino acids 1 to 120. The partial murine constant heavy region is amino acids 121 to 130.

FIG. 18 depicts the DNA sequences (SEQ ID NOS: 20-23) of amplification primers used to convert murine light and heavy chain constant region residues to their human equivalents.

FIG. 19 depicts the DNA sequence (SEQ ID NO: 24) and the amino acid sequence (SEQ ID NO: 25) for the 5.12.14 light chain variable region and the human IgG1 light chain constant region. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable light region is amino acids 1 to 109. The human constant light region is amino acids 110 to 215.

FIGS. 20A-20B depict the DNA sequence (SEQ ID NO: 26) and the amino acid sequence (SEQ ID NO: 27) for the 5.12.14 heavy chain variable region and the heavy chain constant region of human IgG1. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 120. The human constant heavy region is amino acids 121 to 229.

FIG. 21 depicts the DNA sequences (SEQ ID NOS: 1-6) of three primers designed for each of the light and heavy chains. Multiple primers were designed in order to increase the chances of primer hybridization and efficiency of first strand cDNA synthesis for cloning the variable light and heavy regions of monoclonal antibody 6G4.2.5.

FIG. 22 depicts the DNA sequences (SEQ ID NOS: 28-31) of one forward primer and one reverse primer for the 6G4.2.5 light chain variable region amplification.

FIG. 23 depicts the DNA sequences (SEQ ID NOS: 32.33, 11, 15, 14, and 13) of one forward primer and one reverse primer for the 6G4.2.5 heavy chain variable region amplification.

FIG. 24 depicts the DNA sequence (SEQ ID NO: 34) and the amino acid sequence (SEQ ID NO: 35) of the 6G4.2.5 light chain variable region and partial murine constant light region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable light region is amino acids 1 to 114. The partial murine constant light region is amino acids 115 to 131.

FIG. 25 depicts the DNA sequence (SEQ ID NO: 36) and the amino acid sequence (SEQ ID NO: 37) of the 6G4.2.5 heavy chain variable region and partial murine constant heavy region. CDRs are indicated by either X-ray crystallography (underlined amino acids) or by Kabat sequence comparison (amino acids denoted with asterisk). Useful cloning sites are in italics. The signal peptide of STII is amino acids −23 to −1. The murine variable heavy region is amino acids 1 to 122. The partial murine constant heavy region is amino acids 123 to 135.

FIG. 26 depicts the DNA sequences (SEQ ID NOS: 38-40) of primers to convert the murine light chain and heavy chain constant regions to their human equivalents.

FIGS. 27A-27B depict the DNA sequence (SEQ ID NO: 41) and the amino acid sequence (SEQ ID NO: 42) for the chimeric 6G4.2.5 light chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable light region is amino acids 1 to 114. The human constant light region is amino acids 115 to 220.

FIGS. 28A-28B depict the DNA sequence (SEQ ID NO: 43) and the amino acid sequence (SEQ ID NO: 44) for the chimeric 6G4.2.5 heavy chain. CDRs are indicated by either X-ray crystallography (underlined amino acids) or by Kabat sequence comparison (amino acids denoted with asterisk). The human constant region is denoted in italics. The signal peptide of STII is amino acids −23 to −1. The murine variable heavy region is amino acids 1 to 122. The human constant heavy region is amino acids 123 to 231.

FIG. 29 depicts an amino acid sequence alignment of murine 6G425 light chain variable domain (SEQ ID NO: 45), humanized 6G425 F(ab)-1 light chain variable domain (SEQ ID NO: 46), and human light chain κI consensus framework (SEQ ID NO: 47) amino acid sequences, and an amino acid sequence alignment of murine 6G425 heavy chain variable domain (SEQ ID NO: 48), humanized 6G425 F(ab)-1 heavy chain variable domain (SEQ ID NO: 49), and human IgG1 subgroup III heavy chain variable domain (SEQ ID NO: 50) amino acid sequences, used in the humanization of 6G425. Light chain CDRs are labeled L1, L2, L3; heavy chain CDRs are labeled H1, H2, and H3. = and + indicate CDR sequences as defined by X-ray crystallographic contacts and sequence hypervariability, respectively. # indicates a difference between the aligned sequences. Residue numbering is according to Kabat et al. Lower case lettering denotes the insertion of an amino acid residue relative to the humIII consensus sequence numbering.

FIG. 30A presents inhibition data for F(ab)-9 samples at concentrations of 0.06 nM, 6.25 nM, 12.5 nM, 25 nM, 50 nM, and 100 nM, for an isotype control antibody (denoted "4D5") sample at a concentration of 100 nM, and for a no antibody control sample, in the presence of 2 nM human wild type IL-8. FIG. 30B presents inhibition data for F(ab)-9 samples at concentrations of 6.25 nM, 12.5 nM, 25 nM, and 50 nM, for an isotype control antibody (denoted "4D5") sample at a concentration of 100 nM, and for a no antibody control sample, in the presence of 4 nM human monomeric IL-8 (denoted as "BD59" and as "monomeric IL-8"). FIG. 30C presents inhibition data for F(ab)-9 samples at concentrations of 1 nM, 12.5 nM, 25 nM, and 50 nM, for an isotype control antibody (denoted "4D5") sample at a concentration of 100 nM, and for a no antibody control sample, in the presence of 2 nM rhesus IL-8. In addition, FIGS. 30A-30C each presents data for a no IL-8 buffer control sample (denoted as "Buffer") in the respective inhibition assay.

FIG. 31A depicts the amino acid sequences of the humanized anti-IL-8 6G4.2.5V11 light chain in an N-terminal fusion with the STII leader peptide (SEQ ID NO: 51), the humanized anti-IL-8 6G4.2.5V11 heavy chain in an N-terminal fusion with the STII leader peptide (SEQ ID NO: 52), and a peptide linker in a C-terminal fusion with M13 phage geneIII coat protein (SEQ ID NO: 53).

FIG. 31B depicts the nucleic acid sequence (SEQ ID NO: 54) and the translated amino acid sequence (SEQ ID NO: 51) of the humanized anti-IL-8 6G4.2.5V11 light chain in an N-terminal fusion with the STII leader peptide.

FIG. 31C depicts the amino acid sequences of the humanized anti-IL-8 6G4.2.5V19 light chain in an N-terminal fusion with the STII leader peptide (SEQ ID NO: 51), and the humanized anti-IL-8 6G4.2.5V19 heavy chain in an N-terminal fusion with the STII leader peptide (SEQ ID NO: 55).

FIG. 34A presents inhibition data for 6G4.2.5V11N35A Fab samples at concentrations of 0.5, 1, 2, 4, 8, 16, and 33 nM, for an isotype control antibody (denoted "4D5") sample at a concentration of 33 nM, and for a no antibody control (denoted "HuIL-8") sample, in the presence of 2 nM human wild type IL-8. FIG. 34B presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "BD59") sample, in the presence of 2 nM human monomeric IL-8. FIG. 34C presents inhibition data for 6G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted "4D5") sample at a concentration of 33 nM, and for a no antibody control (denoted ?Rab IL-8") sample, in the presence of 2 nM rabbit IL-8. FIG. 34D presents inhibition data for G4.2.5V11N35A Fab samples at concentrations of 0.5, 1, 2, 4, 8, 16, and 33 nM, for an intact 6G4.2.5 mAb sample at a concentration of 33 nM, for an isotype control antibody (denoted as "4D5") sample at a concentration of 33 nM, and for a no antibody control (denoted "Rhe IL-8") sample, in the presence of 2 nM rhesus IL-8. In addition, FIGS. 34B-34D each presents data for human wild type IL-8 control (denoted "HuIL-8") samples at a concentration of 2 nM in the respective assay, and FIGS. 34A-34D each presents data for a no IL-8 buffer control (denoted "Buffer?) sample in the respective assay.

FIG. 35 depicts the amino acid sequences of the humanized anti-IL-8 6G4.2.5V11N35A light chain in an N-terminal fusion with the STII leader peptide (SEQ ID NO: 56), the humanized anti-IL-8 6G4.2.5V11N35A heavy chain in an N-terminal fusion with the STII leader peptide (SEQ ID NO: 52), and the GCN4 leucine zipper peptide (SEQ ID NO: 57). The Ala residue (substituted for the wild type Asn residue) at amino acid position 35 in the 6G4.2.5V11N35A light chain appears in bold case. A putative pepsin cleavage site in the GCN4 leucine zipper sequence is underlined.

FIG. 36 depicts the DNA sequence (SEQ ID NO: 58) and the amino acid sequence (SEQ ID NO: 56) of the humanized anti-IL-8 6G4.2.5V11N35A light chain in an N-terminal fusion with the STII leader peptide. Complementarity determining regions L1, L2, and L3 are underlined FIGS. 37A-37B depict the DNA sequence (SEQ ID NO: 59) and the amino acid sequence (SEQ ID NO: 60) of the humanized anti-IL-8 6G4.2.5V11N35A heavy chain in an N-terminal fusion with the STII leader peptide and in a C-terminal fusion with the GCN4 leucine zipper sequence. Complementarity determining regions H1, H2, and H3 are underlined.

FIGS. 41A-41V depict the nucleic acid sequence (SEQ ID NO: 61) of the p6G4V11N35A.F(ab')$_2$ vector.

FIG. 42 depicts the nucleic acid sequences of the stop template primer (SEQ ID NO: 63) and the NNS randomization primer (SEQ ID NO: 64) used for random mutagenesis of amino acid position 35 in variable light chain CDR-L1 of humanized antibody 6G4V11.

FIG. 43A is a table of data describing the frequencies of different phage display clones obtained from the randomization of amino acid position 35 in variable light chain CDR-L1 of humanized antibody 6G4V11.

FIG. 44 also contains a table of data providing the equilibrium constant for 6G4V11N35A Fab binding to IL-8 (rate constants were not determined "ND"), and the equilibrium and rate constants for 6G4V11N35A F(ab')$_2$ and 6G4V11N35E Fab binding to IL-8.

FIG. 45 depicts the DNA sequence (SEQ ID NO: 65) and amino acid sequence (SEQ ID NO: 62) of the 6G4V11N35E light chain in an N-terminal fusion with the STII leader peptide. Complementarity determining regions L1, L2 and L3 are underlined.

(light columns) mediated neutrophil chemotaxis. Data are presented for 6G4V11N35E Fab samples at concentrations of 0.4, 1.2, 3.7, 11 and 33 nM, and for an isotype control antibody (4D5) sample at a concentration of 100 nM, in the presence of 2 nM human IL-8 or 2 nM rabbit IL-8. In addition, inhibition data are presented for a no IL-8 buffer control sample (denoted "Buffer") and for human and rabbit IL-8 control samples (denoted "IL-8").

FIG. 47 depicts the DNA sequence of the sense (SEQ ID NO: 66) and anti-sense (SEQ ID NO: 67) strands of a PvuII-XhoI synthetic nucleotide encoding amino acids Leu4 to Phe29 of the 6G4V11N35A heavy chain.

FIGS. 48A-48T depict the DNA sequence (SEQ ID NO: 68) of plasmid p6G4V11N35A.choSD9.

FIGS. 49A, 49B, 49C and 49D are graphs of displacement curves depicting the inhibition of $^{125}$I-IL-8 binding to neutrophils exhibited by IL-8 control, intact murine 6G4.2.5 antibody, the full length IgG1 form of variant 6G4V11N35A, and the full length IgG1 form of variant 6G4V11N35E, respectively.

Figure 50A:
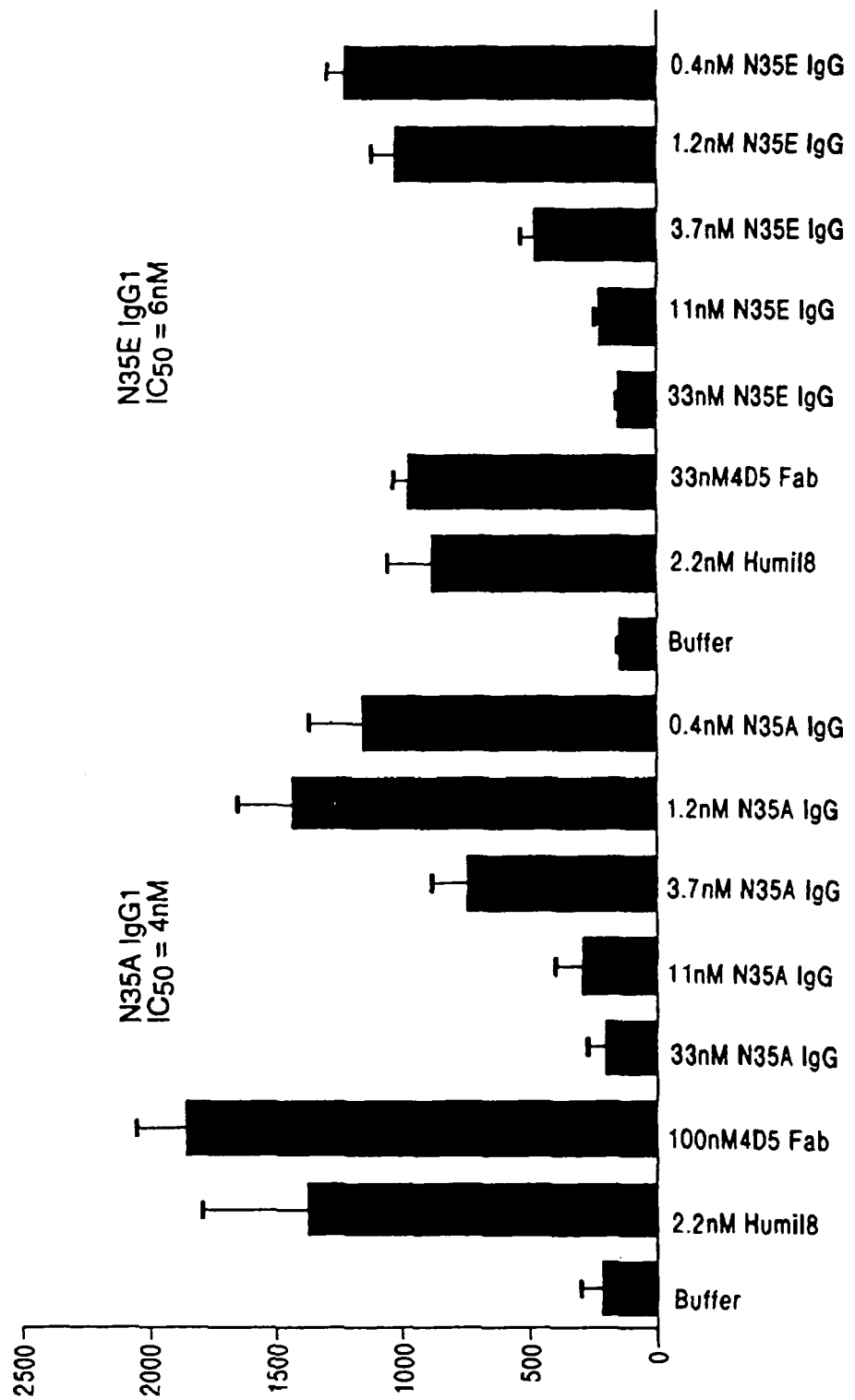
Figure 50B:
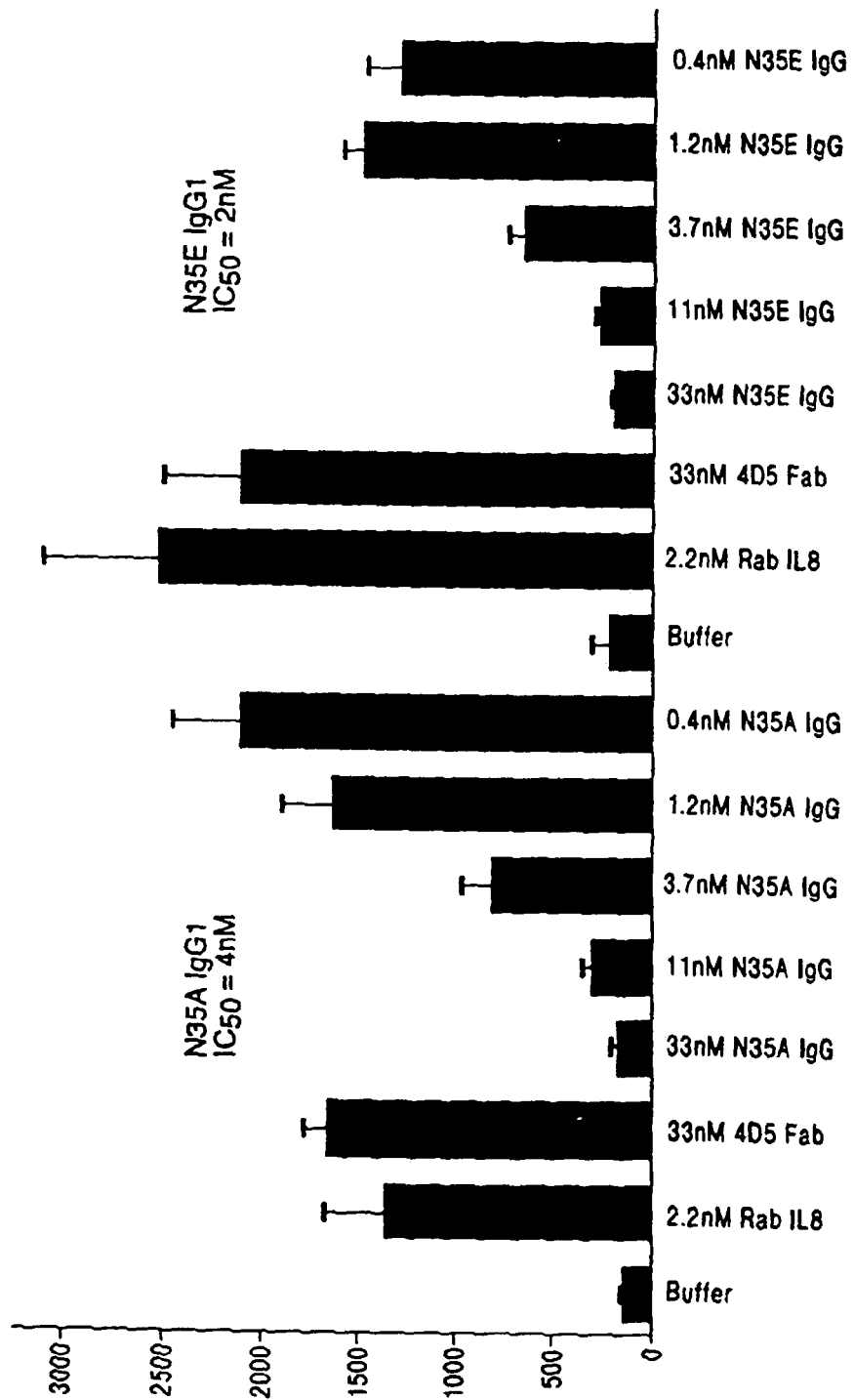

FIGS. 50A-50B are graphs depicting the ability of full length 6G4V11N35A IgG1 and 6G4V11N35E IgG1 to inhibit human IL-8 (FIG. 50A) and rabbit IL-8 (FIG. 50B) mediated neutrophil chemotaxis.

Figure 51:
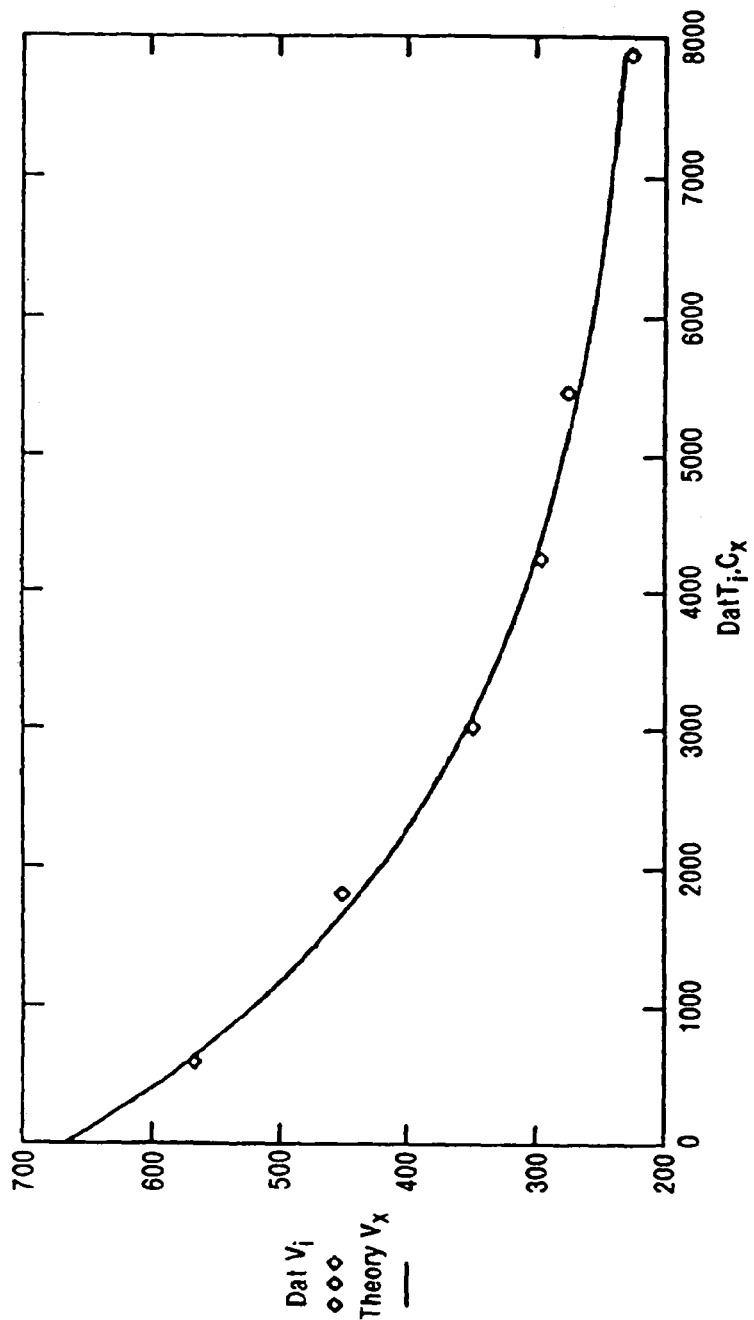

FIG. 51 contains a graph depicting the typical kinetics of a full length anti-IL8 antibody (6G4V11N35A IgG1) binding to IL-8. FIG. 51 also contains a table of data providing the equilibrium and rate constants for full length murine 6G4.2.5 IgG2a, 6G4V11N35A IgG1 and 6G4V11N35E IgG1 binding to IL-8.

Figure 52A:
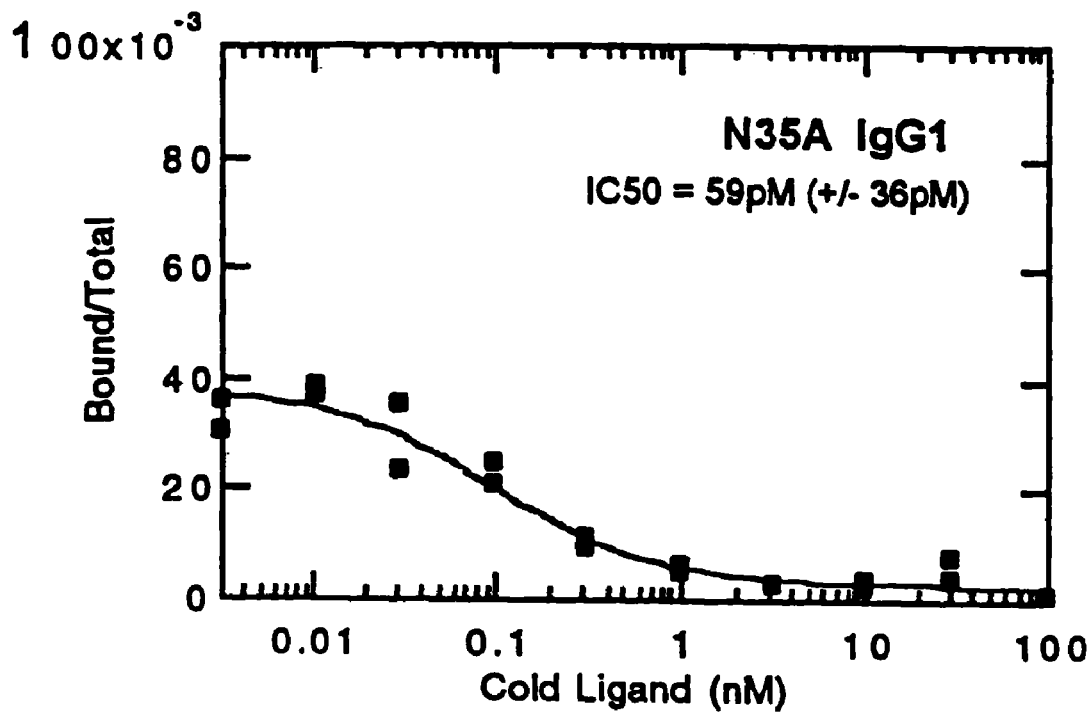
Figure 52B:
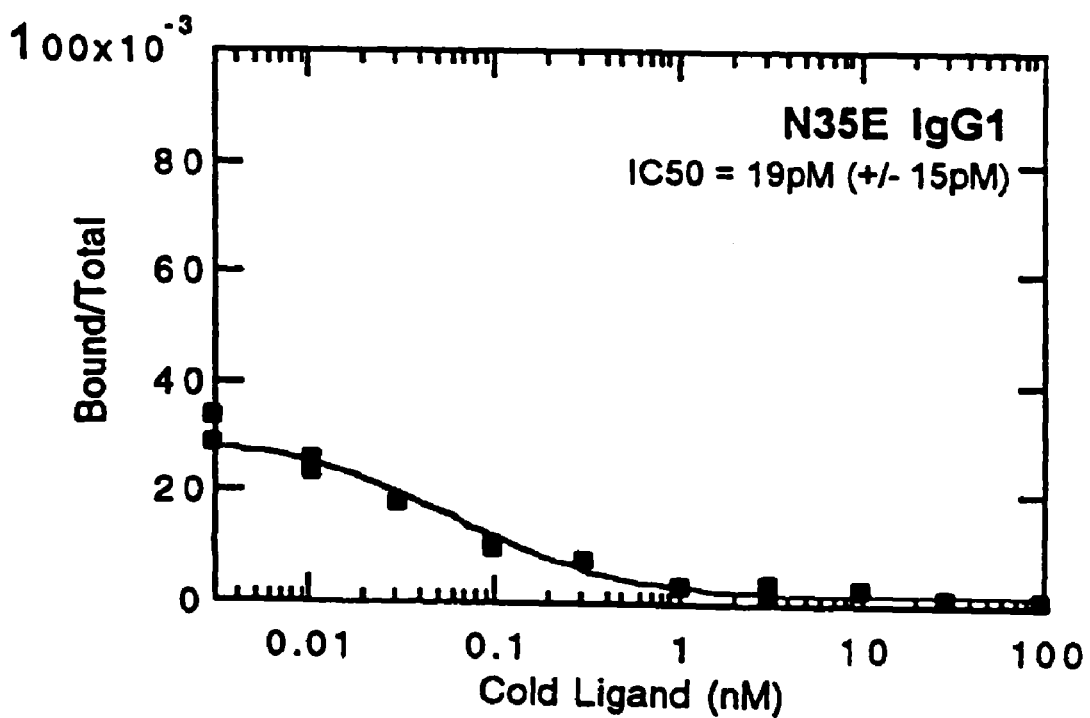

FIGS. 52A and 52B are graphs of displacement curves depicting the results of an unlabeled IL-8/$^{125}$I-IL-8 competition radioimmunoassay performed with full length 6G4V11N35A IgG1 and 6G4V11N35E IgG1, respectively.

FIG. 53 depicts the DNA sequence (SEQ ID NO: 69) and amino acid sequence (SEQ ID NO: 70) of the 6G4V11N35A Fab' heavy chain (6G4V11N35A Fab heavy chain modified to contain a cysteine residue in the hinge region).

Figure 54A:
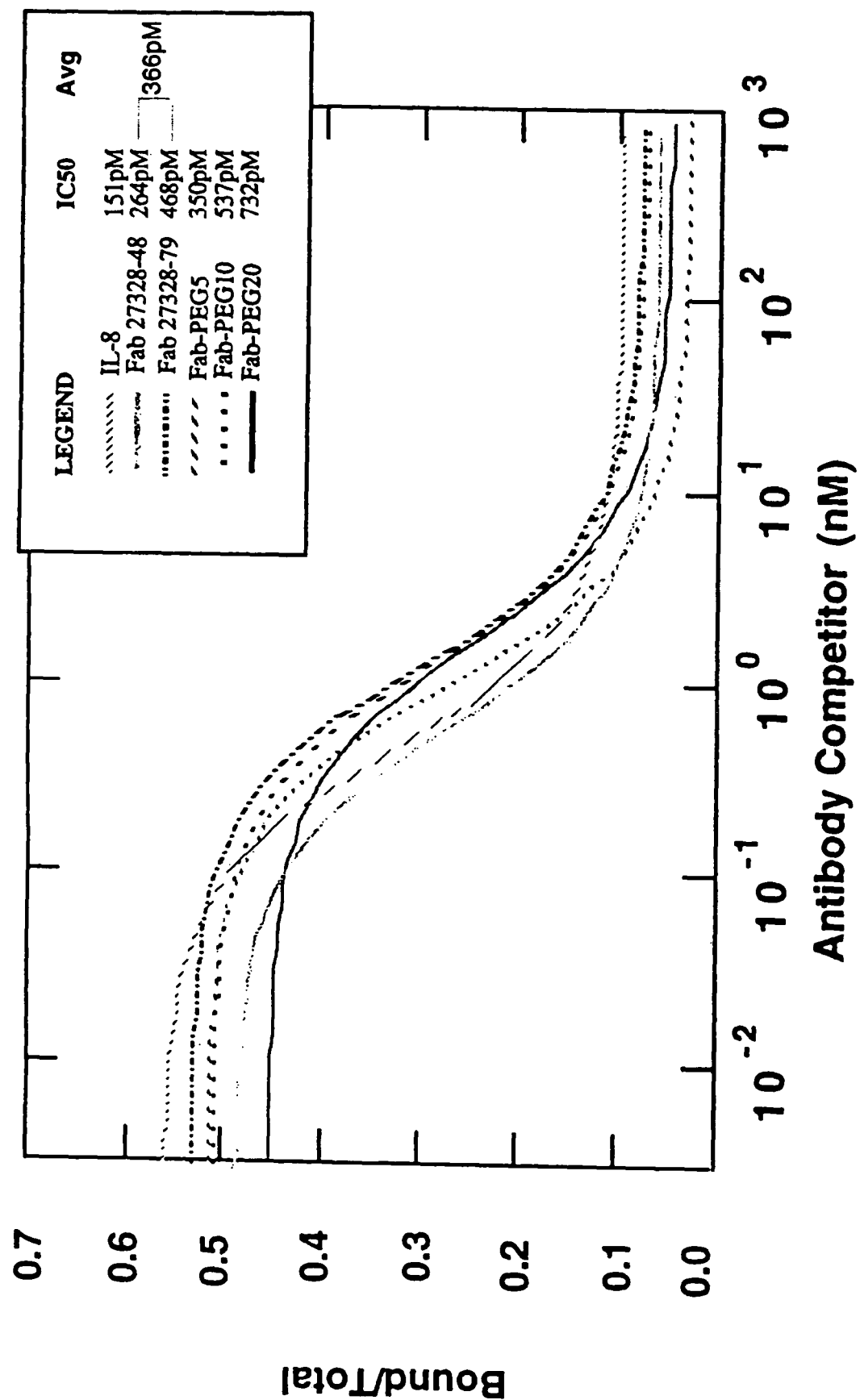
Figure 54B:
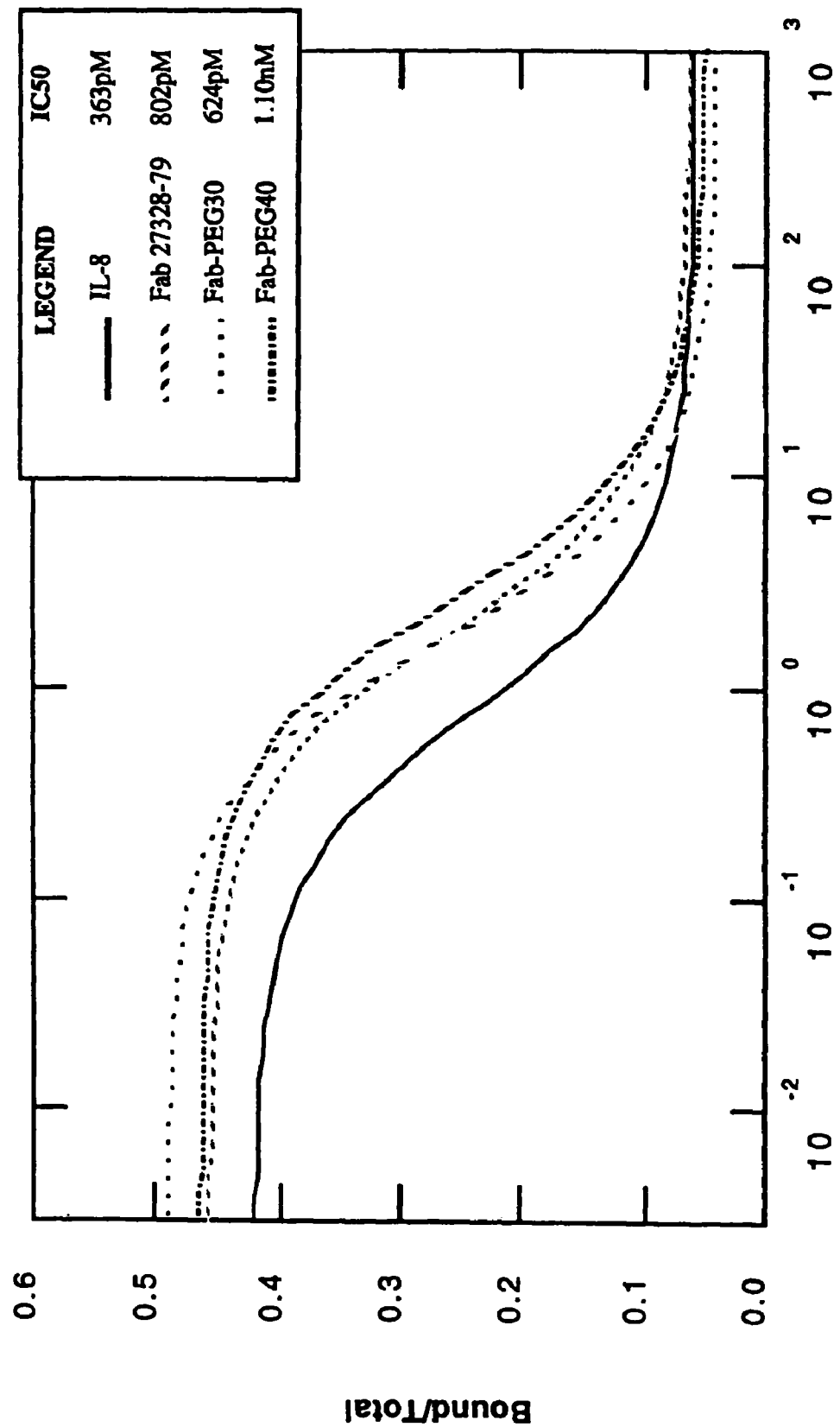
Figure 54C:
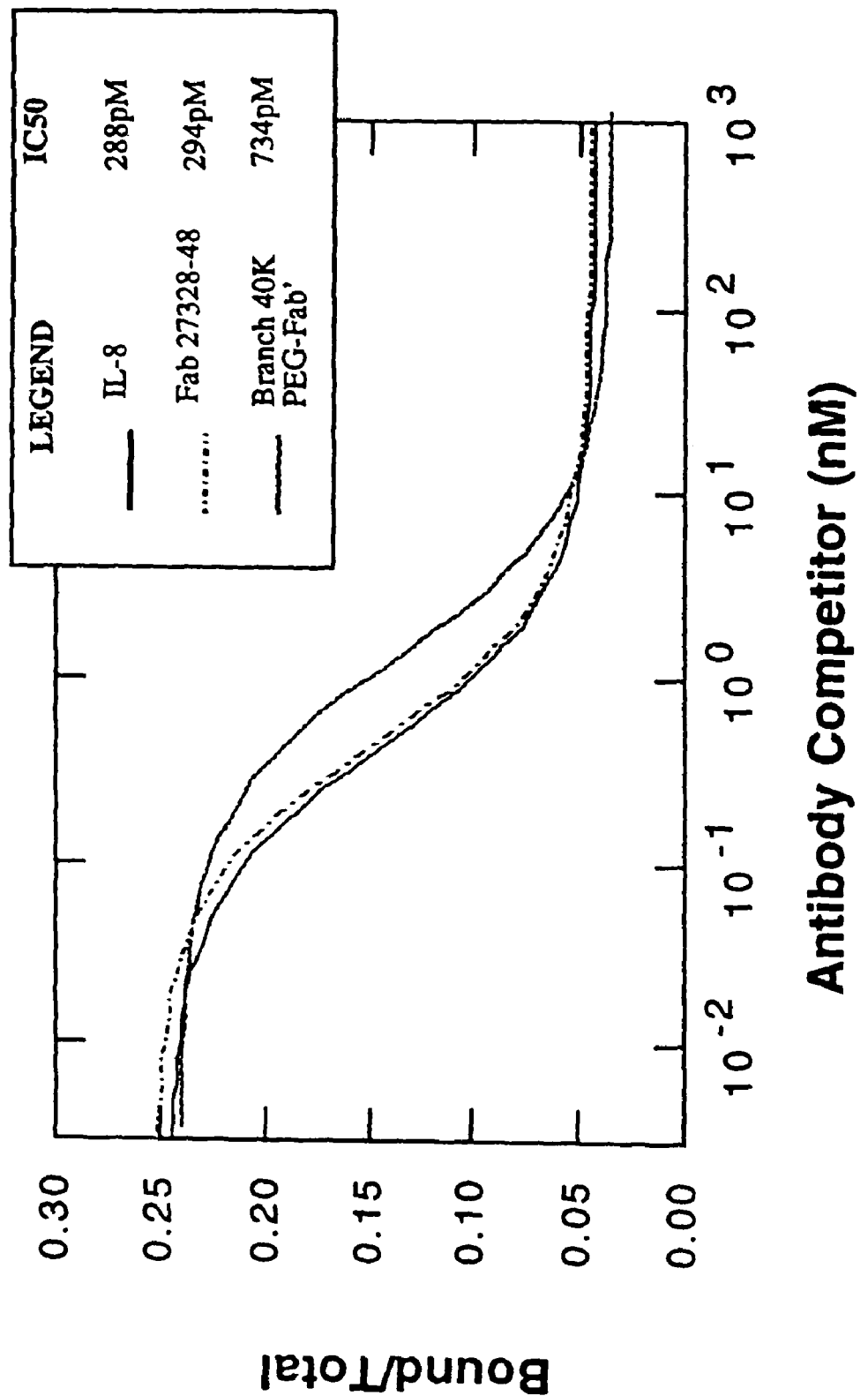

FIGS. 54A-54C contain graphs of displacement curves depicting the IL-8 binding and $IC_{50}$'s for PEG-maleimide modified 6G4V11N35A Fab' molecules.

Figure 55A:
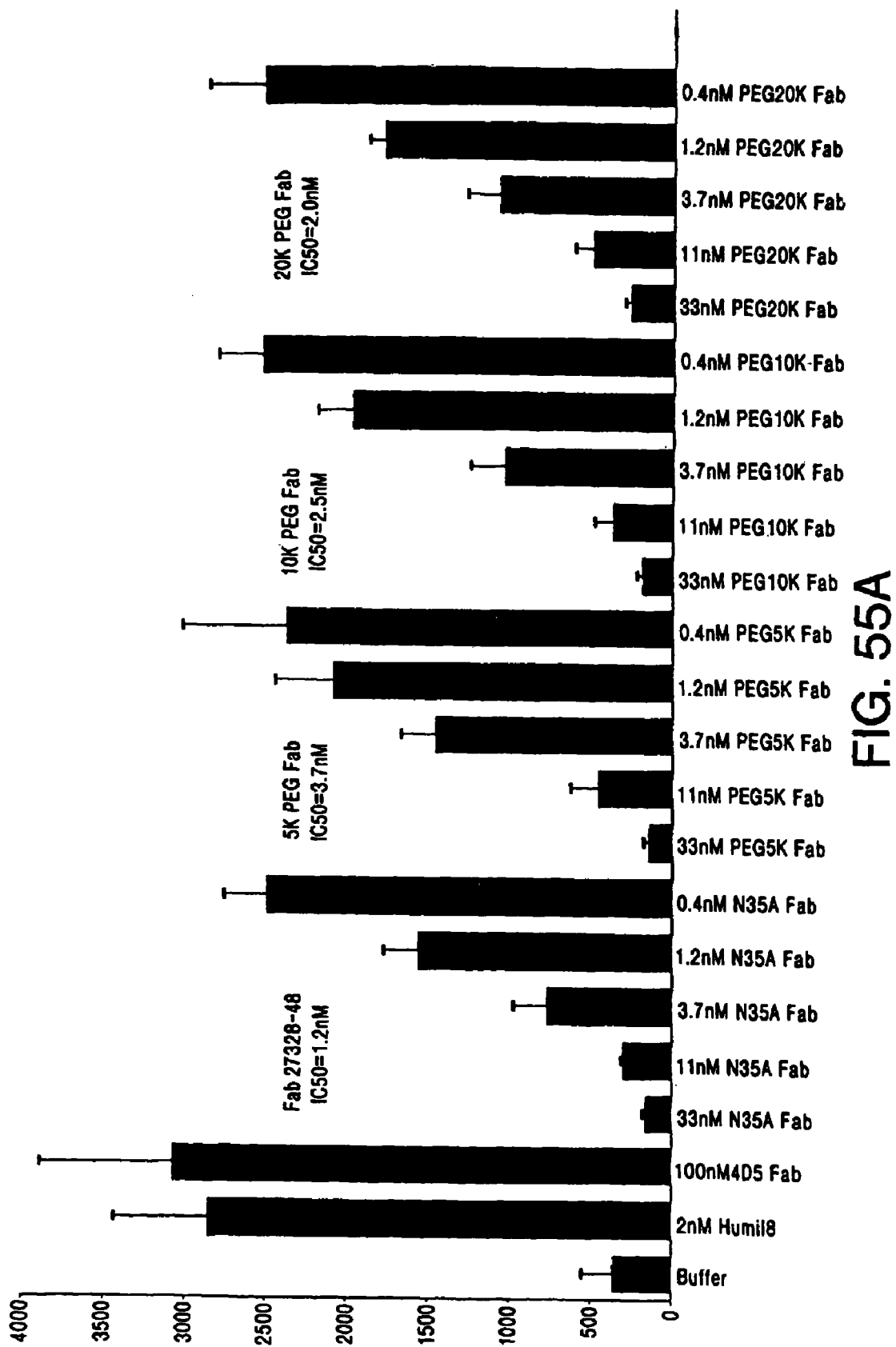
Figure 55B:
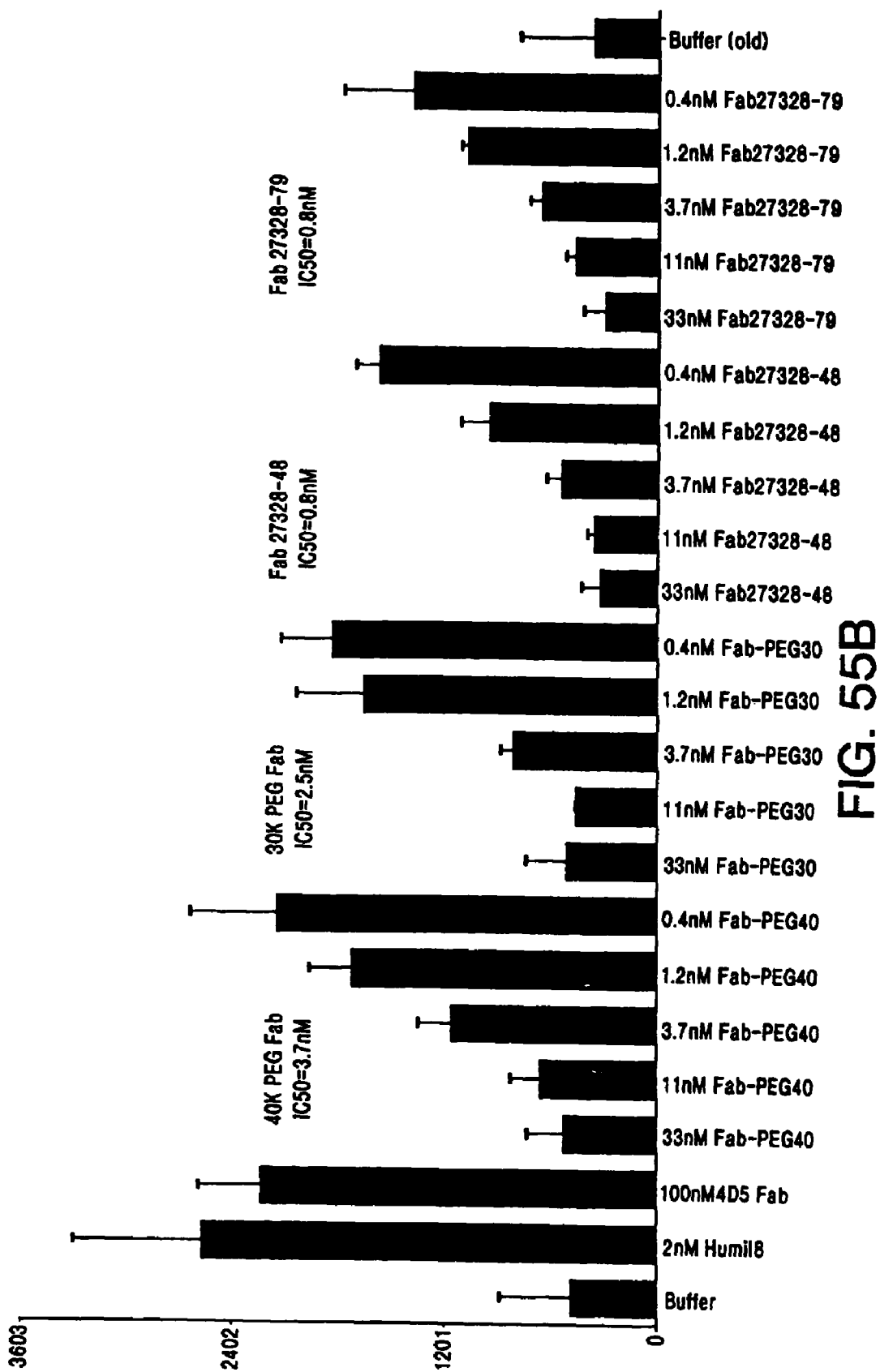

FIGS. 55A-55C are graphs depicting the ability of PEG-maleimide modified 6G4V11N35A Fab' molecules to inhibit human IL-8 and rabbit IL-8 mediated neutrophil chemotaxis.

Figure 56A:
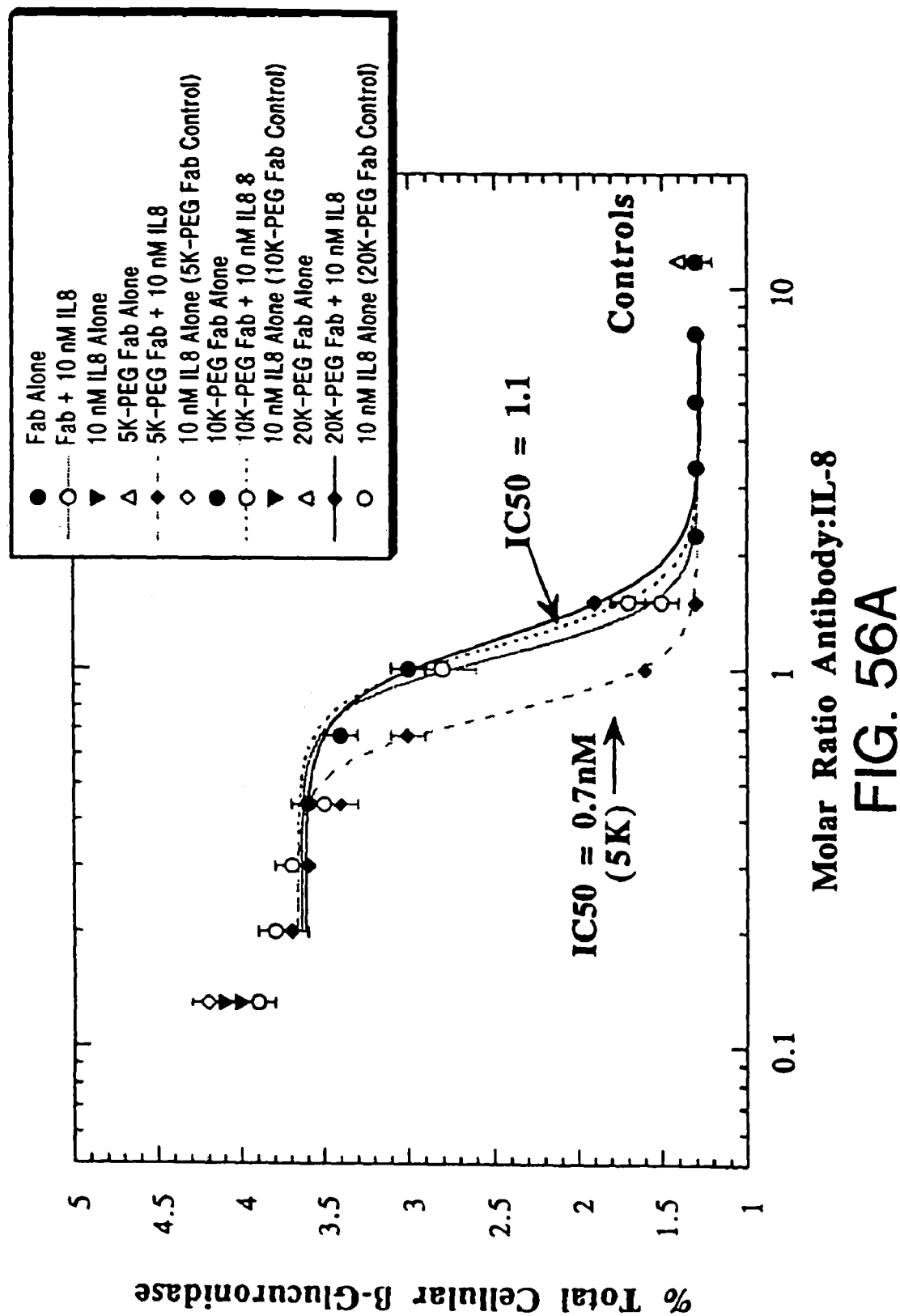
Figure 56B:
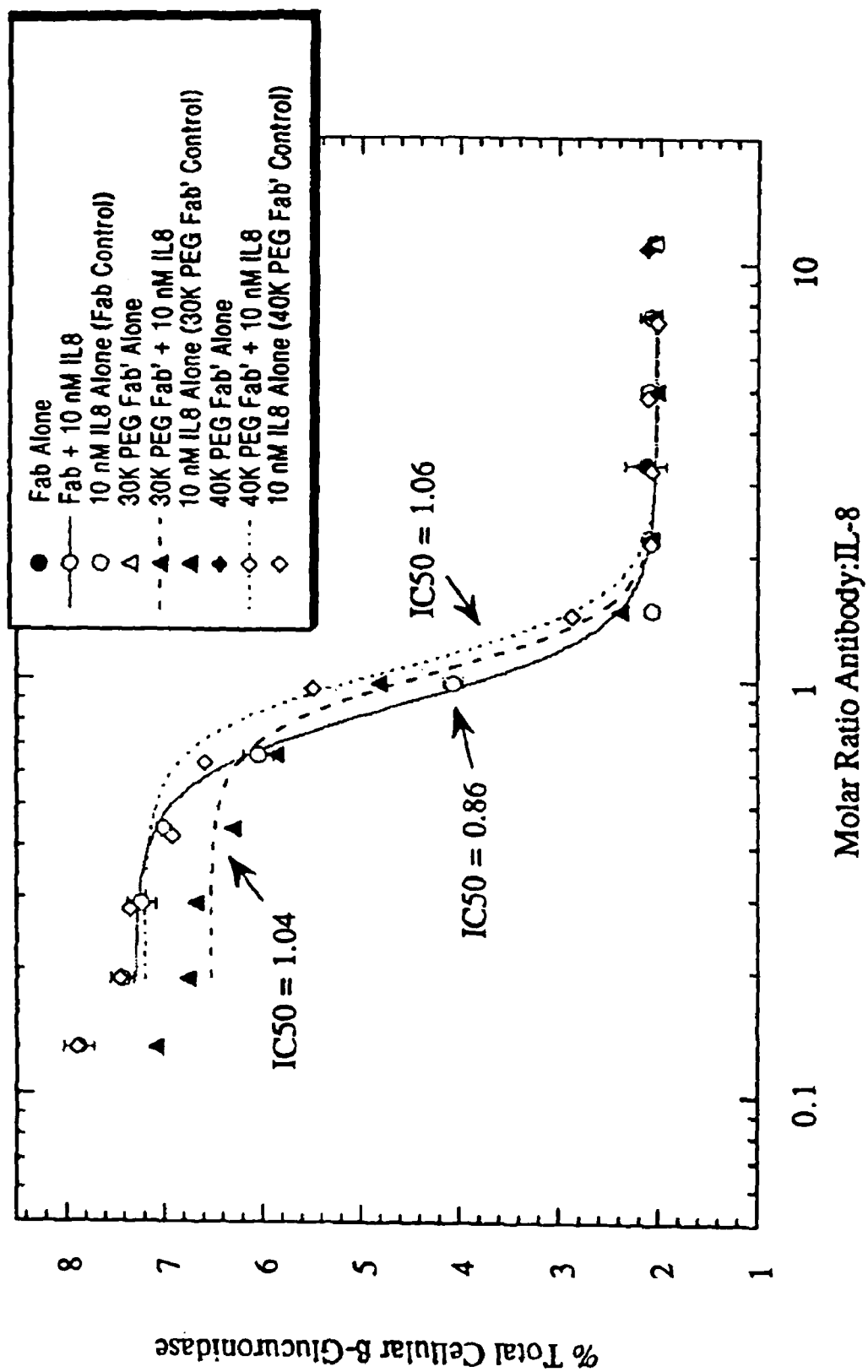
Figure 56C:
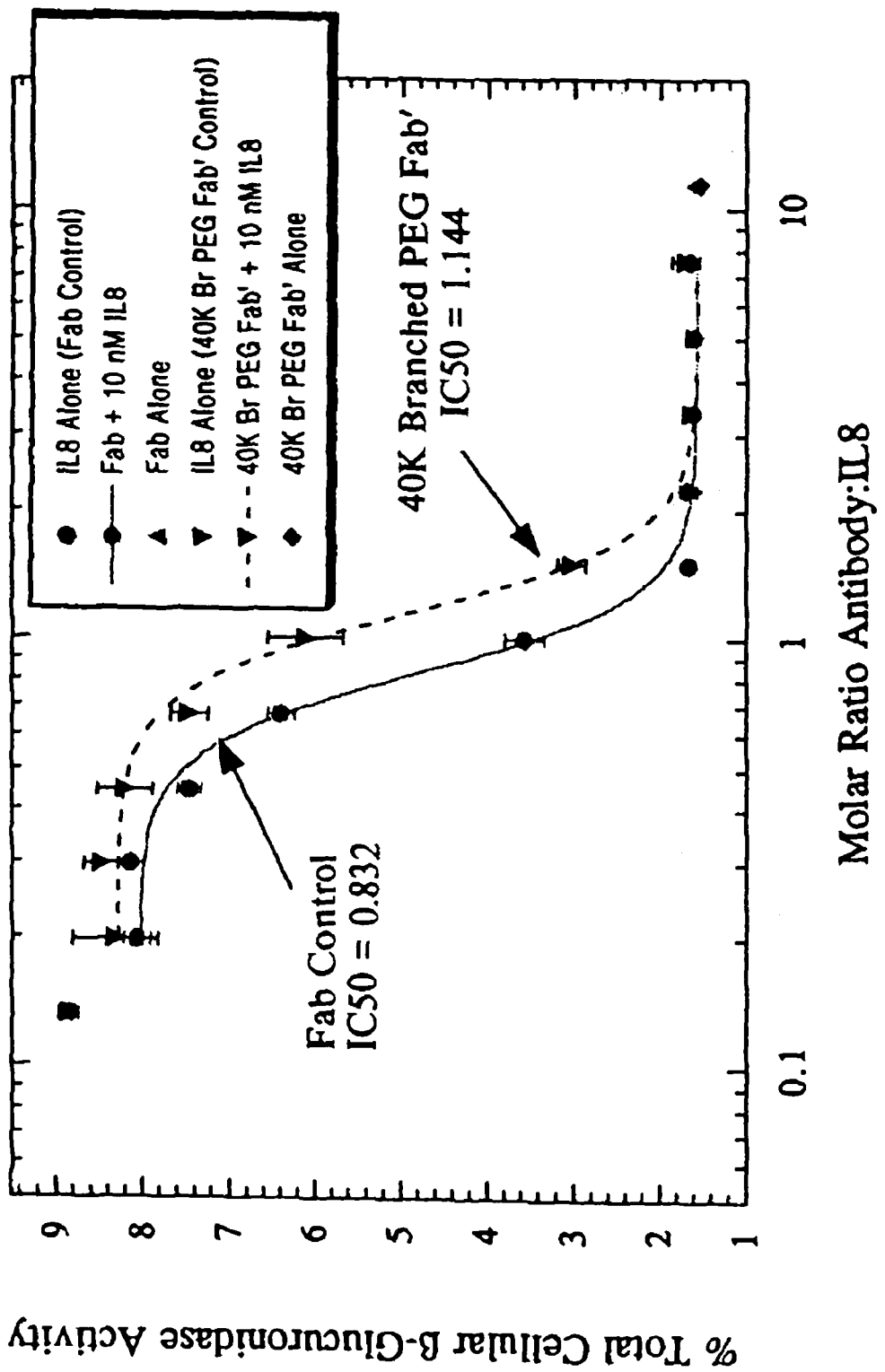

FIGS. 56A-56C are graphs depicting the ability of PEG-maleimide modified 6G4V11N35A Fab' molecules to inhibit IL-8 mediated release of β-glucuronidase from neutrophils.

Figure 57A:
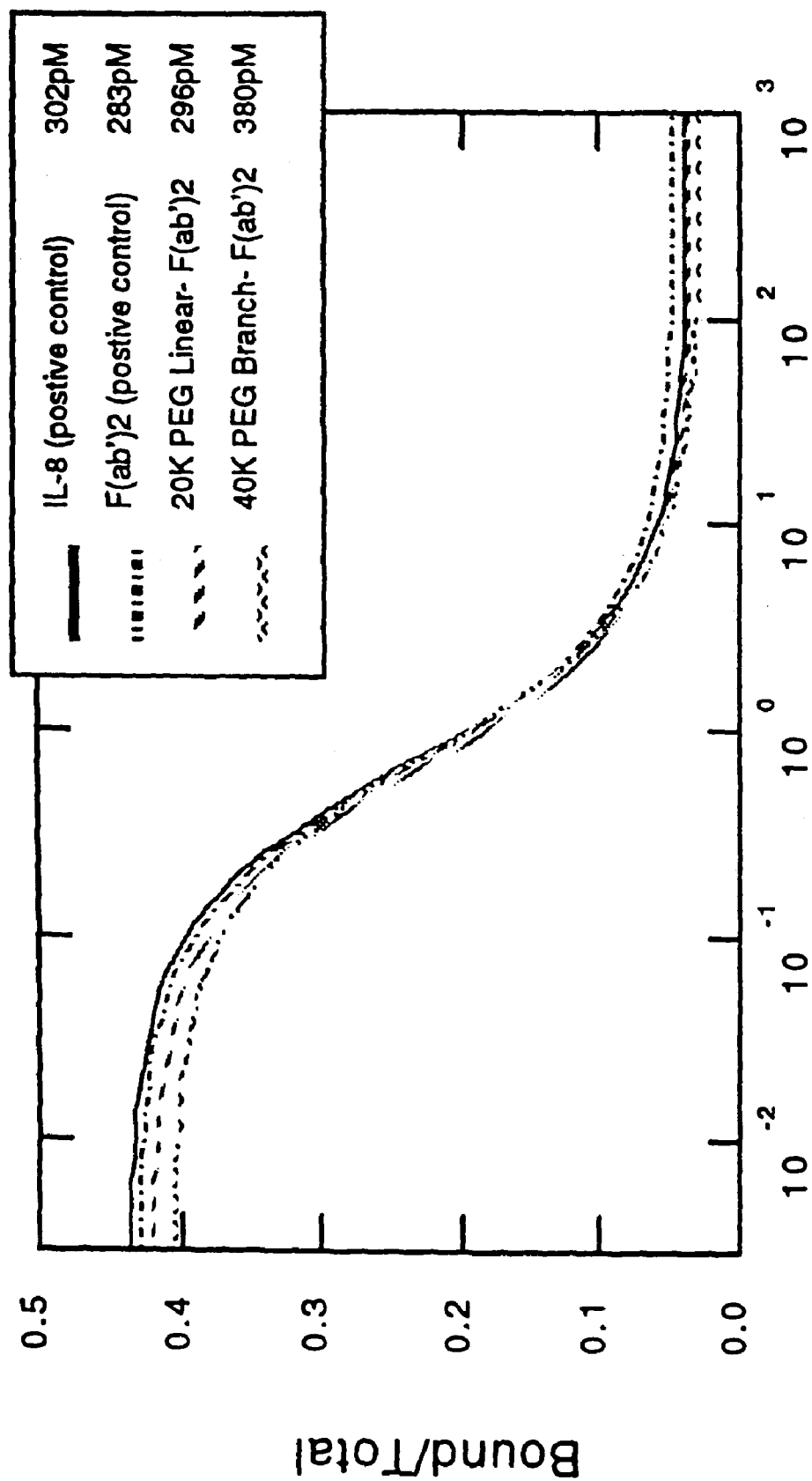
Figure 57B:
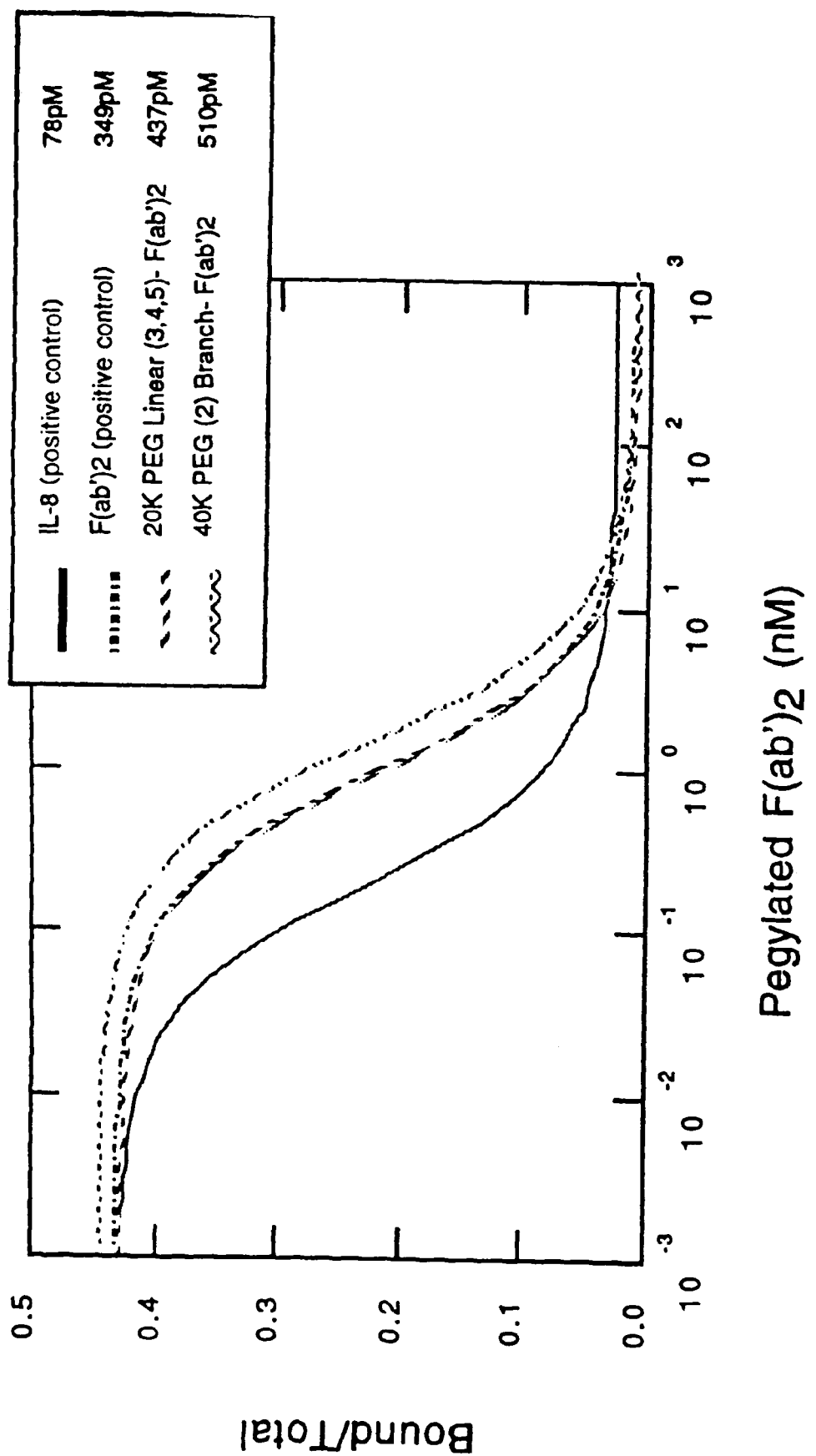

FIGS. 57A-57B contain graphs of displacement curves depicting the inhibition of $^{125}$I-IL-8 binding to neutrophils exhibited by PEG-succinimide modified 6G4V11N35A Fab'$_2$ molecules.

Figure 58A:
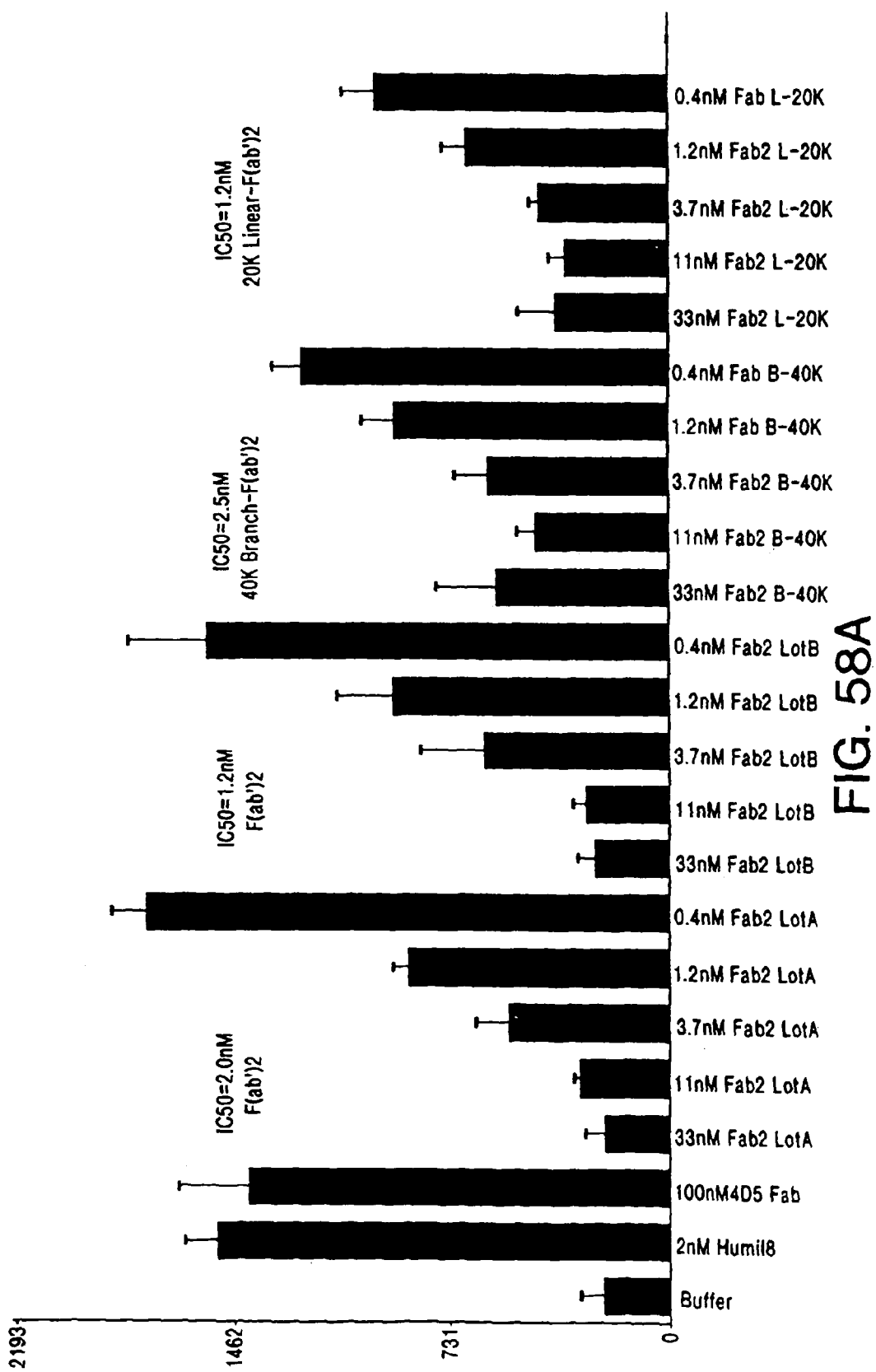
Figure 58B:
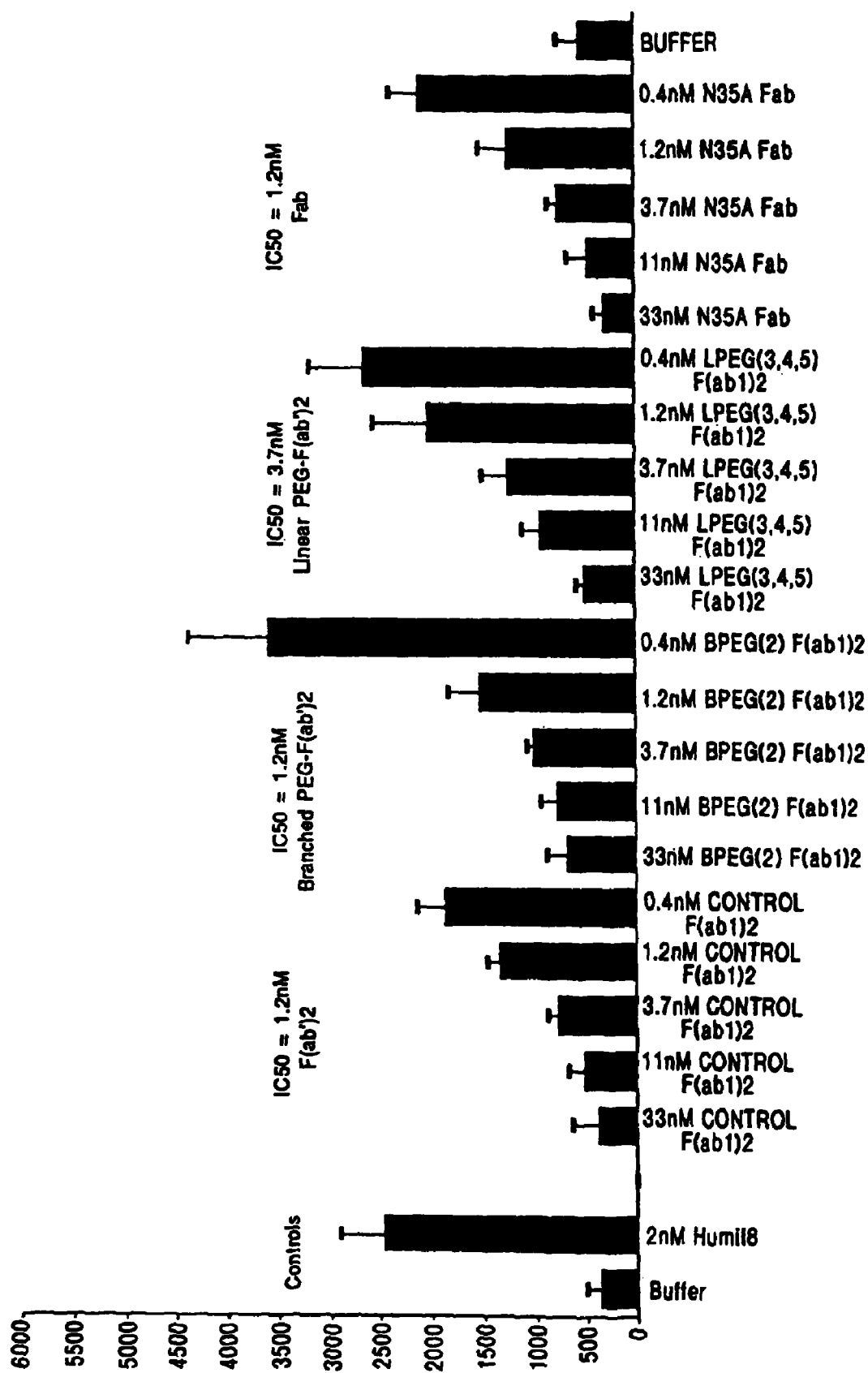

FIGS. 58A-58B are graphs depicting the ability of PEG-succinimide modified 6G4V11N35A F(ab')$_2$ molecules to inhibit human IL-8 mediated neutrophil chemotaxis.

Figure 59A:
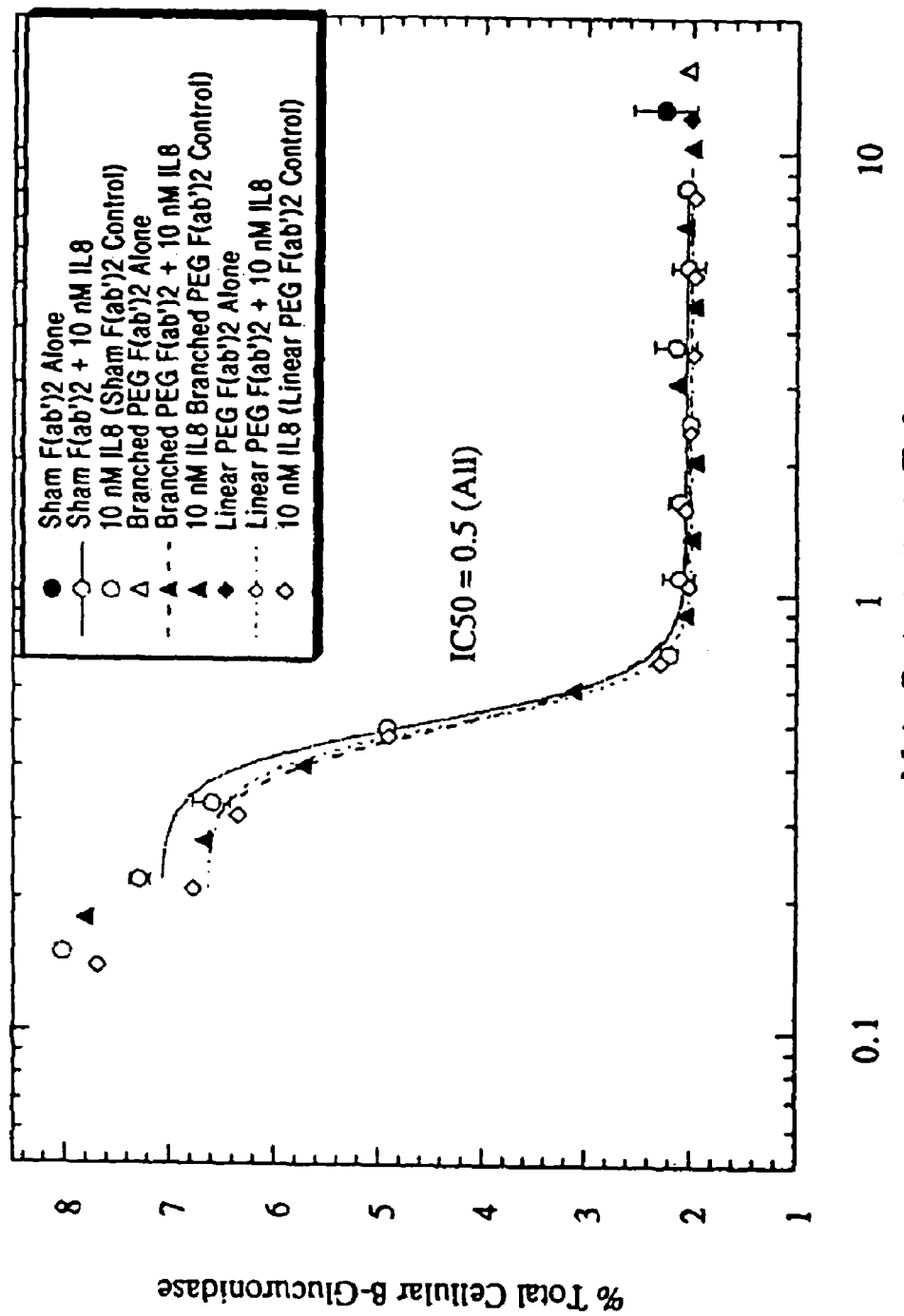

FIGS. 59A-59B are graphs depicting the ability of PEG-succinimide modified 6G4V11N35A F(ab')$_2$ molecules to inhibit human IL-8 mediated release of β-glucuronidase from neutrophils.

Figure 60:
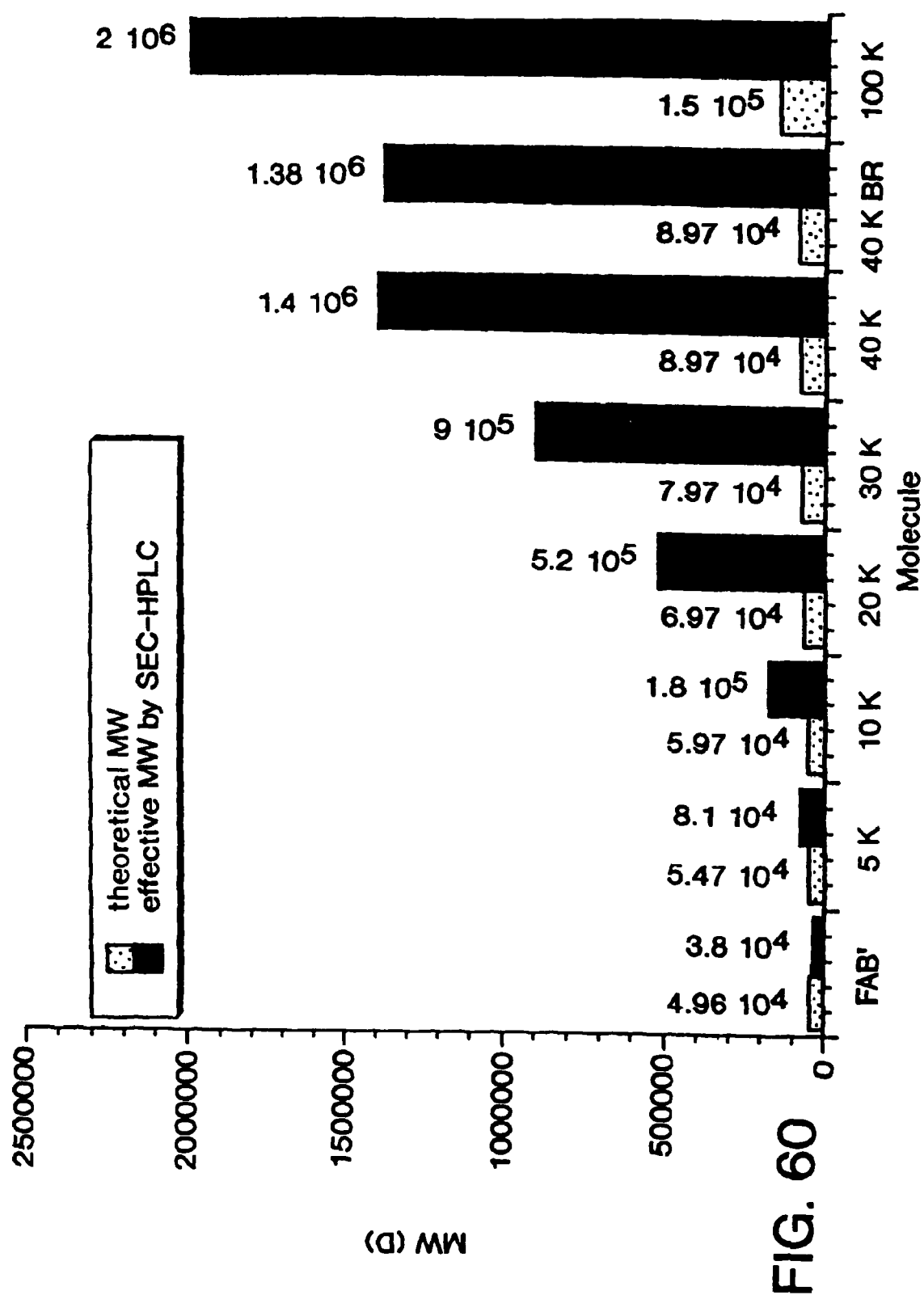

FIG. 60 is a graph depicting the theoretical molecular weight (dotted bars) and effective size (solid bars) of PEG-maleimide modified 6G4V11N35A Fab' molecules as determined by SEC-HPLC.

Figure 61A:
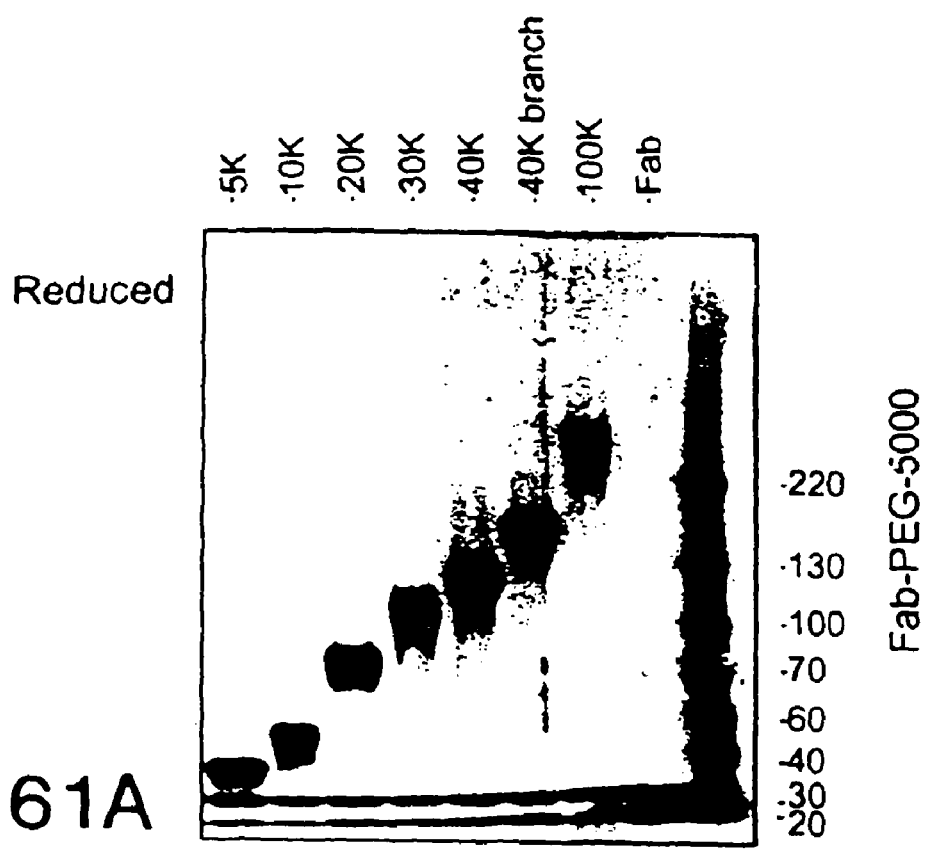
Figure 61B:
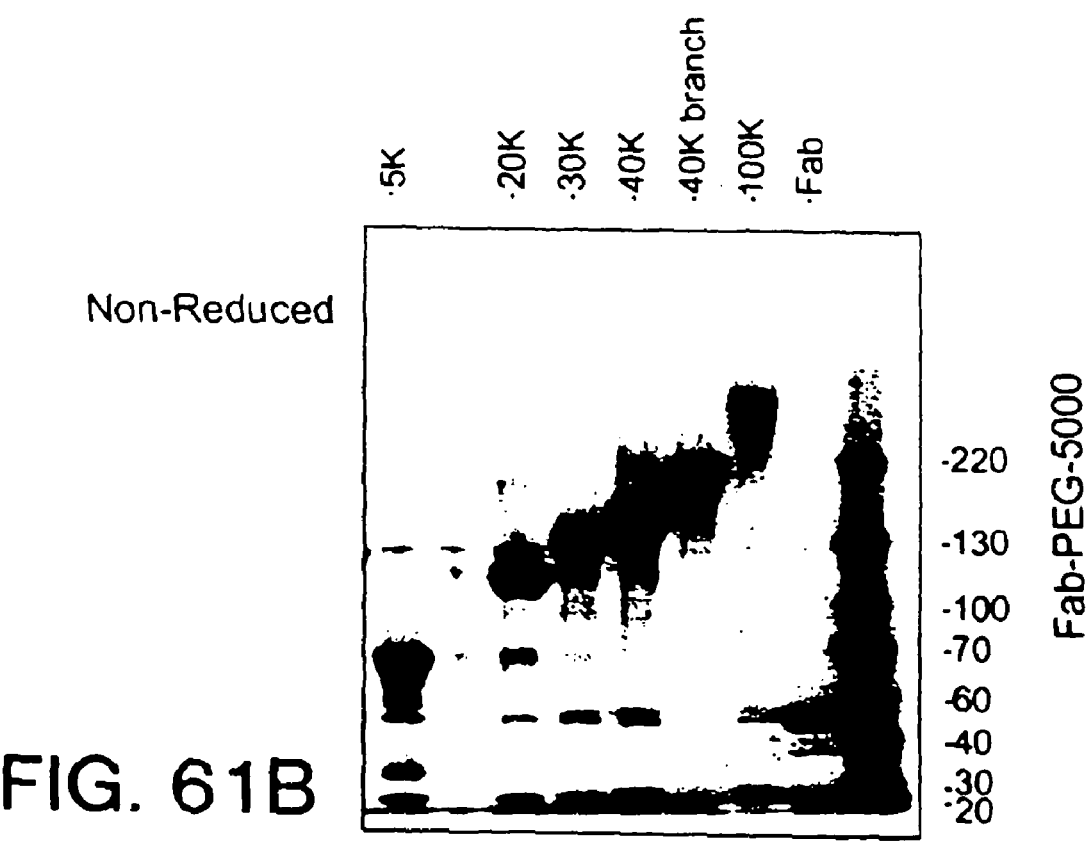

FIGS. 61A and 61B are SDS-PAGE gels depicting the electrophoretic mobility of various PEG-maleimide modified 6G4V11N35A Fab' molecules under reducing and non-reducing conditions, respectively.

Figure 62:
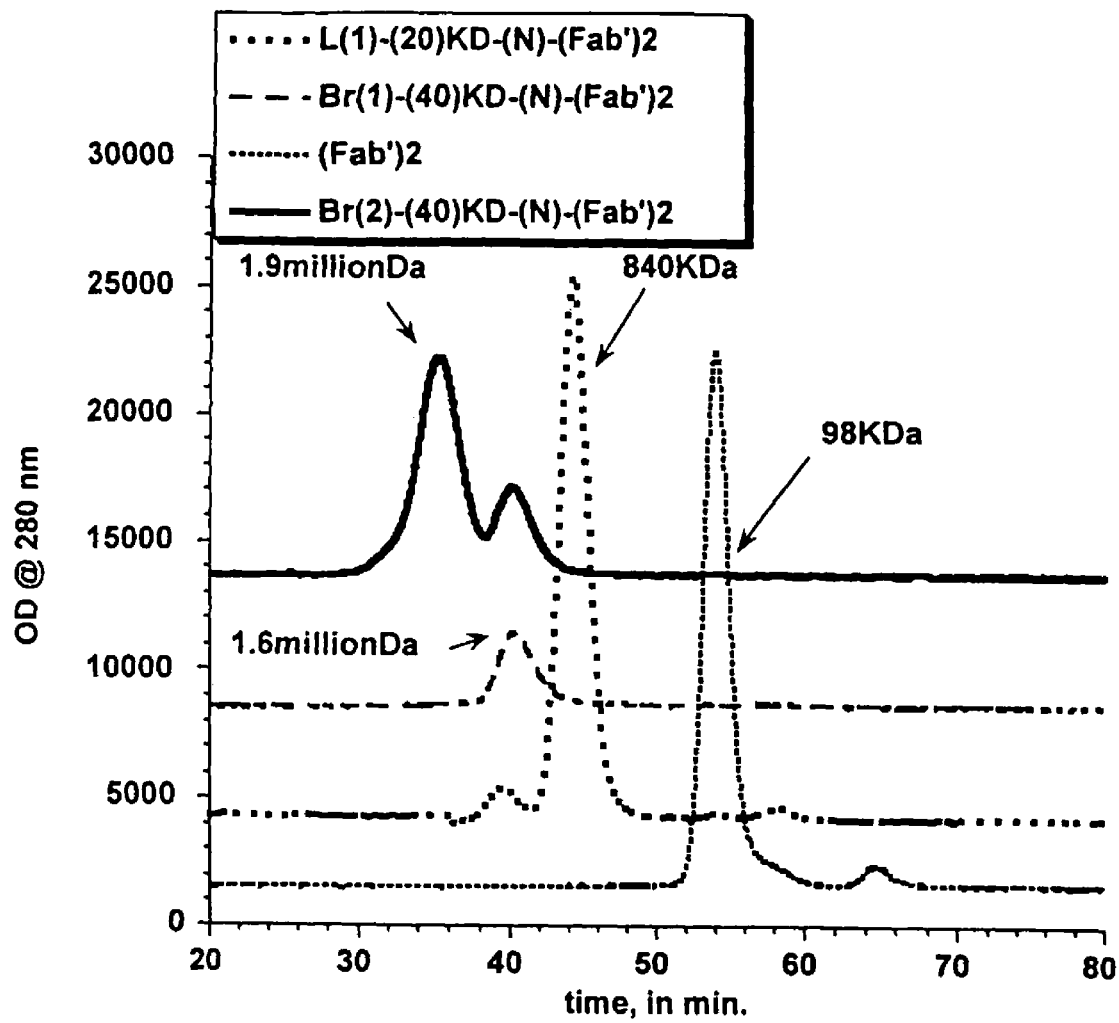

FIG. 62 contains size exclusion chromatograms (SEC-HPLC) depicting the retention times and effective (hydrodynamic) sizes of various PEG-succinimide modified 6G4V11N35A F(ab')$_2$ molecules.

Figure 63:
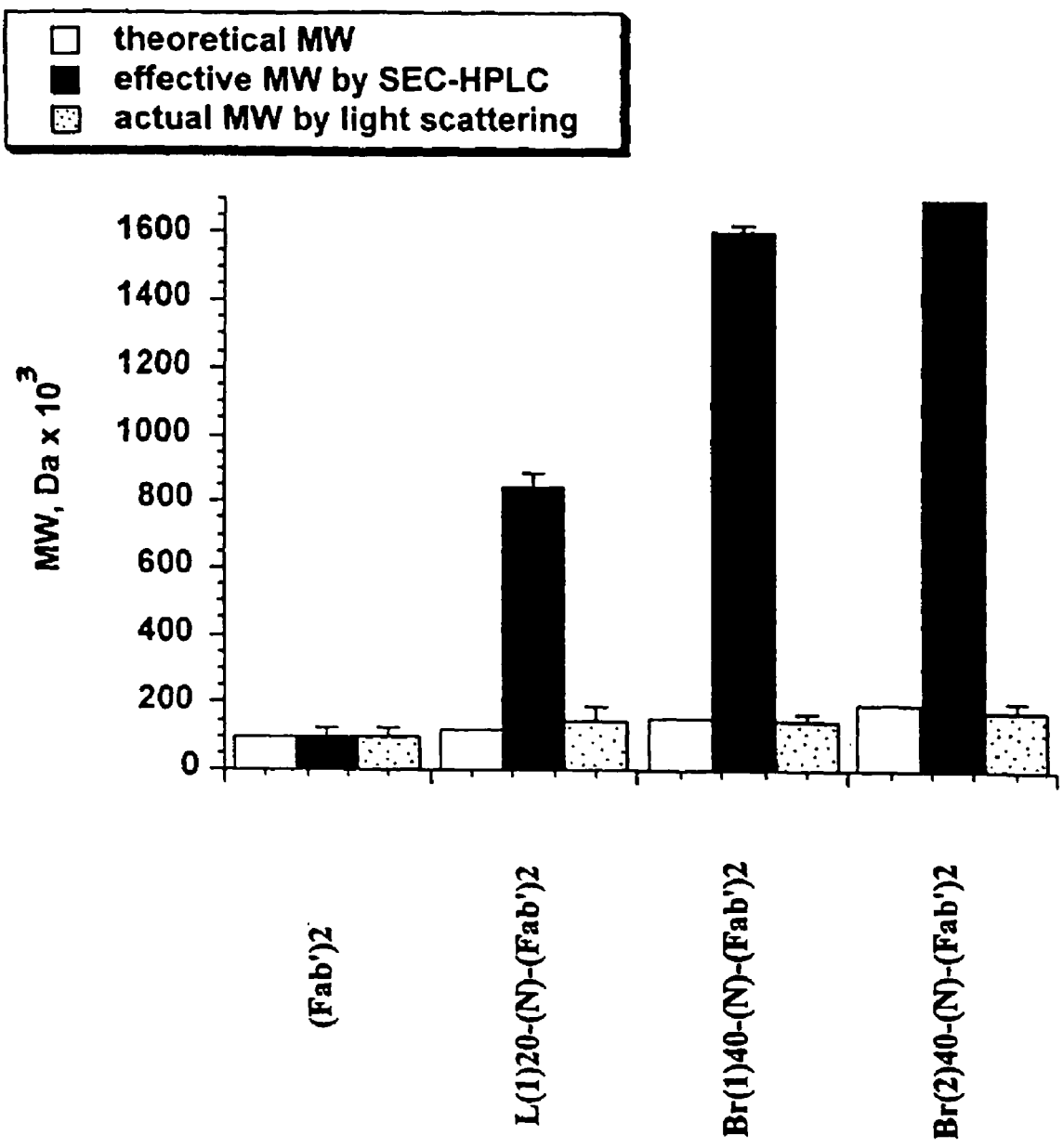

FIG. 63 is a graph depicting the theoretical molecular weight (open columns), effective size determined by SEC-HPLC (solid columns), and the actual molecular weight determined by SEC-light scattering (shaded columns) for various PEG-succinimide modified 6G4V11N35A F(ab')$_2$ molecules.

Figure 64:
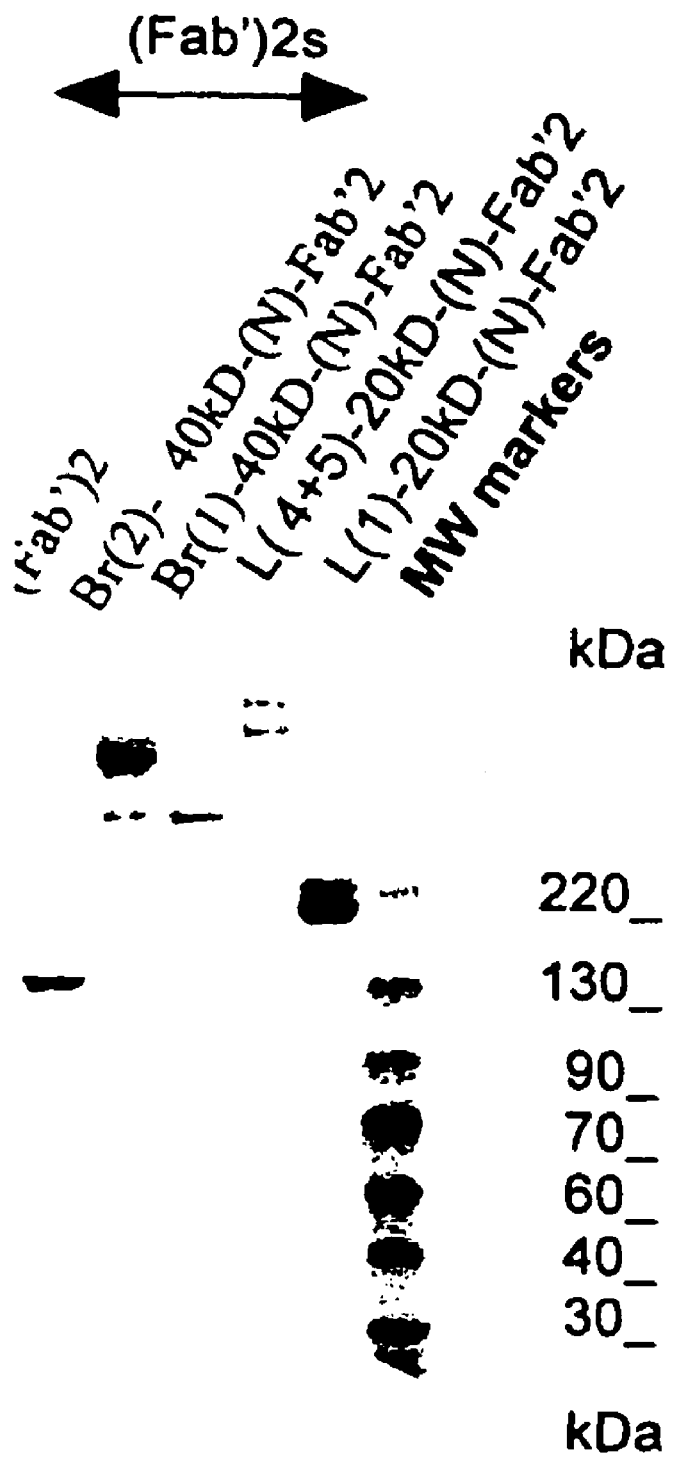

FIG. 64 is an SDS-PAGE gel depicting the electrophoretic mobility of various PEG-succinimide modified 6G4V11N35A F(ab')$_2$ molecules. From left to right, lane 1 contains unmodified F(ab')$_2$, lane 2 contains F(ab')$_2$ coupled to two 40 kD branched PEG-succinimide molecules (denoted "Br(2)-40kD(N)-F(ab')2"), lane 3 contains F(ab')$_2$ coupled to one 40 kD branched PEG-succinimide molecule (denoted "Br(1)-40 kD-(N)-Fab'2"), lane 4 contains a mixture of F(ab')$_2$ coupled to four 20 kD linear PEG-succinimide molecules and F(ab')$_2$ coupled to five 20 kD linear PEG-succinimide molecules (denoted "L(4+5)-20 kD-(N)-Fab'2"), lane 5 contains F(ab')$_2$ coupled to one 20 kD linear PEG-succinimide molecule (denoted "L(1)-20 kD-(N)-Fab'2"), and lane 6 contains molecular weight standards.

Figure 65A:
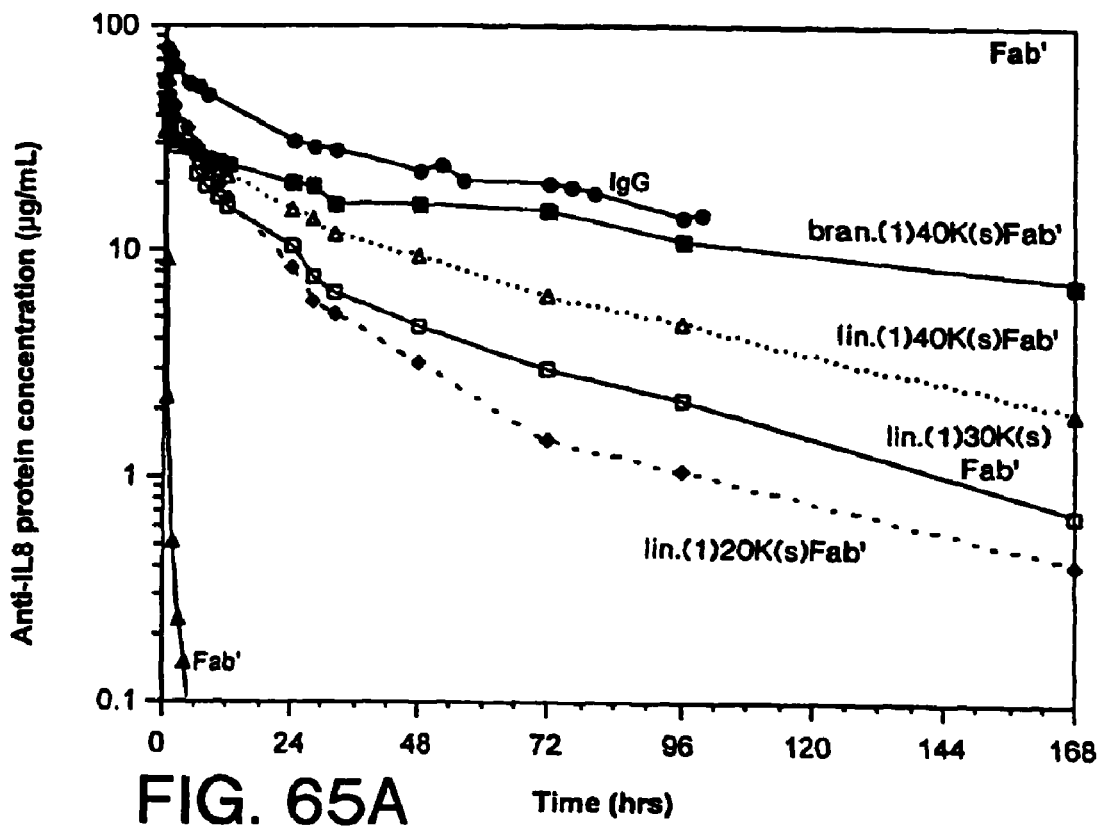
Figure 65B:
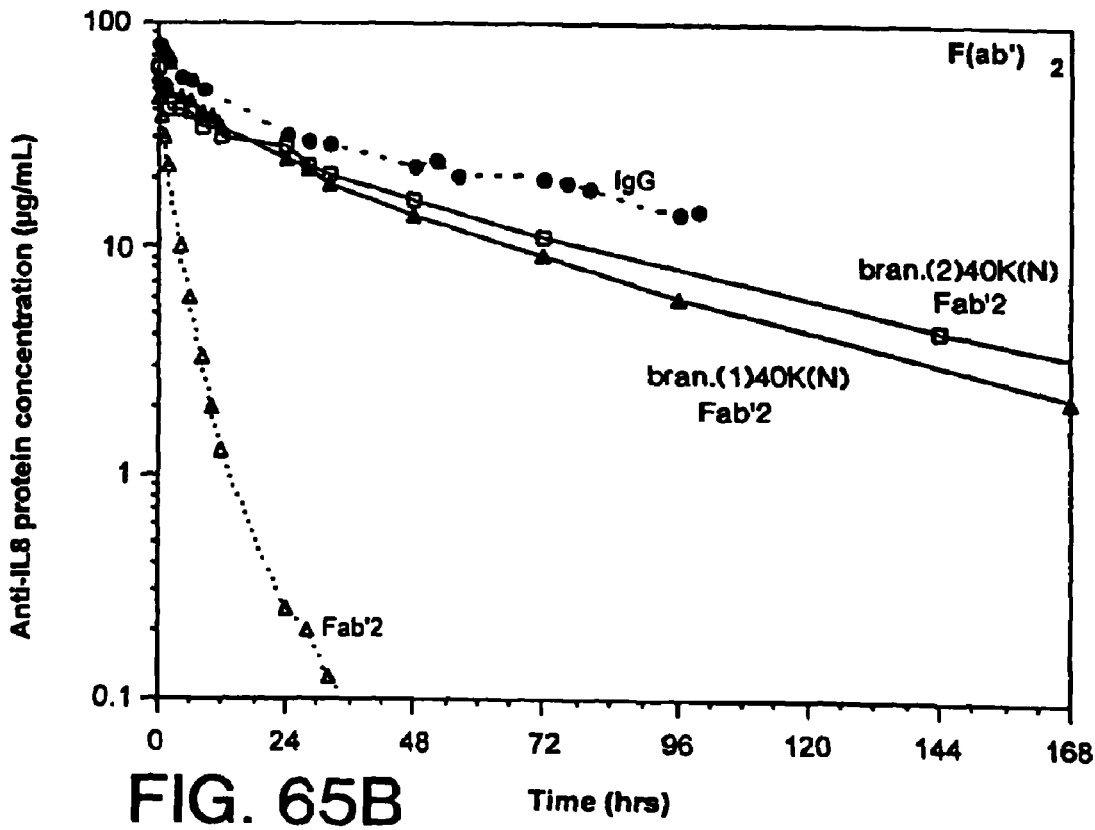

FIGS. 65A and 65B are graphs comparing the serum concentration vs. time profiles of various PEG-maleimide modified 6G4V11N35A Fab' molecules (FIG. 65A) and various PEG-succinimide modified 6G4V11N35A F(ab')$_2$ molecules (FIG. 65B) in rabbits. In FIG. 65A, "bran.(1)40K(s)Fab'" denotes 6G4V11N35A Fab' coupled to one 40 kD branched PEG-maleimide molecule, "lin.(1)40K(s)Fab'" denotes 6G4V11N35A Fab' coupled to one 40 kD linear PEG-maleimide molecule, "lin.(1)30K(s)Fab'" denotes 6G4V11N35A Fab' coupled to one 30 kD linear PEG-maleimide molecule, "lin.(1)20K(s)Fab'" denotes 6G4V11N35A Fab' coupled to one 20 kD linear PEG-maleimide molecule. In FIG. 65B, "bran.(2)40K(N)Fab'2" denotes 6G4V11N35A F(ab')$_2$ coupled to two 40 kD branched PEG-succinimide molecules, "bran.(1)40K(N)Fab'2" denotes 6G4V11N35A F(ab')$_2$ coupled to one 40 kD branched PEG-succinimide molecule, and "Fab'2" denotes unmodified 6G4V11N35A F(ab')$_2$. In both FIGS. 65A and 65B, "IgG" denotes a full length IgG1 equivalent of the human-murine chimeric anti-rabbit IL-8 Fab described in Example F below.

Figure 66:
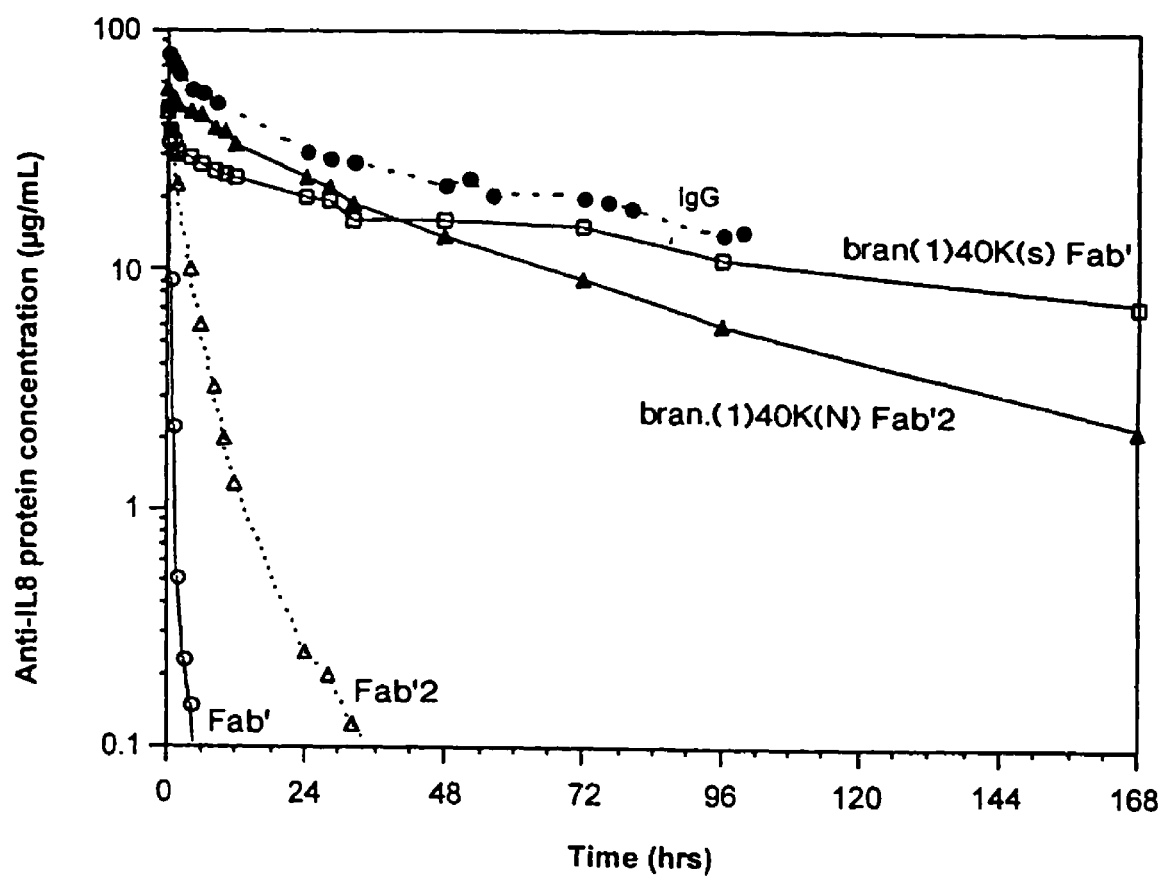

FIG. 66 contains graphs comparing the serum concentration vs. time profiles of 6G4V11N35A Fab' coupled to one 40 kD branched PEG-maleimide molecule (denoted as "bran.(1) 40K(s)Fab'"), 6G4V11N35A F(ab')$_2$ coupled to one 40 kD branched PEG-succinimide molecule (denoted as "bran.(1) 40K(N)Fab'2"), unmodified 6G4V11N35A F(ab')$_2$ (denoted as "Fab'2"), unmodified 6G4V11N35A Fab' (denoted as "Fab'"), and a full length IgG1 (denoted as "IgG") equivalent of the human-murine chimeric anti-rabbit IL-8 Fab described in Example F below.

Figure 67:
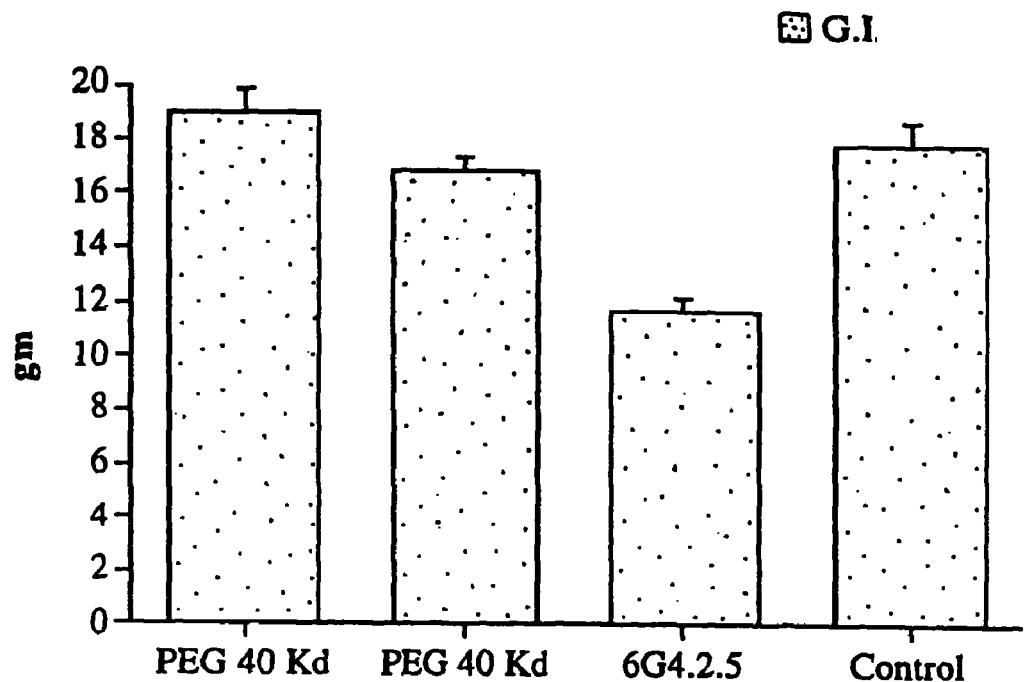

FIG. 67 is a graph depicting the effect of 6G4V11N35A Fab' coupled to one 40 kD branched PEG-maleimide molecule (denoted as "PEG 40 Kd") and murine anti-rabbit IL-8 monoclonal antibody 6G4.2.5 (full length IgG2a) (denoted as "6G4.2.5") on gross weight of entire lung in an ARDS rabbit model.

Figure 68:
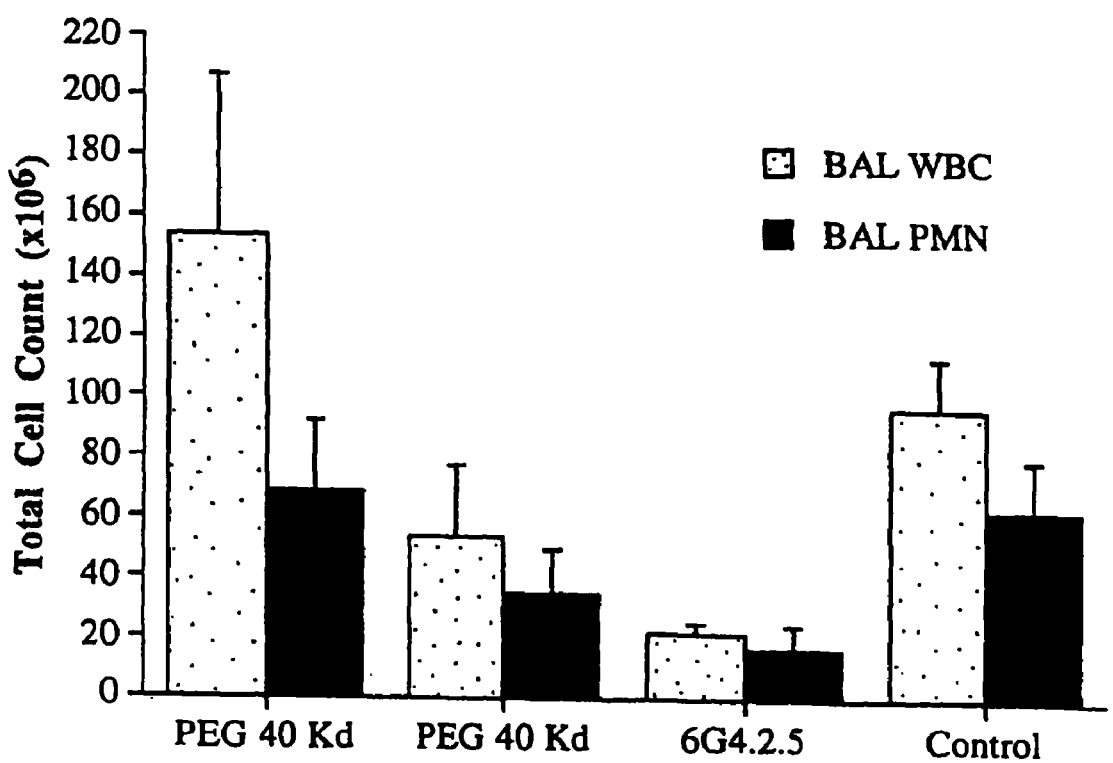

FIG. 68 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on BAL total leukocyte (light columns) and polymorphonuclear cell (dark columns) counts in an ARDS rabbit model. Untreated (no therapeutics) control animal data is denoted as "Control".

Figure 69:
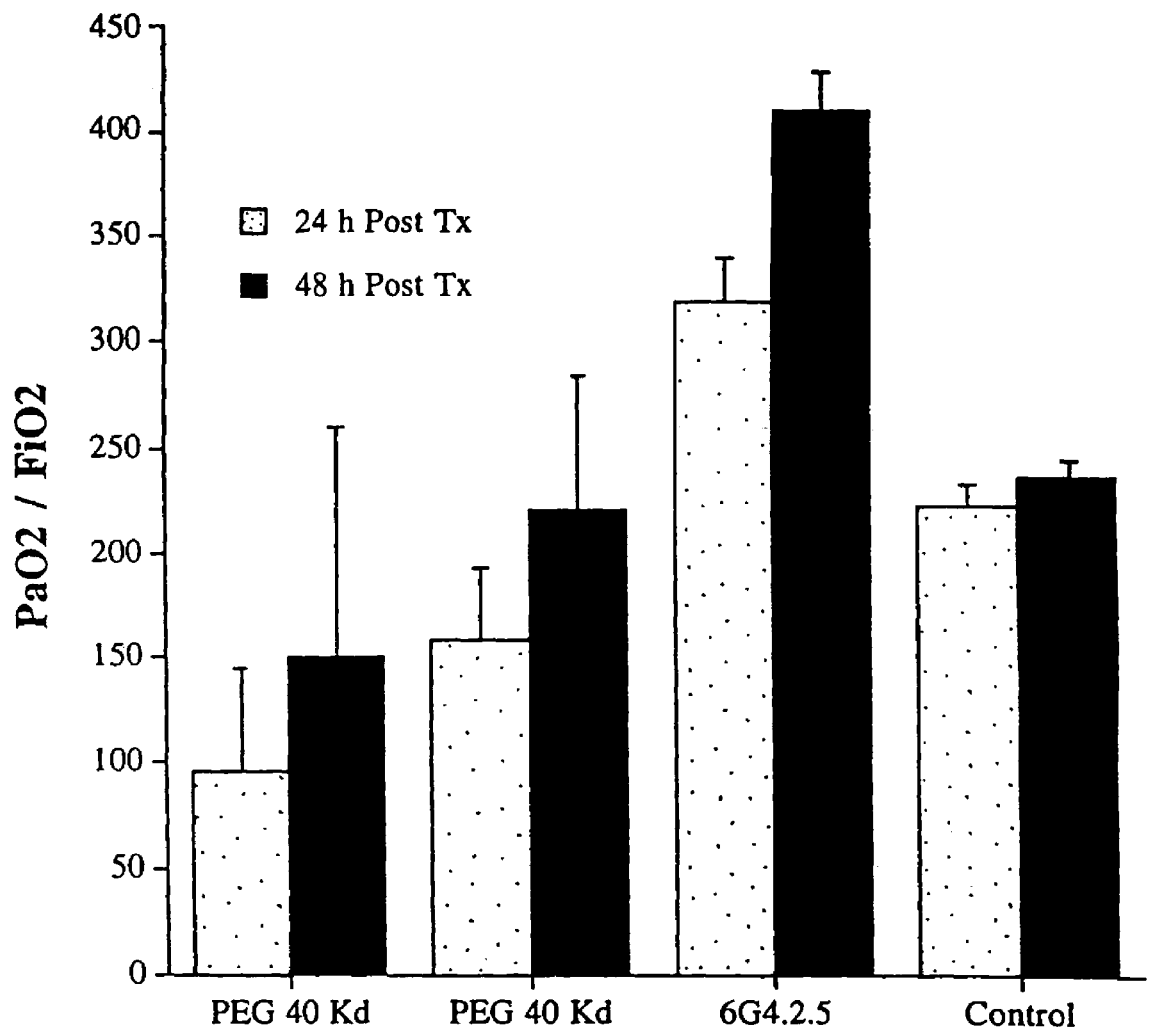

FIG. 69 is a graph depicting the effect of 6G4V11N35A Fab' coupled to one branched 40 kD PEG-maleimide molecule (denoted as "PEG 40 Kd") and murine anti-rabbit IL-8 monoclonal antibody 6G4.2.5 (full length IgG2a) (denoted as "6G4.2.5") on PaO2/FiO2 ratio at 24 hours-post treatment (light columns) and 48 hours post-treatment (dark columns) in an ARDS rabbit model. Untreated (no therapeutics) control animal data is denoted as "Control".

Figure 70A:
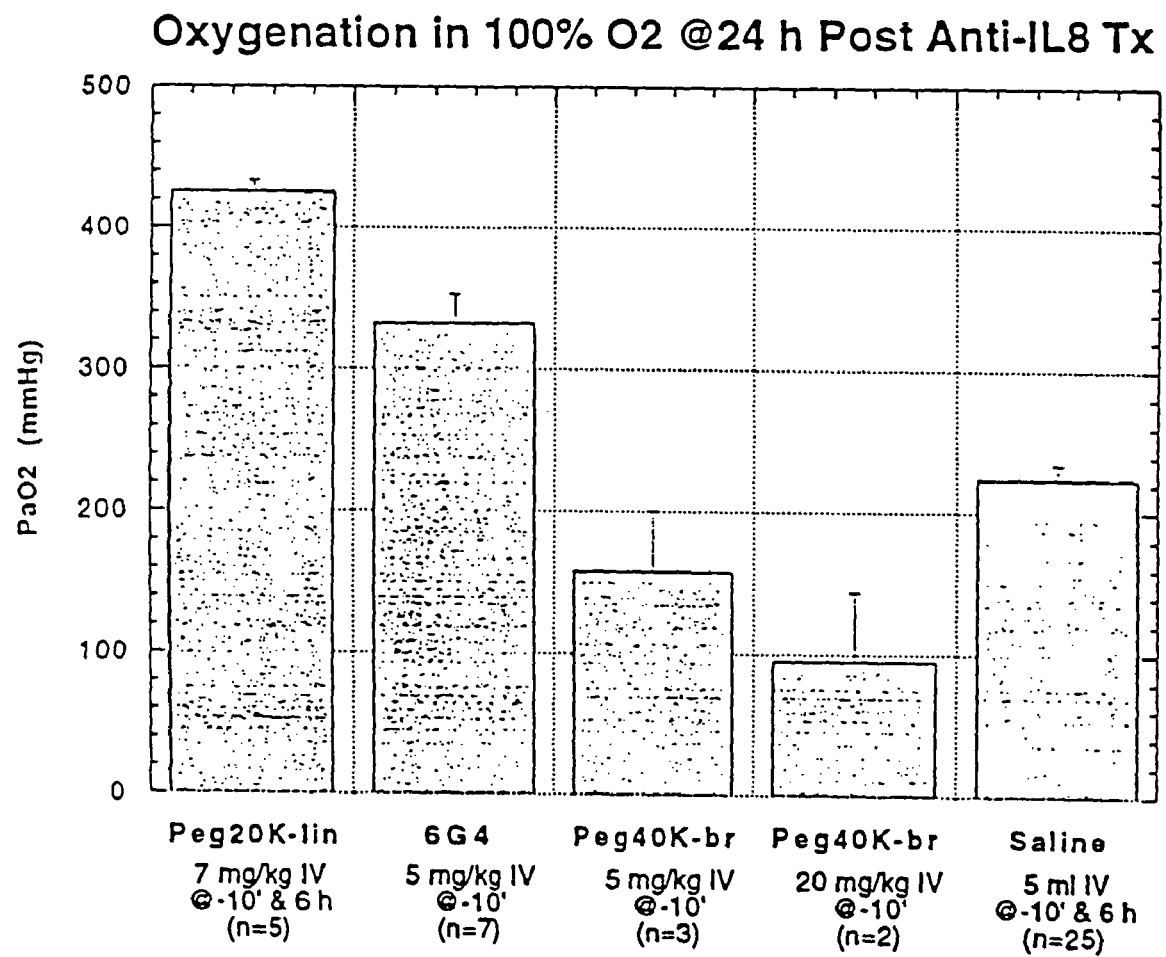

FIG. 70A is a graph depicting PaO2/FiO2 ratios obtained in 100% oxygen at 24 hours after acid instillation for: (1) rabbits (n=5) treated with 7 mg/kg IV 20 kD linear PEG-6G4V11N35E Fab' at 10 minutes before and 6 hours after acid instillation, (2) rabbits (n=7) treated with 5 mg/kg IV full length IgG murine anti-rabbit IL-8 monoclonal antibody 6G4.2.5 at 10 minutes before acid instillation, (3) rabbits (n=3) treated with 5 mg/kg IV 40 kD branched PEG-6G4V11N35A Fab' at 10 minutes before acid instillation, (4) rabbits (n=2) treated with 20 mg/kg IV 40 kD branched PEG-6G4V11N35A Fab' at 10 minutes before acid instillation, and (5) rabbits (n=25) treated with 5 ml IV saline at 10 minutes before and 6 hours after acid instillation.

Figure 70B:
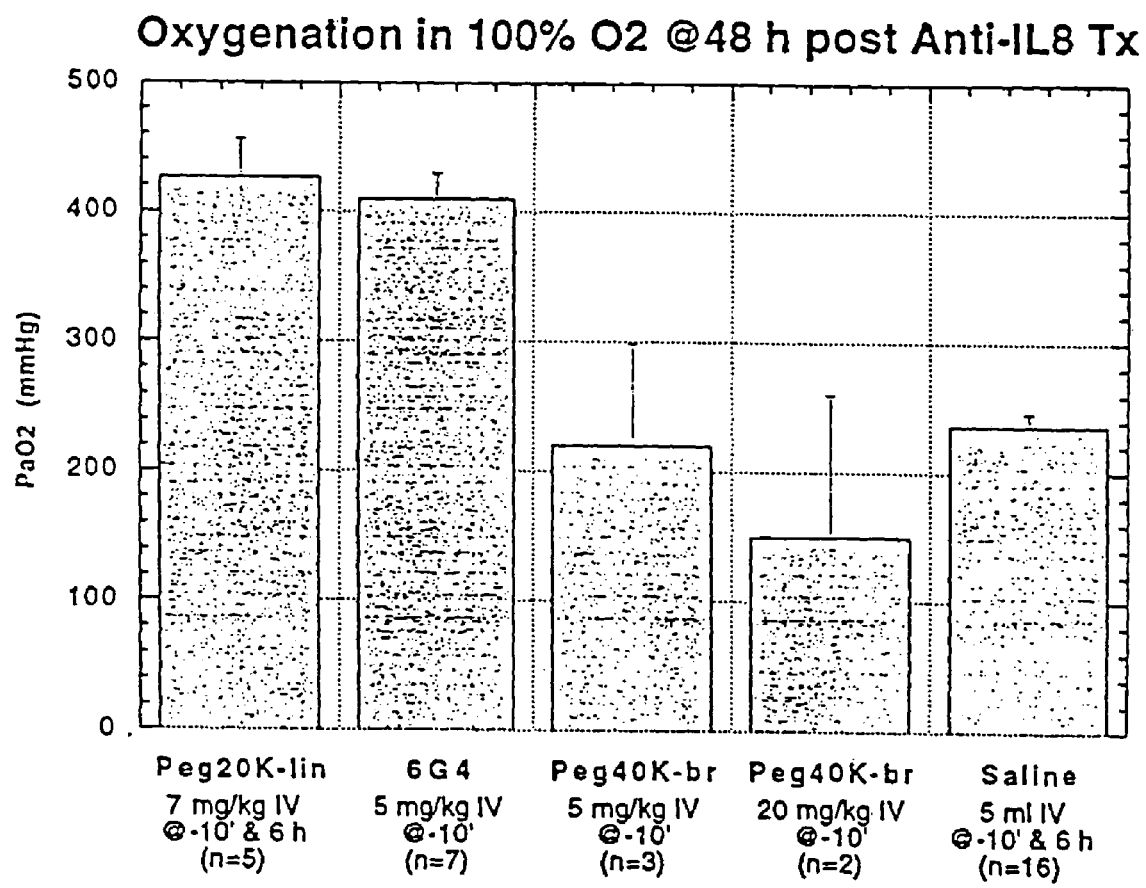

FIG. 70B is a graph depicting PaO2/FiO2 ratios obtained in 100% oxygen at 48 hours after acid instillation for: (1) rabbits (n=5) treated with 7 mg/kg IV 20 kD linear PEG-6G4V11N35E Fab' at 10 minutes before and 6 hours after acid instillation, (2) rabbits (n=7) treated with 5 mg/kg IV full length IgG murine anti-rabbit IL-8 monoclonal antibody 6G4.2.5 at 10 minutes before acid instillation, (3) rabbits (n=3) treated with 5 mg/kg IV 40 kD branched PEG-6G4V11N35A Fab' at 10 minutes before acid instillation, (4) rabbits (n=2) treated with 20 mg/kg IV 40 kD branched PEG-6G4V11N35A Fab' at 10 minutes before acid instillation, and (5) rabbits (n=16) treated with 5 ml IV saline at 10 minutes before and 6 hours after acid instillation.

Figure 70C:
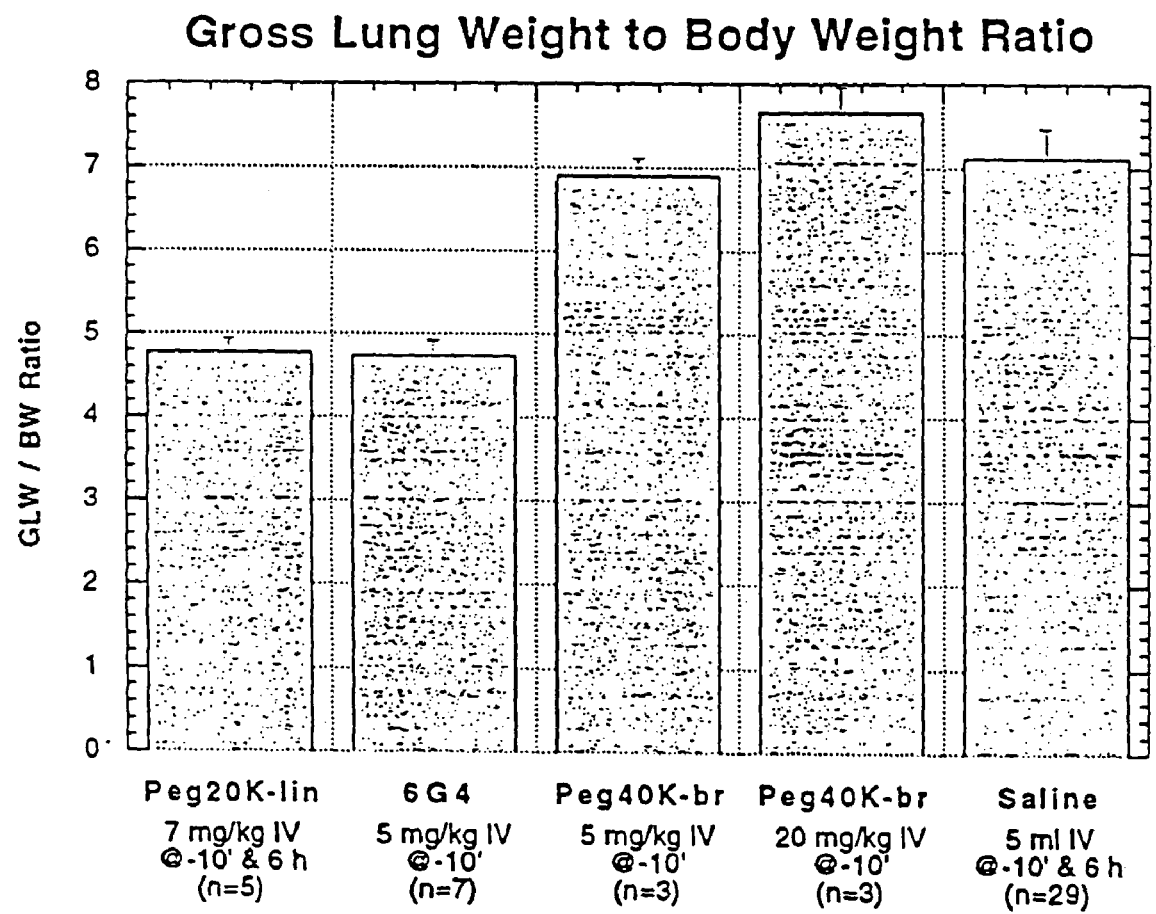

FIG. 70C is a graph depicting gross lung weight (in grams)/body weight (in kilograms) ratios (denoted as "GLW/BW Ratio") obtained at 72 hours post reperfusion for: (1) rabbits (n=5) treated with 7 mg/kg IV 20 kD linear PEG-6G4V11N35E Fab' at 10 minutes before and 6 hours after acid instillation, (2) rabbits (n=7) treated with 5 mg/kg IV full length IgG murine anti-rabbit IL-1-8 monoclonal antibody 6G4.2.5 at 10 minutes before acid instillation, (3) rabbits (n=3) treated with 5 mg/kg IV 40 kD branched PEG-6G4V11N35A Fab' at 10 minutes before acid instillation, (4) rabbits (n=3) treated with 20 mg/kg IV 40 kD branched PEG-6G4V11N35A Fab' at 10 minutes before acid instillation, and (5) rabbits (n=29) treated with 5 ml IV saline at 10 minutes before and 6 hours after acid instillation.

Figure 70D:
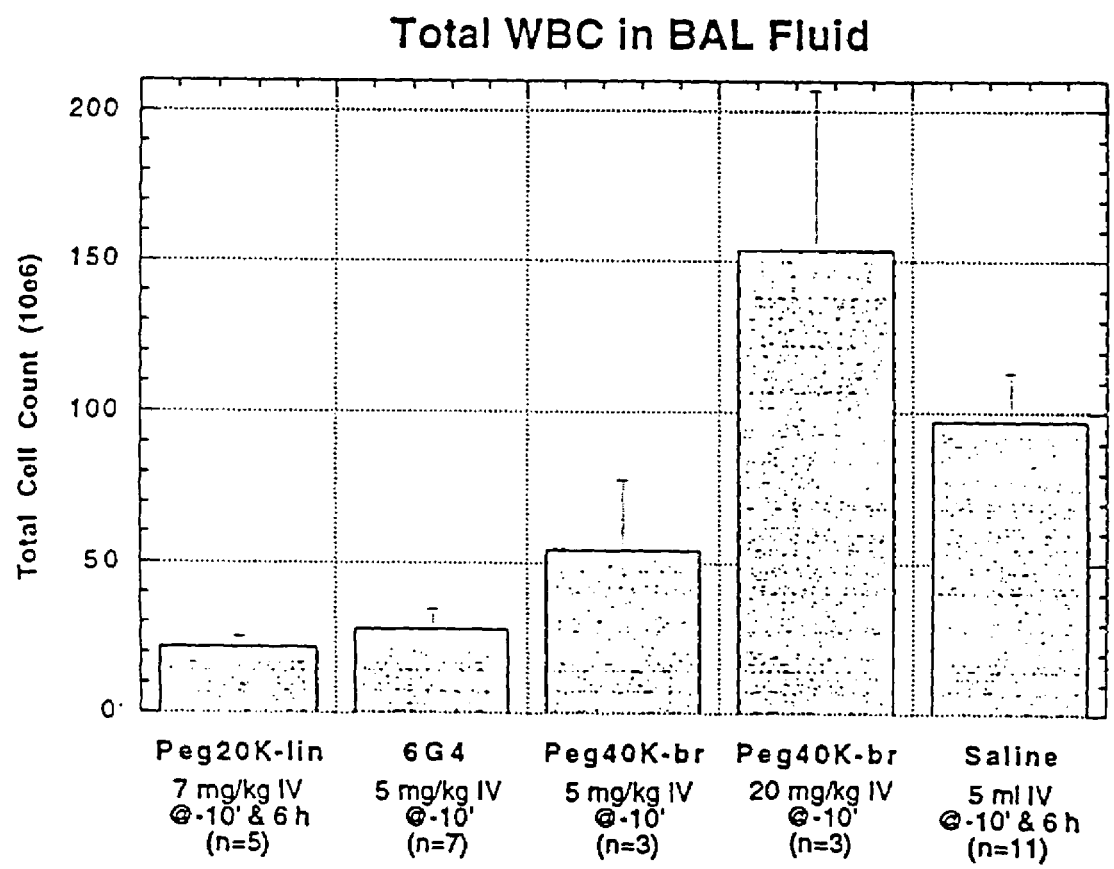

FIG. 70D is a graph depicting total leukocyte (WBC) count in BAL fluid (represented in millions of cells counted in 20 ml BAL fluid) obtained at 72 hours post reperfusion for: (1) rabbits (n=5) treated with 7 mg/kg IV 20 kD linear PEG-6G4V11N35E Fab' at 10 minutes before and 6 hours after acid instillation, (2) rabbits (n=7) treated with 5 mg/kg IV full length IgG murine anti-rabbit IL-8 monoclonal antibody 6G4.2.5 at 10 minutes before acid instillation, (3) rabbits (n=3) treated with 5 mg/kg IV 40 kD branched PEG-6G4V11N35A Fab' at 10 minutes before acid instillation, (4) rabbits (n=3) treated with 20 mg/kg IV 40 kD branched PEG-6G4V11N35A Fab' at 10 minutes before acid instillation, and (5) rabbits (n=11) treated with 5 ml IV saline at 10 minutes before and 6 hours after acid instillation.

Figure 70E:
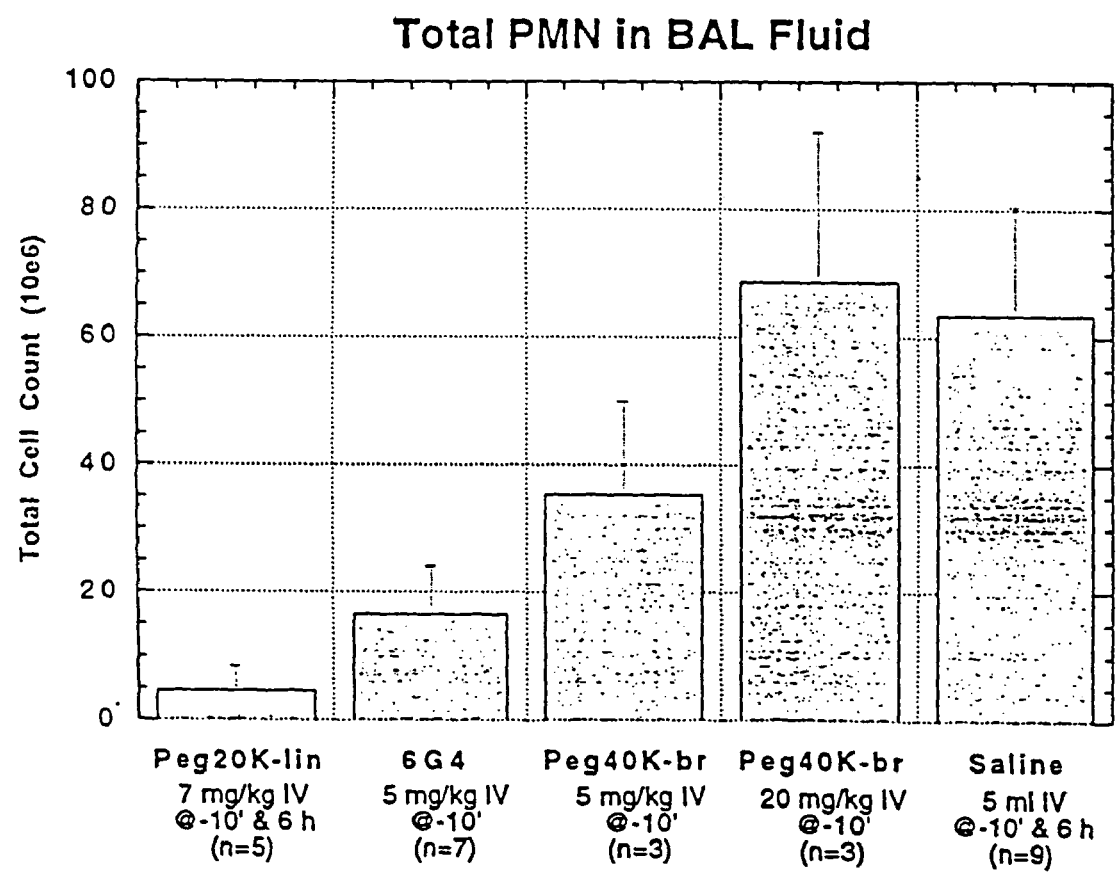

FIG. 70E is a graph depicting total polymorphonuclear (PMN) cell count in BAL fluid (represented in millions of cells counted in 20 ml BAL fluid) obtained at 72 hours post reperfusion for: (1) rabbits (n=5) treated with 7 mg/kg IV 20 kD linear PEG-6G4V11N35E Fab' at 10 minutes before and 6 hours after acid instillation, (2) rabbits (n=7) treated with 5 mg/kg IV full length IgG murine anti-rabbit IL-8 monoclonal antibody 6G4.2.5 at 10 minutes before acid instillation, (3) rabbits (n=3) treated with 5 mg/kg IV 40 kD branched PEG-6G4V11N35A Fab' at 10 minutes before acid instillation, (4) rabbits (n=3) treated with 20 mg/kg IV 40 kD branched PEG-6G4V11N35A Fab' at 10 minutes before acid instillation, and (5) rabbits (n=9) treated with 5 ml IV saline at 10 minutes before and 6 hours after acid instillation.

Figure 71:
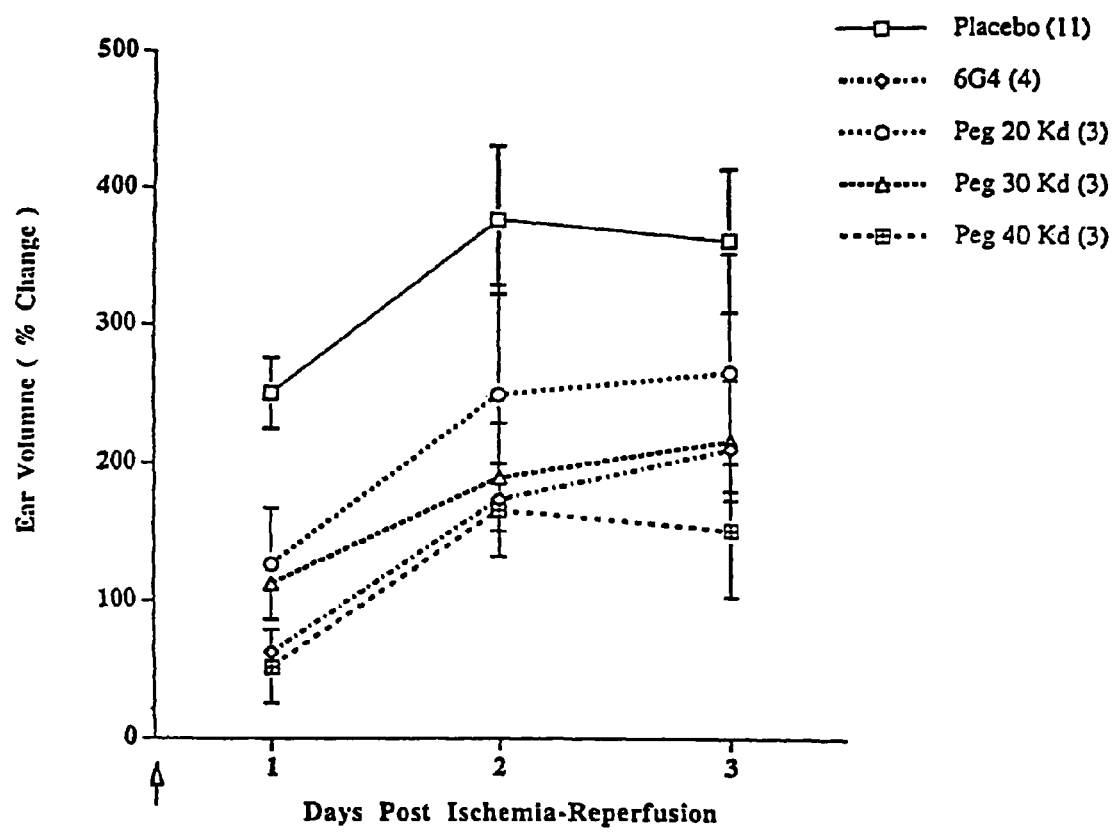

FIG. 71 is a graph depicting the effect of pegylated anti-IL-8 Fab' (as measured by percent change in ear volume at 1, 2 and 3 days post reperfusion) in a rabbit ear model of ischemia reperfusion injury. The data points from animals treated with empty vehicle (n=11), full length IgG murine anti-rabbit IL-8 monoclonal antibody 6G4.2.5 (n=4), 20 kD linear PEG-6G4V11N35E Fab' (n=3), 30 kD linear PEG-6G4V11N35E Fab' (n=3), and 40 kD branched PEG-6G4V11N35E Fab' (n=3) are denoted by open boxes, open diamonds, open circles, open triangles, and crossed boxes, respectively.

Figure 72:
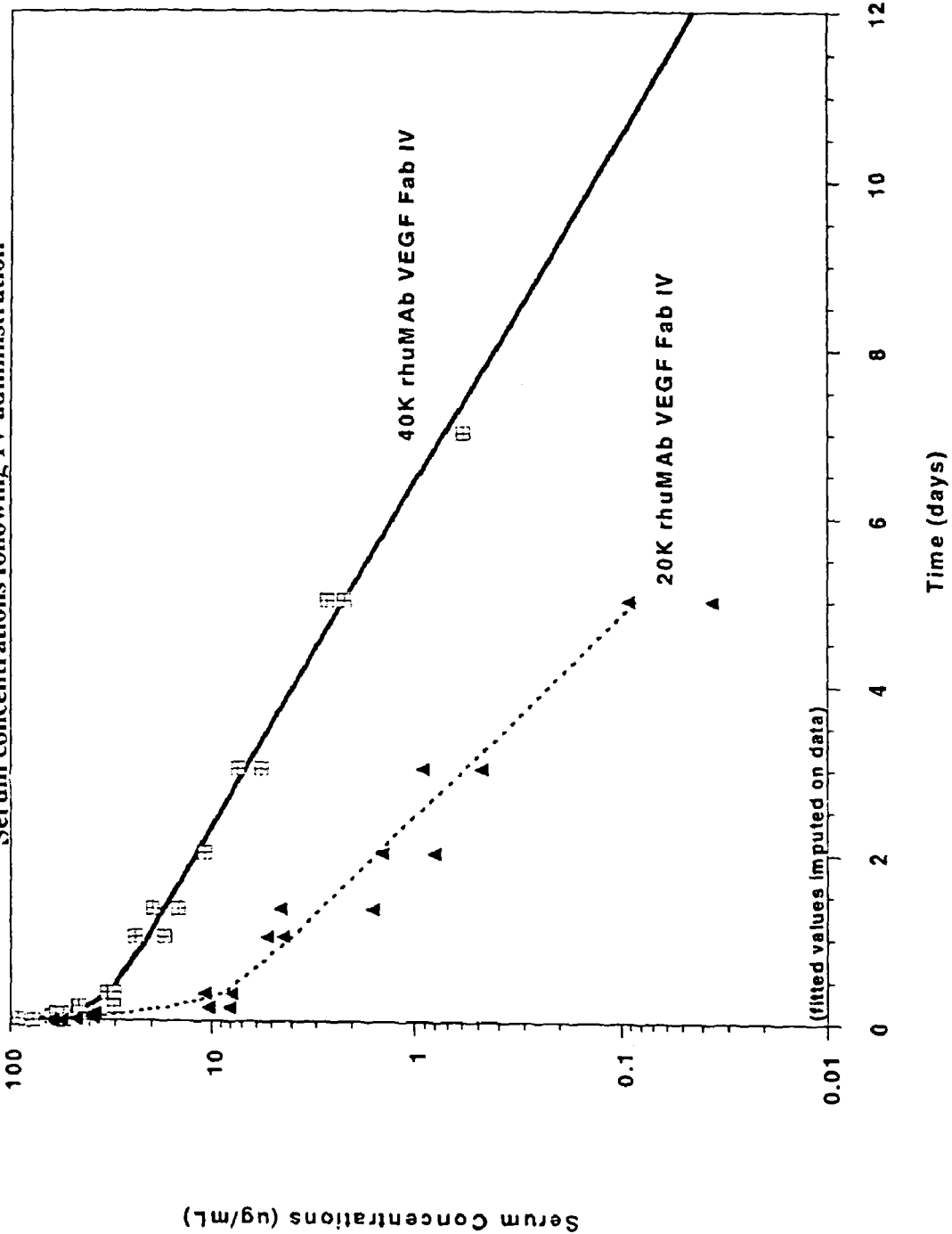

FIG. 72 is a graph comparing the serum concentration vs. time profiles of 20 kD linear PEG-maleimide modified Y0317 anti-human VEGF Fab' (denoted as "20K rhuMAb VEGF Fab IV") and 40 kD branched PEG-maleimide modified Y0317 anti-human VEGF Fab' (denoted as "40K rhuMAb VEGF Fab IV") molecules administered intravenously in mice.

Figure 73:
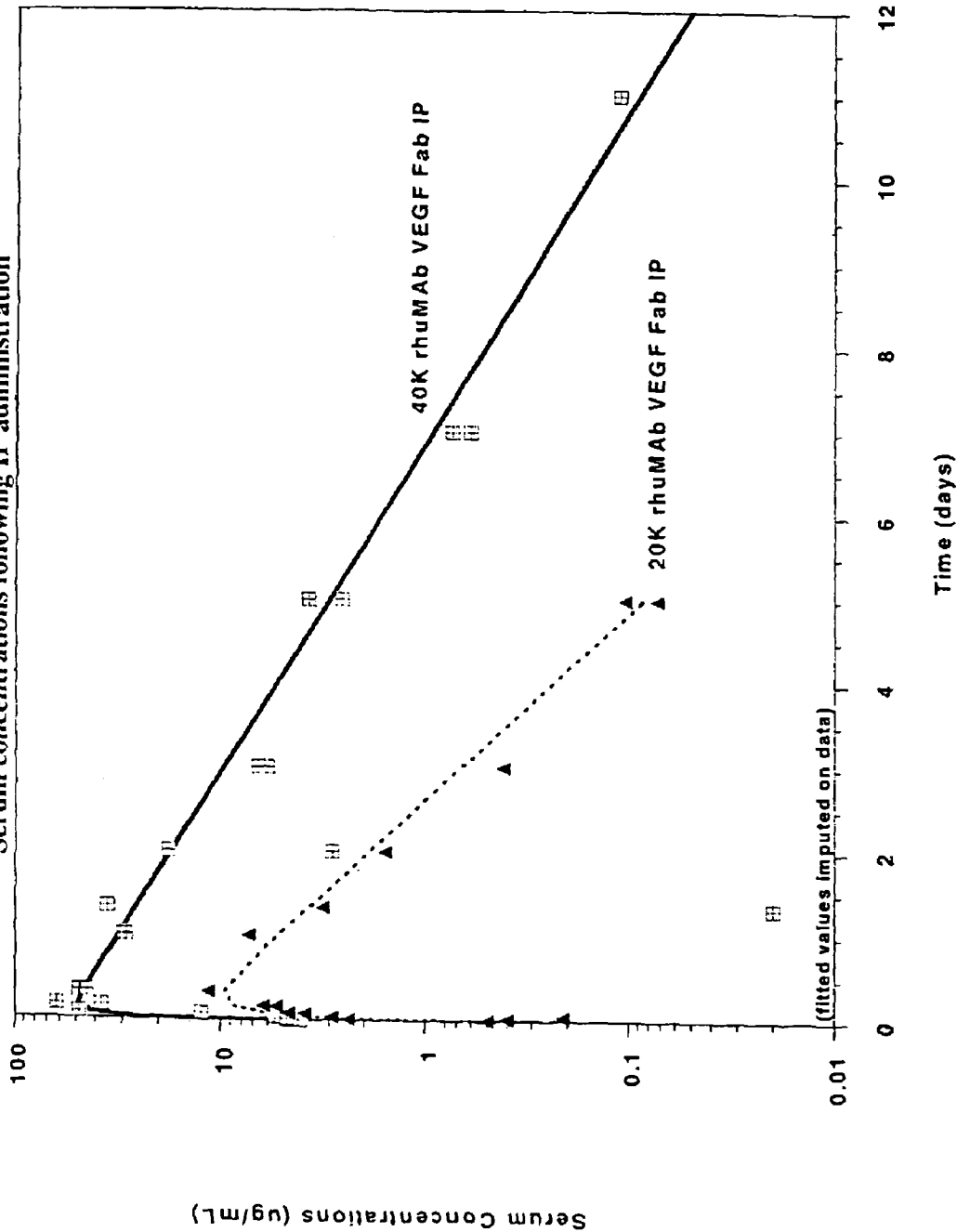

FIG. 73 is a graph comparing the serum concentration vs. time profiles of 20 kD linear PEG-maleimide modified Y0317 anti-human VEGF Fab' (denoted as "20K rhuMAb VEGF Fab IP") and 40 kD branched PEG-maleimide modified Y0317 anti-human VEGF Fab' (denoted as "40K rhuMAb VEGF Fab IP") molecules administered intraperitoneally in mice.

Figure 74:
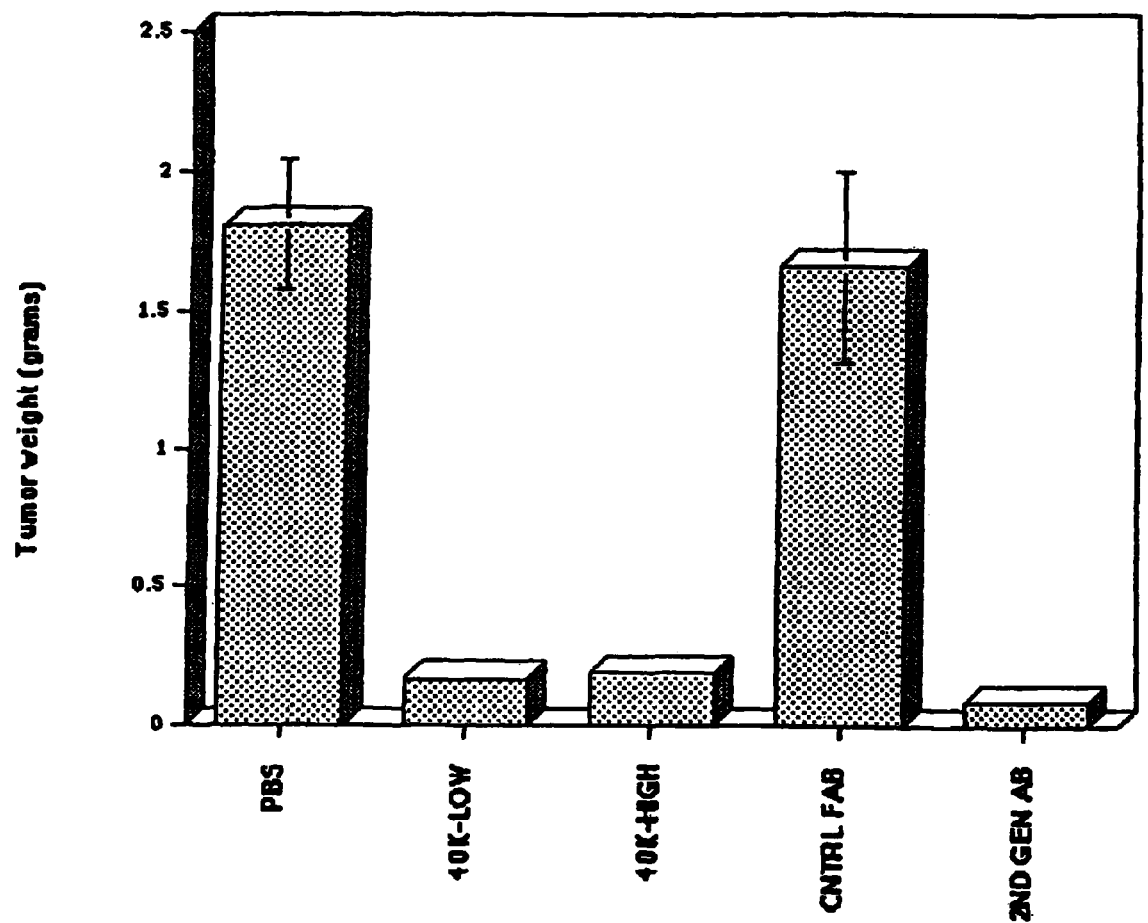

FIG. 74 is a graph comparing inhibition of tumor growth in vivo in mice by intraperitoneal administration of 40 kD branched PEG-maleimide modified Y0317 anti-human VEGF Fab' (2 mg/kg loading dose on day 1 followed by 0.9 mg/kg/day maintenance dose for the remainder of the study) (denoted "40K-LOW"), 40 kD branched PEG-maleimide modified Y0317 anti-human VEGF Fab' (6 mg/kg loading dose on day 1 followed by 2.7 mg/kg/day maintenance dose for the remainder of the study) (denoted "40K-HIGH"), 40 kD branched PEG-6G4V11N35E Fab' (6 mg/kg loading dose on day 1 followed by 2.7 mg/kg/day maintenance dose for the remainder of the study) (denoted "CNTRL FAB'), Y0317 anti-human VEGF MAb (8 mg/kg loading dose on day 1 followed by 0.8 mg/kg maintenance dose every third day for the remainder of the study) (denoted "2ND GEN AB"), and phosphate buffered saline at physiological pH (0.1 ml/day for the duration of the study) (denoted "PBS").

DESCRIPTION OF THE PREFERRED EMBODIMENTS

I. Definitions

In general, the following words or phrases have the indicated definition when used in the description, examples, and claims.

"Polymerase chain reaction" or "PCR" refers to a procedure or technique in which minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.* 51:263 (1987); Erlich, ed., *PCR Technology* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., *J. Mol. Biol.* 186:651 (1985); Novotny and Haber, *Proc. Natl. Acad. Sci. U.S.A.* 82:4592 (1985)).

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab' fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in *The Pharmacology of Monoclonal Anibodies*, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (k) and lambda (l), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ(, and μ, respectively. The subunit structures and three-dimensional configurations of different classes of immunoglobulins are well known.

The term "antibody" is used in the broadest sense and specifically covers single monoclonal antibodies (including agonist and antagonist antibodies) and antibody compositions with polyepitopic specificity.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fe region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). Suitable leucine zipper sequences include the jun and fos leucine zippers taught by Kostelney et al., *J. Immunol.*, 148: 1547-1553 (1992) and the GCN4 leucine zipper described in the Examples below.

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

Unless specifically indicated to the contrary, the terms "polymer", "polymer molecule", "nonproteinaceous polymer", and "nonproteinaceous polymer molecule" are used interchangeably and are defined as a molecule formed by covalent linkage of two or more monomers, wherein none of the monomers is contained in the group consisting of alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), and tyrosine (Tyr) residues.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567 to Cabilly et al.). The "monoclonal antibodies" also include clones of antigen-recognition and binding-site containing antibody fragments (Fv clones) isolated from phage antibody libraries using the techniques described in Clackson et al., *Nature*, 352:624-628 (1991) and Marks et al., *J. Mol. Biol.*, 222:581-597 (1991), for example.

The monoclonal antibodies herein include hybrid and recombinant antibodies produced by splicing a variable (including hypervariable) domain of an anti-IL-8 antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. (See, e.g., U.S. Pat. No. 4,816,567 to Cabilly et al.; Mage and Lamoyi, in *Monoclonal Antibody Production Techniques and Applications*, pp. 79-97 (Marcel Dekker, Inc., New York, 1987).)

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Cabilly et al., supra; Morrison et al., *Proc. Natl. Acad. Sci. U.S.A.* 81:6851 (1984)).

"Humanized" forms of non-human (e.g., murine) antibodies are specific chimeric immunoglobulins, immunoglobulin chains or fragments thereof (such as Fv, Fab, Fab', F(ab')$_2$, or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Furthermore, humanized antibodies can comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details see Jones et al., *Nature* 321:522 (1986); Reichmann et al., *Nature* 332:323 (1988); and Presta, *Curr. Op. Struct. Biol.* 2:593 (1992).

The terms "human vascular endothelial growth factor", "vascular endothelial growth factor", "human VEGF" and "VEGF" are used interchangeably herein to refer to the 165-amino acid human vascular endothelial cell growth factor polypeptide, and related 121-, 189-, and 206-amino acid vascular endothelial cell growth factor polypeptides, described by Leung et al., *Science* 246:1306 (1989), and Houck et al., *Mol. Endocrin.* 5:1806 (1991), together with the naturally occurring allelic and processed forms of such growth factor polypeptides.

The term "human VEGF receptor", "VEGF receptor", "human VEGFr" and "VEGFr" are used interchangeably herein to refer to a cellular receptor for VEGF, ordinarily a cell-surface receptor found on vascular endothelial cells, as well as variants thereof which retain the ability to bind human VEGF. One example of a VEGF receptor is the fms-like tyrosine kinase (flt), a transmembrane receptor in the tyrosine kinase family. DeVries et al., *Science* 255:989 (1992); Shibuya et al., *Oncogene* 5:519 (1990). The flt receptor comprises an extracellular domain, a transmembrane domain, and an intracellular domain with tyrosine kinase activity. The extracellular domain is involved in the binding of VEGF, whereas the intracellular domain is involved in signal transduction. Another example of a VEGF receptor is the flk-1 receptor (also referred to as KDR). Matthews et al., *Proc. Nat. Acad. Sci.* 88:9026 (1991); Terman et al., *Oncogene* 6:1677 (1991); Terman et al., *Biochem. Biophys. Res. Commun.* 187: 1579 (1992). Binding of VEGF to the flt receptor results in the formation of at least two high molecular weight complexes, having apparent molecular weight of 205,000 and 300,000 Daltons. The 300,000 Dalton complex is believed to be a dimer comprising two receptor molecules bound to a single molecule of VEGF.

As used herein, the terms "human p185 receptor-like tyrosine kinase", "c-Erb-B2", "ErbB2", "HER2", and "HER2 receptor" are used interchangeably to refer to the c-Erb-B2 polypeptide described in Yamamoto et al., *Nature*, 319: 230-234 (1986) (Genebank accession number X03363).

As used herein, the terms "human CD20" and "CD20" refer to the B1 cell-surface antigen (CD20) polypeptide described in Tedder et al., *Proc. Natl. Acad. Sci.* (*USA*), 85: 208-212 (1988).

As used herein, the terms "human CD18" and "CD18" refer to the integrin β-chain polypeptide (CD18) described in Kishimoto et al., *Cell*, 48: 681-690 (1987).

As used herein, the terms "human CD11a" and "CD11a" refer to the human CD11a polypeptide described in Edwards et al., *J. Biol. Chem.*, 270: 12635-12640 (1995), van Kooyk et al., *J. Exp. Med.*, 183(3): 1247-1252 (1996), or Champe et al., *J. Biol. Chem.*, 270: 1388-1394 (1995).

As used herein, the terms "human IgE" and "IgE" refer to any human immunoglobulin of the E isotype or class that binds to the human $Fc_\epsilon RI$ receptor α-chain.

As used herein, the terms "human $Fc_\epsilon RI$ receptor α-chain", "$Fc_\epsilon RI$ receptor α-chain", "human $Fc_\epsilon RI$ receptor", "$Fc_\epsilon RI$ receptor", "human $Fc_\epsilon RI$", and "$Fc_\epsilon RI$" are used interchangeably to refer to the human $Fc_\epsilon RI$ α-chain polypeptide described by Shimizu et al., *Proc. Natl. Acad. Sci.* (*USA*), 85: 1907-1911 (1988).

Figure 1:
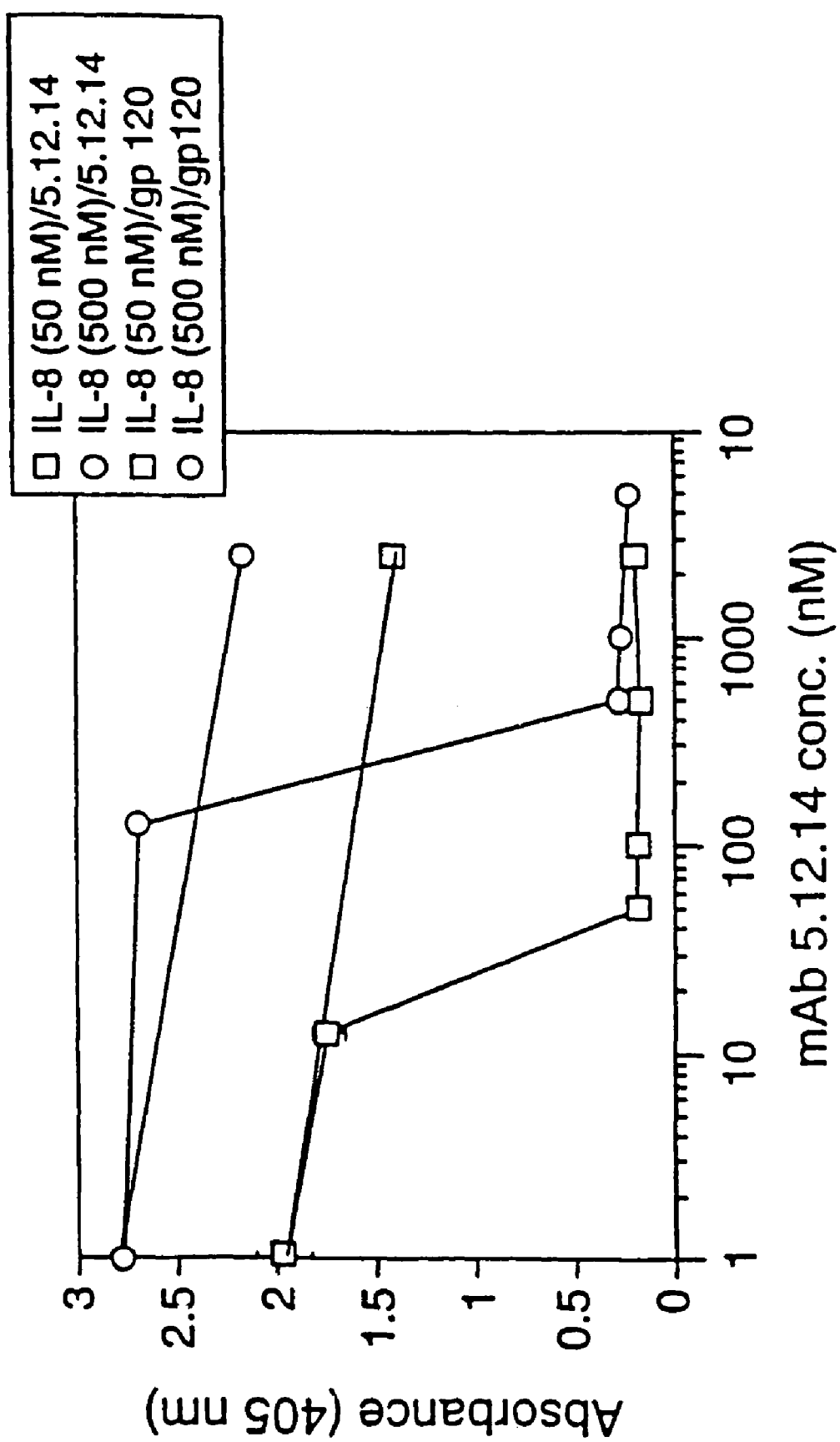
FIG. 1 is a graph depicting the blocking of IL-8 mediated elastase release from neutrophils by anti-IL-8 monoclonal antibody 5.12.14.

As used herein, the terms "human Apo-2 receptor", "Apo-2 receptor", "human Apo-2", and "Apo-2" are used interchangeably to refer to the Apo-2 polypeptide described in FIG. 1 of WO 98/51793 (published Nov. 19, 1998) (International Application No. PCT/US98/09704).

Figure 10:
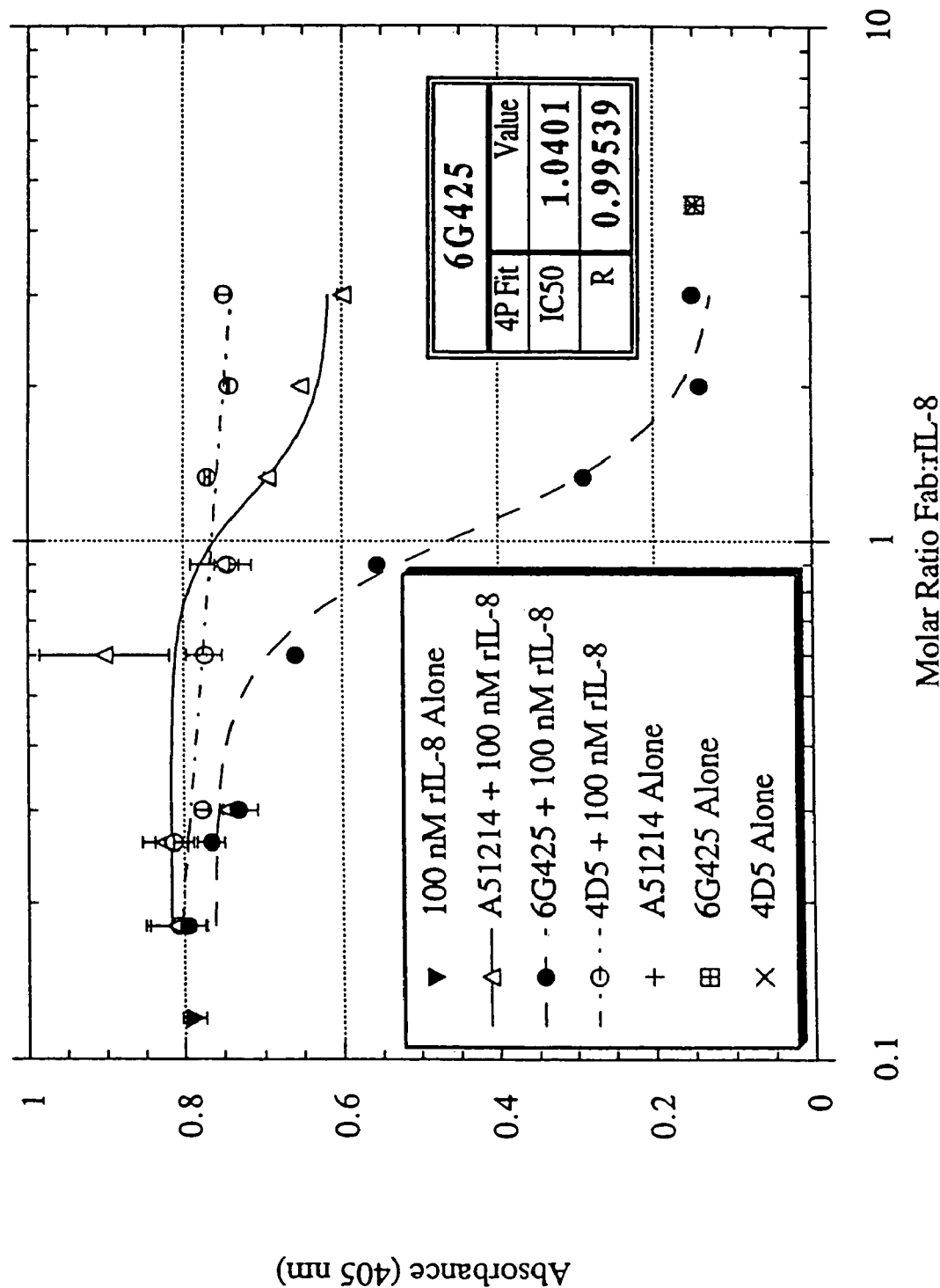
FIG. 10 is a graph depicting the relative abilities of chimeric 6G4.2.5 Fab and chimeric 5.12.14 Fab to inhibit elastase release from human neutrophils stimulated by rabbit IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.
Figure 11B:
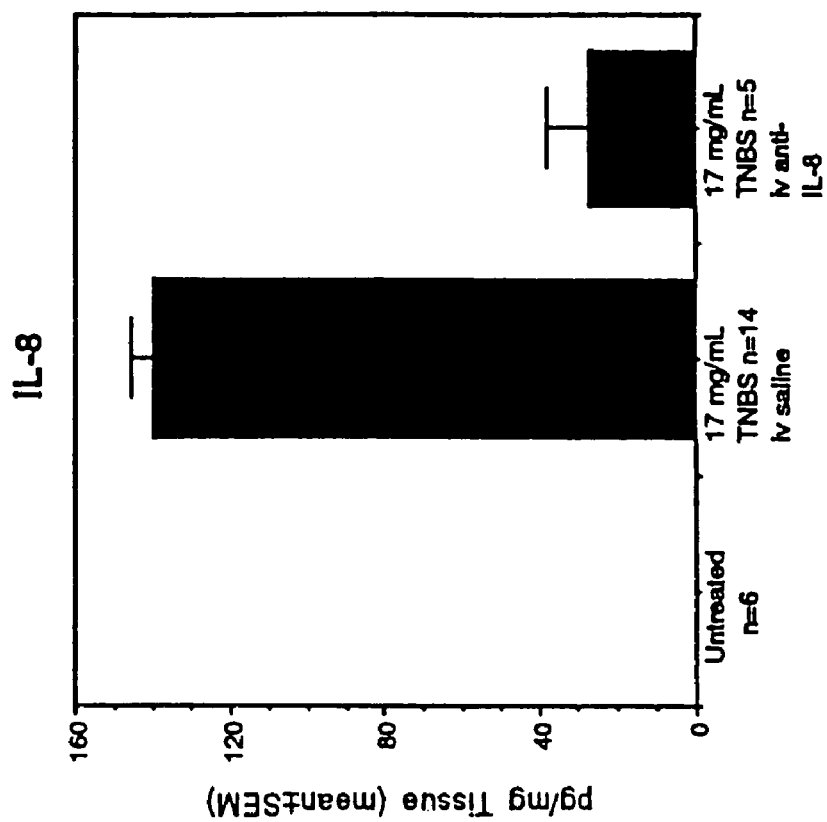
FIGS. 11A-11J are a set of graphs depicting the following parameters in a rabbit ulcerative colitis model.
Figure 11A:
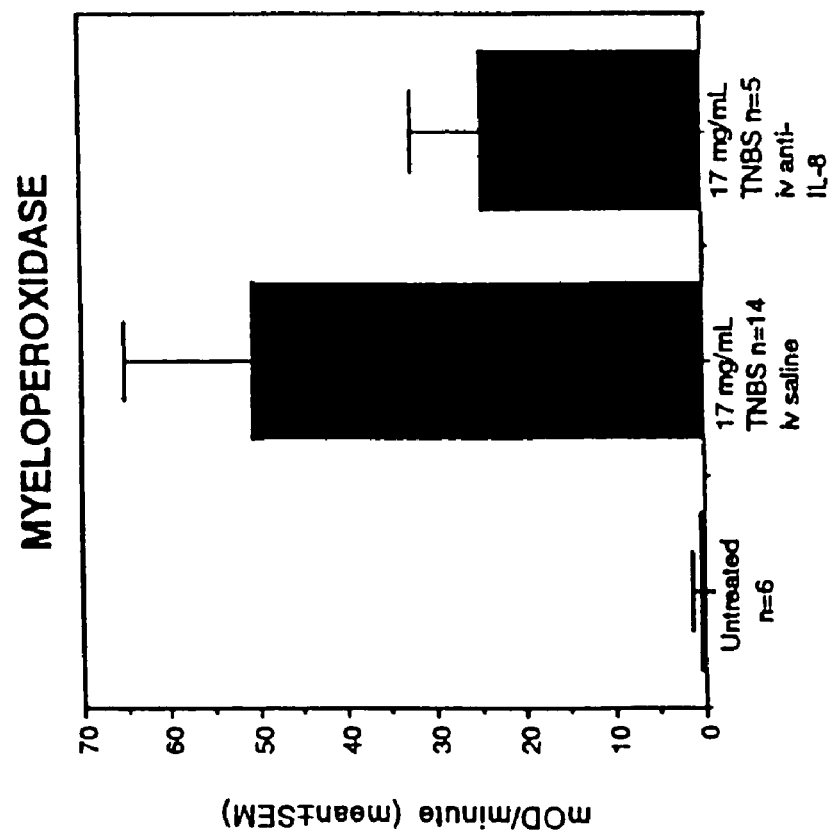
Figure 11D:
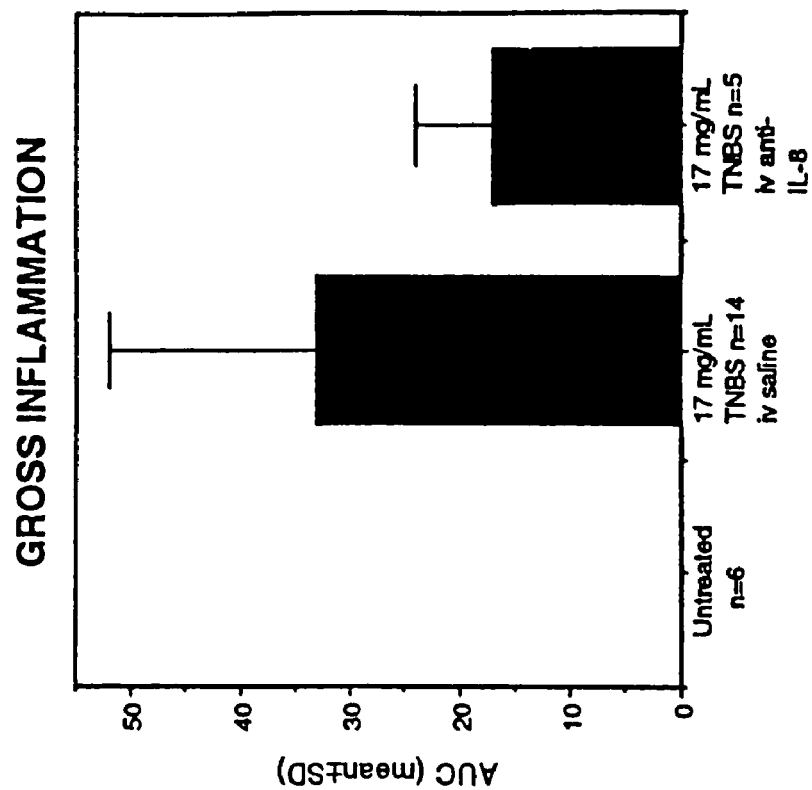
Figure 11C:
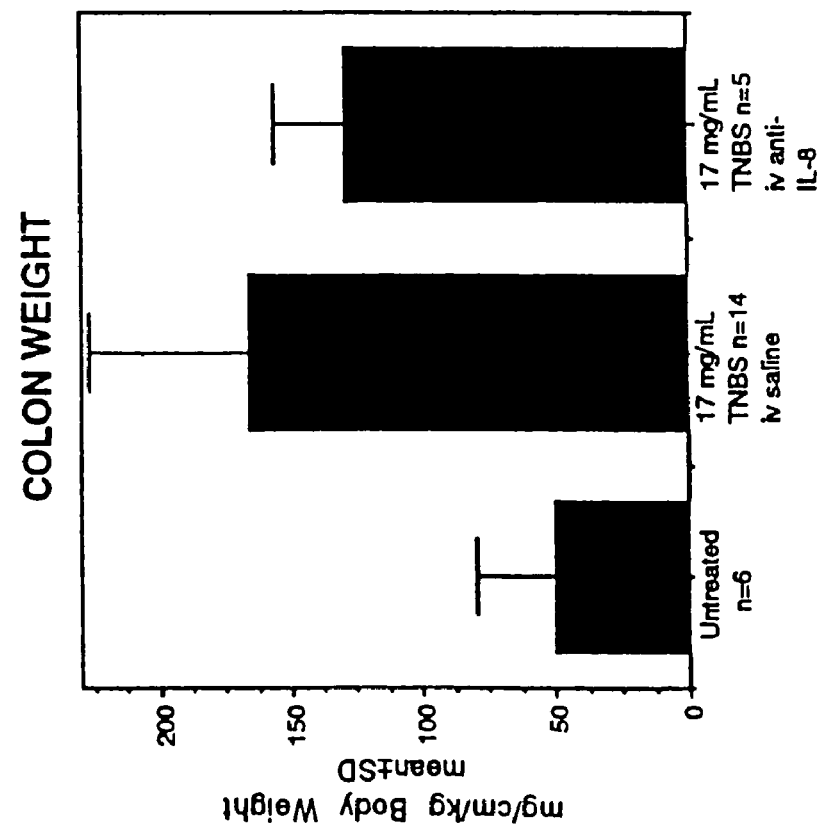
Figure 11F:
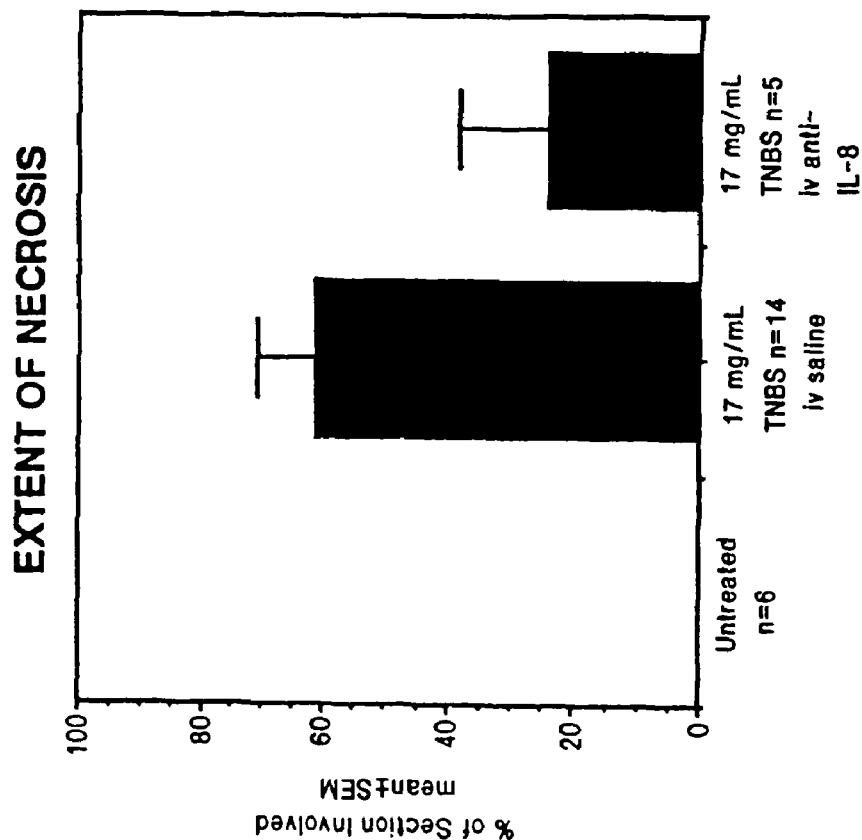
Figure 11E:
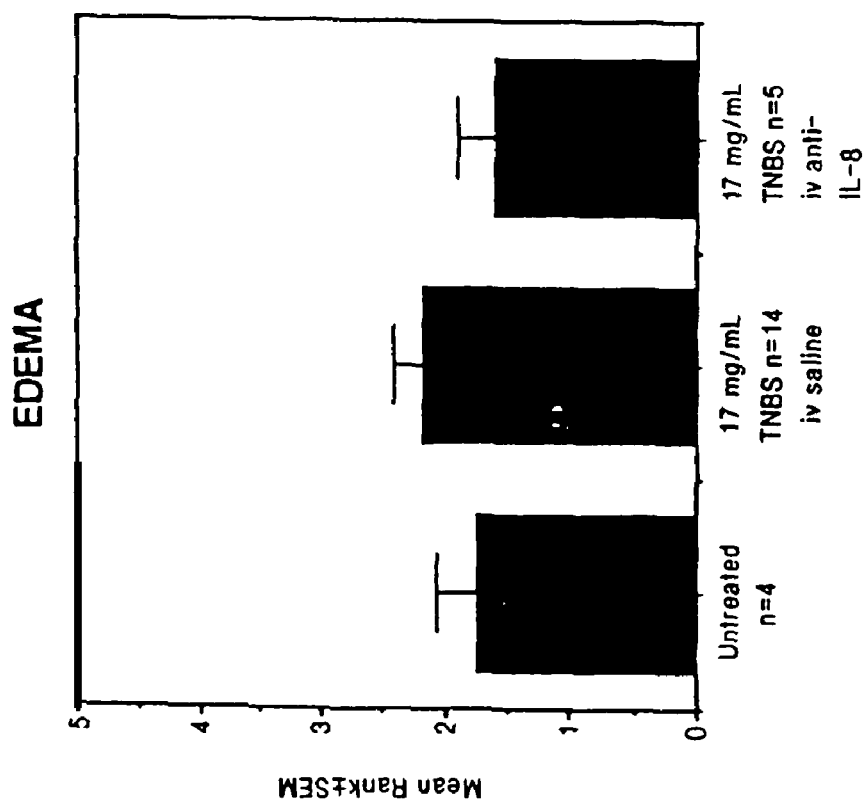
Figure 11H:
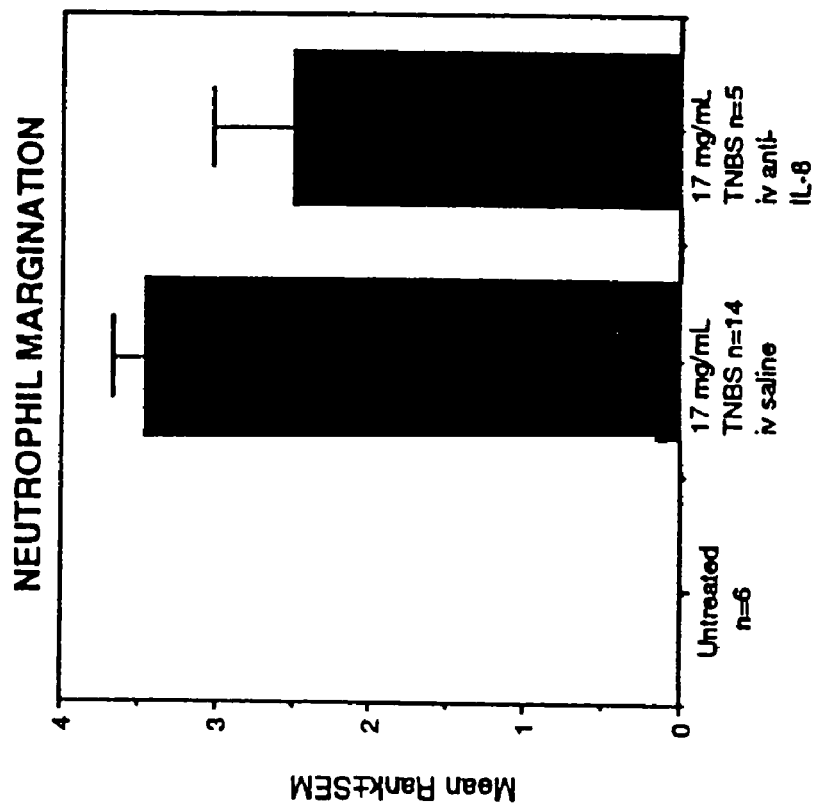
Figure 11G:
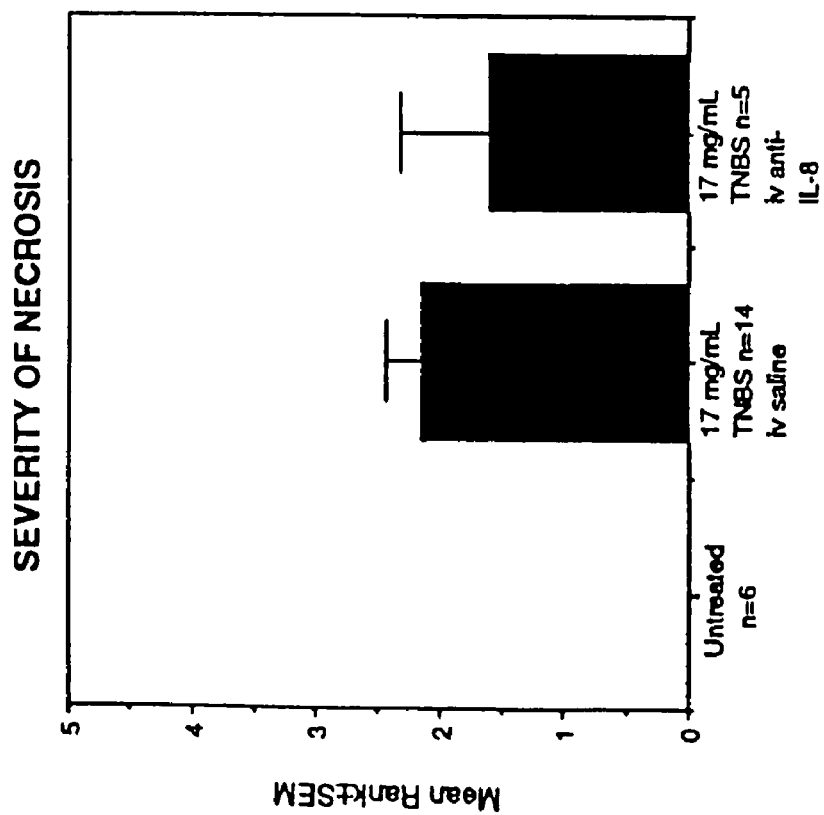
Figure 11J:
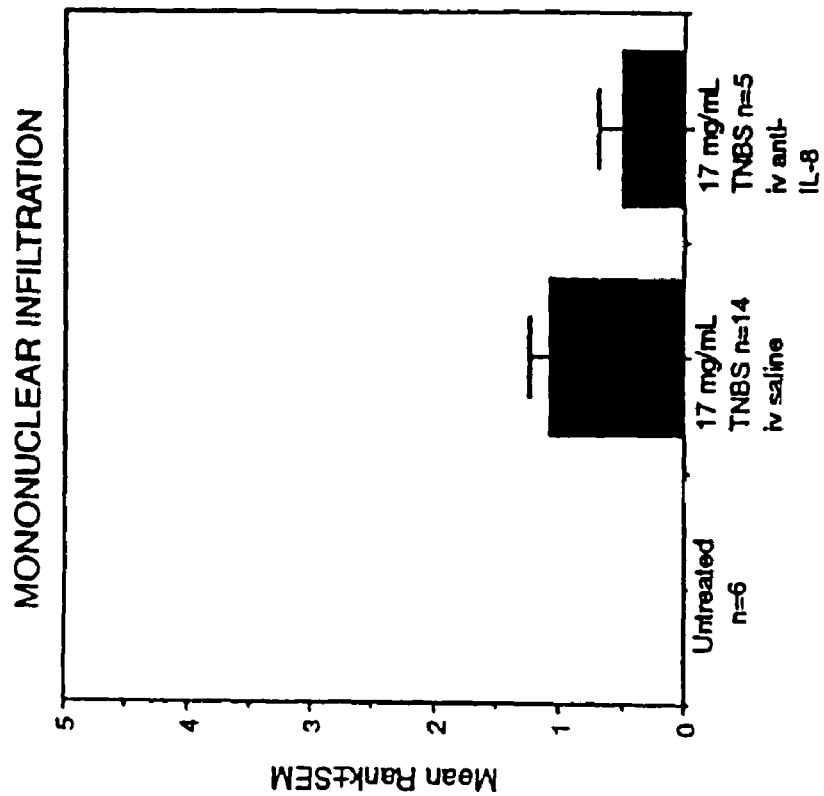
Figure 11I:
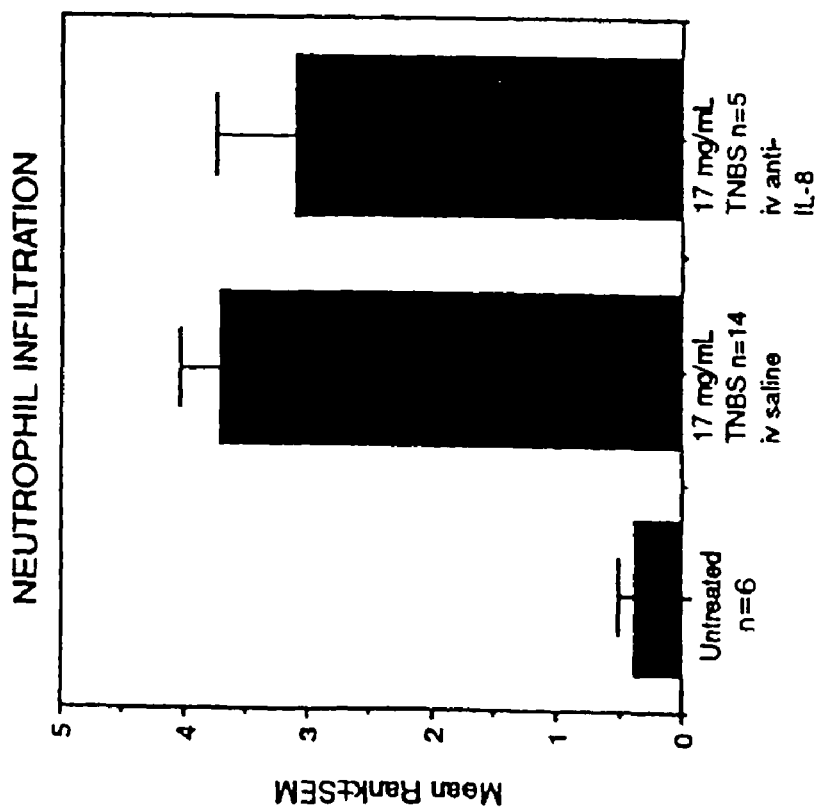

As used herein, the terms "human tumor necrosis factor-α", "tumor necrosis factor-α", "human TNF-α", and "TNF-α" are used interchangeably to refer to the human TNF-α polypeptide described in Pennica et al., *Nature*, 512: 721 (1984) or in FIG. 10 of U.S. Pat. No. 4,650,674.

Figure 2:
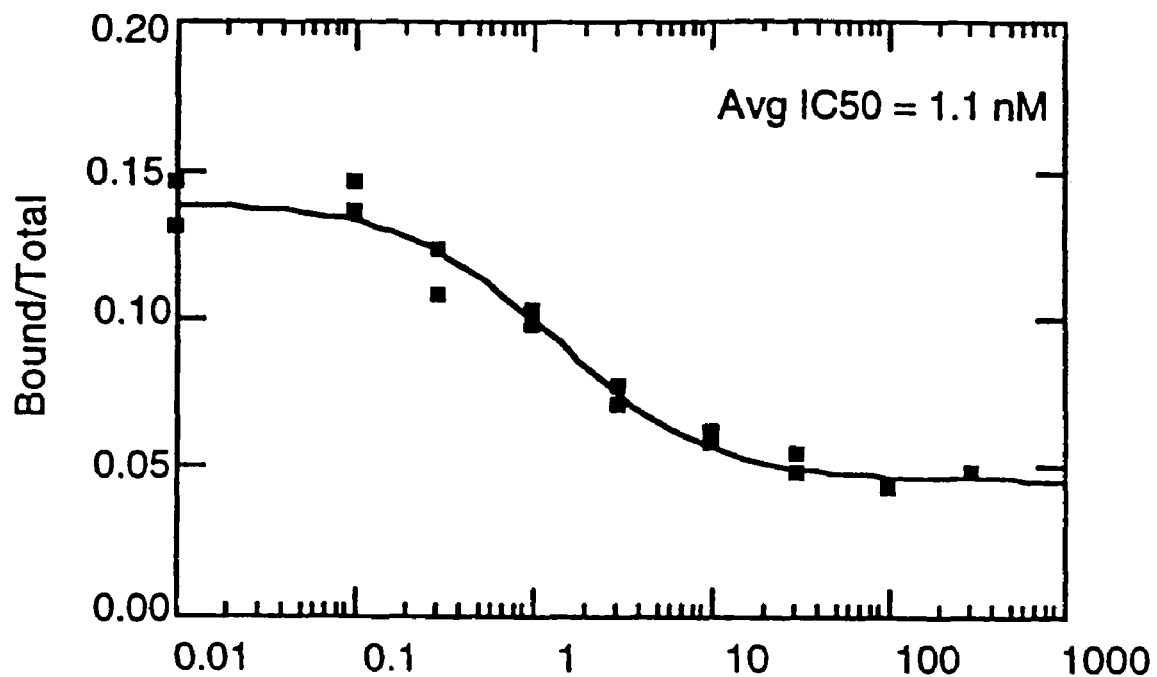
FIG. 2 is a graph depicting the inhibition of $^{125}$I-IL-8 binding to neutrophils by unlabeled IL-8.

As used herein, the terms "human tissue factor" and "tissue factor" are used to refer to the human tissue factor polypeptide described in FIG. 2 of European Patent No. 0 278 776 B1 (granted May 28, 1997).

As used herein, the terms "human $α_4$ integrin", "$α_4$ integrin", "human $α_4$", and "$α_4$" are used interchangeably to refer to the human VLA-4 $α_4$ subunit polypeptide described in Takada et al., *EMBO J.*, 8: 1361-1368 (1989).

As used herein, the terms "human 7 integrin", "$β_7$ integrin", "human $β_7$ and "$β_7$" are used interchangeably to refer to the $β_2$-related integrin polypeptide described in Yuan et al., *International Immunology*, 2: 1097-1108 (1990).

As used herein, the terms "human GPIIIa integrin", "GPIIIa integrin", "human GPIIIa", and "GPIIIa" are used interchangeably to refer to the GPIIIa polypeptide described in Fitzgerald et al., *J. Biol. Chem.*, 262(9): 3936 (1987).

As used herein, the terms "human GPIIb integrin", "GPIIb integrin", "human GPIIb" and "GPIIb" are used interchangeably to refer to the GPIIb polypeptide described in Fitzgerald et al., *Biochem.*, 26: 8158 (1987).

As used herein, the terms "human GPIIb-IIIa integrin", "GPIIb-IIIa integrin", "human GPIIb-IIa", and "GPIIb-IIIa" are used interchangeably to refer to a GPIIb-GPIIIa integrin complex.

As used herein, the terms "human epidermal growth factor receptor", "epidermal growth factor receptor", "human EGFR", and "EGFR" are used interchangeably to refer to the human epidermal growth factor receptor polypeptide described in Ullrich et al., *Nature*, 309: 418-425 (1984).

As used herein, the terms "human CD3" and "CD3" are used interchangeably to refer to the 20K T3 glycoprotein subunit of the human T-cell receptor complex described in van den Elsen et al., *Nature*, 312: 413-418 (1984).

As used herein, the terms "human interleukin-2 receptor α-chain", "interleukin-2 receptor α-chain", "human IL-2R α-chain", "IL-2R α-chain", "human T-cell activation antigen", "human TAC", and "TAC" are used interchangeably to refer to the 272 amino acid interleukin-2 receptor polypeptide described in Leonard et al., *Nature*, 311: 626-631 (1984).

As used herein, the terms "anti-LFA-1 antibody", "anti-LFA-1 monoclonal antibody" and "anti-LFA-1 MAb" refer to an antibody directed against either CD 11a or CD18 or both. The anti-CD11a antibodies include, e.g., MHM24 [Hildreth et al., *Eur. J. Immunol.*, 13: 202-208 (1983)], R3.1 (IgG1) [R. Rothlein, Boehringer Ingelheim Pharmaceuticals, Inc., Ridgefield, Conn.], 25-3 (or 25.3), an IgG1 available from Immunotech, France [Olive et al., in Feldmann, ed., Human T cell Clones. A new Approach to Immune Regulation, Clifton, N.J., Humana, 1986 p. 173], KBA (IgG2a) [Nishimura et al., *Cell. Immunol.*, 107: 32 (1987); Nishimura et al., ibid., 94: 122 (1985)], M7/15 (IgG2b) [Springer et al., *Immunol. Rev.*, 68: 171 (1982)], 10T16 [Vermot Desroches et al., *Scand. J. Immunol.*, 33: 277-286 (1991)], SPVL7 [Vermot Desroches et al., supra], and M17 (IgG2a), available from ATCC, which are rat anti-murine CD11a antibodies.

Examples of anti-CD18 antibodies include MHM23 [Hildreth et al., supra], M18/2 (IgG2a) [Sanches-Madrid et al., *J. Exp. Med.*, 158: 586 (1983)], H52 [Fekete et al., *J. Clin. Lab Immunol.*, 31: 145-149 (1990)], Mas 191c [Vermot Desroches et al., supra], IOT18 [Vermot Desroches et al., supra], 60.3 [Taylor et al., *Clin. Exp. Immunol.*, 71: 324-328 (1988)], and 60.1 [Campana et al., *Eur. J. Immunol.*, 16: 537-542 (1986)].

The term "graft" as used herein refers to biological material derived from a donor for transplantation into a recipient. Grafts include such diverse material as, for example, isolated cells such as islet cells, tissue such as the amniotic membrane of a newborn, bone marrow, hematopoietic precursor cells, and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart and the donor of the graft and the host are matched for HLA class II antigens.

The term "donor" as used herein refers to the mammalian species, dead or alive, from which the graft is derived. Preferably, the donor is human. Human donors are preferably volunteer blood-related donors that are normal on physical examination and of the same major ABO blood group, because crossing major blood group barriers possibly prejudices survival of the allograft. It is, however, possible to transplant, for example, a kidney of a type O donor into an A, B or AB recipient.

The term "transplant" and variations thereof refers to the insertion of a graft into a host, whether the transplantation is syngeneic (where the donor and recipient are genetically identical), allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenically widely separated species, for example, a pig heart valve, or animal beta islet cells or neuronal cells transplanted into a human host.

"Treatment" refers to both therapeutic treatment and prophylactic or preventative measures. Those in need of treatment include those already with the disorder as well as those prone to have the disorder or those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal herein is human.

As used herein, protein, peptide and polypeptide are used interchangeably to denote an amino acid polymer or a set of two or more interacting or bound amino acid polymers.

As used herein, the term "inflammatory disorders" refers to pathological states resulting in inflammation, typically caused by neutrophil chemotaxis. Examples of such disorders include inflammatory skin diseases including psoriasis and atopic dermatitis; systemic scleroderma and sclerosis; responses associated with inflammatory bowel disease (such as Crohn's disease and ulcerative colitis); ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma; hypovolemic shock; asphyxia; adult respiratory distress syndrome; acute lung injury; Behcet's Disease; dermatomyositis; polymyositis; multiple sclerosis; dermatitis; meningitis; encephalitis; uveitis; osteoarthritis; lupus nephritis; autoimmune diseases such as rheumatoid arthritis, Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; etc. The preferred indications include acute lung injury, adult respiratory distress syndrome, ischemic reperfusion (including surgical tissue reperfusion injury, myocardial ischemia, and acute myocardial infarction), hypovolemic shock, asthma, bacterial pneumonia and inflammatory bowel disease such as ulcerative colitis.

As used herein, the term "LFA-1-mediated disorder" refers to pathological states caused by cell adherence interactions involving the LFA-1 receptor on lymphocytes. Examples of such disorders include T cell inflammatory responses such as inflammatory skin diseases including psoriasis; responses associated with inflammatory bowel disease (such as Crohn's disease and ulcerative colitis); adult respiratory distress syndrome; dermatitis; meningitis; encephalitis; uveitis; allergic conditions such as eczema and asthma and other conditions involving infiltration of T cells and chronic inflammatory responses; skin hypersensitivity reactions (including poison ivy and poison oak); atherosclerosis; leukocyte adhesion deficiency; autoimmune diseases such as rheumatoid arthritis, systemic lupus erythematosus (SLE), diabetes mellitus, multiple sclerosis, Reynaud's syndrome, autoimmune thyroiditis, experimental autoimmune encephalomyelitis, Sjorgen's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; diseases involving leukocyte diapedesis; CNS inflammatory disorder, multiple organ injury syndrome secondary to septicaemia or trauma; autoimmune haemolytic anemia; myethemia gravis; antigen-antibody complex mediated diseases; all types of transplantations, including graft vs. host or host vs. graft disease; etc.

As used herein, the term "IgE-mediated disorder" means a condition or disease which is characterized by the overproduction and/or hypersensitivity to the immunoglobulin IgE. Specifically it should be construed to include conditions associated with anaphylactic hypersensitivity and atopic allergies, including for example: asthma, allergic rhinitis & conjunctivitis (hay fever), eczema, urticaria and food allergies. However, the serious physiological condition of anaphylactic shock, usually caused by bee or snake stings or parental medication is also encompassed under the scope of this term.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The terms "allergy" and "atopy" and all their grammatical variants are used synonymously herein to refer to any disease mediated by a Type I (Gell & Coombs classification) hypersensitivity reaction, including allergic rhinitis, atopic dermatitis, anaphylaxis, allergic asthma.

As used herein, the terms "asthma", "asthmatic disorder", "asthmatic disease", and "bronchial asthma" refer to a condition of the lungs in which there is widespread narrowing of lower airways. "Atopic asthma" and "allergic asthma" refer to asthma that is a manifestation of an IgE-mediated hypersensitivity reaction in the lower airways, including, e.g., moderate or severe chronic asthma, such as conditions requiring the frequent or constant use of inhaled or systemic steroids to control the asthma symptoms. A preferred indication is allergic asthma.

The term "allergic rhinitis" as used herein refers to any allergen-induced nasal symptoms, including itching, sneezing, nasal congestion, nasal discharge, and symptoms associated with nasal mucosal inflammation.

The terms "thrombotic disorder" and "prothrombotic disorder" as used interchangeably herein to refer to pathological conditions in which the blood coagulation cascade is activated (see, generally, Hoffbrand & Pettit, *Essential Haematology*, Blackwell Scientific Publications, Oxford (1980)). Such conditions include peripheral arterial obstruction, acute myocardial infarction, deep vein thrombosis, pulmonary embolism, dissecting aneurysm, transient ischemic attack, restenosis, stroke and other occlusive disease or disorders such as unstable angina, disseminated intravascular coagulation, sepsis, surgical or infective shock, postoperative and post-delivery trauma, angioplasty, cardiopulmonary bypass and coronary bypass, incompatible blood transfusion, amotio placentae, thrombotic thrombocytopenic purpura, asthma, chronic or acute renal disease, diabetes, inflammations, atherosclerosis, hemolytic uremic syndrome, symmetric peripheral necrosis, and allograft rejection in mammals including human.

The terms "hydrodynamic size", "apparent size", "apparent molecular weight", "effective size" and "effective molecular weight" of a molecule are used synonymously herein refer to the size of a molecule as determined by comparison to a standard curve produced with globular protein molecular weight standards in a size exclusion chromatography system, wherein the standard curve is created by mapping the actual molecular weight of each standard against its elution time observed in the size exclusion chromatography system. Thus, the apparent size of a test molecule is derived by using the molecule's elution time to extrapolate a putative molecular weight from the standard curve. Preferably, the molecular weight standards used to create the standard curve are selected such that the apparent size of the test molecule falls within the linear portion of the standard curve.

II. Modes for Carrying Out the Invention

In one part, the invention arises from the surprising and unexpected discovery that antibody fragment-polymer conjugates having an effective or apparent size significantly greater than the antibody fragment-polymer conjugates described in the art confers an increase in serum half-life, an increase in mean residence time in circulation (MRT), and/or a decrease in serum clearance rate over underivatized antibody fragment which far exceed the modest changes in such biological property or properties obtained with the art-known antibody fragment-polymer conjugates. The present inventors have determined for the first time that increasing the effective size of an antibody fragment to at least about 500,000 D, or increasing the effective size of an antibody fragment by at least about 8 fold over the effective size of the parental antibody fragment, or derivatizing an antibody fragment with a polymer of at least about 20,000 D in molecular weight, yields a molecule with a commercially useful pharmacokinetic profile. The greatly extended serum half-life, extended MRT, and/or reduced serum clearance rate of the conjugates of the invention makes such conjugates viable alternatives to intact antibodies used for therapeutic treatment of many disease indications. Antibody fragments provide significant advantages over intact antibodies, notably the fact that recombinant antibody fragments can be made in bacterial cell expression systems. Bacterial cell expression systems provide several advantages over mammalian cell expression systems, including reduced time and cost at both the research and development and manufacturing stages of a product.

In another part, the present invention also arises from the humanization of the 6G4.2.5 murine anti-rabbit IL-8 monoclonal antibody ("6G4.2.5") described in WO 95/23865 (PCT/US95/02589 published Sep. 8, 1995), the entire disclosure of which is specifically incorporated herein by reference. The hybridoma producing antibody 6G4.2.5 was deposited on Sep. 28, 1994 with the American Type Culture Collection and assigned ATCC Accession No. HB 11722 as described in the Examples below. In one aspect, the invention provides a humanized derivative of the 6G4.2.5 antibody, variant 11 (referred to herein as "6G4.2.5v11"), in which the murine CDRs of 6G4.2.5 are grafted onto a consensus framework for human light chain 61 and human IgG1 heavy chain subgroup III, followed by importing three framework residues from the murine 6G4.2.5 parent heavy chain variable domain sequence into analogous sites in the heavy chain variable domain of the human template sequence, as described in the Examples below. In another aspect, the invention provides variants of the 6G4.2.5v11 antibody with certain amino acid substitution(s) yielding increased affinity for human IL-8 and/or promoting greater efficiency in recombinant manufacturing processes.

It will be understood that in the context of this Section (II) and all subsections thereof, every reference to "an antibody fragment" or "the antibody fragment" contained in a conjugate shall be a reference to one or more antibody fragment(s) in the conjugate (consistent with the definition of the term "conjugate" set forth in Section (I) above), except where the number of antibody fragment(s) in the conjugate is expressly indicated. It will be understood that in the context of this Section (II) and all subsections thereof, every reference to "a polymer", "a polymer molecule", "the polymer", or "the polymer molecule" contained in a conjugate shall be a reference to one or more polymer molecule(s) in the conjugate (consistent with the definition of the term "conjugate" set forth in Section (I) above), except where the number of polymer molecule(s) in the conjugate is expressly indicated.

1. Large Effective Size Antibody Fragment-Polymer Conjugates

In one aspect, the invention provides an antibody fragment covalently attached to a polymer to form a conjugate having an effective or apparent size of at least about 500,000 Daltons (D). In another aspect, the invention provides an antibody fragment covalently attached to a polymer to form a conjugate having an apparent size that is at least about 8 fold greater than the apparent size of the parental antibody fragment. In yet another aspect, the invention provides an antibody fragment covalently attached to a polymer of at least about 20,000 D in molecular weight (MW). It will be appreciated that the unexpectedly and surprisingly large increase in antibody fragment serum half-life, increase in MRT, and/or decrease in serum clearance rate can be achieved by using any type of polymer or number of polymer molecules which will provide the conjugate with an effective size of at least about 500,000 D, or by using any type of polymer or number of polymer molecules which will provide the conjugate with an effective size that is at least about 8 fold greater than the effective size of the parental antibody fragment, or by using any type or number of polymers wherein each polymer molecule is at least about 20,000 D in MW. Thus, the invention is not dependent on the use of any particular polymer or molar ratio of polymer to antibody fragment in the conjugate.

In addition, the beneficial aspects of the invention extend to antibody fragments without regard to antigen specificity. Although variations from antibody to antibody are to be expected, the antigen specificity of a given antibody will not substantially impair the extraordinary improvement in serum half-life, MRT, and/or serum clearance rate for antibody fragments thereof that can be obtained by derivatizing the antibody fragments as taught herein. The invention can be applied to an antibody fragment specific for any antigen of interest, including, e.g., renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-1 (brain IGF-1), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressing; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

In one embodiment, the conjugate has an effective size of at least about 500,000 D, or at least about 800,000 D, or at least about 900,000 D, or at least about 1,000,000 D, or at least about 1,200,000 D, or at least about 1,400,000 D, or at least about 1,500,000 D, or at least about 1,800,000 D, or at least about 2,000,000 D, or at least about 2,500,000 D.

In another embodiment, the conjugate has an effective size of at or about 500,000 D to at or about 10,000,000 D, or an effective size of at or about 500,000 D to at or about 8,000,000 D, or an effective size of at or about 500,000 D to at or about 5,000,000 D, or an effective size of at or about 500,000 D to at or about 4,000,000 D, or an effective size of at or about 500,000 D to at or about 3,000,000 D, or an effective size of at or about 500,000 D to at or about 2,500,000 D, or an effective size of at or about 500,000 D to at or about 2,000,000 D, or an effective size of at or about 500,000 D to at or about 1,800,000 D, or an effective size of at or about 500,000 D to at or about 1,600,000 D, or an effective size of at or about 500,000 D to at or about 1,500,000 D, or an effective size of at or about 500,000 D to at or about 1,000,000 D.

In another embodiment, the conjugate has an effective size of at or about 800,000 D to at or about 10,000,000 D, or an effective size of at or about 800,000 D to at or about 8,000,000 D, or an effective size of at or about 800,000 D to at or about 5,000,000 D, or an effective size of at or about 800,000 D to at or about 4,000,000 D, or an effective size of at or about 800,000 D to at or about 3,000,000 D, or an effective size of at or about 800,000 D to at or about 2,500,000 D, or an effective size of at or about 800,000 D to at or about 2,000,000 D, or an effective size of at or about 800,000 D to at or about 1,800,000 D, or an effective size of at or about 800,000 D to at or about 1,600,000 D, or an effective size of at or about 800,000 D to at or about 1,500,000 D, or an effective size of at or about 800,000 D to at or about 1,000,000 D.

In another embodiment, the conjugate has an effective size of at or about 900,000 D to at or about 10,000,000 D, or an effective size of at or about 900,000 D to at or about 8,000,000 D, or an effective size of at or about 900,000 D to at or about 5,000,000 D, or an effective size of at or about 900,000 D to at or about 4,000,000 D, or an effective size of at or about 900,000 D to at or about 3,000,000 D, or an effective size of at or about 900,000 D to at or about 2,500,000 D, or an effective size of at or about 900,000 D to at or about 2,000,000 D, or an effective size of at or about 900,000 D to at or about 1,800,000 D, or an effective size of at or about 900,000 D to at or about 1,600,000 D, or an effective size of at or about 900,000 D to at or about 1,500,000 D.

In another embodiment, the conjugate has an effective size of at or about 1,000,000 D to at or about 10,000,000 D, or an effective size of at or about 1,000,000 D to at or about 8,000,000 D, or an effective size of at or about 1,000,000 D to at or about 5,000,000 D, or an effective size of at or about 1,000,000 D to at or about 4,000,000 D, or an effective size of at or about 1,000,000 D to at or about 3,000,000 D, or an effective size of at or about 1,000,000 D to at or about 2,500,000 D, or an effective size of at or about 1,000,000 D to at or about 2,000,000 D, or an effective size of at or about 1,000,000 D to at or about 1,800,000 D, or an effective size of at or about 1,000,000 D to at or about 1,600,000 D, or an effective size of at or about 1,000,000 D to at or about 1,500,000 D.

In a further embodiment, the conjugate has an effective size that is at least about 8 fold greater, or at least about 10 fold greater, or at least about 12 fold greater, or at least about 15 fold greater, or at least about 18 fold greater, or at least about 20 fold greater, or at least about 25 fold greater, or at least about 28 fold greater, or at least about 30 fold greater, or at least about 40 fold greater, than the effective size of the parental antibody fragment.

In another embodiment, the conjugate has an effective size that is about 8 fold to about 100 fold greater, or is about 8 fold to about 80 fold greater, or is about 8 fold to about 50 fold greater, or is about 8 fold to about 40 fold greater, or is about 8 fold to about 30 fold greater, or is about 8 fold to about 28 fold greater, or is about 8 fold to about 25 fold greater, or is about 8 fold to about 20 fold greater, or is about 8 fold to about 18 fold greater, or is about 8 fold to about 15 fold greater, than the effective size of the parental antibody fragment.

In another embodiment, the conjugate has an effective size that is about 12 fold to about 100 fold greater, or is about 12 fold to about 80 fold greater, or is about 12 fold to about 50 fold greater, or is about 12 fold to about 40 fold greater, or is about 12 fold to about 30 fold greater, or is about 12 fold to about 28 fold greater, or is about 12 fold to about 25 fold greater, or is about 12 fold to about 20 fold greater, or is about 12 fold to about 18 fold greater, or is about 12 fold to about 15 fold greater, than the effective size of the parental antibody fragment.

In another embodiment, the conjugate has an effective size that is about 15 fold to about 100 fold greater, or is about 15 fold to about 80 fold greater, or is about 15 fold to about 50 fold greater, or is about 15 fold to about 40 fold greater, or is about 15 fold to about 30 fold greater, or is about 15 fold to about 28 fold greater, or is about 15 fold to about 25 fold greater, or is about 15 fold to about 20 fold greater, or is about 15 fold to about 18 fold greater, than the effective size of the parental antibody fragment.

In another embodiment, the conjugate has an effective size that is about 18 fold to about 100 fold greater, or is about 18 fold to about 80 fold greater, or is about 18 fold to about 50 fold greater, or is about 18 fold to about 40 fold greater, or is about 18 fold to about 30 fold greater, or is about 18 fold to about 28 fold greater, or is about 18 fold to about 25' fold greater, or is about 18 fold to about 20 fold greater, than the effective size of the parental antibody fragment.

In another embodiment, the conjugate has an effective size that is about 20 fold to about 100 fold greater, or is about 20 fold to about 80 fold greater, or is about 20 fold to about 50 fold greater, or is about 20 fold to about 40 fold greater, or is about 20 fold to about 30 fold greater, or is about 20 fold to about 28 fold greater, or is about 20 fold to about 25 fold greater, than the effective size of the parental antibody fragment.

In another embodiment, the conjugate has an effective size that is about 25 fold to about 100 fold greater, or is about 25 fold to about 80 fold greater, or is about 25 fold to about 50 fold greater, or is about 25 fold to about 40 fold greater, or is about 25 fold to about 30 fold greater, or is about 25 fold to about 28 fold greater, than the effective size of the parental antibody fragment.

In another embodiment, the conjugate has an effective size that is about 28 fold to about 100 fold greater, or is about 28 fold to about 80 fold greater, or is about 28 fold to about 50 fold greater, or is about 28 fold to about 40 fold greater, or is about 28 fold to about 30 fold greater, than the effective size of the parental antibody fragment.

In another embodiment, the conjugate has an effective size that is about 30 fold to about 100 fold greater, or is about 30 fold to about 80 fold greater, or is about 30 fold to about 50 fold greater, or is about 30 fold to about 40 fold greater, than the effective size of the parental antibody fragment.

In another embodiment, the conjugate has an effective size that is about 40 fold to about 100 fold greater, or is about 40 fold to about 80 fold greater, or is about 40 fold to about 50 fold greater, than the effective size of the parental antibody fragment.

In still another embodiment, the conjugate is an antibody fragment covalently attached to at least one polymer having an actual MW of at least about 20,000 D.

In a further embodiment, the conjugate is an antibody fragment covalently attached to at least one polymer having an actual MW of at least about 30,000 D.

In yet another embodiment, the conjugate is an antibody fragment covalently attached to at least one polymer having an actual MW of at least about 40,000 D.

In another embodiment, the conjugate is an antibody fragment covalently attached to at least one polymer having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one polymer having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one polymer having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one polymer having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one polymer having an actual MW that is at or about 20,000 D to at or about 40,000 D, or is at or about 30,000 D to at or about 40,000 D.

The conjugates of the invention can be made using any suitable technique now known or hereafter developed for derivatizing antibody fragments with polymers. It will be appreciated that the invention is not limited to conjugates utilizing any particular type of linkage between an antibody fragment and a polymer.

The conjugates of the invention include species wherein a polymer is covalently attached to a non-specific site or non-specific sites on the parental antibody fragment, i.e. polymer attachment is not targeted to a particular region or a particular amino acid residue in the parental antibody fragment. In such embodiments, the coupling chemistry can, for example, utilize the free epsilon amino groups of lysine residues in the parental antibody as attachment sites for the polymer, wherein such lysine residue amino groups are randomly derivatized with polymer.

In addition, the conjugates of the invention include species wherein a polymer is covalently attached to a specific site or specific sites on the parental antibody fragment, i.e. polymer attachment is targeted to a particular region or a particular amino acid residue or residues in the parental antibody fragment. In such embodiments, the coupling chemistry can, for example, utilize the free sulfhydryl group of a cysteine residue not in a disulfide bridge in the parental antibody fragment. In one embodiment, one or more cysteine residue(s) is (are) engineered into a selected site or sites in the parental antibody fragment for the purpose of providing a specific attachment site or sites for polymer. The polymer can be activated with any functional group that is capable of reacting specifically with the free sulfhydryl or thiol group(s) on the parental antibody, such as maleimide, sulfhydryl, thiol, triflate, tesylate, aziridine, exirane, and 5-pyridyl functional groups. The polymer can be coupled to the parental antibody fragment using any protocol suitable for the chemistry of the coupling system selected, such as the protocols and systems described in Section (II)(1)(b) or in Section (T) of the Examples below.

In another embodiment, polymer attachment is targeted to the hinge region of the parental antibody fragment. The location of the hinge region varies according to the isotype of the parental antibody. Typically, the hinge region of IgG, IgD and IgA isotype heavy chains is contained in a proline rich peptide sequence extending between the $C_H1$ and $C_H2$ domains. In a preferred embodiment, a cysteine residue or residues is (are) engineered into the hinge region of the parental antibody fragment in order to couple polymer specifically to a selected location in the hinge region.

In one aspect, the invention encompasses a conjugate having any molar ratio of polymer to antibody fragment that endows the conjugate with an apparent size in the desired range as taught herein. The apparent size of the conjugate will depend in part upon the size and shape of the polymer used, the size and shape of the antibody fragment used, the number of polymer molecules attached to the antibody fragment, and the location of such attachment site(s) on the antibody fragment. These parameters can easily be identified and maximized to obtain the a conjugate with the desired apparent size for any type of antibody fragment, polymer and linkage system.

In another aspect, the invention encompasses a conjugate with a polymer to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer polymer molecules, each polymer molecule having a molecular weight of at least about 20,000 D, or at least about 30,000 D, or at least about 40,000 D. In another embodiment, the conjugate contains an antibody fragment attached to about 5 or fewer polymer molecules, each polymer molecule having a molecular weight of at least about 20,000 D, or at least about 30,000 D, or at least about 40,000 D. In still another embodiment, the conjugate contains an antibody fragment attached to about 4 or fewer polymer molecules, each polymer molecule having a molecular weight of at least about 20,000 D, or at least about 30,000 D, or at least about 40,000 D. In a further embodiment, the conjugate contains an antibody fragment attached to about 3 or fewer polymer molecules, each polymer molecule having a molecular weight of at least about 20,000 D, or at least about 30,000 D, or at least about 40,000 D. In an additional embodiment, the conjugate contains an antibody fragment attached to about 2 or fewer polymer molecules, each polymer molecule having a molecular weight of at least about 20,000 D, or at least about 30,000 D, or at least about 40,000 D. Also provided herein is a conjugate containing an antibody fragment attached to a single polymer molecule having a molecular weight of at least about 20,000 D, or at least about 30,000 D, or at least about 40,000 D.

In still another aspect, the invention encompasses a conjugate wherein every polymer molecule in the conjugate has a molecular weight that is at or about 20,000 D to at or about 300,000 D, or is at or about 30,000 D to at or about 300,000 D, or is at or about 40,000 D to at or about 300,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 100,000 D, or is at or about 30,000 D to at or about 100,000 D, or is at or about 40,000 D to at or about 100,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 70,000 D, or is at or about 30,000 D to at or about 70,000 D, or is at or about 40,000 D to at or about 70,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 50,000 D, or is at or about 30,000 D to at or about 50,000 D, or is at or about 40,000 D to at or about 50,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In still another aspect, the invention encompasses a conjugate wherein every polymer molecule in the conjugate has a molecular weight that is at or about 20,000 D to at or about 40,000 D, or is at or about 30,000 D to at or about 40,000 D, and wherein the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

It is believed that the serum half-life, MRT and/or serum clearance rate of any antibody fragment can be greatly improved by derivatizing the antibody fragment with polymer as taught herein. In one embodiment, the conjugate contains an antibody fragment selected from the group consisting of Fab, Fab', Fab'-SH, Fv, scFv and F(ab')$_2$.

In a preferred embodiment, the conjugate contains an antibody fragment selected from the group consisting of Fab, Fab', and Fab'-SH, wherein every polymer molecule in the conjugate is attached to the hinge region of the antibody fragment.

In another preferred embodiment, the conjugate contains an antibody fragment selected from the group consisting of Fab, Fab', and Fab'-SH, every polymer molecule in the conjugate molecule is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In yet another preferred embodiment, the conjugate contains a F(ab')$_2$ antibody fragment attached to no more than about 2 polymer molecules, wherein every polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In a further embodiment, the conjugate contains an antibody fragment selected from the group consisting of Fab, Fab', and Fab'-SH, wherein the antibody fragment is attached to no more than 1 polymer molecule and the polymer is coupled to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In an additional embodiment, the conjugate contains an antibody fragment selected from the group consisting of Fab, Fab', and Fab'-SH, every polymer molecule in the conjugate is at least about 20,000 D in molecular weight, or at least about 30,000 in molecular weight, or at least about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In another embodiment, the conjugate contains an antibody fragment selected from the group consisting of Fab, Fab', and Fab'-SH, every polymer molecule in the conjugate is at or about 20,000 D to at or about 40,000 D in molecular weight, or is at or about 30,000 D to at or about 40,000 D in molecular weight, every polymer molecule in the conjugate is attached to the hinge region of the antibody fragment, and the conjugate contains no more than about 10 polymer molecules, or no more than about 5 polymer molecules, or no more than about 4 polymer molecules, or no more than about 3 polymer molecules, or no more than about 2 polymer molecules, or no more than 1 polymer molecule.

In a further embodiment, the conjugate contains a F(ab')$_2$ antibody fragment attached to no more than about 2 polymer molecules, wherein every polymer molecule in the conjugate is at least about 20,000 D in molecular weight, or at least about 30,000 D in molecular weight, or at least about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')$_2$ antibody fragment attached to no more than about 2 polymer molecules, wherein every polymer molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')₂ antibody fragment attached to no more than about 2 polymer molecules, wherein every polymer molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains a F(ab')₂ antibody fragment attached to no more than about 2 polymer molecules, wherein every polymer molecule in the conjugate is at or about 20,000 D to at or about 40,000 D in molecular weight, or is at or about 30,000 D to at or about 40,000 D in molecular weight, and wherein every polymer molecule in the conjugate is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In yet another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, wherein the polymer molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another embodiment, the conjugate contains an antibody fragment selected from the group consisting of Fab, Fab', and Fab'-SH, wherein the antibody fragment is attached to no more than 1 polymer molecule, wherein the polymer molecule is at least about 20,000 D in molecular weight, or at least about 30,000 D in molecular weight, or at least about 40,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 300,000 D in molecular weight, or is at or about 30,000 D to at or about 300,000 D in molecular weight, or is at or about 40,000 D to at or about 300,000 D in molecular weight, and wherein the polymer molecule is attached to the hinge region of the antibody fragment.

In another embodiment, the conjugate contains an antibody fragment selected from the group consisting of Fab, Fab', and F'ab'-SH, wherein the antibody fragment is attached to no more than 1 polymer molecule, wherein the polymer molecule is at or about 20,000 D to at or about 100,000 D in molecular weight, or is at or about 30,000 D to at or about 100,000 D in molecular weight, or is at or about 40,000 D to at or about 100,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 70,000 D in molecular weight, or is at or about 30,000 D to at or about 70,000 D in molecular weight, or is at or about 40,000 D to at or about 70,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 50,000 D in molecular weight, or is at or about 30,000 D to at or about 50,000 D in molecular weight, or is at or about 40,000 D to at or about 50,000 D in molecular weight, and wherein the polymer molecule is attached to the hinge region of the antibody fragment.

In another embodiment, the conjugate contains an antibody fragment selected from the group consisting of Fab, Fab', and Fab'-SH, wherein the antibody fragment is attached to no more than 1 polymer molecule, wherein the polymer molecule is at or about 20,000 D to at or about 40,000 D in molecular weight, or is at or about 30,000 D to at or about 40,000 D in molecular weight, and wherein the polymer molecule is attached to the hinge region of the antibody fragment.

Although any type of polymer is contemplated for use in constructing the conjugates of the invention, including the polymers and chemical linkage systems described in Section (II)(1)(b) below, polyethylene glycol (PEG) polymers are preferred for use herein.

In one embodiment, the conjugate is an antibody fragment covalently attached to at least one PEG having an actual MW of at least about 20,000 D.

In another embodiment, the conjugate is an antibody fragment covalently attached to at least one PEG having an actual MW of at least about 30,000 D.

In yet another embodiment, the conjugate is an antibody fragment covalently attached to at least one PEG having an actual MW of at least about 40,000 D.

In another embodiment, the conjugate is an antibody fragment covalently attached to at least one PEG having an actual MW that is at or about 20,000 D to at or about 300,000 D, or is at or about 30,000 D to at or about 300,000 D, or is at or about 40,000 D to at or about 300,000 D.

In another embodiment, the conjugate is an antibody fragment covalently attached to at least one PEG having an actual MW that is at or about 20,000 D to at or about 100,000 D, or is at or about 30,000 D to at or about 100,000 D, or is at or about 40,000 D to at or about 100,000 D.

In another embodiment, the conjugate is an antibody fragment covalently attached to at least one PEG having an actual MW that is at or about 20,000 D to at or about 70,000 D, or is at or about 30,000 D to at or about 70,000 D, or is at or about 40,000 D to at or about 70,000 D.

In another embodiment, the conjugate is an antibody fragment covalently attached to at least one PEG having an actual MW that is at or about 20,000 D to at or about 50,000 D, or is at or about 30,000 D to at or about 50,000 D, or is at or about 40,000 D to at or about 50,000 D.

In another embodiment, the conjugate is an antibody fragment covalently attached to at least one PEG having an actual MW that is at or about 20,000 D to at or about 40,000 D, or is at or about 30,000 D to at or about 40,000 D.

In another aspect, the invention encompasses a conjugate with a PEG to antibody fragment molar ratio of no more than about 10:1, or no more than about 5:1, or no more than about 4:1, or no more than about 3:1, or no more than about 2:1, or no more than 1:1.

In yet another aspect, the invention encompasses a conjugate wherein the antibody fragment is attached to about 10 or fewer PEG molecules, each PEG molecule having a molecular weight of at least about 20,000 D, or at least about 30,000 D, or at least about 40,000 D. In another embodiment, the conjugate contains an antibody fragment attached to about 5 or fewer PEG molecules, each PEG molecule having a molecular weight of at least about 20,000 D, or at least about 30,000 D, or at least about 40,000 D. In still another embodiment, the conjugate contains an antibody fragment attached to about 4 or fewer PEG molecules, each PEG molecule having a molecular weight of at least about 20,000 D, or at least about 30,000 D, or at least about 40,000 D. In a further embodiment, the conjugate contains an antibody fragment attached to about 3 or fewer PEG molecules, each PEG molecule having a molecular weight of at least about 20,000 D, or at least about 30,000 D, or at least about 40,000 D. In an additional embodiment, the conjugate contains an antibody fragment attached to about 2 or fewer PEG molecules, each PEG molecule having a molecular weight of at least about 20,000 D, or at least about 30,000 D, or at least about 40,000 D. Also provided herein is a conjugate containing an antibody fragment attached to a single PEG molecule having a molecular weight of at least about 20,000 D, or at least about 30,000 D, or at least about 40,000 D.

In another aspect, the invention encompasses a conjugate wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In still another aspect, the invention encompasses a conjugate containing an antibody fragment selected from the group consisting of Fab, Fab', Fab'-SH and F(ab')$_2$, wherein the antibody fragment is attached to about 10 or fewer PEG molecules, each PEG molecule having a molecular weight of at least about 20,000 D, or at least about 30,000 D, or at least about 40,000 D. In another embodiment, the foregoing conjugate contains an antibody fragment attached to about 5 or fewer PEG molecules, each PEG molecule having a molecular weight of at least about 20,000 D, or at least about 30,000 D, or at least about 40,000 D. In still another embodiment, the foregoing conjugate contains an antibody fragment attached to about 4 or fewer PEG molecules, each PEG molecule having a molecular weight of at least about 20,000 D, or at least about 30,000 D, or at least about 40,000 D. In a further embodiment, the foregoing conjugate contains an antibody fragment attached to about 3 or fewer PEG molecules, each PEG molecule having a molecular weight of at least about 20,000 D, or at least about 30,000 D, or at least about 40,000 D. In an additional embodiment, the foregoing conjugate contains an antibody fragment attached to about 2 or fewer PEG molecules, each PEG molecule having a molecular weight of at least about 20,000 D, or at least about 30,000 D, or at least about 40,000 D. Also provided herein is the foregoing conjugate that contains an antibody fragment attached to a single PEG molecule having a molecular weight of at least about 20,000 D, or at least about 30,000 D, or at least about 40,000 D.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another aspect, the invention encompasses a conjugate containing an antibody fragment selected from the group consisting of Fab, Fab', Fab'-SH and F(ab')$_2$, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In a preferred embodiment, the conjugate contains an antibody fragment selected from the group consisting of Fab, Fab', and Fab'-SH, wherein the antibody fragment is derivatized with PEG having a molecular weight of at least about 20,000 D, or at least about 30,000 D, or at least about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 300,000 D, or is at or about 30,000 D to at or about 300,000 D, or is at or about 40,000 D to at or about 300,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 100,000 D, or is at or about 30,000 D to at or about 100,000 D, or is at or about 40,000 D to at or about 100,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 70,000 D, or is at or about 30,000 D to at or about 70,000 D, or is at or about 40,000 D to at or about 70,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 50,000 D, or is at or about 30,000 D to at or about 50,000 D, or is at or about 40,000 D to at or about 50,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG having a molecular weight that is at or about 20,000 D to about 40,000 D, or is at or about 30,000 D to at or about 40,000 D, and wherein every PEG molecule in the conjugate is attached to the hinge region of the antibody fragment.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 D in molecular weight, or at least about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein every PEG molecule in the conjugate molecule is attached to the hinge region of the antibody fragment, and wherein the conjugate contains no more than about 10 PEG molecules, or no more than about 5 PEG molecules, or no more than about 4 PEG molecules, or no more than about 3 PEG molecules, or no more than about 2 PEG molecules, or no more than 1 PEG molecule.

In yet another preferred embodiment, the conjugate contains a F(ab')$_2$ antibody fragment derivatized with PEG, wherein every PEG molecule in the conjugate is at least about 20,000 D in molecular weight, or at least about 30,000 D in molecular weight, or at least about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains a F(ab')$_2$ antibody fragment derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than about 2 PEG molecules, and wherein every PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In still another preferred embodiment, the conjugate contains an antibody fragment selected from the group consisting of Fab, Fab', and Fab'-SH, wherein the antibody fragment is derivatized with PEG, wherein every PEG molecule in the conjugate is at least about 20,000 D in molecular weight, or at least about 30,000 in molecular weight, or at least about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 300,000 D in molecular weight, or is at or about 30,000 D to at or about 300,000 D in molecular weight, or is at or about 40,000 D to at or about 300,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 100,000 D in molecular weight, or is at or about 30,000 D to at or about 100,000 D in molecular weight, or is at or about 40,000 D to at or about 100,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 70,000 D in molecular weight, or is at or about 30,000 D to at or about 70,000 D in molecular weight, or is at or about 40,000 D to at or about 70,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 50,000 D in molecular weight, or is at or about 30,000 D to at or about 50,000 D in molecular weight, or is at or about 40,000 D to at or about 50,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

In another preferred embodiment, the conjugate contains an antibody fragment selected from the group consisting of Fab, Fab', and Fab'-SH, wherein the antibody fragment is derivatized with PEG, wherein every PEG molecule in the conjugate is at or about 20,000 D to at or about 40,000 D in molecular weight, or is at or about 30,000 D to at or about 40,000 D in molecular weight, wherein the antibody fragment is attached to no more than 1 PEG molecule, and wherein the PEG molecule is attached to a cysteine residue in the light or heavy chain of the antibody fragment that would ordinarily form the disulfide bridge linking the light and heavy chains, wherein the disulfide bridge is avoided by substituting another amino acid, such as serine, for the corresponding cysteine residue in the opposite chain.

It will be appreciated that all of the above-described embodiments of the invention utilizing PEG polymers include conjugates wherein the PEG polymer(s) is (are) linear or branched. In a preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and at least about 40,000 D in molecular weight. In a particularly surprising and unexpected finding, the inventors discovered that the foregoing conjugate exhibits a serum half-life, MRT and serum clearance rate approaching that of full length antibody as shown in Example X below.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 40,000 D to at or about 50,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and at least 40,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 40,000 D to at or about 50,000 D, and the PEG molecule is attached to the hinge region of the antibody fragment.

In a preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and at least about 40,000 D in molecular weight.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 40,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 40,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 40,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 40,000 D to at or about 50,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and at least 40,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 40,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 40,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 40,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 40,000 D to at or about 50,000 D, and the PEG molecule is attached to the hinge region of the antibody fragment.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at least about 30,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 30,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 30,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 30,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 30,000 D to at or about 50,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 30,000 D to at or about 40,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and at least 30,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 30,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 30,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 30,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 30,000 D to at or about 50,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 30,000 D to at or about 40,000 D, and the PEG molecule is attached to the hinge region of the antibody fragment.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at least about 30,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 30,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 30,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 30,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 30,000 D to at or about 50,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 30,000 D to at or about 40,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and at least 30,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 30,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 30,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 30,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 30,000 D to at or about 50,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 30,000 D to at or about 40,000 D, and the PEG molecule is attached to the hinge region of the antibody fragment.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at least about 20,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 50,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 40,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is linear and has a molecular weight that is at or about 20,000 D to at or about 30,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and at least 20,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 50,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 40,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is linear and has a molecular weight that is at or about 20,000 D to at or about 30,000 D, and the PEG molecule is attached to the hinge region of the antibody fragment.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at least about 20,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 300,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 100,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 70,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 50,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 40,000 D.

In another preferred embodiment, the conjugate contains an antibody fragment selected from the group consisting of Fab, Fab', and Fab'-SH, wherein the antibody fragment is attached to no more than 1 PEG molecule, and wherein the PEG molecule is branched and has a molecular weight that is at or about 20,000 D to at or about 30,000 D.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and at least 20,000 D in molecular weight, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 300,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 100,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 70,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 50,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 40,000 D, and the PEG molecule is attached to the hinge region of the antibody fragment.

In another preferred embodiment, the invention provides a conjugate containing an antibody fragment selected from the group consisting of Fab, Fab', and Fab'-SH, wherein the antibody fragment is attached to no more than 1 PEG molecule, wherein the PEG molecule is branched and has a molecular weight that is at or about 20,000 D to at or about 30,000 D, and the PEG molecule is attached to the hinge region of the antibody fragment.

In one aspect, the invention provides any of the above-described conjugates wherein the conjugate contains no more than one antibody fragment. Additionally provided herein is any of the above-described conjugates wherein the conjugate contains one or more antibody fragment(s) covalently linked to one or more polymer molecule(s), such as conjugates containing two or more antibody fragments covalently linked together by polymer molecule(s). In one embodiment, a polymer molecule is used to link together two antibody fragments to form a dumbbell-shaped structure. Also encompassed herein are conjugates formed by more than two antibody fragments joined by polymer molecule(s) to form a rosette or other shapes. The antibody fragments in such structures can be of the same or different fragment type and can have the same antigen specificity or have different antigen specificities. Such structures can be made by using a polymer molecule derivatized with multiple functional groups permitting the direct attachment, or the attachment by means of bi- or multi-functional linkers, of two or more antibody fragments to the polymer backbone.

In another aspect, the invention encompasses any of the above-described conjugates utilizing an antibody fragment comprising an antigen recognition site that binds to rabbit IL-8 and/or human IL-8. In yet another aspect, the invention encompasses any of the above-described conjugates utilizing an antibody fragment comprising 6G4.2.5LV/L1N35A or 6G4.2.5LV/L1N35E as defined below. In still another aspect, the invention encompasses any of the above-described conjugates utilizing an antibody fragment comprising 6G4.5.2.5HV11 as defined below. In a further aspect, the invention encompasses any of the above-described conjugates utilizing an antibody fragment comprising hu6G4.2.5LV/L1N35A or hu6G4.2.5LV/L1N35E as defined below. In an additional aspect, the invention encompasses any of the above-described conjugates utilizing an antibody fragment comprising hu6G4.2.5HV. Further encompassed herein are any of the above-described conjugates utilizing an antibody fragment comprising 6G4.2.5LV/L1N35A or 6G4.2.5LV/L1N35E and further comprising the CDRs of 6G4.2.5HV as defined below. Also encompassed herein are any of the above described conjugates utilizing an antibody fragment comprising hu6G4.2.5LV/L1N35A or hu6G4.2.5LV/L1N35E and further comprising hu6G4.2.5HV as defined below. Additionally encompassed herein are any of the above-described conjugates utilizing an antibody fragment comprising 6G4.2.5LV11N35A or 6G4.2.5LV11N35E as defined below. Further provided herein are any of the above-described conjugates utilizing an antibody fragment comprising 6G4.2.5LV11N35A or 6G4.2.5LV11N35E and further comprising 6G4.2.5HV11 as defined below.

In another aspect, the invention encompasses any of the above-described conjugates utilizing an antibody fragment comprising an antigen recognition site that binds to human VEGF. In another embodiment, the foregoing antibody fragment competes with VEGF receptor for binding to VEGF. Such anti-VEGF antagonistic antibody fragments are used to construct conjugates that are capable of inhibiting one or more of the biological activities of VEGF, for example, its mitogenic or angiogenic activity. Antagonists of VEGF act by interfering with the binding of VEGF to a cellular receptor, by incapacitating or killing cells which have been activated by VEGF, or by interfering with vascular endothelial cell activation after VEGF binding to a cellular receptor. All such points of intervention used by anti-VEGF antagonists are also suitable therapeutic targets for the anti-VEGF antibody fragment-polymer conjugates of the invention. Anti-human VEGF antibodies capable of interfering with the binding of VEGF to a cellular receptor are described in WO 98/45331 published Oct. 15, 1998 (International Application No. PCT/US98/06604 filed Apr. 3, 1998).

In another aspect, the invention encompasses any of the above-described conjugates utilizing an antibody fragment comprising an antigen recognition site that binds to HER2. In another embodiment, the foregoing antibody fragment binds to the extracellular domain of the human ErbB2 (HER2) receptor. In yet another embodiment, the foregoing antibody fragment is capable of inducing cell death or apoptosis of a HER2-expressing cell. In still another embodiment, the foregoing conjugate utilizing an anti-HER2 antibody fragment further incorporates a radioimaging or radiotherapeutic agent, including radionuclides such as $^{212}$Bi, $^{131}$I, $^{131}$In, $^{90}$Y and $^{186}$Re, or other nonproteinaceous diagnostic label or chemotherapeutic agent, including small molecule toxins such as calicheamicins, maytansinoids, palytoxins, trichothenes, and CC1065.

In another aspect, the invention encompasses any of the above-described conjugates utilizing an antibody fragment comprising an antigen recognition site that binds to human CD20. In another embodiment, the foregoing antibody fragment binds to the extracellular domain of human CD20.

In another aspect, the invention encompasses any of the above-described conjugates utilizing an antibody fragment comprising an antigen recognition site that binds to human CD18. In another embodiment, the foregoing antibody fragment binds to the extracellular domain of human CD18.

In another aspect, the invention encompasses any of the above-described conjugates utilizing an antibody fragment comprising an antigen recognition site that binds to human CD11a. In another embodiment, the foregoing antibody fragment binds to the extracellular domain of human CD11a.

In another aspect, the invention encompasses any of the above-described conjugates utilizing an antibody fragment comprising an antigen recognition site that binds to human IgE. In another embodiment, the foregoing antibody fragment is capable of competing with $Fc_\epsilon RI$ receptor for binding to human IgE, i.e. capable of inhibiting the binding of human IgE to the $FC_\epsilon RI$ receptor. In yet another embodiment, the foregoing antibody fragment binds to membrane-bound IgE on the surface of human B-lymphocytes but does not bind to soluble IgE bound to $Fc_\epsilon RI$ receptor on the surface of human basophils.

In another aspect, the invention encompasses any of the above-described conjugates utilizing an antibody fragment comprising an antigen recognition site that binds to human Apo-2 receptor. In another embodiment, the foregoing antibody fragment binds to the extracellular domain of the human Apo-2 receptor. In yet another embodiment, the foregoing antibody fragment is capable of inducing cell death or apoptosis of an Apo-2 receptor-expressing cell.

In another aspect, the invention encompasses any of the above-described conjugates utilizing an antibody fragment comprising an antigen recognition site that binds to human TNF-α.

In another aspect, the invention encompasses any of the above-described conjugates utilizing an antibody fragment comprising an antigen recognition site that binds to human tissue factor.

In another aspect, the invention encompasses any of the above-described conjugates utilizing an antibody fragment comprising an antigen recognition site that binds to human $\alpha_4\beta_7$ integrin. In another embodiment, the foregoing antibody fragment binds to the extracellular region of a human $\alpha_4\beta_7$ integrin complex.

In another aspect, the invention encompasses any of the above-described conjugates utilizing an antibody fragment comprising an antigen recognition site that binds to human GPIIb-IIIa integrin. In another embodiment, the foregoing antibody fragment binds to the extracellular region of a human GPIIb-IIIa integrin complex.

In another aspect, the invention encompasses any of the above-described conjugates utilizing an antibody fragment comprising an antigen recognition site that binds to human CD3. In another embodiment, the foregoing antibody fragment binds to the extracellular domain of human CD3.

In another aspect, the invention encompasses any of the above-described conjugates utilizing an antibody fragment comprising an antigen recognition site that binds to human interleukin-2 receptor (IL-2R) α-chain (T-cell activation antigen or "TAC"). In another embodiment, the foregoing antibody fragment binds to the extracellular domain of human TAC.

In another aspect, the invention encompasses any of the above-described conjugates utilizing an antibody fragment comprising an antigen recognition site that binds to human EGFR. In another embodiment, the foregoing antibody fragment binds to the extracellular domain of human EGFR.

a. Production of Antibody Fragments

Antibody fragments can be produced by any method known in the art. Generally, an antibody fragment is derived from a parental intact antibody.

(i) Antigen Preparation

The antigen to be used for antibody generation can be prepared by any convenient method, such as recombinant methods. Membrane-bound protein antigens can be presented by cell surface expression in recombinant or non-recombinant cells, which cells can be used as immunogens for raising the desired antibody response against the membrane-bound protein antigen. Alternatively, soluble forms of the membrane-bound protein antigen can be generated, such as isolated extracellular domain fragments of membrane-anchored receptor proteins, or variants of such receptor proteins having deleted or inactivated transmembrane domains. In one embodiment, an extracellular domain is fused to the Fc region of an immunoglobulin to form a chimeric protein immunogen.

A protein antigen of interest can be cloned, genetically engineered as desired to add characteristics useful in antibody generation (such as fusion to an immunoglobulin Fc region), and produced in a recombinant expression host cell system according to known methods. In one embodiment, human VEGF-encoding DNA is obtained as described in U.S. Pat. No. 5,332,671 (issued Jul. 26, 1994) and used for production of human VEGF in recombinant host cells according to the same general methods that are described for antibodies and antibody fragments in Section (II)(4) below, followed by recovery and purification of human VEGF from recombinant host cell culture according to the same general methods that are described for antibodies and antibody fragments in Section (II)(4)(F) below. In another embodiment, human VEGF is obtained as described in U.S. Pat. No. 5,332,671.

In one embodiment, soluble HER2-encoding DNA, such as HER2 extracellular domain (ECD)-encoding DNA, is obtained as described in European Patent No. 0 474 727 B1 (granted Jul. 23, 1997) (European regional phase of WO 90/14357 published Nov. 29, 1990) and used for production of HER2 ECD in recombinant host cells according to the same general methods that are described for antibodies and antibody fragments in Section (II)(4) below, followed by recovery and purification of human HER2 ECD from recombinant host cell culture according to the same general methods that are described for antibodies and antibody fragments in Section (II)(4)(F) below. In another embodiment, HER2 ECD is obtained as described in EP 0 474 727 B1.

In one embodiment, soluble human CD20-encoding DNA, such as human CD20 extracellular domain (ECD)-encoding DNA, is obtained as described in Tedder et al., "Isolation and Structure of a cDNA Encoding the B1 (CD20) Cell-Surface Antigen of Human B Lymphocytes," *Proc. Natl. Acad. Sci. (USA)*, 85: 208-212 (1988) and used for production of CD20 ECD in recombinant host cells according to the same general methods that are described for antibodies and antibody fragments in Section (II)(4) below, followed by recovery and purification of human CD20 ECD from recombinant host cell culture according to the same general methods that are described for antibodies and antibody fragments in Section (II)(4)(F) below.

In one embodiment, soluble human CD11a-encoding DNA, such as human CD11a I-domain-encoding DNA, is obtained as described in van Kooyk et al., *J. Exp. Med.*, 183(3): 1247-1252 (1996), Edwards et al., *J. Biol. Chem.*, 270(21): 12635-12640 (1995), or Champe et al., *J. Biol. Chem.*, 270: 1388-1394 (1995), and used for production of CD11a I-domain in recombinant host cells according to the same general methods that are described for antibodies and antibody fragments in Section (II)(4) below, followed by recovery and purification of human CD11a 1-domain from recombinant host cell culture according to the same general methods that are described for antibodies and antibody fragments in Section (II)(4)(F) below.

In one embodiment, soluble human CD18-encoding DNA, such as human CD18 extracellular domain (ECD)-encoding DNA, is obtained as described in Kishimoto et al., "Cloning of the beta subunit of the leukocyte adhesion proteins: homology to an extracellular matrix receptor defines a novel supergene family," *Cell*, 48:681-690 (1987) and used for production of CD18 ECD in recombinant host cells according to the same general methods that are described for antibodies and antibody fragments in Section (II)(4) below, followed by recovery and purification of human CD18 ECD from recombinant host cell culture according to the same general methods that are described for antibodies and antibody fragments in Section (II)(4)(F) below.

In one embodiment, human membrane-bound IgE extracellular domain-encoding DNA is obtained as described in U.S. Pat. No. 5,091,131 (issued Feb. 25, 1992) and used for production of human membrane-bound IgE ECD in recombinant host cells according to the same general methods that are described for antibodies and antibody fragments in Section (II)(4) below, followed by recovery and purification of human membrane-bound IgE ECD from recombinant host cell culture according to the same general methods that are described for antibodies and antibody fragments in Section (II)(4)(F) below. In another embodiment, human membrane-bound IgE ECD is obtained as described in U.S. Pat. No. 5,091,131.

In one embodiment, soluble human Apo-2 receptor-encoding DNA, such as human Apo-2 receptor extracellular domain (ECD)-encoding DNA, is obtained as described in WO 98/51793 (published Nov. 19, 1998) (International Application No. PCT/US98/09704 filed May 14, 1998) and used for production of human Apo-2 receptor ECD in recombinant host cells according to the same general methods that are described for antibodies and antibody fragments in Section (II)(4) below, followed by recovery and purification of human Apo-2 receptor ECD from recombinant host cell culture according to the same general methods that are described for antibodies and antibody fragments in Section (II)(4)(F) below.

In one embodiment, human TNF-α-encoding DNA is obtained as described in Pennica et al., *Nature*, 512: 721 (1984) or U.S. Pat. No. 4,650,674 (issued Mar. 17, 1987) and used for production of human TNF-α in recombinant host cells according to the same general methods that are described for antibodies and antibody fragments in Section (II)(4) below, followed by recovery and purification of human TNF-α from recombinant host cell culture according to the same general methods that are described for antibodies and antibody fragments in Section (II)(4)(F) below. In another embodiment, human TNF-α is obtained as described in U.S. Pat. No. 4,650,674.

In one embodiment, human tissue factor-encoding DNA is obtained as described in European Patent No. 0 278 776 B1 (granted May 28, 1997) and used for production of human tissue factor in recombinant host cells according to the same general methods that are described for antibodies and antibody fragments in Section (II)(4) below, followed by recovery and purification of human tissue factor from recombinant host cell culture according to the same general methods that are described for antibodies and antibody fragments in Section (II)(4)(F) below. In another embodiment, human tissue factor is obtained as described in European Patent No. 0 278 776 B1.

In one embodiment, soluble human $\alpha_4$ integrin-encoding DNA and soluble human $\beta_7$ integrin encoding DNA, such as human $\alpha_4$ integrin extracellular domain (ECD)-encoding DNA along with human $\beta_7$ integrin extracellular domain (ECD)-encoding DNA, are obtained as described in Takada et al., "The primary structure of the $\alpha_4$ subunit of VLA-4: Homology to other integrins and a possible cell-cell adhesion function", *EMBO J.*, 8: 1361-1368 (1989) and Yuan et al., "Cloning and sequence analysis of a novel $\beta_2$-related integrin transcript from T lymphocytes: homology of integrin cysteine-rich repeats to domain III of laminin B chains", *International Immunology*, 2: 1097-1108 (1990), respectively, and used for co-production of human $\alpha_4$ integrin ECD and human $\beta_7$ integrin ECD in recombinant host cells according to the same general methods that are described for antibodies and antibody fragments in Section (II)(4) below, followed by recovery and purification of $\alpha_4$ ECD-$\beta_7$ ECD complex from recombinant host cell culture according to the same general methods that are described for antibodies and antibody fragments in Section (II)(4)(F) below.

In one embodiment, soluble human GPIIb-encoding DNA and soluble human GPIIIa-encoding DNA, such as human GPIIb extracellular domain (ECD)-encoding DNA along with human GPIIIa extracellular domain (ECD)-encoding DNA, are obtained as described in U.S. Pat. No. 5,726,037 (issued Mar. 10, 1998) and used for co-production of human GPIIb ECD and human GPIIIa ECD in recombinant host cells according to the same general methods that are described for antibodies and antibody fragments in Section (II)(4) below, followed by recovery and purification of GPIIb ECD-GPIIIa ECD complex from recombinant host cell culture according to the same general methods that are described for antibodies and antibody fragments in Section (II)(4)(F) below. Alternatively, human GPIIb-IIIa complex can be produced and secreted from recombinant host cells as described in Example 3 of U.S. Pat. No. 5,726,037.

In one embodiment, soluble human epidermal growth factor receptor (EGFR)-encoding DNA, such as human EGFR extracellular domain (ECD)-encoding DNA, is obtained as described in Ullrich et al., *Nature*, 309: 418-425 (1984) and used for production of human EGFR ECD in recombinant host cells according to the same general methods that are described for antibodies and antibody fragments in Section (II)(4) below, followed by recovery and purification of human EGFR ECD from recombinant host cell culture according to the same general methods that are described for antibodies and antibody fragments in Section (II)(4)(F) below.

In one embodiment, soluble human CD3-encoding DNA, such as human CD3 extracellular domain (ECD)-encoding DNA, is obtained as described in van den Elsen et al., "Isolation of cDNA clones encoding the 20K T3 glycoprotein of human T-cell receptor complex," *Nature*, 312:413-418 (1984) and used for production of human CD3 ECD in recombinant host cells according to the same general methods that are described for antibodies and antibody fragments in Section (II)(4) below, followed by recovery and purification of human CD3 ECD from recombinant host cell culture according to the same general methods that are described for antibodies and antibody fragments in Section (II)(4)(F) below.

In one embodiment, soluble human interleukin-2 receptor (IL-2R) ∀-chain (T-cell activation antigen or "TAC")-encoding DNA, such as human TAC extracellular domain (ECD)-encoding DNA, is obtained as described in Leonard et al., *Science,* 230: 633-639 (1985) and used for production of human TAC ECD in recombinant host cells according to the same general methods that are described for antibodies and antibody fragments in Section (II)(4) below, followed by recovery and purification of human TAC ECD from recombinant host cell culture according to the same general methods that are described for antibodies and antibody fragments in Section (II)(4)(F) below.

(ii) Polyclonal Antibodies

The parental antibody can be generated by raising polyclonal sera against the desired antigen by multiple subcutaneous (sc) or intraperitoneal (ip) injections of antigen and an adjuvant, such as monophosphoryl lipid A (MPL)/trehalose dicrynomycolate (TDM) (Ribi Immunochem. Research, Inc., Hamilton, Mont.), at multiple sites. Two weeks later the animals are boosted. 7 to 14 days later animals are bled and the serum is assayed for anti-antigen titer. Animals are boosted until titer plateaus. Sera are harvested from animals, and polyclonal antibodies are isolated from sera by conventional immunoglobulin purification procedures, such as protein A-Sepharose chromatography, hydroxylapatite chromatography, gel filtration, dialysis, or antigen affinity chromatography. The desired antibody fragments can be generated from purified polyclonal antibody preparations by conventional enzymatic methods, e.g. F(ab')₂ fragments are produced by pepsin cleavage of intact antibody, and Fab fragments are produced by briefly digesting intact antibody with papain.

(iii) Monoclonal Antibodies

Alternatively, antibody fragments are derived from monoclonal antibodies generated against the desired antigen. Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies. Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies. Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In one embodiment, anti-human VEGF monoclonal antibody is obtained as described in WO 98/45331 (published Oct. 15, 1998) (International Application No. PCT/US98/06604 filed Apr. 3, 1998).

In another embodiment, anti-HER2 monoclonal antibody is obtained as described in U.S. Pat. No. 5,725,856 (issued Mar. 10, 1998) or International Application No. CT/US98/26266 (filed Dec. 10, 1998).

In another embodiment, anti-human CD20 monoclonal antibody is obtained as described in WO 94/11026 (published May 26, 1994) (International Application No. PCT/US93/10953 filed Nov. 12, 1993).

In another embodiment, anti-human CD18 monoclonal antibody is obtained as described in U.S. Pat. No. 5,622,700 (issued Apr. 22, 1997). In yet another embodiment, anti-human CD18 monoclonal antibody is obtained as described in WO 97/26912 (published Jul. 31, 1997) (International Application No. PCT/US97/00492 filed Jan. 11, 1997).

In another embodiment, anti-human CD11a monoclonal antibody is obtained as described in U.S. Pat. No. 5,622,700. In yet another embodiment, anti-human CD11a monoclonal antibody is obtained as described in WO 98/23761 (published Jun. 4, 1998) (International Application No. PCT/US97/19041 filed Oct. 20, 1997).

In another embodiment, anti-human IgE monoclonal antibody is obtained as described in U.S. Pat. No. 5,714,338 (issued Feb. 3, 1998). In yet another embodiment, anti-human IgE monoclonal antibody is obtained as described in U.S. Pat. No. 5,091,313 (issued Feb. 25, 1992). In still another embodiment, anti-human IgE monoclonal antibody is obtained as described in WO 93/04173 (published Mar. 4, 1993) (International Application No. PCT/US92/06860 filed Aug. 14, 1992). In an additional embodiment, anti-human IgE monoclonal antibody is obtained as described in International Application No. PCT/US98/13410 (filed Jun. 30, 1998). In a further aspect, the invention comptemplates the use of anti-human IgE monoclonal antibody capable of competing with $Fc_\epsilon RI$ receptor for binding to human IgE, i.e. capable of inhibiting the binding of human IgE to the $Fc_\epsilon RI$ receptor. Such anti-IgE monoclonal antibodies can be selected and identified by any convenient screening method, such an assay for inhibition of IgE-induced basophil cell sensitization as described in U.S. Pat. No. 5,714,338.

In another embodiment, anti-human Apo-2 receptor monoclonal antibody is obtained as described in WO 98/51793 (published Nov. 19, 1998) (International Application No. PCT/US98/09704 filed May 14, 1998). In a further embodiment, the invention contemplates the use of anti-human Apo-2 receptor monoclonal antibody capable of activating the human Apo-2 receptor. Such anti-Apo-2 monoclonal antibodies can be selected and identified by any convenient screening method, such as an assay for induction of Apo-2 mediated 9D cell apoptosis as described in Example 10 of WO 98/51793.

In another embodiment, anti-human TNF-α monoclonal antibody is obtained as described in U.S. Pat. No. 5,672,347 (issued Sep. 30, 1997).

In another embodiment, anti-human tissue factor monoclonal antibody is obtained as described in European Patent No. 0 420 937 B1 (granted Nov. 9, 1994).

In another embodiment, anti-human $\alpha_4$-$\beta_7$ integrin monoclonal antibody is obtained as described in WO 98/06248 (published Feb. 19, 1998) (International Application No. PCT/US97/13884 filed Aug. 6, 1997).

In another embodiment, anti-human EGFR monoclonal antibody is obtained as described in WO 96/40210 (published Dec. 19, 1996) (International Application No. PCT/US96/9847 filed Jun. 7, 1996).

In another embodiment, anti-human CD3 monoclonal antibody is obtained as described in U.S. Pat. No. 4,515,893 (issued May 7, 1985).

In another embodiment, anti-human TAC monoclonal antibody is obtained as described in U.S. Pat. No. 5,693,762 (issued Dec. 2, 1997).

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs.*, 130: 151 (1992).

In a preferred embodiment, the antibody fragment is derived from a humanized antibody. Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. It will be appreciated that variable domain sequences obtained from any non-human animal phage display library-derived Fv clone or from any non-human animal hybridoma-derived antibody clone provided as described herein can serve as the "import" variable domain used in the construction of the humanized antibodies of the invention. Humanization can be essentially performed following the method of Winter and co-workers (Jones et al., Nature, 321: 522 (1986); Riechmann et al., Nature, 332: 323 (1988); Verhoeyen et al., Science, 239: 1534 (1988)), by substituting non-human animal, e.g. rodent, CDRs or CDR sequences for the corresponding sequences of a human antibody. Accordingly, such "humanized" antibodies are chimeric antibodies (Cabilly et al., supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in non-human animal, e.g. rodent, antibodies.

The choice of human variable domains, both light and heavy, to be used in making the humanized antibodies is very important to reduce antigenicity. According to the so-called "best-fit" method, the sequence of the variable domain of a non-human animal, e.g. rodent, antibody is screened against the entire library of known human variable-domain sequences. The human sequence which is closest to that of the non-human animal is then accepted as the human framework (FR) for the humanized antibody (Sims et al., J. Immunol., 151: 2296 (1993); Chothia and Lesk, J. Mol. Biol., 196: 901 (1987)). Another method uses a particular framework derived from the consensus sequence of all human antibodies of a particular subgroup light or heavy chains. The same framework can be used for several different humanized antibodies (Carter et al., Proc. Natl. Acad. Sci USA, 89: 4285 (1992); Presta et al., J. Immunol., 151: 2623 (1993)).

It is also important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind to its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding.

In addition, antibody fragments for use herein can be derived from human monoclonal antibodies. Human monoclonal antibodies against the antigen of interest can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Alternatively, phage display technology (McCafferty et al., Nature 348:552 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson et al., Current Opinion in Structural Biology 3:564 (1993). Several sources of V-gene segments can be used for phage display. Clackson et al., Nature 352:624 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581 (1991), or Griffith et al., EMBO J. 12:725 (1993). In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., Bio/Technol. 10:779 (1992)). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires has been described by Waterhouse et al., Nucl. Acids Res. 21:2265 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

The invention also encompasses the use of bispecific and heteroconjugate antibody fragments having specificities for at least two different antigens. Bispecific and heteroconjugate antibodies can be prepared as full length antibodies or as antibody fragments (e.g. F(ab')$_2$ bispecific antibody fragments). Antibody fragments having more than two valencies (e.g. trivalent or higher valency antibody fragments) are also contemplated for use herein. Bispecific antibodies, heteroconjugate antibodies, and multi-valent antibodies can be prepared as described in Section (II)(3)(C) below.

As described above, DNA encoding the monoclonal antibody or antibody fragment of interest can be isolated from its hybridoma or phage display clone of origin, and then manipulated to create humanized and/or affinity matured constructs. In addition, known techniques can be employed to introduce an amino acid residue or residues into any desired location on the polypeptide backbone of the antibody fragment, e.g. a cysteine residue placed in the hinge region of the heavy chain, thereby providing a site for specific attachment of polymer molecule(s). In one embodiment, the native cysteine residue in either the light or heavy chain of the antibody fragment that would ordinarily form the disulfide bridge linking the light and heavy chains is substituted with another amino acid, such as serine, in order to leave the partner cysteine residue in the opposite chain with a free sulfhydryl for specific attachment of polymer molecule.

Upon construction of the desired antibody or antibody fragment-encoding clone, the clone can be used for recombinant production of the antibody fragment as described in Section (II)(4) below. Finally, the antibody or antibody fragment product can be recovered from host cell culture and purified as described in Section (II)(4)(F) below. In the case of embodiments utilizing an antibody fragment engineered to lack a cysteine residue that ordinarily forms the disulfide bridge between the light and heavy chains as described above, preferred recombinant production systems include bacterial expression and product recovery procedures utilizing the low pH osmotic shock method described in the "Alternative Fab'-SH Purification" section of Example T below. If a full length antibody is produced, the desired antibody fragment can be obtained therefrom by subjecting the intact antibody to enzymatic digestion according to known methods, e.g. as described in Section (II)(4)(G) below.

b. Construction of Antibody Fragment-Polymer Conjugates

The antibody fragment-polymer conjugates of the invention can be made by derivatizing the desired antibody fragment with an inert polymer. It will be appreciated that any inert polymer which provides the conjugate with the desired apparent size or which has the selected actual MW as taught herein is suitable for use in constructing the antibody fragment-polymer conjugates of the invention.

Many inert polymers are suitable for use in pharmaceuticals. See, e.g., Davis et al., *Biomedical Polymers Polymeric Materials and Pharmaceuticals for Biomedical Use*, pp. 441-451 (1980). In all embodiments of the invention, a non-proteinaceous polymer is used. The nonproteinaceous polymer ordinarily is a hydrophilic synthetic polymer, i.e., a polymer not otherwise found in nature. However, polymers which exist in nature and are produced by recombinant or in vitro methods are also useful, as are polymers which are isolated from native sources. Hydrophilic polyvinyl polymers fall within the scope of this invention, e.g. polyvinylalcohol and polyvinylpyrrolidone. Particularly useful are polyalkylene ethers such as polyethylene glycol (PEG); polyoxyalkylenes such as polyoxyethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, silica acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon. The polymer prior to cross-linking need not be, but preferably is, water soluble, but the final conjugate must be water soluble. Preferably, the conjugate exhibits a water solubility of at least about 0.01 mg/ml, and more preferably at least about 0.1 mg/ml, and still more preferably at least about 1 mg/ml. In addition, the polymer should not be highly immunogenic in the conjugate form, nor should it possess viscosity that is incompatible with intravenous infusion or injection if the conjugate is intended to be administered by such routes.

In one embodiment, the polymer contains only a single group which is reactive. This helps to avoid cross-linking of protein molecules. However, it is within the scope herein to maximize reaction conditions to reduce cross-linking, or to purify the reaction products through gel filtration or ion exchange chromatography to recover substantially homogenous derivatives. In other embodiments, the polymer contains two or more reactive groups for the purpose of linking multiple antibody fragments to the polymer backbone. Again, gel filtration or ion exchange chromatography can be used to recover the desired derivative in substantially homogeneous form.

The molecular weight of the polymer can range up to about 500,000 D, and preferably is at least about 20,000 D, or at least about 30,000 D, or at least about 40,000 D. The molecular weight chosen can depend upon the effective size of the conjugate to be achieved, the nature (e.g. structure, such as linear or branched) of the polymer, and the degree of derivatization, i.e. the number of polymer molecules per antibody fragment, and the polymer attachment site or sites on the antibody fragment.

The polymer can be covalently linked to the antibody fragment through a multifunctional crosslinking agent which reacts with the polymer and one or more amino acid residues of the antibody fragment to be linked. However, it is also within the scope of the invention to directly crosslink the polymer by reacting a derivatized polymer with the antibody fragment, or vice versa.

The covalent crosslinking site on the antibody fragment includes the N-terminal amino group and epsilon amino groups found on lysine residues, as well as other amino, imino, carboxyl, sulfhydryl, hydroxyl or other hydrophilic groups. The polymer may be covalently bonded directly to the antibody fragment without the use of a multifunctional (ordinarily bifunctional) crosslinking agent. Covalent binding to amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, activated succinimidyl esters, activated dithiocarbonate PEG, 2,4,5-trichlorophenylcloroformate or P-nitrophenylcloroformate activated PEG.) Carboxyl groups are derivatized by coupling PEG-amine using carbodiimide. Sulfhydryl groups are derivatized by coupling to maleimido-substituted PEG (e.g. alkoxy-PEG amine plus sulfosuccinimidyl 4-(N-maleimidomethyl)cyclohexane-1-carboxylate) as described in WO 97/10847 published Mar. 27, 1997, or PEG-maleimide commercially available from Shearwater Polymers, Inc., Huntsville, Ala.). Alternatively, free amino groups on the antibody fragment (e.g. epsilon amino groups on lysine residues) can be thiolated with 2-imino-thiolane (Traut's reagent) and then coupled to maleimide-containing derivatives of PEG as described in Pedley et al., *Br. J. Cancer,* 70: 1126-1130 (1994).

The polymer will bear a group which is directly reactive with an amino acid side chain, or the N- or C-terminus of the polypeptide linked, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides.

"Water soluble" in reference to the starting polymer means that the polymer or its reactive intermediate used for conjugation is sufficiently water soluble to participate in a derivatization reaction.

The degree of substitution with such a polymer will vary depending upon the number of reactive sites on the antibody fragment, the molecular weight, hydrophilicity and other characteristics of the polymer, and the particular antibody fragment derivatization sites chosen. In general, the conjugate contains from 1 to about 10 polymer molecules, but greater numbers of polymer molecules attached to the antibody fragments of the invention are also contemplated. The desired amount of derivatization is easily achieved by using an experimental matrix in which the time, temperature and other reaction conditions are varied to change the degree of substitution, after which the level of polymer substitution of the conjugates is determined by size exclusion chromatography or other means known in the art.

The polymer, e.g. PEG, is cross-linked to the antibody fragment by a wide variety of methods known per se for the covalent modification of proteins with nonproteinaceous polymers such as PEG. Certain of these methods, however, are not preferred for the purposes herein. Cyanuronic chloride chemistry leads to many side reactions, including protein cross-linking. In addition, it may be particularly likely to lead to inactivation of proteins containing sulfhydryl groups. Carbonyl diimidazole chemistry (Beauchamp et al., *Anal Biochem.* 131, 25-33 [1983]) requires high pH (>8.5), which can inactivate proteins. Moreover, since the "activated PEG" intermediate can react with water, a very large molar excess of "activated PEG" over protein is required. The high concentrations of PEG required for the carbonyl diimidazole chemistry also led to problems in purification, as both gel filtration chromatography and hydrophilic interaction chromatography are adversely affected. In addition, the high concentrations of "activated PEG" may precipitate protein, a problem that per se has been noted previously (Davis, U.S. Pat. No. 4,179,337). On the other hand, aldehyde chemistry (Royer, U.S. Pat. No. 4,002,531) is more efficient since it requires only a 40-fold molar excess of PEG and a 1-2 hr incubation. However, the manganese dioxide suggested by Royer for preparation of the PEG aldehyde is problematic "because of the pronounced tendency of PEG to form complexes with metal-based oxidizing agents" (Harris et al., *J. Polym. Sci. Polym. Chem. Ed.* 22, 341-52 [1984]). The use of a Moffatt oxidation, utilizing DMSO and acetic anhydride, obviates this problem. In addition, the sodium borohydride suggested by Royer must be used at high pH and has a significant tendency to reduce disulfide bonds. In contrast, sodium cyanoborohydride, which is effective at neutral pH and has very little tendency to reduce disulfide bonds is preferred. In another preferred embodiment, maleimido-activated PEG is used for coupling to free thiols on the antibody fragment.

Functionalized PEG polymers to modify the antibody fragments of the invention are available from Shearwater Polymers, Inc. (Huntsville, Ala.). Such commercially available PEG derivatives include, but are not limited to, amino-PEG, PEG amino acid esters, PEG-hydrazide, PEG-thiol, PEG-succinate, carboxymethylated PEG, PEG-propionic acid, PEG amino acids. PEG succinimidyl succinate, PEG succinimidyl propionate, succinimidyl ester of carboxymethylated PEG, succinimidyl carbonate of PEG, succinimidyl esters of amino acid PEGs, PEG-oxycarbonylimidazole, PEG-nitrophenyl carbonate, PEG tresylate, PEG-glycidyl ether, PEG-aldehyde, PEG vinylsulfone, PEG-maleimide, PEG-orthopyridyl-disulfide, heterofunctional PEGs, PEG vinyl derivatives, PEG silanes, and PEG phospholides. The reaction conditions for coupling these PEG derivatives will vary depending on the protein, the desired degree of PEGylation, and the PEG derivative utilized. Some factors involved in the choice of PEG derivatives include: the desired point of attachment (such as lysine or cysteine R-groups), hydrolytic stability and reactivity of the derivatives, stability, toxicity and antigenicity of the linkage, suitability for analysis, etc. Specific instructions for the use of any particular derivative are available from the manufacturer.

The conjugates of this invention are separated from the unreacted starting materials by gel filtration or ion exchange HPLC. Heterologous species of the conjugates are purified from one another in the same fashion.

The conjugates may also be purified by ion-exchange chromatography. The chemistry of many of the electrophilically activated PEG's results in a reduction of amino group charge of the PEGylated product. Thus, high resolution ion exchange chromatography can be used to separate the free and conjugated proteins, and to resolve species with different levels of PEGylation. In fact, the resolution of different species (e.g. containing one or two PEG residues) is also possible due to the difference in the ionic properties of the unreacted amino acids. In one embodiment, species with difference levels of PEGylation are resolved according to the methods described in WO 96/34015 (International Application No. PCT/US96/05550 published Oct. 31, 1996).

In a preferred embodiment, the conjugate is generated by utilizing the derivatization and purification methods described in Section (T) of the Examples below.

In one aspect, the invention provides any of the above-described conjugates formed by its component parts, i.e. one or more antibody fragment(s) covalently attached to one or more polymer molecule(s), without any extraneous matter in the covalent molecular structure of the conjugate.

c. Other Derivatives of Large Effective Size Conjugates

In another aspect, any of the above-described conjugates can be modified to contain one or more component(s) in addition to the antibody fragment component(s) and polymer component(s) that form the conjugate, wherein the modification does not alter the essential functional property of the conjugate, namely, the substantially improved serum half-life, MRT and/or serum clearance rate as compared to that of the parental antibody fragment from which the conjugate is derived. In one embodiment, the invention provides any of the above-described conjugates modified to incorporate one or more nonproteinaceous functional group(s). For example, the conjugate can be modified to incorporate nonproteinaceous labels or reporter molecules, such as radiolabels, including any radioactive substance used in medical treatment or imaging or used as an effector function or tracer in an animal model, such as radioisotopic labels $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{75}Se$, $^{52}Eu$, $^{67}CU$, $^{217}Ci$, $^{211}At$, $^{212}Pb$, $^{47}Sc$, $^{109}Pd$, $^{234}Th$ $^{40}K$, and the like, non-radioisotopic labels such as $^{157}Gd$, $^{55}Mn$, $^{52}Tr$, $^{56}Fe$, etc., fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels, stable free radicals, and the like.

Conventional methods are available to bind these labels covalently to the polypeptide antibody fragment or polymer component of the conjugate. In one aspect, any conjugate of the invention is modified by derivatizing the antibody fragment component with any of the above-described non-proteinaceous labels, wherein the label is directly or indirectly (through a coupling agent) attached to the antibody fragment, and wherein such derivatization of the antibody fragment does not contribute or introduce any polymer moiety into the molecular structure of the conjugate. For instance, coupling agents such as dialdehydes, carbodiimides, dimaleimides, bis-imidates, bis-diazotized benzidine, and the like can be used to tag the antibody fragment with the above-described fluorescent or chemiluminescent labels. See, for example, U.S. Pat. No. 3,940,475 (fluorimetry), Morrison, *Meth. Enzymol.*, 32b, 103 (1974), Svyanen et al., *J. Biol. Chem.*, 284, 3762 (1973), and Bolton and Hunter, *Biochem. J.*, 133, 529 (1973).

In the case of embodiments utilizing radiolabels, both direct and indirect labeling can be used to incorporate the selected radionuclide into the conjugate. As used herein in the context of radiolabeling, the phrases "indirect labeling" and "indirect labeling approach" both mean that a chelating agent is covalently attached to the antibody fragment moiety or polymer moiety of the conjugate and at least one radionuclide is inserted into the chelating agent. Preferred chelating agents and radionuclides are set forth in Srivagtava, S. C. and Mease, R. C., "Progress in Research on Ligands, Nuclides and Techniques for Labeling Monoclonal Antibodies," *Nucl. Med. Bio.*, 18(6): 589-603 (1991). A particularly preferred chelating agent is 1-isothiocycmatobenzyl-3-methyldiothelene triaminepent acetic acid ("MX-DTPA"). As used herein in the context of radiolabeling, the phrases "direct labeling" and "direct labeling approach" both mean that a radionuclide is covalently attached directly to the antibody fragment moiety (typically via an amino acid residue) or to the polymer moiety of the conjugate. Preferred radionuclides for use in direct labeling of conjugate are provided in Srivagtava and Mease, supra. In one embodiment, the conjugate is directly labeled with $^{131}I$ covalently attached to tyrosine residues. In another embodiment, the antibody fragment component of the conjugate is directly or indirectly labeled with any of the above-described radiolabels, wherein such labeling of the antibody fragment does not contribute or introduce any polymer moiety into the molecular structure of the conjugate.

In another embodiment, the conjugate can be modified to incorporate one or more small molecule toxins, such as a calicheamicin, a maytansine (U.S. Pat. No. 5,208,020, expressly incorporated herein by reference), palytoxin, a trichothene, and CC1065. For example, the conjugate of the invention can be derivatized with one or more maytansine molecules (e.g. about 1 to about 10 maytansine molecules per antibody molecule). Maytansine can be converted to May-ss-Me, which can be reduced to May-SH3 and reacted with modified antibody fragment to generate a maytansinoid-derivatized antibody fragment moiety in the conjugate.

In yet another embodiment, the antibody fragment in the conjugate is derivatized with one or more calicheamicin molecules. The calicheamicin family of antibiotics are capable of producing double-stranded DNA breaks at sub-picomolar concentrations. Structural analogues of calicheamicin which may be used include, but are not limited to, $_1^I$, $_2^I$, $_3^I$, N-acetyl-$_1^I$, PSAG and $^I_1$ (Hinman et al., *Cancer R.* 53:3336-3342 [1993]; and Lode et al., *Cancer R.* 58:2925-2928 [1998]).

d. Therapeutic Compositions and Administration of Large Effective Size Conjugates The conjugate of the invention is useful for treating the disease indications that are treated with the parent intact antibody. In one aspect, the invention provides the use of conjugates derived from a parental antibody that binds to an effector molecule selected from the group consisint of human VEGF, HER2, human CD20, human CD18, human CD11a, human IgE, human Apo-2 receptor, human TNF-α, human tissue factor, human $α_4β_7$ integrin, human GPIIb-IIIa integrin, human EGFR, human CD3, human IL-2R α-chain, and human IL-8 in the treatment of a disease that is mediated by the effector molecule.

(i) VEGF-Mediated Disorders

In one embodiment, the invention provides a method for treating a VEGF-mediated disease in a human patient with any of the conjugates described in this Section (II) that is derived from a parental antibody that binds to human VEGF. Such conjugates have prophylactic and therapeutic applications in a broad spectrum of VEGF-mediated disorders, including pathologies supported by blood vessel proliferation, i.e. angiogenesis, in a manner similar to the application of anti-VEGF antibodies in the treatment of such disease indications that is known in the art, which treatment indications include solid tumors ((Kim et al. *Nature* 362:841-844 (1993); Warren et al. *J. Clin. Invest.* 95:1789-1797 (1995); Borgstrom et al. *Cancer Res.* 56:4032-4039 (1996); and Melnyk et al. *Cancer Res.* 56:921-924 (1996)) and intraocular neovascular syndromes such as proliferative retinopathies and age-related macular degeneration (AMD) (Adamis et al. *Arch. Ophthalmol.* 114:66-71 (1996)).

As shown in the Examples below, the conjugates of the invention approximate the in vivo pharmacokinetics (e.g. serum half-life, clearance and mean residence time as shown in FIGS. 72-73 and in Example AB below) and the in vivo therapeutic efficacy (e.g. the treatment of solid tumors as shown in FIG. 74 and in Example AC below) of full length anti-VEGF monoclonal antibody. Since conjugates of the invention derived from anti-VEGF antibodies and fragments display the same or substantially similar in vivo activities as full length anti-VEGF monoclonal antibody across a range of different parameters, including pharmacokinetic characteristics and therapeutic endpoints in an animal tumor model, the data support the efficacy of the conjugates in the same broad spectrum of neovascular disease indications that responds to full length anti-VEGF-antibody treatment.

As noted above, any conjugate described in this Section (II) that is derived from an anti-VEGF antibody or fragment can be advantageously utilized in a method of treating a VEGF-mediated disease or disorder, such as neovascular disorders. In one embodiment, the invention provides a method of treating a neovascular disorder in a human patient comprising administering to the patient an effective amount of any conjugate described in this Section (II) wherein at least one antibody fragment in the conjugate comprises an antigen binding site that binds to human VEGF.

In another embodiment, the invention provides a method of treating a solid tumor disorder in a human patient comprising administering to the patient an effective amount of any conjugate described in this Section (II) wherein at least one antibody fragment in the conjugate comprises an antigen binding site that binds to human VEGF. In yet another embodiment, the solid tumor disorder in the foregoing method is selected from the group consisting of breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), and Meigs' syndrome.

In still another embodiment, the invention provides a method of treating an intraocular neovascular disorder in a human patient comprising administering to the patient an effective amount of any conjugate described in this Section (II) wherein at least one antibody fragment in the conjugate comprises an antigen binding site that binds to human VEGF. In a further embodiment, the intraocular neovascular disorder is selected from the group consisting of diabetic and other proliferative retinopathies including retinopathy of prematurity, retrolental fibroplasia, neovascular glaucoma, and age-related macular degeneration.

In another embodiment, the invention provides a method of inhibiting angiogenesis in a human patient comprising administering to the patient an effective amount of any conjugate described in this Section (II) wherein at least one antibody fragment in the conjugate comprises an antigen binding site that binds to human VEGF.

(ii) Disorders Mediated by HER2-Expressing Cells

In one embodiment, the invention provides a method for treating a human disease mediated by HER2-expressing cells with any of the conjugates described in this Section (II) that is derived from a parental antibody that binds to HER2. Such conjugates have prophylactic and therapeutic applications in a broad spectrum of HER2-expressing cell-mediated disorders, including pathologies supported by the proliferation of cells expressing HER2, such as cancers characterized by overexpression of HER2, in a manner similar to the application of full length anti-HER2 antibodies in the treatment of such disease indications that is known in the art, which treatment indications include HER2-overexpressing breast, ovarian and lung cancers.

In one embodiment, the invention provides a method of treating a HER2-expressing cell mediated disorder in a human patient comprising administering to the patient a therapeutically effective amount of any conjugate described in this Section (II) wherein at least one antibody fragment in the conjugate comprises an antigen binding site that binds to HER2. The disorder can be a HER2-expressing cell proliferative disorder, including a benign or malignant tumor characterized by the overexpression of the ErbB2 receptor, e.g. a cancer, such as, breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. In addition, the invention contemplates the use of the foregoing conjugate in place of full length anti-HER2 antibody in the treatment of HER2-overexpressing cancers as described in U.S. Pat. No. 5,725,856 or International Patent Application No. PCT/US98/26266.

(iii) Disorders Mediated by CD20-Expressing Cells

In one embodiment, the invention provides a method for treating a human disease mediated by CD20-expressing cells with any of the conjugates described in this Section (II) that is derived from a parental antibody that binds to human CD20. Such conjugates have prophylactic and therapeutic applications in a broad spectrum of CD20-expressing cell-mediated disorders, including pathologies supported by the proliferation of CD20-expressing cells, such as cancers of CD20-expressing cells, in a manner similar to the application of full length anti-CD20 antibodies in the treatment of such disease indications that is known in the art, which treatment indications include B-lymphocytic lymphomas.

In one embodiment, the invention provides a method of treating a disorder in a human patient mediated by a CD20-expressing cell, comprising administering to the patient a therapeutically effective amount of any conjugate described in this Section (II) wherein at least one antibody fragment in the conjugate comprises an antigen binding site that binds to human CD20. In another embodiment, the CD20-expressing cell-mediated disorder is a B-lymphocyte proliferative disorder, such as B-lymphocytic lymphoma. In addition, the invention contemplates the use of the foregoing conjugate in place of full length anti-CD20 antibody in the treatment of B-lymphocyte proliferative disorders as described in WO 94/11026 (published May 26, 1994) (International Application No. PCT/US93/10953 filed Nov. 12, 1993).

(iv) Disorders Mediated by CD18-Expressing Cells

In one embodiment, the invention provides a method for treating a human disease mediated by CD18-expressing cells with any of the conjugates described in this Section (II) that is derived from a parental antibody that binds to human CD18. Such conjugates have prophylactic and therapeutic applications in a broad spectrum of CD18-expressing cell-mediated disorders, including pathologies supported by leukocyte adhesion, in a manner similar to the application of full length anti-CD18 antibodies in the treatment of such disease indications that is known in the art, which treatment indications include acute myocardial infarction and stroke.

In one embodiment, the invention provides a method of treating a disorder in a human patient mediated by a CD18-expressing cell, comprising administering to the patient a therapeutically effective amount of any conjugate described in this Section (II) wherein at least one antibody fragment in the conjugate comprises an antigen binding site that binds to human CD18. In another embodiment, the CD18-expressing cell-mediated disorder is an inflammatory disorder, such as an ischemic reperfusion disorder, including acute myocardial infarction and stroke. In addition, the invention contemplates the use of the foregoing conjugate in place of full length anti-CD18 antibody in the treatment of stroke as described in WO 97/26912.

In another embodiment, the invention provides a method of treating a LFA-1-mediated disorder in a human, comprising administering to the patient a therapeutically effective amount of any conjugate described in this Section (II) wherein at least one antibody fragment in the conjugate comprises an antigen binding site that binds to human CD18. In addition, the invention contemplates the use of the foregoing conjugate in place of full length anti-CD18 antibody in the treatment of an LFA-1-mediated disorder, such as psoriasis and graft rejection, in a human patient as described in U.S. Pat. No. 5,622,700.

(v) Disorders Mediated by CD11a-Expressing Cells

In one embodiment, the invention provides a method for treating a human disease mediated by a CD11a-expressing cell with any of the conjugates described in this Section (II) that is derived from a parental antibody that binds to human CD11a. Such conjugates have prophylactic and therapeutic applications in a broad spectrum of CD11a-expressing cell-mediated disorders, including pathologies supported by leukocyte adhesion, in a manner similar to the application of full length anti-CD11a antibodies in the treatment of such disease indications that is known in the art, which treatment indications include psoriasis, asthma, graft rejection, and multiple sclerosis.

In one embodiment, the invention provides a method of treating a disorder in a human patient mediated by a CD11a-expressing cell, comprising administering to the patient a therapeutically effective amount of any conjugate described in this Section (II) wherein at least one antibody fragment in the conjugate comprises an antigen binding site that binds to human CD11a.

In another embodiment, the invention provides a method of treating an inflammatory disorder in a human patient comprising administering to the patient a therapeutically effective amount of any conjugate described in this Section (II) wherein at least one antibody fragment in the conjugate comprises an antigen binding site that binds to human CD11a. In another embodiment, the inflammatory disorder is psoriasis.

In another embodiment, the invention provides a method of treating an immune disorder in a human patient comprising administering to the patient a therapeutically effective amount of any conjugate described in this Section (II) wherein at least one antibody fragment in the conjugate comprises an antigen binding site that binds to human CD11a. In still another embodiment, the immune disorder is graft rejection. In a further embodiment, the immune disorder is multiple sclerosis.

In another embodiment, the invention provides a method of treating asthma in a human patient comprising administering to the patient an therapeutically effective amount of any conjugate described in this Section (II) wherein at least one antibody fragment in the conjugate comprises an antigen binding site that binds to human CD11a.

In another embodiment, the invention provides a method of treating a LFA-1-mediated disorder in a human, comprising administering to the patient a therapeutically effective amount of any conjugate described in this Section (II) wherein at least one antibody fragment in the conjugate comprises an antigen binding site that binds to human CD11a. In addition, the invention contemplates the use of the foregoing conjugate in place of full length anti-CD11a antibody in the treatment of an LFA-1-mediated disorder, such as psoriasis and graft rejection, in a human patient as described in U.S. Pat. No. 5,622,700. In another aspect, the invention contemplates the use of the foregoing conjugate in place of full length anti-CD11a antibody in the treatment of LFA-1-mediated disorders in a human patient as described in WO 98/23761.

(vi) IgE-Mediated Disorders

In one embodiment, the invention provides a method for treating an IgE-mediated disorder in a human patient with any of the conjugates described in this Section (II) that is derived from a parental antibody that binds to human IgE. Such conjugates have prophylactic and therapeutic applications in a broad spectrum of IgE-mediated disorders, including pathologies characterized by the overproduction and/or hypersensitivity to the immunoglobulin IgE, in a manner similar to the application of anti-IgE antibodies in the treatment of such disease indications that is known in the art, which treatment indications include allergic diseases, such as allergic asthma and allergic rhinitis.

In one embodiment, the invention provides a method of treating an IgE-mediated disorder in a human patient comprising administering to the patient a therapeutically effective amount of any conjugate described in this Section (II) wherein at least one antibody fragment in the conjugate comprises an antigen binding site that binds to human IgE. In another embodiment, the IgE-mediated disorder is an allergic disease. In yet another embodiment, the IgE-mediated disorder is allergic asthma. In still another embodiment, the IgE-mediated disorder is allergic rhinitis.

In a further embodiment, the invention provides a method of treating an IgE-mediated disorder in a human patient comprising administering to the patient a therapeutically effective amount of any conjugate described in this Section (II) wherein at least one antibody fragment in the conjugate comprises an antigen binding site that competes with human $Fc_{\epsilon}RI$ for binding to human IgE. In yet another embodiment, the invention provides a method of treating an IgE-mediated disorder in a human patient comprising administering to the patient a therapeutically effective amount of any conjugate described in this Section (II) wherein at least one antibody fragment in the conjugate comprises an antigen binding site that binds to membrane-bound IgE on the surface of human B-lymphocytes but does not bind to soluble IgE bound to $Fc_{\epsilon}RI$ receptor on the surface of human basophils. In addition, the invention contemplates the use of any of the foregoing conjugates in place of full length anti-human IgE antibody in the treatment of an IgE-mediated disorder, such as allergic diseases including allergic asthma and allergic rhinitis, in a human patient as described in International Application No. PCT/US98/13410 (filed Jun. 30, 1998). In another aspect, the invention contemplates the use of any of the foregoing conjugates in place of full length anti-human IgE antibody in the treatment of allergic asthma in a human patient as described in WO 97/04807 (published Feb. 13, 1997) (International Application No. PCT/US96/12275 filed Jul. 24, 1996).

In another embodiment, the invention provides a method of treating an allergic disease in a human patient comprising administering to the patient a therapeutically effective amount of any conjugate described in this Section (II) wherein at least one antibody fragment in the conjugate comprises an antigen binding site that competes with human $Fc_{\epsilon}RI$ for binding to human IgE. In yet another embodiment, the invention provides a method of treating an allergic disease in a human patient comprising administering to the patient a therapeutically effective amount of any conjugate described in this Section (II) wherein at least one antibody fragment in the conjugate comprises an antigen binding site that binds to membrane-bound IgE on the surface of human B-lymphocytes but does not bind to soluble IgE bound to $Fc_\epsilon RI$ receptor on the surface of human basophils.

In another embodiment, the invention provides a method of treating allergic asthma in a human patient comprising administering to the patient a therapeutically effective amount of any conjugate described in this Section (II) wherein at least one antibody fragment in the conjugate comprises an antigen binding site that competes with human $Fc_\epsilon RI$ for binding to human IgE. In yet another embodiment, the invention provides a method of treating allergic asthma in a human patient comprising administering to the patient a therapeutically effective amount of any conjugate described in this Section (II) wherein at least one antibody fragment in the conjugate comprises an antigen binding site that binds to membrane-bound IgE on the surface of human B-lymphocytes but does not bind to soluble IgE bound to $Fc_\epsilon RI$ receptor on the surface of human basophils.

In another embodiment, the invention provides a method of treating allergic rhinitis in a human patient comprising administering to the patient a therapeutically effective amount of any conjugate described in this Section (II) wherein at least one antibody fragment in the conjugate comprises an antigen binding site that competes with human $Fc_\epsilon RI$ for binding to human IgE. In yet another embodiment, the invention provides a method of treating allergic rhinitis in a human patient comprising administering to the patient a therapeutically effective amount of any conjugate described in this Section (II) wherein at least one antibody fragment in the conjugate comprises an antigen binding site that binds to membrane-bound IgE on the surface of human B-lymphocytes but does not bind to soluble IgE bound to $Fc_\epsilon RI$ receptor on the surface of human basophils.

(vii) Disorders Mediated by Cells Expressing Apo-2 Receptor

In one embodiment, the invention provides a method for treating a human disease mediated by cells expressing Apo-2 receptor with any of the conjugates described in this Section (II) that is derived from, a parental antibody that binds to human Apo-2 receptor. Such conjugates have prophylactic and therapeutic applications in a broad spectrum of Apo-2 receptor-expressing cell-mediated disorders, including cancers susceptible to Apo-2 receptor-mediated apoptosis, in a manner similar to the application of full length anti-Apo-2 receptor antibodies in the treatment of such disease indications that is known in the art, which treatment indications include cancers.

In one embodiment, the invention provides a method of treating a proliferative disorder in a human patient comprising administering to the patient a therapeutically effective amount of any conjugate described in this Section (II) wherein at least one antibody fragment in the conjugate comprises an antigen binding site that binds to human Apo-2 receptor. The proliferative disorder can be a benign or malignant tumor characterized by cells expressing the Apo-2 receptor, e.g. a cancer, such as breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

In another embodiment, the invention provides a method of treating a proliferative disorder in a human patient comprising administering to the patient a therapeutically effective amount of any conjugate described in this Section (II) wherein at least one antibody fragment in the conjugate comprises an antigen binding site that binds to the human Apo-2 receptor, and wherein the conjugate is an agonist of the human Apo-2 receptor, i.e. capable of inducing Apo-2 receptor-mediated cell apoptosis. The proliferative disorder can be a benign or malignant tumor characterized by cells expressing the Apo-2 receptor, e.g. a cancer, such as breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. In addition, the invention contemplates the use of the foregoing conjugate in place of full length anti-Apo-2 receptor agonist antibody in the treatment of cancers, e.g. colon cancer, as described in WO 98/51793 (published Nov. 19, 1998) (International Application No. PCT/US98/09704 filed May 14, 1998).

(vi) TNF-α-Mediated Disorders

In one embodiment, the invention provides a method for treating a TNF-α-mediated disease with any of the conjugates described in this Section (II) that is derived from a parental antibody that binds to human TNF-α. Such conjugates have prophylactic and therapeutic applications in a broad spectrum of TNF-α-mediated disorders, including inflammatory disorders and immune disorders, in a manner similar to the application of full length anti-human TNF-α antibodies in the treatment of such disease indications that is known in the art, which treatment indications include Crohn's disease, inflammatory bowel disease, and rheumatoid arthritis.

In one embodiment, the invention provides a method of treating a TNF-α-mediated disorder in a human patient comprising administering to the patient a therapeutically effective amount of any conjugate described in this Section (II) wherein at least one antibody fragment in the conjugate comprises an antigen binding site that binds to human TNF-α.

In one embodiment, the invention provides a method of treating an inflammatory disorder in a human patient comprising administering to the patient a therapeutically effective amount of any conjugate described in this Section (II) wherein at least one antibody fragment in the conjugate comprises an antigen binding site that binds to human TNF-α. In another embodiment, the inflammatory disorder is Crohn's disease. In yet another embodiment, the inflammatory disorder is inflammatory bowel disease. In still another embodiment, the inflammatory disorder is rheumatoid arthritis. In addition, the invention contemplates the use of the foregoing conjugate in place of full length anti-human TNF-α antibody in the treatment of TNF-α-mediated disorders, including inflammatory disorders and immune disorders such as graft-versus-host disease (GHVD) as described in U.S. Pat. No. 5,672,347 (issued Sep. 30, 1997). In another aspect, the invention contemplates the use of the foregoing conjugate in place of full length anti-human TNF-α antibody in the treatment of Crohn's disease as described in U.S. Pat. No. 5,656,272 (issued Aug. 12, 1997). In yet another aspect, the invention contemplates the use of the foregoing conjugate in place of full length anti-human TNF-α antibody in the treatment of rheumatoid arthritis as described in U.S. Pat. No. 5,698,195 (issued Dec. 16, 1997).

(vii) Tissue Factor-Mediated Disorders

In one embodiment, the invention provides a method for treating a tissue factor-mediated disease with any of the conjugates described in this Section (II) that is derived from a parental antibody that binds to human tissue factor. Such conjugates have prophylactic and therapeutic applications in a broad spectrum of tissue factor-mediated disorders, including pathologies supported by blood coagulation, in a manner similar to the application of full length anti-human tissue factor antibodies in the treatment of such disease indications that is known in the art, which treatment indications include deep vein thrombosis and arterial thrombosis.

In one embodiment, the invention provides a method of treating a tissue factor-mediated disorder in a human patient comprising administering to the patient a therapeutically effective amount of any conjugate described in this Section (II) wherein at least one antibody fragment in the conjugate comprises an antigen binding site that binds to human tissue factor.

In one embodiment, the invention provides a method of treating a thrombotic or prothrombotic disorder in a human patient comprising administering to the patient a therapeutically effective amount of any conjugate described in this Section (II) wherein at least one antibody fragment in the conjugate comprises an antigen binding site that binds to human tissue factor. The thrombotic or prothrombotic disorder can be any disorder characteristically associated with a hyperthrombotic state leading to intravascular thrombi or emboli, including diseases involving vascular narrowing or occlusion, such as deep vein thrombosis, arterial thrombosis, atherosclerosis, vascular stenosis, myocardial ischemic diseases including acute myocardial infarction, reocclusion following angioplasty or atherectomy or thrombolytic treatment for acute myocardial infarction, angina, cerebral ischemic diseases including stroke, venous thrombophlebitis, and pulmonary embolism. In yet another aspect, the invention contemplates the use of the foregoing conjugate in place of full length anti-human tissue factor antibody in the treatment of thrombotic and prothrombotic diseases, such as coronary artery thrombotic diseases as described in European Patent No 0 420 937 B1 (granted Nov. 19, 1994).

In another embodiment, the invention provides a method of inhibiting blood coagulation in a human patient comprising administering to the patient a therapeutically effective amount of any conjugate described in this Section (II) wherein at least one antibody fragment in the conjugate comprises an antigen binding site that binds to human tissue factor.

(viii) Disorders Mediated by α4β7 Integrin-Expressing Cells

In one embodiment, the invention provides a method for treating a human disease mediated by an $\alpha_4\beta_7$ integrin-expressing cell with any of the conjugates described in this Section (II) that is derived from a parental antibody that binds to human $\alpha_4\beta_7$ integrin. Such conjugates have prophylactic and therapeutic applications in a broad spectrum of $\alpha_4\beta_7$ integrin-expressing cell-mediated disorders, including pathologies supported by leukocyte adhesion, in a manner similar to the application of full length anti-$\alpha_4\beta_7$ integrin antibodies in the treatment of such disease indications that is known in the art, which treatment indications include inflammatory bowel disease.

In one embodiment, the invention provides a method of treating a disorder in a human patient mediated by an $\alpha_4\beta_7$ integrin-expressing cell, comprising administering to the patient a therapeutically effective amount of any conjugate described in this Section (II) wherein at least one antibody fragment in the conjugate comprises an antigen binding site that binds to human $\alpha_4\beta_7$ integrin.

In another embodiment, the invention provides a method of treating an inflammatory disorder in a human patient comprising administering to the patient a therapeutically effective amount of any conjugate described in this Section (II) wherein at least one antibody fragment in the conjugate comprises an antigen binding site that binds to human $\alpha_4\beta_7$ integrin. In another embodiment, the inflammatory disorder is inflammatory bowel disease. In another aspect, the invention contemplates the use of the foregoing conjugate in place of full length anti-human $\alpha_4\beta_7$ integrin antibody in the treatment of inflammatory disorders in a human patient as described in WO 98/06248 (published Feb. 19, 1998) (International Patent Application No. PCT/US97/13884 filed Aug. 6, 1997).

(ix) GPIIb-IIIa Integrin-Expressing Cell-Mediated Disorders

In one embodiment, the invention provides a method for treating a human disease mediated by a GPIIb-IIIa integrin-expressing cell with any of the conjugates described in this Section (II) that is derived from a parental antibody that binds to human GPIIb-IIIa integrin. Such conjugates have prophylactic and therapeutic applications in a broad spectrum of GPIIa-IIIB integrin-expressing cell-mediated disorders, including pathologies supported by platelet aggregation, such as thrombotic disorders and prothrombotic disorders, in a manner similar to the application of full length anti-human GPIIb-IIIa integrin antibodies in the treatment of such disease indications that is known in the art, which treatment indications include unstable angina and reocclusion following angioplasty or thrombolytic treatment of acute myocardial infarction.

In one embodiment, the invention provides a method of treating a thrombotic or prothrombotic disorder in a human patient comprising administering to the patient a therapeutically effective amount of any conjugate described in this Section (II) wherein at least one antibody fragment in the conjugate comprises an antigen binding site that binds to human GPIIb-IIIa integrin. The thrombotic or prothrombotic disorder can be any disorder characteristically associated with a hyperthrombotic state leading to intravascular thrombi or emboli, including diseases involving vascular narrowing or occlusion, such as deep vein thrombosis, arterial thrombosis, atherosclerosis, vascular stenosis, myocardial ischemic diseases including acute myocardial infarction, reocclusion following angioplasty or atherectomy or thrombolytic treatment for acute myocardial infarction, angina, cerebral ischemic diseases including stroke, venous thrombophlebitis, and pulmonary embolism. In another aspect, the invention contemplates the use of the foregoing conjugate in place of full-length anti-human GIIb-IIIa antibody in a method for inhibition of thrombus formation in a human patient as described in U.S. Pat. No. 5,387,413 (issued Feb. 7, 1995). In yet another aspect, the invention contemplates the use of the foregoing conjugate in place of unpegylated anti-human GPIIb-IIIa antibody fragment, e.g. Fab, Fab' or F(ab')$_2$, in the treatment of thrombotic and prothrombotic diseases, including coronary artery thrombotic diseases such as restenosis following percutaneous coronary artery transluminal angioplasty or atherectomy as described for REOPRO®abciximab in *Physician's Desk Reference*, 52$^{nd}$ Edition (1998), pp. 1498-1501.

In another embodiment, the invention provides a method of inhibiting blood coagulation in a human patient comprising administering to the patient a therapeutically effective amount of any conjugate described in this Section (II) wherein at least one antibody fragment in the conjugate comprises an antigen binding site that binds to human GPIIb-IIIa integrin.

In still another embodiment, the invention provides a method of inhibiting platelet aggregation in a human patient comprising administering to the patient a therapeutically effective amount of any conjugate described in this Section (II) wherein at least one antibody fragment in the conjugate comprises an antigen binding site that binds to human GPIIb-IIIa integrin.

(x) Disorders Mediated by EGFR-Expressing Cells

In one embodiment, the invention provides a method for treating a human disease mediated by EGFR-expressing cells with any of the conjugates described in this Section (II) that is derived from a parental antibody that binds to human EGFR. Such conjugates have prophylactic and therapeutic applications in a broad spectrum of EGFR-expressing cell-mediated disorders, including pathologies supported by the proliferation of cells expressing EGFR, such as cancers characterized by overexpression of EGFR, in a manner similar to the application of full length anti-EGFR antibodies in the treatment of such disease indications that is known in the art, which treatment indications include EGFR-overexpressing cancers of the breast, ovary, head and neck, brain, bladder, pancreas, and lung.

In one embodiment, the invention provides a method of treating a cell proliferation disorder in a human patient characterized by overexpression of epidermal growth factor receptor (EGFR) comprising administering to the patient a therapeutically effective amount of any conjugate described in this Section (II) wherein at least one antibody fragment in the conjugate comprises an antigen binding site that binds to human EGFR. The disorder can be a benign or malignant tumor characterized by the overexpression of the EGFR, e.g. a cancer, such as, breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. In addition, the invention contemplates the use of the foregoing conjugate in place of full length anti-EGFR antibody in the treatment of EGFR-overexpressing cancers as described in WO 96/40210 (published Dec. 19, 1996) (International Application No. PCT/US96/9847 filed Jun. 7, 1996).

(xi) Disorders Mediated by CD3-Expressing Cells

In one embodiment, the invention provides a method for treating a human disease mediated by CD3-expressing cells with any of the conjugates described in this Section (II) that is derived from a parental antibody that binds to human CD3. Such conjugates have prophylactic and therapeutic applications in a broad spectrum of CD3-expressing cell-mediated disorders, including pathologies supported by the proliferation or activation of cells expressing CD3, such as immune disorders mediated by T-lymphocytes, in a manner similar to the application of full length anti-human CD3 antibodies in the treatment of such disease indications that is known in the art, which treatment indications include graft rejection in transplant recipients.

In one embodiment, the invention provides a method of treating a disorder in a human patient mediated by a CD3-expressing cell, comprising administering to the patient a therapeutically effective amount of any conjugate described in this Section (II) wherein at least one antibody fragment in the conjugate comprises an antigen binding site that binds to human CD3. In another embodiment, the CD3-expressing cell-mediated disorder is characterized by the activation or proliferation of T-lymphocytes, including immune disorders such as graft rejection in transplant recipients. In addition, the invention contemplates the use of the foregoing conjugate in place of full length anti-human CD3 antibody in the treatment of T-lymphocyte mediated disorders as described in U.S. Pat. No. 4,515,893 (issued May 7, 1985). In another aspect, the invention contemplates the use of the foregoing conjugate in place of full length anti-human CD3 antibody in the treatment of acute allograft rejection in renal transplant recipients as described for ORTHOCLONE OKT3®muromonab-CD3 in *Physician's Desk Reference,* $52^{nd}$ Edition (1998), pp. 1971-1974.

(xii) Disorders Mediated by TAC-Expressing Cells

In one embodiment, the invention provides a method for treating a human disease mediated by interleukin-2 receptor α-chain (TAC)-expressing cells with any of the conjugates described in this Section (II) that is derived from a parental antibody that binds to human TAC. Such conjugates have prophylactic and therapeutic applications in a broad spectrum of TAC-expressing cell-mediated disorders, including pathologies supported by the proliferation or activation of cells expressing TAC, such as immune disorders mediated by T-lymphocytes or B-lymphocytes, in a manner similar to the application of full length anti-human TAC antibodies in the treatment of such disease indications that is known in the art, which treatment indications include graft rejection in transplant recipients.

In one embodiment, the invention provides a method of treating a disorder in a human patient mediated by a TAC-expressing cell, comprising administering to the patient a therapeutically effective amount of any conjugate described in this Section (II) wherein at least one antibody fragment in the conjugate comprises an antigen binding site that binds to human TAC. In another embodiment, the TAC-expressing cell-mediated disorder is characterized by the activation or proliferation of T-lymphocytes or B-lymphocytes, including immune disorders such as graft rejection in transplant recipients. In addition, the invention contemplates the use of the foregoing conjugate in place of full length anti-human TAC antibody in the treatment of T-lymphocyte or B-lymphocyte mediated disorders, including graft-versus-host disease (GHVD), graft rejection in transplant recipients, such as acute graft rejection in renal transplant recipients, and autoimmune diseases such as Type I diabetes, multiple sclerosis, rheumatoid arthritis, systemic lupus erythematosus, and myasthenia gravis, as described in U.S. Pat. No. 5,693,761.

(xiii) IL-8-Mediated Disorders

In one embodiment, the invention provides a method for treating an IL-8-mediated disease with any of the conjugates described in this Section (II) that is derived from a parental antibody that binds to rabbit or human IL-8. For example, a conjugate derived from an anti-IL-8 antibody or fragment is useful in the treatment of inflammatory disorders as described in Section (II)(5)(B) below. Such conjugates have prophylactic and therapeutic applications in a broad spectrum of IL-8 mediated diseases, such as inflammatory diseases and asthma, in a manner similar to the widespread efficacy of anti-IL-8 antibodies in the treatment of such disease indications that is known in the art, which treatment indications include: (1) ischemic reperfusion injury of the lung (Sekido et al., *Nature,* 365: 654 (1993)); (2) acute lung injury and ARDS (WO 96/22785 published Aug. 1, 1996; Folkesson et al., *J.*

Clin. Invest., 96: 107-116 (1995); Mulligan et al., J. Immunol., 150: 5585-5595 (1993)); (3) hypovolemic shock (Hebert, C., "Humanized Anti-IL-8: Potential Therapy for Shock and ARDS", seminar presented at Keystone Conference on *The Role of Cytokines in Leukocyte Trafficking and Disease*, held at Copper Mountain Resort, Colo., Mar. 31-Apr. 5, 1997; Sharar, S. A., Harlan, J. H., Patterson, C. A., Hebert, C. A., and Winn, R. K., "Reperfusion Injury After Hemorrhagic Shock in Rabbits is Reduced Similarly by IL-8 or CD-18 Monoclonal Antibodies", manuscript submitted 1998); (4) myocardial infarction (WO 97/40215 published Oct. 30, 1997); (5) cerebral reperfusion injury (Matsumoto et al., *Laboratory Invest.*, 77: 119-125 (1997)); (6) bacterial pneumonia (U.S. Pat. Nos. 5,702,946, 5,677,426, 5,707,622, and 5,686,070); (7) ulcerative colitis (U.S. Pat. Nos. 5,702,946, 5,677,426, 5,707,622, and 5,686,070); and asthma (WO 97/01354 published Jan. 16, 1997).

As shown in the Examples below, the conjugates of the invention mimic the in vitro activities of full-length anti-IL-8 monoclonal antibody (e.g. inhibition of IL-8 binding and activation of human neutrophils as shown in FIGS. 54A-54C, 55A-55C and 56A-56C and in Example V below), approximate the in vivo pharmacokinetics (e.g. serum half-life, clearance rate and mean residence time as shown in FIG. 65 and in Example X below) and the in vivo therapeutic efficacy (e.g. the treatment of acute lung injury and ARDS as shown in FIGS. 70A-70I and in Example Z below and the treatment of ischemic reperfusion injury as shown in FIG. 71 and in Example AA below) of full length anti-IL-8 monoclonal antibody. Since conjugates of the invention derived from anti-IL-8 antibodies and fragments display the same or substantially similar in vitro and in vivo activities as full length anti-IL-8 monoclonal antibody across a range of different parameters, including pharmacokinetic characteristics and therapeutic endpoints in various animal models, the data support the efficacy of the conjugates in the same broad spectrum of disease indications that responds to full length anti-IL-8 antibody treatment.

As noted above, any conjugate of the invention derived from an anti-IL-8 antibody or fragment can be advantageously utilized in a method of treating an IL-8 mediated disease or disorder, such as inflammatory diseases. In one embodiment, the invention provides a method of treating an inflammatory disorder in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating inflammatory disorders wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses any of the foregoing methods of treating an inflammatory disorder wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating ischemic reperfusion injury in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating ischemic reperfusion injury wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses the foregoing methods of treating ischemic reperfusion injury wherein the ischemic reperfusion injury is induced by or incident to a surgical procedure, i.e. a surgical tissue reperfusion injury.

In still another aspect, the invention encompasses the foregoing methods of treating ischemic reperfusion injury wherein the ischemic reperfusion injury is a myocardial ischemic reperfusion injury, such as myocardial infarction, reperfusion after cardiac surgery, cardiac arrest, and constriction after percutaneous transluminal coronary angioplasty.

In yet another aspect, the invention encompasses any of the foregoing methods of treating ischemic reperfusion injury wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating acute lung injury in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating acute lung injury wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35 E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses the foregoing methods of treating acute lung injury wherein the acute lung injury includes adult respiratory distress syndrome (ARDS).

In a further aspect, the invention encompasses any of the foregoing methods of treating acute lung injury wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD.

In a further aspect, the invention encompasses any of the foregoing methods of treating acute lung injury, wherein the patient is selected for prophylactic treatment prior to onset of acute lung injury (with or without progression to ARDS), such as at least 2 hours prior to onset, or at least 90 minutes prior to onset, or at least 60 minutes prior to onset, or at least 30 minutes prior to onset, by the assessment of biological parameters displayed in the patient's condition that indicate likely progression of disease to acute lung injury which may include ARDS, e.g. by using any of the prognostic methods described in Section (II)(5)(B) below, wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating hypovolemic shock in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating hypovolemic shock wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses any of the foregoing methods of treating hypovolemic shock wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating an inflammatory bowel disease in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating an inflammatory bowel disease wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5V11N35E and further comprising 6G4.2.5HV11 as defined below.

In still another aspect, the invention encompasses the foregoing methods of treating an inflammatory bowel disease wherein the inflammatory bowel disease is ulcerative colitis.

In yet another aspect, the invention encompasses any of the foregoing methods of treating inflammatory bowel disease wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating a bacterial pneumonia in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating bacterial pneumonia wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses any of the foregoing methods of treating bacterial pneumonia wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In another embodiment, the invention provides a method of treating an asthmatic disease in a mammal comprising administering to the mammal an effective amount of a conjugate selected from the group consisting of: (1) every conjugate described in Section (II)(1) above formed by its component parts, i.e. the antibody fragment or fragments and the nonproteinaceous polymer or polymer molecules that form the conjugate, without any extraneous matter in the covalent molecular structure of the conjugate, (2) every conjugate described in Section (II)(1) above modified to contain one or more additional components, in addition to the antibody fragment component(s) and polymer component(s) that form the conjugate, wherein the modification does not alter the essential functional property of the conjugate of substantially improved serum half-life, MRT and/or serum clearance rate as compared to that of the parental antibody fragment from which the conjugate is derived, (3) every conjugate described in Section (II)(1) above modified to incorporate one or more nonproteinaceous labels or reporter molecules, and (4) every conjugate described in Section (II)(1) above modified to incorporate one or more radiolabels; wherein at least one antibody fragment in the conjugate comprises an antigen binding site that binds to human IL-8.

In another aspect, the invention encompasses the foregoing method of treating an asthmatic disease wherein at least one antibody fragment in the conjugate is selected from the group consisting of: (1) an antibody fragment comprising 6G4.2.5LV/L1N35A as defined below; (2) an antibody fragment comprising 6G4.2.5LV/L1N35E as defined below; (3) an antibody fragment comprising 6G4.2.5HV11 as defined below; (4) an antibody fragment comprising hu6G4.2.5LV/L1N35A as defined below; (5) an antibody fragment comprising hu6G4.2.5LV/L1N35E as defined below; (6) an antibody fragment comprising hu6G4.2.5HV as defined below; (7) an antibody fragment comprising 6G4.2.5LV/L1N35A and further comprising the CDRs of 6G4.2.5HV11 as defined below; (8) an antibody fragment comprising 6G4.2.5LV/L1N35E and further comprising the CDRs of 6G4.2.5HV11 as defined below; (9) an antibody fragment comprising hu6G4.2.5LV/L1N35A and further comprising hu6G4.2.5HV as defined below; (10) an antibody fragment comprising hu6G4.2.5LV/L1N35E and further comprising hu6G4.2.5HV as defined below; (11) an antibody fragment comprising 6G4.2.5LV11N35A as defined below; (12) an antibody fragment comprising 6G4.2.5LV11N35E as defined below; (13) an antibody fragment comprising 6G4.2.5LV11N35A and further comprising 6G4.2.5HV11 as defined below; and (14) an antibody fragment comprising 6G4.2.5LV11N35E and further comprising 6G4.2.5HV11 as defined below.

In yet another aspect, the invention encompasses the foregoing methods of treating asthmatic disease wherein the asthmatic disease is allergic asthma.

In yet another aspect, the invention encompasses any of the foregoing methods of treating an asthmatic disease wherein the conjugate contains no more than one antibody fragment, wherein the antibody fragment is selected from the group consisting of Fab, Fab' and Fab'-SH, wherein the antibody fragment is covalently attached to no more than one nonproteinaceous polymer molecule, and wherein the nonproteinaceous polymer molecule is a linear polyethylene glycol having a molecular weight of at least at or about 20 kD, or at least at or about 30 kD or at least at or about 40 kD, or is a branched polyethylene glycol having a molecular weight of at least at or about 40 kD.

In a preferred embodiment, the invention encompasses any of the foregoing methods of treating inflammatory diseases or asthmatic diseases wherein the mammal is a human.

Therapeutic formulations of the conjugate of the invention can be prepared by utilizing the same procedures described for the formulation of the anti-IL-8 antibodies and fragments of the invention in Section (II)(5)(B) below. The conjugate of the invention can be administered in place of the parent antibody for a given disease indication by modifying the formulation, dosage, administration protocol, and other aspects of a therapeutic regimen as required by the different pharmacodynamic characteristics of the conjugate and as dictated by common medical knowledge and practice.

e. Reagent Uses for Large Effective Size Conjugates

The conjugate of the invention also finds application as a reagent in an animal model system for in vivo study of the biological functions of the antigen recognized by the conjugate. The conjugate would enable the practitioner to inactivate or detect the cognate antigen in circulation or in tissue for a far greater period of time than would be possible with art-known constructs while removing any Fc interaction (which could attend the use of an intact antibody) from the system. In addition, the increased half-life of the conjugate of the invention can be applied advantageously to the induction of tolerance for the underivatized antibody fragment in a test animal by employing the Wie et al., *Int. Archs. Allergy Appl. Immunol.*, 64: 84-99 (1981) method for allergen tolerization, which would permit the practitioner to repeatedly challenge the tolerized animal with the underivatized parental antibody fragment without generating an immune response against the parental fragment.

2. Humanized 6G4.2.5 Monoclonal Antibodies and Antibody Fragments

In one embodiment, the invention provides an antibody fragment or full length antibody comprising a heavy chain comprising the amino acid sequence of amino acids 1-230 (herein referred to as "6G4.2.5HV11") of the humanized anti-IL-8 6G4.2.5v11 heavy chain polypeptide amino acid sequence of FIGS. 37A-37B (SEQ ID NO: 60).

The invention encompasses a single chain antibody fragment comprising the 6G4.2.5HV11, with or without any additional amino acid sequence. In one embodiment, the invention provides a single chain antibody fragment comprising the 6G4.2.5HV11 without any associated light chain amino acid sequence, i.e. a single chain species that makes up one half of a Fab fragment.

Further provided herein are an antibody or antibody fragment comprising the 6G4.2.5HV11, and further comprising a light chain comprising the amino acid sequence of amino acids 1-219 (herein referred to as "6G4.2.5LV11") of the humanized anti-IL-8 6G4.2.5v11 light chain polypeptide amino acid sequence of FIG. 31B (SEQ ID NO: 51).

In one embodiment, the invention provides a single chain antibody fragment wherein the 6G4.2.5HV11 and the 6G4.2.5LV11 are contained in a single chain polypeptide species. In a preferred embodiment, the single chain antibody fragment comprises the 6G4.2.5HV11 joined to the 6G4.2.5LV11 by means of a flexible peptide linker sequence, wherein the heavy chain and light chain domains can associate in a ?dimeric? structure analogous to that formed in a two-chain Fab species. In another embodiment, the single chain antibody fragment is a species comprising the 6G4.2.5HV11 joined to the 6G4.2.5LV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the 6G4.2.5HV11 and a second polypeptide chain comprises the 6G4.2.5LV11 and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

The invention also provides an antibody or antibody fragment comprising a heavy chain containing the 6G4.2.5HV11 and optionally further comprising a light chain containing the 6G4.2.5LV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the antibody or antibody fragment comprises the 6G4.2.5HV11 in a heavy chain that is fused to or contains a leucine zipper sequence. The leucine zipper can increase the affinity and/or production efficiency of the antibody or antibody fragment of interest. Suitable leucine zipper sequences include the jun and fos leucine zippers taught by Kostelney et al., *J. Immunol.*, 148: 1547-1553 (1992) and the GCN4 leucine zipper described in the Examples below. In a preferred embodiment, the antibody or antibody fragment comprises the 6G4.2.5HV11 fused at its C-terminus to the GCN4 leucine zipper to yield the amino acid sequence of amino acids 1-275 (herein referred to as "6G4.2.5HV11 GCN4") of the heavy chain polypeptide amino acid sequence of FIGS. 37A-37B (SEQ ID NO: 60).

3. Variants of Humanized 6G4.2.5 Monoclonal Antibodies and Antibody Fragments

The invention additionally encompasses humanized anti-IL-8 monoclonal antibody and antibody fragments comprising variants of the 6G4.2.5 complementarity determining regions (CDRs) or variants of the 6G4.2.5v11 variable domains which exhibit higher affinity for human IL-8 and/or possess properties that yield greater efficiency in recombinant production processes.

A. 6G4.2.5LV Variants

In one aspect, the invention provides humanized anti-IL-8 monoclonal antibodies and antibody fragments comprising the complementarity determining regions (referred to herein as the "CDRs of 6G4.2.5LV") L1, L2, and L3 of the 6G4.2.5 light chain variable domain amino acid sequence of FIG. 24, wherein L1 corresponds to amino acids 24-39 of the amino acid sequence of FIG. 24, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35).

In addition, the invention provides a variant 6G4.2.5 humanized antibody or antibody fragment comprising a humanized light chain variable domain comprising a variant (hereinafter referred to a "6G4.2.5LV CDRs variant") of the complementarity determining regions L1, L2, and L3 of the 6G4.2.5 variable light chain domain amino acid sequence of FIG. 24 (SEQ ID NO: 35). In one embodiment, the invention provides a variant 6G4.2.5 humanized antibody or antibody fragment comprising a 6G4.2.5LV CDRs variant (herein referred to as "6G4.2.5LV/L1N35X$_{35}$") wherein L1 corresponds to amino acids 24-39 of the amino acid sequence of FIG. 24 (SEQ ID NO: 35) with the proviso that any amino acid other than Asn (denoted as "X$_{35}$") is substituted for Asn at amino acid position 35, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/ L1N35A") wherein L1 corresponds to amino acids 24-39 of the amino acid sequence of FIG. 24 (SEQ ID NO: 35) with the proviso that Ala is substituted for Asn at amino acid position 35, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35). In another preferred embodiment, the invention provides a variant 6G4.2.5 humanized antibody or antibody fragment comprising a 6G4.2.5LV CDRs variant (herein referred to as "6G4.2.5LV/L1N35E") wherein L1 corresponds to amino acids 24-39 of the amino acid sequence of FIG. 24 (SEQ ID NO: 35) with the proviso that Glu is substituted for Asn at amino acid position 35, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35).

In a second aspect, the invention provides a variant 6G4.2.5 humanized antibody or antibody fragment comprising a 6G4.2.5LV CDRs variant (herein referred to as "6G4.2.5LV/L1S26$X_{26}$") wherein L1 corresponds to amino acids 24-39 of the amino acid sequence of FIG. 24 (SEQ ID NO: 35) with the proviso that any amino acid other than Ser (denoted as "$X_{26}$") is substituted for Ser at amino acid position 26, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35). In a preferred embodiment, the invention provides a variant 6G4.2.5 humanized antibody or antibody fragment comprising a 6G4.2.5LV CDRs variant (herein referred to as "6G4.2.5LV/L1S26A") wherein L1, corresponds to amino acids 24-39 of the amino acid sequence of FIG. 24 (SEQ ID NO: 35) with the proviso that Ala is substituted for Ser at amino acid position 26, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35).

In a third aspect, the invention provides a variant 6G4.2.5 humanized antibody or antibody fragment comprising a 6G4.2.5LV CDRs variant (herein referred to as "6G4.2.5LV/L3H98$X_{98}$") wherein L1 corresponds to amino acids 24-39 of the amino acid sequence of FIG. 24 (SEQ ID NO: 35), L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L3H98A") wherein L1 corresponds to amino acids 24-39 of the amino acid sequence of FIG. 24 (SEQ ID NO: 35), L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35) with the proviso that Ala is substituted for His at amino acid position 98.

In a fourth aspect, the invention provides a variant 6G4.2.5 humanized antibody or antibody fragment comprising a 6G4.2.5LV CDRs variant (herein referred to as "6G4.2.5LV/L1S26$X_{26}$,N35$X_{35}$") wherein L1 corresponds to amino acids 24-39 of the amino acid sequence of FIG. 24 (SEQ ID NO: 35) with the proviso that any amino acid other than Ser (denoted as "$X_{26}$") is substituted for Ser at amino acid position 26 and any amino acid other than Asn (denoted as "$X_{35}$") is substituted for Asn at amino acid position 35, L2 corresponds to amino acids 55-61 of the amino acid sequence of FIG. 24 (SEQ ID NO:35), and L3 corresponds to amino acids 94-102 of the amino acid sequence of FIG. 24 (SEQ ID NO:35). In a preferred embodiment, the invention provides a variant 6G4.2.5 humanized antibody or antibody fragment comprising a 6G4.2.5LV CDRs variant (herein referred to as "6G4.2.5LV/L1S26A,N35A") wherein L1 corresponds to amino acids 24-39 of the amino acid sequence of FIG. 24 (SEQ ID NO:35) with the proviso that Ala is substituted for Ser at amino acid position 26 and Ala is substituted for Asn at amino acid position 35, L2 corresponds to amino acids 55-61 of the amino acid sequence of FIG. 24 (SEQ ID NO 35), and L3 corresponds to amino acids 94-102 of the amino acid sequence of FIG. 24 (SEQ ID NO 35).

In a fifth aspect, the invention provides a variant 6G4.2.5 humanized antibody or antibody fragment comprising a 6G4.2.5LV CDRs variant (herein referred to as "6G4.2.5LV/L1N35$X_{35}$/L3H98$X_{98}$") wherein L1 corresponds to amino acids 24-39 of the amino acid sequence of FIG. 24 (SEQ ID NO 35) with the proviso that any amino acid other than Asn (denoted as "$X_{35}$") is substituted for Asn at amino acid position 35, L2 corresponds to amino acids 55-61 of the amino acid sequence of FIG. 24 (SEQ ID NO 35), and L3 corresponds to amino acids 94-102 of the amino acid sequence of FIG. 24 (SEQ ID NO 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1N35A/L3H98A") wherein L1 corresponds to amino acids 24-39 of the amino acid sequence of FIG. 24 (SEQ ID NO 35) with the proviso that Ala is substituted for Asn at amino acid position 35, L2 corresponds to amino acids 55-61 of the amino acid sequence of FIG. 24 (SEQ ID NO 35), and L3 corresponds to amino acids 94-102 of the amino acid sequence of FIG. 24 (SEQ ID NO 35) with the proviso that Ala is substituted for His at amino acid position 98.

In a sixth aspect, the invention provides a variant 6G4.2.5 humanized antibody or antibody fragment comprising a 6G4.2.5LV CDRs variant (herein referred to as "6G4.2.5LV/L1S26$X_{26}$/L3H98$X_{98}$") wherein L1 corresponds to amino acids 24-39 of the amino acid sequence of FIG. 24 (SEQ ID NO 35) with the proviso that any amino acid other than Ser (denoted as "$X_{26}$") is substituted for Ser at amino acid position 26, L2 corresponds to amino acids 55-61 of the amino acid sequence of FIG. 24 (SEQ ID NO 35), and L3 corresponds to amino acids 94-102 of the amino acid sequence of FIG. 24 (SEQ ID NO 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (herein referred to as "6G4.2.5LV/L1S26A/L3H98A") wherein L1 corresponds to amino acids 24-39 of the amino acid sequence of FIG. 24 (SEQ ID NO 35) with the proviso that Ala is substituted for Ser at amino acid position 26, L2 corresponds to amino acids 55-61 of the amino acid sequence of FIG. 24 SEQ ID NO 35), and L3 corresponds to amino acids 94-102 of the amino acid sequence of FIG. 24 (SEQ ID NO: 35) with the proviso that Ala is substituted for His at amino acid position 98.

In a seventh aspect, the invention provides a variant 6G4.2.5 humanized antibody or antibody fragment comprising a 6G4.2.5LV CDRs variant (here referred to as "6G4.2.5LV/L1S26$X_{26}$,N35$X_{35}$/L3H98$X_{98}$") wherein L1 corresponds to amino acids 24-39 of the amino acid sequence of FIG. 24 (SEQ ID NO: 35) with the proviso that any amino acid other than Ser (denoted as "$X_{26}$") is substituted for Ser at amino acid position 26 and any amino acid other than Asn (denoted as "$X_{35}$") is substituted for Asn at amino acid position 35, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35) with the proviso that any amino acid other than His (denoted as "$X_{98}$") is substituted for His at amino acid position 98. In a preferred embodiment, the invention provides a variant 6G4.2.5 humanized antibody or antibody fragment comprising a 6G4.2.5LV CDRs variant (here referred to as "6G4.2.5LV/L1S26A,N35A/L3H98A") wherein L1 corresponds to amino acids 24-39 of the amino acid sequence of FIG. 24 (SEQ ID NO: 35) with the proviso that Ala is substituted for Ser at amino acid position 26 and Ala is substituted for Asn at amino acid position 35, L2 corresponds to amino acids 55-61 of the amino acid sequence of FIG. 24 (SEQ ID NO: 35), and L3 corresponds to amino acids 94-102 of the amino acid sequence of FIG. 24 (SEQ ID NO: 35) with the proviso that Ala is substituted for His at amino acid position 98.

The humanized light chain variable domains of the invention can be constructed by using any of the techniques for antibody humanization known in the art. Humanization can be essentially performed following the method of Winter and co-workers (Jones et al., *Nature* 321:522 (1986); Riechmann et al., *Nature* 332:323 (1988); Verhoeyen et al., *Science* 239: 1534 (1988)), by substituting the CDRs of 6G4.2.5LV or the CDRs of a 6G4.2.5LV CDRs variant for the corresponding sequences of a human antibody light chain variable domain. Accordingly, such "humanized" derivatives containing the CDRs of 6G4.2.5LV or the CDRs of a 6G4.2.5VL CDRs variant are chimeric (Cabilly et al., supra). The humanized light chain variable domain comprising the CDRs of 6G4.2.5LV or the CDRs of a 6G4.2.5LV CDRs variant can also contain some FR residues that are substituted by residues from analogous sites in the murine 6G4.2.5 antibody light chain variable domain ("6G4.2.5LV"). The complete amino acid sequence of 6G4.2.5LV is set out as amino acids 1-114 of the amino acid sequence of FIG. 24 (SEQ ID NO: 35).

The invention further provides a humanized antibody or antibody fragment comprising a humanized light chain variable domain comprising the CDRs of 6G4.2.5LV or the CDRs of a 6G4.2.5LV CDRs variant as described above, and further comprising a humanized heavy chain variable domain comprising the complementarity determining regions (CDRs) H1, H2, and H3 of the 6G4.2.5 (murine monoclonal antibody) variable heavy chain domain amino acid sequence of FIG. 25 (SEQ ID NO: 37), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37). The above-described H1, H-2, and H3 CDRs of the 6G4.2.5 heavy chain variable domain ("6G4.2.5HV") are collectively referred to as the "CDRs of 6G4.2.5HV".

In another embodiment, the invention provides a humanized antibody or antibody fragment comprising a humanized light chain variable domain comprising the CDRs of 6G4.2.5LV or the CDRs of a 6G4.2.5LV CDRs variant as described above, and further comprising a humanized heavy chain variable domain comprising a variant (herein referred to as a "6G4.2.5HV CDRs variant") of the H1, H2, and H3CDRs of the 6G4.2.5 (murine monoclonal antibody) variable heavy chain domain amino acid sequence of FIG. 25 (SEQ ID NO: 37). In one 6G4.2.5HV CDRs variant (referred to herein as "6G4.2.5HV/H1S31$Z_{31}$"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37). In a preferred 6G4.2.5HV CDRs variant (referred to herein as "6G4.2.5HV/H1S31A"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37).

In a second 6G4.2.5HV CDRs variant (referred to herein as "6G4.2.5HV/H2S54$Z_{54}$"), 111 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37). In a preferred 6G4.2.5HV CDRs variant (referred to herein as "6G4.2.5HV/H2S54A"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and F13 corresponds to amino acids 99-111 of the amino acid sequence of FIG. 25 (SEQ ID NO: 37).

In a third 6G4.2.5HV CDRs variant (referred to herein as "6G4.2.5H/H3D100E"), wherein 11 correspond to amino acids 26-35 of the amino acid sequence of FIG. 25 (SEQ ID NO: 37), wherein 1-12 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Glu is substituted for Asp at amino acid position 100.

In a fourth 6G4.2.5HV CDRs variant (referred to herein as "6G4.2.5HV/H3R102K"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Lys is substituted for Arg at amino acid position 102.

In a fifth 6G4.2.5HV CDRs variant (referred to herein as "6G4.2.5HV/H3D106E"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Glu is substituted for Asp at amino acid position 106.

In a seventh 6G4.2.5HV CDRs variant (referred to herein as "6G4.2.5HV/H3D100E,R102K"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102.

In an eighth 6G4.2.5HV CDRs variant (referred to herein as "6G4.2.5HV/H3R102K,D106E"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106.

In a ninth 6G4.2.5HV CDRs variant (referred to herein as "6G4.2.5HV/H3D100E,D106E"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106.

In a tenth 6G4.2.5HV CDRs variant (referred to herein as "6G4.2.5HV/H-13D100E,R102K,D106E"), wherein H1 correspond to amino acids 26-35 of the amino acid sequence of FIG. 25 (SEQ ID NO: 37), wherein H2 corresponds to amino acids 50-66 of the amino acid sequence of FIG. 25 (SEQ ID NO: 37), and wherein 113 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102, and Glu is substituted for Asp at amino acid position 106.

In an eleventh 6G4.2.5HV CDRs variant (referred to herein as "6G4.2.5HV/H1S31$Z_{31}$/H2S54$Z_{54}$"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37). In a preferred 6G4.2.5HV CDRs variant (referred to herein as "6G4.2.5HV/H1S31A/H2S54A"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and 113 corresponds to amino acids 99-111 of the amino acid sequence of FIG. 25 (SEQ ID NO: 37).

In a twelfth 6G4.2.5HV CDRs variant (referred to herein as "6G4.2.5HV/H1S31$Z_{31}$/H3D100E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H3D100E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100.

In a thirteenth 6G4.2.5HV CDRs variant (referred to herein as "6G4.2.5HV/H1S31$Z_{31}$/H3R102K"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H1S31A/H3R102K"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Lys is substituted for Arg at amino acid position 102.

A fourteenth 6G4.2.5HV CDRs variant (referred to herein as "6G4.2.5HV/H1S31$Z_{31}$/H3D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, 142 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H3D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 106.

A fifteenth 6G4.2.5HV CDRs variant (referred to herein as "6G4.2.5HV/H1S31$Z_{31}$/H3D100E,R102K"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H3D100E,R102K"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and 1-13 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102.

In a sixteenth 6G4.2.5HV CDRs variant (referred to herein as "6G4.2.5HV/H1S31$Z_{31}$/H3R102K,D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H3R102K,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106.

In a seventeenth 6G4.2.5HV CDRs variant (referred to herein as "6G4.2.5HV/H1S31$Z_{31}$/H3D100E,D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H3D100E,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106.

In an eighteenth 6G4.2.5HV CDRs variant (referred to herein as "6G4.2.5HV/H1S31$Z_{31}$/H3D100E,R102K, D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred G4.2.5HV CDRs variant (referred to herein as "6G4.2.5HV/H1S31A/H3D100E,R102K,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37), and H3 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a nineteenth 6G4.2.5HV CDRs variant (referred to herein as "6G4.2.5HV/H2S54$Z_{54}$/H3D100E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H2S54A/H3D100E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100.

In a twentieth 6G4.2.5HV CDRs variant (referred to herein as "6G4.2.5HV/H2S54$Z_{54}$/H3R102K"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and 1-13 corresponds to amino acids 99-111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H2S54A/H3R102K"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102.

In a twenty-first 6G4.2.5HV CDRs variant (referred to herein as "6G4.2.5HV/42S54$Z_{54}$/H3D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H2S54A/H3D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 106.

In a twenty-second 6G4.2.5HV CDRs variant (referred to herein as "6G4.2.5HV/H2S54$Z_{54}$/H3D100E,R102K"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H2S54A/H3D100E,R102K"), H1 corresponds to amino acids 26-35 of the amino acid sequence of FIG. 25 (SEQ ID NO: 37), 1-12 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102.

In a twenty-third 6G4.2.5HV CDRs variant (referred to herein as "6G4.2.5HV/H2S54$Z_{54}$/H3R102K,D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H2S54Z$_{54}$A/H3R102K,D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106.

In a twenty-fourth 6G4.2.5HV CDRs variant (referred to herein as "6G4.2.5HV/H2S54Z$_{54}$/H3D100E,D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H2S54A/H3D100E,D106E"), H1 corresponds to amino acids, 26-35 of the amino acid sequence of FIG. 25 (SEQ ID NO: 37), H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106.

In a twenty-fifth 6G4.2.5HV CDRs variant (referred to herein as "6G4.2.5HV/H2S54Z$_{54}$/H3D100E,R102K,D106E"), H1 corresponds to amino acids 26-35 of the amino acid sequence of FIG. 25 (SEQ ID NO: 37), H2 corresponds to amino acids 50-66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H2S54A/H3D100E,R102K,D106E"), H1 corresponds to amino acids 26-35 of the amino acid sequence of FIG. 25 (SEQ ID NO: 37), 142 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

In a twenty-sixth 6G4.2.5HV CDRs variant (referred to herein as "6G4.2.5HV/H1S31Z$_{31}$/H2S54Z$_{54}$/H3D100E"), H1 correspond to amino acids 26-35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100. In a preferred 6G4.2.5HV CDRs variant (referred to herein as "6G4.2.5HV/H1S31A/H2S54A/H3D100E"), 1-11 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100.

In a twenty-seventh 6G4.2.5HV CDRs variant (referred to herein as "6G4.2.5HV/H1S31Z$_{31}$/H2S54Z$_{54}$/H3R102K"), H1 correspond to amino acids 26-35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "Z$_{54}$") is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102. In a preferred 6G4.2.5HV CDRs variant (referred to herein as "6G4.2.5HV/H1S31A/H2S54A/H3R102K"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102.

In a twenty-eighth 6G4.2.5HV CDRs variant (referred to herein as "6G4.2.5HV/H1S31Z$_{31}$/H2S54Z$_{54}$/H3D106E"), H1 correspond to amino acids 26-35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50-66 of the amino acid sequence of FIG. 25 (SEQ ID NO: 37), with the proviso that any amino acid other than Ser (denoted as "Z$_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 106. In a preferred 6G4.2.5HV CDRs variant (referred to herein as "6G4.2.5HV/H1S31A/H2S54A/H3D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 106.

In a twenty-ninth 6G4.2.5HV CDRs variant (referred to herein as "6G4.2.5HV/H1S31Z$_{31}$/H2S54Z$_{54}$/H3D100E, R102K"), H1 correspond to amino acids 26-35 of the amino acid sequence of FIG. 25 (SEQ ID NO: 37) with the proviso that any amino acid other than Ser (denoted as "Z$_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102. In a preferred 6G4.2.5HV CDRs variant (referred to herein as "6G4.2.5HV/H1S31A/H2S54A/ H3D100E,R102K"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Lys is substituted for Arg at amino acid position 102.

In a thirtieth 6G4.2.5HV CDRs variant (referred to herein as "6G4.2.5HV/H1S31$Z_{31}$/H2S54$Z_{54}$/H3R102K,D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/ H3R102K,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Lys is substituted for Arg at amino acid position 102 and Glu is substituted for Asp at amino acid position 106.

In a thirty-first 6G4.2.5HV CDRs variant (referred to herein as "6G4.2.5HV/H1S31$Z_{31}$/H2S54$Z_{54}$/H3D100E, D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106. In a preferred 6G4.2.5HV CDRs variant (referred to herein as "6G4.2.5HV/H1S31A/H2S54A/ H3D100E,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100 and Glu is substituted for Asp at amino acid position 106.

In a thirty-second 6G4.2.5HV CDRs variant (referred to herein as "6G4.2.5HV/H1S31$Z_{31}$/H2S54$Z_{54}$/1-13D100E, R102K,D106E"), H1 correspond to amino acids 26-35 of the amino acid sequence of FIG. 25 (SEQ ID NO: 37) with the proviso that any amino acid other than Ser (denoted as "$Z_{31}$") is substituted for Ser at amino acid position 31, H2 corresponds to amino acids 50-66 of the amino acid sequence of FIG. 25 (SEQ ID NO: 37) with the proviso that any amino acid other than Ser (denoted as "$Z_{54}$") is substituted for Ser at amino acid position 54, and 113 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106. In a preferred 6G4.2.5HV CDRs variant (referred to herein as "6G4.2.5HV/H1S31A/H2S54A/ H3D100E,R102K,D106E"), H1 correspond to amino acids 26-35 of the amino acid sequence of FIG. 25 (SEQ ID NO: 37) with the proviso that Ala is substituted for Ser at amino acid position 31, H2 corresponds to amino acids 50-66 of the amino acid sequence of FIG. 25 (SEQ ID NO: 37) with the proviso that Ala is substituted for Ser at amino acid position 54, and H3 corresponds to amino acids 99-111 of the amino acid sequence of FIG. 25 (SEQ ID NO: 37) with the proviso that Glu is substituted for Asp at amino acid position 100, Lys is substituted for Arg at amino acid position 102 and Glu is substituted for Asp at amino acid position 106.

As in the humanization of the light chain variable domain described above, a humanized heavy chain variable domain is constructed by substituting the CDRs of 6G4.2.5HV or the CDRs of a 6G4.2.5HV CDRs variant for the corresponding sequences in a human heavy chain variable domain. The humanized heavy chain variable domain comprising the CDRs of 6G4.2.5HV or the CDRs of a 6G4.2.5HV CDRs variant can also contain some FR residues that are substituted by residues from analogous sites in the murine 6G4.2.5 antibody heavy chain variable domain. The complete amino acid sequence of 6G4.2.5HV is set out as amino acids 1-122 of the amino acid sequence of FIG. 25 (SEQ ID NO: 37).

The choice of human variable domains, both light and heavy, to be used in making the humanized antibodies and antibody fragments is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., *J. Immunol.* 151: 2296 (1993); Chothia and Lesk, *J. Mol. Biol.* 196:901 (1987)). Another method uses a particular framework derived from the consensus sequence of all human antibodies of a particular subgroup of light or heavy chains. The same framework can be used for several different humanized antibodies (Carter et al., *Proc. Natl. Acad. Sci. U.S.A.* 89:4285 (1992); Presta et al., *J. Immunol.* 151:2623 (1993)).

It is also important that the antibodies and antibody fragments of the invention be humanized with retention of high affinity for human IL-8 and other favorable biological properties. To achieve this goal, according to a preferred method, the humanized antibodies and antibody fragments of the invention are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and parental sequences so that the desired antibody characteristic, such as increased affinity for the target antigen(s), is achieved.

Any and all humanized light chain variable domain amino acid sequences which comprise the CDRs of 6G4.2.5LV are collectively referred to herein as "hu6G4.2.5LV".

Any and all humanized light chain variable domain amino acid sequences which comprise the CDRs of 6G4.2.5LV/L1N35$X_{35}$ are collectively referred to herein as "hu 6G4.2.5LV/L1N35$X_{35}$".

Any and all humanized light chain variable domain amino acid sequences which comprise the CDRs of 6G4.2.5LV/L1N35A are collectively referred to herein as "hu6G4.2.5LV/L1N35A".

Any and all humanized light chain variable domain amino acid sequences which comprise the CDRs of 6G4.2.5LV/L1N35E are collectively referred to herein as "hu6G4.2.5LV/L1N35E".

Any and all humanized light chain variable domain amino acid sequences which comprise the CDRs of 6G4.2.5LV/L1S26$X_{26}$ are collectively referred to herein as "hu6G4.2.5LV/L1S26$X_{26}$".

Any and all humanized light chain variable domain amino acid sequences which comprise the CDRs of 6G4.2.5LV/L1S26A are collectively referred to herein as "hu6G4.2.5LV/L1S26A".

Any and all humanized light chain variable domain amino acid sequences which comprise the CDRs of 6G4.2.5LV/L3H98$X_{98}$ are collectively referred to herein as "hu6G4.2.5LV/L3H98$X_{98}$".

Any and all humanized light chain variable domain amino acid sequences which comprise the CDRs of 6G4.2.5LV/L3H98A are collectively referred to herein as "hu6G4.2.5LV/L3H98A".

Any and all humanized light chain variable domain amino acid sequences which comprise the CDRs of 6G4.2.5LV/L1S26$X_{26}$,N35$X_{35}$ are collectively referred to herein as "hu6G4.2.5LV/L1S26$X_{26}$,N35$X_{35}$".

Any and all humanized light chain variable domain amino acid sequences which comprise the CDRs of 6G4.2.5LV/L1S26A,N35A are collectively referred to herein as "hu6G4.2.5LV/L1S26A,N35A".

Any and all humanized light chain variable domain amino acid sequences which comprise the CDRs of 6G4.2.5LV/L1N35$X_{35}$/L3H98$X_{98}$ are collectively referred to herein as "hu6G4.2.5LV/L1N35$X_{35}$/L3H98$X_{98}$".

Any and all humanized light chain variable domain amino acid sequences which comprise the CDRs of 6G4.2.5LV/L1N35A/L3H98A are collectively referred to herein as "hu6G4.2.5LV/L1N35A/L3H98A".

Any and all humanized light chain variable domain amino acid sequences which comprise the CDRs of 6G4.2.5LV/L1S26$X_{26}$/L3H98$X_{98}$ are collectively referred to herein as "hu6G4.2.5LV/L1S26$X_{26}$/L3H98$X_{98}$".

Any and all humanized light chain variable domain amino acid sequences which comprise the CDRs of 6G4.2.5LV/L1S26$X_{26}$/L3H98A are collectively referred to herein as "hu6G4.2.5LV/L1S26A/L3H98A".

Any and all humanized light chain variable domain amino acid sequences which comprise the CDRs of 6G4.2.5LV/L1S26$X_{26}$,N35$X_{35}$/L3H98$X_{98}$ are collectively referred to herein as "hu6G4.2.5LV/L1S26$X_{26}$,N35$X_{35}$/L3H98$X_{98}$".

Any and all humanized light chain variable domain amino acid sequences which comprise the CDRs of 6G4.2.5LV/L1S26A,N35A/L3H98A are collectively referred to herein as "hu6G4.2.5LV/L1S26A,N35A/L3H98A".

The humanized light chain variable domain amino acid sequences of hu6G4.2.5LV/L1N35$X_{35}$, hu6G4.2.5LV/L1S26$X_{26}$, hu6G4.2.5LV/L1S26$X_{26}$/L3H98$X_{98}$, hu6G4.2.5LV/L1S26$X_{26}$,N35$X_{35}$, hu6G4.2.5LV/L1N35$X_{35}$/L3H98$X_{98}$, hu6G4.2.5LV/L1S26$X_{26}$/L3H98$X_{98}$, and hu6G4.2.5LV/L1S26$X_{26}$,N35$X_{35}$/L3H98$X_{98}$ are collectively referred to herein as "hu6G4.2.5LV/vL1-3X".

The humanized light chain variable domain amino acid sequences of hu6G4.2.5LV/L1N35A, hu6G4.2.5LV/L1S26A, hu6G4.2.5LV/L1S26A/L3H98A, hu6G4.2.5LV/L1S26A,N35A, hu6G4.2.5LV/L1N35A/L3H98A, hu6G4.2.5LV/L1S26A/L3H98A, hu6G4.2.5LV/L1S26A,N35A/L3H98A are collectively referred to herein as "hu6G4.2.5LV/vL1-3A".

Any and all humanized heavy chain variable domain amino acid sequences which comprise the CDRs of 6G4.2.5HV are collectively referred to herein as "hu6G4.2.5HV".

Any and all humanized heavy chain variable domain amino acid sequences which comprise the CDRs of 6G4.2.5HV/H1S31$Z_{31}$ are collectively referred to herein as "hu6G4.2.5HV/H1S31$Z_{31}$".

Any and all humanized heavy chain variable domain amino acid sequences which comprise the CDRs of 6G4.2.5HV/H1S31A are collectively referred to herein as "hu6G4.2.5HV/H1S31A".

Any and all humanized heavy chain variable domain amino acid sequences which comprise the CDRs of 6G4.2.5HV/H2S54$Z_{54}$ are collectively referred to herein as "hu6G4.2.5HV/H2S54$Z_{54}$".

Any and all humanized heavy chain variable domain amino acid sequences which comprise the CDRs of 6G4.2.5HV/H2S54A are collectively referred to herein as "hu6G4.2.5HV/H2S54A".

Any and all humanized heavy chain variable domain amino acid sequences which comprise the CDRs of 6G4.2.5HV/H3D100E are collectively referred to herein as "hu6G4.2.5HV/H3D100E".

Any and all humanized heavy chain variable domain amino acid sequences which comprise the CDRs of 6G4.2.5HV/H3R102K are collectively referred to herein as "hu6G4.2.5HV/H3R102K".

Any and all humanized heavy chain variable domain amino acid sequences which comprise the CDRs of 6G4.2.5HV/H3D106E are collectively referred to herein as "hu6G4.2.5HV/H3D106E".

Any and all humanized heavy chain variable domain amino acid sequences which comprise the CDRs of 6G4.2.5HV/H3D100E,R102K are collectively referred to herein as "hu6G4.2.5HV/H3D100E,R102K".

Any and all humanized heavy chain variable domain amino acid sequences which comprise the CDRs of 6G4.2.5HV/H3R102K,D106E are collectively referred to herein as "hu6G4.2.5HV/H3R102K,D106E".

Any and all humanized heavy chain variable domain amino acid sequences which comprise the CDRs of 6G4.2.5HV/H3D100E,D106E are collectively referred to herein as "hu6G4.2.5HV/H3D100E,D106E".

Any and all humanized heavy chain variable domain amino acid sequences which comprise the CDRs of 6G4.2.5HV/ H3D100E,R102K,D106E are collectively referred to herein as "hu6G4.2.5HV/H3D100E,R102K,D106E".

Any and all humanized heavy chain variable domain amino acid sequences which comprise the CDRs of 6G4.2.5HV/ H1S31$Z_{31}$/H2S54$Z_{54}$ are collectively referred to herein as "hu6G4.2.5HV/H1S31$Z_{31}$/1-12S54$Z_{54}$".

Any and all humanized heavy chain variable domain amino acid sequences which comprise the CDRs of 6G4.2.5HV/ H1S31$Z_{31}$/H3D100E are collectively referred to herein as "hu6G4.2.5HV/H1S31$Z_{31}$/H3D100E".

Any and all humanized heavy chain variable domain amino acid sequences which comprise the CDRs of 6G4.2.5HV/ H1S31$Z_{31}$/H3R102K are collectively referred to herein as "hu6G4.2.5HV/H1S31$Z_{31}$/H3R102K".

Any and all humanized heavy chain variable domain amino acid sequences which comprise the CDRs of 6G4.2.5HV/ H1S31$Z_{31}$/H3D106E are collectively referred to herein as "hu6G4.2.5HV/H1S31$Z_{31}$/H3D106E".

Any and all humanized heavy chain variable domain amino acid sequences which comprise the CDRs of 6G4.2.5HV/ H1S31$Z_{31}$/H3D100E,R102K are collectively referred to herein as "hu6G4.2.5HV/H1S31$Z_{31}$/H3D100E,R102K".

Any and all humanized heavy chain variable domain amino acid sequences which comprise the CDRs of 6G4.2.5HV/ H1S31$Z_{31}$/H3R102K,D106E are collectively referred to herein as "hu6G4.2.5HV/H1S31$Z_{31}$/H3R102K,D106E".

Any and all humanized heavy chain variable domain amino acid sequences which comprise the CDRs of 6G4.2.5HV/ H1S31$Z_{31}$/H3D100E,D106E are collectively referred to herein as "hu6G4.2.5HV/H1S31$Z_{31}$/H3D100E,D106E".

Any and all humanized heavy chain variable domain amino acid sequences which comprise the CDRs of 6G4.2.5HV/ H1S31$Z_{31}$/H3D100E,R102K,D106E are collectively referred to herein as "hu6G4.2.5HV/H1S31$Z_{31}$/H3D100E, R102K,D106E".

Any and all humanized heavy chain variable domain amino acid sequences which comprise the CDRs of 6G4.2.5HV/ H2S54$Z_{54}$/H3D100E are collectively referred to herein as "hu6G4.2.5HV/H2S54$Z_{54}$/H3D100E".

Any and all humanized heavy chain variable domain amino acid sequences which comprise the CDRs of 6G4.2.5HV/ H2S54$Z_{54}$/H3R102K are collectively referred to herein as "hu6G4.2.5HV/H2S54$Z_{54}$/H3R102K".

Any and all humanized heavy chain variable domain amino acid sequences which comprise the CDRs of 6G4.2.5HV/ H2S54$Z_{54}$/H3D106E are collectively referred to herein as "hu6G4.2.5HV/H2S54$Z_{54}$/H3D106E".

Any and all humanized heavy chain variable domain amino acid sequences which comprise the CDRs of 6G4.2.5HV/ H2S54$Z_{54}$/H3R102K,D106E are collectively referred to herein as "hu6G4.2.5HV/H2S54$Z_{54}$/H3R102K,D106E".

Any and all humanized heavy chain variable domain amino acid sequences which comprise the CDRs of 6G4.2.5HV/ H2S54$Z_{54}$/H3D100E,D106E are collectively referred to herein as "hu6G4.2.5HV/H2S54$Z_{54}$/H3D100E,D106E".

Any and all humanized heavy chain variable domain amino acid sequences which comprise the CDRs of 6G4.2.5HV/ H2S54$Z_{54}$/H3D100E,R102K,D106E are collectively referred to herein as "hu6G4.2.5HV/H2S54$Z_{54}$/H3D100E, R102K,D106E".

Any and all humanized heavy chain variable domain amino acid sequences which comprise the CDRs of 6G4.2.5HV/ H1S31$Z_{31}$/H2S54$Z_{54}$/H3D100E are collectively referred to herein as "hu6G4.2.5HV/H1S31$Z_{31}$/H2S54$Z_{54}$/H3D100E".

Any and all humanized heavy chain variable domain amino acid sequences which comprise the CDRs of 6G4.2.5HV/ H1S31$Z_{31}$/H2S54$Z_{54}$/H3R102K are collectively referred to herein as "hu6G4.2.5HV/H1S31$Z_{31}$/H2S54$Z_{54}$/H3R102K".

Any and all humanized heavy chain variable domain amino acid sequences which comprise the CDRs of 6G4.2.5HV/ H1S31$Z_{31}$/H2S54$Z_{54}$/H3D106E are collectively referred to herein as "hu6G4.2.5HV/H1S31$Z_{31}$/H2S54$Z_{54}$/H3D106E".

Any and all humanized heavy chain variable domain amino acid sequences which comprise the CDRs of 6G4.2.5HV/ H1S31$Z_{31}$/H2S54$Z_{54}$/H3D100E,R102K are collectively referred to herein as "hu6G4.2.5HV/H1S31$Z_{31}$/H2S54$Z_{54}$/ H3D100E,R102K".

Any and all humanized heavy chain variable domain amino acid sequences which comprise the CDRs of 6G4.2.5HV/ H1S31$Z_{31}$/H2S54$Z_{54}$/H3R102K,D106E are collectively referred to herein as "hu6G4.2.5HV/H1S31$Z_{31}$/H2S54$Z_{54}$/ H3R102K,D106E".

Any and all humanized heavy chain variable domain amino acid sequences which comprise the CDRs of 6G4.2.5HV/ H1S31$Z_{31}$/H2S54$Z_{54}$/H3D100E,D106E are collectively referred to herein as "hu6G4.2.5HV/H1S31$Z_{31}$/H2S54$Z_{54}$/ H3D100E,D106E".

Any and all humanized heavy chain variable domain amino acid sequences which comprise the CDRs of 6G4.2.5HV/ H1S31$Z_{31}$/H2S54$Z_{54}$/H3D100E,R102K,D106E are collectively referred to herein as "hu6G4.2.5HV/H1S31$Z_{31}$/ H2S54$Z_{54}$/H3D100E,R102K,D106E".

Any and all humanized heavy chain variable domain amino acid sequences which comprise the CDRs of 6G4.2.5HV/ H1S31A/H2S54A are collectively referred to herein as "hu6G4.2.5HV/H1S31A/H2S54A".

Any and all humanized heavy chain variable domain amino acid sequences which comprise the CDRs of 6G4.2.5HV/ H1S31A/H3D100E are collectively referred to herein as "hu6G4.2.5HV/H1S31A/H3D100E".

Any and all humanized heavy chain variable domain amino acid sequences which comprise the CDRs of 6G4.2.5HV/ H1S31A/H3R102K are collectively referred to herein as "hu6G4.2.5H/H1S31A/H3R102K".

Any and all humanized heavy chain variable domain amino acid sequences which comprise the CDRs of 6G4.2.5HV/ H1S31A/H3D106E are collectively referred to herein as "hu6G4.2.5HV/H1S31A/H3D106E".

Any and all humanized heavy chain variable domain amino acid sequences which comprise the CDRs of 6G4.2.5HV/ H1S31A/H3D100E,R102K are collectively referred to herein as "hu6G4.2.5HV/H1S31A/H3D100E,R102K".

Any and all humanized heavy chain variable domain amino acid sequences which comprise the CDRs of 6G4.2.5HV/ H1S31A/H3R102K,D106E are collectively referred to herein as "hu6G4.2.5HV/H1S31A/H3R102K,D106E".

Any and all humanized heavy chain variable domain amino acid sequences which comprise the CDRs of 6G4.2.5HV/ H1S31A/H3D100E,D106E are collectively referred to herein as "hu6G4.2.5HV/H1S31A/H3D100E,D106E".

Any and all humanized heavy chain variable domain amino acid sequences which comprise the CDRs of 6G4.2.5HV/ H1S31A/H3D100E,R102K,D106E are collectively referred to herein as "hu6G4.2.5HV/H1S31A/H3 D100E,R102K, D106E".

Any and all humanized heavy chain variable domain amino acid sequences which comprise the CDRs of 6G4.2.5HV/ H2S54A/H3D100E are collectively referred to herein as "hu6G4.2.5HV/H2S54A/H3D100E".

Any and all humanized heavy chain variable domain amino acid sequences which comprise the CDRs of 6G4.2.5HV/

H2S54A/H3R102K are collectively referred to herein as "hu6G4.2.5HV/H2S54A/H3R102K".

Any and all humanized heavy chain variable domain amino acid sequences which comprise the CDRs of 6G4.2.5HV/H2S54A/H3D106E are collectively referred to herein as "hu6G4.2.5HV/H2S54A/H3D106E".

Any and all humanized heavy chain variable domain amino acid sequences which comprise the CDRs of 6G4.2.5HV/H2S54A/H3R102K,D106E are collectively referred to herein as "hu6G4.2.5HV/H2S54A/H3R102K,D106E".

Any and all humanized heavy chain variable domain amino acid sequences which comprise the CDRs of 6G4.2.5HV/H2S54A/H3D100E,D106E are collectively referred to herein as "hu6G4.2.5HV/H2S54A/H3D100E,D106E".

Any and all humanized heavy chain variable domain amino acid sequences which comprise the CDRs of 6G4.2.5HV/H2S54A/H3D100E,R102K,D106E are collectively referred to as "hu6G4.2.5HV/H2S54A/H3D100E,R102K,D106E".

Any and all humanized heavy chain variable domain amino acid sequences which comprise the CDRs of 6G4.2.5HV/H1S31A/H2S54A/H3D100E are collectively referred to herein as "hu6G4.2.5HV/H1S31A/H2S54A/H3D100E".

Any and all humanized heavy chain variable domain amino acid sequences which comprise the CDRs of 6G4.2.5HV/H1S31A/H2S54A/H3R102K are collectively referred to herein as "hu6G4.2.5HV/H1S31A/H2S54A/H3R102K".

Any and all humanized heavy chain variable domain amino acid sequences which comprise the CDRs of 6G4.2.5HV/H1S31A/H2S54A/H3D106E are collectively referred to herein as "hu6G4.2.5HV/H1S31A/H2S54A/H3D106E".

Any and all humanized heavy chain variable domain amino acid sequences which comprise the CDRs of 6G4.2.5HV/H1S31A/H2S54A/H3D100E,R102K are collectively referred to herein as "hu6G4.2.5HV/H1S31A/H2S54A/H3D100E,R102K".

Any and all humanized heavy chain variable domain amino acid sequences which comprise the CDRs of 6G4.2.5HV/H1S31A/H2S54A/H3R102K,D106E are collectively referred to herein as "hu6G4.2.5HV/H1S31A/H2S54A/H3R102K,D106E".

Any and all humanized heavy chain variable domain amino acid sequences which comprise the CDRs of 6G4.2.5HV/H1S31A/H2S54A/H3D100E,D106E are collectively referred to herein as "hu6G4.2.5 HV/H1S31A/H2S54A/H3D100E,D106E".

Any and all humanized heavy chain variable domain amino acid sequences which comprise the CDRs of 6G4.2.5HV/H1S31A/H2S54A/H3D100E,R102K,D106E are collectively referred to herein as "hu6G4.2.5HV/H1S31A/H2S54A/H3D100E,R102K,D106E".

The humanized heavy chain variable domain amino acid sequences of hu6G4.2.5HV/H1S31$Z_{31}$, hu6G4.2.5HV/H2S54$Z_{54}$, hu6G4.2.5HV/H3D100E, hu6G4.2.5HV/H3R102K, hu6G4.2.5HV/H3D106E, hu6G4.2.5HV/H3D100E,R102K, hu6G4.2.5HV/H3R102K,D106E, hu6G4.2.5HV/H3D100E,D106E, hu6G4.2.5HV/H3D100E,R102K,D106E, hu6G4.2.5HV/H1S31$Z_{31}$/H2S54$Z_{54}$, hu6G4.2.5HV/H1S31$Z_{31}$/H3D100E, hu6G4.2.5HV/H1S31$Z_{31}$/H3R102K, hu6G4.2.5HV/H1S31$Z_{31}$/H3D106E, hu6G4.2.5HV/H1S31$Z_{31}$/H3D100E,R102K, hu6G4.2.5HV/H1S31$Z_{31}$/H3R102K,D106E, hu6G4.2.5HV/H1S31$Z_{31}$/H3D100E,D106E, hu6G4.2.5HV/H1S31$Z_{31}$/H3D100E,R102K,D106E, hu6G4.2.5HV/H2S54$Z_{54}$/H3R102K, hu6G4.2.5HV/H2S54$Z_{54}$/H3D106E, hu6G4.2.5HV/H2S54$Z_{54}$/H3R102K,D106E, hu6G4.2.5HV/H2S54$Z_{54}$/H3D100E,D106E, hu6G4.2.5HV/H2S54$Z_{54}$/1-13D100E,R102K,D106E, hu6G4.2.5HV/H1S31$Z_{31}$/H2S54$Z_{54}$/H3D100E, hu6G4.2.5HV/H1S31$Z_{31}$/H2S54$Z_{54}$/H3R102K, hu6G4.2.5HV/H1S31$Z_{31}$/H2S54$Z_{54}$/H3D106E, hu6G4.2.5HV/H1S31$Z_{31}$/H2S54$Z_{54}$/H3D100E,R102K, hu6G4.2.5HV/H1S31$Z_{31}$/H2S54$Z_{54}$/H3R102K,D106E, hu6G4.2.5HV/H1S31$Z_{31}$/H2S54$Z_{54}$/H3D100E,D106E, and hu6G4.2.5HV/H1S31$Z_{31}$/H2S54$Z_{54}$/H3D100E,R102K,D106E are collectively referred to herein as "hu6G4.2.5HV/vH1-3Z".

The humanized heavy chain variable domain amino acid sequences of hu6G4.2.5HV/H1S31A, hu6G4.2.5HV/H2S54A, hu6G4.2.5HV/H3D100E, hu6G4.2.5HV/H3R102K, hu6G4.2.5HV/H3D106E, hu6G4.2.5HV/H3D100E,R102K, hu6G4.2.5HV/H3R102K,D106E, hu6G4.2.5HV/H3D100E,D106E, hu6G4.2.5HV/H3D100E,R102K,D106E, hu6G4.2.5HV/H1S31A/H2S54A, hu6G4.2.5HV/H1S31A/H3D100E, hu6G4.2.5HV/H1S31A/H3R102K, hu6G4.2.5HV/H1S31A/H3D106E, hu6G4.2.5HV/H1S31A/H3D100E,R102K, hu6G4.2.5HV/H1S31A/H3R102K,D106E, hu6G4.2.5HV/H1S31A/H3D100E,D106E, hu6G4.2.5HV/H1S31A/H3D100E,R102K,D106E, hu6G4.2.5HV/H2S54A/H3D100E, hu6G4.2.5HV/H2S54A/H3R102K, hu6G4.2.5HV/H2S54A/H3D106E, hu6G4.2.5HV/H2S54A/H3R102K,D106E, hu6G4.2.5HV/H2S54A/H3D100E,D106E, hu6G4.2.5HV/H2S54A/H3D100E,R102K,D106E, hu6G4.2.5HV/H1S31A/H2S54A/H3D100E, hu6G4.2.5HV/H1S31A/H2S54A/H3R102K, hu6G4.2.5HV/H1S31A/H2S54A/H3D106E, hu6G4.2.5HV/H1S31A/H2S54A/H3D100E,R102K, hu6G4.2.5HV/H1S31A/H2S54A/H3R102K,D106E, hu6G4.2.5HV/H1S31A/H2S54A/H3D100E,D106E, and hu6G4.2.5HV/H1S31A/H2S54A/H3D100E,R102K,D106E are collectively referred to herein as "hu6G4.2.5HV/vH1-3A".

The invention provides a humanized antibody or antibody fragment that comprises a light chain variable domain comprising the hu6G4.2.5LV/vL1-3X. In another embodiment, the invention provides a humanized antibody or antibody fragment that comprises a light chain variable domain comprising the hu6G4.2.5LV/vL1-3A. In yet another embodiment, the invention provides a humanized antibody or antibody fragment that comprises a light chain variable domain comprising the hu6G4.2.5LV/L1N35$X_{35}$. In still another embodiment, the invention provides a humanized antibody or antibody fragment that comprises a light chain variable domain comprising the hu6G4.2.5LV/L1N35A. In a further embodiment, the invention provides a humanized antibody or antibody fragment that comprises a light chain variable domain comprising the hu6G4.2.5LV/L1N35E.

The invention additionally provides a humanized antibody or antibody fragment that comprises a light chain variable domain comprising the hu6G4.2.5LV/vL1-3X, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV or hu6G4.2.5HV/vH1-3Z. In yet another embodiment, the invention provides a humanized antibody or antibody fragment that comprises a light chain variable domain comprising the hu6G4.2.5LV/vL1-3A, and further comprises a heavy chain variable domain comprising the hu6G4.2.5HV/vH1-3A.

In a further embodiment, the invention provides a humanized antibody or antibody fragment that comprises a light chain variable domain comprising the hu6G4.2.5LV/ L1N35X$_{35}$, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/ N35X$_{35}$, and further comprises a heavy chain variable domain comprising the hu6G4.2.5HV/vH1-3A. In a preferred embodiment, the antibody or antibody fragment comprises a light chain variable domain comprising the hu6G4.2.5LV/L1N35X$_{35}$ and further comprises a humanized heavy chain comprising the amino acid sequence of 6G4.2.5HV11.

In an additional embodiment, the invention provides a humanized antibody or antibody fragment that comprises a light chain variable domain comprising the hu6G4.2.5LV/ L1N35A, and further comprises a heavy chain variable domain comprising the hu6G4.2.5HV or hu6G4.2.5HV/vH1-3Z. In another embodiment, the invention provides a humanized antibody or antibody fragment that comprises a light chain variable domain comprising the hu6G4.2.5LV/N35A, and further comprises a heavy chain variable domain comprising the hu6G4.2.5HV/vH1-3A. In still another embodiment, the humanized antibody or antibody fragment comprises a light chain variable domain comprising the hu6G4.2.5LV/L1N35A, and further comprises a heavy chain variable domain comprising the hu6G4.2.5HV. In a further embodiment, the humanized antibody or antibody fragment comprises a light chain variable domain comprising the hu6G4.2.5LV/L1N35E, and further comprises a heavy chain variable domain comprising the hu6G4.2.5HV. In a preferred embodiment, the antibody or antibody fragment comprises a light chain variable domain comprising the hu6G4.2.5LV/ L1N35A and further comprises a humanized heavy chain comprising the amino acid sequence of 6G4.2.5HV11. In another preferred embodiment, the antibody or antibody fragment comprises a light chain variable domain comprising the hu6G4.2.5LV/L1N35E and further comprises a humanized heavy chain comprising the amino acid sequence of 6G4.2.5HV11.

The invention encompasses a single chain antibody fragment comprising the hu6G4.2.5LV/vL1-3X, with or without any additional amino acid sequence. In one embodiment, the invention provides a single chain antibody fragment comprising the hu6G4.2.5LV/vL1-3X without any associated heavy chain variable domain amino acid sequence, i.e. a single chain species that makes up one half of an Fv fragment. In another embodiment, the invention provides a single chain antibody fragment comprising the hu6G4.2.5LV/vL1-3A without any associated heavy chain variable domain amino acid sequence. In still another embodiment, the invention provides a single chain antibody fragment comprising the hu6G4.2.5LV/L1N35X$_{35}$ without any associated heavy chain variable domain amino acid sequence. In a preferred embodiment, the invention provides a single chain antibody fragment comprising the hu6G4.2.5LV/L1N35A without any associated heavy chain variable domain amino acid sequence. In another preferred embodiment, the invention provides a single chain antibody fragment comprising the hu6G4.2.5LV/L1N35E without any associated heavy chain variable domain amino acid sequence.

In one embodiment, the invention provides a single chain antibody fragment wherein the hu6G4.2.5LV/vL1-3X and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/vL1-3X joined to the hu6G4.2.5HV or hu6G4.2.5HV/vH1-3Z by means of a flexible peptide linker sequence, wherein the heavy chain and light chain variable domains can associate in a ?dimeric? structure analogous to that formed in a two-chain Fv species. In another embodiment, the single chain antibody fragment is a species comprising the hu6G4.2.5LV/vL1-3X joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In another embodiment, the invention provides a single chain antibody fragment wherein the hu6G4.2.5LV/vL1-3A and the hu6G4.2.5HV or hu6G4.2.5HV/vH1-3Z are contained in a single chain polypeptide species. In a preferred embodiment, the single chain antibody fragment is a scfv species comprising the hu6G4.2.5LV/vL1-3A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/vL1-3A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

In yet another embodiment, the invention provides a single chain antibody fragment wherein the hu6G4.2.5LV/vL1-3A and the hu6G4.2.5HV/vH1-3A are contained in a single chain polypeptide species. In a preferred embodiment, the single chain antibody fragment is a scFv species comprising the hu6G4.2.5LV/vL1-3A joined to the hu6G4.2.5HV/vH1-3A by means of a flexible peptide linker sequence, wherein the heavy chain and light chain variable domains can associate in a ?dimeric? structure analogous to that formed in a two-chain Fv species. In another embodiment, the single chain antibody fragment is a species comprising the hu6G4.2.5LV/vL1-3A joined to the hu6G4.2.5HV/vH1-3A by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/ L1N35X$_{35}$ and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35X$_{35}$ joined to the hu6G4.2.5HV or hu6G4.2.5HV/vH1-3Z by means of a flexible peptide linker sequence, wherein the heavy chain and light chain variable domains can associate in a ?dimeric? structure analogous to that formed in a two-chain Fv species. In another embodiment, the single chain antibody fragment is a species comprising the hu6G4.2.5LV/ L1N35X$_{35}$ joined to the hu6G4.2.5HV or hu6G4.2.5HV/ vH1-3Z by a linker that is too short to permit intramolecular pairing of the two variable domains, i.e. a single chain polypeptide monomer that forms a diabody upon dimerization with another monomer.

In a further embodiment, the invention provides a single chain antibody fragment wherein the hu6G4.2.5LV/ L1N35X$_{35}$ and the hu6G4.2.5HV/vH1-3A are contained in a single chain polypeptide species. In a preferred embodiment, the single chain antibody fragment is a scFv species comprising the hu6G4.2.5LV/L1N35X$_{35}$ joined to the hu6G4.2.5HV/ vH1-3A by means of a flexible peptide linker sequence, wherein the heavy chain and light chain variable domains can associate in a ?dimeric? structure analogous to that formed in a two-chain Fv species. In another embodiment, the single chain antibody fragment is a species comprising the hu6G4.2.5LV/L1N35X$_{35}$ joined to the hu6G4.2.5HV/vH1-3A by a linker that is too short to permit intramolecular pairing of the two variable domains, i.e. a single chain polypeptide monomer that forms a diabody upon dimerization with another monomer.

In an additional embodiment, the invention provides a single chain antibody fragment wherein the hu6G4.2.5LV/L1N35A and the hu6G4.2.5HV or hu6G4.2.5HV/vH1-3Z are contained in a single chain polypeptide species. In a preferred embodiment, the single chain antibody fragment is a scFv species comprising the hu6G4.2.5LV/L1N35A joined to the hu6G4.2.5HV or hu6G4.2.5HV/vH1-3Z by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35A joined to the hu6G4.2.5HV or hu6G4.2.5HV/vH1-3Z by a linker that is too short to permit intramolecular pairing of the two variable domains, i.e. a single chain polypeptide monomer that forms a diabody upon dimerization with another monomer.

Also provided herein is a single chain antibody fragment wherein the hu6G4.2.5LV/L1N35E and the hu6G4.2.5HV are contained in a single chain polypeptide species. In a preferred embodiment, the single chain antibody fragment is a scFv species comprising the hu6G4.2.5LV/L1N35E joined to the hu6G4.2.5HV by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5LV/L1N35E joined to the hu6G4.2.5HV by a linker that is too short to permit intramolecular pairing of the two variable domains, i.e. a single chain polypeptide monomer that forms a diabody upon dimerization with another monomer.

In still another embodiment, the invention provides a single chain antibody fragment wherein the hu6G4.2.5LV/L1N35A and the hu6G4.2.5HV/vH1-3A are contained in a single chain polypeptide species. In a preferred embodiment, the single chain antibody fragment is a scFv species comprising the hu6G4.2.5LV/L1N35A joined to the hu6G4.2.5HV/vH1-3A by means of a flexible peptide linker sequence, wherein the heavy chain and light chain variable domains can associate in a ?dimeric? structure analogous to that formed in a two-chain Fv species. In another embodiment, the single chain antibody fragment is a species comprising the hu6G4.2.5LV/L1N35A joined to the hu6G4.2.5HV/vH1-3A by a linker that is too short to permit intramolecular pairing of the two variable domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3X and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3X and a second polypeptide chain comprises the amino acid sequence of 6G4.2.5HV11 and the two polypeptide chains are covalently linked by one or more interchain disulfide bonds.

In a further embodiment, the invention provides an antibody fragment comprising a plurality of polypeptide chains, wherein one polypeptide chain comprises the hu6G4.2.5LV/vL1-3A and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/vL1-3A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/vL1-3A and a second polypeptide chain comprises the amino acid sequence of 6G4.2.5HV11 and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35X$_{35}$ and a second polypeptide chain comprises the hu6G4.2.5HV or hu6G4.2.5HV/vH1-3Z and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35X$_{35}$ and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35X$_{35}$ and a second polypeptide chain comprises the amino acid sequence of 6G4.2.5HV11 and the two polypeptide chains are covalently linked by one or more interchain disulfide bonds.

The invention further encompasses an antibody fragment comprising a plurality of polypeptide chains, wherein one polypeptide chain comprises the hu6G4.2.5LV/L1N35A and a second polypeptide chain comprises the hu6G4.2.5HV or hu6G4.2.5HV/vH1-3Z and the two polypeptide chains are covalently linked by one or more interchain disulfide bonds.

The invention also encompasses an antibody fragment comprising a plurality of polypeptide chains, wherein one polypeptide chain comprises the hu6G4.2.5LV/L1N35E and a second polypeptide chain comprises the hu6G4.2.5HV and the two polypeptide chains are covalently linked by one or more interchain disulfide bonds.

In still another embodiment, the invention provides an antibody fragment comprising a plurality of polypeptide chains, wherein one polypeptide chain comprises the hu6G4.2.5LV/L1N35A and a second polypeptide chain comprises the hu6G4.2.5HV/vH1-3A and the two polypeptide chains are covalently linked by one or more interchain disulfide bonds. In a preferred embodiment, the invention provides an antibody fragment comprising a plurality of polypeptide chains, wherein one polypeptide chain comprises the hu6G4.2.5LV/L1N35A and a second polypeptide chain comprises the amino acid sequence of 6G4.2.5HV11 and the two polypeptide chains are covalently linked by one or more interchain disulfide bonds. In another preferred embodiment, the invention provides an antibody fragment comprising a plurality of polypeptide chains, wherein one polypeptide chain comprises the hu6G4.2.5LV/L1N35E and a second polypeptide chain comprises the amino acid sequence of 6G4.2.5HV11 and the two polypeptide chains are covalently linked by one or more interchain disulfide bonds.

In a preferred embodiment, any of the foregoing two-chain antibody fragments are selected from the group consisting of Fab, Fab', Fab'-SH, Fv, and F(ab')$_2$. In another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35X$_{35}$ and a second polypeptide chain comprising the hu6G4.2.5HV. In yet another preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35A and a second polypeptide chain comprising the hu6G4.2.5HV. In a further preferred embodiment, the antibody fragment is selected from the group consisting of Fab, Fab', Fab'-SH, Fv, and F(ab')$_2$, wherein the antibody fragment comprises one polypeptide chain comprising the hu6G4.2.5LV/L1N35E and a second polypeptide chain comprising the hu6G4.2.5HV. In still another preferred embodiment, the antibody fragment is a F(ab')$_2$ that comprises one polypeptide chain comprising the hu6G4.2.5LV/L1N35A and a second polypeptide chain comprising the amino acid sequence of 6G4.2.5HV11. In an additional preferred embodiment, the antibody fragment is a F(ab')$_2$ that comprises one polypeptide chain comprising the hu6G4.2.5LV/L1N35E and a second polypeptide chain comprising the amino acid sequence of 6G4.2.5HV11.

The invention also provides an antibody or antibody fragment comprising a light chain variable domain containing the hu6G4.2.5LV/vL1-3X and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/vL1-3X and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain variable domain containing the hu6G4.2.5LV/L1N35X$_{35}$ and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35X$_{35}$ and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention also encompasses an antibody or antibody fragment comprising a light chain variable domain containing the hu6G4.2.5LV/L1N35A and optionally further comprising a heavy chain variable domain containing the hu6G4.2.5HV or hu6G4.2.5HV/vH1-3Z, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain variable domain containing the hu6G4.2.5LV/L1N35A and optionally further comprising a heavy chain variable domain containing the hu6G4.2.5HV/vH1-3A, wherein the light chain variable domain, and optionally the heavy chain variable domain, is (are) fused to an additional moiety, such as a immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally encompasses an antibody or antibody fragment comprising a light chain variable domain containing the hu6G4.2.5LV/L1N35A and optionally further comprising a heavy chain containing the amino acid sequence of 6G4.2.5HV11, wherein the light chain variable domain, and optionally the heavy chain, is (are) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further encompasses an antibody or antibody fragment comprising a light chain variable domain containing the hu6G4.2.5LV/L1N35E and optionally further comprising a heavy chain containing the amino acid sequence of 6G4.2.5HV11, wherein the light chain variable domain, and optionally the heavy chain, is (are) fused to an additional moiety, such as immunoglobulin constant domain sequences. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the antibody or antibody fragment comprises a light chain variable domain containing the hu6G4.2.5LV/vL1-3X, and further comprises the hu6G4.2.5HV or hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547-1553 (1992) and the GCN4 leucine zipper described in the Examples below.

In particular, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 (herein referred to as "6G4.2.5LV11N35$X_{35}$").

In another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 (herein referred to as "6G4.2.5LV11S26$X_{26}$").

In yet another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than His (denoted as "$X_{98}$") is substituted for L is at amino acid position 98 (herein referred to as "6G4.2.5LV11H98$X_{98}$").

In still another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than Asn (denoted as "$X_{35}$") is substituted for Asn at amino acid position 35 (herein referred to as "6G4.2.5LV11S26$X_{26}$/N35$X_{35}$").

In a further embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11N35$X_{35}$/H98$X_{98}$").

In an additional embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26 and any amino acid other than His (denoted as "$X_{98}$") is substituted for His at amino acid position 98 (herein referred to as "6G4.2.5LV11S26$X_{26}$/H98$X_{98}$").

The invention also encompasses an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that any amino acid other than Ser (denoted as "$X_{26}$") is substituted for Ser at amino acid position 26, any amino acid other than Asn (denoted as "$X_{35}$") is substituted for Asn at amino acid position 35 and any amino acid other than His (denoted as "$X_{98}$") is substituted for His at amino acid position 98 (herein referred to as "6G4.2.5LV11S26$X_{26}$/N35$X_{35}$/H98$X_{98}$").

Additionally, the invention provides an antibody or antibody fragment comprising a light chain comprising the amino acid sequence of amino acids 1-219 of the variant humanized anti-IL-8 6G4.2.5v11 light chain polypeptide amino acid sequence (SEQ ID NO: 56) of FIG. 36 (herein referred to as "6G4.2.5LV11N35A").

Further provided herein is an antibody or antibody fragment comprising a light chain comprising the amino acid sequence of amino acids 1-219 of the variant humanized anti-IL-8 6G4.2.5v11 light chain polypeptide amino acid sequence (SEQ ID NO: 62) of FIG. 45 (herein referred to as "6G4.2.5LV11N35E").

In another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that Ala is substituted for Ser at amino acid position 26 (herein referred to as "6G4.2.5LV11S26A").

In yet another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that Ala is substituted for His at amino acid position 98 (herein referred to as "6G4.2.5LV11H98A").

In still another embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for Asn at amino acid position 35 (herein referred to as "6G4.2.5LV11S26A/N35A").

In a further embodiment, the invention provides an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that Ala is substituted for Ser at amino acid position 26 and Ala is substituted for His at amino acid position 98 (herein referred to as "6G4.2.5LV11S26A/H98A").

The invention also encompasses an antibody or antibody fragment comprising a light chain comprising the amino acid sequence of amino acids 1-219 of the variant humanized anti-IL-8 6G4.2.5v11 light chain polypeptide amino acid sequence of FIG. 31B (SEQ ID NO: 51) with the proviso that Ala is substituted for Asn at amino acid position 35 and Ala is substituted for His at amino acid position 98 (herein referred to as "6G4.2.5LV11N35A/H98A").

The invention further encompasses an antibody or antibody fragment comprising a light chain comprising the amino acid sequence of amino acids 1-219 of the variant humanized anti-1 L-8 6G4.2.5v11 light chain polypeptide amino acid sequence of FIG. 31B (SEQ ID NO: 51) with the proviso that Ala is substituted for Ser at amino acid position 26, Ala is substituted for Asn at amino acid position 35, and Ala is substituted for His at amino acid position 98 (herein referred to as "6G4.2.5LV11S26A/N35A/H98A").

The invention provides a single chain antibody fragment comprising a variant light chain selected from the group consisting of 6G4.2.5LV11N35$X_{35}$, 6G4.2.5LV11S26$X_{26}$, 6G4.2.5LV11H98$X_{98}$, 6G4.2.5LV11S26$X_{26}$/N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$/N35$X_{35}$/H98$X_{98}$, with or without any additional amino acid sequence. It will be understood that the group consisting of 6G4.2.5LV11N35$X_{35}$, 6G4.2.5LV11S26$X_{26}$, 6G4.2.5LV11H98$X_{98}$, 6G4.2.5LV11S26$X_{26}$/N35$X_{35}$, 6G4.2.5LV11N35$X_{35}$/H98$X_{98}$, 6G4.2.5LV11S26$X_{26}$/H98$X_{98}$, and 6G4.2.5LV11S26$X_{26}$/N35$X_{35}$/H98$X_{98}$, is collectively referred to herein as the "group of 6G4.2.5LV11X variants", and that individual members of this group are generically referred to herein as a "6G4.2.5LV11X variant." In one embodiment, the invention provides a single chain antibody fragment comprising a 6G4.2.5LV11X variant without any associated heavy chain amino acid sequence, i.e. a single chain species that makes up one half of a Fab fragment. In a preferred embodiment, the invention provides a 6G4.2.5LV11N35$X_{35}$ variant without any associated heavy chain amino acid sequence.

The invention encompasses a single chain antibody fragment comprising a variant light chain selected from the group consisting of 6G4.2.5LV11N35A, 6G4.2.5LV11S26A, 6G4.2.5LV11H98A, 6G4.2.5LV11S26A/N35A, 6G4.2.5LV11N35A/H98A, 6G4.2.5LV11S26A/H98A, and 6G4.2.5LV11S26A/N35A/H98A, with or without any additional amino acid sequence. It will be understood that the group consisting of 6G4.2.5LV11N35A, 6G4.2.5LV11S26A, 6G4.2.5LV11H98A, 6G4.2.5LV11S26A/N35A, 6G4.2.5LV11N35A/H98A, 6G4.2.5LV11S26A/H98A, and 6G4.2.5LV11S26A/N35A/H98A is collectively referred to herein as the "group of 6G4.2.5LV11A variants", and that individual members of this group are generically referred to herein as a "6G4.2.5LV11A variant." In one embodiment, the invention provides a single chain antibody fragment comprising a 6G4.2.5LV11A variant without any associated heavy chain amino acid sequence, i.e. a single chain species that makes up one half of a Fab fragment. In a preferred embodiment, the invention provides the 6G4.2.5LV11N35A without any associated heavy chain amino acid sequence.

Further provided herein are an antibody or antibody fragment comprising a light chain comprising a 6G4.2.5LV11X variant, and further comprising a heavy chain comprising the G4.2.5HV11. In a preferred embodiment, the invention provides an antibody or antibody fragment comprising a 6G4.2.5LV11N35$X_{35}$ variant and further comprising the 6G4.2.5HV11. In a preferred embodiment, the invention provides an antibody or antibody fragment comprising the 6G4.2.5LV11N35A and further comprising the 6G4.2.5HV11. In another preferred embodiment, the invention provides an antibody or antibody fragment comprising the 6G4.2.5LV11N35E and further comprising the 6G4.2.5HV11.

In one embodiment, the invention provides a single chain antibody fragment wherein a 6G4.2.5LV11X variant and the 6G4.2.5HV11 are contained in a single chain polypeptide species. In a preferred embodiment, the single chain antibody fragment comprises a 6G4.2.5LV11X variant joined to the 6G4.2.5HV11 by means of a flexible peptide linker sequence, wherein the heavy chain and light chain domains can associate in a ?dimeric? structure analogous to that formed in a two-chain Fab species. In another embodiment, the single chain antibody fragment is a species comprising a 6G4.2.5LV11X variant joined to the 6G4.2.5HV11 by a linker that is too short to permit intramolecular pairing of complementary domains, i.e. a single chain polypeptide monomer that forms a diabody upon dimerization with another monomer.

In still another embodiment, the invention provides a single chain antibody fragment wherein a 6G4.2.5LV11N35$X_{35}$ variant and the 6G4.2.5HV11 are contained in a single chain polypeptide species. In a preferred embodiment, the single chain antibody fragment comprises a 6G4.2.5LV11N35$X_{35}$ variant joined to the 6G4.2.5HV11 by means of a flexible peptide linker sequence, wherein the heavy chain and light chain domains can associate in a ?dimeric? structure analogous to that formed in a two-chain Fab species. In another embodiment, the single chain antibody fragment is a species comprising a 6G4.2.5LV11N35$X_{35}$ variant joined to the 6G4.2.5HV11 by a linker that is too short to permit intramolecular pairing of complementary domains, i.e. a single chain polypeptide monomer that forms a diabody upon dimerization with another monomer.

In a further embodiment, the invention provides a single chain antibody fragment wherein the 6G4.2.5LV11N35A and the 6G4.2.5HV11 are contained in a single chain polypeptide species. In a preferred embodiment, the single chain antibody fragment comprises the 6G4.2.5LV11N35A joined to the 6G4.2.5HV11 by means of a flexible peptide linker sequence, wherein the heavy chain and light chain domains can associate in a ?dimeric? structure analogous to that formed in a two-chain Fab species. In another embodiment, the single chain antibody fragment is a species comprising the 6G4.2.5LV11N35A joined to the 6G4.2.5HV11 by a linker that is too short to permit intramolecular pairing of complementary domains, i.e. a single chain polypeptide monomer that forms a diabody upon dimerization with another monomer.

In an additional embodiment, the invention provides a single chain antibody fragment wherein the 6G4.2.5V11N35E and the 6G4.2.5HV11 are contained in a single chain polypeptide species. In a preferred embodiment, the single chain antibody fragment comprises the 6G4.2.5V11N35E joined to the 6G4.2.5HV11 by means of a flexible peptide linker sequence, wherein the heavy chain and light chain domains can associate in a ?dimeric? structure analogous to that formed in a two-chain Fab species. In another embodiment, the single chain antibody fragment is a species comprising the 6G4.2.5LV11N35E joined to the 6G4.2.5HV11 by a linker that is too short to permit intramolecular pairing of complementary domains, i.e. a single chain polypeptide monomer that forms a diabody upon dimerization with another monomer.

In yet another embodiment, the invention provides an antibody fragment comprising a plurality of polypeptide chains, wherein one polypeptide chain comprises a 6G4.2.5V11X variant and a second polypeptide chain comprises the 6G4.2.5HV11 and the two polypeptide chains are covalently linked by one or more interchain disulfide bonds. In still another embodiment, the invention provides an antibody fragment comprising a plurality of polypeptide chains, wherein one polypeptide chain comprises a 6G4.2.5V11N35$X_{35}$ variant and a second polypeptide chain comprises the 6G4.2.5HV11 and the two polypeptide chains are covalently linked by one or more interchain disulfide bonds. In a preferred embodiment, any of the foregoing two-chain antibody fragments is selected from the group consisting of Fab, Fab', Fab'-SH, and F(ab')$_2$. In still another preferred embodiment, the two-chain antibody fragment is a F(ab')$_2$ wherein one polypeptide chain comprises the 6G4.2.5LV11N35A and the second polypeptide chain comprises the 6G4.2.5HV11. In a further preferred embodiment, the antibody fragment is a Fab, Fab', Fab'-SH, or F(ab')$_2$ wherein one polypeptide chain comprises the 6G4.2.5LV11N35E and the second polypeptide chain comprises the 6G4.2.5HV11. A particularly preferred embodiment, the antibody fragment is the 6G4V11N35A F(ab')$_2$ GCN4 leucine zipper species described in the Examples below. In another particularly preferred embodiment, the antibody fragment is the 6G4V11N35E F(ab')$_2$ GCN4 leucine zipper species described in the Examples below. In yet another particularly preferred embodiment, the antibody fragment is the 6G4V11N35E Fab described in the Examples below.

The invention also provides an antibody or antibody fragment comprising a light chain containing a 6G4.2.5LV11X variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention additionally provides an antibody or antibody fragment comprising a light chain containing a 6G4.2.5V11N35$X_{35}$ variant and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35A and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

The invention further provides an antibody or antibody fragment comprising a light chain containing the 6G4.2.5LV11N35E and optionally further comprising a heavy chain containing the 6G4.2.5HV11, wherein the light chain, and optionally the heavy chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the antibody or antibody fragment comprises a light chain containing a 6G4.2.5LV11X variant, and further comprises the 6G4.2.5HV11 in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547-1553 (1992) and the GCN4 leucine zipper described in the Examples below. In another preferred embodiment, the antibody or antibody fragment comprises a light chain containing the 6G4.2.5LV11N35A, and further comprises a heavy chain containing the 6G4.2.5HV11 fused to the GCN4 leucine zipper. In yet another preferred embodiment, the antibody or antibody fragment comprises a light chain containing the 6G4.2.5LV11N35E, and further comprises a heavy chain containing the 6G4.2.5HV11 fused to the GCN4 leucine zipper.

B. 6G4.2.5HV Variants

The invention provides humanized antibodies and antibody fragments comprising the CDRs of a 6G4.2.5HV CDR variant. The use of a 6G4.2.5HV CDRs variant in the humanized antibodies and antibody fragments of the invention confer the advantages of higher affinity for human IL-8 and/or improved recombinant manufacturing economy.

A heavy chain variable domain comprising the CDRs of a 6G4.2.5HV CDRs variant can be humanized in conjunction with a light chain comprising the CDRs of 6G4.2.5LV or the CDRs of a 6G4.2.5LV CDRs variant, essentially as described in Section (II)(2)(A) above. In one embodiment, the invention provides a humanized antibody or antibody fragment comprising a 6G4.2.5HV CDRs variant selected from the group consisting of 6G4.2.5HV/H1S31$Z_{31}$, 6G4.2.5HV/H2S54$Z_{54}$, and 6G4.2.5HV/H1S31$Z_{31}$/H2S54$Z_{54}$. In addition, the invention provides a humanized antibody or antibody fragment comprising a 6G4.2.5HV CDRs variant selected from the group consisting of 6G4.2.5HV/H1S31A, 6G4.2.5HV/H2S54A, and 6G4.2.5HV/H1S31A/H2S54A. In particular, the 6G4.2.5HV CDRs variants can be used to construct a humanized antibody or antibody comprising the hu6G4.2.5HV/vH1-3Z as described in Section (II)(2)(A) above.

The invention additionally provides a humanized antibody or antibody fragment that comprises a heavy chain variable domain comprising the hu6G4.2.5HV/vH1-3Z, and further comprises a light chain variable domain comprising the hu6G4.2.5LV or hu6G4.2.5LV/vL1-3X.

The invention further encompasses a single chain humanized antibody fragment comprising the hu6G4.2.5HV/vH1-3Z, with or without any additional amino acid sequence. In one embodiment, the invention provides a single chain antibody fragment comprising the hu6G4.2.5HV/vH1-3Z without any associated heavy chain variable domain amino acid sequence, i.e. a single chain species that makes up one half of an Fv fragment.

In one embodiment, the invention provides a single chain humanized antibody fragment wherein the hu6G4.2.5HV/vH1-3Z and the hu6G4.2.5LV or hu6G4.2.5LV/vL1-3X are contained in a single chain polypeptide species. In a preferred embodiment, the single chain antibody fragment is a scFv species comprising the hu6G4.2.5HV/vH1-3Z joined to the hu6G4.2.5LV or hu6G4.2.5LV/vL1-3X by means of a flexible peptide linker sequence, wherein the heavy chain and light chain variable domains can associate in a "dimeric" structure analogous to that formed in a two-chain Fv species. In another embodiment, the single chain antibody fragment is a species comprising the hu6G4.2.5HV/vH1-3Z joined to the hu6G4.2.5LV or hu6G4.2.5LV/vL1-3X by a linker that is too short to permit intramolecular pairing of the two variable domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises the hu6G4.2.5HV/vH1-3Z and a second polypeptide chain comprises the hu6G4.2.5LV or hu6G4.2.5LV/vL1-3X and the two polypeptide chains are covalently linked by one or more interchain disulfide bonds. In a preferred embodiment, the foregoing two-chain antibody fragment is selected from the group consisting of Fab, Fab', Fab'-SH, Fv, and F(ab')$_2$.

The invention also provides a humanized antibody or antibody fragment comprising a heavy chain variable domain containing the hu6G4.2.5HV/vH1-3Z and optionally further comprising a light chain variable domain containing the hu6G4.2.5LV or hu6G4.2.5LV/vL1-3X, wherein the heavy chain variable domain, and optionally the light chain variable domain, is (are) fused to an additional moiety, such as an immunoglobulin constant domain. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al.

In a preferred embodiment, the humanized antibody or antibody fragment comprises the hu6G4.2.5HV/vH1-3Z in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547-1553 (1992) and the GCN4 leucine zipper described in the Examples below.

In addition, the invention provides a humanized antibody or antibody fragment comprising a heavy chain comprising the amino acid sequence of amino acids 1-230 of the 6G4.2.5HV11 polypeptide amino acid sequence of FIGS. 37A-37B (SEQ ID NO: 60) with the proviso that Ala is substituted for Ser at amino acid position 31 (hereinafter referred to as "6G4.2.5HV11 S31A").

In another embodiment, the invention provides a humanized antibody or antibody fragment comprising a heavy chain comprising the amino acid sequence of amino acids 1-230 of the 6G4.2.5HV11 polypeptide amino acid sequence of FIGS. 37A-37B (SEQ ID NO: 60) with the proviso that Ala is substituted for Ser at amino acid position 54 (hereinafter referred to as "6G4.2.5HV11 S54A").

In yet another embodiment, the invention provides a humanized antibody or antibody fragment comprising a heavy chain comprising the amino acid sequence of amino acids 1-230 of the 6G4.2.5HV11 polypeptide amino acid sequence of FIGS. 37A-37B (SEQ ID NO: 60) with the proviso that Ala is substituted for Ser at amino acid position 31 and Ala is substituted for Ser at amino acid position 54 (hereinafter referred to as "6G4.2.5HV11S31A/S54A").

Further provided herein is a humanized antibody or antibody fragment that comprises any of the light and heavy chain combinations listed in Tables 1-2 below.

TABLE 1

| Heavy Chain | Light Chain |
| --- | --- |
| 6G4.2.5HV11S31A | 6G4.2.5LV11 |
| 6G4.2.5HV11S31A | 6G4.2.5LV11N35A |
| 6G4.2.5HV11S31A | 6G4.2.5LV11S26A |
| 6G4.2.5HV11S31A | 6G4.2.5LV11H98A |
| 6G4.2.5HV11S31A | 6G4.2.5LV11S26A/N35A |
| 6G4.2.5HV11S31A | 6G4.2.5LV11S26A/H98A |
| 6G4.2.5HV11S31A | 6G4.2.5LV11N35A/H98A |
| 6G4.2.5HV11S31A | 6G4.2.5LV11S26A/N35A/H98A |
| 6G4.2.5HV11S54A | 6G4.2.5LV11 |
| 6G4.2.5HV11S54A | 6G4.2.5LV11N35A |
| 6G4.2.5HV11S54A | 6G4.2.5LV11S26A |
| 6G4.2.5HV11S54A | 6G4.2.5LV11H98A |
| 6G4.2.5HV11S54A | 6G4.2.5LV11S26A/N35A |
| 6G4.2.5HV11S54A | 6G4.2.5LV11S26A/H98A |
| 6G4.2.5HV11S54A | 6G4.2.5LV11N35A/H98A |
| 6G4.2.5HV11S54A | 6G4.2.5LV11S26A/N35A/H98A |
| 6G4.2.5HV11S31A/S54A | 6G4.2.5LV11 |
| 6G4.2.5HV11S31A/S54A | 6G4.2.5LV11N35A |
| 6G4.2.5HV11S31A/S54A | 6G4.2.5LV11S26A |
| 6G4.2.5HV11S31A/S54A | 6G4.2.5LV11H98A |
| 6G4.2.5HV11S31A/S54A | 6G4.2.5LV11S26A/N35A |
| 6G4.2.5HV11S31A/S54A | 6G4.2.5LV11S26A/H98A |

TABLE 1-continued

| Heavy Chain | Light Chain |
| --- | --- |
| 6G4.2.5HV11S31A/S54A | 6G4.2.5LV11N35A/H98A |
| 6G4.2.5HV11S31A/S54A | 6G4.2.5LV11S26A/N35A/H98A |

TABLE 2

| Heavy Chain | Light Chain |
| --- | --- |
| 6G4.2.5HV11S31A | 6G4.2.5LV11 |
| 6G4.2.5HV11S31A | 6G4.2.5LV11N35X$_{35}$ |
| 6G4.2.5HV11S31A | 6G4.2.5LV11S26X$_{26}$ |
| 6G4.2.5HV11S31A | 6G4.2.5LV11H98X$_{98}$ |
| 6G4.2.5HV11S31A | 6G4.2.5LV11S26X$_{26}$/N35X$_{35}$ |
| 6G4.2.5HV11S31A | 6G4.2.5LV11S26X$_{26}$/H98X$_{98}$ |
| 6G4.2.5HV11S31A | 6G4.2.5LV11N35X$_{35}$/H98X$_{98}$ |
| 6G4.2.5HV11S31A | 6G4.2.5LV11S26X$_{26}$/N35X$_{35}$/H98X$_{98}$ |
| 6G4.2.5HV11S54A | 6G4.2.5LV11 |
| 6G4.2.5HV11S54A | 6G4.2.5LV11N35X$_{35}$ |
| 6G4.2.5HV11S54A | 6G4.2.5LV11S26X$_{26}$ |
| 6G4.2.5HV11S54A | 6G4.2.5LV11H98X$_{98}$ |
| 6G4.2.5HV11S54A | 6G4.2.5LV11S26X$_{26}$/N35X$_{35}$ |
| 6G4.2.5HV11S54A | 6G4.2.5LV11S26X$_{26}$/H98X$_{98}$ |
| 6G4.2.5HV11S54A | 6G4.2.5LV11N35X$_{35}$/H98X$_{98}$ |
| 6G4.2.5HV11S54A | 6G4.2.5LV11S26X$_{26}$/N35X$_{35}$/H98X$_{98}$ |
| 6G4.2.5HV11S31A/S54A | 6G4.2.5LV11 |
| 6G4.2.5HV11S31A/S54A | 6G4.2.5LV11N35X$_{35}$ |
| 6G4.2.5HV11S31A/S54A | 6G4.2.5LV11S26X$_{26}$ |
| 6G4.2.5HV11S31A/S54A | 6G4.2.5LV11H98X$_{98}$ |
| 6G4.2.5HV11S31A/S54A | 6G4.2.5LV11S26X$_{26}$/N35X$_{35}$ |
| 6G4.2.5HV11S31A/S54A | 6G4.2.5LV11S26X$_{26}$/H98X$_{98}$ |
| 6G4.2.5HV11S31A/S54A | 6G4.2.5LV11N35X$_{35}$/H98X$_{98}$ |
| 6G4.2.5HV11S31A/S54A | 6G4.2.5LV11S26X$_{26}$/N35X$_{35}$/H98X$_{98}$ |

The invention encompasses a single chain humanized antibody fragment comprising a variant heavy chain selected from the group consisting of 6G4.2.5HV11S31A, 6G4.2.5HV11S54A, and 6G4.2.5HV11S31A/S54A, with or without any additional amino acid sequence. It will be understood that the group consisting of 6G4.2.5HV11S31A, 6G4.2.5HV11S54A, and 6G4.2.5HV11S31A/S54A is collectively referred to herein as the "group of 6G4.2.5HV11A variants", and that individual members of this group are generically referred to herein as a ?6G4.2.5HV11A variant.? In one embodiment, the invention provides a single chain humanized antibody fragment comprising a 6G4.2.5HV11A variant without any associated light chain amino acid sequence, i.e. a single chain species that makes up one half of a Fab fragment.

Further provided herein are a humanized antibody or antibody fragment comprising a heavy chain comprising a 6G4.2.5HV11A variant, and further comprising a light chain comprising a 6G4.2.5LV11A variant or a 6G4.2.5LV11X variant. In another embodiment, the humanized antibody or antibody fragment comprises any combination of light and heavy chains listed in Tables 1 and 2 above. In one embodiment, the invention provides a humanized antibody or antibody fragment comprising a 6G4.2.5HV11A variant and further comprising the 6G4.2.5LV11N35X$_{35}$. In a preferred embodiment, the invention provides a humanized antibody or antibody fragment comprising a 6G4.2.5HV11A variant and further comprising the 6G4.2.5LV11N35A.

In yet another embodiment, the invention provides a single chain humanized antibody fragment wherein a 6G4.2.5HV11A variant and the 6G4.2.5LV11 are contained in a single chain polypeptide species. In another embodiment, the invention provides a single chain humanized antibody fragment wherein any pair of light and heavy chains listed in Tables 1-2 above is contained in a single chain polypeptide species. In yet another embodiment, the invention provides a single chain humanized antibody fragment wherein a 6G4.2.5HV11A variant and a 6G4.2.5LV11X variant are contained in a single chain polypeptide species. In still another embodiment, the invention provides a single chain humanized antibody fragment wherein a 6G4.2.5HV11A variant and a 6G4.2.5LV11N35X$_{35}$ variant are contained in a single chain polypeptide species. In an additional embodiment, the invention provides a single chain humanized antibody fragment wherein a 6G4.2.5HV11A variant and the 6G4.2.5LV11N35A variant are contained in a single chain polypeptide species.

In a preferred embodiment, the single chain humanized antibody fragment comprises a 6G4.2.5HV11A variant joined to a 6G4.2.5LV11X variant, 6G4.2.5LV11N35X$_{35}$ variant, 6G4.2.5LV11N35A variant, or 6G4.2.5LV11 by means of a flexible peptide linker sequence, wherein the heavy chain and light chain domains can associate in a ?dimeric? structure analogous to that formed in a two-chain Fab species. In a further embodiment, the single chain humanized antibody fragment is a species comprising a 6G4.2.5HV11A variant joined to a G4.2.5LV11X variant, 6G4.2.5LV11N35X$_{35}$ variant, 6G4.2.5LV11N35A variant, or 6G4.2.5LV11 by a linker that is too short to permit intramolecular pairing of complementary domains, i.e. a single chain polypeptide monomer that forms a diabody upon dimerization with another monomer.

In still another embodiment, the single chain humanized antibody fragment comprises any pair of light and heavy chains listed in Table 1 above joined by means of a flexible peptide linker sequence, wherein the heavy chain and light chain domains can associate in a ?dimeric? structure analogous to that formed in a two-chain Fab species. In an additional embodiment, the single chain humanized antibody fragment comprises any pair of light and heavy chains listed in Tables 1-2 above joined by a linker that is too short to permit intramolecular pairing of complementary domains, i.e. a single chain polypeptide monomer that forms a diabody upon dimerization with another monomer.

In yet another embodiment, the invention provides a humanized antibody fragment comprising a plurality of polypeptide chains, wherein one polypeptide chain comprises a 6G4.2.5HV11A variant and a second polypeptide chain comprises a 6G4.2.5LV11X variant, 6G4.2.5LV11N35X$_{35}$ variant, 6G4.2.5LV11N35A variant, or 6G4.2.5V11, and the two polypeptide chains are covalently linked by one or more interchain disulfide bonds. In a preferred embodiment, the foregoing two-chain antibody fragment is selected from the group consisting of Fab, Fab', Fab'-SH, and F(ab')$_2$.

In an additional embodiment, the invention provides a two-chain humanized antibody fragment comprising any pair of heavy and light chains listed in Tables 1-2 above, wherein each chain is contained on a separate molecule. In another embodiment, the two-chain antibody fragment comprising any pair of heavy and light chains listed in Tables 1-2 above is selected from the group consisting of Fab, Fab', Fab'-SH, and F(ab')$_2$. In a preferred embodiment, the two-chain humanized antibody fragment is a F(ab')$_2$ comprising any pair of heavy and light chains listed in Tables 1-2 above. In another preferred embodiment, the two-chain humanized antibody fragment is a F(ab')$_2$ wherein one polypeptide chain comprises a 6G4.2.5HV11A variant and the second polypeptide chain comprises the 6G4.2.5V11N35A.

The invention also provides a humanized antibody or antibody fragment comprising a heavy chain containing a 6G4.2.5HV11A variant and optionally further comprising a light chain containing a 6G4.2.5LV11X variant, 6G4.2.5V11N35X$_{35}$ variant, 6G4.2.5LV11N35A, or 6G4.2.5HV11, wherein the heavy chain, and optionally the light chain, is (are) fused to an additional moiety, such as additional immunoglobulin constant domain sequence. Constant domain sequence can be added to the heavy chain and/or light chain sequence(s) to form species with full or partial length heavy and/or light chain(s). It will be appreciated that constant regions of any isotype can be used for this purpose, including IgG, IgM, IgA, IgD, and IgE constant regions, and that such constant regions can be obtained from any human or animal species. Preferably, the constant domain sequence is human in origin. Suitable human constant domain sequences can be obtained from Kabat et al. (supra).

In a preferred embodiment, the humanized antibody or antibody fragment comprises a 6G4.2.5HV11A variant in a heavy chain that is fused to or contains a leucine zipper sequence. The leucine zipper can increase the affinity or production efficiency of the antibody or antibody fragment of interest. Suitable leucine zipper sequences include the jun and fos leucine zippers taught by Kostelney et al., *J. Immunol.*, 148: 1547-1553 (1992) and the GCN4 leucine zipper described in the Examples below.

C. Bispecific Antibodies

Bispecific antibodies are monoclonal, preferably human or humanized, antibodies that have binding specificities for at least two different antigens. In the present case, one of the binding specificities is for IL-8, the other one is for any other antigen. For example, bispecific antibodies specifically binding a IL-8 and neurotrophic factor, or two different types of IL-8 polypeptides are within the scope of the present invention.

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature* 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published 13 May 1993, and in Traunecker et al., *EMBO J.* 10:3655 (1991).

According to a different and more preferred approach, antibody-variable domains with the desired binding specificities (antibody-antigen combining sites) are fused to immunoglobulin constant-domain sequences. The fusion preferably is with an immunoglobulin heavy-chain constant domain, comprising at least part of the hinge, CH2, and CH3 regions. It is preferred to have the first heavy-chain constant region (CH1), containing the site necessary for light-chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the maximum yields. It is, however, possible to insert the coding sequences for two or all three polypeptide chains in one expression vector when the production of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation. For further details of generating bispecific antibodies, see, for example, Suresh et al., *Methods in Enzymology* 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676, 980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science,* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.,* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies were by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

4. Production of Humanized Anti-IL-8 6G4.2.5 Monoclonal Antibody, Antibody Fragments, and Variants The antibodies and antibody fragments of the invention can be produced using any convenient antibody manufacturing process known in the art. Typically, the antibody or antibody fragment is made using recombinant expression systems. A multiple polypeptide chain antibody or antibody fragment species can be made in a single host cell expression system wherein the host cell produces each chain of the antibody or antibody fragment and assembles the polypeptide chains into a multimeric structure to form the antibody or antibody fragment in vivo, followed by recovery of the antibody or antibody fragment from the host cell. For example, suitable recombinant expression systems for the production of complete antibody or antibody fragment are described in Lucas et al., *Nucleic Acids Res.*, 24: 1774-1779 (1996). Alternatively, the separate polypeptide chains of the desired antibody or antibody fragment can be made in separate expression host cells, separately recovered from the respective host cells, and then mixed in vitro under conditions permitting the formation of the multi-subunit antibody or antibody fragment of interest. For example, U.S. Pat. No. 4,816,567 to Cabilly et al. and Carter et al., *Bio/Technology*, 10: 163-167 (1992) provide methods for recombinant production of antibody heavy and light chains in separate expression hosts followed by assembly of antibody from separate heavy and light chains in vitro.

The following discussion of recombinant expression methods applies equally to the production of single chain antibody polypeptide species and multi-subunit antibody and antibody fragment species. All recombinant procedures for the production of antibody or antibody fragment provided below shall be understood to describe: (1) manufacture of single chain antibody species as the desired end-product; (2) manufacture of multi-subunit antibody or antibody fragment species by production of all subunits in a single host cell, subunit assembly in the host cell, optionally followed by host cell secretion of the multi-subunit end-product into the culture medium, and recovery of the multi-subunit end-product from the host cell and/or culture medium; and (3) manufacture of multi-subunit antibody or antibody fragment by production of subunits in separate host cells (optionally followed by host cell secretion of subunits into the culture medium), recovery of subunits from the respective host cells and/or culture media, followed by in vitro subunit assembly to form the multi-subunit end-product. In the case of a multi-subunit antibody or antibody fragment produced in a single host cell, it will be appreciated that production of the various subunits can be effected by expression of multiple polypeptide-encoding nucleic acid sequences carried on a single vector or by expression of polypeptide-encoding nucleic acid sequences carried on multiple vectors contained in the host cell.

A. Construction of DNA Encoding Humanized 6G4.2.5 Monoclonal Antibodies, Antibody, Fragments, and Variants Following the selection of the humanized antibody or antibody fragment of the invention according to the methods described above, the practitioner can use the genetic code to design DNAs encoding the desired antibody or antibody fragment. In one embodiment, codons preferred by the expression host cell are used in the design of a DNA encoding the antibody or antibody fragment of interest. DNA encoding the desired antibody or antibody fragment can be prepared by a variety of methods known in the art. These methods include, but are not limited to, chemical synthesis by any of the methods described in Engels et al., *Agnew. Chem. Int. Ed. Engl.* 28: 716-734 (1989), the entire disclosure of which is incorporated herein by reference, such as the triester, phosphite, phosphoramidite and H-phosphonate methods.

A variation on the above procedures contemplates the use of gene fusions, wherein the gene(s) encoding the antibody or antibody fragment is associated, in the vector, with a gene encoding another protein or a fragment of another protein. This results in the antibody or antibody fragment being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is advantageous to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., Ed., Academic, London, Vol. 4, p. 127 (1983); Uhlen, M. & Moks, T., *Methods Enzymol.* 185:129-143 (1990)). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144-161 (1990)). It has also been shown that many heterologous proteins are degraded when expressed directly in *E. coli*, but are stable when expressed as fusion proteins (Marston, F. A. O., *Biochem J.* 240:1 (1986)).

Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the antibody or antibody fragment gene(s).

Alternatively, one can employ proteolytic cleavage of fusion proteins, which has been recently reviewed (Carter, P. (1990) in *Protein Purification. From Molecular Mechanisms to Large-Scale Processes*, Ladisch, M. R., Willson, R. C., Painton, C. C., and Builder, S. E., eds., American Chemical Society Symposium Series No. 427, Ch 13, 181-193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as humanized anti-IL-8 antibody or antibody fragment. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

Various techniques are also available which may now be employed to produce variant humanized antibodies or antibody fragments, which encodes for additions, deletions, or changes in amino acid sequence of the resultant protein(s) relative to the parent humanized antibody or antibody fragment.

By way of illustration, with expression vectors encoding humanized antibody or antibody fragment in hand, site specific mutagenesis (Kunkel et al., *Methods Enzymol.* 204:125-139 (1991); Carter, P., et al., *Nucl. Acids. Res.* 13:4331 (1986); Zoller, M. J. et al., *Nucl. Acids Res.* 10:6487 (1982)), cassette mutagenesis (Wells, J. A., et al., *Gene* 34:315 (1985)), restriction selection mutagenesis (Wells, J. A., et al., *Philos. Trans*, R. Soc. London SerA 317, 415 (1986)) or other known techniques may be performed on the antibody or antibody fragment DNA. The variant DNA can then be used in place of the parent DNA by insertion into the aforementioned expression vectors. Growth of host bacteria containing the expression vectors with the mutant DNA allows the production of variant humanized antibodies or antibody fragments, which can be isolated as described herein.

B. Insertion of DNA into a Cloning Vehicle

The DNA encoding the antibody or antibody fragment is inserted into a replicable vector for further cloning (amplification of the DNA) or for expression. Many vectors are available, and selection of the appropriate vector will depend on (1) whether it is to be used for DNA amplification or for DNA expression, (2) the size of the DNA to be inserted into the vector, and (3) the host cell to be transformed with the vector. Each vector contains various components depending on its function (amplification of DNA or expression of DNA) and the host cell for which it is compatible. The vector components generally include, but are not limited to, one or more of the following: a signal sequence, an origin of replication, one or more marker genes, an enhancer element, a promoter, and a transcription termination sequence.

(i) Signal Sequence Component

In general, a signal sequence may be a component of the vector, or it may be a part of the antibody or antibody fragment DNA that is inserted into the vector. Preferably, a heterologous signal sequence selected and fused to the antibody or antibody fragment DNA such that the signal sequence in the corresponding fusion protein is recognized, transported and processed (i.e., cleaved by a signal peptidase) in the host cell's protein secretion system. In the case of prokaryotic host cells, the signal sequence is selected, for example, from the group of the alkaline phosphatase, penicillinase, lpp, or heat-stable enterotoxin II leaders. In a preferred embodiment, the STII signal sequence is used as described in the Examples below. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, or the signal described in WO 90/13646. In mammalian cell expression, mammalian signal sequences as well as viral secretory leaders, for example, the herpes simplex gD signal, are available.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2: plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using *Bacillus* species as hosts, for example, by including in the vector a DNA sequence that is homologous to a sequence found in *Bacillus* genomic DNA. Transfection of *Bacillus* with this vector results in homologous recombination with the genome and insertion of the antibody or antibody fragment DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g. ampicillin, neomycin, methotrexate, or tetracycline, (b) complement auxotrophic deficiencies, or (c) supply critical nutrients not available from complex media, e.g. the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin (Southern et al., *J. Molec. Appl. Genet.*, 1: 327 (1982)), mycophenolic acid (Mulligan et al., *Science*, 209: 1422 (1980)) or hygromycin (Sugden et al., *Mol. Cell. Biol.*, 5: 410-413 (1985)). The three examples given above employ bacterial genes under eukaryotic control to convey resistance to the appropriate drug (G418 or neomycin (geneticin), xgpt (mycophenolic acid), and hygromycin, respectively.)

Another example of suitable selectable markers for mammalian cells are those that enable the identification of cells competent to take up the antibody or antibody fragment nucleic acid, such as dihydrofolate reductase (DHFR) or thymidine kinase. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the antibody or antibody fragment. Amplification is the process by which genes in greater demand for the production of a protein critical for growth are reiterated in tandem within the chromosomes of successive generations of recombinant cells. Increased quantities of the antibody or antibody fragment are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA,* 77: 4216 (1980). The transformed cells are then exposed to increased levels of methotrexate. This leads to the synthesis of multiple copies of the DHFR gene, and, concomitantly, multiple copies of other DNA comprising the expression vectors, such as the DNA encoding the antibody or antibody fragment. This amplification technique can be used with any otherwise suitable host, e.g., ATCC No. CCL61 CHO-K1, notwithstanding the presence of endogenous DHFR if, for example, a mutant DHFR gene that is highly resistant to Mtx is employed (EP 117,060). Alternatively, host cells (particularly wild-type hosts that contain endogenous DHFR) transformed or co-transformed with DNA sequences encoding the antibody or antibody fragment, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7. Stinchcomb et al., *Nature,* 282: 39 (1979); Kingsman et al., *Gene,* 7: 141 (1979); or Tschemper et al., *Gene,* 10: 157 (1980). The trp1 gene provides a selection marker for a mutant strain of yeast lacking the ability to grow in tryptophan, for example, ATCC No. 44076 or PEP4-1. Jones, *Genetics,* 85: 12 (1977). The presence of the trp1 lesion in the yeast host cell genome then provides an effective environment for detecting transformation by growth in the absence of tryptophan. Similarly, Leu2-deficient yeast strains (ATCC 20,622 or 38,626) are complemented by known plasmids bearing the Leu2 gene.

(iv) Promoter Component

Expression vectors usually contain a promoter that is recognized by the host organism and is operably linked to the antibody or antibody fragment nucleic acid. Promoters are untranslated sequences located upstream (5') to the start codon of a structural gene (generally within about 100 to 1000 bp) that control the transcription and translation of a particular nucleic acid sequence, such as the antibody or antibody fragment encoding sequence, to which they are operably linked. Such promoters typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

Promoters suitable for use with prokaryotic hosts include the β-lactamase and lactose promoter systems (Chang et al., *Nature,* 275: 615 (1978); and Goeddel et al., *Nature,* 281: 544 (1979)), alkaline phosphatase, a tryptophan (trp) promoter system (Goeddel, *Nucleic Acids Res.,* 8: 4057 (1980) and EP 36,776) and hybrid promoters such as the tac promoter (deBoer et al., *Proc. Natl. Acad. Sci. USA,* 80: 21-25 (1983)). However, other known bacterial promoters are suitable. Their nucleotide sequences have been published, thereby enabling a skilled worker to operably ligate them to DNA encoding the antibody or antibody fragment (Siebenlist et al., *Cell,* 20: 269 (1980)) using linkers or adaptors to supply any required restriction sites. Promoters for use in bacterial systems also generally will contain a Shine-Dalgarno (S.D.) sequence operably linked to the DNA encoding the antibody or antibody fragment.

Suitable promoting sequences for use with yeast hosts include the promoters for 3-phosphoglycerate kinase (Hitzeman et al., *J. Biol. Chem.,* 255: 2073 (1980)) or other glycolytic enzymes (1-less et al., *J. Adv. Enzyme Reg.,* 7: 149 (1968); and Holland, *Biochemistry,* 17: 4900 (1978)), such as enolase, glyceraldehyde-3-phosphate dehydrogenase, hexokinase, pyruvate decarboxylase, phospho fructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

Vector driven transcription of antibody or antibody fragment encoding DNA in mammalian host cells can be controlled by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, and from heat-shock promoters, provided such promoters are compatible with the host cell systems.

The early and late promoters of the SV40 virus are conveniently obtained as an SV40 restriction fragment that also contains the SV40 viral origin of replication. Fiers et al., *Nature,* 273: 113 (1978); Mulligan and Berg, *Science,* 209: 1422-1427 (1980); Pavlakis et al., *Proc. Natl. Acad. Sci. USA,* 78: 7398-7402 (1981). The immediate early promoter of the human cytomegalovirus is conveniently obtained as a HindIII E restriction fragment. Greenaway et al., *Gene,* 18: 355-360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature,* 295: 503-508 (1982) on expressing cDNA encoding immune interferon in monkey cells, Reyes et al., *Nature,* 297: 598-601 (1982) on expression of human-interferon cDNA in mouse cells under the control of a thymidine kinase promoter from herpes simplex virus, Canaani and Berg, *Proc. Natl. Acad. Sci. USA,* 79: 5166-5170 (1982) on expression of the human interferon I gene in cultured mouse and rabbit cells, and Gorman et al., *Proc. Natl. Acad. Sci. USA,* 79: 6777-6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding antibody or antibody fragment by higher eukaryotic host cells is often increased by inserting an enhancer sequence into the vector. Enhancers are cis-acting elements of DNA, usually about from 10-300 bp, that act on a promoter to increase its transcription. Enhancers are relatively orientation and position independent having been found 5' (Laimins et al., *Proc. Natl. Acad. Sci. USA,* 78: 993 (1981)) and 3' (Lusky et al., *Mol. Cell Bio.,* 3: 1108 (1983)) to the transcription unit, within an intron (Banerji et al., *Cell,* 33: 729 (1983)) as well as within the coding sequence itself (Osborne et al., *Mol. Cell Bio.,* 4: 1293 (1984)). Many enhancer sequences are now known from mammalian genes (globin, elastase, albumin, -fetoprotein and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature,* 297: 17-18 (1982) on enhancing elements for activation of eukaryotic promoters. The enhancer may be spliced into the vector at a position 5' or 3' to the antibody or antibody fragment DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the antibody or antibody fragment. The 3' untranslated regions also include transcription termination sites.

Suitable vectors containing one or more of the above listed components and the desired coding and control sequences are constructed by standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. Coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9: 309 (1981) or by the method of Maxam et al., *Methods in Enzymology,* 65: 499 (1980).

Particularly useful in the practice of this invention are expression vectors that provide for the transient expression in mammalian cells of DNA encoding the antibody or antibody fragment. In general, transient expression involves the use of an expression vector that is able to replicate efficiently in a host cell, such that the host cell accumulates many copies of the expression vector and, in turn, synthesizes high levels of a desired polypeptide encoded by the expression vector.

Other methods, vectors, and host cells suitable for adaptation to the synthesis of the antibody or antibody fragment in recombinant vertebrate cell culture are described in Gething et al., *Nature,* 293: 620-625 (1981); Mantei et al., *Nature,* 281: 40-46 (1979); Levinson et al., EP 117,060; and EP 117,058. A particularly useful plasmid for mammalian cell culture expression of the IgE peptide antagonist is pRK5 (EP pub. no. 307,247) or pSVI6B (PCT pub. no. WO 91/08291 published 13 Jun. 1991).

C. Selection and Transformation of Host Cells

Suitable host cells for cloning or expressing the vectors herein are the prokaryote, yeast, or higher eukaryote cells described above. Suitable prokaryotes include eubacteria, such as Gram-negative or Gram-positive organisms, for example, *E. coli,* Bacilli such as *B. subtilis, Pseudomonas* species such as *P. aeruginosa, Salmonella typhimurium,* or *Serratia marcescens.* One preferred *E. coli* cloning host is *E. coli* 294 (ATCC 31,446), although other strains such as *E. coli* B, *E. coli* 1776 (ATCC 31,537), and *E. coli* W3110 (ATCC 27,325) are suitable. These examples are illustrative rather than limiting. Preferably the host cell should secrete minimal amounts of proteolytic enzymes. In a preferred embodiment, the *E. coli* strain 49D6 is used as the expression host as described in the Examples below. Review articles describing the recombinant production of antibodies in bacterial host cells include Skerra et al., *Curr. Opinion in Immunol.,* 5: 256 (1993) and Pluckthun, *Immunol. Revs.,* 130: 151 (1992).

In addition to prokaryotes, eukaryotic microbes such as filamentous fungi or yeast are suitable hosts for vectors containing antibody or antibody fragment DNA. *Saccharomyces cerevisiae,* or common baker's yeast, is the most commonly used among lower eukaryotic host microorganisms. However, a number of other genera, species, and strains are commonly available and useful herein, such as *S. pombe* (Beach and Nurse, *Nature,* 290: 140 (1981)), *Kluyveromyces lactis* (Louvencourt et al., *J. Bacteriol.,* 737 (1983)), *yarrowia* (EP 402,226), *Pichia pastoris* (EP 183,070), *Trichoderma reesia* (EP 244,234), *Neurospora crassa* (Case et al., *Proc. Natl. Acad. Sci. USA,* 76: 5259-5263 (1979)), and *Aspergillus* hosts such as *A. nidulans* (Ballance et al., *Biochem. Biophys. Res. Commun.,* 112: 284-289 (1983); Tilburn et al., *Gene,* 26: 205-221 (1983); Yelton et al., *Proc. Natl. Acad. Sci. USA,* 81: 1470-1474 (1984)) and *A. niger* (Kelly and Hynes, *EMBO J.,* 4: 475-479 (1985)).

Host cells derived from multicellular organisms can also be used in the recombinant production of antibody or antibody fragment. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* host cells have been identified. See, e.g., Luckow et al., *Bio/Technology,* 6: 47-55 (1988); Miller et al., in *Genetic Engineering,* Setlow, J. K. et al., 8: 277-279 (Plenum Publishing, 1986), and Maeda et al., *Nature,* 315: 592-594 (1985). A variety of such viral strains are publicly available, e.g., the L-1 variant of *Aulographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the antibody or antibody fragment DNA. During incubation of the plant cell culture with *A. tumefaciens*, the DNA encoding antibody or antibody fragment is transferred to the plant cell host such that it is transfected, and will, under appropriate conditions, express the antibody or antibody fragment DNA. In addition, regulatory and signal sequences compatible with plant cells are available, such as the nopaline synthase promoter and polyadenylation signal sequences. Depicker et al., *J. Mol. Appl. Gen.,* 1: 561 (1982). In addition, DNA segments isolated from the upstream region of the T-DNA 780 gene are capable of activating or increasing transcription levels of plant-expressible genes in recombinant DNA-containing plant tissue. See EP 321,196 published 21 Jun. 1989.

Vertebrate cell culture is preferred for the recombinant production of full length antibodies. The propagation of vertebrate cells in culture (tissue culture) has become a routine procedure in recent years (*Tissue Culture*, Academic Press, Kruse and Patterson, editors (1973)). Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.,* 36: 59 (1977)); baby hamster kidney cells (BHK, ATCC CCL 10); Chinese hamster ovary cells/–DHFR (CHO, Urlaub and Chasin, *Proc. Natl. Acad. Sci. USA,* 77: 4216 (1980)); mouse sertoli cells (TM4, Mather, *Biol. Reprod.,* 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.,* 383: 44-68 (1982)); MRC 5 cells; FS4 cells; and a human hepatoma cell line (Hep G2). Preferred host cells are human embryonic kidney 293 and Chinese hamster ovary cells. Myeloma cells that do not otherwise produce immunoglobulin protein are also useful host cells for the recombinant production of full length antibodies.

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with *Agrobacterium tumefaciens* is used for transformation of certain plant cells, as described by Shaw et al., *Gene,* 23: 315 (1983) and WO 89/05859 published 29 Jun. 1989. For mammalian cells without such cell walls, the calcium phosphate precipitation method described in sections 16.30-16.37 of Sambrook et al., supra, is preferred. General aspects of mammalian cell host system transformations have been described by Axel in U.S. Pat. No. 4,399,216 issued 16 Aug. 1983. Transformations into yeast are typically carried out according to the method of Van Solingen et al., *J. Bact.,* 130: 946 (1977) and Hsiao et al., *Proc. Natl. Acad. Sci.* (*USA*), 76: 3829 (1979). However, other methods for introducing DNA into cells such as by nuclear injection, electroporation, or by protoplast fusion may also be used.

D. Culturing the Host Cells

Prokaryotic cells used to produce the antibody or antibody fragment are cultured in suitable media as described generally in Sambrook et al., supra.

The mammalian host cells used to produce the antibody or antibody fragment can be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host-cells. In addition, any of the media described in Ham and Wallace, *Meth. Enz.,* 58: 44 (1979), Barnes and Sato, *Anal. Biochem.,* 102: 255 (1980), U.S. Pat. No. 4,767,704; 4,657,866; 4,927,762; or 4,560,655; WO 90/03430; WO 87/00195; U.S. Pat. Re. No. 30,985; or U.S. Pat. No. 5,122,469, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

E. Detecting Gene Amplification/Expression

Gene amplification and/or expression may be measured in a sample directly, for example, by conventional Southern blotting, northern blotting to quantitate the transcription of mRNA (Thomas, *Proc. Natl. Acad. Sci. USA,* 77: 5201-5205 (1980)), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product, where the labels are usually visually detectable, such as enzymatic labels, fluorescent labels, luminescent labels, and the like. A particularly sensitive staining technique suitable for use in the present invention is described by Hsu et al., *Am. J. Clin. Path.*, 75: 734-738 (1980).

F. Purification of the Antibody or Antibody Fragment

In the case of a host cell secretion system, the antibody or antibody fragment is recovered from the culture medium. Alternatively, the antibody can be produced intracellularly, or produced in the periplasmic space of a bacterial host cell. If the antibody is produced intracellularly, as a first step, the host cells are lysed, and the resulting particulate debris is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fe domain that is present in the antibody. Protein A can be used to purify antibodies that are based on human (1, (2, or (4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin Sepharose chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

G. Production of Antibody Fragments

Various techniques have been developed for the production of the humanized antibody fragments of the invention, including Fab, Fab', Fab'-SH, or $F(ab')_2$ fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science,* 229:81 (1985)). However, these fragments can now be produced directly by recombinant host cells. For example, Fab'-SH fragments can be directly recovered from *E. coli* and chemically coupled to form $F(ab')_2$ fragments (Carter et al., *Bio/Technology,* 10:163-167 (1992)). According to another approach, $F(ab')_2$ fragments can be isolated directly from recombinant host cell culture. Other techniques for the production of antibody fragments will be apparent to the skilled practitioner.

5. Uses of Anti-IL-8 Antibodies

A. Diagnostic Uses

For diagnostic applications requiring the detection or quantitation of IL-8, the antibodies or antibody fragments of the invention typically will be labeled with a detectable moiety. The detectable moiety can be any one which is capable of producing, either directly or indirectly, a detectable signal. For example, the detectable moiety can be a radioisotope, such as $^3H$, $^{14}C$, $^{32}P$, $^{35}S$, or $^{125}I$; a fluorescent or chemiluminescent compound, such as fluorescein isothiocyanate, rhodamine, or luciferin; radioactive isotopic labels, such as, e.g., $^{125}I$, $^{32}P$, $^{14}C$, or $^3H$; or an enzyme, such as alkaline phosphatase, beta-galactosidase, or horseradish peroxidase.

Any method known in the art for separately conjugating the antibody or antibody fragment to the detectable moiety can be employed, including those methods described by Hunter et al., *Nature* 144:945 (1962); David et al., *Biochemistry* 13:1014 (1974); Pain et al., *J. Immunol. Meth.* 40:219 (1981); and Nygren, *J. Histochem. and Cytochem.* 30:407 (1982).

The antibodies and antibody fragments of the present invention can be employed in any known assay method, such as competitive binding assays, direct and indirect sandwich assays, and immunoprecipitation assays. For example, see Zola, *Monoclonal Antibodies: A Manual of Techniques,* pp. 147-158 (CRC Press, Inc., 1987).

Competitive binding assays rely on the ability of a labeled standard (which can be a IL-8 or an immunologically reactive portion thereof) to compete with the test sample analyte (IL-8) for binding with a limited amount of antibody or antibody fragment. The amount of IL-8 in the test sample is inversely proportional to the amount of standard that becomes bound to the antibodies. To facilitate determining the amount of standard that becomes bound, the antibodies or antibody fragments generally are insolubilized before or after the competition, so that the standard and analyte that are bound to the antibodies can conveniently be separated from the standard and analyte which remain unbound.

Sandwich assays involve the use of two antibodies, each capable of binding to a different antigenic portion, or epitope, of the protein (IL-8) to be detected. In a sandwich assay, the test sample analyte is bound by a first antibody which is immobilized on a solid support, and thereafter a second antibody binds to the analyte, thus forming an insoluble three-part complex (U.S. Pat. No. 4,376,110). The second antibody can itself be labeled with a detectable moiety (direct sandwich assays) or can be measured using an anti-immunoglobulin antibody that is labeled with a detectable moiety (indirect sandwich assay). For example, one type of sandwich assay is an ELISA assay, in which case the detectable moiety is an enzyme (e.g., horseradish peroxidase).

IL-8 antibodies and antibody fragments also are useful for the affinity purification of IL-8 from recombinant cell culture or natural sources. For example, these antibodies can be fixed to a solid support by techniques well known in the art so as to purify IL-8 from a source such as culture supernatant or tissue.

B. Therapeutic Compositions and Administration of Anti-IL-8 Antibody

The humanized anti-IL-8 antibodies and antibody fragments of the invention are useful in the treatment of inflammatory disorders, including inflammations of the lung, such as adult respiratory distress syndrome (ARDS) and any stage of acute lung injury in the pathogenesis of ARDS described in Bernard et al., *Am. J. Respir. Crit. Care Med.*, 149: 818-824 (1994), bacterial pneumonia, hypovolemic shock, ischemic reperfusion disorders such as surgical tissue reperfusion injury, myocardial ischemic conditions such as myocardial infarction, reperfusion after cardiac surgery, cardiac arrest, and constriction after percutaneous transluminal coronary angioplasty, inflammatory bowel disorders such is ulcerative colitis, and autoimmune diseases such as rheumatoid arthritis. In addition, the humanized anti-IL-8 antibodies and antibody fragments of the invention are useful in the treatment of asthmatic diseases, such as allergic asthma.

Therapeutic formulations of the humanized anti-IL-8 antibodies and antibody fragments are prepared for storage by mixing the antibody or antibody fragment having the desired degree of purity with optional physiologically acceptable carriers, excipients, or stabilizers (*Remington's Pharmaceutical Sciences*, supra), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween. Pluronics or polyethylene glycol (PEG).

The humanized anti-IL-8 mAb or antibody fragment to be used for in vivo administration must be sterile. This is readily accomplished by filtration through sterile filtration membranes, prior to or following lyophilization and reconstitution. The humanized anti-IL-8 mAb or antibody fragment ordinarily will be stored in lyophilized form or in solution.

Therapeutic humanized anti-IL-8 mAb or antibody fragment compositions generally are placed into a container having a sterile access port, for example, an intravenous solution bag or vial having a stopper pierceable by a hypodermic injection needle.

The route of humanized anti-IL-8 mAb or antibody fragment administration is in accord with known methods, e.g., inhalation, injection or infusion by intravenous, intraperitoneal, intracerebral, intramuscular, intraocular, intraarterial, or intralesional routes, by enema or suppository, or by sustained release systems as noted below. Preferably the antibody is given systemically or at a site of inflammation.

In one embodiment, the invention provides for the treatment of asthmatic diseases by administration of humanized anti-IL-8 mAb or antibody fragment to the respiratory tract. The invention contemplates formulations comprising humanized anti-IL-8 mAb or antibody fragment for use in a wide variety of devices that are designed for the delivery of pharmaceutical compositions and therapeutic formulations to the respiratory tract. In one aspect, humanized anti-IL-8 mAb or antibody fragment is administered in aerosolized or inhaled form. The humanized anti-IL-8 mAb or antibody fragment, combined with a dispersing agent, or dispersant, can be administered in an aerosol formulation as a dry powder or in a solution or suspension with a diluent.

Suitable dispersing agents are well known in the art, and include but are not limited to surfactants and the like. Surfactants are generally used in the art to reduce surface induced aggregation of protein caused by atomization of the solution forming the liquid aerosol. Examples of such surfactants include polyoxyethylene fatty acid esters and alcohols, and polyexyethylene sorbitan fatty acid esters. Amounts of surfactants used will vary, being generally within the range of about 0.001 to 4% by weight of the formulation. In a specific aspect, the surfactant is polyoxyethylene sorbitan monooleate or sorbitan trioleate.

Liquid aerosol formulations contain the humanized anti-IL-8 mAb or antibody fragment and a dispersing agent in a physiologically acceptable diluent. The dry powder formulations of the invention consist of a finely divided solid form of the humanized anti-IL-8 mAb or antibody fragment and a dispersing agent, and optionally a bulking agent, such as lactose, sorbitol, sucrose, or mannotil, and the like, to facilitate dispersal of the powder. With either the liquid or dry powder aerosol formulation, the formulations must be aerosolized. It must be broken down into liquid or solid particles in order to ensure that the aerosolized dose actually reaches the bronchii and/or alveoli, as desired. For example, in the methods for treatment of asthma provided herein, it is preferable to deliver aerosolized humanized anti-IL-8 mAb or antibody fragment to the bronchii. In other embodiments, such as the present methods for treating ARDS and any stage of acute lung injury in the pathogenesis of ARDS, it is preferable to deliver aerosolized humanized anti-IL-8 mAb or antibody fragment to the alveoli. In general, the mass median dynamic diameter will be 5 micrometers (:m) or less to ensure that the drug particles reach the lung bronchii or alveoli (Wearly, L. L., 1991, Crit. Rev. in Ther. Drug Carrier Systems, 8:333).

With regard to construction of the delivery device, any form of aerosolization known in the art, including but not limited to nebulization, atomization or pump aerosolization of a liquid formulation, and aerosolization of a dry powder formulation, can be used in the practice of the invention. A delivery device that is uniquely designed for administration of solid formulations is envisioned. Often, the aerosolization of a liquid or a dry powder formulation will require a propellent. The propellent can be any propellent generally used in the art. Examples of useful propellants include chlorofluorocarbons, hydrofluorocarbons, hydrochlorofluorocarbons, and hydrocarbons, including trifluoromethane, dichlorofluoromethane, dichlorotetrafluoroethanol, and 1,1,1,2-tetrafluoroethane, and combinations thereof.

In a preferred aspect of the invention, the device for aerosolization is a metered dose inhaler. A metered dose inhaler provides a specific dosage when administered, rather than a variable dose depending on administration. Such a metered dose inhaler can be used with either a liquid or a dry powder aerosol formulation.

Systems of aerosol delivery, such as the pressurized metered dose inhaler and the dry powder inhaler are disclosed in Newman, S. P., *Aerosols and the Lung*, Clarke, S. W. and Davia, D. editors, pp. 197-22 and can be used in connection with the present invention.

Sustained release systems can be used in the practice of the methods of the invention. Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman et al., *Biopolymers* 22:547 (1983)), poly(2-hydroxyethyl-methacrylate) (Langer et al., *J. Biomed. Mater. Res.* 15:167 (1981) and Langer, *Chem. Tech.* 12:98 (1982)), ethylene vinyl acetate (Langer et al., supra) or poly-D-(−)-3-hydroxybutyric acid (EP 133,988). Sustained-release humanized anti-IL-8 antibody or antibody fragment compositions also include liposomally entrapped antibody or antibody fragment. Liposomes containing an antibody or antibody fragment are prepared by methods known per se: DE 3,218, 121; Epstein et al., *Proc. Natl. Acad. Sci. U.S.A.* 82:3688 (1985); Hwang et al., *Proc. Natl. Acad. Sci. U.S.A.* 77:4030 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the liposomes are of the small (about 200-800 Angstroms) unilamelar type in which the lipid content is greater than about 30 mole percent cholesterol, the selected proportion being adjusted for the most efficacious antibody or antibody fragment therapy.

An "effective amount" of the humanized anti-IL-8 antibody or antibody fragment to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer the humanized anti-IL-8 antibody or antibody fragment until a dosage is reached that achieves the desired effect. The progress of this therapy is easily monitored by conventional assays.

In the treatment and prevention of an inflammatory disorder or asthmatic disorder with a humanized anti-IL-8 antibody or antibody fragment of the invention, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the inflammatory disorder, including treating acute or chronic respiratory diseases and reducing inflammatory responses. Such amount is preferably below the amount that is toxic to the host or renders the host significantly more susceptible to infections.

As a general proposition, the initial pharmaceutically effective amount of the antibody or antibody fragment administered parenterally per dose will be in the range of about 0.1 to 50 mg/kg of patient body weight per day, with the typical initial range of antibody used being 0.3 to 20 mg/kg/day, more preferably 0.3 to 15 mg/kg/day.

In one embodiment, using systemic administration, the initial pharmaceutically effective amount will be in the range of about 2 to 5 mg/kg/day.

For methods of the invention using administration by inhalation, the initial pharmaceutically effective amount will be in the range of about 1 microgram (:g)/kg/day to 100 mg/kg/day.

The invention provides for both prophylactic and therapeutic treatment of inflammatory disorders. Without intending to limit the methods of the invention to a particular mechanism of action or a particular disease intervention strategy, it is noted that in some indications it is beneficial to treat the disease in question prior to or early on in the stage of the underlying disease that involves neutrophil activation, recruitment and infiltration at sites of inflammation. Accordingly, it may be advantageous to utilize the humanized anti-IL-8 mAb or antibody fragment in a prophylactic treatment regimen for an inflammatory disease indication in order to attenuate or eliminate a pathogenic neutrophil response that may or will arise during the course of the disease.

In patients at risk of developing acute lung injury with possible or likely progression to ARDS, it is desirable to employ a prophylactic course of treatment in order to ameliorate or prevent the deterioration of lung function and the pathogenesis of associated disease sequelae (which may greatly increase patient morbidity and mortality) prior to the onset of such conditions. Certain biological parameters, such as IL-8 levels in bronchial alveolar lavage (BAL) fluid and ferritin levels in serum, can be used for prognosis of acute lung injury and ARDS in patients who are predisposed to such disease progression, i.e. patients suffering from diseases or other insults that commonly precipitate acute lung injury and ARDS, such as aspiration, diffuse pulmonary infection, near-drowning, toxic inhalation, lung contusion, multiple trauma, pancreatitis, perforated bowel, sepsis, and the like. In one embodiment, acute lung injury and ARDS at-risk patients presenting BAL fluid IL-8 concentrations of at or above 0.2 ng/ml are selected for prophylactic treatment according to the methods of the invention. Any suitable method for assay of IL-8 in patient BAL fluid may be employed, such as the method described in Donnelly et al., *Lancet*, 341: 643-647 (1993).

In another embodiment, acute lung injury/ARDS at-risk female and male patients presenting ferritin serum concentrations of at or above 270 ng/ml and 680 ng/ml, respectively, are selected for prophylactic treatment according to the methods of the invention. Any suitable method for assay of ferritin in patient serum may be employed, such as the method described in U.S. Pat. No. 5,679,532 for "Serum Ferritin as a Predictor of the Acute Respiratory Distress Syndrome" to Repine issued on Oct. 21, 1997.

In patients presenting ischemic conditions or undergoing surgical procedures that generate ischemic conditions in tissue and concomitant risk of tissue injury upon reperfusion, it is desirable to employ a course of treatment wherein the humanized anti-IL-8 mAb or antibody fragment is administered to the patient prior to the reperfusion of ischemic tissue, or prior to or as soon as possible after the onset of an inflammatory response following reperfusion of ischemic tissue. In the patients presenting acute myocardial infarction, for example, it is advantageous to employ a course of treatment wherein the humanized anti-IL-8 mAb or antibody fragment is administered to the patient prior to or concomitant with recanalization therapy, including pharmaceutical recanalization therapies such as the administration of tissue plasminogen activators, streptokinase, or other thrombolytic drugs with or without anti-clotting agents such as platelet-fibrin binding antagonists (e.g. anti-IIbIIa integrin antibody), blood thinning agents such as heparin, or other anti-reocclusion agents such as aspirin, and the like, and including mechanical recanalization therapies such as percutaneous transluminal coronary angioplasty, or wherein the humanized anti-IL-8 mAb or antibody fragment is administered to the patient prior to or as soon as possible after the onset of an inflammatory response following reperfusion of ischemic myocardium. In yet another embodiment, the humanized anti-IL-8 mAb or antibody fragment of the invention can be employed in the methods of treating acute myocardial infarction with anti-IL-8 antibody described in WO 97/40215 published Oct. 30, 1997.

The invention provides for both prophylactic and therapeutic treatment of asthma with humanized anti-IL-8 mAb and antibody fragment. In the case of prophylactic treatment for allergic asthma with the antibodies or antibody fragments of the invention, it is desirable to administer about 0.1 to 10 mg/kg of the antibody agent to the patient up to about 24 hours prior to anticipated exposure to allergen or prior to onset of allergic asthma. In the case of therapeutic treatment for acute asthma, including allergic asthma, it is desirable to treat the asthmatic patient as early as possible following onset of an asthma attack. In one embodiment, an episode of acute asthma is treated within 24 hours of the onset of symptoms by administration of about 0.1 to 10 mg/kg of an anti-IL-8 antibody agent. However, it will be appreciated that the methods of the invention can be used to ameliorate symptoms at any point in the pathogenesis of asthmatic disease. Additionally, the methods of the invention can be used to alleviate symptoms of chronic asthmatic conditions.

The antibody or antibody fragment need not be, but is optionally formulated with one or more agents currently used to prevent or treat the inflammatory disorder or asthmatic disease in question. For example, in rheumatoid arthritis, the antibody can be given in conjunction with a glucocorticosteroid. In the case of treating asthmatic diseases with anti-IL-8 antibody or antibody fragment, the invention contemplates the coadministration of antibody or antibody fragment and one or more additional agents useful in treating asthma, such as bronchodilators, antihistamines, epinephrine, and the like. The effective amount of such other agents depends on the amount of antibody or antibody fragment present in the formulation, the type of disorder or treatment, and other factors discussed above. These are generally used in the same dosages and with administration routes as used hereinbefore or about from 1 to 99% of the heretofore employed dosages.

The following examples are offered by way of illustration and not by way of limitation. The disclosures of all references cited in the specification, and the disclosures of all citations in such references, are expressly incorporated herein by reference.

EXAMPLES

A. Generation and Characterization of Monoclonal Antibodies Against Human IL-8

Balb/c mice were immunized in each hind footpad or intraperitoneally with 10:g of recombinant human IL-8 (produced as a fusion of (ser-IL-8)$_{72}$ with ubiquitin (Hebert et al. *J. Immunology* 145:3033-3040 (1990)); IL-8 is available commercially from PeproTech, Inc., Rocky Hill, N.J.) resuspended in MPL/TDM (Ribi Immunochem. Research Inc., Hamilton, Mont.) and boosted twice with the same amount of IL-8. In these experiments, "IL-8" is intended to mean (ser-IL-8)$_{72}$ unless otherwise specified. A final boost of 10 µg of IL-8 was given 3 days before the fusion. Spleen cells or popliteal lymph node cells were fused with mouse myeloma P3X63Ag8U.1 (ATCC CRL1597), a non-secreting clone of the myeloma P3X63Ag8, using 35% polyethylene glycol as described before. Ten days after the fusion, culture supernatant was screened for the presence of monoclonal antibodies to IL-8 by ELISA.

The ELISA was performed as follows. Nunc 96-well immunoplates (Flow Lab, McLean, Va.) were coated with 50 µl/well of 2 µg/ml IL-8 in phosphate-buffered saline (PBS) overnight at 4° C. The remaining steps were carried out at room temperature. Nonspecific binding sites were blocked with 0.5% bovine serum albumin (BSA) for 1 hour (hr). Plates were then incubated with 50:l/well of hybridoma culture supernatants from 672 growing parental fusion wells for 1 hr, followed by the incubation with 50 µl/well of 1:1000 dilution of a 1 mg/ml stock solution of alkaline phosphatase-conjugated goat anti-mouse Ig (Tago Co., Foster City, Calif.) for 1 hr. The level of enzyme-linked antibody bound to the plate was determined by the addition of 100:µ/well of 0.5 mg/ml of r-nitrophenyl phosphate in sodium bicarbonate buffer, pH 9.6. The color reaction was measured at 405 nm with an ELISA plate reader (Titertrek Multiscan, Flow Lab, McLean, Va.). Between each step, plates were washed three times in PBS containing 0.05% Tween 20.

Culture supernatants which promoted 4-fold more binding of IL-8 than did control medium were selected as positives. According to this criterion, 16 of 672 growing parental fusion wells (2%) were positive. These positive hybridoma cell lines were cloned at least twice by using the limiting dilution technique.

Seven of the positive hybridomas were further characterized as follows. The isotypes of the monoclonal antibodies were determined by coating Nunc 96-well immunoplates (Flow Lab, McLean, Va.) with IL-8 overnight, blocking with BSA, incubating with culture supernatants followed by the addition of predetermined amount of isotype-specific alkaline phosphatase-conjugated goat anti-mouse Ig (Fisher Biotech, Pittsburgh, Pa.). The level of conjugated antibodies bound to the plate was determined by the addition of r-nitrophenyl phosphate as described above.

All the monoclonal antibodies tested belonged to either IgG$_1$ or IgG$_2$ immunoglobulin isotype. Ascites fluid containing these monoclonal antibodies had antibody titers in the range of 10,000 to 100,000 as determined by the reciprocal of the dilution factor which gave 50% of the maximum binding in the ELISA.

To assess whether these monoclonal antibodies bound to the same epitopes, a competitive binding ELISA was performed. At a ratio of biotinylated mAb to unlabeled mAb of 1:100, the binding of biotinylated mAb 5.12.14 was significantly inhibited by its homologous mAb but not by mAb 4.1.3, while the binding of biotinylated mAb 4.1.3 was inhibited by mAb 4.1.3 but not by mAb 5.12.14. Monoclonal antibody 5.2.3 behaved similarly to mAb 4.1.3, while monoclonal antibodies 4.8 and 12.3.9 were similar to mAb 5.12.14. Thus, mAb 4.1.3 and mAb 5.2.3 bind to a different epitope(s) than the epitope recognized by monoclonal antibodies 12.3.9, 4.8 and 5.12.14.

Immunodot blot analysis was performed to assess antibody reactivity to IL-8 immobilized on nitrocellulose paper. All seven antibodies recognized IL-8 immobilized on paper, whereas a control mouse IgG antibody did not.

The ability of these monoclonal antibodies to capture soluble $^{125}$I-IL-8 was assessed by a radioimmune precipitation test (RIP). Briefly, tracer $^{125}$I-IL-8 (4×10$^4$ cpm) was incubated with various dilutions of the monoclonal anti-IL-8 antibodies in 0.2 ml of PBS containing 0.5% BSA and 0.05% Tween 20 (assay buffer) for 1 hr at room temperature. One hundred microliters of a predetermined concentration of goat anti-mouse Ig antisera (Pel-Freez, Rogers, Ark.) were added and the mixture was incubated at room temperature for 1 hr. Immune complexes were precipitated by the addition of 0.5 ml of 6% polyethylene glycol (M.W. 8000) kept at 4° C. After centrifugation at 2,000×g for 20 min at 4° C., the supernatant was removed by aspiration and the radioactivity remaining in the pellet was counted in a gamma counter. Percent specific binding was calculated as (precipitated cpm−background cpm)/(total cpm−background cpm). Monoclonal antibodies 4.1.3, 5.2.3, 4.8, 5.12.14 and 12.3.9 captured $^{125}$I-IL-8 very efficiently, while antibodies 9.2.4 and 8.9.1 were not able to capture soluble $^{125}$I-IL-8 in the RIP even though they could bind to IL-8 coated onto ELISA plates (Table 1).

The dissociation constants of these monoclonal antibodies were determined using a competitive binding RIP assay. Briefly, competitive inhibition of the binding each antibody to $^{125}$I-IL-8 (20,000-40,000 cpm per assay) by various amounts of unlabeled IL-8 was determined by the RIP described above. The dissociation constant (affinity) of each mAb was determined by using Scatchard plot analysis (Munson, et al., *Anal. Biochem.* 107:220 (1980)) as provided in the VersaTerm-PRO computer program (Synergy Software, Reading, Pa.). The $K_d$'s of these monoclonal antibodies (with the exception of 9.2.4. and 8.9.1) were in the range from $2 \times 10^{-8}$ to $3 \times 10^{-10}$ M. Monoclonal antibody 5.12.14 with a $K_d$ of $3 \times 10^{-10}$ M showed the highest affinity among all the monoclonal antibodies tested (Table 3).

TABLE 3

Characterization of Anti-IL-8 Monoclonal Antibodies

| Antibody | % Specific Binding to IL-8 | $K_d$ (M) | Isotype | pI |
|---|---|---|---|---|
| 4.1.3 | 58 | $2 \times 10^{-9}$ | IgG$_1$ | 4.3-6.1 |
| 5.2.3 | 34 | $2 \times 10^{-8}$ | IgG$_1$ | 5.2-5.6 |
| 9.2.4 | 1 | — | IgG$_1$ | 7.0-7.5 |
| 8.9.1 | 2 | — | IgG$_1$ | 6.8-7.6 |
| 4.8 | 62 | $3 \times 10^{-8}$ | IgG$_{2a}$ | 6.1-7.1 |
| 5.12.14 | 98 | $3 \times 10^{-10}$ | IgG$_{2a}$ | 6.2-7.4 |
| 12.3.9 | 86 | $2 \times 10^{-9}$ | IgG$_{2a}$ | 6.5-7.1 |

To assess the ability of these monoclonal antibodies to neutralize IL-8 activity, the amount of $^{125}$I-IL-8 bound to human neutrophils in the presence of various amounts of culture supernatants and purified monoclonal antibodies was measured. Neutrophils were prepared by using Mono-Poly Resolving Medium (M-PRM) (Flow Lab. Inc., McLean, Va.). Briefly fresh, heparinized human blood was loaded onto M-PRM at a ratio of blood to medium, 3.5:3.0, and centrifuged at 300×g for 30 min at room temperature. Neutrophils enriched at the middle layer were collected and washed once in PBS. Such a preparation routinely contained greater than 95% neutrophils according to the Wright's Giemsa staining. The receptor binding assay was done as follows. 50:1 of $^{125}$I-IL-8 (5 ng/ml) was incubated with 50:1 of unlabeled IL-8 (100:g/ml) or monoclonal antibodies in PBS containing 0.1% BSA for 30 min at room temperature. The mixture was then incubated with 100:1 of neutrophils ($10^7$ cells/ml) for 15 min at 37° C. The $^{125}$I-IL-8 bound was separated from the unbound material by loading mixtures onto 0.4 ml of PBS containing 20% sucrose and 0.1% BSA and by centrifugation at 300×g for 15 min. The supernatant was removed by aspiration and the radioactivity associated with the pellet was counted in a gamma counter.

Monoclonal antibodies 4.1.3, 5.2.3, 4.8, 5.12.14, and 12.3.9 inhibited greater than 85% of the binding of IL-8 to human neutrophils at a 1:25 molar ratio of IL-8 to mAb. On the other hand, monoclonal antibodies 9.2.4 and 8.9.1 appeared to enhance the binding of IL-8 to its receptors on human neutrophils. Since a control mouse IgG also enhanced the binding of IL-8 on neutrophils, the enhancement of IL-8 binding to its receptors by mAb 9.2.4 and 8.9.1 appears to be nonspecific. Thus, monoclonal antibodies, 4.1.3, 5.1.3, 4.8, 5.12.14, and 12.3.9 are potential neutralizing monoclonal antibodies while monoclonal antibodies 8.9.1 and 9.2.4 are non-neutralizing monoclonal antibodies.

The ability of the anti-IL-8 antibodies to block neutrophil chemotaxis induced by IL-8 was tested as follows. Neutrophil chemotaxis induced by IL-8 was determined using a Boyden chamber method (Larsen, et al. *Science* 243:1464 (1989)). One hundred μl of human neutrophils ($10^6$ cells/ml) resuspended in RPMI containing 0.1% BSA were placed in the upper chamber and 29 μl of the IL-8 (20 nM) with or without monoclonal antibodies were placed in the lower chamber. Cells were incubated for 1 hr at 37° C. Neutrophils migrated into the lower chamber were stained with Wright's Giemsa stain and counted under the microscope (100× magnification). Approximately 10 different fields per experimental group were examined. Neutralizing monoclonal antibodies 5.12.14 and 4.1.3 blocked almost 70% of the neutrophil chemotactic activity of IL-8 at 1:10 ratio of IL-8 to mAb.

The isoelectric focusing (IEF) pattern of each mAb was determined by applying purified antibodies on an IEF polyacrylamide gel (pH 3-9, Pharmacia) using the Fast gel system (Pharmacia, Piscataway, N.J.). The IEF gel was pretreated with pharmalyte containing 1% Triton X100 (Sigma, St. Louis, Mo.) for 10 min before loading the samples. The IEF pattern was visualized by silver staining according to the instructions from the manufacturer. All of the monoclonal antibodies had different IEF patterns, confirming that they originated from different clones. The pI values for the antibodies are listed in Table 3.

All these monoclonal antibodies bound equally well to both (ala-IL-8)77 and (ser-IL-8)72 forms of IL-8. Because IL-8 has greater than 30% sequence homology with certain other members of the platelet factor 4 (PF4) family of inflammatory cytokines such as ∃-TG (Van Damme et al., *Eur. J. Biochem.* 181:337 (1989); Tanaka et al., *FEB* 236(2):467 (1988)) and PF4 (Deuel et al., *Proc. Natl. Acad. Sci. U.S.A.* 74:2256 (1977)), they were tested for possible cross reactivity to β-TG and PF4, as well as to another neutrophil activating factor, C5a. No detectable binding to any of these proteins was observed, with the exception of mAb 4.1.3, which had a slight cross reactivity to β-TG.

One of the antibodies, mAb 5.12.14, was further studied to determine whether it could block the IL-8 mediated release of elastase by neutrophils. Briefly, human neutrophils were resuspended in Hanks balanced salt solution (Gibco, Grand Island, N.Y.) containing 1.0% BSA, Fraction V (Sigma, St. Louis, Mo.), 2 mg/ml alpha-D-glucose (Sigma), 4.2 mM sodium bicarbonate (Sigma) and 0.01 M HEPES, pH 7.1 (JRH Bioscience, Lenexa, Kans.). A stock of cytochalasin B (Sigma) was prepared (5 mg/ml in dimethylsulfoxide (Sigma) and stored at 2-8° C. Cytochalasin B was added to the neutrophil preparation to produce a final concentration of 5:g/ml, and incubated for 15 min at 37° C. Human IL-8 was incubated with mAb 5.12.14 (20:1), or a negative control antibody, in 1 ml polypropylene tubes (DBM Scientific, San Fernando, Calif.) for 30 min at 37° C. The final assay concentrations of IL-8 were 50 and 500 nM. The monoclonal antibodies were diluted to produce the following ratios (IL-8:Mab): 1:50, 1:10, 1:2, 1:1, and 1:0.25. Cytochalasin B-treated neutrophils were added (100 μl/tube) and incubated for 2 hours at 25° C. The tubes were centrifuged (210×g, 2-8° C.) for 10 min, and supernatants were transferred to 96 well tissue culture plates (30 μl/well). Elastase substrate stock, 10 mM methoxysuccinyl-alanyl-alanyl-propyl-valyl-p-nitroanilide (Calbiochem, La Jolla, Calif.) in DMSO was prepared and stored at 2-8° C. Elastase substrate solution (1.2 mM substrate, 1.2 M NaCl (Mallinckrodt, Paris, Ky.), 0.12 M HEPES pH 7.2 in distilled water) was added (170:l/well) to the supernatants and incubated for 0.5 to 2 hours at 37° C. (until control O.D. of 1.0 was reached). Absorbance was measured at 405 nm (SLT 340 ATTC plate reader, SLT Lab Instruments, Austria).

The results are shown in FIG. 1. At a 1:1 ratio of IL-8 to mAb 5.12.14, the antibody was able to effectively block the release of elastase from neutrophils.

The hybridoma producing antibody 5.12.14 was deposited on Feb. 15, 1993 with the American Type Culture Collection, 12301 Parklawn Drive, Rockville, Md., U.S.A. (ATCC) and assigned ATTC Accession No. HB 11553.

B. Generation and Characterization of Monoclonal Antibodies Against Rabbit IL-8

Antibodies against rabbit IL-8 were generated in essentially the same process as anti-human IL-8 antibodies using rabbit IL-8 as immunogen (kindly provided by C. Broaddus; see also Yoshimura et al. *J. Immunol.* 146:3483 (1991)). The antibody was characterized as described above for binding to other cytokines coated onto ELISA plates; no measurable binding was found to MGSA, fMLP, C5a, b-TG, TNF, PF4, or IL-1.

The hybridoma producing antibody 6G4.2.5 was deposited on Sep. 28, 1994, with the American Type Culture Collection, 12301 Parklawn Drive, Rockville, Md., U.S.A. (ATCC) and assigned ATTC Accession No. HB 11722.

Recombinant human-murine chimeric Fabs for 5.12.14 and 6G4.2.5 were constructed as described below. A chimeric 6G.4.25 Fab is compared with a chimeric 5.12.14 Fab in detail below.

1. Inhibition of IL-8 Binding to Human Neutrophils by 5.12.14-Fab and 6G4 2.5-Fab The ability of the two chimeric Fabs, 5.12.14-Fab and 6G4.2.5-Fab, to efficiently bind IL-8 and prevent IL-8 from binding to IL-8 receptors on human neutrophils was determined by performing a competition binding assay which allows the calculation of the $IC_{50}$— concentration required to achieve 50% inhibition of IL-8 binding.

Figure 3:
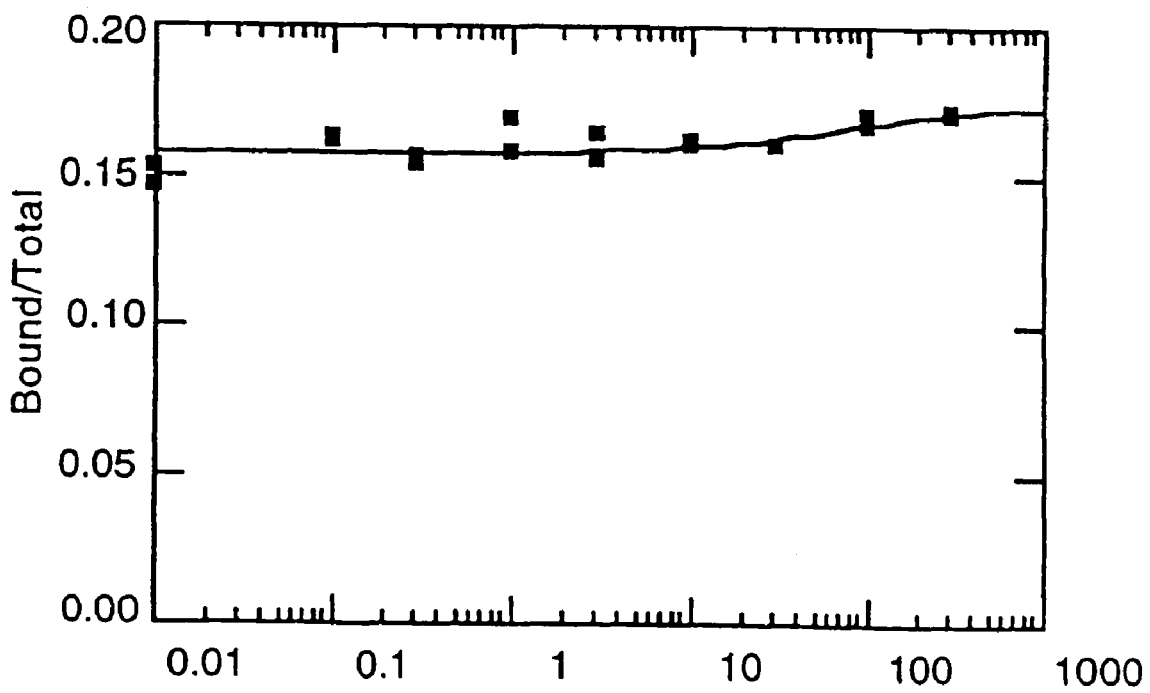
FIG. 3 demonstrates that a isotype matched negative control Fab (denoted as "4D5 Fab") does not inhibit the binding of $^{125}$I-IL-8 to human neutrophils.
Figure 4:
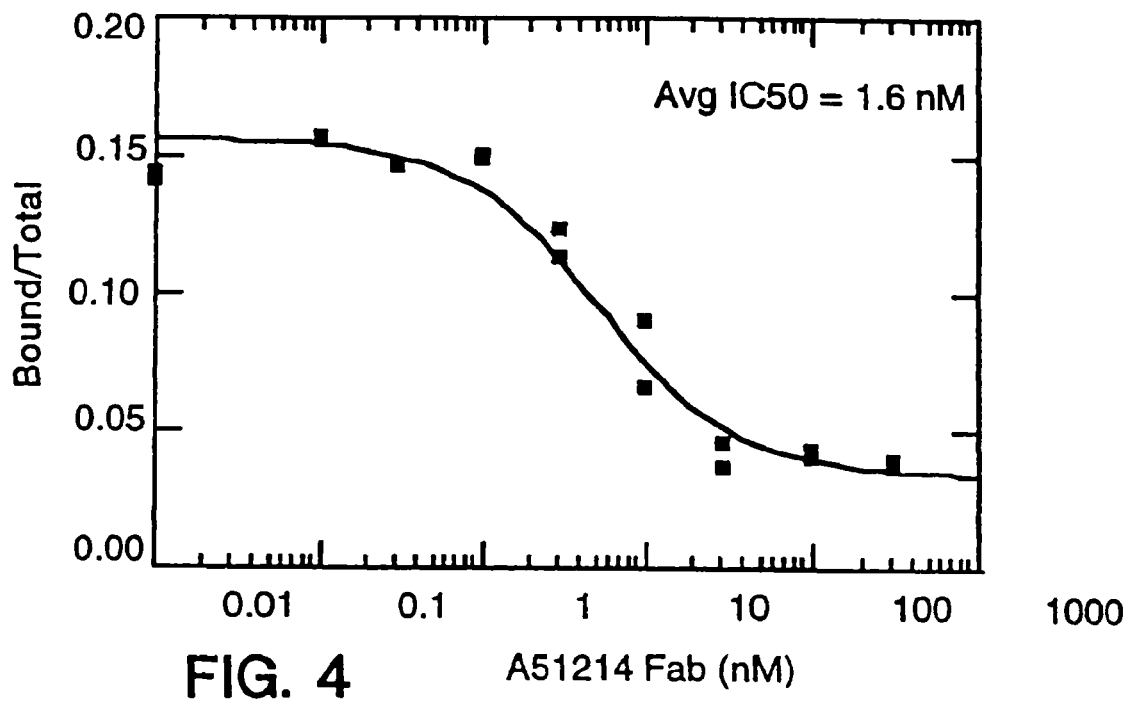
FIG. 4 is a graph depicting the inhibition of binding of $^{125}$I-IL-8 to human neutrophils by chimeric 5.12.14 Fab with an average $IC_{50}$ of 1.6 nM.
Figure 5:
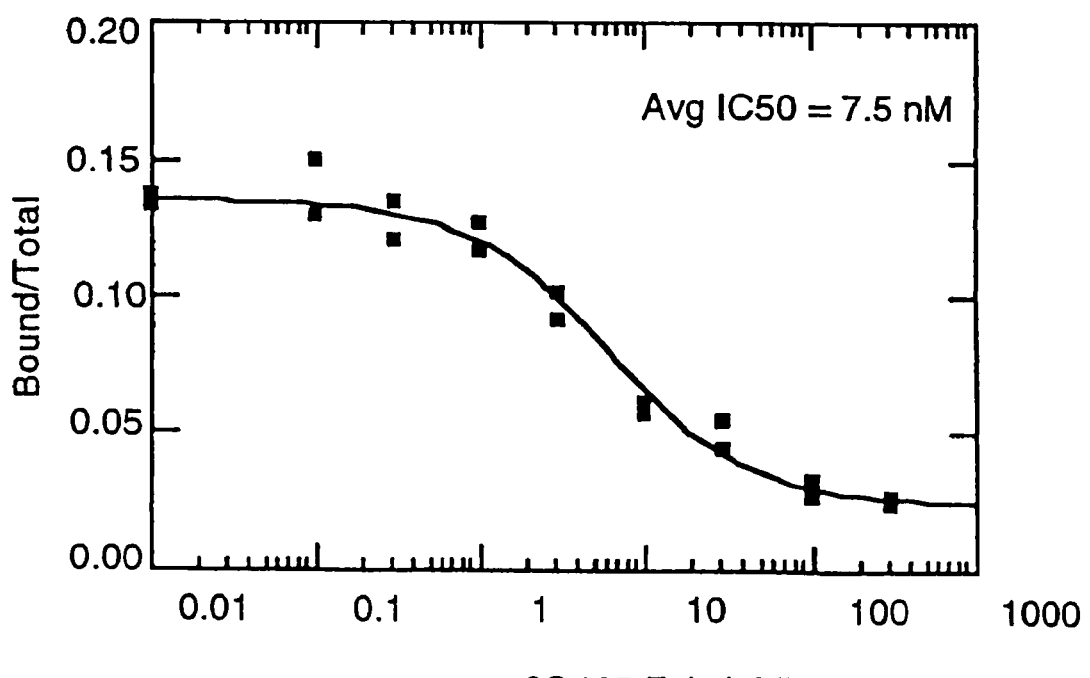
FIG. 5 is a graph depicting the inhibition of binding of $^{125}$I-IL-8 to human neutrophils by chimeric 6G.4.25 Fab with an average $IC_{50}$ of 7.5 nM.

Human neutrophils ($5\times10^5$) were incubated for 1 hour at 4° C. with 0.5 nM $^{125}$I-IL-8 in the presence of various concentrations (0 to 300 nM) of 5.12.14-Fab, 6G4.2.5-Fab, an isotype control (4D5-Fab) or unlabeled IL-8. After the incubation, the unbound $^{125}$I-IL-8 was removed by centrifugation through a solution of 20% sucrose and 0.1% bovine serum albumin in phosphate buffered saline and the amount of $^{125}$I-IL-8 bound to the cells was determined by counting the cell pellets in a gamma counter. FIG. 2 demonstrates the inhibition of $^{125}$I-IL-8 binding to neutrophils by unlabeled IL-8. FIG. 3 demonstrates that a negative isotype matched Fab does not inhibit the binding of $^{125}$I-IL-8 to human neutrophils. Both the anti-IL-8 Fabs, 5.12.14 Fab (FIG. 4) and 6G.4.25 Fab (FIG. 5) were able to inhibit the binding of $^{125}$I-IL-8 to human neutrophils with an average $IC_{50}$ of 1.6 nM and 7.5 nM, respectively.

2. Inhibition of IL-8-Mediated Neutrophil Chemotaxis by 5.12.14-Fab and 6G4.2.5-Fab Human neutrophils were isolated, counted and resuspended at $5\times10^6$ cells/ml in Hank's balanced salt solution (abbreviated HBSS; without calcium and magnesium) with 0.1% bovine serum albumin. The neutrophils were labeled by adding calcein AM (Molecular Probe, Eugene, Oreg.) at a final concentration of 2.0 µM. Following a 30 minute incubation at 37° C., cells were washed twice with HBSS-BSA and resuspended at $5\times10^6$ cells/ml.

Chemotaxis experiments were carried out in a Neuro Probe (Cabin John, Md.) 96-well chamber, model MBB96. Experimental samples (buffer only control, IL-8 alone or IL-8+ Fabs) were loaded in a Polyfiltronics 96-well View plate (Neuro Probe Inc.) placed in the lower chamber. 100 µl of the calcein AM-labeled neutrophils were added to the upper chambers and allowed to migrate through a 5 micrometer porosity PVP free polycarbonate framed filter (Neuro Probe Inc.) toward the bottom chamber sample. The chemotaxis apparatus was then incubated for 40 to 60 minutes at 37° C. with 5% $CO_2$. At the end of the incubation, neutrophils remaining in the upper chamber were aspirated and upper chambers were washed three times with PBS. Then the polycarbonate filter was removed, non-migrating cells were wiped off with a squeegee wetted with PBS, and the filter was air dried for 15 minutes.

The relative number of neutrophils migrating through the filter (Neutrophil migration index) was determined by measuring fluorescence intensity of the filter and the fluorescence intensity of the contents of the lower chamber and adding the two values together. Fluorescence intensity was measured with a CytoFluor 2300 fluorescent plate reader (Millipore Corp. Bedford, Mass.) configured to read a Corning 96-well plate using the 485-20 nm excitation filter and a 530-25 emission filter, with the sensitivity set at 3.

Figure 6:
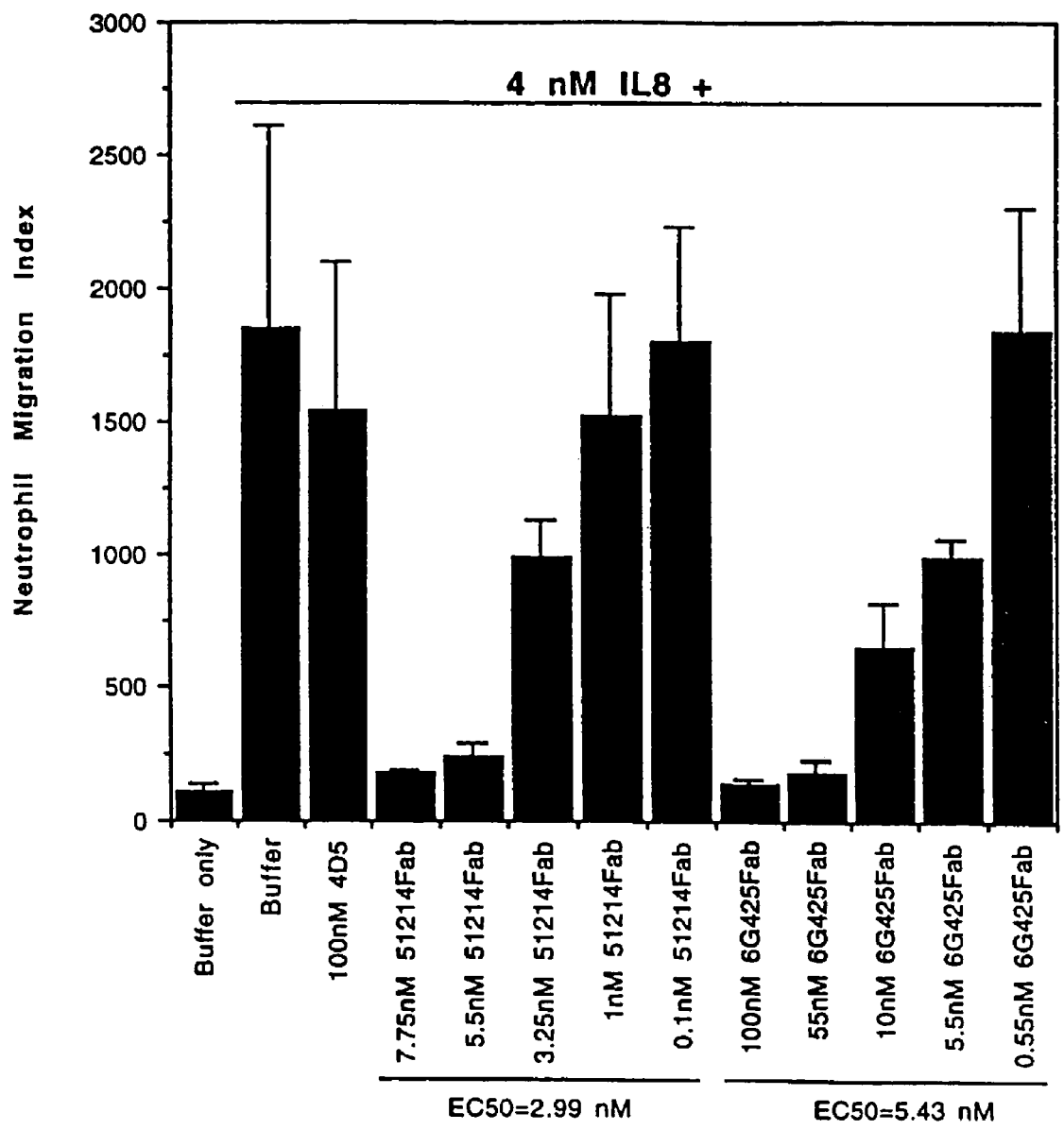
FIG. 6 demonstrates the inhibition of human IL-8 mediated neutrophil chemotaxis by chimeric 6G4.2.5 Fab and chimeric 5.12.14 Fab.
Figure 7:
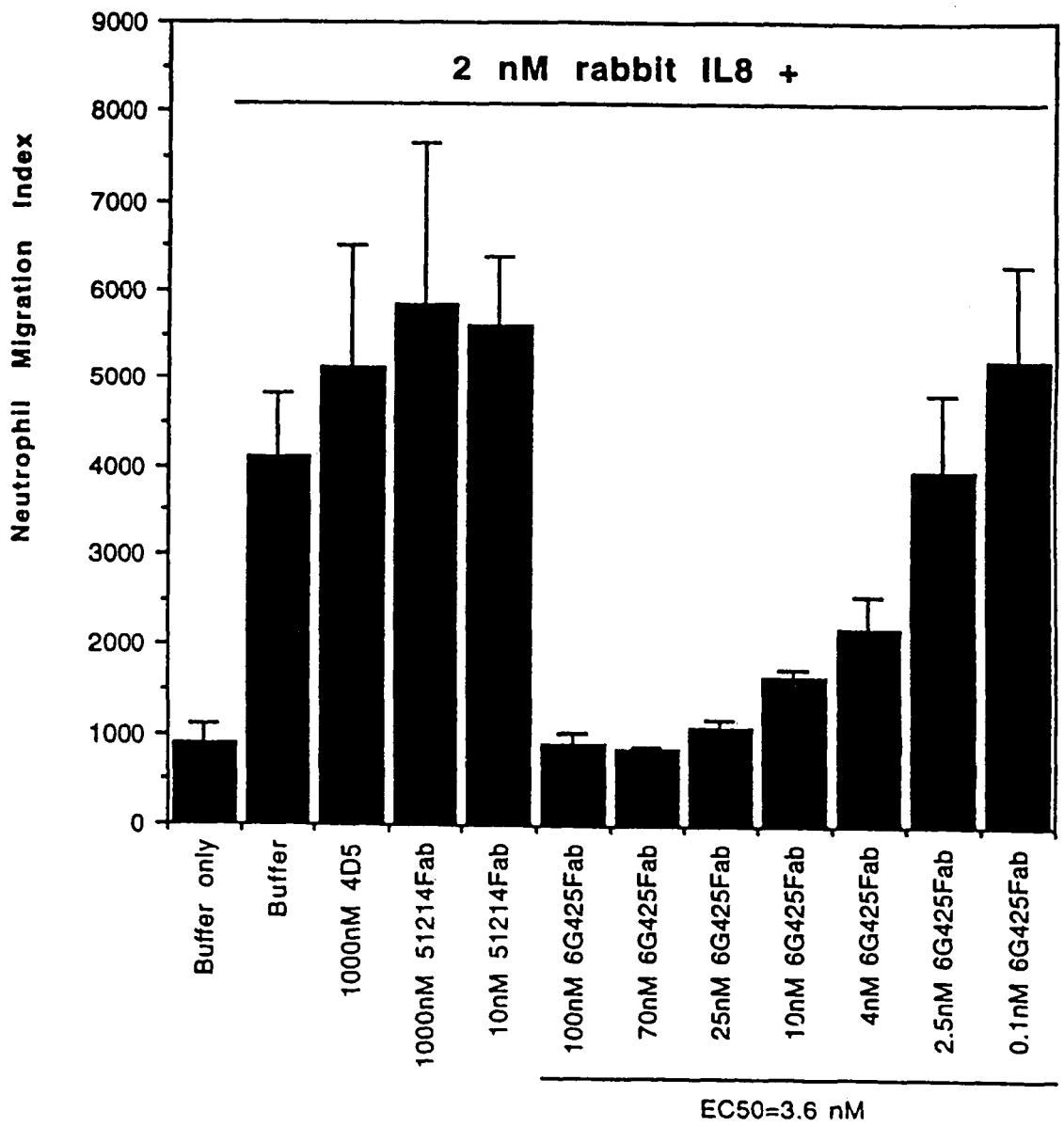
FIG. 7 demonstrates the relative abilities of chimeric 6G4.2.5 Fab and chimeric 5.12.14 Fab to inhibit rabbit IL-8 mediated neutrophil chemotaxis.

The results are shown in FIGS. 6 and 7. FIG. 6 demonstrates the inhibition of human IL-8 mediated neutrophil chemotaxis by chimeric 6G4.2.5 and 5.12.14 Fabs. FIG. 7 demonstrates the relative abilities of chimeric 6G4.2.5 and 5.12.14 Fabs to inhibit rabbit IL-8 mediated neutrophil chemotaxis.

3. Inhibition of IL-8-Mediated Neutrophil Elastase Release by Various Concentrations of 6G4.2.5 and 5.12.14 Fabs Blood was drawn from healthy male donors into heparinized syringes. Neutrophils were isolated by dextran sedimentation, centrifugation over Lymphocyte Separation Medium (Organon Teknika, Durham, N.C.), and hypotonic lysis of contaminating red blood cells as described by Berman et al. (*J. Cell Biochem.* 52:183 (1993)). The final neutrophil pellet was suspended at a concentration of $1\times10^7$ cells/ml in assay buffer, which consisted of Hanks Balanced Salt Solution (GIBCO, Grand Island, N.Y.) supplemented with 1.0% BSA (fraction V, Sigma, St. Louis, Mo.), 2 mg/ml glucose, 4.2 mM sodium bicarbonate, and 0.01 M HEPES, pH 7.2. The neutrophils were stored at 4° C. for not longer than 1 hr.

Figure 8:
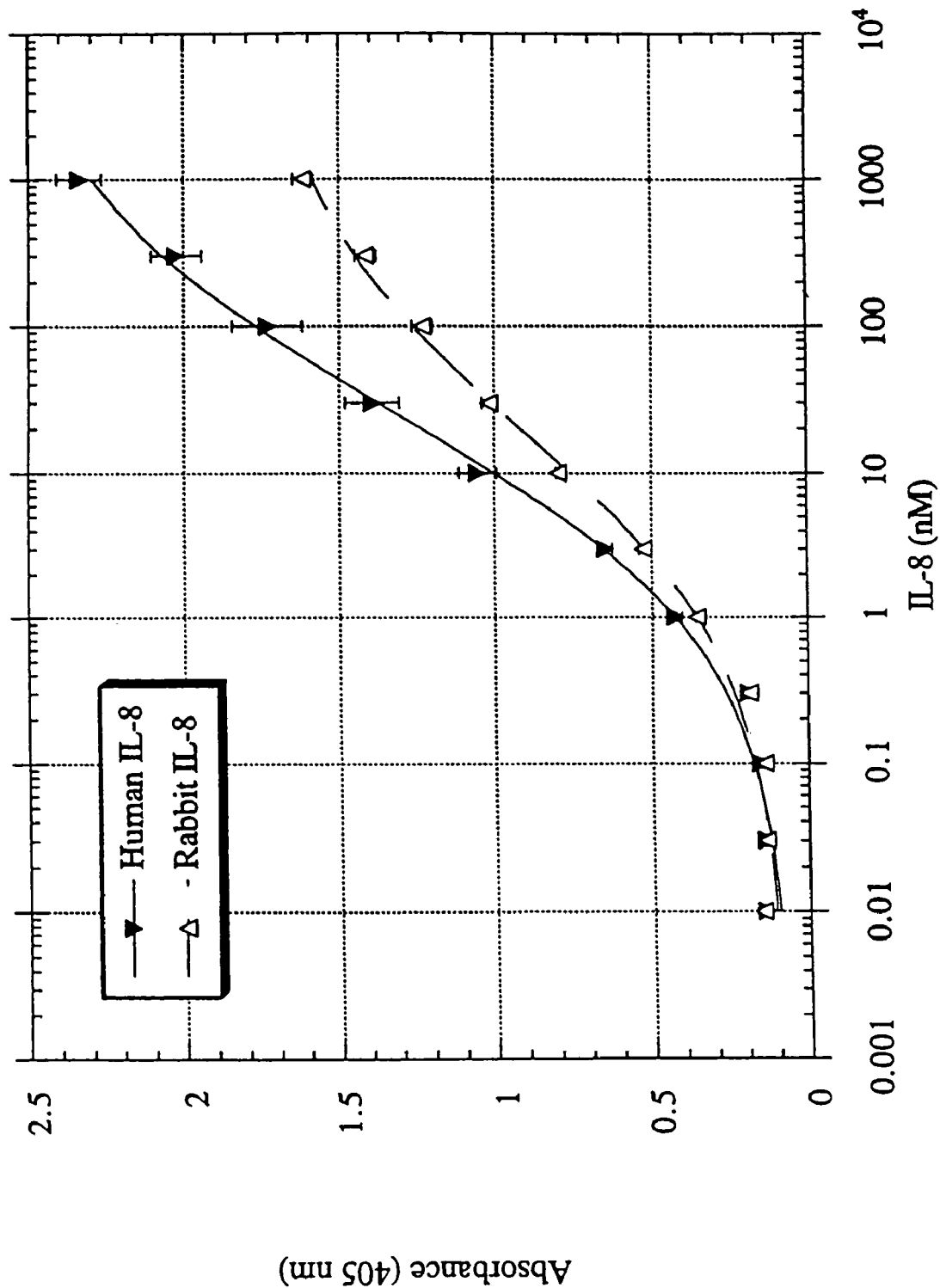
FIG. 8 depicts the stimulation of elastase release from human neutrophils by various concentrations of human and rabbit IL-8. The relative extent of elastase release was quantitated by measurement of absorbance at 405 nm. The data represent mean±SEM of triplicate samples.
Figure 9:
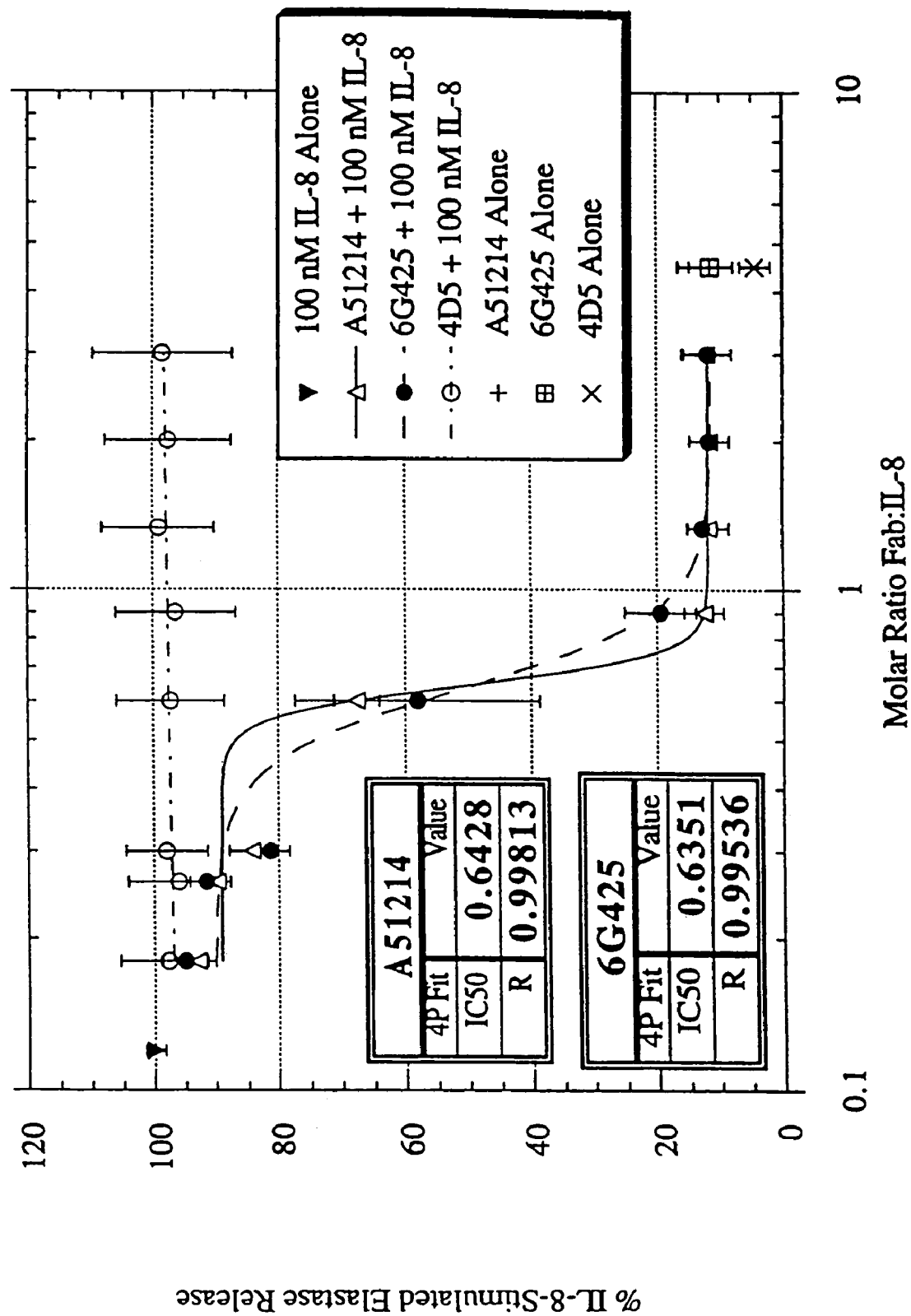
FIG. 9 is a graph depicting the ability of chimeric 6G4.2.5 Fab and chimeric 5.12.14 Fab to inhibit elastase release from human neutrophils stimulated by human IL-8. The results were normalized to reflect the percentage of elastase release elicited by 100 nM IL-8 alone. The data represent the mean±SEM of three separate experiments performed on different days with different blood donors. $IC_{50}$ values were calculated by four parameter fit.

IL-8 (10 µl) was mixed with anti-IL-8 Fab, an isotype control Fab, or buffer (20 µl) in 1 ml polypropylene tubes and incubated in a 37° C. water bath for 30 min. IL-8 was used at final concentrations ranging from 0.01 to 1000 nM in dose response studies (FIG. 8) and at a final concentration of 100 nM in the experiments addressing the effects of the Fabs on elastase release (FIGS. 9 and 10). Fab concentrations ranged from approximately 20 nM to 300 nM, resulting in Fab:IL-8 molar ratios of 0.2:1 to 3:1. Cytochalasin B (Sigma) was added to the neutrophil suspension at a concentration of 5:g/ml (using a 5 mg/ml stock solution made up in DMSO), and the cells were incubated for 15 min in a 37° C. water bath. Cytochalasin B-treated neutrophils (100 µl) were then added to the IL-8/Fab mixtures. After a 3 hr incubation at room temperature, the neutrophils were pelleted by centrifugation (200×g for 5 min), and aliquots of the cell-free supernatants were transferred to 96 well plates (30 µl/well). The elastase substrate, methoxysuccinyl-alanyl-alanyl-prolyl-valyl-p-nitroanilide (Calbiochem, La Jolla, Calif.), was prepared as a 10 mM stock solution in DMSO and stored at 4° C. Elastase substrate working solution was prepared just prior to use (1.2 mM elastase substrate, 1.2 M NaCl, 0.12 M HEPES, pH 7.2), and 170 µl was added to each sample-containing well. The plates were placed in a 37° C. tissue culture incubator for 30 min or until an optical density reading for the positive controls reached at least 1.0. Absorbance was measured at 405 nm using an SLT 340 plate reader (SLT Lab Instruments, Austria).

FIG. 9 demonstrates the ability of the chimeric anti-IL-8 Fabs to inhibit elastase release from human neutrophils stimulated by human IL-8; FIG. 10 demonstrates the relative abilities of the chimeric anti-IL-8 Fabs to inhibit elastase release from human neutrophils stimulated by rabbit IL-8.

C. Molecular Cloning of the Variable Light and Heavy Regions of the Murine 5.12.14 (Anti-IL-8) Monoclonal Antibody Total RNA was isolated from $1 \times 10^8$ cells (hybridoma cell line ATCC HB-11722) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat, E. A. et al. (1991) NIH Publication 91-3242, V 1-3.). Three primers (SEQ ID NOS: 1-6) were designed for each of the light and heavy chains to increase the chances of primer hybridization and efficiency of first strand cDNA synthesis (FIG. 13). Amplification of the first strand cDNA to double-stranded (ds) DNA was accomplished using two sets of synthetic DNA oligonucleotide primers: one forward primer (SEQ ID NOS: 7-9) and one reverse primer (SEQ ID NO: 10) for the light chain variable region amplification (FIG. 14) and one forward primer (SEQ ID NOS: 11-14) and one reverse primer (SEQ ID NOS: 11, 15, 14 and 13) for the heavy chain variable region amplification (FIG. 15). The N-terminal sequence of the first eight amino acids of either the light or heavy chains of 5.12.14 was used to generate a putative murine DNA sequence corresponding to this region. (A total of 29 amino acids was sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, MluI for both the light chain variable region forward primer and the heavy chain variable region forward primer to facilitate ligation to the 3' end of the STII element in the cloning vector. The reverse amplification primers were designed to anneal with the murine DNA sequence corresponding to a portion of the constant region of the light or heavy chains near the variable/constant junction. The light chain variable region reverse primer contained a unique BstBI restriction site and the heavy chain variable region reverse primer contained a unique ApaI restriction site for ligation to the 5' end of either the human IgG1 constant light or IgG1 constant heavy regions in the vectors, pB13.1 (light chain) and pB14 (heavy chain). The polymerase chain reaction using these primer sets yielded DNA fragments of approximately 400 bp. The cDNA encoding the 5.12.14 light chain variable region was cloned into the vector pB13.1, to form pA51214VL and the 5.12.14 heavy chain variable region was cloned into the vector, pB14, to form pA51214VH. The cDNA inserts were characterized by DNA sequencing and are presented in the DNA sequence (SEQ ID NO: 16) and amino acid sequence (SEQ ID NO: 17) of FIG. 16 (murine light chain variable region) and in the DNA sequence (SEQ ID NO: 18) and amino acid (SEQ ID NO: 19) of FIG. 17 (murine heavy chain variable region).

D. Construction of a 5.12.14 Fab Vector

In the initial construct, pA51214VL, the amino acids between the end of the 5.12.14 murine light chain variable sequence and the unique cloning site, BstBI, in the human IgG1 constant light sequence were of murine origin corresponding to the first 13 amino acids of the murine IgG1 constant region (FIG. 16). Therefore, this plasmid contained a superfluous portion of the murine constant region separating the 5.12.14 murine light chain variable region and the human light chain IgG1 constant region. This intervening sequence would alter the amino acid sequence of the chimera and most likely produce an incorrectly folded Fab. This problem was addressed by immediately truncating the cDNA clone after A109 and re-positioning the BstBI site to the variable/constant junction by the polymerase chain reaction. FIG. 18 shows the amplification primers used to make these modifications. The forward primer, VL.front (SEQ ID NO: 20), was designed to match the last five amino acids of the STII signal sequence, including the MluI cloning site, and the first 4 amino acids of the 5.12.14 murine light chain variable sequence. The sequence was altered from the original cDNA in the third position of the first two codons D1 (T to C) and I2 (C to T) to create a unique EcoRV cloning site which was used for later constructions. The reverse primer, VL.rear (SEQ ID NO: 21), was designed to match the first three amino acids of the human IgG1 constant light sequence and the last seven amino acids of the 5.12.14 light chain variable sequence which included a unique BstBI cloning site. In the process of adding the BstBI site, the nucleotide sequence encoding several amino acids were altered: L106 (TTG to CTT), K107 (AAA to CGA) resulting in a conservative amino acid substitution to arginine, and R108 (CGG to AGA). The PCR product encoding the modified 5.12.14 light chain variable sequence was then subcloned into pB13.1 in a two-part ligation. The MluI-BstBI digested 5.12.14 PCR product encoding the light chain variable region was ligated into MluI-BstBI digested vector to form the plasmid, pA51214VL'. The modified cDNA was characterized by DNA sequencing. The coding sequence for the 5.12.14 light chain is shown in FIG. 19.

Likewise, the DNA sequence between the end of the heavy chain variable region and the unique cloning site, ApaI, in the human IgG1 heavy chain constant domain of pA51214VH was reconstructed to change the amino acids in this area from murine to human. This was done by the polymerase chain reaction. Amplification of the murine 5.12.14 heavy chain variable sequence was accomplished using the primers shown in FIG. 18. The forward PCR primer (SEQ ID NO: 22) was designed to match nucleotides 867-887 in pA51214VH upstream of the STII signal sequence and the putative cDNA sequence encoding the heavy chain variable region and included the unique cloning site SpeI. The reverse PCR primer (SEQ ID NO: 23) was designed to match the last four amino acids of the 5.12.14 heavy chain variable sequence and the first six amino acids corresponding to the human IgG1 heavy constant sequence which also included the unique cloning site, ApaI. The PCR product encoding the modified 5.12.14 heavy chain variable sequence was then subcloned to the expression plasmid, pMHM24.2.28 in a two-part ligation. The vector was digested with SpeI-ApaI and the SpeI-ApaI digested 5.12.14 PCR product encoding the heavy chain variable region was ligated into it to form the plasmid, pA51214VH'. The modified cDNA was characterized by DNA sequencing. The coding sequence for the 5.12.14 heavy chain is shown in the DNA sequence (SEQ ID NO: 26) and amino acid sequence (SEQ ID NO: 27) of FIGS. 20A-20B.

The first expression plasmid, pantiIL-8.1, encoding the chimeric Fab of 5.12.14 was made by digesting pA51214VH' with EcoRV and BpuI 1021 to replace the EcoRV-BpuI 1021 fragment with a EcoRV-BpuI 1021 fragment encoding the murine 5.12.14 light chain variable region of pA51214VL'. The resultant plasmid thus contained the murine-human variable/constant regions of both the light and heavy chains of 5.12.14.

Preliminary analysis of Fab expression using pantiIL-8.1 showed that the light and heavy chains were produced intracellularly but very little was being secreted into the periplasmic space of *E. coli*. To correct this problem, a second expression plasmid was constructed.

The second expression plasmid, pantiIL-8.2, was constructed using the plasmid, pmy187, as the vector. Plasmid pantiIL-8.2 was made by digesting pmy187 with MluI and SphI and the MluI (partial)-SphI fragment encoding the murine 5.12.14 murine-human chimeric Fab of pantiIL-8.1 was ligated into it. The resultant plasmid thus contained the murine-human variable/constant regions of both the light and heavy chains of 5.12.14.

The plasmid pantiIL-8.2 was deposited on Feb. 10, 1995 with the American Type Culture Collection, 12301 Parklawn Drive, Rockville, Md., U.S.A. (ATCC) and assigned ATTC Accession No. ATCC 97056.

E. Molecular Cloning of the Variable Light and Heavy Regions of the Murine 6G4.2.5 Monoclonal Antibody Total RNA was isolated from 1×10⁸ cells (hybridoma cell line 6G4.2.5) using the procedure described by Chomczynski and Sacchi (*Anal. Biochem.* 162:156 (1987)). First strand cDNA was synthesized by specifically priming the mRNA with synthetic DNA oligonucleotides designed to hybridize with regions of the murine RNA encoding the constant region of the kappa light chain or the IgG2a heavy chain (the DNA sequence of these regions are published in *Sequences of Proteins of Immunological Interest*, Kabat et al. (1991) NIH Publication 91-3242, V 1-3). Three primers (SEQ ID NOS: SEQ ID NOS: 1-6) were designed for each the light and heavy chains to increase the chances of primer hybridization and efficiency of first strand cDNA synthesis (FIG. 21). Amplification of the first strand cDNA to double-stranded (ds) DNA was accomplished using two sets of synthetic DNA oligonucleotide primers: one forward primer (SEQ ID NOS: 28-30) and one reverse primer (SEQ ID NO: 31) for the light chain variable region amplification (FIG. 22) and one forward primer (SEQ ID NOS: 32-33) and one reverse primer (SEQ ID NOS: 11, 15, 14 and 13) for the heavy chain variable region amplification (FIG. 23). The N-terminal sequence of the first eight amino acids of either the light or heavy chains of 6G4.2.5 was used to generate a putative murine DNA sequence corresponding to this region. (A total of 29 amino acids were sequenced from the N-terminus of both the light chain and heavy chain variable regions using the Edman degradation protein sequencing technique.) This information was used to design the forward amplification primers which were made degenerate in the third position for some codons to increase the chances of primer hybridization to the natural murine DNA codons and also included the unique restriction site, NsiI, for the light chain variable region forward primer and the unique restriction site, MluI, for the heavy chain variable region forward primer to facilitate ligation to the 3' end of the STII element in the vector, pchimFab. The reverse amplification primers were designed to anneal with the murine DNA sequence corresponding to a portion of the constant region of the light or heavy chains near the variable/constant junction. The light chain variable region reverse primer contained a unique MunI restriction site and the heavy chain variable region reverse primer contained a unique ApaI restriction site for ligation to the 5' end of either the human IgG1 constant light or IgG1 constant heavy regions in the vector, pchimFab. The polymerase chain reaction using these primer sets yielded DNA fragments of approximately 400 bp and were cloned individually into the vector, pchimFab, to form p6G425VL and p6G425VH. The cDNA inserts were characterized by DNA sequencing and are presented in the DNA sequence (SEQ ID NO: 34) and amino acid sequence (SEQ ID NO: 35) of FIG. 24 (murine light chain variable region) and the DNA sequence (SEQ ID NO: 36) and amino acid sequence (SEQ ID NO: 37) of FIG. 25 (murine heavy chain variable region).

F. Construction of a 6G4.2.5 chimeric Fab Vector

In the initial construct, p6G425VL, the amino acids between the end of the 6G4.2.5 murine light chain variable sequence and the unique cloning site, MunI, in the human IgG1 constant light sequence were of murine origin. These amino acids must match the human IgG1 amino acid sequence to allow proper folding of the chimeric Fab. Two murine amino acids, D115 and S121, differed dramatically from the amino acids found in the loops of the β-strands of the human IgG1 constant domain and were converted to the proper human amino acid residues, V115 and F121, by site-directed mutagenesis using the primers (SEQ ID NOS: 38, 39, 40) shown in FIG. 26. These specific mutations were confirmed by DNA sequencing and the modified plasmid named p6G425VL'. The coding sequence is shown in the DNA sequence (SEQ ID NO: 41) and amino acid sequence (SEQ ID NO: 42) of FIGS. 27A-27B.

Likewise, the DNA sequence between the end of the heavy chain variable region and the unique cloning site, ApaI, in the human IgG1 heavy chain constant domain of p6G425VH was reconstructed to change the amino acids in this area from murine to human. This process was facilitated by the discovery of a BstEII site near the end of the heavy chain variable region. This site and the ApaI site were used for the addition of a synthetic piece of DNA encoding the corresponding IgG human amino acid sequence. The synthetic oligo-nucleotides shown in FIG. 26 were designed as complements of one another to allow the formation of a 27 bp piece of ds DNA. The construction was performed as a three-part ligation because the plasmid, p6G425V11, contained an additional BstEII site within the vector sequence. A 5309 bp fragment of p6G425VH digested with MluI-ApaI was ligated to a 388 bp fragment carrying the 6G4.2.5 heavy chain variable region and a 27 bp synthetic DNA fragment encoding the first six amino acids of the human IgG1 constant region to form the plasmid, p6G425VH'. The insertion of the synthetic piece of DNA was confirmed by DNA sequencing. The coding sequence is shown in the DNA sequence (SEQ ID NO: 43) and amino acid sequence (SEQ ID NO: 44) of FIGS. 28A-28B.

The expression plasmid, p6G425chim2, encoding the chimeric Fab of 6G4.2.5 was made by digesting p6G425chimVL' with MluI and ApaI to remove the STII-murine HPC4 heavy chain variable region and replacing it with the MluI-ApaI fragment encoding the STII-murine 6G4.2.5 heavy chain variable region of p6G425chimVH'.

The resultant plasmid thus contained the murine-human variable/constant regions of both the light and heavy chains of 6G4.2.5.

lysozyme was omitted from the purification protocol. The variant antibodies were analyzed by SDS-PAGE, electrospray mass spectroscopy and amino acid analysis.

TABLE 4

Humanized 6G425 Variants

| Variant | Version | Template | Changes[a] | Purpose[b] | IC50[c] Mean | S.D. | N |
|---|---|---|---|---|---|---|---|
| F(ab)-1 | version 1 | | CDR Swap | | 63.0 | 12.3 | 4 |
| F(ab)-2 | version 2 | F(ab)-1 | PheH67*Ala* | packaging w/ CDR H2 | 106.0 | 17.0 | 2 |
| F(ab)-3 | version 3 | F(ab)-1 | ArgH71*Val* | packaging w/ CDRs H1, H2 | 79.8 | 42.2 | 4 |
| F(ab)-4 | version 6 | F(ab)-1 | IleH69*Leu* | packaging w/ CDR H2 | 44.7 | 9.0 | 3 |
| F(ab)-5 | version 7 | F(ab)-1 | LeuH78*Ala* | packaging w/ CDRs H1, H2 | 52.7 | 31.0 | 9 |
| F(ab)-6 | version 8 | F(ab)-1 | IleH69*Leu* LeuH78*Ala* | combine F(ab)-4 and -5 | 34.6 | 6.7 | 7 |
| F(ab)-7 | version 16 | F(ab)-6 | LeuH80*Val* | packaging w/ CDR H1 | 38.4 | 9.1 | 2 |
| F(ab)-8 | version 19 | F(ab)-6 | ArgH38*Lys* | packaging w/ CDR H2 | 14.0 | 5.7 | 2 |
| F(ab)-9 | version 11 | F(ab)-6 | GluH6*Gln* | packaging w/ CDR H3 | 19.0 | 5.1 | 7 |
| Chimeric[d] F(ab) | | | | | 11.4 | 7.0 | 1 3 |
| rhu4D5[e] F(ab) | | | | | >200:M | | 5 |

[a]Amino acid changes made relative to the template used. Murine residues are in bold italics and residue numbering is according to Kabat et al.
[b]Purpose for making changes based upon interactions observed in molecular models of the humanized and murine variable domains.
[c]nM concentration of variant necessary to inhibit binding of iodinated IL-8 to human neutrophils in the competitive binding assay.
[d]Chimeric F(ab) is a (F(ab) which carries the murine heavy and light chain variable domains fused to the human light chain kI constant domain and the human heavy chain subgroup III constant domain I respectively.
[e]rhu4D5F(ab) is of the same isotype as the humanized 6G425 F(ab)s and is a humanized anti-HER2 F(ab) and therefore should not bind to IL8.

The plasmid p6G425chim2 was deposited on Feb. 10, 1995 with the American Type Culture Collection, 12301 Parklawn Drive, Rockville, Md., U.S.A. (ATCC) and assigned ATTC Accession No. 97055.

G. Construction of Humanized Versions of Anti-IL-8 Antibody 6G4.2.5

Figure 30A:
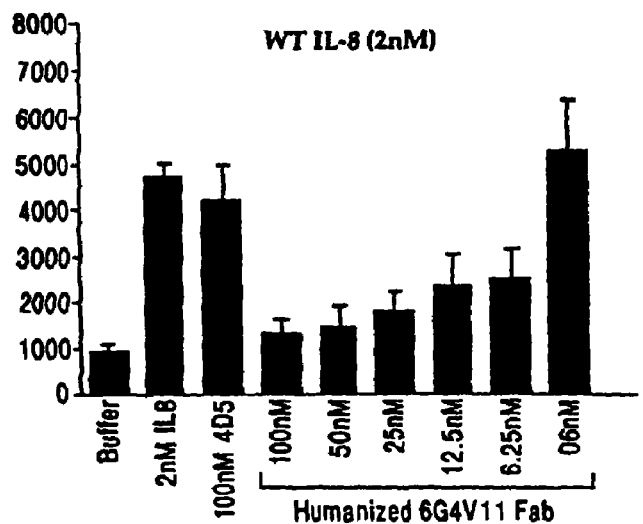
FIGS. 30A, 30B and 30C are graphs depicting the ability of F(ab)-9 (humanized 6G4V11 Fab) to inhibit human wild type IL-8, human monomeric IL-8, and rhesus IL-8 mediated neutrophil chemotaxis, respectively.
Figure 30B:
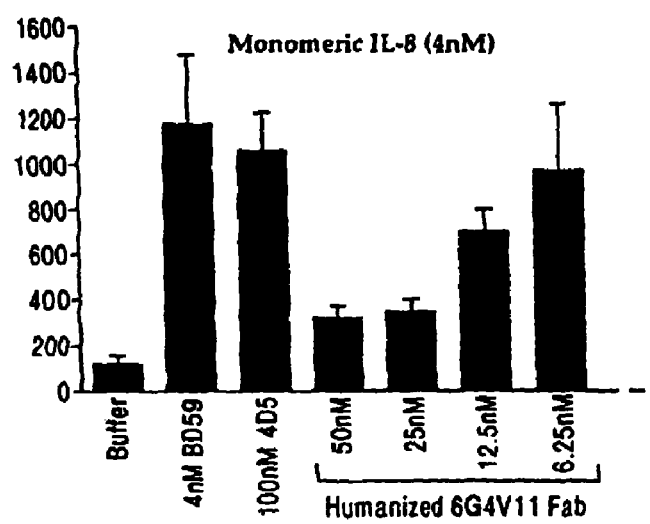
Figure 30C:
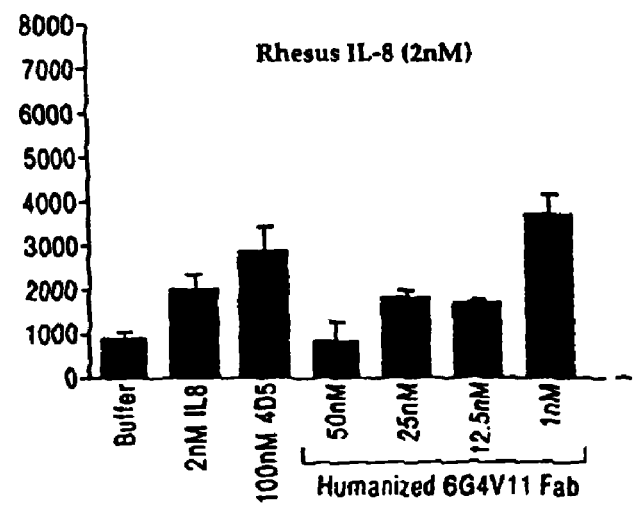

The murine cDNA sequence information obtained from the hybridoma cell line, 6G4.2.5, was used to construct recombinant humanized variants of the murine anti-IL-8 antibody. The first humanized variant, F(ab)-1, was made by grafting synthetic DNA oligonucleotide primers encoding the murine CDRs of the heavy and light chains onto a phagemid vector, pEMX1 (Werther et al., *J. Immunol*, 157: 4986-4995 (1996)), which contains a human 6-subgroup I light chain and a human IgG1 subgroup III heavy chain (FIG. 29). Amino acids comprising the framework of the antibody that were potentially important for maintaining the conformations necessary for high affinity binding to IL-8 by the complementarity-determining regions (CDR) were identified by comparing molecular models of the murine and humanized 6G4.2.5 (F(ab)-1) variable domains using methods described by Carter et al., PNAS 89:4285 (1992) and Eigenbrot, et. al., J. Mol. Biol. 229:969 (1993). Additional humanized framework variants (F(ab) 2-9) were constructed from the information obtained from these models and are presented in Table 2 below. In these variants, the site-directed mutagenesis methods of Kunkel, *Proc. Natl. Acad. Sci. USA*), 82:488 (1985) were utilized to exchange specific human framework residues with their corresponding 6G4.2.5 murine counterparts. Subsequently, the entire coding sequence of each variant was confirmed by DNA sequencing. Expression and purification of each F(ab) variant was performed as previously described by Werther et. al., supra, with the exception that hen egg white The first humanized variant, F(ab)-1, was an unaltered CDR swap in which all the murine CDR amino acids defined by both x-ray crystallography and sequence hypervariability were transferred to the human framework. When the purified F(ab) was tested for its ability to inhibit $^{125}$I-IL-8 binding to human neutrophils according to the methods described in Section (B)(1) above, a 5.5 fold reduction in binding affinity was evident as shown in Table 4 above. Subsequent versions of F(ab)-1 were engineered to fashion the 3-dimensional structure of the CDR loops into a more favorable conformation for binding IL-8. The relative affinities of the F(ab) variants determined from competition binding experiments using human neutrophils as described in Section (B)(1) above are presented in Table 4 above. A slight decrease in IL-8 binding (<2 fold) was observed for F(ab)-2-3 while only slight increases in IL-8 binding were noted for F(ab)3-5. Variant F(ab)-6 had the highest increase in affinity for IL-8 (approximately 2 fold), exhibiting an IL-8 binding affinity of 34.6 nM compared to the F(ab)-11L-8 binding affinity of 63 nM. The substitutions of murine Leu for Ile at H69 and murine Ala for Leu at H78 are predicted to influence the packing of CDRs H1 and H2. Further framework substitutions using the F (ab)-6 variant as template were made to bring the binding affinity closer to that of the chimeric F(ab). In-vitro binding experiments revealed no change in affinity for F(ab)-7 (38.4 nM) but a significant improvement in affinity for F(ab)-8/9 of 14 nM and 19 nM, respectively. By analysis of a 3-D computer-generated model of the anti-IL-8 antibody, it was hypothesized that the substitution of murine Lys for Arg at H38 in F(ab)-8 influences CDR-H2 while a change at 1-16 of murine Gln for Glu in F(ab)-9 affects CDR-H3. Examination of the human antibody sequences with respect to amino acid variability revealed that the frequency of Arg at residue H38 is >99% whereas residue H6 is either Gln ~20% or Glu ~80% (Kabat et. al. Sequences of Proteins of Immunological Interest 5th Ed. (1991)). Therefore, to reduce the likelihood of causing an immune response to the antibody, F(ab)-9 was chosen over F(ab)-8 for further affinity maturation studies. Variant F(ab)-9 was also tested for its ability to inhibit IL-8-mediated chemotaxis (FIG. 30). This antibody was able to block neutrophil migration induced by wild-type human IL-8, human monomeric IL-8 and Rhesus IL-8 with $IC_{50}$=s of approximately 12 nM, 15 nM, and 22 nM, respectively, in IL-8 mediated neutrophil chemotaxis inhibition assays performed as described in Section (B)(2) above. The amino acid sequence for variant F(ab)-8 is provided in FIG. 31c. The F(ab)-8 was found to block human and rhesus IL-8-mediated chemotaxis with $IC_{50}$=s of 12 nM and 10 nM, respectively, in IL-8 mediated neutrophil chemotaxis inhibition assays performed as described in Section (B)(2) above.

H. Construction of an Anti-IL-8-Gene III Fusion Protein for Phage Display and Alanine Scanning Mutagenesis An expression plasmid, pPh6G4.V11, encoding a fusion protein (heavy chain of the humanized 6G4.2.5 version 11 antibody and the M13 phage gene-III coat protein) and the light chain of the humanized 6G4.2.5 version 11 antibody was assembled to produce a monovalent display of the anti-IL-8 antibody on phage particles. The construct was made by digesting the plasmid, pFPHX, with EcoRV and ApaI to remove the existing irrelevant antibody coding sequence and replacing it with a 1305 bp EcoRV-ApaI fragment from the plasmid, p6G4.V11, encoding the humanized 6G4.2.5 version 11 anti-IL-8 antibody. The translated sequence of the humanized 6G4.2.5 version 11 heavy chain (SEQ ID NO: 52), peptide linker and gene III coat protein (SEQ ID NO: 53) is shown in FIG. 31A. The pFPHX plasmid is a derivative of phGHam-3 which contains an in-frame amber codon (TAG) between the human growth hormone and gene-III DNA coding sequences. When transformed into an amber suppressor strain of E. coli, the codon (TAG) is read as Glutamate producing a growth hormone (hGH)-gene III fusion protein. Likewise, in a normal strain of E. coli, the codon (TAG) is read as a stop preventing translational read-through into the gene-III sequence and thus allowing the production of soluble hGH. The pGHam-3 plasmid is described in Methods: A Companion to Methods in Enzymology, 3:205 (1991). The final product, pPh6G4.V11, was used as the template for the alanine scanning mutagenesis of the CDRs and for the construction of randomized CDR libraries of the humanized 6G4.V11 antibody.

I. Alanine Scanning Mutagenesis of Humanized Antibody 6G4.2.5 Version 11

The solvent exposed amino acid residues in the CDRs of the humanized anti-IL-8 6G4.2.5 version 11 antibody (h6G4V11) were identified by analysis of a 3-D computer-generated model of the anti-IL-8 antibody. In order to determine which solvent exposed amino acids in the CDRs affect binding to interleukin-8, each of the solvent exposed amino acids was individually changed to alanine, creating a panel of mutant antibodies wherein each mutant contained an alanine substitution at a single solvent exposed residue. The alanine scanning mutagenesis was performed as described by Leong et. al., *J. Biol. Chem.*, 269: 19343 (1994)).

The $IC_{50}$'s (relative affinities) of h6G4V11 wt and mutated antibodies were established using a Competition Phage ELISA Assay described by Cunningham et. al., (EMBO J. 13:2508 (1994)) and Lee et. al., (Science 270:1657 (1995)). The assay measures the ability of each antibody to bind IL-8 coated onto a 96-well plate in the presence of various concentrations of free IL-8 (0.2 to 1 uM) in solution. The first step of the assay requires that the concentrations of the phage carrying the wild type and mutated antibodies be normalized, allowing a comparison of the relative affinities of each antibody. The normalization was accomplished by titering the phage on the IL-8 coated plates and establishing their $EC_{50}$. Sulfhydryl coated 96-well binding plates (Corning-Costar; Wilmington, Mass.) were incubated with a 0.1 mg/ml solution of K64C IL-8 (Lysine 64 is substituted with Cysteine to allow the formation of a disulfide bond between the free thiol group of K64C IL-8 and the sulfhydryl coated plate, which results in the positioning of the IL-8 receptor binding domains towards the solution interface) in phosphate buffered saline (PBS) pH 6.5 containing 1 mM EDTA for 1 hour at 25° C. followed by three washes with PBS and a final incubation with a solution of PBS containing 1.75 mg/ml of L-cysteine-HCl and 0.1 M $NaHCO_3$ to block any free reactive sulfhydryl groups on the plate. The plates were washed once more and stored covered at 4° C. with 200 ul of PBS/well. Phage displaying either the reference antibody, h6G4V11, or the mutant h6G4V11 antibodies were grown and harvested by PEG precipitation. The phage were resuspended in 500 ul 10 mM Tris-HCl pH 7.5, 1 mM EDTA and 100 mM NaCl and held at 4° C. for no longer than 3 hours. An aliquot of each phage was diluted 4-fold in PBS containing 0.05% Tween-20 (BioRad, Richmond, Calif.) and 0.5% BSA RIA grade (Sigma, St. Louis, Mo.) (PBB) and added to IL-8 coated plates blocked for at least 2 hours at 25° C. with 50 mg/ml skim milk powder in 25 mM Carbonate Buffer pH 9.6. The phage were next serially diluted in 3 fold steps down the plate from well A through H. The plates were incubated for 1 hour at 25° C. followed by nine quick washes with PBS containing 0.05% Tween-20 (PBST). The plates were then incubated with a 1:3200 dilution of rabbit anti-phage antibody and a 1:1600 dilution of secondary goat-anti-rabbit Fc HRP-conjugated antibody for 15 minutes at 25° C. followed by nine quick washes with PBST. The plates were developed with 80 ul/well of 1 mg/ml OPD (Sigma, St. Louis, Mo.) in Citrate Phosphate buffer pH 5.0 containing 0.015% $H_2O_2$ for 4 minutes at 25° C. and the reaction stopped with the addition of 40 ul of 4.5M $H_2SO_4$. The plates were analyzed at wavelength 8492 in a SLT model 340ATTC plate reader (SLT Lab Instruments). The individual $EC_{50}$=s were determined by analyzing the data using the program Kaleidagraph (Synergy Software, Reading, Pa.) and a 4-parameter fit equation. The phage held at 4° C. were then immediately diluted in PBB to achieve a final concentration corresponding to their respective $EC_{50}$ or target $OD_{492}$ for the competition segment of the experiment, and dispensed into a 96 well plate containing 4-fold serial dilutions of soluble IL-8 ranging from 1 uM in well A and ending with 0.2 uM in well H. Using a 12-channel pipet, 100 ul of the phage/IL-8 mixture was transferred to an IL-8 coated 96-well plate and executed as described above. Each sample was done in triplicate –3 columns/sample.

TABLE 5

Relative Affinities (IC50) for
Alanine-scan Anti-IL-8 6G4V11 CDR Mutants

| CDR | Amino Acid Residue | Avg IC50 (nM) | Std Dev |
|---|---|---|---|
| V11 | Reference | 11.5 | 6.4 |
| CDR-L1 | S26 | 6.3 | 2.9 |
|  | Q27 | 10.2 | 2.4 |
|  | S28 | 14.2 | 5.2 |
|  | V30 | 29.1 | 12.3 |
|  | H31 | 580.3 | 243.0 |
|  | I33 | 64.2 | 14.6 |
|  | N35 | 3.3 | 0.7 |
|  | T36 | 138.0 | nd |
|  | Y37 | NDB | nd |
| CDR-L2 | K55 | 24.2 | 14.9 |
|  | V56 | 15.5 | 3.8 |
|  | S57 | 12.4 | 4.0 |
|  | N58 | 17.6 | 3.7 |
|  | R59 | nd | nd |
| CDR-L3 | S96 | 10.8 | 4.4 |
|  | T97 | 70.6 | 55.2 |
|  | H98 | 8.0 | 1.2 |
|  | V99 | 19.6 | 1.9 |
| CDR-H1 | S28 | 8.6 | 3.1 |
|  | S30 | nd | nd |
|  | S31 | 7.8 | 2.5 |
|  | H32 | 13.3 | 5.8 |
|  | Y53 | 48.2 | 15.8 |
| CDR-H2 | Y50 | 35.6 | 13.0 |
|  | D52 | 13.3 | 7.5 |
|  | S53 | 6.0 | 3.4 |
|  | N54 | 96.0 | 5.8 |
|  | E56 | 15.8 | 4.5 |
|  | T57 | 8.4 | 1.6 |
|  | T58 | 11.3 | 1.8 |
|  | Y59 | 9.1 | 3.7 |
|  | Q61 | 12.6 | 6.4 |
|  | K64 | 18.5 | 12.1 |
| CDR-H3 | D96 | NDB | nd |
|  | Y97 | NDB | nd |
|  | R98 | 36.6 | 15.3 |
|  | Y99 | 199.5 | nd |
|  | N100 | 278.3 | 169.4 |
|  | D102 | 159.2 | 44 |
|  | W103 | NDB | nd |
|  | F104 | NDB | nd |
|  | F105 | 209.4 | 72.3 |
|  | D106 | 25.3 | 21.7 |

Each sample performed in triplicate/experiment.
NDB = No Detectable Binding/
nd = value not determined*
Residue numbering is according to Kabat et al.

Figure 32:
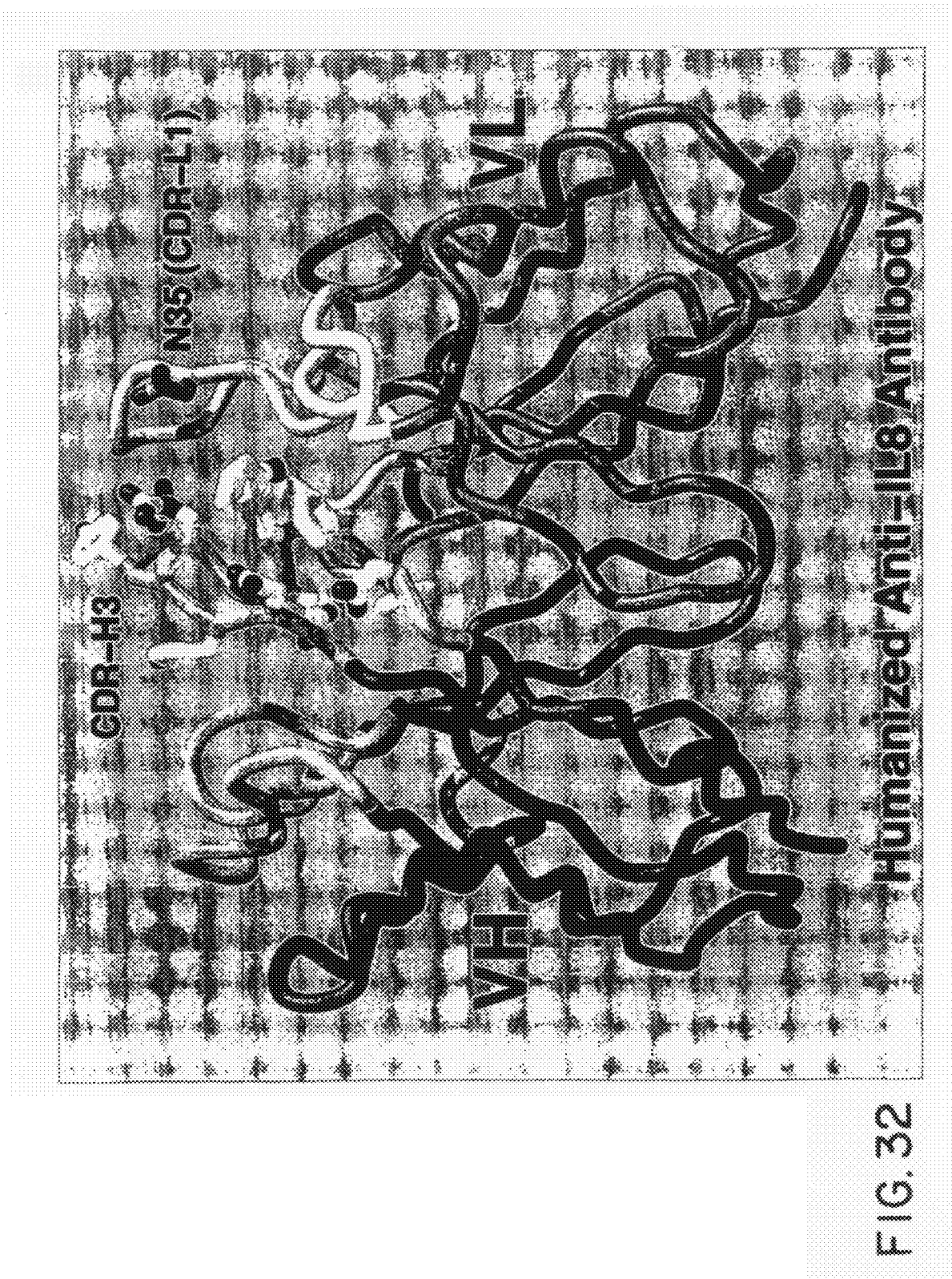
FIG. 32 is a three dimensional computer model of the humanized anti-IL-8 6G4.2.5V11 antibody. Heavy chain CDR loops and variable domain regions appear in purple, and CDR-H3 side chain residues appear in yellow. Heavy chain constant domain regions appear in red. Light chain CDR loops and variable domain regions appear in off-white, and the Asn residue at amino acid position 35 (N35) in CDR L1 appears in green. Light chain constant domain regions appear in amber.

The results of the alanine-scan are summarized in Table 5 above. The alanine substitutions in of many of the mutant antibodies had little or no adverse effects (<3 fold) on the binding affinity for IL-8. Mutants that were found to exhibit no detectable binding of IL-8 (NDB) presumably contained disruptions in the conformational structure of the antibody conferred by crucial structural or buried amino acids in the CDR. Based on the results of the scan, CDR-H3 (heavy chain, 3rd CDR) was identified as the dominant binding epitope for binding IL-8. Alanine substitutions in this CDR resulted in a 3 to >26 fold decrease in binding affinity. The amino acids, Y597, Y599 and D602 are of particular interest because it was determined from the computer generated model of the anti-IL-8 antibody that these residues are solvent exposed and that these residues might participate in hydrogen bonding or charge interactions with IL-8 or other amino acids of the antibody that influence either binding to IL-8 or the conformation of the CDR-H3 loop structure. (See the model depicted in FIG. 32). Unexpected increases in binding affinity (1.8>2.7 fold) were noted for S528 and S531 of CDR-H1 and S553 of CDR-H2.

Surprisingly, a significant increase in binding affinity was observed in the alanine mutant N35A located in CDR-L1 (light chain, 1st CDR). A 3-6 fold increase in affinity was observed compared to the wild-type h6G4V11 antibody. This augmentation of IL-8 binding could be the result of the close proximity of N35A to CDR-H3. The alanine substitution may have imparted a slight change in the conformation of CDR-L1 which alters the packing interaction of neighboring amino acid residues on CDR-H3, thereby tweaking the loop of CDR-H3 into a conformation that facilitates more appropriate contacts with IL-8. Similarly, N35A may also influence the orientation of amino acids in CDR-L1 or its interaction directly with IL-8. Unexpected increases in affinity (~2 fold) were also observed for S26 of CDR-L1 and H98 of CDR-L3.

J. Characterization of Humanized Anti-IL-8 Antibody 6G4V11N35A

Figure 33:
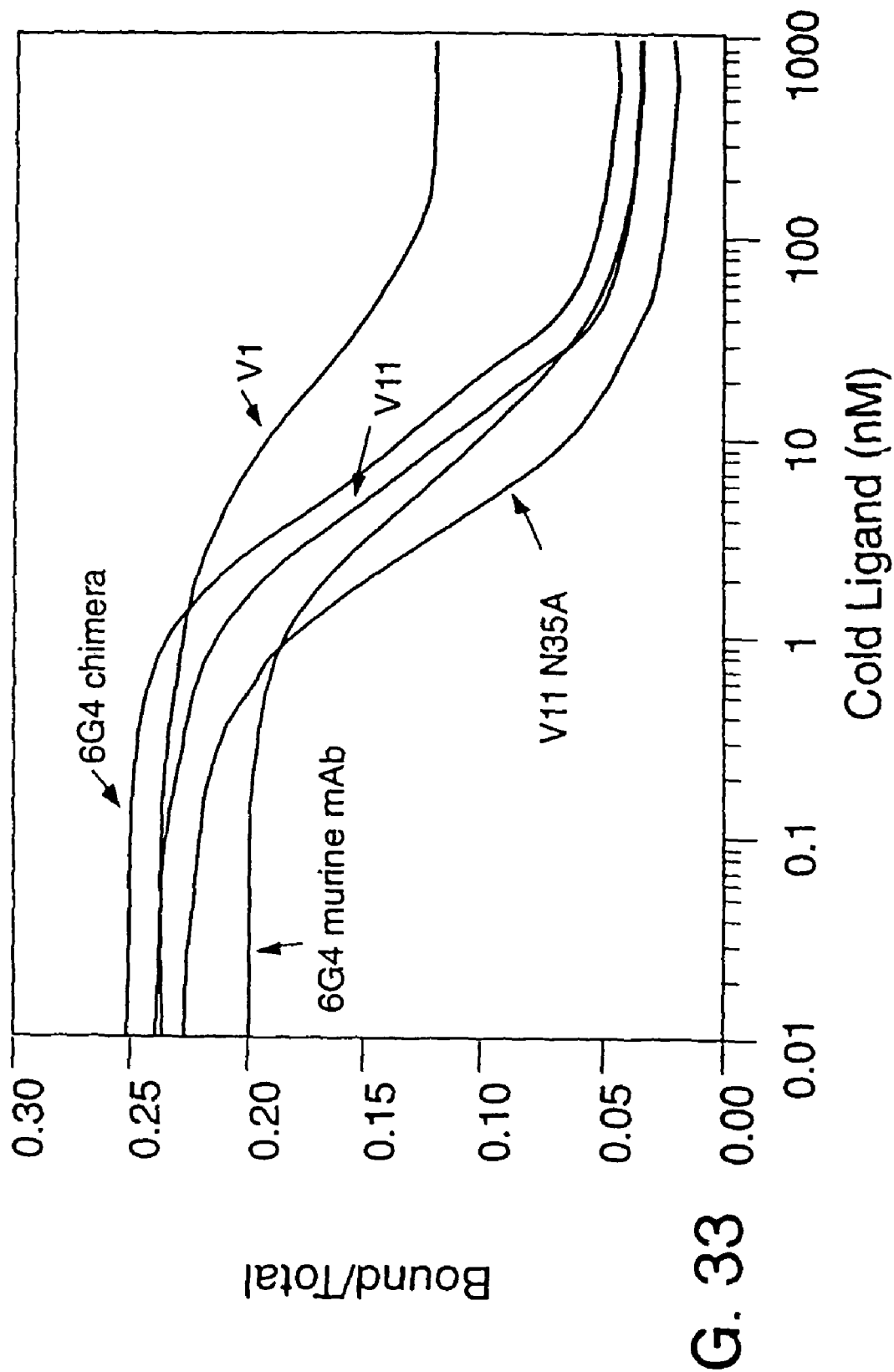
FIG. 33 is a Scatchard plot depicting the inhibition of $^{125}$I-IL-8 binding to human neutrophils exhibited by intact murine 6G4.2.5 antibody (denoted 6G4 murine mAb), 6G4.2.5 murine-human chimera Fab (denoted 6G4 chimera), humanized 6G4.2.5 Fab versions 1 and 11 (denoted V1 and V11), and variant 6G4.2.5V11N35A Fab (denoted V11N35A).
Figure 34A:
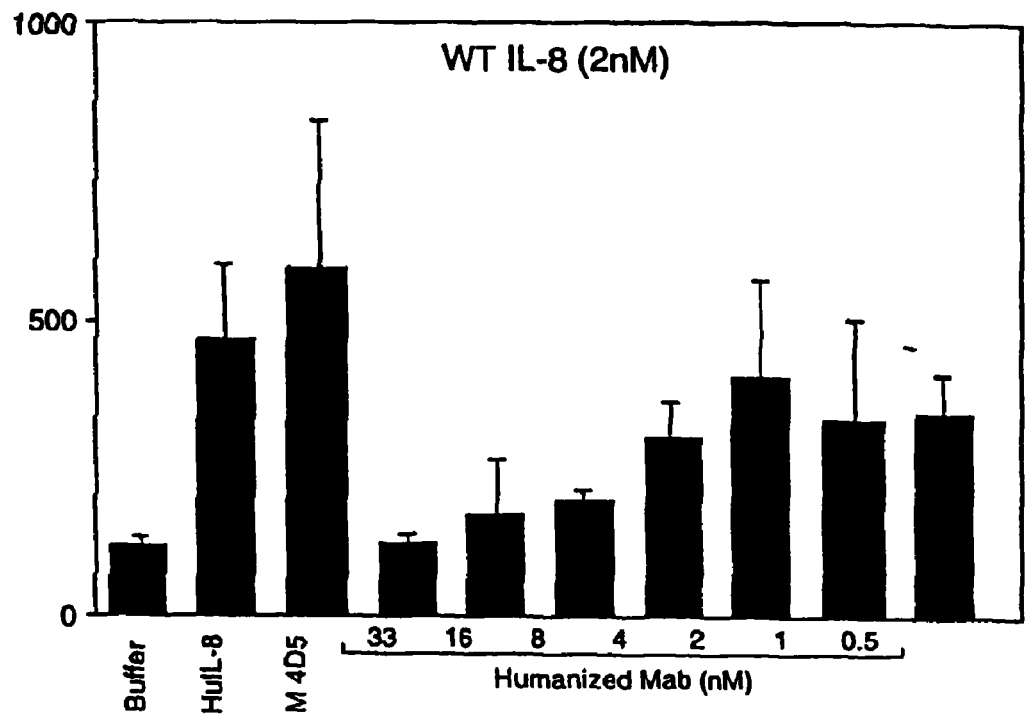
FIGS. 34A, 34B, 34C and 34D are graphs depicting the ability of 6G4.2.5V11N35A Fab to inhibit human wild type IL-8, human monomeric IL-8, rabbit IL-8, and rhesus IL-8 mediated neutrophil chemotaxis, respectively.
Figure 34B:
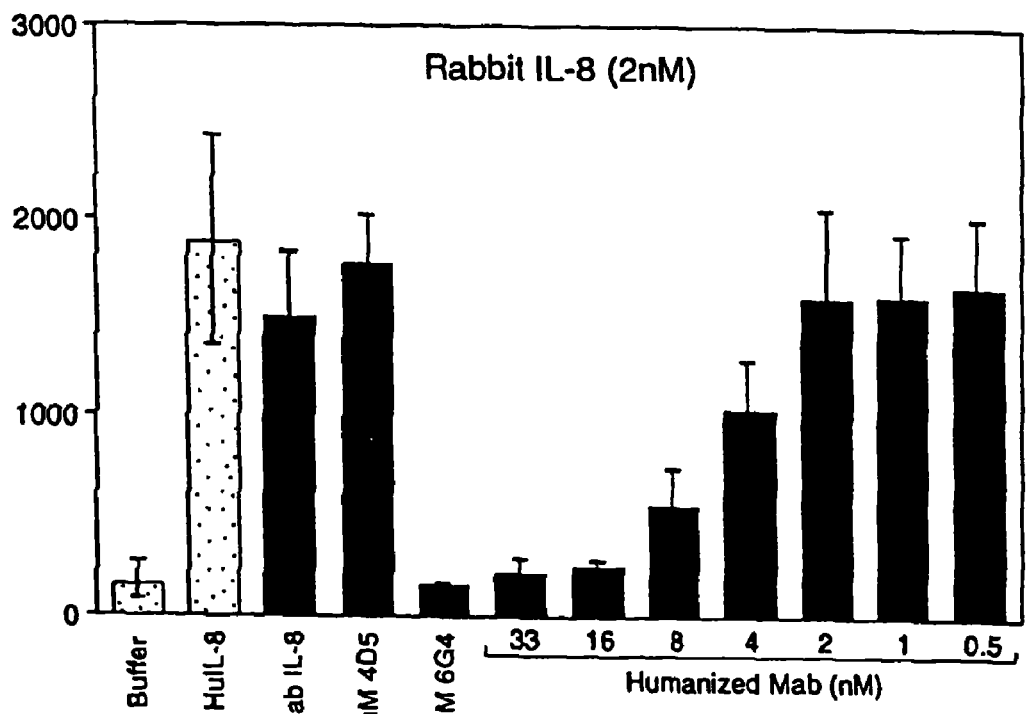
Figure 34C:
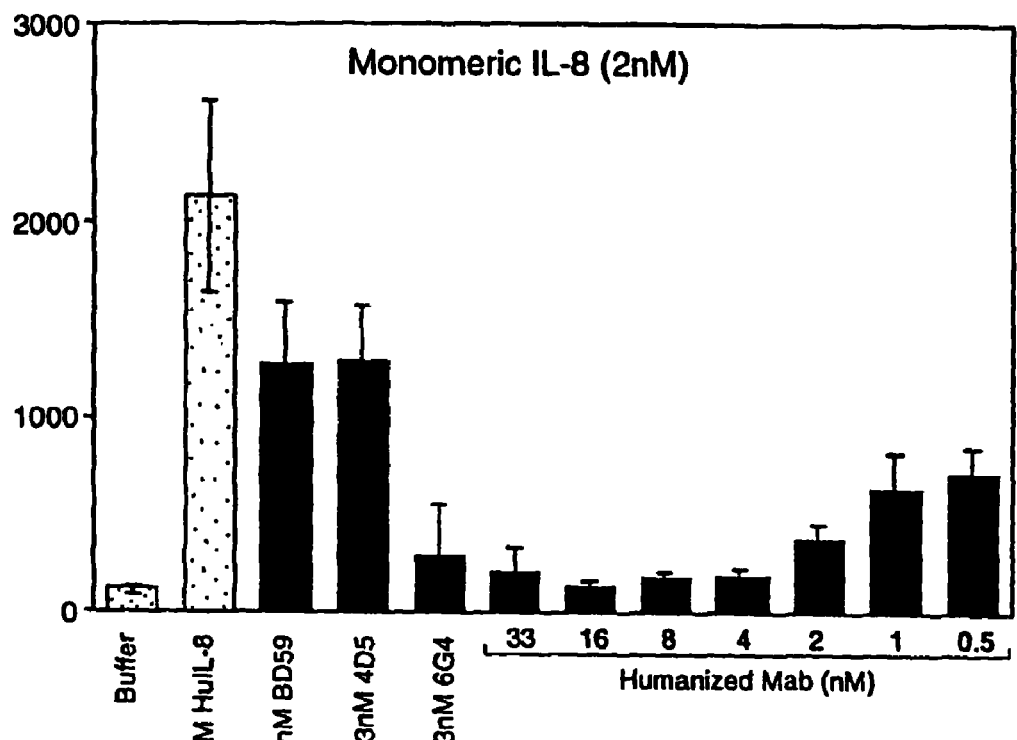
Figure 34D:
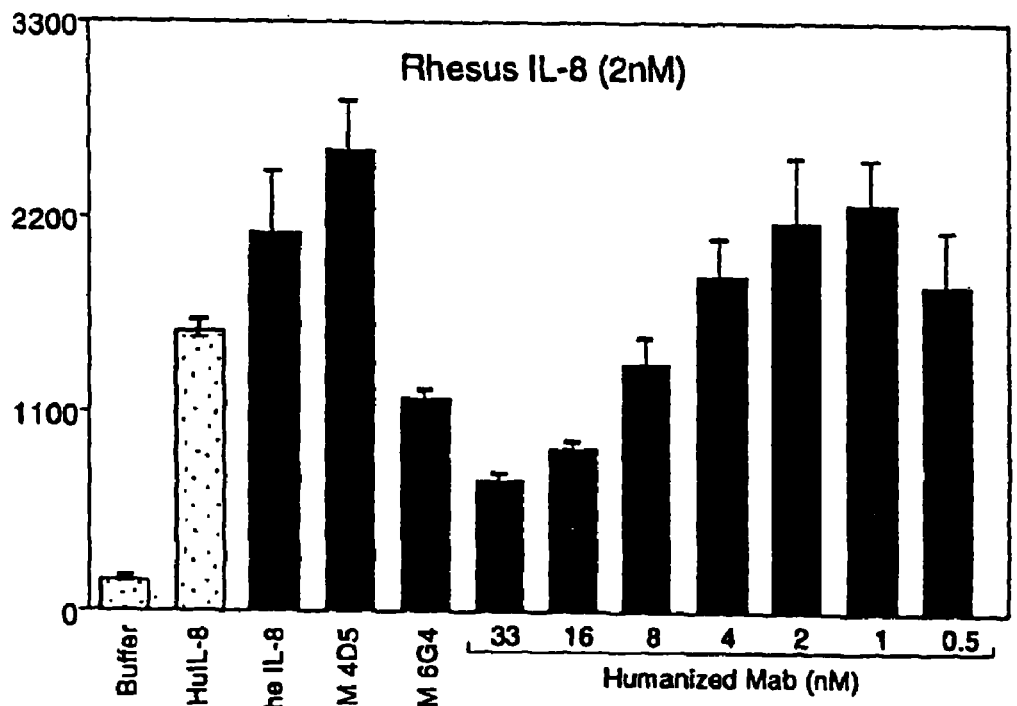

Soluble 6G4V11N35A Fab antibody was made by transforming an amber non-suppressor strain of E. coli, 34B8, with pPh6G4.V11 and growing the culture in low phosphate medium for 24 hours. The periplasmic fraction was collected and passed over a Hi-Trap Protein-G column (Pharmacia, Piscataway, N.J.) followed by a desalting and concentration step. The protein was analyzed by SDS-PAGE, mass spectrometry and amino acid analysis. The protein had the correct size and amino acid composition (FIG. 35). The 6G4V11N35A Fab was tested for its ability to inhibit $^{125}$I-IL-8 binding to human neutrophils and to inhibit IL-8 mediated neutrophil chemotaxis as described in Section (B)(1) and (B)(2) above. As shown in FIG. 33, hybridoma-derived intact murine antibody (6G4 murine mAB), recombinant 6G4 murine-human chimera Fab, recombinant humanized Fab versions 1 and 11, and 6G4V11N35A Fab were found to inhibit $^{125}$I-IL-8 binding to human neutrophils with an average $IC_{50}$ of 5 nM, 8 nM, 40 nM, 10 nM and 3 nM, respectively. The 6G4V11N35A Fab had at least a 2-fold higher affinity than the 6G4.2.5 chimera Fab and a 3-fold higher affinity than 6G4V11. As shown in FIG. 34, the 6G4V11N35A Fab was found to inhibit IL-8 mediated neutrophil chemotaxis induced by both wild type and monomeric human IL-8, and by two different animal species of IL-8, namely, rabbit and rhesus. The irrelevant isotype control Fab (4D5) did not inhibit neutrophil migration. The average $IC_{50}$ values were 3 nM (wt IL-8), 1 nM (monomeric IL-8), 5 nM (Rabbit IL-8), and 10 nM (Rhesus IL-8).

K. Construction of a 6G4V11N35A F(ab')$_2$ Leucine Zipper

Production of a F(ab')$_2$ version of the humanized anti-IL-8 6G4V11N35A Fab was accomplished by constructing a fusion protein with the yeast GCN4 leucine zipper. The expression plasmid p6G4V11N35A.F(ab')$_2$ was made by digesting the plasmid p6G425chim2.fab2 with the restriction enzymes bsaI and apaI to remove the DNA sequence encoding the 6G4.2.5 murine-human chimeric Fab and replacing it with a 2620 bp bsaI-apaI fragment from pPh6G4.V11N35A. The plasmid p6G425chim2.fab2 is a derivative of pS1130 which encodes a fusion protein (the GCN4 leucine zipper fused to the heavy chain of anti-CD18) and the light chain of anti-CD18 antibody. The expression plasmid p6G4V11N35A.F(ab')$_2$ was deposited on Feb. 20, 1996 with the American Type Culture Collection, 12301 Parklawn Drive, Rockville, Md., U.S.A. (ATCC) and assigned ATCC Accession No. 97890. A pepsin cleavage site in the hinge region of the antibody facilitates the removal of the leucine zipper leaving the two immunoglobin monomers joined by the cysteines that generate the interchain disulfide bonds. The DNA and protein sequence of the h6G4V11N35A.F(ab')$_2$ are depicted in FIGS. 35-37.

An expression host cell was obtained by transforming *E. coli* strain 49D6 with p6G4V11N35A.F(ab')$_2$ essentially as described in Section (II)(3)(C) above. The transformed host *E. coli* 49D6 (p6G4V11N35A.F(ab')$_2$) was deposited on Feb. 20, 1997 at the ATCC and assigned ATCC Accession No. 98332. Transformed host cells were grown in culture, and the 6G4V11N35A F(ab')$_2$ product was harvested from the host cell periplasmic space essentially as described in Section (II)(3)(F) above.

L. Characterization of the Humanized 6G4V11N35A F(ab')$_2$ Leucine Zipper

Figure 38:
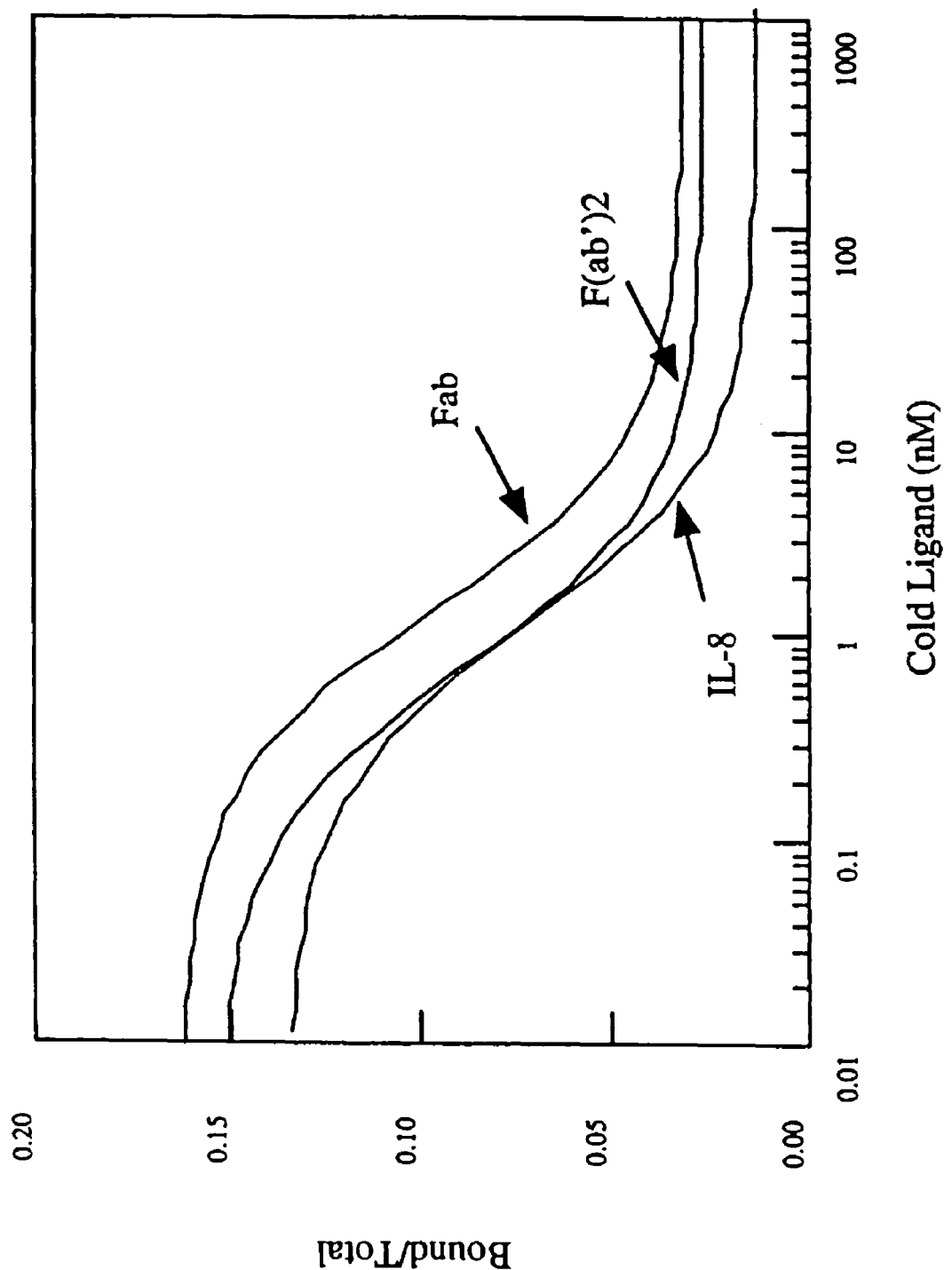
FIG. 38 is a Scatchard plot depicting the inhibition of $^{125}$I-IL-8 binding to human neutrophils exhibited by 6G4.2.5V11N35A Fab (denoted Fab), 6G4.2.5V11N35A F(ab')$_2$ (denoted F(ab')$_2$), and human wild type IL-8 control (denoted IL-8).

The 6G4V11N35A Fab and F(ab')$_2$ were tested for their ability to inhibit $^{125}$I-IL-8 binding to neutrophils according to the procedures described in Section (B)(1) above. The displacement curves from a representative binding experiment performed in duplicate is depicted in FIG. 38. Scatchard analysis of this data shows that 6G4V11N35A F(ab')$_2$ inhibited $^{125}$I-IL-8 binding to human neutrophils with an average IC$_{50}$ of 0.7 nM (+/−0.2). This is at least a 7 fold increase in affinity compared to the hybridoma-derived intact murine antibody (average IC$_{50}$ of 5 nM) and at least a 2.8 fold increase in affinity over the Fab version (average IC$_{50}$ of 2 nM).

Figure 39:
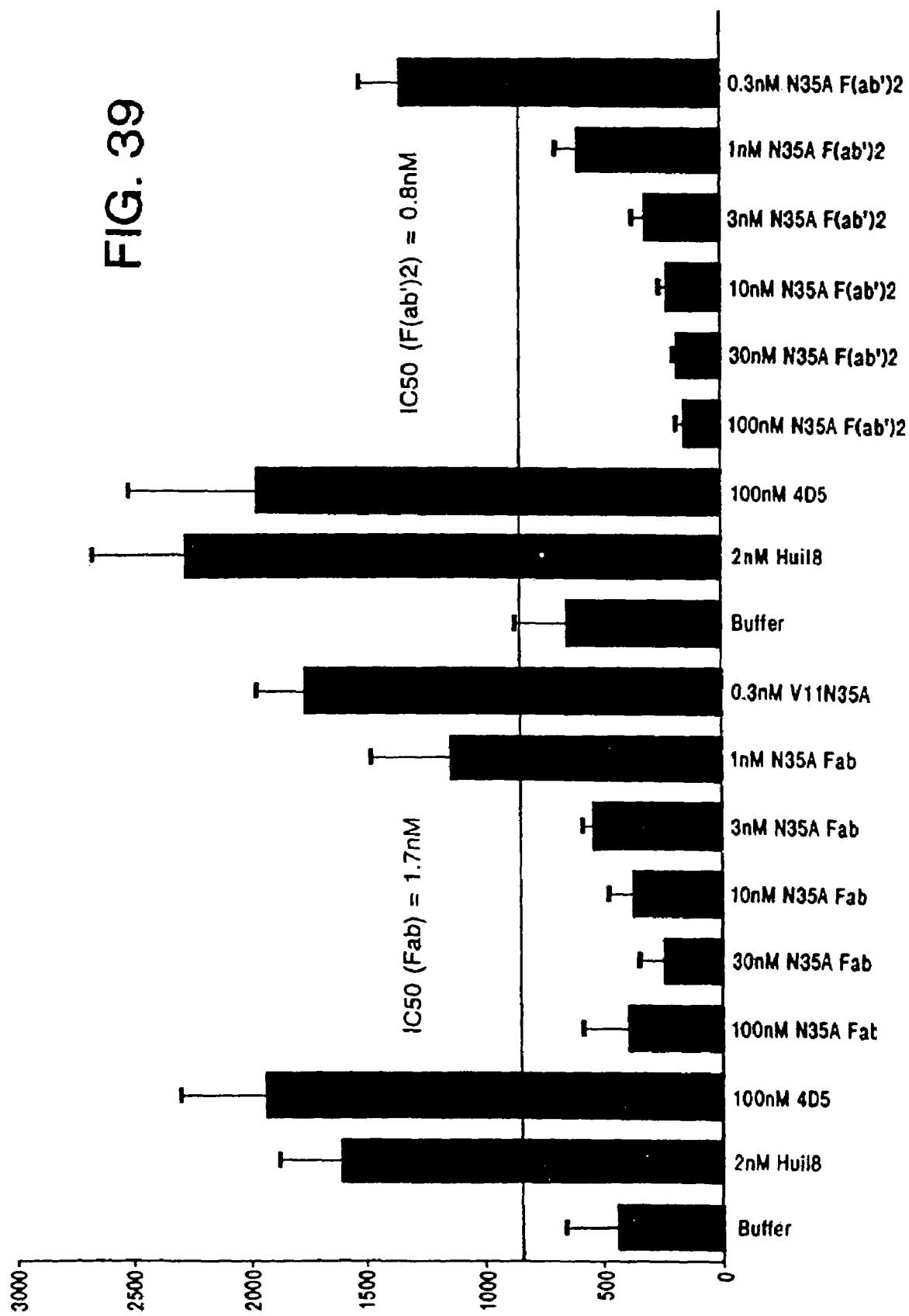
FIG. 39 is a graph depicting a comparison of the wild type human IL-8 mediated neutrophil chemotaxis inhibition activities of the 6G4.2.5V11N35A F(ab')$_2$ and 6G4.2.5V11N35A Fab. Inhibition data are presented for 6G4.2.5V11N35A Fab samples (denoted "N35A Fab") and 6G4.2.5V11N35A F(ab')$_2$ samples (denoted N35A F(ab')$_2$) at concentrations of 0.3, 1, 3, 10, 30, and 100 nM, for an isotype control antibody (denoted as "4D5") sample at a concentration of 100 nM, and for a no antibody control sample, in the presence of 2 nM human wild type IL-8. In addition, inhibition data are presented for no IL-8 buffer control samples (denoted "Buffer").
Figure 40:
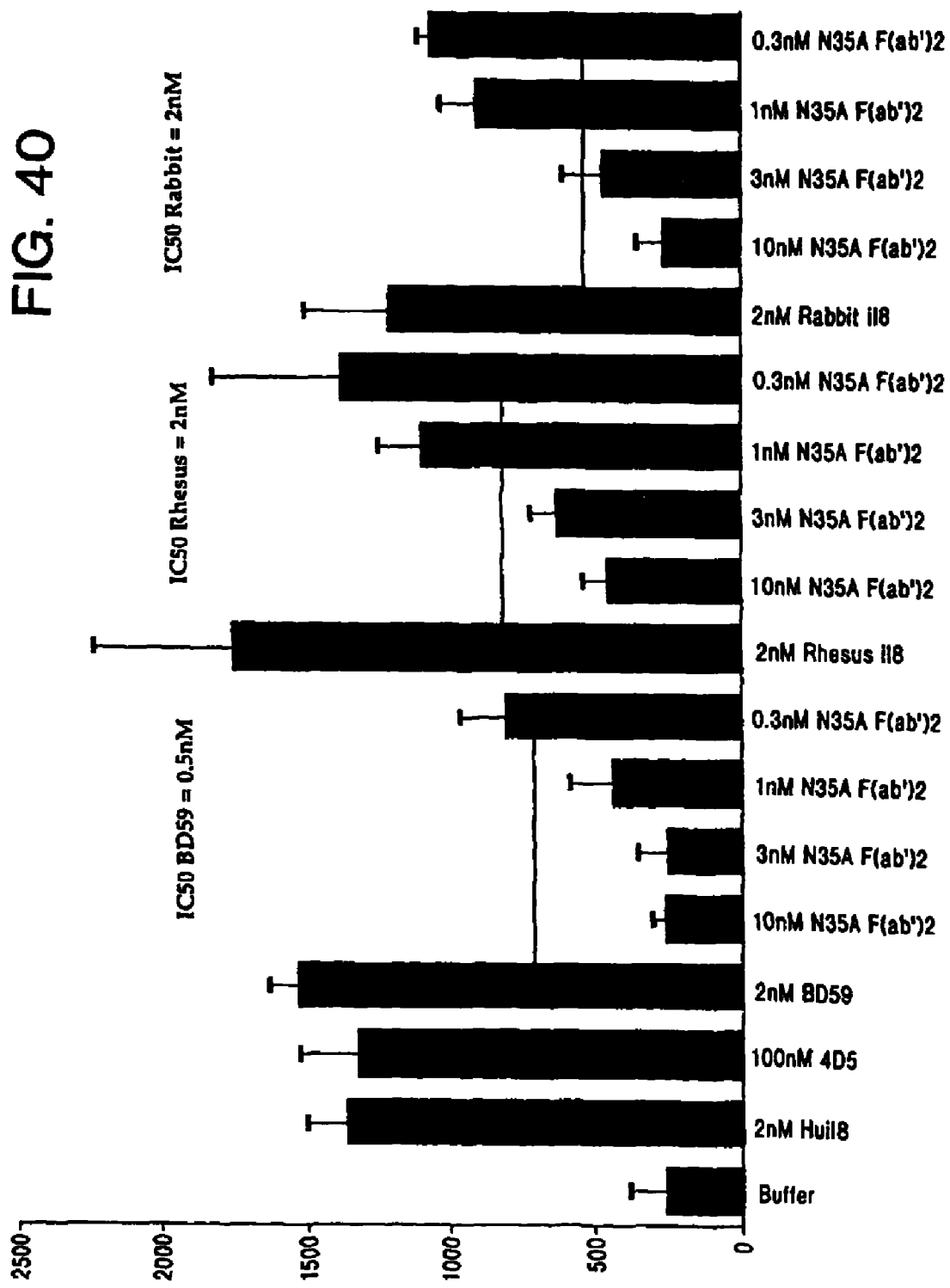
FIG. 40 is a graph depicting the ability of 6G4.2.5V11N35A F(ab')$_2$ to inhibit human monomeric IL-8, rhesus IL-8, and rabbit IL-8 mediated neutrophil chemotaxis. Human monomeric IL-8 mediated neutrophil chemotaxis data are presented for 6G4.2.5V11N35A F(ab')$_2$ samples at concentrations of 0.3, 1, 3, and 10 nM, for an isotype control antibody (denoted as "4D5") sample at a concentration of 100 nM, and for a no. antibody control sample (denoted as "BD59"), in the presence of human monomeric IL-8 (denoted as "BD59") at a concentration of 0.5 nM. Rhesus IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rhesus IL-8 at a concentration of 2 nM. Rabbit IL-8 mediated neutrophil chemotaxis data are presented for 6G4.2.5V11N35A F(ab')$_2$ samples at concentrations of 0.3, 1, 3, and 10 nM, and for a no antibody control sample, in the presence of rabbit IL-8 at a concentration of 2 nM. In addition, inhibition data are presented for a no IL-8 buffer control sample (denoted as "Buffer") and for a 2 nM human wild type IL-8 (denoted as "HuIL-8").

The 6G4V11N35A F(ab')$_2$ was also tested for its ability to inhibit IL-8 mediated neutrophil chemotaxis according to the procedures described in Section (B)(2) above. The results of a representative chemotaxis experiment performed in quadruplicate are depicted in FIG. 39. As shown in FIG. 39, the 6G4V11N35A F(ab')$_2$ inhibited human IL-8 mediated neutrophil chemotaxis. The 6G4V11N35A F(ab')$_2$ exhibited an average IC$_{50}$ value of 1.5 nM versus 2.7 nM for the 6G4V11N35A Fab, which represents an approximately 2 fold improvement in the antibody's ability to neutralize the effects of IL-8. The irrelevant isotype control Fab (4D5) did not inhibit neutrophil migration. Furthermore, the 6G4V11N35A F(ab')$_2$ antibody retained its ability to inhibit IL-8 mediated neutrophil chemotaxis by monomeric IL-8 and by two different animal species of IL-8, namely rabbit and rhesus, in neutrophil chemotaxis experiments conducted as described above. An individual experiment is shown in FIG. 40. The average IC$_{50}$ values were 1 nM (monomeric IL-8), 4 nM (Rabbit IL-8), and 2.0 nM (Rhesus IL-8).

M. Random Mutagenesis of Light Chain Amino acid (N35A) in CDR-L1 of Humanized Antibody 6G4V11

A 3-fold improvement in the IC$_{50}$ for inhibiting $^{125}$I-IL-8 binding to human neutrophils was observed when alanine was substituted for asparagine at position 35 in CDR-L1 (light chain) of the humanized 6G4V11 mAb as described in Section (I) above. This result might be attributed to an improvement in the contact between the antigen-antibody binding interfaces as a consequence of the replacement of a less bulky nonpolar side chain (R-group) that may have altered the conformation of CDR-L1 or neighboring CDR-H3 (heavy chain) to become more accessible for antigen docking. The acceptance of alanine at position 35 of CDR-L1 suggested that this position contributed to improved affinity and that an assessment of the re-modeling of CDR loops/antigen-binding region(s) by other amino acids at this location was warranted. Selection of an affinity matured version of the humanized 6G4.V11 mAB (Kunkel, T. A., *Proc. Natl. Acad. Sci. USA*, 82:488 (1995)) was accomplished by randomly mutagenizing position 35 of CDR-L1 and constructing an antibody-phage library. The codon for Asparagine (N) at position 35 of CDR-L1, was targeted for randomization to any of the 20 known amino acids.

Initially, a stop template, pPh6G4.V11-stop, was made to eliminate contaminating wild-type N35 sequence from the library. This was accomplished by performing site-directed mutagenesis (Muta-Gene Kit, Biorad, Ricmond, Calif.) of pPH6G4V11 (described in Section (H) above) to replace the codon (AAC) for N35 with a stop codon (TAA) using the primer SL.97.2 (SEQ ID NO:63)(FIG. 42). The incorporation of the stop codon was confirmed by DNA sequencing. Subsequently, uracil containing single-stranded DNA derived from *E. coli* CJ236 transformed with the stop template was used to generate an antibody-phage library following the method described by Lowman (*Methods in Molecular Biology*, 87 Chapter 25:1-15 (1997). The variants generated from this library were predicted to produce a collection of antibodies containing one of the 20 known amino acids at position N35 in CDR-L1. The amino acid substitutions were accomplished by site-directed mutagenesis using the degenerate oligonucleotide primer (SL.97.3) with the sequence NNS (N=A/G/T/C; S=G/C;) (SEQ ID NO: 64) (FIG. 42). This codon usage should allow for the expression of any of the 20 amino acids—including the amber stop codon (TAG). The collection of antibody-phage variants was transfected into *E. coli* strain XL-1 blue (Stratagene, San Diego, Calif.) by electroporation and grown at 37° C. overnight to amplify the library. Selection of tight binding humanized 6G4V11 Fab's were accomplished by panning the library on IL-8 coated 96-well plates as described in Section (I) above. Prior to panning, the number of phage/library was normalized to 1.1×10$^{13}$ phage/ml (which produces a maximum OD$_{270}$ reading=1 OD unit) and IL-8 coated plates were incubated with blocking solution (25 mN Carbonate buffer containing 50 mg/ml skim milk) for 2 hours before the addition of phage (each sort used eight IL-8 coated wells/library). After the blocking and washing steps, every sort began with the addition of 100 ul of antibody-phage (titered at 1.1×10$^{13}$ phage/ml) to each of eight IL-8 coated wells followed by an 1 hour incubation at 25° C. The non-specifically bound antibody-phage were removed by 10 quick washes with PBS-0.05% Tween 20 (PBS-Tween). For sort #1, a low stringency wash (100 ul PBS-Tween/well for 10 minutes at 25° C.) was employed to capture the small proportion of tight binding antibody-phage bound to the immobilized IL-8. The antibody-phage variants specifically bound to IL-8 were eluted with 100 ul/well of 200 mM Glycine pH 2.0 for 5 minutes at 25° C. The eluted antibody-phage variants from the 8 wells were then pooled and neutralized with 1M Tris-HCl pH 8.0 (⅓ the elution volume). The phage were titered and propagated as described in Section (I) above. The stringency of the washes were successively increased with each round of panning depending upon the percent recovery of phage at the end of a sort. The wash conditions were as follows: sort #2 (4×15 minute intervals; total time=60 minutes) and sort #3 (either #3a: 8×15 minute intervals or #3b: 12×10 minute intervals; total time=120 minutes). The total number of phage recovered was progressively reduced after each sort suggesting that non- or weak-binders were being selected against. The recovery of the negative control (the antibody-phage stop variant) was constant throughout the panning (approximately 0.0001 to 0.00001 percent).

Eighteen random variants from sort #3 were analyzed by DNA sequencing to look for an amino acid consensus at position 35 of CDR-L1. The data presented in FIG. 43A showed that Glycine occupied position 35 in 33% of the variants sequenced. However, after correcting for the number of NNS codon combinations/amino acid, the frequency of Glycine was reduced to 16.6%. Glutamic Acid was represented with the highest frequency (22%) followed by Aspartic Acid and Glycine (16.6%). The frequencies of recovery of the wild-type Asparagine and substituted Alanine were only 5.6%. Interestingly, the high frequency of Glycine may suggest that a much wider range of conformations might be allowed for the loop of CDR-L1 which may be attributed to the reduction in steric hindrance of bond angle ($\phi$-$\psi$) pairing as a result of the single hydrogen atom as the side chain. Conversely, Glutamic Acid at position 35 might restrict the flexibility of the loop by imposing less freedom of rotation imposed by the more rigid and bulky charged polar side chain.

Figure 43B:
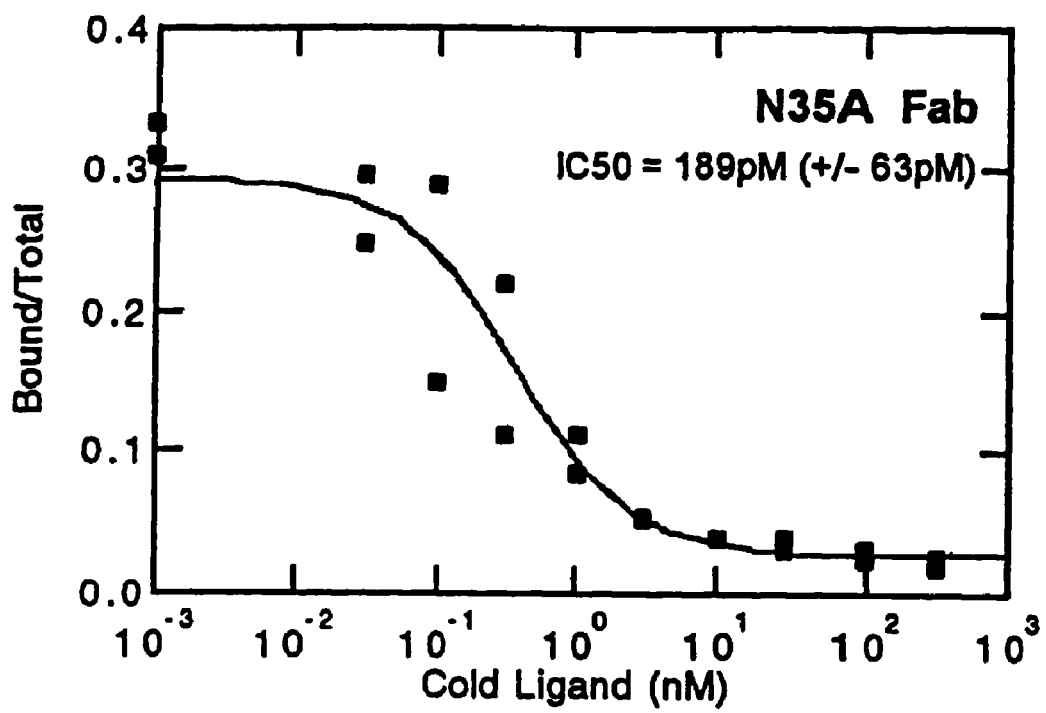
FIGS. 43B, 43C, 43D and 43E are graphs of displacement curves depicting the inhibition of $^{125}$I-IL-8 binding to neutrophils exhibited by the 6G4V11N35A, 6G4V11N35D, 6G4V11N35E and 6G4V11N35G Fab's.
Figure 43C:
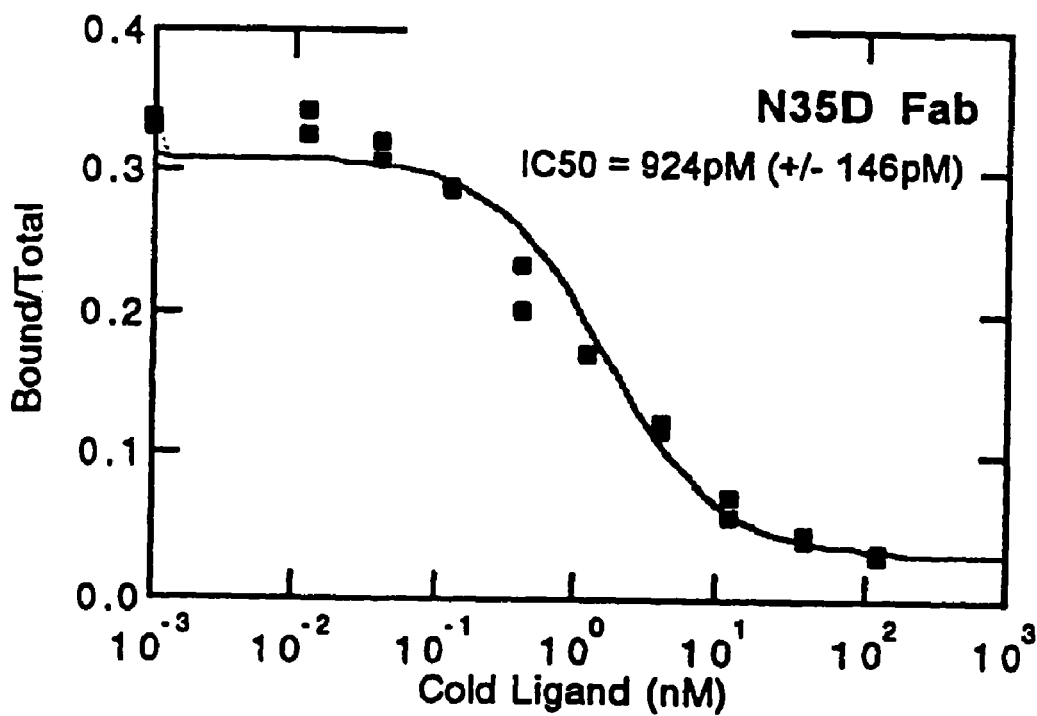
Figure 43D:
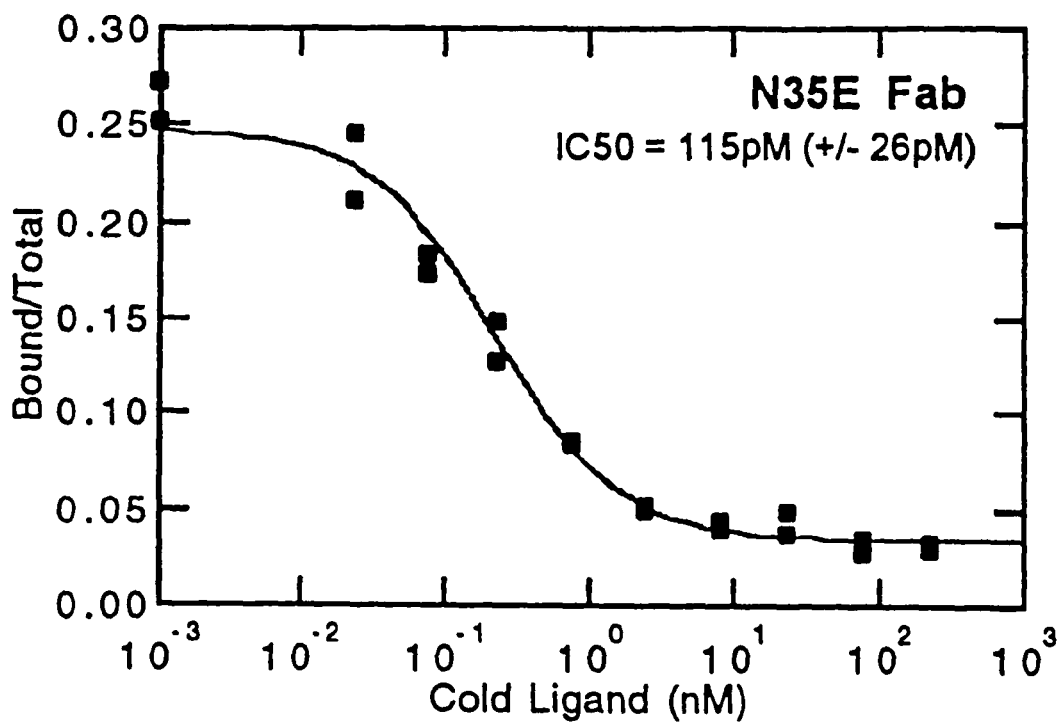
Figure 43E:
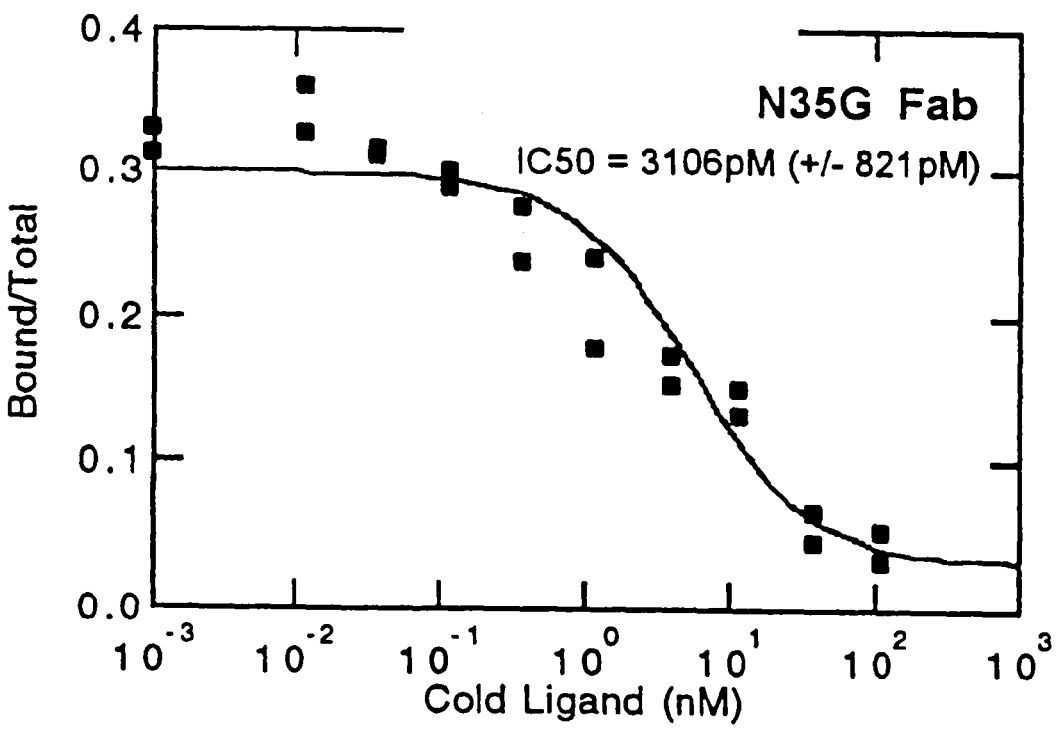

Soluble Fab's of the affinity matured variants (N35G, N35D, N35E and N35A) were made as described in Section (J) above for evaluating their ability to block IL-8 binding. As shown in FIG. 43B, variants N35A, N35D, N35E and N35G were found to inhibit $^{125}$I-IL-8 binding to human neutrophils with an approximate IC$_{50}$ of 0.2 nM, 0.9 nM, 0.1 nM and 3.0 nM, respectively. All of the affinity matured variants showed an improvement in binding IL-8 ranging from 3-100 fold compared to the humanized 6G4V11 mAb. The affinity-matured variant, 6G4V11N35E, was 2-fold more potent in blocking IL-8 binding to human neutrophils than the alanine-scan variant, 6G4V11N35A.

Equilibrium and kinetic measurements of variants 6G4V11N35A and 6G4V11N35E were determined using KinEXA™ automated immunoassay system (Sapidyne Instruments Inc., Id. City, Id.) as described by Blake et al., *J. Biol. Chem.* 271: 27677 (1996). The procedure for preparing the antigen-coated particles was modified as follows: 1 ml of activated agarose beads (Reacti-Gel 6X; Pierce, Rockford, Ill.) were coated with antigen in 50 mM Carbonate buffer pH 9.6 containing 20 ug/ml of human IL-8 and incubated with gentle agitation on a rocker overnight at 25° C. The IL-8 coated beads were then washed twice with 1M Tris-HCl pH 7.5 to inactivate any unreactive groups on the beads and blocked with Superblock (Pierce, Rockford, Ill.) for 1 hour at 25° C. to reduce non-specific binding. The beads were resuspended in assay buffer (0.1% bovine serum albumin in PBS) to a final volume of 30 ml. A 550 ul aliquot of the IL-8 coated bead suspension was used each time to pack a fresh 4 mm high column in the KinEXA observation cell. The amount of unbound antibody from the antibody-antigen mixtures captured by the IL-8-coated beads in both the equilibrium and kinetic experiments was quantified using a fluorescently labeled secondary antibody. Murine 6G4.2.5 was detected with a R-PE AffiniPure F(ab')$_2$ goat anti-mouse IgG, Fc fragment specific 2° antibody (Jackson Immuno Research Laboratories, West Grove, Pa.) and humanized affinity matured N35A (Fab and F(ab')$_2$) and N35E Fab were detected with a R-PE AffiniPure F(ab')$_2$ donkey anti-human IgG (H+L) 2° antibody (Jackson Immunoresearch Laboratories, West Grove, Pa.); both at a 1:1000 dilution.

Equilibrium measurements were determined by incubating a constant amount of anti-IL-8 antibody (0.005 ug/ml) with various concentrations of human IL-8 (0, 0.009, 0.019, 0.039, 0.078, 0.156, 0.312, 0.625, 1.25, 2.5 nM). The antibody-antigen mixture was incubated for 2 hours at 25° C. to allow the molecules to reach equilibrium. Subsequently, each sample was passed over a naive IL-8 coated bead pack in the KinEXA observation cell at a flow rate of 0.5 ml/minute for a total of 9 minutes/sample. The equilibrium constant (Kd) was calculated using the software provided by Sapidyne Instruments Inc.

Rates of association (ka) and dissociation (kd) were determined by incubating together a constant amount of antibody and antigen, and measuring the amount of uncomplexed anti-IL-8 bound to the IL-8 coated beads over time. The concentration of antibody used in the kinetic experiments was identical to that used in the equilibrium experiment described above. Generally, the amount of human IL-8 used was the concentration derived from the binding curves of the equilibrium experiment that resulted in 70% inhibition of anti-IL-8 binding to the IL-8 coated beads. Measurements were made every 15 minutes to collect approximately nine data points. The ka was calculated using the software provided by Sapidyne Instruments, Inc. The off rate was determined using the equation: kd=Kd/ka.

Figure 44:
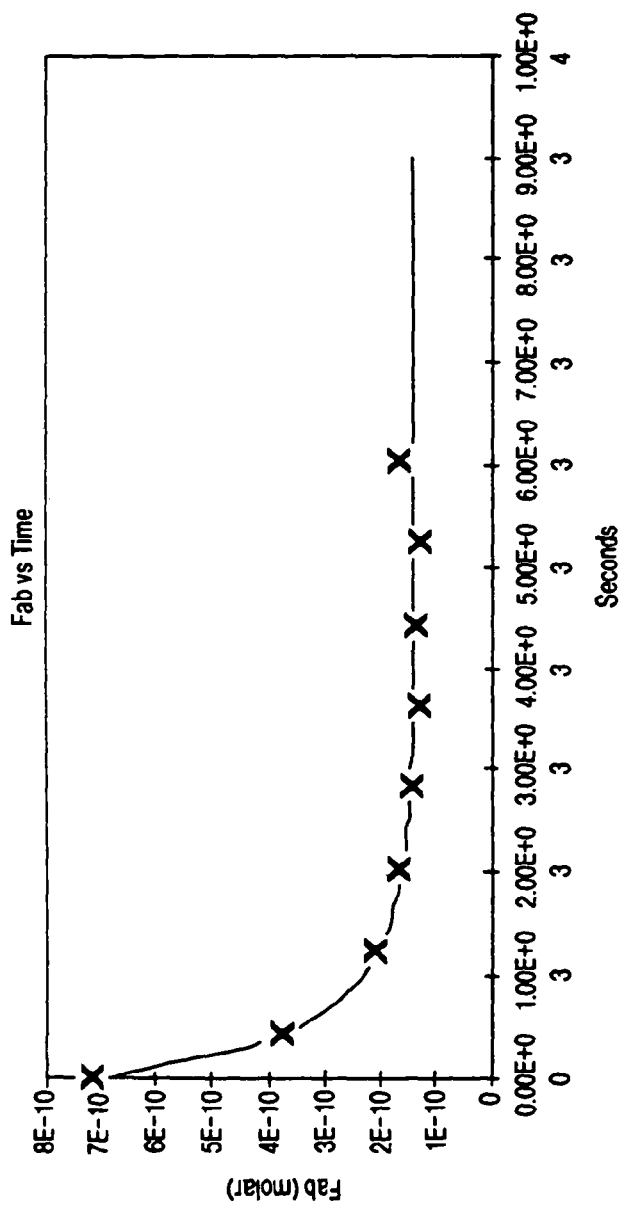
FIG. 44 contains a graph depicting the typical kinetics of an anti-IL-8 antibody fragment (6G4V11N35A F(ab')$_2$) binding to IL-8.

FIG. 44 shows the equilibrium constants (Kd) for the affinity matured variants 6G4V11N35E and 6G4V11N35A Fab's were approximately 54 pM and 114 pM, respectively. The improvement in affinity of 6G4V11N35E Fab for IL-8 can be attributed to a 2-fold faster rate of association ($K_{on}$) of 4.7× $10^6$ for 6G4V11N35E Fab versus 2.0×$10^6$ for 6G4V11N35A F(ab')$_2$. (The Kd of the 6G4V11N35A F(ab')2 and 6G4V11N35A Fab are similar.) The dissociation rates ($K_{off}$) were not significantly different. Molecular modeling suggests that substitution of Aspargine with Glutamic Acid might either affect the antibody's interaction with IL-8 directly or indirectly by neutralizing the charge of neighboring residues R98 (CDR-H3) or K50 (CDR-L2) in the CDR's to facilitate contact with IL-8. Another effect might be the formation of a more stable loop conformation for CDR-L1 that could have facilitated more appropriate contacts of other CDR-L1 loop residues with IL-8. The DNA (SEQ ID NO: 65) and amino acid (SEQ ID NO:62) sequences of p6G4V11N35E.Fab showing the Asparagine to Glutamic Acid substitution in the light chain are presented in FIG. 45.

N. Characterization of Humanized Anti-IL-8 Variant 6G4V11N35E Fab

Figure 46:
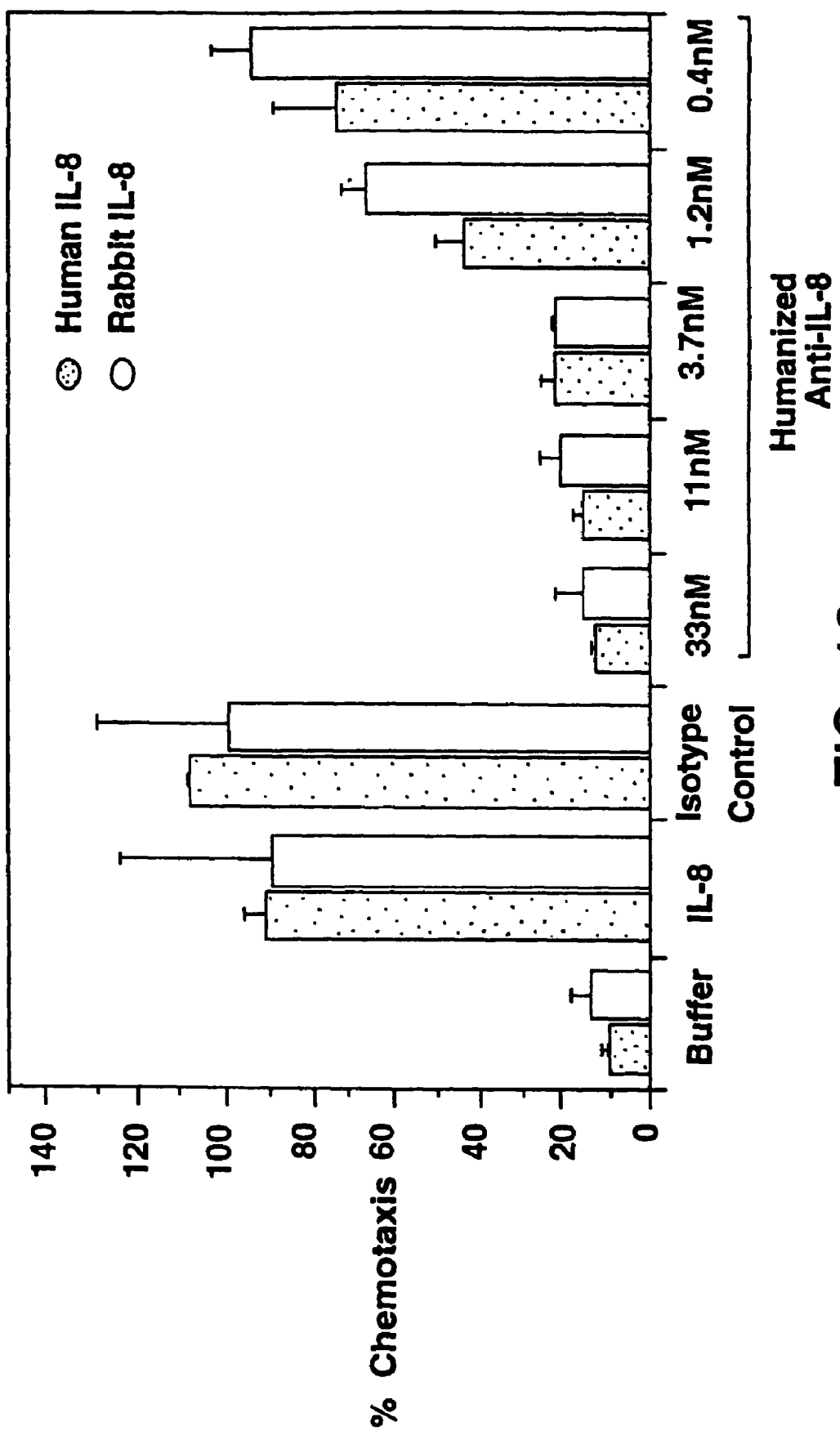
FIG. 46 is a graph depicting the ability of 6G4V11N35E Fab to inhibit human IL-8 (dark columns) and rabbit IL-8
Figure 49A:
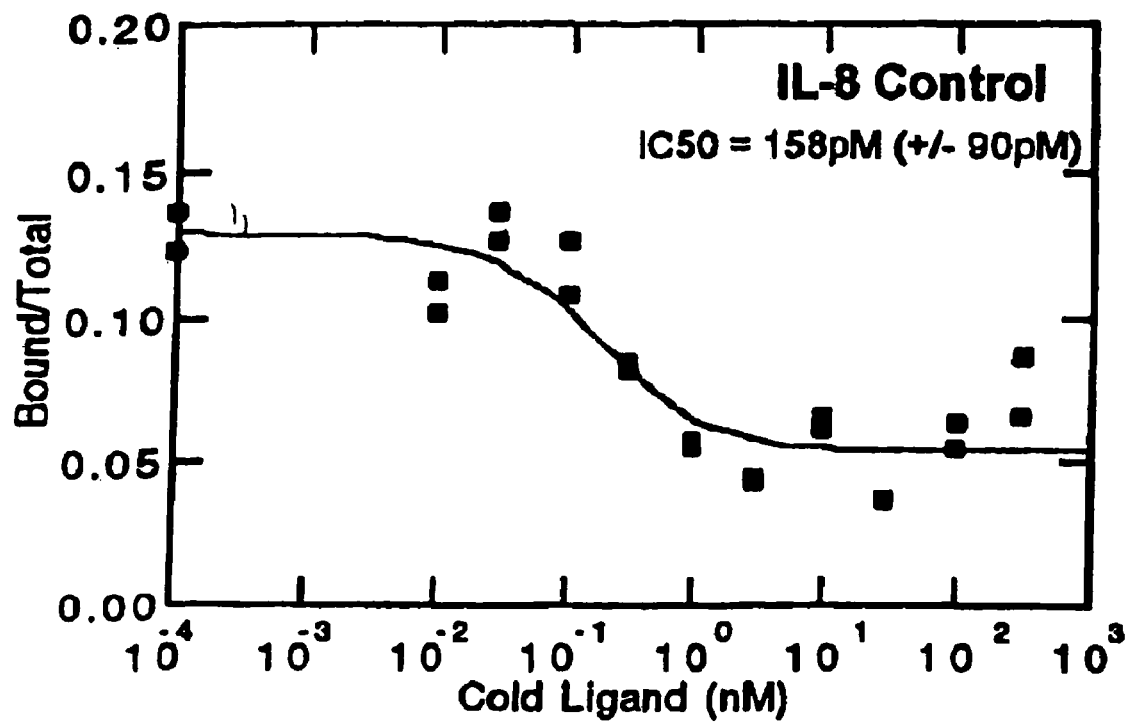
Figure 49B:
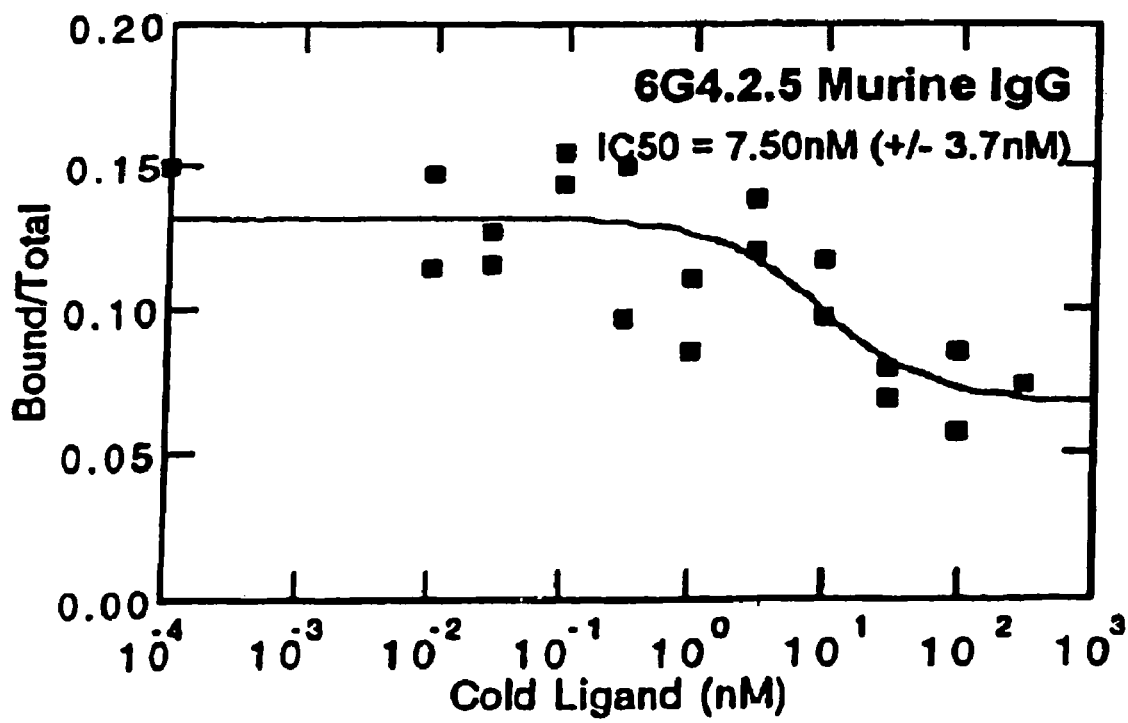
Figure 49C:
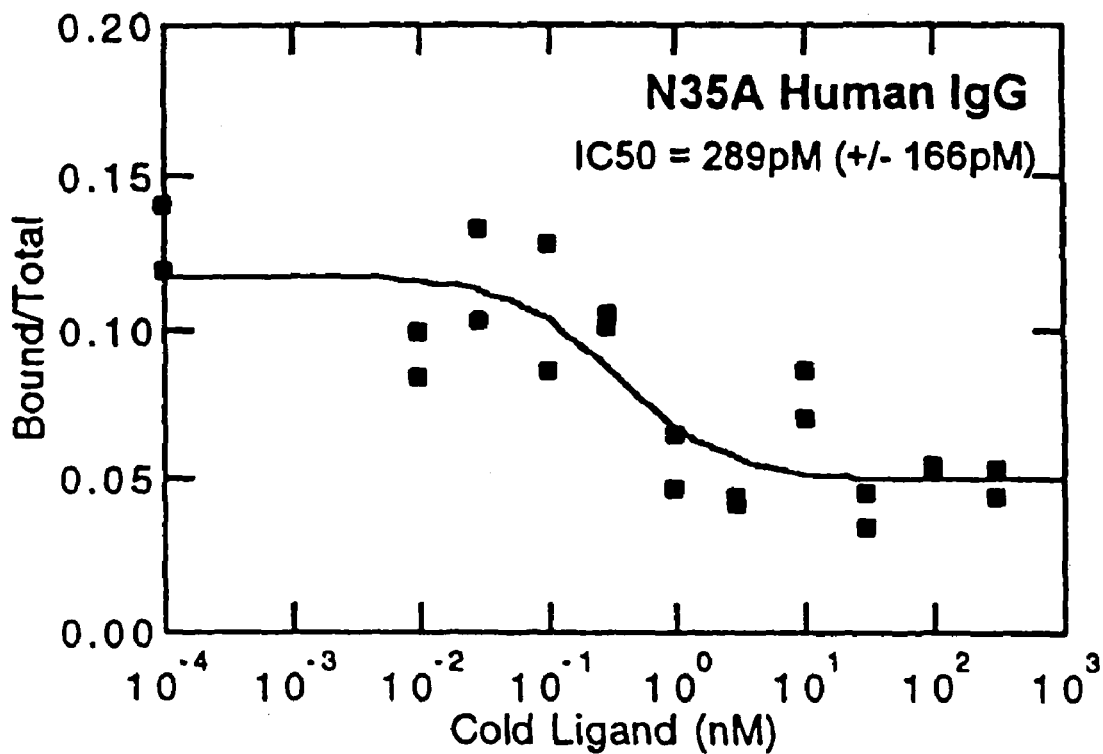
Figure 49D:
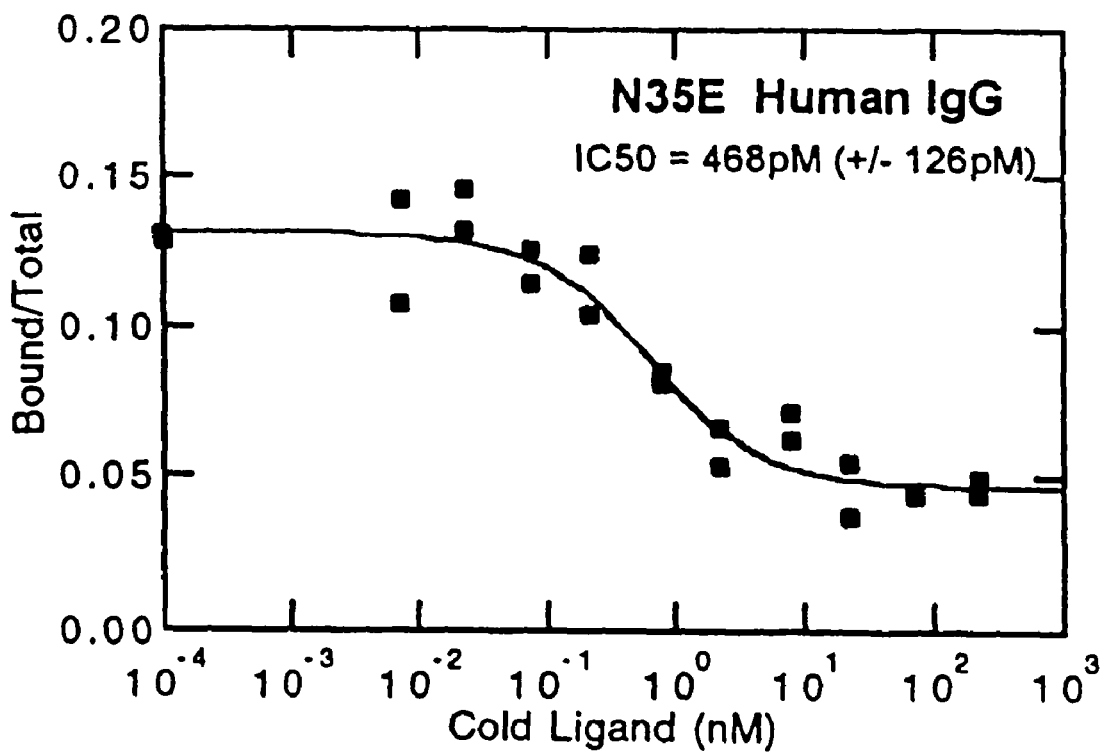

The affinity matured Fab variant, 6G4V11N35E, was tested for its ability to inhibit IL-8 mediated neutrophil chemotaxis as described in Section (B)(2) above. The reuseable 96-well chemotaxis chamber described in Section (B)(2) was replaced with endotoxin-free disposable chemotaxis chambers containing 5-micron PVP-free polycarbonate filters (ChemoTx101-5, Neuro Probe, Inc. Cabin John, Md.). As illustrated in FIG. 46, variant N35E effectively blocks IL-8 mediated neutrophil chemotaxis induced by a 2 nM stimulus of either rabbit or human IL-8. In fact, the level of inhibition at antibody concentrations between 3.7 nM-33 nM was not significantly different from the buffer control indicating variant N35E could completely inhibit this response. The IC$_{50}$'s for both rabbit and human IL-8 were approximately 2.8 nM and 1.2 nM, respectively. The irrelevant isotype control Fab (4D5) did not inhibit neutrophil migation indicating the results observed for the affinity matured variant, N35E, is IL-8 specific.

O. Construction of humanized 6G4V11N35E F(ab')$_2$ Leucine Zipper

A F(ab')$_2$ expression plasmid for 6G4V11N35E was constructed using methods similar to those described in Section (K) above. The expression plasmid, p6G4V11N35E.F(ab')₂, was made by digesting the plasmid p6G4V11N35A.F(ab')₂ (described in Section (K) above) with the restriction enzymes ApaI and NdeI to isolate a 2805 bp fragment encoding the heavy chain constant domain—GCN4 leucine zipper and ligating it to a 3758 bp ApaI-NdeI fragment of the pPH6G4V11N35E phage display clone (encoding 6G4V11N35E Fab) obtained as described in Section (M) above. The integrity of the entire coding sequence was confirmed by DNA sequencing.

P. Construction of the full length humanized 6G4V11N35A IgG Expression Plasmid The full length IgG₁ version of the humanized anti-IL8 variant 6G4V11N35A was made using a dicistronic DHFR-Intron expression vector (Lucas et al., *Nucleic Acids Res.*, 24: 1774-1779 (1996)) which contained the full length recombinant murine-human chimera of the 6G4.2.5 anti-IL8 mAb. The expression plasmid encoding the humanized variant 6G4V11N35A was assembled as follows. First an intermediate plasmid (pSL-3) was made to shuttle the sequence encoding the variable heavy chain of humanized anti-IL-8 variant 6G4V11N35A to pRK56G4chim.2Vh—which contains the variable heavy region of the chimeric 6G4.5 anti-IL8 antibody. The vector pRK56G4chim.Vh was digested with PvuII and ApaI to remove the heavy chain variable region of the chimeric antibody and religated with an 80 bp PvuII-XhoI synthetic oligonucleotide (encoding Leu4 to Phe29 of 6G4V11N35A) (FIG. 47) and a 291 bp XhoI-ApaI fragment from p6G4V11N35A.7 carrying the remainder of the variable heavy chain sequence of 6G4V11N35A to create pSL-3. This intermediate plasmid was used in conjunction with 2 other plasmids, p6G4V11N35A.F(ab')₂ and p6G425chim2.choSD, to create the mammalian expression plasmid, p6G4V11N35AchoSD.9 (identified as p6G425V11N35A.choSD in a deposit made on Dec. 16, 1997 with the ATCC and assigned ATCC Accession No. 209552). This expression construct was assembled in a 4-part ligation using the following DNA fragments: a 5,203 bp ClaI-BipI fragment encoding the regulatory elements of the mammalian expression plasmid (p6G425 chim2.choSD), a 451 bp ClaI-ApaI fragment containing the heavy chain variable region of the humanized 6G4V11N35A antibody (pSL-3), a 1,921 bp ApaI-EcoRV fragment carrying the heavy chain constant region of 6G4V11N35A (p6G425chim2.choSD) and a 554 bp EcoRV-BlpI fragment encoding the light chain variable and constant regions of 6G4V11N35A (p6G4V11N35A.F(ab')₂). The DNA sequence (SEQ ID NO: 68) of clone p6G4V11N35A.choSD.9 was confirmed by DNA sequencing and is presented in FIG. 48.

Q. Construction of the full length humanized 6G4V11N35E IgG Expression Plasmid A mammalian expression vector for the humanized 6G4V11N35E was made by swapping the light chain variable region of 6G4V11N35A with 6G4V11N35E as follows: a 7,566 bp EcoRV-BlpI fragment (void of the 554 bp fragment encoding the light chain variable region of 6G4V11N35A) from p6G4V11N35A.choSD.9 was ligated to a 554 bp EcoRV-BlpI fragment (encoding the light chain variable region of 6G4V11N35E) from pPH6G4V11N35E.7. The mutation at position N35 of the light chain of p6G4V11N35E.choSD.10 was confirmed by DNA sequencing.

R. Stable Cho Cell Lines for Variants N35A and N35E

For stable expression of the final humanized IgG1 variants (6G4V11N35A and 6G4V11N35E), Chinese hamster ovary (CHO) DP-12 cells were transfected with the above-described dicistronic vectors (p6G4V11N35A.choSD.9 and p6G4V11N35E.choSD.10, respectively) designed to coexpress both heavy and light chains (Lucas et al., *Nucleic Acid Res.* 24:1774-79 (1996)). Plasmids were introduced into CHO DP12 cells via lipofection and selected for growth in GHT-free medium (Chisholm, V. High efficiency gene transfer in mammalian cells. In: Glover, D M, Hames, B D. *DNA Cloning* 4. *Mammalian systems.* Oxford Univ. Press, Oxford pp 1-41 (1996)). Approximately 20 unamplified clones were randomly chosen and reseeded into 96 well plates. Relative specific productivity of each colony was monitored using an ELISA to quantitate the full length human IgG accumulated in each well after 3 days and a fluorescent dye, Calcien AM, as a surrogate marker of viable cell number per well. Based on these data, several unamplified clones were chosen for further amplification in the presence of increasing concentrations of methotrexate. Individual clones surviving at 10, 50, and 100 nM methotrexate were chosen and transferred to 96 well plates for productivity screening. One clone for each antibody (clone/1933 aIL8.92 NB 28605/12 for 6G4V11N35A; clone#1934 aIL8.42 NB 28605/14 for 6G4V11N35E), which reproducibly exhibited high specific productivity, was expanded in T-flasks and used to inoculate a spinner culture. After several passages, the suspension-adapted cells were used to inoculate production cultures in GHT-containing, serum-free media supplemented with various hormones and protein hydrolysates. Harvested cell culture fluid containing recombinant humanized anti-IL8 was purified using protein A-Sepharose CL-4B. The purity after this step was approximately 99%. Subsequent purification to homogeneity was carried out using an ion exchange chromatography step. Production titer of the humanized 6G4V11N35E IgG1 antibody after the first round of amplification and 6G4V11N35A IgG1 after the second round of amplification were 250 mg/L and 150 mg/L, respectively.

S. Characterization of the humanized 6G4V11N35A/E IgG Variants

The humanized full length IgG variants of 6G4.2.5 were tested for their ability to inhibit $^{125}$I-IL-8 binding and to neutralize activation of human neutrophils; the procedures are described in Sections (B)(1) and (B)(2) above. As shown in FIG. 49, the full length IgG1 forms of variants 6G4V11N35A and 6G4V11N35E equally inhibited 125I-IL-8 binding to human neutrophils with approximate IC$_{50}$'s of 0.3 nM and 0.5 nM, respectively. This represents a 15-25 fold improvement in blocking binding of IL-8 compared to the full length murine mAb (IC$_{50}$=7.5 nM). Similarly, the two anti-IL-8 variants showed equivalent neutralizing capabilities with respect to inhibiting IL-8 mediated human neutrophil chemotaxis (FIGS. 50A-50B). The IC$_{50}$'s of 6G4V11N35A IgG1 and 6G4V11N35E IgG1 for human IL-8 were 4.0 nM and 6.0 nM, respectively, and for rabbit IL-8 were 4.0 nM and 2.0 nM, respectively. The irrelevant isotype control Fab (4D5) did not inhibit neutrophil migration.

The affinity for IL-8 of these variants relative to the murine 6G4.2.5 mAb was determined using KinExA as described in Section (M). FIG. 51 shows the equilibrium constant (Kd) for the full length affinity matured variants 6G4V11N35E IgG1 and 6G4V11N35A IgG1 were approximately 49 pM and 88 pM, respectively. The Kd for 6G4V11N35A IgG1 was determined directly from the kinetic experiment. As reported with their respective Fabs, this improvement in affinity might be attributed to an approximate 2-fold increase in the on-rate of 6G4V11N35E IgG1 (ka=3.0×10$^6$) compared to that of 6G4V11N35A IgG1 (ka=8.7×10$^5$). In addition, these results were confirmed by a competition radio-immune assay using iodinated human IL-8. 50 pM of 6G4V11N35A IgG1 or 6G4V11N35E IgG1 was incubated for 2 hours at 25° C. with 30-50 pM of $^{125}$I-IL-8 and varying concentrations (0 to 100 nM) of unlabeled IL-8. The antibody-antigen mixture was then incubated for 1 hour at 4° C. with 10 ul of a 70% slurry of Protein-A beads (pre-blocked with 0.1% BSA). The beads were briefly spun in a microcentrifuge and the supernatant discarded to remove the unbound $^{125}$I-IL-8. The amount of $^{125}$I-IL-8 specifically bound to the anti-IL-8 antibodies was determined by counting the protein-A pellets in a gamma counter. The approximate Kd values were similar to those determined by KinEXA. The average Kd for 6G4V11N35A IgG1 and 6G4V11N35E IgG1 were 54 pM (18-90 pM) and 19 pM (5-34 pM), respectively (FIG. 52).

T. Construction of humanized 6G4V11N35A/E Fab's for modification by Polyethylene Glycol A Fab' expression vector for 6G4V11N35A was constructed by digesting p6G4V11N35A.F(ab')$_2$ with the restriction enzymes ApaI and NdeI to remove the 2805 bp fragment encoding the human IgG$_1$ constant domain fused with the yeast GCN4 leucine zipper and replacing it with the 2683 bp ApaI-NdeI fragment from the plasmid pCDNA.18 described in Eigenbrot et al., *Proteins: Struct. Funct. Genet.*, 18: 49-62 (1994). The pCDNA.18 ApaI-NdeI fragment carries the coding sequence for the human constant IgG1 heavy domain, including the free cysteine in the hinge region that was used to attach the PEG molecule. The 3758 bp ApaI-NdeI fragment (encodes the light chain and heavy variable domain of 6G4V11N35A) isolated from p6G4V11N35A.F(ab')$_2$ was ligated to the 2683 bp ApaI-NdeI fragment of pCDNA.18 to create p6G4V11N35A.PEG-1. The integrity of the entire coding sequence was confirmed by DNA sequencing. The nucleotide and translated amino acid sequences of heavy chain constant domain with the cysteine in the hinge are presented in FIG. 53.

A Fab' expression plasmid for 6G4V11N35E was made similarly by digesting pPH6G4V11N35E (from Section (O) above) with the restriction enzymes ApaI and NdeI to isolate the 3758 bp ApaI-NdeI DNA fragment carrying the intact light chain and heavy variable domain of 6G4V11N35E and ligating it to the 2683 bp ApaI-NdeI DNA fragment from p6G4V11N35A.PEG-1 to create p6G4V11N35E.PEG-3. The integrity of the entire coding sequence was confirmed by DNA sequencing.

Anti-IL-8 6G4V11N35A Fab' variant was modified with 20 kD linear methoxy-PEG-maleimide, 30 kD linear methoxy-PEG-maleimide, 40 kD linear methoxy-PEG-maleimide, or 40 kD branched methoxy-PEG-maleimide as described below. All PEG's used were obtained commercially from Shearwater Polymers, Inc.

a. Materials and Methods

Fab'-SH Purification

A Fab'-SH antibody fragment of the affinity matured antibody 6G4V11N35A was expressed in *E. coli* grown to high cell density in the fermentor as described by Carter et al., *BioTechnology* 10, 163-167 (1992). Preparation of Fab'-SH fragments was accomplished by protecting the Fab'-SH fragments with 4',4'-dithiodipyridine (PDS), partially purifying the protected Fab'-PDS fragments, deprotect the Fab'-PDS with dithiothreitol (DTT) and finally isolate the free Fab'-SH by using gel permeation chromatography.

Protection of Fab'-SH with PDS

Fermentation paste samples were dissolved in 3 volumes of 20 mM MES, 5 mM EDTA, pH 6.0 containing 10.7 mg of 4',4'-dithiodipyridine per gram fermentation paste, resulting in a suspension with a pH close to 6.0 The suspension was passed through a homogenizer followed by addition of 5% PEI (w/v), pH 6 to the homogenate to a final concentration of 0.25%. The mixture was then centrifuged to remove solids and the clear supernatant was conditioned to a conductivity of less than 3 mS by the addition of cold water.

Partial Purification of the Fab'-SH Molecule Using Ion Exchange Chromatography

The conditioned supernatant was loaded onto an ABX (Baker) column equilibrated in 20 mM MES, pH 6.0. The column was washed with the equilibration buffer followed by elution of the Fab'-SH with a 15 column volume linear gradient from 20 mM MES, pH 6.0 to 20 mM MES, 350 mM sodium chloride. The column was monitored by absorbance at 280 nm, and the eluate was collected in fractions.

Deprotection of the Fab'-SH antibody fragments with DTT

The pH of the ABX pool was adjusted to 4.0 by the addition of dilute HCl. The pH adjusted solution was then deprotected by adding DTT to a final concentration of 0.2 mM. The solution was incubated for about 30 minutes and then applied to a gel filtration Sephadex G25 column, equilibrated with 15 mM sodium phosphate, 25 mM MES, pH 4.0. After elution, the pH of the pool was raised to pH 5.5 and immediately flash frozen at −70° C. for storage or derivatized with PEG-MAL as described below.

Alternative Fab'-SH Purification

Alternatively Fab'-SH fragments can be purified using the following procedure. 100 g fermentation paste is thawed in the presence of 200 ml 50 mM acetic acid, pH 2.8, 2 mM EDTA, 1 mM PMSF. After mixing vigorously for 30 min at room temperature, the extract is incubated with 100 mg hen egg white lysozyme. DEAE fast flow resin (approximately 100 mL) is equilibrated with 10 mM MES, pH 5.5, 1 mM EDTA on a sintered glass funnel. The osmotic shock extract containing the Fab'-SH fragment is then filtered through the resin.

A protein G Sepharose column is equilibrated with 10 mM MES, pH 5.5, 1 mM EDTA and then loaded with the DEAE flow-through sample. The column is washed followed by three 4 column volume washes with 10 mM MES, pH 5.5, 1 mM EDTA. The Fab'-SH antibody fragment containing a free thiol is eluted from the column with 100 mM acetic acid, pH 2.8, 1 mM EDTA. After elution, the pH of the pool is raised to pH 5.5 and immediately flash frozen at −70° C. for storage or derivatized with PEG-MAL as described below.

Preparation of Fab'-S-PEG

The free thiol content of the Fab'-SH preparation obtained as described above was determined by reaction with 5,5'-dithiobis(2-nitrobenzoic acid) (DTNB) analysis according to the method of Creighton in *Protein Structure: A Practical Approach*, Creighton, T. E., ed, IRL Press (Oxford, UK: 1990), pp. 155-167. The concentration of free thiol was calculated from the increase on absorbance at 412 nm, using $e_{412}$=14,150 cm$^{-1}$M$^{-1}$ for the thionitrobenzoate anion and a $M_r$=48,690 and $e_{280}$=1.5 for the Fab'-SH antibody. To the Fab'-SH protein G Sepharose pool, or the deprotected Fab'-

SH gel permeation pool, 5 molar equivalents of PEG-MAL were added and the pH was immediately adjusted to pH 6.5 with 10% NaOH.

The Fab'-S-PEG was purified using a 2.5×20 cm cation exchange column (Poros 50-HS). The column was equilibrated with a buffer containing 20 mM MES, pH 5.5. The coupling reaction containing the PEGylated antibody fragment was diluted with deionized water to a conductivity of approximately 2.0 mS. The conditioned coupling reaction was then loaded onto the equilibrated Poros 50 HS column. Unreacted PEG-MAL was washed from the column with 2 column volumes of 20 mM MES, pH 5.5. The Fab'-S-PEG was eluted from the column using a linear gradient from 0 to 400 mM NaCl, in 20 mM MES pH 5.5, over 15 column volumes.

Alternatively a Bakerbond ABX column can be used to purify the Fab'-S-PEG molecule. The column is equilibrated with 20 mM MES, pH 6.0 (Buffer A). The coupling reaction is diluted with deionized water until the conductivity equaled that of the Buffer A (approximately 2.0 mS) and loaded onto the column. Unreacted PEG-MAL is washed from the column with 2 column volumes of 20 mM MES, pH 6.0. The Fab'-S-PEG is eluted from the column using a linear gradient from 0 to 100 mM $(NH_4)_2SO_4$, in 20 mM MES pH 6.0, over 15 column volumes.

Size Exclusion Chromatography

The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

b. Results

Size Exclusion Chromatography

The effective size of each modified species was characterized using size exclusion chromatography. The results are shown in FIG. 60 below. The theoretical molecular weight of the anti-IL8 Fab fragments modified with PEG 5 kD, 10 kD, 20 kD, 30 kD, 40 kD (linear), 40 kD (branched) or 100,000 kD is shown along with the apparent molecular weight of the PEGylated fragments obtained by HPLC size exclusion chromatography. When compared to the theoretical molecular weight of the Fab'-S-PEG fragments, the apparent molecular weight (calculated by size exclusion HPLC) increases dramatically by increasing the size of the PEG attached to the fragments. Attachment of a small molecular weight PEG, for example PEG 10,000 D only increases the theoretical molecular weight of the PEGylated antibody fragment (59,700 D) by 3 fold to an apparent molecular weight of 180,000D. In contrast attachment of a larger molecular weight PEG for example 100,000 D PEG to the antibody fragment increases the theoretical molecular weight of the PEGylated antibody fragment (158,700 D) by 12 fold to an apparent molecular weight of 2,000,000D.

SDS-PAGE

In FIG. 61, the upper panel shows the size of the anti-IL-8 Fab fragments modified with PEG of molecular weight 5 kD (linear), 10 kD (linear), 20 kD (linear), 30 kD (linear), kD (linear), 40 kD (branched) or 100 kD (linear) under reduced conditions. The unmodified Fab is shown in lane 2 from right to left. Both the heavy and light chains of the Fab had a molecular weight of approximately 30 kD as determined by PAGE. Each PEGylated fragment sample produced two bands: (1) a first band (attributed to the light chain) exhibiting a molecular weight of 30 kD; and (2) a second band (attributed to the heavy chain to which the PEG is attached specifically at the hinge SH) exhibiting increasing molecular weights of 40, 45, 70, 110, 125, 150 and 300 kD. This result suggested that PEGylation was specifically restricted to the heavy chain of the Fab's whereas the light chain remained unmodified.

The lower panel is non-reduced PAGE showing the size of the anti-IL-8 Fab fragments modified with PEG of molecular weight 5 kD (linear), 20 kD (linear), 30 kD (linear), 40 kD (linear), 40 kD (branched), or 100 kD (linear). The PEGylated fragments exhibited molecular weights of approximately 70 kD, 115 kD, 120 kD, 140 kD, 200 kD and 300 kD.

The SDS PAGE gels confirm that all Fab'-S-PEG molecules were purified to homogeneity and that the molecules differed only with respect to the size of the PEG molecule attached to them.

U. Amine Specific Pegylation of Anti-IL-8 F(ab')$_2$ Fragments

Pegylated F(ab')$_2$ species were generated by using large MW or branched PEGs in order to achieve a large effective size with minimal protein modification which might affect activity. Modification involved N-hydroxysuccinamide chemistry which reacts with primary amines (lysines and the N-terminus). To decrease the probability of modifying the N-terminus, which is in close proximity to the CDR region, a reaction pH of 8, rather than the commonly used pH of 7, was employed. At pH 8.0, the amount of the reactive species (charged $NH_3^+$) would be considerably more for the $\epsilon$-NH2 group of lysines ($pK_a$=10.3) than for the $\alpha$-NH2 group ($pK_a$ of approximately 7) of the amino-terminus. For the linear PEGs, a methoxy-succinimidyl derivative of an NHS-PEG was used because of the significantly longer half-life in solution (17 minutes at 25° C. at pH 8.0) compared to the NHS esters of PEGs (which have 5-7 minute half life under the above conditions). By using a PEG that is less prone to hydrolysis, a greater extent of modification is achieved with less PEG. Branched PEGs were used to induce a large increase in effective size of the antibody fragments.

a. Materials

All PEG reagents were purchased from Shearwater Polymers and stored at −70° C. in a desiccator: branched N-hydroxysuccinamide-PEG (PEG2-NHS-40 KDa) has a 20 kDa PEG on each of the two branches, methoxy-succinimidyl-propionic acid-PEG (M-SPA-20000) is a linear PEG molecule with 20 kDa PEG. Protein was recombinantly produced in *E. coli* and purified as a (Fab)'$_2$ as described in Sections (K) and (O) above.

b. Methods

IEX method: A J. T. Baker Wide-Pore Carboxy-sulfone (CSX), 5 micron, 7.75×100 mm HPLC column was used for fractionation of the different pegylated products, taking advantage of the difference in charge as the lysines are modified. The column was heated at 40° C. A gradient as shown in Table 7 below was used where Buffer A was 25 mM sodium Borate/25 mM sodium phosphate pH 6.0, and Buffer B was 1 M ammonium sulfate, and Buffer C was 50 mM sodium acetate pH 5.0.

TABLE 7

| Time (min) | % B | % C | flow mL/min |
|---|---|---|---|
| 0 | 10 | 10 | 1.5 |
| 20 | 18 | 7.5 | 1.5 |
| 25 | 25 | 7.5 | 1.5 |
| 27 | 70 | 3.0 | 2.5 |
| 29 | 70 | 3.0 | 2.5 |
| 30 | 10 | 10 | 2.5 |
| 33 | 10 | 10 | 2.5 |

SEC-HPLC: The hydrodynamic or effective size of each molecule was determined using a Pharmacia Superose-6 HR 10/30 column (10×300 mm). The mobile phase was 200 mM NaCl, 50 mM sodium phosphate pH 6.0. Flow rate was at 0.5 ml/min and the column was kept at ambient temperature. Absorbance at 280 nm was monitored where PEG contributed little signal. Biorad MW standards containing cyanocobalamin, myoglobin, ovalbumin, IgG, Thyroglobulin monomer and dimer were used to generate a standard curve from which the effective size of the pegylated species was estimated.

SEC-HPLC-Light Scattering: For determination of the exact molecular weight, this column was connected to an on-line light scattering detector (Wyatt Minidawn) equipped with three detection angles of 50°, 90°, and 135° C. A refractive index detector (Wyatt) was also placed on-line to determine concentration. All buffers were filtered with Millipore 0.11 filters; in additional 0.02µ Whatman Anodisc 47 was placed on-line prior to the column.

The intensity of scattered light is directly proportional to the molecular weight (M) of the scattering species, independent of shape, according to:

$$M = R_0 / K \cdot c$$

where $R_0$ is the Rayleigh ratio, K is an optical constant relating to the refractive index of the solvent, the wavelength of the incident light, and dn/dc, the differential refractive index between the solvent and the solute with respect to the change in solute concentration, c. The system was calibrated with toluene ($R_0$ of $1.406 \times 10^{-5}$ at 632.8 nm); a dn/dc of 0.18, and an extinction coefficient of 1.2 was used. The system had a mass accuracy of 5%.

SDS-PAGE: 4-12% Tris-Glycine Novex minigels were used along with the Novex supplied Tris-Glycine running buffers. 10-20 ug of protein was applied in each well and the gels were run in a cold box at 150 mV/gel for 45 minutes. Gels were then stained with colloidal Coomassie Blue (Novex) and then washed with water for a few hours and then preserved and dried in drying buffer (Novex)

Preparation of a linear(1)20 KDa-(N)-(Fab')2: A 4 mg/ml solution of anti-IL8 formulated initially in a pH 5.5 buffer was dialyzed overnight against a pH 8.0 sodium phosphate buffer. 5 mL protein was mixed at a molar ratio of 3:1. The reaction was carried out in a 15 ml polypropylene Falcon tube and the PEG was added while vortexing the sample at low speed for 5 seconds. It was then placed on a nutator for 30 minutes. The extent of modification was evaluated by SDS-PAGE. The whole 5 ml reaction mixture was injected on the IEX for removal of any unreacted PEG and purification of singly or doubly pegylated species. The above reaction generated a mixture of 50% singly-labeled anti-IL8. The other 50% unreacted anti-IL8 was recycled through the pegylation/purification steps. The pooled pegylated product was dialyzed against a pH 5.5 buffer for in vitro assays and animal PK studies. Endotoxin levels were measured before administration to animals or for the cell based assays. Levels were below 0.5 eu/ml. The fractions were also run on SDS-PAGE to confirm homogeneity. Concentration of the final product was assessed by absorbance at 280 nm using an extinction coefficient of 1.34, as well as by amino acid analysis.

Preparation of a Branched(1)40 KDa-(N)-(Fab')2: A 4 mg/mL solution of anti-IL8 (Fab')$_2$ formulated in a pH 5.5 buffer was dialyzed overnight against a pH 8.0 phosphate buffer. Solid PEG powder was added to 5 mL protein in two aliquots to give a final PEG:protein molar ratio of 6:1. Each solid PEG aliquot was added to the protein in a 15 mL polypropylene Falcon tube while vortexing at low speed for 5 sec, and then placing the sample on a nutator for 15 minutes. The extent of modification was evaluated by SDS-PAGE using a 4-12% Tris-Glycine (Novex) gel and stained with colloidal Coomasie blue (Novex). The 5 mL PEG-protein mixture was injected on the ion exchange column for removal of any unreacted PEG. The above reaction generated a mixture of unreacted (37%), singly-labelled (45%), doubly and triply-labeled (18%) species. These were the optimal conditions for obtaining the greatest recovery of the protein with only 1 PEG per antibody rather than the higher molecular weight adducts. The unmodified anti-IL8 was recycled. The pegylated products were separated and fractionated in falcon tubes and then dialyzed against a pH 5.5 buffer for assays and animal PK studies. Endotoxin levels were below 0.5 eu/ml. The fractions were also run on SDS-PAGE to confirm homogeneity. The concentration of the final product was assessed by absorbance at 280 nm using an extinction coefficient of 1.34, as well as by amino acid analysis.

Preparation of branched(2)-40 KDa-(N)(Fab')2: This molecule was most efficiently made by adding three times in 15 minute intervals a 3:1 molar ratio of PEG to the already modified branched(1)-40 KDa-(N)-(Fab')$_2$. The molecule was purified on IEX as 50% branched(2)-40 KDa-(N)-(Fab')$_2$. The unmodified molecule was recycled until ~20 mg protein was isolated for animal PK studies. The product was characterized by SEC-light scattering and SDS-PAGE.

c. Results

PEGs increased the hydrodynamic or effective size of the product significantly as determined by gel filtration (SEC-HPLC). FIG. 62 shows the SEC profile of the pegylated F(ab')$_2$ species with UV detection at 280 nm. The hydrodynamic size of each molecule was estimated by reference to the standard MW calibrators. As summarized in FIG. 62, the increase in the effective size of (Fab')$_2$ was about 7-fold by adding one linear 20 kDa PEG molecule and about 11-fold by adding one branched ("Br(1)") 40 kDa PEG molecule, and somewhat more with addition of two branched ("Br(2)") PEG molecules.

Light scattering detection gave the exact molecular weight of the products and confirmed the extent of modification (FIG. 63). The homogeneity of the purified material was shown by SDS-PAGE (FIG. 64). Underivatized F(ab')$_2$ migrated as a 120 kDa species, the linear(1)20 KD-(N)-F(ab')$_2$ migrated as a band at 220 kDa, the Br(1)-40 KD(N)-F(ab')$_2$ migrated as one major band at 400 kDa, and the Br(2)-40 KD-(N)-F(ab')$_2$ migrated as a major band at around 500 kDa. The proteins appeared somewhat larger than their absolute MW due to the steric effect of PEG.

V. In vitro Activity Characterization of PEG Modified Fab' Fragments of 6G4V11N35A (Maleimide Chemical Coupling Method)

Anti-IL-8 6G4V11N35A Fab' variants modified with 5-40 kD linear PEG molecules and a 40 kD branched PEG molecule were tested for their ability to inhibit both IL-8 binding and activation of human neutrophils; the procedures were described in Sections (B)(1), (B)(2) and (B)(3) above. The binding curves and IC$_{50}$'s for PEG-maleimide modified 6G4V11N35A Fab' molecules are presented in FIGS. 54A-54C. The IC$_{50}$ of the 5 kD pegylated Fab' (350 pM) and the average IC$_{50}$ of the Fab control (366 pM) were not significantly different, suggesting that the addition of a 5 kD MW PEG did not affect the binding of IL-8 to the modified Fab' (FIG. 54A). However, a decrease in the binding of IL-8 to the 10 kD and 20 kD pegylated Fab' molecules was observed as depicted by the progressively higher IC$_{50}$'s (537 pM and 732 pM, respectively) compared to the average IC$_{50}$ of the native Fab. These values represent only a minimal loss of binding activity (between 1.5- and 2.0-fold). A less pronounced difference in IL-8 binding was observed for the 30 kD and 40 kD linear PEG antibodies (FIG. 54B). The IC$_{50}$'s were 624 pM and 1.1 nM, respectively, compared to the 802 pM value of the Fab control. The 40 kD branched PEG Fab' showed the largest decrease in IL-8 binding (2.5 fold) relative to the native Fab (FIG. 54C). Nevertheless, the reduction in binding of IL-8 by these pegylated Fab's is minimal.

The ability of the pegylated antibodies to block IL-8 mediated activation of human neutrophils was demonstrated using the PMN chemotaxis (according to the method described in Section B(2) above) and β-glucuronidase release (according to the method described in Lowman et al., *J. Biol. Chem.*, 271: 14344 (1996)) assays. The IC$_{50}$'s for blocking IL-8 mediated chemotaxis are shown in FIGS. 55A-55C. The 5-20 kD linear pegylated Fab' antibodies were able to block IL-8 mediated chemotaxis within 2-3 fold of the unpegylated Fab control (FIG. 55A). This difference is not significant because the inherent variation can be up to 2 fold for this type of assay. However, a significant difference was detected for the 30 kD and 40 kD linear pegylated Fab' antibodies as illustrated by the higher IC$_{50}$'s of the 30 kD linear PEG-Fab' (2.5 nM) and 40 kD linear PEG-Fab' (3.7 nM) compared to the Fab control (0.8 nM) (FIG. 55B). The ability of the 40 kD branched PEG Fab' molecule to block IL-8 mediated chemotaxis was similar to that of the 40 kD linear PEG Fab' (FIG. 55C). At most, the ability of the pegylated Fab' antibodies to block IL-8 mediated chemotaxis was only reduced 2-3 fold. Furthermore, release of β-glucuronidase from the granules of neutrophils was used as another criteria for assessing IL-8 mediated activation of human PMNs. FIG. 56A (depicting results obtained with 5 kD, 10 kD and 20 kD linear PEGs), FIG. 56B (depicting results obtained with 30 kD and 40 kD linear PEGs), and FIG. 56C (depicting results obtained with 40 kD branched PEG) show that all the pegylated Fab' antibodies were able to inhibit IL-8 mediated release of β-glucuronidase as well as or better than the unpegylated Fab control. The data collectively shows that the pegylated Fab' variants are biological active and are capable of inhibiting high amounts of exogenous IL-8 in in-vitro assays using human neutrophils.

W. In Vitro Activity Characterization of PEG Modified F(ab')$_2$ Fragments of 6G4V11N35A (Succinimidyl Chemical Coupling Method)

The anti-IL-8 variant 6G4V11N35A F(ab')$_2$ modified with (a) a single 20 kD linear PEG molecule per F(ab')$_2$, (b) a single 40 kD branched PEG molecule per F(ab')$_2$, (c) with three, four, or five 20 kD linear PEG molecules per F(ab')$_2$ (a mixture of: (1) species having three 20 kD linear PEG molecules per F(ab')$_2$; (2) species having four 20 kD linear PEG molecules per F(ab')$_2$; and (3) species having five 20 kD linear PEG molecules per F(ab')$_2$; denoted as "20 kD linear PEG (3,4,5) F(ab')$_2$"), or (d) with two 40 kD branched PEG molecules per F(ab')$_2$ (denoted as "40 kD branch PEG (2) F(ab')$_2$"), were tested for their ability to inhibit [125]I-IL-8 binding and to neutralize activation of human neutrophils. The procedures used are described in Sections (B)(1), (B)(2) and (B)(3) above. The binding curves for pegylated F(ab')$_2$ variants are shown in FIGS. 57A-57B. No significant differences were observed amongst the F(ab')$_2$ control, the single 20 kD linear PEG-modified F(ab')$_2$, and the single 40 kD branched PEG-modified F(ab')$_2$ (FIG. 57A). However, the F(ab')$_2$ variants containing multiple PEG molecules showed a slight reduction (less than 2-fold) in their ability to bind IL-8. The IC$_{50}$'s of the kD linear PEG (3,4,5) F(ab')$_2$ and 40 kD branch PEG (2) F(ab')$_2$ variants were 437 pM and 510 pM, respectively, compared to 349 pM of the F(ab')$_2$ control (FIG. 57B).

The ability of these pegylated F(ab')$_2$ variants to block IL-8 mediated neutrophil chemotaxis is presented in FIGS. 58A-58B. Consistent with the PMN binding data, the single linear and branched PEG F(ab')$_2$ variants were able to block IL-8 mediated chemotaxis similar to the unpegylated F(ab')$_2$ control (FIG. 58A). The ability of the 40 kD branch PEG (2) F(ab')$_2$ variant to inhibit PMN chemotaxis was identical to the control F(ab')$_2$ while the 20 kD linear PEG (3,4,5) F(ab')$_2$ mixture was able to inhibit within 3-fold of the control antibody (FIG. 58B).

Shown in FIGS. 59A and 59B are the results of the β-glucuronidase release assay which is a measure of degranulation by IL-8 stimulated human neutrophils. The single 20 kD linear PEG-modified F(ab')$_2$ and the single 40 kD branched PEG-modified F(ab')$_2$ variants were able to inhibit release of ∃-glucuronidase as well as the F(ab')$_2$ control (FIG. 59A). The 40 kD branch PEG (2) F(ab')$_2$ inhibited this response within 2-fold of the F(ab')$_2$ control (FIG. 59B). The 20 kD linear PEG (3,4,5) molecule was not tested. Overall, the F(ab')$_2$ pegylated anti-IL-8 antibodies were biologically active and effectively prevented IL-8 binding to human neutrophils and the signaling events leading to cellular activation.

X. Pharmacokinetic and Safety Study of Eight Constructs of Pegylated Anti-IL-8 (Humanized) F(ab')2 And Fab' Fragments in Normal Rabbits Following Intravenous Administration The objective of this study was to evaluate the effect of pegylation on the pharmacokinetics and safety of six pegylated humanized anti-IL-8 constructs (pegylated 6G4V11N35A.Fab' and pegylated 6G4V11N35A.F(ab')$_2$ obtained as described in Sections (T) and (U) above) relative to the non-pegylated fragments in normal rabbits. Eight groups of two/three male rabbits received equivalent protein amounts of pegylated 6G4V11N35A.Fab' or pegylated 6G4V11N35A.F(ab')$_2$ constructs (2 mg/kg) via a single intravenous (IV) bolus dose of one anti-IL8 construct. Serum samples were collected according to the schedule shown in Table 8 below and analyzed for anti-IL8 protein concentrations and antibody formation against anti-IL8 constructs by ELISA.

TABLE 8

| Group No. | Dose level/ Route | Material | Blood Collection |
|---|---|---|---|
| 1 | 2 mg/kg (protein conc.) | Fab' control | 0, 5, 30 min; 1, 2, 3, 4, 6, 8, 10, 14, 20, 24, 360 hr |
| 2 | IV bolus | linear(1)20K(s)Fab' | 0, 5, 30 min; 1, 2, 4, 6, 8, 10, 12, |
| 3 | | linear(1)40K(s)Fab' | 24, 28, 32, 48, 72, 96, 168, 216, |

TABLE 8-continued

| Group No. | Dose level/ Route | Material | Blood Collection |
|---|---|---|---|
| 4 | | branched(1)40K(N)F(ab')$_2$ | 264, 336, 360 hr |
| 5 | | F(ab')$_2$ control | 0, 5, 30 min; 1, 2, 4, 6, 8, 10, 12, 24, 28, 32, 48, 52, 56, 336 hr |
| 6 | | branched(2)40K(s)Fab' | 0, 5, 30 min; 1, 2, 4, 6, 8, 10, 12, 24, 28, 32, 48, 72, 96, 168, 216, 264, 336 hr; Day 17, 21, 25 |
| 7 | | branched(2)40K(N)F(ab')$_2$ | 0, 5, 30 min; 1, 2, 4, 6, 8, 10, 12, 24, 28, 32, 48, 72, 144, 192, 240 hr; Day 13, 16, 20, 23 |
| 8 | | linear(1)30K(s)Fab' | 0, 5, 30 min; 1, 2, 4, 6, 8, 10, 12, 24, 28, 32, 48, 72, 96, 168, 216, 264, 336 hr; Day 17, 21, 25 | a. Methods

Three male New Zealand White (NZW) rabbits per group (with exception to Group 7, n=2) received an equivalent amount of 6G4V11N35A protein (Fab' or F(ab')$_2$) construct at 2 mg/kg via an IV bolus dose in a marginal ear vein. Amino acid composition analysis and absorbance at 280 nm using extinction coefficients of 1.26 for 6G4V11N35A Fab' constructs and 1.34 for 6G4V11N35A F(ab')$_2$ constructs were performed to determine the protein concentration. Whole blood samples were collected via an ear artery cannulation (ear opposing dosing ear) at the above time points. Samples were harvested for serum and assayed for free G4V11N35A Fab' or F(ab')$_2$ constructs using an IL-8 Binding ELISA. Assays were conducted throughout the study as samples became available. All animals were sacrificed following the last blood draw, and necropsies were performed on all animals in Groups 1, 4-8. Due to the development of antibodies against the 6G4V11N35A constructs, non-compartmental pharmacokinetic analysis was conducted on concentration versus time data only up to 168 hours.

b. Results

In four animals (Animals B, P, Q, V), interference to rabbit serum in the ELISA assay was detected (i.e. measurable concentrations of anti-IL8 antibodies at pre-dose). However, because these values were at insignificant levels and did not effect the pharmacokinetic analysis, the data were not corrected for this interference.

One animal (Animal G; Group 3) was exsanguinated before the termination of the study and was excluded from the pharmacokinetic analysis. At 4 hours, the animal showed signs of a stroke that was not believed to be drug related, as this can occur in rabbits following blood draws via ear artery cannulation.

The mean concentration-time profiles of the eight anti-IL8 constructs in normal rabbits are depicted in FIG. 65, and the pharmacokinetic parameters for the eight constructs are summarized in Table 9 below. Significant antibodies to the anti-IL-8 constructs were present at Day 13/14 in all dose groups except Group 1 (Fab' control).

TABLE 9

Pharmacokinetic parameters.

| | Molecule | | | | | | | |
|---|---|---|---|---|---|---|---|---|
| | Fab' | | | | | F(ab')$_2$ | | |
| | Group No. | | | | | | | |
| | 1 | 2 | 8 | 3 | 6 | 5 | 4 | 7 |
| | PEG structure | | | | | | | |
| | — | linear | linear | linear | branched | — | branched | branched |
| | Number of PEGs | | | | | | | |
| | — | 1 | 1 | 1 | 1 | — | 1 | 2 |
| | PEG MW | | | | | | | |
| | — | 20K | 30K | 40K | 40K | — | 40K | 40K |
| Dose (mg/kg) | 2 | 2 | 2 | 2 | 2 | 2 | 2 | 2 |
| $V_c$ (mL/kg)$^a$ | 58 ± 3 | 36 ± 3 | 35 ± 1 | 34 | 44 ± 1 | 45 ± 5 | 36 ± 1 | 32 |
| $V_{ss}$ (mL/kg)$^b$ | 68 ± 8 | 80 ± 8 | 110 ± 15 | 79 | 88 ± 21 | 59 ± 4 | 50 ± 3 | 52 |
| Cmax (μg/mL)$^c$ | 35 ± 1 | 58 ± 3 | 57 ± 1 | 60 | 45 ± 1 | 45 ± 6 | 56 ± 2 | 62 |
| Tmax (min)$^d$ | 5 | 5 | 5 | 5 | 5 | 5 | 5 | 5 |
| $t_{1/2}$ term (hr)$^e$ | 3.0 ± 0.9 | 44 ± 2 | 43 ± 7 | 50 | 105 ± 11 | 8.5 ± 2.1 | 45 ± 3 | 48 |
| AUC$_{0-8}$ (hr · μg/mL)$^f$ | 18 ± 3 | 80 ± 74 | 910 ± 140 | 1600 | 3400 ± 1300 | 140 ± 3 | 2200 ± 77 | 2500 |
| CL (mL/hr/kg)$^g$ | 110 ± 17 | 2.5 ± 0.2 | 2.2 ± 0.4 | 1.3 | 0.63 ± 0.20 | 14 ± 0 | 0.92 ± 0.03 | 0.83 |

TABLE 9-continued

Pharmacokinetic parameters.

| | | Molecule | | | | | | |
|---|---|---|---|---|---|---|---|---|
| | | Fab' | | | | F(ab')₂ | | |
| | | Group No. | | | | | | |
| | 1 | 2 | 8 | 3 | 6 | 5 | 4 | 7 |
| | | | | PEG structure | | | | |
| | — | linear | linear | linear | branched | — | branched | branched |
| | | | | Number of PEGs | | | | |
| | — | 1 | 1 | 1 | 1 | — | 1 | 2 |
| | | | | PEG MW | | | | |
| | — | 20K | 30K | 40K | 40K | — | 40K | 40K |
| MRT (hr)$^h$ | 0.61 ± 0.15 | 32 ± 2 | 45 ± 9 | 63 | 140 ± 18 | 4.2 ± 0.3 | 55 ± 3 | 64 |
| No. of Animals | 3 | 3 | 3 | 2 | 3 | 3 | 3 | 2 |

$^a$Initial volume of distribution.
$^b$Volume of distribution at steady state.
$^c$Observed maximum concentration.
$^d$Observed time to Cmax.
$^e$t$_{1/2}$ term = half-life associated with the terminal phase of the concentration vs. time profile.
$^f$Area under the concentration versus time curve (extrapolated to infinity).
$^g$CL = serum clearance.
$^h$MRT = Mean residence time.

The initial volume of distribution approximated the plasma volume for both the Fab' and F(ab')₂. Pegylation decreased serum CL of anti-IL8 fragments and extended both the terminal half-life and MRT as shown in Table 10 below.

TABLE 10

Fold decrease/increase in clearance, terminal half-life & MRT of pegylated anti-IL8 fragments.

| | | anti-IL8 fragment | | | | | | | |
|---|---|---|---|---|---|---|---|---|---|
| | | Fab' | | | | | F(ab')₂ | | |
| | | Group No. | | | | | | | |
| | | 1 | 2 | 8 | 3 | 6 | 5 | 4 | 7 |
| | | | | | PEG structure | | | | |
| | | — | linear | linear | linear | bran. | — | bran. | bran. |
| | | | | | No. of PEGs | | | | |
| | | — | 1 | 1 | 1 | 1 | — | 1 | 2 |
| | | | | | PEG MW | | | | |
| | | — | 20K | 30K | 40K | 40K | — | 40K | 40K |
| CL: | mean (mL/hr/kg) | 110 | 2.5 | 2.2 | 1.3 | 0.63 | 14 | 0.92 | 0.83 |
| | fold decrease | 1 | 46 | 51 | 90 | 180 | 1 | 15 | 17 |
| t½ term: | mean (hr) | 3.0 | 44 | 43 | 50 | 110 | 8.5 | 45 | 48 |
| | fold increase | 1 | 14 | 14 | 17 | 35 | 1 | 5.3 | 5.7 |
| MRT: | mean (hr) | 0.61 | 32 | 45 | 63 | 140 | 4.2 | 55 | 64 |
| | fold increase | 1 | 53 | 73 | 100 | 240 | 1 | 13 | 15 |

For the pegylated anti-IL8 Fab' fragments, CL decreased by 46 to 180-fold. Terminal half-life and MRT increased 14 to 35-fold and 53 to 240-fold, respectively. For pegylated anti-IL8 F(ab')₂ molecules, CL decreased 15 to 17-fold with pegylation, and terminal half-life and MRT increased by greater than 5-fold and 13-fold, respectively. The changes in these parameters increased for both pegylated Fab' and F(ab')₂ molecules with increasing PEG molecular weight and approached the values of the full-length anti-IL8 (terminal half-life of 74 hours, MRT of 99 hours and CL of 0.47 mL/hr/kg). In comparing the branched(1)40K Fab' (Group 6) and branched(1)40K F(ab')₂ (Group 4), unexpected pharmacokinetics were observed. The pegylated Fab' molecule appeared to remain in the serum longer than the pegylated F(ab')₂ (see FIG. 66). The mean CL of branched(1)40K Fab' was 0.63 mL/hr/kg, but a higher CL was observed for branched(1)40 kD F(ab')₂ (CL 0.92 mL/hr/kg). The terminal half-life, likewise, was longer for the Fab' than the F(ab')₂ pegylated molecule (110 vs 45 hours).

The pharmacokinetic data demonstrated that pegylation decreased CL and increased terminal t1/2 and MRT of anti-IL8 fragments (Fab' and F(ab')₂) to approach that of the full-length anti-IL8. Clearance was decreased with pegylation 46 to 180-fold for the Fab' and approximately 16-fold for the F(ab')$_2$. The terminal half-life of the Fab' anti-IL8 fragment was increased by 14 to 35-fold and approximately 5-fold for the F(ab')$_2$ anti-IL8. MRT, likewise, were extended by 53 to 240-fold for the Fab' and approximately 14-fold for the F(ab')$_2$. The branched(1) 40 kD Fab' had a longer terminal half-life and lower clearance compared to the branched(1) 40 kD F(ab')$_2$.

Y. In Vivo Efficacy Testing of Anti-IL-8 Antibody Reagents in Rabbit Model of Ischemia/Reperfusion and Acid Aspiration-Induced Acute Respiratory Distress Syndrome (ARDS)

Full length murine anti-rabbit IL-8 monoclonal antibody 6G4.2.5, 40 kD branched PEG-6G4V11N35A Fab', and control antibody (anti-HIV gp120 monoclonal antibody 9E3.1F10) were tested in a rabbit ARDS model. The animals were weighed and anaesthetized by intramuscular injection of ketamine (50 mg/kg body weight), xylazine (5 mg/kg body weight), and acepromazine (0.75 mg/kg body weight). A second dose (20% of the first dosage) was given IM 15 minutes before removal of vascular clip, and third dose (60% of the first dosage) was given at tracheotomy. Intra-arterial catheter (22G, 1 in. Angiocath) and intra-venous catheter (24G, 1 in. angiocath) were be placed in the ear central artery and posterior marginal ear vein for blood samplings (arterial blood gases and CBC) and anti-IL-8 and fluid administration, respectively. The anaesthetized animals were transferred in a supine position to an operating tray; the abdominal area was shaved and prepared for surgery. Via a midline laparotomy, the superior mesenteric artery (SMA) was isolated and a microvascular arterial clip applied at the aortic origin. Before the temporary closure of the abdomen using 9 mm wound clip (Autoclip, Baxter), 15 ml of normal saline was given intraperitoneally as fluid supplement. After 110 minutes of intestinal ischemia, the abdominal incision was reopened and the arterial clip was released to allow reperfusion. Before closure, 5 ml of normal saline was given intraperitoneally for fluid replacement. The laparotomy incision was closed in two layers and the animals allowed to awaken.

After surgery, the animals were placed on a heating pad (38° C.) and continuously monitored for up to 6 hours post reperfusion and lactated Ringer's 8-12 ml/kg/hr IV was given as fluid supplement.

At 22-24 hr post-reperfusion, a tracheotomy was performed under anesthesia. Normal physiologic saline was diluted 1:3 with water and adjusted to pH 1.5 (adjusted by using 1N HCL); 3 ml/kg body weight was then instilled intra-tracheally. Rectal temperature was maintained at 37+/-1 degree C. using a homeothermic heat therapy pad (K-Mod II, Baxter). Fluid supplements (LRS) at a rate of 5 ml/kg/hour IV were given. Blood gases were monitored every hour. The rabbits were returned to the cage after 6 hr of continuous monitoring.

Just prior to aspiration, animals were treated with saline, the control monoclonal antibody (anti-HIV gp-120 IgG 9E3.1F10), the full length murine anti-rabbit IL8 (6g4.2.5 murine IgG2a anti-rabbit IL8) or the pegylated 6G4V11N35A Fab' (6G4V11N35A Fab' modified with 40 kD branched PEG-maleimide as described in Section T above, denoted as "40 kD branched PEG-6G4V11N35A Fab'"). Data from saline or control antibody treated animals was combined and presented as "Control". Arterial blood gases and A-a PO2 gradient measurements were taken daily, and IV fluid supplementation was performed daily. A-a PO2 gradient was measured at 96 hr of reperfusion. The A-a PO2 gradient was calculated as:

$$A\text{-}aPO2 = [FIO2(PB-PH2O)-(PaCO2/RQ)]-PaO2.$$

PaO2/FiO2 ratios were measured at 24 hr and 48 hr in room air and 100% oxygen.

After the final A-a PO2 gradient measurement, the animals were anesthetized with Nembutal 100 mg/kg i.v. and the animals were euthanized by transecting the abdominal aorta in order to reduce red blood cell contamination of bronchoalveolar lavage fluid (BAL). The lungs were removed en bloc. The entire lung was weighed and then lavaged with an intratracheal tube (Hi-Lo tracheal tube, 3 mm) using 30 ml of HBSS and lidocain. Total and differential leukocyte counts in the BAL were determined. Lesions/changes were verified by histological examination of each lobe of the right lung of each animal.

The gross lung weight, total leukocyte and polymorphonuclear cell counts in BAL, and PaO2/FiO2 data obtained are depicted in FIGS. 67, 68 and 69, respectively. Treatment with 40 kD branched PEG-6G4V11N35A Fab' exhibited no effect on the biological parameters measured in the model as compared to the "Control" group. However, the data do not contradict the pharmacokinetic analysis or the in vitro activity analysis for the 40 kD branched PEG-6G4V11N35A Fab' presented in Sections (V) and (X) above. In addition, these data do not contradict the ability of the 40 kD branched PEG-6G4V11N35A Fab' to reach and act on disease effector targets in circulation or other tissues.

Z. Additional In Vivo Efficacy Testing of Anti-IL-8 Antibody Reagents in Rabbit Model of Ischemia/Reperfusion and Acid Aspiration-Induced Acute Respiratory Distress Syndrome (ARDS)

Full length murine anti-rabbit IL-8 monoclonal antibody 6G4.2.5 and 20 kD linear PEG-6G4V11N35E Fab' were tested in a rabbit model of ischemia/reperfusion- and acid aspiration-induced acute respiratory distress syndrome (ARDS).

Antibodies

A Fab'-SH antibody fragment of the affinity matured anti-IL-8 antibody 6G4V11N35E was expressed using the Fab' expression plasmid for 6G4V11N35E (described in Section (T) above) in *E. coli* grown to high density in the fermentor as described by Carter et al., *Bio/Technology*, 10: 163-167 (1992). Anti-IL-8 6G4V11N35E Fab' variant was purified from fermentation paste and modified with 20 kD linear methoxy-PEG-maleimide as described in Example T above. Pegylated material was formulated in phosphate buffered saline (PBS) at physiological pH. Full length 6G4.2.5 antibody was obtained from hybridoma cell line 6G4.2.5 as described in Section (B) above and formulated in phosphate buffered saline (PBS) at physiological pH.

Sterile Surgical Procedures and Post-Operative Care

Male New Zealand White rabbits weighing 2.2 to 2.5 kg (obtained from Western Oregon Rabbit Company) were anaesthetized by intramuscular injection of ketamine (50 mg/kg body weight), xylazine (5 mg/kg body weight), and acepromazine (0.75 mg/kg body weight). Intra-arterial catheter (22G, 1 in. Angiocath) and intra-venous catheter (24G, 1 in. angiocath) were be placed in the ear central artery and posterior marginal ear vein for blood samplings (arterial blood gases and CBC) and anti-IL-8 (or fluid) administration, respectively. The anaesthetized animals were transferred in a supine position to an operating tray; the abdominal area was shaved and prepared for surgery. Via a midline laparotomy, the superior mesenteric artery (SMA) was isolated and a microvascular arterial clip applied at the aortic origin. Before the temporary closure of the abdomen using 9 mm wound clip (Autoclip, Baxter), 15 ml of normal saline (38° C.) was given intraperitoneally as fluid supplement. After 110 minutes of intestinal ischemia, the abdominal incision was reopened and the arterial clip was released to allow reperfusion. Before closure, 5 ml of normal saline (38° C.) was given intraperitoneally for fluid replacement. The laparotomy incision was closed in two layers and the animals allowed to awaken.

After surgery, the animals were placed on a heating pad (38° C.) and continuously monitored for up to 6 hours post reperfusion and lactated Ringer's 8-12 ml/kg/hr IV was given as fluid supplement.

At 22-24 hr post-reperfusion, a tracheotomy was performed under anesthesia using ketamine, xylazine and acepromazine as described above. Normal physiologic saline was diluted 1:3 with water and adjusted to pH 1.5 (adjusted by using 1N HCL), and 3 ml/kg body weight was then instilled intra-tracheally through an uncuffed tracheal tube (2.0 mm I.D., Mallinckrodt Medical, Inc.). After instillation, the trachea was closed with 3-0 silk suture and the rabbits were allowed to recover. Rectal temperature was maintained at 37° C.+/−1° C. using a homeothermic heat therapy pad (K-Mod II, Baxter). Fluid supplements (LRS) at a rate of 5 ml/kg/hour IV were given. The rabbits were observed and blood gases in room air and in 100% oxygen were measured daily.

Dose Administration

Treated animals received an intravenous injection of 7 mg/kg 20 kD linear PEG-6G4V11N35E Fab' (n=5 animals) at 10 minutes before and 6 hours after acid instillation.

Oxygenation Measurement

Alveolar-arterial oxygen pressure gradient (A-a PO2 gradient) was calculated as follows:

$$A\text{-}aPO2=[FiO2(PB-PH2O)-(PaCO2/RQ)]-PaO2$$

where FiO2 is fraction of inspired oxygen, PB is barometric pressure, PH2O is partial pressure of water vapor, PaCO2 is arterial carbon dioxide pressure, RQ is respiratory quotient, and PaO2 is arterial oxygen pressure.

A-a PO2 gradient and PaO2/FiO2 ratios for each rabbit were measured at baseline (pre-op), before acid instillation, every hour up to 6 hours after acid instillation, and every 24 hours thereafter.

Bronchoalveolar Lavage (BAL)

After blood gases measurement at 72 hours post reperfusion, the rabbits were anesthetized with Nembutal 50 mg/kg i.v. and were euthanized by exsanguination. The abdominal aorta was transected to reduce red blood cell contamination of bronchial alveolar lavage fluid (BALF). The lung and heart were removed en bloc. The right lung was lavaged with an intratracheal tube (Hi-Lo tracheal tube, 3.0 mm) using 20 ml of HBSS and lidocain. Total and differential leukocyte counts of BALF were determined.

Gross Lung Weight

The whole lung from each rabbit was weighed immediately after harvest and was expressed as g/kg of body weight.

Peripheral Blood Count

Blood samples (0.05 ml for CBC, 0.2 ml for blood gases) were collected from the ear central artery catheter at baseline (pre-op), 2 hours, 4 hours, 6 hours, and 22 hours post reperfusion (prior to acid or saline instillation) and at 1 hour, 2 hours, 3 hours, 4 hours, 6 hours and every 24 hours after acid instillation. Hematology parameters were determined by Automated Hematology Analyzer according to the standard hematological procedures.

Pharmacokinetics

Blood samples (0.5 ml) were collected from the ear central artery catheter at baseline (pre-op), 4 hours, and 22 hours post reperfusion and at 1 hour, 4 hours, and every 24 hours after acid instillation.

Results and Discussion

In the rabbit model of ARDS, lung injury is manifested by hypoxemia (low PaO2—the pressure of O2 in the arterial blood, as measured by a blood gas machine), lung edema (evidenced by an elevated lung weight to body weight ratio) and pro-inflammatory infiltrates into the alveolar space (evidenced by high white blood cell (WBC) and neutrophil (PMN) numbers). Although 40 kD branched PEG-6G4V11N35A Fab' did not protect rabbits from lung injury at any of the doses tried (5 mg/kg and 20 mg/kg) (see Section (Y) above), the 20 kD linear PEG-6G4V11N35E Fab' had efficacy equal to, and, for some end-points, superior to that of the full length IgG murine anti-rabbit IL-8 monoclonal antibody 6G4.2.5 and prevented lung injury in the rabbits as shown in FIGS. 70A-70E. (The data points for 40 kD branched PEG-6G4V11N35A Fab' treated animals, full length 6G4.2.5 treated animals, and saline treated animals appearing in FIGS. 70A-70E are taken from the data displayed in FIGS. 67-69 and generated in Example Y above.) In addition, these data indicate that large effective size anti-IL-8 Fab'-PEG conjugates can exhibit useful levels of efficacy in acute lung injury and ARDS.

AA. In Vivo Efficacy Testing of Anti-IL-8 Antibody Reagents in Rabbit Ear Model of Tissue Ischemia and Reperfusion Full length murine anti-rabbit IL-8 monoclonal antibody 6G4.2.5, 20 kD linear PEG-6G4V11N35E Fab', 30 kD linear PEG-6G4V11N35E Fab', and 40 kD branched PEG-6G4V11N35E Fab' were tested in a rabbit ear model of tissue ischemia and reperfusion injury.

Antibodies

A Fab'-SH antibody fragment of the affinity matured anti-IL-8 antibody 6G4V11N35E was expressed using the Fab' expression plasmid for 6G4V11N35E (described in Example T above) in *E. coli* grown to high density in the fermentor as described by Carter et al., *Bio/Technology*, 10: 163-167 (1992). Anti-IL-8 6G4V11N35E Fab' variant was purified from fermentation paste and modified with 20 kD linear methoxy-PEG-maleimide, 30 kD linear methoxy-PEG-maleimide, or 40 kD branched methoxy-PEG-maleimide as described in Example T above. Pegylated material was formulated in phosphate buffered saline (PBS) at physiological pH.

Animals 1.0 to 1.5 kg New Zealand White rabbits were obtained from Western Oregon Rabbit Company.

Surgical Procedure and Animal Evaluation

The procedure was essentially described by Vedder et al., *Proc. Natl. Acad. Sci. (USA)*, 87: 2643-2646 (1990). Briefly, general anesthesia was achieved by intramuscular injections of Ketamine (50 mg/kg) plus Xylazine (5 mg/kg) and Acepromazine (2 mg/kg). The right external ear was prepared for surgery and under sterile procedure the ear was transected at its base, leaving intact only the central artery and vein. All nerves were transected to ensure that the ear was completely anesthetic. A straight microaneurysm clip (1.5×10 mm) was placed across the artery to produce complete ischemia. The ear was reattached with the clip exiting through the wound. The rabbits were then housed at 26° C. and 6 hours later the clip was removed to effect reperfusion. Untreated rabbits (n=11 animals) received an intravenous injection of vehicle (10 mM sodium acetate, 8% trehalose and 0.01% polysorbate-20 at pH 5.5) immediately prior to reperfusion. Treated animals received 5 mg/kg full length IgG murine anti-rabbit IL-8 monoclonal antibody 6G4.2.5 (n=4 animals), 20 kD linear PEG-6G4V11N35E Fab' (n=3 animals), 30 kD linear PEG-6G4V11N35E Fab' (n=3 animals), or 40 kD branched PEG-6G4V11N35E Fab' (n=3 animals) immediately prior to reperfusion.

The ear volume and necrosis were measured daily by procedures described in Vedder et al., supra. Briefly, the ear was submerged in a beaker of water containing 1.2% Povidone iodine (Baxter) up to the intertragic incisure and the ear volume determined by the volume of fluid displaced. The ears were monitored in this manner for 7 days. The data are represented (in FIG. 71) as percent change in ear volume calculated as follows:

$$\% \text{ change in ear volume} = \frac{(\text{Ear vol. at day } x - \text{Ear vol. at day 0})}{\text{Ear vol. at day 0}} \times 100\%$$

Animals were sacrificed at day 1 and day 7 for histological evaluation of the ear and the same section of ear was taken from all animals.

To determine that the therapeutic agents did not adversely affect any hematological parameter, aliquots of blood were withdrawn for complete blood counts and differentials immediately before reperfusion and at 24 hour intervals. In a separate experiment, blood samples were taken at 1, 5, 15, and 30 minutes and at 1 hour and 4 hours.

Results and Discussion

In the rabbit model of ear ischemia reperfusion injury, antibody was administered intravenously at a single dose (5 mg/kg) at the time of reperfusion. In this model, ischemia reperfusion injury is characterized by tissue damage, edema and sometimes necrosis; all attributable in part to neutrophil-mediated damage. Monitoring of ear volume over time is a surrogate end-point for evaluating edema in the ear tissue. The resulting data (depicted in FIG. 71) showed that treatment with 20 kD linear PEG-, 30 kD linear PEG- and 40 kD branched PEG-conjugated Fab's effectively reduced ear swelling and edema at all time points of observation (days 1, 3 and 5). In fact, the efficacy of all three PEGylated Fab's was statistically indistinguishible from that of the full length IgG murine anti-rabbit IL-8 monoclonal antibody 6G4.2.5 at all time points observed. These data support the efficacy of large effective size anti-IL-8 Fab'-PEG conjugates in ischemic reperfusion injury and specifically support the ability of 40 kD branched PEG-conjugated Fab' molecules to reach and act on disease effector targets in circulation and other tissues.

AB. Pharmacokinetic Studies of Two Constructs of Pegylated Anti-VEGF Fab' Fragments Following Intravenous and Intraperitoneal Administration in Normal Mice The objective of this study was to characterize and compare the pharmacokinetics of two pegylated species of the Y0317 affinity matured variant of humanized anti-VEGF F(ab)-12 (Y0317 is described in WO 98/45331 published Oct. 15, 1998) (International Application No. PCT/US98/06604 filed Apr. 3, 1998) when administered intravenously and intraperitoneally in normal mice.

Methods

The Y0317 anti-VEGF Fab' was obtained as described in Example 3 of WO 98/45331. The Y0317 anti-VEGF Fab' was pegylated with 20 kD linear PEG or 40 kD branched PEG using the thiol protection/deprotection maleimide coupling method described in Example T above to form 20 kD linear PEG-Y0317 Fab' and 40 kD branched PEG-Y0317 Fab', respectively. Pegylated Fab's were formulated in phosphate buffered saline (PBS) at physiological pH.

Male CD-1 mice (Charles River Laboratories, Hollister, Calif.), weighing between 18.9 and 28.8 grams, were injected with a single intravenous (IV) or intraperitoneal (IP) dose of either 20 kD linear or 40 kD branched PEG-Y0317 Fab' at approximately 3 mg protein/kg. Blood was collected via cardiac puncture upon terminal sacrifice at the following time points (n=2 per time point): pre-dose, 5 and 30 minutes; 1, 2, 4, 8, 24, 32 hours; Days 2, 3, 5, 7 10 and 14. Serum was harvested and analyzed for PEGylated Y0317 Fab' concentrations by ELISA. In addition, approximately 0.2 mL of serum was collected pre-dose from the Day 7 and 14 mice (orbital bleed) as controls for potential antibody analysis.

For each PEGylated Y0317 Fab', the pooled individual serum PEGylated Y0317 Fab' concentration data following IV and IP administration were analyzed using a two-compartment and one-compartment pharmacokinetic model, respectively. Concentration values that were below the lower limit of the assay were not used in the analysis.

Results

Table 11 below summarizes the compartmental pharmacokinetic parameters of the 20 kD linear and 40 kD branched PEG-Y0317 Fab'. FIGS. 1 and 2 display the serum concentration versus time profiles following IV and IP administration, respectively, for the 20 kD linear and 40 kD branched PEG-Y0317 Fab'.

TABLE 11

Summary of PK parameters

| | 20K | | 40K | |
| --- | --- | --- | --- | --- |
| | IV | IP | IV | IP |
| Dose (mg/kg) | 3 | 3 | 3.4 | 3.4 |
| Cmax (µg/mL) | 58.1 | 11.5 | 74.6 | 49.8 |
| Tmax | 5 min | 8 hr | 30 min | 4 hr |
| CL (mL/day/kg) | 179 | 236 | 49.4 | 37.0 |
| $t_{1/2} \alpha$ (hr) | 1.34 | — | 1.78 | — |
| $t_{1/2} \beta$ (hr) | 16.6 | 16.0[a] | 29.8 | 28.3[a] |
| AUC (day · µg/mL) | 16.8 | 12.7 | 68.9 | 91.8 |
| Vss (mL/kg) | 139 | 228 | 82.8 | 63.3 |
| BA (%) | — | 75.6 | — | 133 |

[a] K10 half-life was reported for IP.

After intravenous administration, the clearance of the 20 kD linear PEG-Y0317 Fab' was 179 mL/day/kg and decreased to 49.4 mL/day/kg with the 40 kD branched PEG-Y0317 Fab'. Vss, also decreasing with a larger PEG size, was 139 and 82.8 for the 20 kD and 40 kD PEGylated species, respectively. In accord with the decrease in clearance and volume of distribution, an increased terminal half-life was observed for the larger PEG size (terminal $t_{1/2}$ of approximately 17 and 30 hours for the 20 kD and 40 kD PEGylated species, respectively). After IP administration, the bioavailability was approximately 76 and 133% for the 20 kD and 40 kD PEGylated species, respectively. Results from previous pharmacokinetic studies with intravenous administration of an anti-CD18 Fab in a normal mouse model (Zapata et al., "Site Specific Coupling of Monomethoxypoly(ethylene) glycol to a single-sulfhydryl humanized Fab'", poster presented at the American Society for Biochemistry and Molecular Biology FASEB Meeting held in San Francisco, Calif. on May 21-25, 1995; Abstract No. 1288 published in Zapata et al., *FASEB J.*, 9(6): A1479 (1995)) indicated that the clearance of a non-PEGylated Fab' was approximately 4500 mL/day/kg and the terminal half-life was approximately 30 minutes. Taken together, these data indicate that 20 kD (linear) and 40 kD (branched) PEGylation of the Y0317 Fab' resulted in an approximately 25-fold to 90-fold decrease in clearance and a 29-fold and 52-fold increase in terminal $t_{1/2}$, respectively.

AC. In Vivo Efficacy Testing of Anti-VEGF Antibody Reagents in Mouse Model of Tumor Growth 40 kD branched PEG-Y0317 anti-human VEGF Fab' was tested in a mouse tumor growth model.

Methods 40 kD branched PEG-Y0317 anti-human VEGF Fab' was obtained as described in Example AB above. Y0317 anti-human VEGF MAb (full length IgG1) was obtained by fusing the Y0317 variable light (VL) and variable heavy (VH) domain sequences to constant light (CL) and constant heavy (CH) domain sequences, respectively, in separate pRK expression vectors as described in Eaton et al., *Biochemistry*, 25: 8343-8347 (1986), co-transfecting the expression constructs into 293 cells or CHO cells, and harvesting antibody from transfected cell culture supernatant essentially as described in Example 1 of WO 98/45331 (published Oct. 15, 1998) (International Application No. PCT/US98/06604 filed Apr. 3, 1998). Control 40 kD branched PEG-6G4V11N35E anti-rabbit IL-8 Fab' was obtained as described in Example AA above.

Human A673 rhabdomyosarcoma cells (ATCC; CRL 1598) were cultured as previously described in DMEM/F12 supplemented with 10% fetal bovine serum, 2 mM glutamine and antibiotics (Kim et al. *Nature* 362:841-844 (1993) and Borgström et al. *Cancer Res.* 56:4032-4039 (1996)). Female Beige nude mice, 6-10 weeks old (Harlan Sprague Dawley), were injected subcutaneously in the dorsal area with $2.5 \times 10^6$ A673 tumor cells in a volume of 100 μl of matrigel. Animals were then treated with 40 kD branched PEG-Y0317 Fab', Y0317 MAb, control 40 kD branched PEG-6G4V11N35E anti-rabbit IL-8 Fab', or phosphate buffered saline (PBS) at physiological pH.

In the low dose 40 kD branched PEG-Y0317 Fab' treatment group, 40 kD branched PEG-Y0317 Fab' was administered at a loading dose of 2 mg/kg on day 1, followed by maintenance doses of 0.9 mg/kg daily for the remainder of the study.

In the high dose 40 kD branched PEG-Y0317 Fab' treatment group, 40 kD branched PEG-Y0317 Fab' was administered at a loading dose of 6 mg/kg on day 1, followed by maintenance doses of 2.7 mg/kg daily for the remainder of the study.

In the Y0317 MAb treatment group, Y0317 MAb was administered at a loading dose of 8 mg/kg on day 1, followed by maintenance doses of 0.8 mg/kg every third day for the remainder of the study.

In the control Fab' treatment group, 40 kD branched PEG-6G4V11N35E anti-rabbit IL-8 Fab' was administered at a loading dose of 6 mg/kg on day 1, followed by maintenance doses of 2.7 mg/kg daily for the remainder of the study.

In the PBS control group, 0.1 ml/day of PBS was administered for the duration of the study. All doses were administered intraperitoneally in a volume of 100 μl, starting 24 hr after tumor cell inoculation.

Each group initially consisted of 10 mice. Tumor size (length×width×height) was determined at weekly intervals. 17 days after tumor cell inoculation, animals were euthanized and the tumors were removed and weighed. Statistical analysis was performed by ANOVA.

Results

As shown in FIG. 74, at both doses tested (2 and 6 mg/kg), the 40 kD branched PEG-Y0317 Fab' markedly suppressed tumor growth as assessed by tumor weight measurements three weeks after tumor cell inoculation. The decreases were 91% and 90%, respectively, in animals treated with the low and high doses of 40 kD branched PEG-Y0317 Fab' versus 95% in animals treated with Y0317 MAb.

The following biological materials have been deposited with the American Type Culture Collection, 12301 Parklawn Drive, Rockville, Md., USA (ATCC):

| Material | ATCC Accession No. | Deposit Date |
| --- | --- | --- |
| hybridoma cell line 5.12.14 | HB 11553 | Feb. 15, 1993 |
| hybridoma cell line 6G4.2.5 | HB 11722 | Sep. 28, 1994 |
| pantiIL-8.2, *E. coli* strain 294 mm | 97056 | Feb. 10, 1995 |
| p6G425chim2, *E. coli* strain 294 mm | 97055 | Feb. 10, 1995 |
| p6G4V11N35A.F(ab')₂ | 97890 | Feb. 20, 1997 |
| *E. coli* strain 49D6(p6G4V11N35A.F(ab')₂) | 98332 | Feb. 20, 1997 |
| p6G425V11N35A.choSD | 209552 | Dec. 16, 1997 |
| clone#1933 aIL8.92 NB 28605/12 | CRL-12444 | Dec. 11, 1997 |
| clone#1934 aIL8.42 NB 28605/14 | CRL-12445 | Dec. 11, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable deposit for 30 years from the date of deposit. These cell lines will be made available by ATCC under the terms of the Budapest Treaty, and subject to an agreement between Genentech, Inc. and ATCC, which assures permanent and unrestricted availability of the cell lines to the public upon issuance of the pertinent U.S. patent or upon laying open to the public of any U.S. or foreign patent application, whichever comes first, and assures availability of the cell lines to one determined by the U.S. Commissioner of Patents and Trademarks to be entitled thereto according to 35 USC §122 and the Commissioner's rules pursuant thereto (including 37 CFR §1.14 with particular reference to 8860G 638).

The assignee of the present application has agreed that if the deposited cell lines should be lost or destroyed when cultivated under suitable conditions, they will be promptly replaced on notification with a specimen of the same cell line. Availability of the deposited cell lines is not to be construed as a license to practice the invention in contravention of the rights granted under the authority of any government in accordance with its patent laws.

SEQUENCE LISTING

<160> NUMBER OF SEQ ID NOS: 72

<210> SEQ ID NO 1
<211> LENGTH: 22
<212> TYPE: DNA
<213> ORGANISM: Mus musculus

<400> SEQUENCE: 1
cagtccaact gttcaggacg cc                                          22

<210> SEQ ID NO 2
<211> LENGTH: 22
<212> TYPE: DNA
<213> ORGANISM: Mus musculus

<400> SEQUENCE: 2
gtgctgctca tgctgtaggt gc                                          22

<210> SEQ ID NO 3
<211> LENGTH: 23
<212> TYPE: DNA
<213> ORGANISM: Mus musculus

<400> SEQUENCE: 3
gaagttgatg tcttgtgagt ggc                                         23

<210> SEQ ID NO 4
<211> LENGTH: 24
<212> TYPE: DNA
<213> ORGANISM: Mus musculus

<400> SEQUENCE: 4
gcatcctaga gtcaccgagg agcc                                        24

<210> SEQ ID NO 5
<211> LENGTH: 22
<212> TYPE: DNA
<213> ORGANISM: Mus musculus

<400> SEQUENCE: 5
cactggctca gggaaataac cc                                          22

<210> SEQ ID NO 6
<211> LENGTH: 22
<212> TYPE: DNA
<213> ORGANISM: Mus musculus

<400> SEQUENCE: 6
ggagagctgg gaaggtgtgc ac                                          22

<210> SEQ ID NO 7
<211> LENGTH: 35
<212> TYPE: DNA
<213> ORGANISM: Mus musculus

<400> SEQUENCE: 7
acaaacgcgt acgctgacat cgtcatgacc cagtc                            35

<210> SEQ ID NO 8
<211> LENGTH: 35
<212> TYPE: DNA
<213> ORGANISM: Mus musculus

<400> SEQUENCE: 8
acaaacgcgt acgctgatat tgtcatgact cagtc        35

<210> SEQ ID NO 9
<211> LENGTH: 35
<212> TYPE: DNA
<213> ORGANISM: Mus musculus

<400> SEQUENCE: 9
acaaacgcgt acgctgacat cgtcatgaca cagtc        35

<210> SEQ ID NO 10
<211> LENGTH: 37
<212> TYPE: DNA
<213> ORGANISM: Mus musculus

<400> SEQUENCE: 10
gctcttcgaa tggtgggaag atggatacag ttggtgc      37

<210> SEQ ID NO 11
<211> LENGTH: 39
<212> TYPE: DNA
<213> ORGANISM: Mus musculus

<400> SEQUENCE: 11
cgatgggccc ggatagaccg atggggctgt tgttttggc    39

<210> SEQ ID NO 12
<211> LENGTH: 39
<212> TYPE: DNA
<213> ORGANISM: Mus musculus

<400> SEQUENCE: 12
cgatgggccc ggatagactg atggggctgt cgttttggc    39

<210> SEQ ID NO 13
<211> LENGTH: 39
<212> TYPE: DNA
<213> ORGANISM: Mus musculus

<400> SEQUENCE: 13
cgatgggccc ggatagacgg atggggctgt tgttttggc    39

<210> SEQ ID NO 14
<211> LENGTH: 39
<212> TYPE: DNA
<213> ORGANISM: Mus musculus

<400> SEQUENCE: 14
cgatgggccc ggatagacag atggggctgt tgttttggc    39

<210> SEQ ID NO 15
<211> LENGTH: 39
<212> TYPE: DNA
<213> ORGANISM: Mus musculus

<400> SEQUENCE: 15

-continued

```
cgatgggccc ggatagactg atggggctgt tgttttggc                          39
```

<210> SEQ ID NO 16
<211> LENGTH: 369
<212> TYPE: DNA
<213> ORGANISM: Mus musculus

<400> SEQUENCE: 16

```
gacattgtca tgacacagtc tcaaaaattc atgtccacat cagtaggaga              50
cagggtcagc gtcacctgca aggccagtca gaatgtgggt actaatgtag             100
cctggtatca acagaaacca gggcaatctc ctaaagcact gatttactcg             150
tcatcctacc ggtacagtgg agtccctgat cgcttcacag gcagtggatc             200
tgggacagat ttcactctca ccatcagcca tgtgcagtct gaagacttgg             250
cagactattt ctgtcagcaa tataacatct atcctctcac gttcggtcct             300
gggaccaagc tggagttgaa acgggctgat gctgcaccac caactgtatc             350
catcttccca ccattcgaa                                               369
```

<210> SEQ ID NO 17
<211> LENGTH: 123
<212> TYPE: PRT
<213> ORGANISM: Mus musculus

<400> SEQUENCE: 17

```
Asp Ile Val Met Thr Gln Ser Gln Lys Phe Met Ser Thr Ser Val
  1               5                  10                  15

Gly Asp Arg Val Ser Val Thr Cys Lys Ala Ser Gln Asn Val Gly
                 20                  25                  30

Thr Asn Val Ala Trp Tyr Gln Gln Lys Pro Gly Gln Ser Pro Lys
                 35                  40                  45

Ala Leu Ile Tyr Ser Ser Ser Tyr Arg Tyr Ser Gly Val Pro Asp
                 50                  55                  60

Arg Phe Thr Gly Ser Gly Ser Gly Thr Asp Phe Thr Leu Thr Ile
                 65                  70                  75

Ser His Val Gln Ser Glu Asp Leu Ala Asp Tyr Phe Cys Gln Gln
                 80                  85                  90

Tyr Asn Ile Tyr Pro Leu Thr Phe Gly Pro Gly Thr Lys Leu Glu
                 95                 100                 105

Leu Lys Arg Ala Asp Ala Ala Pro Pro Thr Val Ser Ile Phe Pro
                110                 115                 120

Pro Phe Glu
        123
```

<210> SEQ ID NO 18
<211> LENGTH: 417
<212> TYPE: DNA
<213> ORGANISM: Mus musculus

<400> SEQUENCE: 18

```
ttctattgct acaaacgcgt acgctgaggt gcagctggtg gagtctgggg              50
gaggcttagt gccgcctgga gggtccctga actctcctg tgcagcctct              100
ggattcatat tcagtagtta tggcatgtct tgggttcgcc agactccagg             150
caagagcctg gagttggtcg caaccattaa taataatggt gatagcacct             200
attatccaga cagtgtgaag ggccgattca ccatctcccg agacaatgcc             250
```

```
aagaacaccc tgtacctgca aatgagcagt ctgaagtctg aggacacagc              300
catgttttac tgtgcaagag ccctcattag ttcggctact tggtttggtt              350
actggggcca agggactctg gtcactgtct ctgcagccaa acaacagcc               400 ccatctgtct atccggg                                                  417
```

```
<210> SEQ ID NO 19
<211> LENGTH: 130
<212> TYPE: PRT
<213> ORGANISM: Mus musculus

<400> SEQUENCE: 19
```

| Glu | Val | Gln | Leu | Val | Glu | Ser | Gly | Gly | Gly | Leu | Val | Pro | Pro | Gly |
|---|---|---|---|---|---|---|---|---|---|---|---|---|---|---|
| 1 | | | | 5 | | | | | 10 | | | | | 15 |

| Gly | Ser | Leu | Lys | Leu | Ser | Cys | Ala | Ala | Ser | Gly | Phe | Ile | Phe | Ser |
|---|---|---|---|---|---|---|---|---|---|---|---|---|---|---|
| | | | | 20 | | | | | 25 | | | | | 30 |

| Ser | Tyr | Gly | Met | Ser | Trp | Val | Arg | Gln | Thr | Pro | Gly | Lys | Ser | Leu |
|---|---|---|---|---|---|---|---|---|---|---|---|---|---|---|
| | | | | 35 | | | | | 40 | | | | | 45 |

| Glu | Leu | Val | Ala | Thr | Ile | Asn | Asn | Gly | Asp | Ser | Thr | Tyr | Tyr |
|---|---|---|---|---|---|---|---|---|---|---|---|---|---|
| | | | | 50 | | | | | 55 | | | | 60 |

| Pro | Asp | Ser | Val | Lys | Gly | Arg | Phe | Thr | Ile | Ser | Arg | Asp | Asn | Ala |
|---|---|---|---|---|---|---|---|---|---|---|---|---|---|---|
| | | | | 65 | | | | | 70 | | | | | 75 |

| Lys | Asn | Thr | Leu | Tyr | Leu | Gln | Met | Ser | Ser | Leu | Lys | Ser | Glu | Asp |
|---|---|---|---|---|---|---|---|---|---|---|---|---|---|---|
| | | | | 80 | | | | | 85 | | | | | 90 |

| Thr | Ala | Met | Phe | Tyr | Cys | Ala | Arg | Ala | Leu | Ile | Ser | Ser | Ala | Thr |
|---|---|---|---|---|---|---|---|---|---|---|---|---|---|---|
| | | | | 95 | | | | | 100 | | | | | 105 |

| Trp | Phe | Gly | Tyr | Trp | Gly | Gln | Gly | Thr | Leu | Val | Thr | Val | Ser | Ala |
|---|---|---|---|---|---|---|---|---|---|---|---|---|---|---|
| | | | | 110 | | | | | 115 | | | | | 120 |

| Ala | Lys | Thr | Thr | Ala | Pro | Ser | Val | Tyr | Pro |
|---|---|---|---|---|---|---|---|---|---|
| | | | | 125 | | | | | 130 |

```
<210> SEQ ID NO 20
<211> LENGTH: 31
<212> TYPE: DNA
<213> ORGANISM: Artificial Sequence
<220> FEATURE:
<221> NAME/KEY: Artificial Sequence
<222> LOCATION: 1-31
<223> OTHER INFORMATION: recombinant immunoglobulin

<400> SEQUENCE: 20
acaaacgcgt acgctgatat cgtcatgaca g                                   31

<210> SEQ ID NO 21
<211> LENGTH: 31
<212> TYPE: DNA
<213> ORGANISM: Artificial Sequence
<220> FEATURE:
<221> NAME/KEY: Artificial Sequence
<222> LOCATION: 1-31
<223> OTHER INFORMATION: recombinant immunoglobulin

<400> SEQUENCE: 21
gcagcatcag ctcttcgaag ctccagcttg g                                   31

<210> SEQ ID NO 22
<211> LENGTH: 21
<212> TYPE: DNA
<213> ORGANISM: Escherichia coli

<400> SEQUENCE: 22
```

```
ccactagtac gcaagttcac g                                              21
```

<210> SEQ ID NO 23
<211> LENGTH: 33
<212> TYPE: DNA
<213> ORGANISM: Artificial Sequence
<220> FEATURE:
<221> NAME/KEY: Artificial Sequence
<222> LOCATION: 1-33
<223> OTHER INFORMATION: recombinantimmunoglobulin

<400> SEQUENCE: 23

```
gatgggccct tggtggaggc tgcagagaca gtg                                 33
```

<210> SEQ ID NO 24
<211> LENGTH: 714
<212> TYPE: DNA
<213> ORGANISM: Artificial Sequence
<220> FEATURE:
<221> NAME/KEY: Artificial Sequence
<222> LOCATION: 1-714
<223> OTHER INFORMATION: recombinant immunoglobulin

<400> SEQUENCE: 24

```
atgaagaaga atatcgcatt tcttcttgca tctatgttcg tttttttctat              50
tgctacaaac gcgtacgctg atatcgtcat gacacagtct caaaaattca              100
tgtccacatc agtaggagac agggtcagcg tcacctgcaa ggccagtcag              150
aatgtgggta ctaatgtagc ctggtatcaa cagaaaccag gcaatctcc               200
taaagcactg atttactcgt catcctaccg gtacagtgga gtccctgatc              250
gcttcacagg cagtggatct gggacagatt tcactctcac catcagccat              300
gtgcagtctg aagacttggc agactatttc tgtcagcaat ataacatcta              350
tcctctcacg ttcggtcctg ggaccaagct ggagcttcga agagctgtgg              400
ctgcaccatc tgtcttcatc ttcccgccat ctgatgagca gttgaaatct              450
ggaactgctt ctgttgtgtg cctgctgaat aacttctatc ccagagaggc              500
caaagtacag tggaaggtgg ataacgccct ccaatcgggt aactcccagg              550
agagtgtcac agagcaggac agcaaggaca gcacctacag cctcagcagc              600
accctgacgc tgagcaaagc agactacgag aaacacaaag tctacgcctg              650
cgaagtcacc catcagggcc tgagctcgcc cgtcacaaag agcttcaaca              700
ggggagagtg ttaa                                                     714
```

<210> SEQ ID NO 25
<211> LENGTH: 237
<212> TYPE: PRT
<213> ORGANISM: Artificial Sequence
<220> FEATURE:
<221> NAME/KEY: Artificial Sequence
<222> LOCATION: 1-237
<223> OTHER INFORMATION: recombinant immunoglobulin

<400> SEQUENCE: 25

```
Met Lys Lys Asn Ile Ala Phe Leu Leu Ala Ser Met Phe Val Phe
 1               5                  10                  15

Ser Ile Ala Thr Asn Ala Tyr Ala Asp Ile Val Met Thr Gln Ser
                20                  25                  30

Gln Lys Phe Met Ser Thr Ser Val Gly Asp Arg Val Ser Val Thr
                35                  40                  45
```

-continued

```
Cys Lys Ala Ser Gln Asn Val Gly Thr Asn Val Ala Trp Tyr Gln
            50                  55                  60

Gln Lys Pro Gly Gln Ser Pro Lys Ala Leu Ile Tyr Ser Ser Ser
            65                  70                  75

Tyr Arg Tyr Ser Gly Val Pro Asp Arg Phe Thr Gly Ser Gly Ser
            80                  85                  90

Gly Thr Asp Phe Thr Leu Thr Ile Ser His Val Gln Ser Glu Asp
            95                  100                 105

Leu Ala Asp Tyr Phe Cys Gln Gln Tyr Asn Ile Tyr Pro Leu Thr
            110                 115                 120

Phe Gly Pro Gly Thr Lys Leu Glu Leu Arg Arg Ala Val Ala Ala
            125                 130                 135

Pro Ser Val Phe Ile Phe Pro Pro Ser Asp Glu Gln Leu Lys Ser
            140                 145                 150

Gly Thr Ala Ser Val Val Cys Leu Leu Asn Asn Phe Tyr Pro Arg
            155                 160                 165

Glu Ala Lys Val Gln Trp Lys Val Asp Asn Ala Leu Gln Ser Gly
            170                 175                 180

Asn Ser Gln Glu Ser Val Thr Glu Gln Asp Ser Lys Asp Ser Thr
            185                 190                 195

Tyr Ser Leu Ser Ser Thr Leu Thr Leu Ser Lys Ala Asp Tyr Glu
            200                 205                 210

Lys His Lys Val Tyr Ala Cys Glu Val Thr His Gln Gly Leu Ser
            215                 220                 225

Ser Pro Val Thr Lys Ser Phe Asn Arg Gly Glu Cys
            230                 235     237
```

```
<210> SEQ ID NO 26
<211> LENGTH: 756
<212> TYPE: DNA
<213> ORGANISM: Artificial Sequence
<220> FEATURE:
<221> NAME/KEY: Artificial Sequence
<222> LOCATION: 1-756
<223> OTHER INFORMATION: recombinant immunoglobulin

<400> SEQUENCE: 26
atgaaaaaga atatcgcatt tcttcttgca tctatgttcg ttttttctat         50
tgctacaaac gcgtacgctg aggtgcagct ggtggagtct ggggggaggct        100 tagtgccgcc tggagggtcc ctgaaactct cctgtgcagc ctctggattc        150
atattcagta gttatggcat gtcttgggtt cgccagactc caggcaagag        200
cctggagttg gtcgcaacca ttaataataa tggtgatagc acctattatc        250 agacagtgt gaagggccga ttcaccatct cccgagacaa tgccaagaac         300
accctgtacc tgcaaatgag cagtctgaag tctgaggaca cagccatgtt        350
ttactgtgca agagccctca ttagttcggc tacttggttt ggttactggg        400 gccaaggcgac tctggtcact gtctctgcag cctccaccaa gggcccatcg       450
gtcttccccc tggcaccctc ctccaagagc acctctgggg gcacagcggc        500
cctgggctgc ctggtcaagg actacttccc cgaaccggtg acggtgtcgt        550
ggaactcagg cgccctgacc agcggcgtgc acaccttccc ggctgtccta        600
cagtcctcag gactctactc cctcagcagc gtggtgaccg tgccctccag        650
cagcttgggc acccagacct acatctgcaa cgtgaatcac aagcccagca        700
```

```
acaccaaggt ggacaagaaa gttgagccca atcttgtga caaaactcac         750 acatga                                                        756
```

<210> SEQ ID NO 27
<211> LENGTH: 251
<212> TYPE: PRT
<213> ORGANISM: Artificial Sequence
<220> FEATURE:
<221> NAME/KEY: Artificial Sequence
<222> LOCATION: 1-251
<223> OTHER INFORMATION: recombinant immunglobulin

<400> SEQUENCE: 27

```
Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Glu Ser
                20                  25                  30

Gly Gly Gly Leu Val Pro Pro Gly Gly Ser Leu Lys Leu Ser Cys
                35                  40                  45

Ala Ala Ser Gly Phe Ile Phe Ser Ser Tyr Gly Met Ser Trp Val
                50                  55                  60

Arg Gln Thr Pro Gly Lys Ser Leu Glu Leu Val Ala Thr Ile Asn
                65                  70                  75

Asn Asn Gly Asp Ser Thr Tyr Tyr Pro Asp Ser Val Lys Gly Arg
                80                  85                  90

Phe Thr Ile Ser Arg Asp Asn Ala Lys Asn Thr Leu Tyr Leu Gln
                95                 100                 105

Met Ser Ser Leu Lys Ser Glu Asp Thr Ala Met Phe Tyr Cys Ala
               110                 115                 120

Arg Ala Leu Ile Ser Ser Ala Thr Trp Phe Gly Tyr Trp Gly Gln
               125                 130                 135

Gly Thr Leu Val Thr Val Ser Ala Ala Ser Thr Lys Gly Pro Ser
               140                 145                 150

Val Phe Pro Leu Ala Pro Ser Ser Lys Ser Thr Ser Gly Gly Thr
               155                 160                 165

Ala Ala Leu Gly Cys Leu Val Lys Asp Tyr Phe Pro Glu Pro Val
               170                 175                 180

Thr Val Ser Trp Asn Ser Gly Ala Leu Thr Ser Gly Val His Thr
               185                 190                 195

Phe Pro Ala Val Leu Gln Ser Ser Gly Leu Tyr Ser Leu Ser Ser
               200                 205                 210

Val Val Thr Val Pro Ser Ser Leu Gly Thr Gln Thr Tyr Ile
               215                 220                 225

Cys Asn Val Asn His Lys Pro Ser Asn Thr Lys Val Asp Lys Lys
               230                 235                 240

Val Glu Pro Lys Ser Cys Asp Lys Thr His Thr
               245                 250 251
```

<210> SEQ ID NO 28
<211> LENGTH: 37
<212> TYPE: DNA
<213> ORGANISM: Mus musculus

<400> SEQUENCE: 28

```
ccaatgcata cgctgacatc gtgatgaccc agacccc                       37
```

<210> SEQ ID NO 29

```
<211> LENGTH: 37
<212> TYPE: DNA
<213> ORGANISM: Mus musculus

<400> SEQUENCE: 29
ccaatgcata cgctgatatt gtgatgactc agactcc                              37

<210> SEQ ID NO 30
<211> LENGTH: 37
<212> TYPE: DNA
<213> ORGANISM: Mus musculus

<400> SEQUENCE: 30
ccaatgcata cgctgacatc gtgatgacac agacacc                              37

<210> SEQ ID NO 31
<211> LENGTH: 35
<212> TYPE: DNA
<213> ORGANISM: Mus musculus

<400> SEQUENCE: 31
agatgtcaat tgctcactgg atggtgggaa gatgg                                35

<210> SEQ ID NO 32
<211> LENGTH: 32
<212> TYPE: DNA
<213> ORGANISM: Mus musculus

<400> SEQUENCE: 32
caaacgcgta cgctgagatc cagctgcagc ag                                   32

<210> SEQ ID NO 33
<211> LENGTH: 32
<212> TYPE: DNA
<213> ORGANISM: Mus musculus

<400> SEQUENCE: 33
caaacgcgta cgctgagatt cagctccagc ag                                   32

<210> SEQ ID NO 34
<211> LENGTH: 391
<212> TYPE: DNA
<213> ORGANISM: Mus musculus

<400> SEQUENCE: 34
gatatcgtga tgacacagac accactctcc ctgcctgtca gtcttggaga                50
tcaggcctcc atctcttgca gatctagtca gagccttgta cacggtattg               100
gaaacaccta tttacattgg tacctgcaga agccaggcca gtctccaaag               150
ctcctgatct acaaagtttc caaccgattt tctggggtcc cagacaggtt               200
cagtggcagt ggatcaggga cagatttcac actcaggatc agcagagtgg               250
aggctgagga tctgggactt tatttctgct ctcaaagtac acatgttccg               300
ctcacgttcg gtgctgggac caagctggag ctgaaacggg ctgatgctgc               350
accaactgta tccatcttcc caccatccag tgagcaattg a                        391

<210> SEQ ID NO 35
<211> LENGTH: 131
<212> TYPE: PRT
<213> ORGANISM: Mus musculus

<400> SEQUENCE: 35
```

Asp Ile Val Met Thr Gln Thr Pro Leu Ser Leu Pro Val Ser Leu
1               5                   10                  15

Gly Asp Gln Ala Ser Ile Ser Cys Arg Ser Ser Gln Ser Leu Val
                20                  25                  30

His Gly Ile Gly Asn Thr Tyr Leu His Trp Tyr Leu Gln Lys Pro
            35                  40                  45

Gly Gln Ser Pro Lys Leu Leu Ile Tyr Lys Val Ser Asn Arg Phe
            50                  55                  60

Ser Gly Val Pro Asp Arg Phe Ser Gly Ser Gly Ser Gly Thr Asp
            65                  70                  75

Phe Thr Leu Arg Ile Ser Arg Val Glu Ala Glu Asp Leu Gly Leu
            80                  85                  90

Tyr Phe Cys Ser Gln Ser Thr His Val Pro Leu Thr Phe Gly Ala
            95                  100                 105

Gly Thr Lys Leu Glu Leu Lys Arg Ala Asp Ala Ala Pro Thr Val
            110                 115                 120

Ser Ile Phe Pro Pro Ser Ser Glu Gln Leu Lys
            125                 130 131

<210> SEQ ID NO 36
<211> LENGTH: 405
<212> TYPE: DNA
<213> ORGANISM: Mus musculus

<400> SEQUENCE: 36
gagattcagc tgcagcagtc tggacctgag ctgatgaagc ctggggcttc        50
agtgaagata tcctgcaagg cttctggtta ttcattcagt agccactaca       100
tgcactgggt gaagcagagc catggaaaga gccttgagtg gattggctac       150
attgatcctt ccaatggtga aactacttac aaccagaaat tcaagggcaa       200
ggccacattg actgtagaca catcttccag cacagccaac gtgcatctca       250
gcagcctgac atctgatgac tctgcagtct atttctgtgc aagaggggac       300
tatagataca acggcgactg gttttttcgat gtctggggcg cagggaccac       350
ggtcaccgtc tcctccgcca aaaccgacag ccccatcggt ctatccgggc       400
ccatc                                                        405

<210> SEQ ID NO 37
<211> LENGTH: 135
<212> TYPE: PRT
<213> ORGANISM: Mus musculus

<400> SEQUENCE: 37

Glu Ile Gln Leu Gln Gln Ser Gly Pro Glu Leu Met Lys Pro Gly
1               5                   10                  15

Ala Ser Val Lys Ile Ser Cys Lys Ala Ser Gly Tyr Ser Phe Ser
                20                  25                  30

Ser His Tyr Met His Trp Val Lys Gln Ser His Gly Lys Ser Leu
            35                  40                  45

Glu Trp Ile Gly Tyr Ile Asp Pro Ser Asn Gly Glu Thr Thr Tyr
            50                  55                  60

Asn Gln Lys Phe Lys Gly Lys Ala Thr Leu Thr Val Asp Thr Ser
            65                  70                  75

Ser Ser Thr Ala Asn Val His Leu Ser Ser Leu Thr Ser Asp Asp
            80                  85                  90

```
Ser Ala Val Tyr Phe Cys Ala Arg Gly Asp Tyr Arg Tyr Asn Gly
             95                 100                 105

Asp Trp Phe Phe Asp Val Trp Gly Ala Gly Thr Thr Val Thr Val
            110                 115                 120

Ser Ser Ala Lys Thr Asp Ser Pro Ile Gly Leu Ser Gly Pro Ile
            125                 130                 135

<210> SEQ ID NO 38
<211> LENGTH: 22
<212> TYPE: DNA
<213> ORGANISM: Artificial Sequence
<220> FEATURE:
<221> NAME/KEY: Artifical Sequence
<222> LOCATION: 1-22
<223> OTHER INFORMATION: recombinant immunoglobulin

<400> SEQUENCE: 38
cttggtggag gcggaggaga cg                                          22

<210> SEQ ID NO 39
<211> LENGTH: 38
<212> TYPE: DNA
<213> ORGANISM: Artificial Sequence
<220> FEATURE:
<221> NAME/KEY: Artificial Sequence
<222> LOCATION: 1-38
<223> OTHER INFORMATION: recombinant immunoglobulin

<400> SEQUENCE: 39
gaaacgggct gttgctgcac caactgtatt catcttcc                         38

<210> SEQ ID NO 40
<211> LENGTH: 31
<212> TYPE: DNA
<213> ORGANISM: Artificial Sequence
<220> FEATURE:
<221> NAME/KEY: Artificial Sequence
<222> LOCATION: 1-31
<223> OTHER INFORMATION: recombinant immunoglobulin

<400> SEQUENCE: 40
gtcaccgtct cctccgcctc caccaagggc c                                31

<210> SEQ ID NO 41
<211> LENGTH: 729
<212> TYPE: DNA
<213> ORGANISM: Artificial Sequence
<220> FEATURE:
<221> NAME/KEY: Artifical Sequence
<222> LOCATION: 1-729
<223> OTHER INFORMATION: recombinant immunoglobulin

<400> SEQUENCE: 41
atgaagaaga atatcgcatt tcttcttgca tctatgttcg ttttttctat            50
tgctacaaat gcatacgctg atatcgtgat gacacagaca ccactctccc           100
tgcctgtcag tcttggagat caggcctcca tctcttgcag atctagtcag           150
agccttgtac acggtattgg aaacacctat ttacattggt acctgcagaa           200
gccaggccag tctccaaagc tcctgatcta caaagtttcc aaccgatttt           250
ctggggtccc agacaggttc agtggcagtg gatcagggac agatttcaca           300
ctcaggatca gcagagtgga ggctgaggat ctggactttt atttctgctc           350
tcaaagtaca catgttccgc tcacgttcgg tgctgggacc aagctggagc           400
```

```
tgaaacgggc tgttgctgca ccaactgtat tcatcttccc accatccagt         450
gagcaattga atctggaac tgcctctgtt gtgtgcctgc tgaataactt          500
ctatcccaga gaggccaaag tacagtggaa ggtggataac gccctccaat         550
cgggtaactc ccaggagagt gtcacagagc aggacagcaa ggacagcacc         600
tacagcctca gcagcaccct gacgctgagc aaagcagact acgagaaaca         650
caaagtctac gcctgcgaag tcacccatca gggcctgagc tcgcccgtca         700
caaagagctt caacagggga gagtgttaa                                729
```

<210> SEQ ID NO 42
<211> LENGTH: 242
<212> TYPE: PRT
<213> ORGANISM: Artificial Sequence
<220> FEATURE:
<221> NAME/KEY: Artificial Sequence
<222> LOCATION: 1-242
<223> OTHER INFORMATION: recombinant immunoglobulin

<400> SEQUENCE: 42

```
Met Lys Lys Asn Ile Ala Phe Leu Leu Ala Ser Met Phe Val Phe
 1               5                  10                  15

Ser Ile Ala Thr Asn Ala Tyr Ala Asp Ile Val Met Thr Gln Thr
                20                  25                  30

Pro Leu Ser Leu Pro Val Ser Leu Gly Asp Gln Ala Ser Ile Ser
                35                  40                  45

Cys Arg Ser Ser Gln Ser Leu Val His Gly Ile Gly Asn Thr Tyr
                50                  55                  60

Leu His Trp Tyr Leu Gln Lys Pro Gly Gln Ser Pro Lys Leu Leu
                65                  70                  75

Ile Tyr Lys Val Ser Asn Arg Phe Ser Gly Val Pro Asp Arg Phe
                80                  85                  90

Ser Gly Ser Gly Ser Gly Thr Asp Phe Thr Leu Arg Ile Ser Arg
                95                 100                 105

Val Glu Ala Glu Asp Leu Gly Leu Tyr Phe Cys Ser Gln Ser Thr
               110                 115                 120

His Val Pro Leu Thr Phe Gly Ala Gly Thr Lys Leu Glu Leu Lys
               125                 130                 135

Arg Ala Val Ala Ala Pro Thr Val Phe Ile Phe Pro Pro Ser Ser
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
242
```

<210> SEQ ID NO 43
<211> LENGTH: 762
<212> TYPE: DNA
<213> ORGANISM: Artificial Sequence
<220> FEATURE:
<221> NAME/KEY: Artificial Sequence
<222> LOCATION: 1-762
<223> OTHER INFORMATION: recombinant immunoglobulin

<400> SEQUENCE: 43

```
atgaaaaaga atatcgcatt tcttcttgca tctatgttcg ttttttctat         50
tgctacaaac gcgtacgctg agattcagct gcagcagtct ggacctgagc        100
tgatgaagcc tggggcttca gtgaagatat cctgcaaggc ttctggttat        150
tcattcagta gccactacat gcactgggtg aagcagagcc atggaaagag        200
ccttgagtgg attggctaca ttgatccttc caatggtgaa actacttaca        250
accagaaatt caagggcaag gccacattga ctgtagacac atcttccagc        300
acagccaacg tgcatctcag cagcctgaca tctgatgact ctgcagtcta        350
tttctgtgca agaggggact atagatacaa cggcgactgg ttttttcgatg       400
tctggggcgc agggaccacg gtcaccgtct cctccgcctc caccaagggc        450
ccatcggtct tccccctggc accctcctcc aagagcacct ctgggggcac        500
agcggccctg ggctgcctgg tcaaggacta cttccccgaa ccggtgacgg        550
tgtcgtggaa ctcaggcgcc ctgaccagcg gcgtgcacac cttcccggct        600
gtcctacagt cctcaggact ctactccctc agcagcgtgg tgaccgtgcc        650
ctccagcagc ttgggcaccc agacctacat ctgcaacgtg aatcacaagc        700
ccagcaacac caaggtggac aagaaagttg agcccaaatc ttgtgacaaa        750
actcacacat ga                                                  762
```

<210> SEQ ID NO 44
<211> LENGTH: 253
<212> TYPE: PRT
<213> ORGANISM: Artificial Sequence
<220> FEATURE:
<221> NAME/KEY: Artificial Sequence
<222> LOCATION: 1-253
<223> OTHER INFORMATION: recombinant immunoglobulin

<400> SEQUENCE: 44

```
Met Lys Lys Asn Ile Ala Phe Leu Leu Ala Ser Met Phe Val Phe
  1               5                  10                  15

Ser Ile Ala Thr Asn Ala Tyr Ala Glu Ile Gln Leu Gln Gln Ser
                 20                  25                  30

Gly Pro Glu Leu Met Lys Pro Gly Ala Ser Val Lys Ile Ser Cys
                 35                  40                  45

Lys Ala Ser Gly Tyr Ser Phe Ser His Tyr Met His Trp Val
                 50                  55                  60

Lys Gln Ser His Gly Lys Ser Leu Glu Trp Ile Gly Tyr Ile Asp
                 65                  70                  75

Pro Ser Asn Gly Glu Thr Thr Tyr Asn Gln Lys Phe Lys Gly Lys
                 80                  85                  90

Ala Thr Leu Thr Val Asp Thr Ser Ser Thr Ala Asn Val His
                 95                 100                 105

Leu Ser Ser Leu Thr Ser Asp Asp Ser Ala Val Tyr Phe Cys Ala
                110                 115                 120
```

```
Arg Gly Asp Tyr Arg Tyr Asn Gly Asp Trp Phe Phe Asp Val Trp
            125                 130                 135

Gly Ala Gly Thr Thr Val Thr Val Ser Ser Ala Ser Thr Lys Gly
            140                 145                 150

Pro Ser Val Phe Pro Leu Ala Pro Ser Ser Lys Ser Thr Ser Gly
            155                 160                 165

Gly Thr Ala Ala Leu Gly Cys Leu Val Lys Asp Tyr Phe Pro Glu
            170                 175                 180

Pro Val Thr Val Ser Trp Asn Ser Gly Ala Leu Thr Ser Gly Val
            185                 190                 195

His Thr Phe Pro Ala Val Leu Gln Ser Ser Gly Leu Tyr Ser Leu
            200                 205                 210

Ser Ser Val Val Thr Val Pro Ser Ser Ser Leu Gly Thr Gln Thr
            215                 220                 225

Tyr Ile Cys Asn Val Asn His Lys Pro Ser Asn Thr Lys Val Asp
            230                 235                 240

Lys Lys Val Glu Pro Lys Ser Cys Asp Lys Thr His Thr
            245                 250         253

<210> SEQ ID NO 45
<211> LENGTH: 114
<212> TYPE: PRT
<213> ORGANISM: Mus musculus

<400> SEQUENCE: 45

Asp Ile Val Met Thr Gln Thr Pro Leu Ser Leu Pro Val Ser Leu
  1               5                  10                  15

Gly Asp Gln Ala Ser Ile Ser Cys Arg Ser Ser Gln Ser Leu Val
             20                  25                  30

His Gly Ile Gly Asn Thr Tyr Leu His Trp Tyr Leu Gln Lys Pro
             35                  40                  45

Gly Gln Ser Pro Lys Leu Leu Ile Tyr Lys Val Ser Asn Arg
             50                  55                  60

Phe Ser Gly Val Pro Asp Arg Phe Ser Asp Ser Gly Ser Gly Thr
             65                  70                  75

Asp Phe Thr Leu Arg Ile Ser Arg Val Glu Ala Glu Asp Leu Gly
             80                  85                  90

Leu Tyr Phe Cys Ser Gln Ser Thr His Val Pro Leu Thr Phe Gly
             95                 100                 105

Ala Gly Thr Lys Leu Glu Leu Lys Arg
            110                 114

<210> SEQ ID NO 46
<211> LENGTH: 114
<212> TYPE: PRT
<213> ORGANISM: Artificial Sequence
<220> FEATURE:
<221> NAME/KEY: Artificial Sequence
<222> LOCATION: 1-114
<223> OTHER INFORMATION: recombinant immunoglobulin

<400> SEQUENCE: 46

Asp Ile Gln Met Thr Gln Ser Pro Ser Ser Leu Ser Ala Ser Val
  1               5                  10                  15

Gly Asp Arg Val Thr Ile Thr Cys Arg Ser Ser Gln Ser Leu Val
             20                  25                  30

His Gly Ile Gly Asn Thr Tyr Leu His Trp Tyr Gln Gln Lys Pro
             35                  40                  45
```

Gly Lys Ala Pro Lys Leu Leu Ile Tyr Tyr Lys Val Ser Asn Arg
            50                  55                  60

Phe Ser Gly Val Pro Ser Arg Phe Ser Gly Ser Gly Ser Gly Thr
            65                  70                  75

Asp Phe Thr Leu Thr Ile Ser Ser Leu Gln Pro Glu Asp Phe Ala
            80                  85                  90

Thr Tyr Tyr Cys Ser Gln Ser Thr His Val Pro Leu Thr Phe Gly
            95                 100                 105

Gln Gly Thr Lys Val Glu Ile Lys Arg
            110             114

<210> SEQ ID NO 47
<211> LENGTH: 109
<212> TYPE: PRT
<213> ORGANISM: Homo sapiens

<400> SEQUENCE: 47

Asp Ile Gln Met Thr Gln Ser Pro Ser Ser Leu Ser Ala Ser Val
 1               5                  10                  15

Gly Asp Arg Val Thr Ile Thr Cys Arg Ala Ser Lys Thr Ile Ser
            20                  25                  30

Lys Tyr Leu Ala Trp Tyr Gln Gln Lys Pro Gly Lys Ala Pro Lys
            35                  40                  45

Leu Leu Ile Tyr Tyr Ser Gly Ser Thr Leu Glu Ser Gly Val Pro
            50                  55                  60

Ser Arg Phe Ser Gly Ser Gly Ser Gly Thr Asp Phe Thr Leu Thr
            65                  70                  75

Ile Ser Ser Leu Gln Pro Glu Asp Phe Ala Thr Tyr Tyr Cys Gln
            80                  85                  90

Gln His Asn Glu Tyr Pro Leu Thr Phe Gly Gln Gly Thr Lys Val
            95                 100                 105

Glu Ile Lys Arg
        109

<210> SEQ ID NO 48
<211> LENGTH: 117
<212> TYPE: PRT
<213> ORGANISM: Mus Musculus

<400> SEQUENCE: 48

Glu Ile Gln Leu Gln Gln Ser Gly Pro Glu Leu Met Lys Pro Gly
 1               5                  10                  15

Ala Ser Val Lys Ile Ser Cys Lys Ala Ser Gly Tyr Ser Phe Ser
            20                  25                  30

Ser His Tyr Met His Trp Val Lys Gln Ser His Gly Lys Ser Leu
            35                  40                  45

Glu Trp Ile Gly Tyr Ile Asp Pro Ser Asn Gly Glu Thr Thr Tyr
            50                  55                  60

Asn Gln Lys Phe Lys Gly Lys Ala Thr Leu Thr Val Asp Thr Ser
            65                  70                  75

Ser Ser Thr Ala Asn Val His Leu Ser Ser Leu Thr Ser Asp Asp
            80                  85                  90

Ser Ala Val Tyr Phe Cys Ala Ala Arg Gly Asp Tyr Arg Tyr Asn
            95                 100                 105

Gly Asp Trp Phe Phe Asp Val Trp Gly Ala Gly Thr
            110             115     117

<210> SEQ ID NO 49
<211> LENGTH: 117
<212> TYPE: PRT
<213> ORGANISM: Artificial Sequence
<220> FEATURE:
<221> NAME/KEY: Artificial Sequence
<222> LOCATION: 1-117
<223> OTHER INFORMATION: recombinant immunoglobulin

<400> SEQUENCE: 49

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Phe Ser
                20                  25                  30

Ser His Tyr Met His Trp Val Arg Gln Ala Pro Gly Lys Gly Leu
                35                  40                  45

Glu Trp Val Gly Tyr Ile Asp Pro Ser Asn Gly Glu Thr Thr Tyr
                50                  55                  60

Asn Gln Lys Phe Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Ala Arg Gly Asp Tyr Arg Tyr Asn
                95                 100                 105

Gly Asp Trp Phe Phe Asp Val Trp Gly Gln Gly Thr
               110                 115     117
```

<210> SEQ ID NO 50
<211> LENGTH: 116
<212> TYPE: PRT
<213> ORGANISM: Homo sapiens

<400> SEQUENCE: 50

```
Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Ser Phe Thr
                20                  25                  30

Gly His Trp Met Asn Trp Val Arg Gln Ala Pro Gly Lys Gly Leu
                35                  40                  45

Glu Trp Val Gly Met Ile His Pro Ser Asp Ser Glu Thr Arg Tyr
                50                  55                  60

Ala Asp Ser Val Lys Gly Arg Phe Thr Ile Ser Arg Asp Asn Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Ala Arg Gly Ile Tyr Phe Tyr Gly
                95                 100                 105

Thr Thr Tyr Phe Asp Tyr Trp Gly Gln Gly Thr
               110                 115 116
```

<210> SEQ ID NO 51
<211> LENGTH: 242
<212> TYPE: PRT
<213> ORGANISM: Artificial Sequence
<220> FEATURE:
<221> NAME/KEY: Artificial Sequence
<222> LOCATION: 1-242
<223> OTHER INFORMATION: recombinant immunoglobulin

```
<400> SEQUENCE: 51

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ser Ser Gln Ser Leu Val His Gly Ile Gly Asn Thr Tyr
                50                  55                  60

Leu His Trp Tyr Gln Gln Lys Pro Gly Lys Ala Pro Lys Leu Leu
                65                  70                  75

Ile Tyr Lys Val Ser Asn Arg Phe Ser Gly Val Pro Ser Arg Phe
                80                  85                  90

Ser Gly Ser Gly Ser Gly Thr Asp Phe Thr Leu Thr Ile Ser Ser
                95                 100                 105

Leu Gln Pro Glu Asp Phe Ala Thr Tyr Tyr Cys Ser Gln Ser Thr
               110                 115                 120

His Val Pro Leu Thr Phe Gly Gln Gly Thr Lys Val Glu Ile Lys
               125                 130                 135

Arg Thr Val Ala Ala Pro Ser Val Phe Ile Phe Pro Pro Ser Asp
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
   242

<210> SEQ ID NO 52
<211> LENGTH: 253
<212> TYPE: PRT
<213> ORGANISM: Artificial Sequence
<220> FEATURE:
<221> NAME/KEY: Artificial Sequence
<222> LOCATION: 1-253
<223> OTHER INFORMATION: recombinant immunoglobulin

<400> SEQUENCE: 52

Met Lys Lys Asn Ile Ala Phe Leu Leu Ala Ser Met Phe Val Phe
 1               5                  10                  15

Ser Ile Ala Thr Asn Ala Tyr Ala Glu Val Gln Leu Val Gln Ser
                20                  25                  30

Gly Gly Gly Leu Val Gln Pro Gly Gly Ser Leu Arg Leu Ser Cys
                35                  40                  45

Ala Ala Ser Gly Tyr Ser Phe Ser Ser His Tyr Met His Trp Val
                50                  55                  60

Arg Gln Ala Pro Gly Lys Gly Leu Glu Trp Val Gly Tyr Ile Asp
                65                  70                  75
```

```
Pro Ser Asn Gly Glu Thr Thr Tyr Asn Gln Lys Phe Lys Gly Arg
            80                  85                  90

Phe Thr Leu Ser Arg Asp Asn Ser Lys Asn Thr Ala Tyr Leu Gln
            95                  100                 105

Met Asn Ser Leu Arg Ala Glu Asp Thr Ala Val Tyr Tyr Cys Ala
            110                 115                 120

Arg Gly Asp Tyr Arg Tyr Asn Gly Asp Trp Phe Phe Asp Val Trp
            125                 130                 135

Gly Gln Gly Thr Leu Val Thr Val Ser Ala Ser Thr Lys Gly
            140                 145                 150

Pro Ser Val Phe Pro Leu Ala Pro Ser Ser Lys Ser Thr Ser Gly
            155                 160                 165

Gly Thr Ala Ala Leu Gly Cys Leu Val Lys Asp Tyr Phe Pro Glu
            170                 175                 180

Pro Val Thr Val Ser Trp Asn Ser Gly Ala Leu Thr Ser Gly Val
            185                 190                 195

His Thr Phe Pro Ala Val Leu Gln Ser Ser Gly Leu Tyr Ser Leu
            200                 205                 210

Ser Ser Val Val Thr Val Pro Ser Ser Ser Leu Gly Thr Gln Thr
            215                 220                 225

Tyr Ile Cys Asn Val Asn His Lys Pro Ser Asn Thr Lys Val Asp
            230                 235                 240

Lys Lys Val Glu Pro Lys Ser Cys Asp Lys Thr His Thr
            245                 250             253

<210> SEQ ID NO 53
<211> LENGTH: 159
<212> TYPE: PRT
<213> ORGANISM: Artificial Sequence
<220> FEATURE:
<221> NAME/KEY: Artificial Sequence
<222> LOCATION: 1-159
<223> OTHER INFORMATION: recombinant phage protein

<400> SEQUENCE: 53

Ser Gly Gly Gly Ser Gly Ser Gly Asp Phe Asp Tyr Glu Lys Met
 1               5                  10                  15

Ala Asn Ala Asn Lys Gly Ala Met Thr Glu Asn Ala Asp Glu Asn
            20                  25                  30

Ala Leu Gln Ser Asp Ala Lys Gly Lys Leu Asp Ser Val Ala Thr
            35                  40                  45

Asp Tyr Gly Ala Ala Ile Asp Gly Phe Ile Gly Asp Val Ser Gly
            50                  55                  60

Leu Ala Asn Gly Asn Gly Ala Thr Gly Asp Phe Ala Gly Ser Ser
            65                  70                  75

Asn Ser Gln Met Ala Gln Val Gly Asp Gly Asp Asn Ser Pro Leu
            80                  85                  90

Met Asn Asn Phe Arg Gln Tyr Leu Pro Ser Leu Pro Gln Ser Val
            95                  100                 105

Glu Cys Arg Pro Phe Val Phe Ser Ala Gly Lys Pro Tyr Glu Phe
            110                 115                 120

Ser Ile Asp Cys Asp Lys Ile Asn Leu Phe Arg Gly Val Phe Ala
            125                 130                 135

Phe Leu Leu Tyr Val Ala Thr Phe Met Tyr Val Phe Ser Thr Phe
            140                 145                 150
```

Ala Asn Ile Leu Arg Asn Lys Glu Ser
            155            159

```
<210> SEQ ID NO 54
<211> LENGTH: 780
<212> TYPE: DNA
<213> ORGANISM: Artificial Sequence
<220> FEATURE:
<221> NAME/KEY: Artificial Sequence
<222> LOCATION: 1-780
<223> OTHER INFORMATION: recombinant immunglobulin

<400> SEQUENCE: 54
atgaaaaaga atatcgcatt tcttcttgca tctatgttcg tttttttctat         50 tgctacaaac gcatacgctg atatccagat gacccagtcc ccgagctccc        100
tgtccgcctc tgtgggcgat agggtcacca tcacctgcag gtcaagtcaa        150
agcttagtac atggtatagg taacacgtat ttacactggt atcaacagaa        200
accaggaaaa gctccgaaac tactgattta caaagtatcc aatcgattct        250
ctggagtccc ttctcgcttc tctggatccg gttctgggac ggatttcact        300
ctgaccatca gcagtctgca gccagaagac ttcgcaactt attactgttc        350
acagagtact catgtcccgc tcacgtttgg acagggtacc aaggtggaga        400
tcaaacgaac tgtggctgca ccatctgtct tcatcttccc gccatctgat        450
gagcagttga atctggaac tgcttctgtt gtgtgcctgc tgaataactt        500
ctatcccaga gaggccaaag tacagtggaa ggtggataac gccctccaat        550
cgggtaactc ccaggagagt gtcacagagc aggacagcaa ggacagcacc        600
tacagcctca gcagcaccct gacgctgagc aaagcagact acgagaaaca        650
caaagtctac gcctgcgaag tcacccatca gggcctgagc tcgcccgtca        700
caaagagctt caacagggga gagtgttaag ctgatcctct acgccggacg        750
catcgtggcc ctagtacgca actagtcgta                              780

<210> SEQ ID NO 55
<211> LENGTH: 253
<212> TYPE: PRT
<213> ORGANISM: Artificial Sequence
<220> FEATURE:
<221> NAME/KEY: Artificial Sequence
<222> LOCATION: 1-253
<223> OTHER INFORMATION: recombinant immunoglobulin

<400> SEQUENCE: 55
```

Met Lys Lys Asn Ile Ala Phe Leu Leu Ala Ser Met Phe Val Phe
  1            5                  10                15

Ser Ile Ala Thr Asn Ala Tyr Ala Glu Val Gln Leu Val Glu Ser
            20                25                30

Gly Gly Gly Leu Val Gln Pro Gly Gly Ser Leu Arg Leu Ser Cys
            35                40                45

Ala Ala Ser Gly Tyr Ser Phe Ser Ser His Tyr Met His Trp Val
            50                55                60

Lys Gln Ala Pro Gly Lys Gly Leu Glu Trp Val Gly Tyr Ile Asp
            65                70                75

Pro Ser Asn Gly Glu Thr Thr Tyr Asn Gln Lys Phe Lys Gly Arg
            80                85                90

Phe Thr Leu Ser Arg Asp Asn Ser Lys Asn Thr Ala Tyr Leu Gln
            95                100             105

```
Met Asn Ser Leu Arg Ala Glu Asp Thr Ala Val Tyr Tyr Cys Ala
            110                 115                 120

Arg Gly Asp Tyr Arg Tyr Asn Gly Asp Trp Phe Phe Asp Val Trp
            125                 130                 135

Gly Gln Gly Thr Leu Val Thr Val Ser Ala Ser Thr Lys Gly
            140                 145                 150

Pro Ser Val Phe Pro Leu Ala Pro Ser Ser Lys Ser Thr Ser Gly
            155                 160                 165

Gly Thr Ala Ala Leu Gly Cys Leu Val Lys Asp Tyr Phe Pro Glu
            170                 175                 180

Pro Val Thr Val Ser Trp Asn Ser Gly Ala Leu Thr Ser Gly Val
            185                 190                 195

His Thr Phe Pro Ala Val Leu Gln Ser Ser Gly Leu Tyr Ser Leu
            200                 205                 210

Ser Ser Val Val Thr Val Pro Ser Ser Leu Gly Thr Gln Thr
            215                 220                 225

Tyr Ile Cys Asn Val Asn His Lys Pro Ser Asn Thr Lys Val Asp
            230                 235                 240

Lys Lys Val Glu Pro Lys Ser Cys Asp Lys Thr His Thr
            245                 250         253

<210> SEQ ID NO 56
<211> LENGTH: 242
<212> TYPE: PRT
<213> ORGANISM: Artificial Sequence
<220> FEATURE:
<221> NAME/KEY: Artificial Sequence
<222> LOCATION: 1-242
<223> OTHER INFORMATION: recombinant immunoglobulin

<400> SEQUENCE: 56

Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
            20                  25                  30

Pro Ser Ser Leu Ser Ala Ser Val Gly Asp Arg Val Thr Ile Thr
            35                  40                  45

Cys Arg Ser Ser Gln Ser Leu Val His Gly Ile Gly Ala Thr Tyr
            50                  55                  60

Leu His Trp Tyr Gln Gln Lys Pro Gly Lys Ala Pro Lys Leu Leu
            65                  70                  75

Ile Tyr Lys Val Ser Asn Arg Phe Ser Gly Val Pro Ser Arg Phe
            80                  85                  90

Ser Gly Ser Gly Ser Gly Thr Asp Phe Thr Leu Thr Ile Ser Ser
            95                  100                 105

Leu Gln Pro Glu Asp Phe Ala Thr Tyr Tyr Cys Ser Gln Ser Thr
            110                 115                 120

His Val Pro Leu Thr Phe Gly Gln Gly Thr Lys Val Glu Ile Lys
            125                 130                 135

Arg Thr Val Ala Ala Pro Ser Val Phe Ile Phe Pro Pro Ser Asp
            140                 145                 150

Glu Gln Leu Lys Ser Gly Thr Ala Ser Val Val Cys Leu Leu Asn
            155                 160                 165

Asn Phe Tyr Pro Arg Glu Ala Lys Val Gln Trp Lys Val Asp Asn
            170                 175                 180
```

```
Ala Leu Gln Ser Gly Asn Ser Gln Glu Ser Val Thr Glu Gln Asp
                185                 190                 195

Ser Lys Asp Ser Thr Tyr Ser Leu Ser Ser Thr Leu Thr Leu Ser
                200                 205                 210

Lys Ala Asp Tyr Glu Lys His Lys Val Tyr Ala Cys Glu Val Thr
                215                 220                 225

His Gln Gly Leu Ser Ser Pro Val Thr Lys Ser Phe Asn Arg Gly
                230                 235                 240

Glu Cys
    242

<210> SEQ ID NO 57
<211> LENGTH: 45
<212> TYPE: PRT
<213> ORGANISM: Artificial Sequence
<220> FEATURE:
<221> NAME/KEY: Artificial Sequence
<222> LOCATION: 1-45
<223> OTHER INFORMATION: recombinant leucine zipper peptide

<400> SEQUENCE: 57

Cys Pro Pro Cys Pro Ala Pro Glu Leu Leu Gly Gly Arg Met Lys
 1               5                  10                  15

Gln Leu Glu Asp Lys Val Glu Glu Leu Leu Ser Lys Asn Tyr His
                20                  25                  30

Leu Glu Asn Glu Val Ala Arg Leu Lys Lys Leu Val Gly Glu Arg
                35                  40                  45

<210> SEQ ID NO 58
<211> LENGTH: 780
<212> TYPE: DNA
<213> ORGANISM: Artificial Sequence
<220> FEATURE:
<221> NAME/KEY: Artificial Sequence
<222> LOCATION: 1-780
<223> OTHER INFORMATION: recombinant immunoglobulin

<400> SEQUENCE: 58
atgaaaaaga atatcgcatt tcttcttgca tctatgttcg tttttttctat           50 tgctacaaac gcatacgctg atatccagat gacccagtcc ccgagctccc          100
tgtccgcctc tgtgggcgat agggtcacca tcacctgcag gtcaagtcaa          150
agcttagtac atggtatagg tgctacgtat ttacactggt atcaacagaa          200
accaggaaaa gctccgaaac tactgattta caaagtatcc aatcgattct          250
ctggagtccc ttctcgcttc tctggatccg gttctgggac ggatttcact          300
ctgaccatca gcagtctgca gccagaagac ttcgcaactt attactgttc          350
acagagtact catgtcccgc tcacgtttgg acagggtacc aaggtggaga          400
tcaaacgaac tgtggctgca ccatctgtct tcatcttccc gccatctgat          450
gagcagttga aatctggaac tgcttctgtt gtgtgcctgc tgaataactt          500
ctatcccaga gaggccaaag tacagtggaa ggtggataac gccctccaat          550
cgggtaactc ccaggagagt gtcacagagc aggacagcaa ggacagcacc          600
tacagcctca gcagcaccct gacgctgagc aaagcagact acgagaaaca          650
caaagtctac gcctgcgaag tcacccatca gggcctgagc tcgcccgtca          700
caaagagctt caacagggga gagtgttaag ctgatcctct acgccggacg          750
catcgtggcc ctagtacgca actagtcgta                               780
```

<210> SEQ ID NO 59
<211> LENGTH: 927
<212> TYPE: DNA
<213> ORGANISM: Artificial Sequence
<220> FEATURE:
<221> NAME/KEY: Artificial Sequence
<222> LOCATION: 1-927
<223> OTHER INFORMATION: recombinant immunoglobulin

<400> SEQUENCE: 59

```
aaaagggtat ctagaggttg aggtgatttt atgaaaaaga atatcgcatt          50
tcttcttgca tctatgttcg ttttttctat tgctacaaac gcgtacgctg         100
aggttcagct agtgcagtct ggcggtggcc tggtgcagcc aggggggctca        150
ctccgtttgt cctgtgcagc ttctggctac tccttctcga gtcactatat         200
gcactgggtc cgtcaggccc cgggtaaggg cctggaatgg gttggatata         250
ttgatccttc caatggtgaa actacgtata atcaaaagtt caagggccgt         300
ttcactttat ctcgcgacaa ctccaaaaac acagcatacc tgcagatgaa         350
cagcctgcgt gctgaggaca ctgccgtcta ttactgtgca agaggggatt         400
atcgctacaa tggtgactgg ttcttcgacg tctggggtca aggaaccctg         450
gtcaccgtct cctcggcctc caccaagggc ccatcggtct tccccctggc         500
accctcctcc aagagcacct ctgggggcac agcggccctg ggctgcctgg         550
tcaaggacta cttccccgaa ccggtgacgg tgtcgtggaa ctcaggcgcc         600
ctgaccagcg gcgtgcacac cttcccggct gtcctacagt cctcaggact         650
ctactccctc agcagcgtgg tgaccgtgcc ctccagcagc ttgggcaccc         700
agacctacat ctgcaacgtg aatcacaagc ccagcaacac caaggtcgac         750
aagaaagttg agcccaaatc ttgtgacaaa actcacacat gcccgccgtg         800
cccagcacca gaactgctgg gcggccgcat gaaacagcta gaggacaagg         850
tcgaagagct actctccaag aactaccacc tagagaatga agtggcaaga         900
ctcaaaaagc ttgtcgggga gcgctaa                                  927
```

<210> SEQ ID NO 60
<211> LENGTH: 298
<212> TYPE: PRT
<213> ORGANISM: Artificial Sequence
<220> FEATURE:
<221> NAME/KEY: Artificial Sequence
<222> LOCATION: 1-298
<223> OTHER INFORMATION: recombinant immunoglobulin

<400> SEQUENCE: 60

```
Met Lys Lys Asn Ile Ala Phe Leu Leu Ala Ser Met Phe Val Phe
  1               5                  10                  15

Ser Ile Ala Thr Asn Ala Tyr Ala Glu Val Gln Leu Val Gln Ser
                 20                  25                  30

Gly Gly Gly Leu Val Gln Pro Gly Gly Ser Leu Arg Leu Ser Cys
                 35                  40                  45

Ala Ala Ser Gly Tyr Ser Phe Ser Ser His Tyr Met His Trp Val
                 50                  55                  60

Arg Gln Ala Pro Gly Lys Gly Leu Glu Trp Val Gly Tyr Ile Asp
                 65                  70                  75

Pro Ser Asn Gly Glu Thr Thr Tyr Asn Gln Lys Phe Lys Gly Arg
```

```
                    80                  85                  90
Phe Thr Leu Ser Arg Asp Asn Ser Lys Asn Thr Ala Tyr Leu Gln
                95                 100                 105
Met Asn Ser Leu Arg Ala Glu Asp Thr Ala Val Tyr Tyr Cys Ala
               110                 115                 120
Arg Gly Asp Tyr Arg Tyr Asn Gly Asp Trp Phe Phe Asp Val Trp
               125                 130                 135
Gly Gln Gly Thr Leu Val Thr Val Ser Ser Ala Ser Thr Lys Gly
               140                 145                 150
Pro Ser Val Phe Pro Leu Ala Pro Ser Ser Lys Ser Thr Ser Gly
               155                 160                 165
Gly Thr Ala Ala Leu Gly Cys Leu Val Lys Asp Tyr Phe Pro Glu
               170                 175                 180
Pro Val Thr Val Ser Trp Asn Ser Gly Ala Leu Thr Ser Gly Val
               185                 190                 195
His Thr Phe Pro Ala Val Leu Gln Ser Ser Gly Leu Tyr Ser Leu
               200                 205                 210
Ser Ser Val Val Thr Val Pro Ser Ser Ser Leu Gly Thr Gln Thr
               215                 220                 225
Tyr Ile Cys Asn Val Asn His Lys Pro Ser Asn Thr Lys Val Asp
               230                 235                 240
Lys Lys Val Glu Pro Lys Ser Cys Asp Lys Thr His Thr Cys Pro
               245                 250                 255
Pro Cys Pro Ala Pro Glu Leu Leu Gly Gly Arg Met Lys Gln Leu
               260                 265                 270
Glu Asp Lys Val Glu Glu Leu Leu Ser Lys Asn Tyr His Leu Glu
               275                 280                 285
Asn Glu Val Ala Arg Leu Lys Lys Leu Val Gly Glu Arg
               290                 295         298

<210> SEQ ID NO 61
<211> LENGTH: 6563
<212> TYPE: DNA
<213> ORGANISM: Artificial Sequence
<220> FEATURE:
<221> NAME/KEY: Artificial Sequence
<222> LOCATION: 1-6563
<223> OTHER INFORMATION: recombinant immunoglobulin

<400> SEQUENCE: 61
gaattcaact tctccatact ttggataagg aaatacagac atgaaaaatc            50
tcattgctga gttgttattt aagcttgccc aaaaagaaga agagtcgaat            100
gaactgtgtg cgcaggtaga agctttggag attatcgtca ctgcaatgct            150
tcgcaatatg gcgcaaaatg accaacagcg gttgattgat caggtagagg            200
gggcgctgta cgaggtaaag cccgatgcca gcattcctga cgacgatacg            250
gagctgctgc gcgattacgt aaagaagtta ttgaagcatc ctcgtcagta            300
aaaagttaat ctttcaaca gctgtcataa agttgtcacg gccgagactt             350
atagtcgctt tgtttttatt ttttaatgta tttgtaacta gaattcgagc            400
tcggtacccg gggatcctct cgaggttgag gtgattttat gaaaaagaat            450
atcgcatttc ttcttgcatc tatgttcgtt ttttctattg ctacaaacgc            500
atacgctgat atccagatga cccagtcccc gagctccctg tccgcctctg            550
tgggcgatag ggtcaccatc acctgcaggt caagtcaaag cttagtacat            600
```

```
ggtataggtg ctacgtattt acactggtat caacagaaac caggaaaagc       650
tccgaaacta ctgatttaca aagtatccaa tcgattctct ggagtccctt       700
ctcgcttctc tggatccggt tctgggacgg atttcactct gaccatcagc       750
agtctgcagc cagaagactt cgcaacttat tactgttcac agagtactca       800
tgtcccgctc acgtttggac agggtaccaa ggtggagatc aaacgaactg       850
tggctgcacc atctgtcttc atcttcccgc catctgatga gcagttgaaa       900
tctggaactg cttctgttgt gtgcctgctg aataacttct atcccagaga       950
ggccaaagta cagtggaagg tggataacgc cctccaatcg ggtaactccc      1000
aggagagtgt cacagagcag gacagcaagg acagcaccta cagcctcagc      1050
agcaccctga cgctgagcaa agcagactac gagaaacaca agtctacgc       1100
ctgcgaagtc acccatcagg gcctgagctc gcccgtcaca aagagcttca      1150
acaggggaga gtgttaagct gatcctctac gccggacgca tcgtggccct      1200
agtacgcaac tagtcgtaaa aagggtatct agaggttgag gtgattttat      1250
gaaaagaat atcgcatttc ttcttgcatc tatgttcgtt ttttctattg       1300
ctacaaacgc gtacgctgag gttcagctag tgcagtctgg cggtggcctg      1350
gtgcagccag ggggctcact ccgtttgtcc tgtgcagctt ctggctactc      1400
cttctcgagt cactatatgc actgggtccg tcaggcccg ggtaagggcc       1450
tggaatgggt tggatatatt gatccttcca atggtgaaac tacgtataat      1500
caaaagttca agggccgttt cactttatct cgcgacaact ccaaaaacac      1550
agcatacctg cagatgaaca gcctgcgtgc tgaggacact gccgtctatt      1600
actgtgcaag aggggattat cgctacaatg gtgactggtt cttcgacgtc      1650
tggggtcaag aaccctggt caccgtctcc tcggcctcca ccaagggccc       1700
atcggtcttc cccctggcac cctcctccaa gagcacctct gggggcacag      1750
cggccctggg ctgcctggtc aaggactact tccccgaacc ggtgacggtg      1800
tcgtggaact caggcgccct gaccagcggc gtgcacacct tcccggctgt      1850
cctacagtcc tcaggactct actccctcag cagcgtggtg accgtgccct      1900
ccagcagctt gggcacccag acctacatct gcaacgtgaa tcacaagccc      1950
agcaacacca aggtcgacaa gaaagttgag cccaaatctt gtgacaaaac      2000
tcacacatgc ccgccgtgcc cagcaccaga actgctgggc ggccgcatga      2050
aacagctaga ggacaaggtc gaagagctac tctccaagaa ctaccaccta      2100
gagaatgaag tggcaagact caaaaagctt gtcggggagc gctaagcatg      2150
cgacggccct agagtcccta acgctcggtt gccgccgggc gttttttat       2200
gttaactcat gtttgacagc ttatcatcga taagctttaa tgcggtagtt      2250
tatcacagtt aaattgctaa cgcagtcagg caccgtgtat gaaatctaac      2300
aatgcgctca tcgtcatcct cggcaccgtc accctggatg ctgtaggcat      2350
aggcttggtt atgccggtac tgccgggcct cttgcgggat atcgtccatt      2400
ccgacagcat cgccagtcac tatggcgtgc tgctagcgct atatgcgttg      2450
atgcaatttc tatgcgcacc cgttctcgga gcactgtccg accgctttgg      2500
ccgccgccca gtcctgctcg cttcgctact tggagccact atcgactacg      2550
```

| | |
|---|---|
| cgatcatggc gaccacaccc gtcctgtgga tcctctacgc cggacgcatc | 2600 |
| gtggccggca tcaccggcgc cacaggtgcg gttgctggcg cctatatcgc | 2650 |
| cgacatcacc gatggggaag atcgggctcg ccacttcggg ctcatgagcg | 2700 |
| cttgtttcgg cgtgggtatg gtggcaggcc ccgtggccgg gggactgttg | 2750 |
| ggcgccatct ccttgcacgc accattcctt gcggcggcgg tgctcaacgg | 2800 |
| cctcaaccta ctactgggct gcttcctaat gcaggagtcg cataagggag | 2850 |
| agcgtcgtcc gatgcccttg agagccttca acccagtcag ctccttccgg | 2900 |
| tgggcgcggg gcatgactat cgtcgccgca cttatgactg tcttctttat | 2950 |
| catgcaactc gtaggacagg tgccggcagc gctctgggtc attttcggcg | 3000 |
| aggaccgctt tcgctggagc gcgacgatga tcggcctgtc gcttgcggta | 3050 |
| ttcggaatct tgcacgccct cgctcaagcc ttcgtcactg gtcccgccac | 3100 |
| caaacgtttc ggcgagaagc aggccattat cgccggcatg gcggccgacg | 3150 |
| cgctgggcta cgtcttgctg gcgttcgcga cgcgaggctg gatggccttc | 3200 |
| cccattatga ttcttctcgc ttccggcggc atcgggatgc ccgcgttgca | 3250 |
| ggccatgctg tccaggcagg tagatgacga ccatcaggga cagcttcaag | 3300 |
| gatcgctcgc ggctcttacc agcctaactt cgatcactgg accgctgatc | 3350 |
| gtcacggcga tttatgccgc ctcggcgagc acatggaacg ggttggcatg | 3400 |
| gattgtaggc gccgccctat accttgtctg cctccccgcg ttgcgtcgcg | 3450 |
| gtgcatggag ccgggccacc tcgacctgaa tggaagccgg cggcacctcg | 3500 |
| ctaacggatt caccactcca agaattggag ccaatcaatt cttgcggaga | 3550 |
| actgtgaatg cgcaaaccaa cccttggcag aacatatcca tcgcgtccgc | 3600 |
| catctccagc agccgcacgc ggcgcatctc gggcagcgtt gggtcctggc | 3650 |
| cacgggtgcg catgatcgtg ctcctgtcgt tgaggacccg gctaggctgg | 3700 |
| cggggttgcc ttactggtta gcagaatgaa tcaccgatac gcgagcgaac | 3750 |
| gtgaagcgac tgctgctgca aaacgtctgc gacctgagca acaacatgaa | 3800 |
| tggtcttcgg tttccgtgtt tcgtaaagtc tggaaacgcg gaagtcagcg | 3850 |
| ccctgcacca ttatgttccg gatctgcatc gcaggatgct gctggctacc | 3900 |
| ctgtggaaca cctacatctg tattaacgaa gcgctggcat tgaccctgag | 3950 |
| tgatttttct ctggtcccgc cgcatccata ccgccagttg tttaccctca | 4000 |
| caacgttcca gtaaccgggc atgttcatca tcagtaaccc gtatcgtgag | 4050 |
| catcctctct cgtttcatcg gtatcattac ccccatgaac agaaattccc | 4100 |
| ccttacacgg aggcatcaag tgaccaaaca ggaaaaaacc gcccttaaca | 4150 |
| tggcccgctt tatcagaagc cagacattaa cgcttctgga gaaactcaac | 4200 |
| gagctggacg cggatgaaca ggcagacatc tgtgaatcgc ttcacgacca | 4250 |
| cgctgatgag ctttaccgca gctgcctcgc gcgtttcggt gatgacggtg | 4300 |
| aaaacctctg acacatgcag ctcccggaga cggtcacagc ttgtctgtaa | 4350 |
| gcggatgccg ggagcagaca agcccgtcag ggcgcgtcag cgggtgttgg | 4400 |
| cgggtgtcgg ggcgcagcca tgacccagtc acgtagcgat agcggagtgt | 4450 |
| atactggctt aactatgcgg catcagagca gattgtactg agagtgcacc | 4500 |
| atatgcggtg tgaaataccg cacagatgcg taaggagaaa ataccgcatc | 4550 |

```
aggcgctctt ccgcttcctc gctcactgac tcgctgcgct cggtcgttcg      4600
gctgcggcga gcggtatcag ctcactcaaa ggcggtaata cggttatcca      4650
cagaatcagg ggataacgca ggaaagaaca tgtgagcaaa aggccagcaa      4700
aaggccagga accgtaaaaa ggccgcgttg ctggcgtttt tccataggct      4750
ccgcccccct gacgagcatc acaaaaatcg acgctcaagt cagaggtggc      4800
gaaacccgac aggactataa agataccagg cgtttccccc tggaagctcc      4850
ctcgtgcgct ctcctgttcc gaccctgccg cttaccggat acctgtccgc      4900
ctttctccct tcgggaagcg tggcgctttc tcatagctca cgctgtaggt      4950
atctcagttc ggtgtaggtc gttcgctcca agctgggctg tgtgcacgaa      5000
ccccccgttc agcccgaccg ctgcgcctta tccggtaact atcgtcttga      5050
gtccaacccg gtaagacacg acttatcgcc actggcagca gccactggta      5100
acaggattag cagagcgagg tatgtaggcg gtgctacaga gttcttgaag      5150
tggtggccta actacggcta cactagaagg acagtatttg gtatctgcgc      5200
tctgctgaag ccagttacct tcggaaaaag agttggtagc tcttgatccg      5250
gcaaacaaac caccgctggt agcggtggtt ttttgtttg caagcagcag       5300 attacgcgca gaaaaaaagg atctcaagaa gatcctttga tcttttctac      5350
ggggtctgac gctcagtgga acgaaaactc acgttaaggg attttggtca      5400
tgagattatc aaaaaggatc ttcacctaga tccttttaaa ttaaaaatga      5450
agttttaaat caatctaaag tatatatgag taaacttggt ctgacagtta      5500
ccaatgctta atcagtgagg cacctatctc agcgatctgt ctatttcgtt      5550
catccatagt tgcctgactc cccgtcgtgt agataactac gatacgggag      5600
ggcttaccat ctggccccag tgctgcaatg ataccgcgag acccacgctc      5650
accggctcca gatttatcag caataaacca gccagccgga agggccgagc      5700
gcagaagtgg tcctgcaact ttatccgcct ccatccagtc tattaattgt      5750
tgccgggaag ctagagtaag tagttcgcca gttaatagtt tgcgcaacgt      5800
tgttgccatt gctgcaggca tcgtggtgtc acgctcgtcg tttggtatgg      5850
cttcattcag ctccggttcc caacgatcaa ggcgagttac atgatccccc      5900
atgttgtgca aaaagcggt tagctccttc ggtcctccga tcgttgtcag       5950
aagtaagttg gccgcagtgt tatcactcat ggttatggca gcactgcata      6000
attctcttac tgtcatgcca tccgtaagat gcttttctgt gactggtgag      6050
tactcaacca agtcattctg agaatagtgt atgcggcgac cgagttgctc      6100
ttgcccggcg tcaacacggg ataataccgc gccacatagc agaactttaa      6150
aagtgctcat cattggaaaa cgttcttcgg ggcgaaaact ctcaaggatc      6200
ttaccgctgt tgagatccag ttcgatgtaa cccactcgtg cacccaactg      6250
atcttcagca tcttttactt tcaccagcgt ttctgggtga gcaaaaacag      6300
gaaggcaaaa tgccgcaaaa aagggaataa gggcgacacg gaaatgttga      6350
atactcatac tcttcctttt tcaatattat tgaagcattt atcagggtta      6400
ttgtctcatg agcggataca tatttgaatg tatttagaaa aataaacaaa      6450 tagggggttcc gcgcacattt ccccgaaaag tgccacctga cgtctaagaa      6500
```

```
accattatta tcatgacatt aacctataaa aataggcgta tcacgaggcc         6550
ctttcgtctt caa                                                  6563
```

<210> SEQ ID NO 62
<211> LENGTH: 242
<212> TYPE: PRT
<213> ORGANISM: Artificial Sequence
<220> FEATURE:
<221> NAME/KEY: Artificial Sequence
<222> LOCATION: 1-242
<223> OTHER INFORMATION: recombinant immunoglobulin

<400> SEQUENCE: 62

```
Met Lys Lys Asn Ile Ala Phe Leu Leu Ala Ser Met Phe Val Phe
 1               5                  10                  15

Ser Ile Ala Thr Asn Ala Tyr Ala Asp Ile Gln Met Thr Gln Ser
                20                  25                  30

Pro Ser Ser Leu Ser Ala Ser Val Gly Asp Arg Val Thr Ile Thr
                35                  40                  45

Cys Arg Ser Ser Gln Ser Leu Val His Gly Ile Gly Glu Thr Tyr
                50                  55                  60

Leu His Trp Tyr Gln Gln Lys Pro Gly Lys Ala Pro Lys Leu Leu
                65                  70                  75

Ile Tyr Lys Val Ser Asn Arg Phe Ser Gly Val Pro Ser Arg Phe
                80                  85                  90

Ser Gly Ser Gly Ser Gly Thr Asp Phe Thr Leu Thr Ile Ser Ser
                95                 100                 105

Leu Gln Pro Glu Asp Phe Ala Thr Tyr Tyr Cys Ser Gln Ser Thr
               110                 115                 120

His Val Pro Leu Thr Phe Gly Gln Gly Thr Lys Val Glu Ile Lys
               125                 130                 135

Arg Thr Val Ala Ala Pro Ser Val Phe Ile Phe Pro Pro Ser Asp
               140                 145                 150

Glu Gln Leu Lys Ser Gly Thr Ala Ser Val Val Cys Leu Leu Asn
               155                 160                 165

Asn Phe Tyr Pro Arg Glu Ala Lys Val Gln Trp Lys Val Asp Asn
               170                 175                 180

Ala Leu Gln Ser Gly Asn Ser Gln Glu Ser Val Thr Glu Gln Asp
               185                 190                 195

Ser Lys Asp Ser Thr Tyr Ser Leu Ser Ser Thr Leu Thr Leu Ser
               200                 205                 210

Lys Ala Asp Tyr Glu Lys His Lys Val Tyr Ala Cys Glu Val Thr
               215                 220                 225

His Gln Gly Leu Ser Ser Pro Val Thr Lys Ser Phe Asn Arg Gly
               230                 235                 240

Glu Cys
   242
```

<210> SEQ ID NO 63
<211> LENGTH: 27
<212> TYPE: DNA
<213> ORGANISM: Artificial Sequence
<220> FEATURE:
<221> NAME/KEY: Artificial Sequence
<222> LOCATION: 1-27
<223> OTHER INFORMATION: recombinant immunoglobulin

<400> SEQUENCE: 63
catggtatag gttaaactta tttacac                                    27

<210> SEQ ID NO 64
<211> LENGTH: 27
<212> TYPE: DNA
<213> ORGANISM: Artificial Sequence
<220> FEATURE:
<221> NAME/KEY: Artificial Sequence
<222> LOCATION: 1-27
<223> OTHER INFORMATION: recombinant immunoglobulin
<220> FEATURE:
<221> NAME/KEY: n
<222> LOCATION: 13, 14
<223> OTHER INFORMATION: a or g or c or t

<400> SEQUENCE: 64
catggtatag gtnnsactta tttacac                                    27

<210> SEQ ID NO 65
<211> LENGTH: 780
<212> TYPE: DNA
<213> ORGANISM: Artificial Sequence
<220> FEATURE:
<221> NAME/KEY: Artificial Sequence
<222> LOCATION: 1-780
<223> OTHER INFORMATION: recombinant immunoglobulin

<400> SEQUENCE: 65
atgaaaaaga atatcgcatt tcttcttgca tctatgttcg ttttttctat            50
tgctacaaac gcatacgctg atatccagat gacccagtcc ccgagctccc           100
tgtccgcctc tgtgggcgat agggtcacca tcacctgcag gtcaagtcaa           150
agcttagtac atggtatagg tgagacgtat ttacactggt atcaacagaa           200
accaggaaaa gctccgaaac tactgattta caaagtatcc aatcgattct           250
ctggagtccc ttctcgcttc tctggatccg gttctgggac ggatttcact           300
ctgaccatca gcagtctgca gccagaagac ttcgcaactt attactgttc           350
acagagtact catgtcccgc tcacgtttgg acagggtacc aaggtggaga           400
tcaaacgaac tgtggctgca ccatctgtct tcatcttccc gccatctgat           450
gagcagttga aatctggaac tgcttctgtt gtgtgcctgc tgaataactt           500
ctatcccaga gaggccaaag tacagtggaa ggtggataac gccctccaat           550
cgggtaactc ccaggagagt gtcacagagc aggacagcaa ggacagcacc           600
tacagcctca gcagcaccct gacgctgagc aaagcagact acgagaaaca           650
caaagtctac gcctgcgaag tcacccatca gggcctgagc tcgcccgtca           700
caaagagctt caacagggga gagtgttaag ctgatcctct acgccggacg           750
catcgtggcc ctagtacgca actagtcgta                                 780

<210> SEQ ID NO 66
<211> LENGTH: 78
<212> TYPE: DNA
<213> ORGANISM: Artificial Sequence
<220> FEATURE:
<221> NAME/KEY: Artificial Sequence
<222> LOCATION: 1-78
<223> OTHER INFORMATION: recombinant immunoglobulin

<400> SEQUENCE: 66
ctagtgcagt ctggcggtgg cctggtgcag ccagggggct cactccgttt            50
gtcctgtgca gcttctggct actccttc                                    78

<210> SEQ ID NO 67
<211> LENGTH: 82
<212> TYPE: DNA
<213> ORGANISM: Artificial Sequence
<220> FEATURE:
<221> NAME/KEY: Artificial Sequence
<222> LOCATION: 1-82
<223> OTHER INFORMATION: recombinant immunoglobulin

<400> SEQUENCE: 67

```
tcgagaagga gtagccagaa gctgcacagg acaaacggag tgagccccct         50
ggctgcacca ggccaccgcc agactgcact ag                            82
```

<210> SEQ ID NO 68
<211> LENGTH: 8120
<212> TYPE: DNA
<213> ORGANISM: Artificial Sequence
<220> FEATURE:
<221> NAME/KEY: Artificial Sequence
<222> LOCATION: 1-8120
<223> OTHER INFORMATION: recombinant immunoglobulin

<400> SEQUENCE: 68

```
ttcgagctcg cccgacattg attattgact agagtcgatc gacagctgtg         50
gaatgtgtgt cagttagggt gtggaaagtc cccaggctcc ccagcaggca        100
gaagtatgca aagcatgcat ctcaattagt cagcaaccag gtgtggaaag        150
tccccaggct cccagcagg cagaagtatg caaagcatgc atctcaatta         200
gtcagcaacc atagtcccgc ccctaactcc gcccatcccg cccctaactc        250
cgcccagttc cgcccattct ccgccccatg gctgactaat tttttttatt        300
tatgcagagg ccgaggccgc ctcggcctct gagctattcc agaagtagtg        350
aggaggcttt tttggaggcc taggcttttg caaaaagcta gcttatccgg        400
ccgggaacgg tgcattggaa cgcggattcc ccgtgccaag agtgacgtaa        450
gtaccgccta tagagcgata agaggatttt atccccgctg ccatcatggt        500
tcgaccattg aactgcatcg tcgccgtgtc ccaaaatatg gggattggca        550
agaacggaga cctaccctgg cctccgctca ggaacgagtt caagtacttc        600
caaagaatga ccacaacctc ttcagtggaa ggtaaacaga atctggtgat        650
tatgggtagg aaaacctggt tctccattcc tgagaagaat cgacctttaa        700
aggacagaat taatatagtt ctcagtagag aactcaaaga accaccacga        750
ggagctcatt tcttgccaa aagtttggat gatgccttaa gacttattga        800
acaaccggaa ttggcaagta agtagacat ggtttggata gtcggaggca         850
gttctgttta ccaggaagcc atgaatcaac caggccacct tagactcttt        900
gtgacaagga tcatgcagga attttgaaagt gacacgtttt tcccagaaat        950
tgatttgggg aaatataaac ctctcccaga tacccaggc gtcctctctg        1000 aggtccagga ggaaaaaggc atcaagtata agtttgaagt ctacgagaag        1050
aaagactaac aggaagatgc tttcaagttc tctgctcccc tcctaaagct        1100
atgcattttt ataagaccat gggacttttg ctggctttag atccccttgg        1150
cttcgttaga acgcagctac aattaataca taaccttatg tatcatacac        1200
atacgattta ggtgacacta tagataacat ccactttgcc tttctctcca        1250
```

```
caggtgtcca ctcccaggtc caactgcacc tcggttctat cgattgaatt         1300
ccaccatggg atggtcatgt atcatccttt ttctagtagc aactgcaact         1350
ggagtacatt cagaagttca gctagtgcag tctggcggtg gcctggtgca         1400 gccaggggc  tcactccgtt tgtcctgtgc agcttctggc tactccttct         1450
cgagtcacta tatgcactgg gtccgtcagg ccccgggtaa gggcctggaa         1500
tgggttggat atattgatcc ttccaatggt gaaactacgt ataatcaaaa         1550
gttcaagggc cgtttcactt tatctcgcga caactccaaa aacacagcat         1600
acctgcagat gaacagcctg cgtgctgagg acactgccgt ctattactgt         1650
gcaagagggg attatcgcta caatggtgac tggttcttcg acgtctgggg         1700
tcaaggaacc ctggtcaccg tctcctcggc ctccaccaag ggcccatcgg         1750
tcttccccct ggcaccctcc tccaagagca cctctggggg cacagcggcc         1800
ctgggctgcc tggtcaagga ctacttcccc gaaccggtga cggtgtcgtg         1850
gaactcaggc gccctgacca gcggcgtgca caccttcccg gctgtcctac         1900
agtcctcagg actctactcc ctcagcagcg tggtgactgt gccctctagc         1950
agcttgggca cccagaccta catctgcaac gtgaatcaca agcccagcaa         2000
caccaaggtg gacaagaaag ttgagcccaa atcttgtgac aaaactcaca         2050
catgcccacc gtgcccagca cctgaactcc tggggggacc gtcagtcttc         2100
ctcttccccc caaaacccaa ggacaccctc atgatctccc ggacccctga         2150
ggtcacatgc gtggtggtgg acgtgagcca cgaagaccct gaggtcaagt         2200
tcaactggta cgtggacggc gtggaggtgc ataatgccaa gacaaagccg         2250
cgggaggagc agtacaacag cacgtaccgt gtggtcagcg tcctcaccgt         2300
cctgcaccag gactggctga atggcaagga gtacaagtgc aaggtctcca         2350
acaaagccct cccagccccc atcgagaaaa ccatctccaa agccaaaggg         2400
cagccccgag aaccacaggt gtacaccctg cccccatccc gggaagagat         2450
gaccaagaac caggtcagcc tgacctgcct ggtcaaaggc ttctatccca         2500
gcgacatcgc cgtggagtgg gagagcaatg ggcagccgga gaacaactac         2550
aagaccacgc ctcccgtgct ggactccgac ggctccttct tcctctacag         2600
caagctcacc gtggacaaga gcaggtggca gcaggggaac gtcttctcat         2650
gctccgtgat gcatgaggct ctgcacaacc actacacgca gaagagcctc         2700
tccctgtctc cgggtaaatg agtgcgacgg ccctagagtc gacctgcaga         2750
agcttggccg ccatggccca acttgtttat tgcagcttat aatggttaca         2800
aataaagcaa tagcatcaca aatttcacaa ataaagcatt ttttcactg          2850 cattctagtt gtggtttgtc caaactcatc aatgtatctt atcatgtctg         2900
gatcgatcgg gaattaattc ggcgcagcac catggcctga ataacctct          2950 gaaagaggaa cttggttagg taccttctga ggcggaaaga accatctgtg         3000
gaatgtgtgt cagttagggt gtggaaagtc cccaggctcc ccagcaggca         3050
gaagtatgca aagcatgcat ctcaattagt cagcaaccag gtgtggaaag         3100
tccccaggct ccccagcagg cagaagtatg caaagcatgc atctcaatta         3150
gtcagcaacc atagtcccgc ccctaactcc gcccatcccg ccctaactc          3200 cgcccagttc cgcccattct ccgccccatg gctgactaat ttttttttatt       3250
```

```
tatgcagagg ccgaggccgc ctcggcctct gagctattcc agaagtagtg       3300
aggaggcttt tttggaggcc taggcttttg caaaaagcta gcttatccgg       3350
ccgggaacgt tgcattggaa cgcggattcc ccgtgccaag agtcaggtaa       3400
gtaccgccta tagagtctat aggcccaccc ccttggcttc gttagaacgc       3450
ggctacaatt aatacataac cttttggatc gatcctactg acactgacat       3500
ccactttttc tttttctcca caggtgtcca ctcccaggtc caactgcacc       3550
tcggttcgcg aagctagctt gggctgcatc gattgaattc caccatggga       3600
tggtcatgta tcatcctttt tctagtagca actgcaactg gagtacattc       3650
agatatccag atgacccagt ccccgagctc cctgtccgcc tctgtgggcg       3700
atagggtcac catcacctgc aggtcaagtc aaagcttagt acatggtata       3750
ggtgctacgt atttacactg gtatcaacag aaaccaggaa aagctccgaa       3800
actactgatt tacaaagtat ccaatcgatt ctctggagtc ccttctcgct       3850
tctctggatc cggttctggg acggatttca ctctgaccat cagcagtctg       3900
cagccagaag acttcgcaac ttattactgt tcacagagta ctcatgtccc       3950
gctcacgttt ggacagggta ccaaggtgga gatcaaacga actgtggctg       4000
caccatctgt cttcatcttc cgccatctg atgagcagtt gaaatctgga       4050
actgcttctg ttgtgtgcct gctgaataac ttctatccca gagaggccaa       4100
agtacagtgg aaggtggata acgccctcca atcgggtaac tcccaggaga       4150
gtgtcacaga gcaggacagc aaggacagca cctacagcct cagcagcacc       4200
ctgacgctga gcaaagcaga ctacgagaaa cacaaagtct acgcctgcga       4250
agtcacccat cagggcctga gctcgcccgt cacaaagagc ttcaacaggg       4300
gagagtgtta agcttggccg ccatggccca acttgtttat tgcagcttat       4350
aatggttaca aataaagcaa tagcatcaca aatttcacaa ataaagcatt       4400
tttttcactg cattctagtt gtggtttgtc caaactcatc aatgtatctt       4450
atcatgtctg gatcgatcgg gaattaattc ggcgcagcac catggcctga       4500
aataacctct gaaagaggaa cttggttagg taccttctga ggcggaaaga       4550
accagctgtg aatgtgtgt cagttagggt gtggaaagtc cccaggctcc       4600
ccagcaggca gaagtatgca aagcatgcat ctcaattagt cagcaaccag       4650
gtgtggaaag tccccaggct ccccagcagg cagaagtatg caaagcatgc       4700
atctcaatta gtcagcaacc atagtcccgc ccctaactcc gcccatcccg       4750
cccctaactc cgcccagttc cgcccattct ccgccccatg gctgactaat       4800
ttttttatt tatgcagagg ccgaggccgc ctcggcctct gagctattcc       4850
agaagtagtg aggaggcttt tttggaggcc taggcttttg caaaaagctg       4900
ttacctcgag cggccgctta attaaggcgc gccatttaaa tcctgcaggt       4950
aacagcttgg cactggccgt cgttttacaa cgtcgtgact gggaaaaccc       5000
tggcgttacc caacttaatc gccttgcagc acatccccc ttcgccagct       5050
ggcgtaatag cgaagaggcc cgcaccgatc gcccttccca acagttgcgt       5100
agcctgaatg gcgaatggcg cctgatgcgg tattttctcc ttacgcatct       5150
gtgcggtatt tcacaccgca tacgtcaaag caaccatagt acgcgccctg       5200
```

```
tagcggcgca ttaagcgcgg cgggtgtggt ggttacgcgc agcgtgaccg       5250
ctacacttgc cagcgcccta gcgcccgctc ctttcgcttt cttcccttcc       5300
tttctcgcca cgttcgccgg ctttccccgt caagctctaa atcgggggct       5350
ccctttaggg ttccgattta gtgctttacg gcacctcgac cccaaaaaac       5400
ttgatttggg tgatggttca cgtagtgggc catcgccctg atagacggtt       5450
tttcgccctt tgacgttgga gtccacgttc tttaatagtg actcttgtt        5500
ccaaactgga acaacactca accctatctc gggctattct tttgatttat       5550
aagggatttt gccgatttcg gcctattggt aaaaaatga gctgatttaa        5600
caaaaattta acgcgaattt taacaaaata ttaacgttta caattttatg       5650
gtgcactctc agtacaatct gctctgatgc cgcatagtta agccaactcc       5700
gctatcgcta cgtgactggg tcatggctgc gccccgacac ccgccaacac       5750
ccgctgacgc gccctgacgg gcttgtctgc tcccggcatc cgcttacaga       5800
caagctgtga ccgtctccgg gagctgcatg tgtcagaggt tttcaccgtc       5850
atcaccgaaa cgcgcgaggc agtattcttg aagacgaaag gcctcgtga        5900
tacgcctatt tttataggtt aatgtcatga taataatggt ttcttagacg       5950
tcaggtggca cttttcgggg aaatgtgcgc ggaaccccta tttgtttatt       6000
tttctaaata cattcaaata tgtatccgct catgagacaa taaccctgat       6050
aaatgcttca ataatattga aaaggaaga gtatgagtat tcaacatttc         6100
cgtgtcgccc ttattccctt ttttgcggca ttttgccttc ctgttttttgc       6150
tcacccagaa acgctggtga agtaaaaga tgctgaagat cagttgggtg         6200
cacgagtggg ttacatcgaa ctggatctca acagcggtaa gatccttgag        6250
agttttcgcc ccgaagaacg ttttccaatg atgagcactt ttaaagttct        6300
gctatgtggc gcggtattat cccgtgatga cgccgggcaa gagcaactcg       6350
gtcgccgcat acactattct cagaatgact tggttgagta ctcaccagtc        6400
acagaaaagc atcttacgga tggcatgaca gtaagagaat tatgcagtgc       6450
tgccataacc atgagtgata acactgcggc caacttactt ctgacaacga       6500
tcggaggacc gaaggagcta accgcttttt tgcacaacat gggggatcat       6550
gtaactcgcc ttgatcgttg ggaaccggag ctgaatgaag ccataccaaa       6600
cgacgagcgt gacaccacga tgccagcagc aatggcaaca acgttgcgca       6650
aactattaac tggcgaacta cttactctag cttcccggca acaattaata       6700
gactggatgg aggcggataa agttgcagga ccacttctgc gctcggccct       6750
tccggctggc tggtttattg ctgataaatc tggagccggt gagcgtgggt       6800
ctcgcggtat cattgcagca ctggggccag atggtaagcc ctcccgtatc       6850
gtagttatct acacgacggg gagtcaggca actatggatg aacgaaatag       6900
acagatcgct gagataggtg cctcactgat taagcattgg taactgtcag       6950
accaagttta ctcatatata ctttagattg atttaaaact tcatttttaa       7000
tttaaaagga tctaggtgaa gatcctttt gataatctca tgaccaaaat        7050
cccttaacgt gagttttcgt tccactgagc gtcagacccc gtagaaaaga       7100
tcaaaggatc ttcttgagat cctttttttc tgcgcgtaat ctgctgcttg       7150
caaacaaaaa aaccaccgct accagcggtg gtttgtttgc cggatcaaga       7200
```

| | |
|---|---|
| gctaccaact cttttttccga aggtaactgg cttcagcaga gcgcagatac | 7250 |
| caaatactgt ccttctagtg tagccgtagt taggccacca cttcaagaac | 7300 |
| tctgtagcac cgcctacata cctcgctctg ctaatcctgt taccagtggc | 7350 |
| tgctgccagt ggcgataagt cgtgtcttac cgggttggac tcaagacgat | 7400 |
| agttaccgga taaggcgcag cggtcgggct gaacggggggg ttcgtgcaca | 7450 |
| cagcccagct tggagcgaac gacctacacc gaactgagat acctacagcg | 7500 |
| tgagcattga gaaagcgcca cgcttcccga agggagaaag gcggacaggt | 7550 |
| atccggtaag cggcagggtc ggaacaggag agcgcacgag ggagcttcca | 7600 |
| ggggggaaacg cctggtatct ttatagtcct gtcgggtttc gccacctctg | 7650 |
| acttgagcgt cgatttttgt gatgctcgtc agggggggcgg agcctatgga | 7700 |
| aaaacgccag caacgcggcc ttttttacggt tcctggcctt ttgctggcct | 7750 |
| tttgctcaca tgttctttcc tgcgttatcc cctgattctg tggataaccg | 7800 |
| tattaccgcc tttgagtgag ctgataccgc tcgccgcagc cgaacgaccg | 7850 |
| agcgcagcga gtcagtgagc gaggaagcgg aagagcgccc aatacgcaaa | 7900 |
| ccgcctctcc ccgcgcgttg gccgattcat taatccagct ggcacgacag | 7950 |
| gtttcccgac tggaaagcgg gcagtgagcg caacgcaatt aatgtgagtt | 8000 |
| acctcactca ttaggcaccc caggctttac actttatgct tccggctcgt | 8050 |
| atgttgtgtg gaattgtgag cggataacaa tttcacacag gaaacagcta | 8100 |
| tgaccatgat tacgaattaa | 8120 |

<210> SEQ ID NO 69
<211> LENGTH: 800
<212> TYPE: DNA
<213> ORGANISM: Artificial Sequence
<220> FEATURE:
<221> NAME/KEY: Artificial Sequence
<222> LOCATION: 1-800
<223> OTHER INFORMATION: recombinant immunoglobulin

<400> SEQUENCE: 69

| | |
|---|---|
| aaaagggtat ctagaggttg aggtgatttt atgaaaaaga atatcgcatt | 50 |
| tcttcttgca tctatgttcg tttttttctat tgctacaaac gcgtacgctg | 100 |
| aggttcagct agtgcagtct ggcggtggcc tggtgcagcc aggggggctca | 150 |
| ctccgtttgt cctgtgcagc ttctggctac tccttctcga gtcactatat | 200 |
| gcactgggtc cgtcaggccc cgggtaaggg cctggaatgg gttggatata | 250 |
| ttgatccttc caatggtgaa actacgtata atcaaaagtt caagggccgt | 300 |
| ttcactttat ctcgcgacaa ctccaaaaac acagcatacc tgcagatgaa | 350 |
| cagcctgcgt gctgaggaca ctgccgtcta ttactgtgca agaggggatt | 400 |
| atcgctacaa tggtgactgg ttcttcgacg tctggggtca aggaaccctg | 450 |
| gtcaccgtct cctcggcctc caccaagggc ccatcggtct tccccctggc | 500 |
| accctcctcc aagagcacct ctgggggcac agcggccctg gctgcctgg | 550 |
| tcaaggacta cttccccgaa ccggtgacgg tgtcgtggaa ctcaggcgcc | 600 |
| ctgaccagcg gcgtgcacac cttcccggct gtcctacagt cctcaggact | 650 |
| ctactccctc agcagcgtgg tgaccgtgcc ctccagcagc ttgggcaccc | 700 |

-continued

```
agacctacat ctgcaacgtg aatcacaagc ccagcaacac caaggtcgac          750
aagaaagttg agcccaaatc ttgtgacaaa actcacacat gcccgcctga          800
```

<210> SEQ ID NO 70
<211> LENGTH: 256
<212> TYPE: PRT
<213> ORGANISM: Artificial Sequence
<220> FEATURE:
<221> NAME/KEY: Artificial Sequence
<222> LOCATION: 1-256
<223> OTHER INFORMATION: recombinant immunoglobulin

<400> SEQUENCE: 70

| Met | Lys | Lys | Asn | Ile | Ala | Phe | Leu | Leu | Ala | Ser | Met | Phe | Val | Phe |
|---|---|---|---|---|---|---|---|---|---|---|---|---|---|---|
| 1 |  |  |  | 5 |  |  |  |  | 10 |  |  |  |  | 15 |

| Ser | Ile | Ala | Thr | Asn | Ala | Tyr | Ala | Glu | Val | Gln | Leu | Val | Gln | Ser |
|  |  |  |  | 20 |  |  |  |  | 25 |  |  |  |  | 30 |

| Gly | Gly | Gly | Leu | Val | Gln | Pro | Gly | Gly | Ser | Leu | Arg | Leu | Ser | Cys |
|  |  |  | 35 |  |  |  |  | 40 |  |  |  |  | 45 |  |

| Ala | Ala | Ser | Gly | Tyr | Ser | Phe | Ser | Ser | His | Tyr | Met | His | Trp | Val |
|  |  | 50 |  |  |  |  | 55 |  |  |  |  | 60 |  |  |

| Arg | Gln | Ala | Pro | Gly | Lys | Gly | Leu | Glu | Trp | Val | Gly | Tyr | Ile | Asp |
| 65 |  |  |  |  | 70 |  |  |  |  | 75 |  |  |  |  |

| Pro | Ser | Asn | Gly | Glu | Thr | Thr | Tyr | Asn | Gln | Lys | Phe | Lys | Gly | Arg |
|  |  |  | 80 |  |  |  |  | 85 |  |  |  |  | 90 |  |

| Phe | Thr | Leu | Ser | Arg | Asp | Asn | Ser | Lys | Asn | Thr | Ala | Tyr | Leu | Gln |
|  |  | 95 |  |  |  |  | 100 |  |  |  |  | 105 |  |  |

| Met | Asn | Ser | Leu | Arg | Ala | Glu | Asp | Thr | Ala | Val | Tyr | Tyr | Cys | Ala |
|  | 110 |  |  |  |  | 115 |  |  |  |  | 120 |  |  |  |

| Arg | Gly | Asp | Tyr | Arg | Tyr | Asn | Gly | Asp | Trp | Phe | Phe | Asp | Val | Trp |
| 125 |  |  |  |  | 130 |  |  |  |  | 135 |  |  |  |  |

| Gly | Gln | Gly | Thr | Leu | Val | Thr | Val | Ser | Ser | Ala | Ser | Thr | Lys | Gly |
|  |  |  | 140 |  |  |  |  | 145 |  |  |  |  | 150 |  |

| Pro | Ser | Val | Phe | Pro | Leu | Ala | Pro | Ser | Ser | Lys | Ser | Thr | Ser | Gly |
|  |  | 155 |  |  |  |  | 160 |  |  |  |  | 165 |  |  |

| Gly | Thr | Ala | Ala | Leu | Gly | Cys | Leu | Val | Lys | Asp | Tyr | Phe | Pro | Glu |
|  | 170 |  |  |  |  | 175 |  |  |  |  | 180 |  |  |  |

| Pro | Val | Thr | Val | Ser | Trp | Asn | Ser | Gly | Ala | Leu | Thr | Ser | Gly | Val |
| 185 |  |  |  |  | 190 |  |  |  |  | 195 |  |  |  |  |

| His | Thr | Phe | Pro | Ala | Val | Leu | Gln | Ser | Ser | Gly | Leu | Tyr | Ser | Leu |
|  |  |  | 200 |  |  |  |  | 205 |  |  |  |  | 210 |  |

| Ser | Ser | Val | Val | Thr | Val | Pro | Ser | Ser | Ser | Leu | Gly | Thr | Gln | Thr |
|  |  | 215 |  |  |  |  | 220 |  |  |  |  | 225 |  |  |

| Tyr | Ile | Cys | Asn | Val | Asn | His | Lys | Pro | Ser | Asn | Thr | Lys | Val | Asp |
|  | 230 |  |  |  |  | 235 |  |  |  |  | 240 |  |  |  |

| Lys | Lys | Val | Glu | Pro | Lys | Ser | Cys | Asp | Lys | Thr | His | Thr | Cys | Pro |
| 245 |  |  |  |  | 250 |  |  |  |  | 255 |  |  |  |  |

Pro
256

<210> SEQ ID NO 71
<211> LENGTH: 452
<212> TYPE: PRT
<213> ORGANISM: Artificial Sequence
<220> FEATURE:
<221> NAME/KEY: Artificial Sequence
<222> LOCATION: 1-452
<223> OTHER INFORMATION: recombinant immunoglobulin

<400> SEQUENCE: 71

```
Glu Val Gln Leu Val Gln Ser Gly Gly Gly Leu Val Gln Pro Gly
1               5                   10                  15
Gly Ser Leu Arg Leu Ser Cys Ala Ala Ser Gly Tyr Ser Phe Ser
                20                  25                  30
Ser His Tyr Met His Trp Val Arg Gln Ala Pro Gly Lys Gly Leu
            35                  40                  45
Glu Trp Val Gly Tyr Ile Asp Pro Ser Asn Gly Glu Thr Thr Tyr
        50                  55                  60
Asn Gln Lys Phe Lys Gly Arg Phe Thr Leu Ser Arg Asp Asn Ser
65                  70                  75
Lys Asn Thr Ala Tyr Leu Gln Met Asn Ser Leu Arg Ala Glu Asp
                80                  85                  90
Thr Ala Val Tyr Tyr Cys Ala Arg Gly Asp Tyr Arg Tyr Asn Gly
            95                  100                 105
Asp Trp Phe Phe Asp Val Trp Gly Gln Gly Thr Leu Val Thr Val
        110                 115                 120
Ser Ser Ala Ser Thr Lys Gly Pro Ser Val Phe Pro Leu Ala Pro
125                 130                 135
Ser Ser Lys Ser Thr Ser Gly Gly Thr Ala Ala Leu Gly Cys Leu
                140                 145                 150
Val Lys Asp Tyr Phe Pro Glu Pro Val Thr Val Ser Trp Asn Ser
            155                 160                 165
Gly Ala Leu Thr Ser Gly Val His Thr Phe Pro Ala Val Leu Gln
        170                 175                 180
Ser Ser Gly Leu Tyr Ser Leu Ser Ser Val Val Thr Val Pro Ser
185                 190                 195
Ser Ser Leu Gly Thr Gln Thr Tyr Ile Cys Asn Val Asn His Lys
                200                 205                 210
Pro Ser Asn Thr Lys Val Asp Lys Lys Val Glu Pro Lys Ser Cys
            215                 220                 225
Asp Lys Thr His Thr Cys Pro Pro Cys Pro Ala Pro Glu Leu Leu
        230                 235                 240
Gly Gly Pro Ser Val Phe Leu Phe Pro Pro Lys Pro Lys Asp Thr
245                 250                 255
Leu Met Ile Ser Arg Thr Pro Glu Val Thr Cys Val Val Val Asp
                260                 265                 270
Val Ser His Glu Asp Pro Glu Val Lys Phe Asn Trp Tyr Val Asp
            275                 280                 285
Gly Val Glu Val His Asn Ala Lys Thr Lys Pro Arg Glu Glu Gln
        290                 295                 300
Tyr Asn Ser Thr Tyr Arg Val Val Ser Val Leu Thr Val Leu His
305                 310                 315
Gln Asp Trp Leu Asn Gly Lys Glu Tyr Lys Cys Lys Val Ser Asn
                320                 325                 330
Lys Ala Leu Pro Ala Pro Ile Glu Lys Thr Ile Ser Lys Ala Lys
            335                 340                 345
Gly Gln Pro Arg Glu Pro Gln Val Tyr Thr Leu Pro Pro Ser Arg
        350                 355                 360
Glu Glu Met Thr Lys Asn Gln Val Ser Leu Thr Cys Leu Val Lys
365                 370                 375
Gly Phe Tyr Pro Ser Asp Ile Ala Val Glu Trp Glu Ser Asn Gly
```

-continued

```
                380             385             390

Gln Pro Glu Asn Asn Tyr Lys Thr Thr Pro Pro Val Leu Asp Ser
                395             400             405

Asp Gly Ser Phe Phe Leu Tyr Ser Lys Leu Thr Val Asp Lys Ser
                410             415             420

Arg Trp Gln Gln Gly Asn Val Phe Ser Cys Ser Val Met His Glu
                425             430             435

Ala Leu His Asn His Tyr Thr Gln Lys Ser Leu Ser Leu Ser Pro
                440             445             450

Gly Lys
    452

<210> SEQ ID NO 72
<211> LENGTH: 219
<212> TYPE: PRT
<213> ORGANISM: Artificial Sequence
<220> FEATURE:
<221> NAME/KEY: Artficial Sequence
<222> LOCATION: 1-219
<223> OTHER INFORMATION: recombinant imunoglobulin

<400> SEQUENCE: 72

Asp Ile Gln Met Thr Gln Ser Pro Ser Ser Leu Ser Ala Ser Val
  1               5              10              15

Gly Asp Arg Val Thr Ile Thr Cys Arg Ser Ser Gln Ser Leu Val
                 20              25              30

His Gly Ile Gly Ala Thr Tyr Leu His Trp Tyr Gln Gln Lys Pro
                 35              40              45

Gly Lys Ala Pro Lys Leu Leu Ile Tyr Lys Val Ser Asn Arg Phe
                 50              55              60

Ser Gly Val Pro Ser Arg Phe Ser Gly Ser Gly Ser Gly Thr Asp
                 65              70              75

Phe Thr Leu Thr Ile Ser Ser Leu Gln Pro Glu Asp Phe Ala Thr
                 80              85              90

Tyr Tyr Cys Ser Gln Ser Thr His Val Pro Leu Thr Phe Gly Gln
                 95             100             105

Gly Thr Lys Val Glu Ile Lys Arg Thr Val Ala Ala Pro Ser Val
                110             115             120

Phe Ile Phe Pro Pro Ser Asp Glu Gln Leu Lys Ser Gly Thr Ala
                125             130             135

Ser Val Val Cys Leu Leu Asn Asn Phe Tyr Pro Arg Glu Ala Lys
                140             145             150

Val Gln Trp Lys Val Asp Asn Ala Leu Gln Ser Gly Asn Ser Gln
                155             160             165

Glu Ser Val Thr Glu Gln Asp Ser Lys Asp Ser Thr Tyr Ser Leu
                170             175             180

Ser Ser Thr Leu Thr Leu Ser Lys Ala Asp Tyr Glu Lys His Lys
                185             190             195

Val Tyr Ala Cys Glu Val Thr His Gln Gly Leu Ser Ser Pro Val
                200             205             210

Thr Lys Ser Phe Asn Arg Gly Glu Cys
                215             219
```

We claim:

1. A conjugate consisting essentially of an antibody fragment covalently modified by one or two nonproteinaceous polymer molecules at a free sulfhydryl group of a cysteine residue within the hinge region of the antibody fragment,
wherein said antibody fragment is engineered to both (1) provide an unpaired cysteine within the hinge region, so as to provide said free sulfhydryl group, and (2) to avoid disulfide bridge formation between said cysteine and an amino acid in the opposite chain of said antibody fragment,
wherein (a) the average actual molecular weight of each nonproteinaceous polymer molecule is at least 20 kD, (b) the conjugate binds the same antigen as the parental molecule that is not covalently modified by one or two nonproteinaceous polymer molecules, and wherein the antibody fragment comprises an antigen binding site that binds to a human tumor necrosis factor-α (TNF-α) polypeptide.

2. The conjugate of claim 1, wherein the apparent size of the conjugate is at least about 800 kD.

3. The conjugate of claim 1, wherein the apparent size of the conjugate is at least about 1,400 kD.

4. The conjugate of claim 1, wherein the apparent size of the conjugate is at least about 1,800 kD.

5. The conjugate of claim 1, wherein the apparent size of the conjugate is at least about 15 fold greater than the apparent size of at least one antibody fragment.

6. The conjugate of claim 5, wherein the apparent size of the conjugate is at least about 25 fold greater than the apparent size of at least one antibody fragment.

7. The conjugate of claim 1 wherein the antibody fragment is selected from the group consisting of Fab, Fab', Fab'-SH, Fv, scFv and F(ab')$_2$.

8. The conjugate of claim 7 wherein the antibody fragment is selected from the group consisting of Fab, Fab' and Fab'-SH.

9. The conjugate of claim 7 wherein the antibody fragment is a F(ab')$_2$ fragment.

10. The conjugate of claim 7 wherein the antibody fragment is a Fab' fragment.

11. The conjugate of claim 1 wherein the antibody fragment is attached to no more than 1 nonproteinaceous polymer molecule.

12. The conjugate of claim 7 wherein the antibody fragment is covalently attached to no more than 1 nonproteinaceous polymer molecule.

13. The conjugate of claim 9 wherein the antibody fragment is covalently attached to no more than 1 nonproteinaceous polymer molecule.

14. The conjugate of claim 10 wherein the antibody fragment is covalently attached to no more than 1 nonproteinaceous polymer molecule.

15. The conjugate of claim 1 wherein at least one nonproteinaceous polymer is a polyethylene glycol (PEG).

16. The conjugate of claim 15 wherein the PEG has an average molecular weight of at least about 20 kD.

17. The conjugate of claim 15 wherein the PEG has an average molecular weight of at least about 40 kD.

18. The conjugate of claim 15 wherein the PEG is a single chain molecule.

19. The conjugate of claim 15 wherein the PEG is a branched chain molecule.

20. The conjugate of claim 15, wherein the antibody fragment is selected from the group consisting of Fab, Fab', Fab'-SH, Fv, scFv and F(ab')$_2$ and is covalently attached to no more than one PEG molecule.

21. The conjugate of claim 15, wherein the antibody fragment is selected from the group consisting of Fab, Fab' and Fab'-SH and is covalently attached to no more than one PEG molecule.

22. The conjugate of claim 1, wherein the antibody fragment is selected from the group consisting of Fab, Fab' and Fab'-SH, wherein the antibody fragment is, covalently attached to no more than one nonproteinaceous polymer molecule, and wherein the nonproteinaceous polymer molecule is a PEG having an average molecular weight of at least about 20 kD.

23. The conjugate of claim 22 wherein the PEG has an average molecular weight of at least about 30 kD.

24. The conjugate of claim 22 wherein the PEG has an average molecular weight of at least about 40 kD.

25. The conjugate of claim 22 wherein the PEG is a single chain molecule.

26. The conjugate of claim 22 wherein the PEG is a branched chain molecule.

27. The conjugate of claim 1 wherein the antibody fragment comprising the antigen binding site is humanized.

28. The conjugate of claim 1, wherein the covalent structure of the conjugate is free of any matter other than the antibody fragment and nonproteinaceous polymer molecules that form the conjugate.

29. The conjugate of claim 1, wherein the covalent structure of the conjugate incorporates one or more nonproteinaceous labels, and wherein the covalent structure of the conjugate is free of any matter other than the antibody fragment, nonproteinaceous polymer and nonproteinaceous label molecules that form the conjugate.

30. The conjugate of claim 29 wherein at least one nonproteinaceous label is a radiolabel.

31. A composition comprising the conjugate of claim 1 and a carrier.

32. The composition of claim 31 that is sterile.

33. A conjugate consisting essentially of an antibody fragment covalently modified by one or two nonproteinaceous polymer molecules at a free sulfhydryl group of a cysteine residue within the hinge region of the antibody fragment,
wherein said antibody fragment is engineered to both (1) provide an unpaired cysteine within the hinge region, so as to provide said free sulfhydryl group, and (2) to avoid disulfide bridge formation between said cysteine and an amino acid in the opposite chain of said antibody fragment,
wherein the conjugate binds the same antigen as the parental molecule that is not covalently modified by one or two nonproteinaceous polymer molecules, and wherein the antibody fragment comprises an antigen binding site that binds to a human tumor necrosis factor-α (TNF-α) polypeptide.

34. A conjugate consisting essentially of an antibody fragment covalently modified by one or two nonproteinaceous polymer molecules at a free sulfhydryl group of a cysteine residue within the hinge region of the antibody fragment,
wherein said antibody fragment is engineered to both (1) provide an unpaired cysteine within the hinge region, so as to provide said free sulfhydryl group, and (2) to avoid disulfide bridge formation between said cysteine and an amino acid in the opposite chain of said antibody fragment,
wherein the apparent molecular weight of the conjugate, as determined by size exclusion chromatography is at least 500 kD, and the conjugate binds the same antigen as the parental molecule that is not covalently modified by one or two nonproteinaceous polymer molecules, and wherein the antibody fragment comprises an antigen binding site that binds to a human tumor necrosis factor-α (TNF-α) polypeptide.

35. A conjugate consisting essentially of an antibody fragment covalently modified by one or two nonproteinaceous polymer molecules at a free sulfhydryl group of a cysteine residue within the hinge region of the antibody fragment,
  wherein said antibody fragment is engineered to both (1) provide an unpaired cysteine within the hinge region, so as to provide said free sulfhydryl group, and (2) to avoid disulfide bridge formation between said cysteine and an amino acid in the opposite chain of said antibody fragment,
  wherein (a) the apparent molecular weight of the conjugate, as determined by size exclusion chromatography is at least 500 kD, (b) the average actual molecular weight of each nonproteinaceous polymer molecule is at least 20 kD, and (c) the conjugate binds the same antigen as, the parental molecule that is not covalently modified by one or two nonproteinaceous polymer molecules, and wherein the antibody fragment comprises an antigen binding site that binds to a human tumor necrosis factor-α (TNF-α) polypeptide.

36. A conjugate consisting essentially of an antibody fragment covalently modified by one or two nonproteinaceous polymer molecules at a free sulfhydryl group of a cysteine residue within the hinge region of the antibody fragment,
  wherein said antibody fragment is engineered to both (1) provide an unpaired cysteine within the hinge region, so as to provide said free sulfhydryl group, and (2) to avoid disulfide bridge formation between said cysteine and an amino acid in the opposite chain of said antibody fragment,
  (a) the apparent molecular weight of the conjugate, as determined by size exclusion chromatography is at least 500 kD, (b) the average actual molecular weight of each nonproteinaceous polymer molecule is at least 20 kD, (c) wherein the conjugate has an apparent size that is about 8-fold greater than the apparent size of the parental antibody fragment, wherein the conjugate binds the same antigen as the parental molecule that is not covalently modified by one or two nonproteinaceous polymer molecules, and wherein the antibody fragment comprises an antigen binding site that binds to a human tumor necrosis factor-α (TNF-α) polypeptide.

* * * * *